(12) United States Patent
Player et al.

(10) Patent No.: US 7,951,829 B2
(45) Date of Patent: May 31, 2011

(54) BENZIMIDAZOLE MODULATORS OF VR1

(75) Inventors: Mark R. Player, Phoenixville, PA (US);
Scott L. Dax, Landenberg, PA (US);
William H. Parsons, Belle Mead, NJ (US); Michael Richard Brandt, Flemington, NJ (US); Raul R. Calvo, Royerford, PA (US); Sharmila Patel, Jamison, PA (US); Jian Liu, Manalapan, NJ (US); Wing S. Cheung, Plainsboro, NJ (US); Michele C. Jetter, Norristown, PA (US); Yu-Kai Lee, Exton, PA (US); Mark A. Youngman, Warminster, PA (US); Wenxi Pan, Glenmore, PA (US); Kenneth M. Wells, Hillsborough, NJ (US); Derek A. Beauchamp, Watchung, NJ (US)

(73) Assignee: Janssen Pharmaceutica NV (BE)

( * ) Notice: Subject to any disclaimer, the term of this patent is extended or adjusted under 35 U.S.C. 154(b) by 599 days.

(21) Appl. No.: 11/734,984

(22) Filed: Apr. 13, 2007

(65) Prior Publication Data

US 2007/0259936 A1 Nov. 8, 2007

Related U.S. Application Data

(60) Provisional application No. 60/797,504, filed on May 3, 2006.

(51) Int. Cl.
*A01N 43/52* (2006.01)
*C07D 235/00* (2006.01)

(52) U.S. Cl. .................................. 514/394; 548/304.4

(58) Field of Classification Search .................. None
See application file for complete search history.

(56) References Cited

U.S. PATENT DOCUMENTS 6,299,796 B1 10/2001 Igarashi

OTHER PUBLICATIONS

Newman et al., DDT vol. 8, Oct. 2003, p. 898-90.*
Chawla et al., CRIPS vol. 5, No. 1, Jan.-Mar. 2004, p. 9-12.*
Boyd et al., caplus an 1995:252332.*
Alzheimer's Disease Treatment Phases, http://www.alzheimerstreatment.org/treatment/disease-treatment.htm.*
Alzheimer's Drugs, Consumer Reports Best Buy Drugs (p. 1-5).*
CriticalReviewControlledClinicalTrials, http://www.ncbi.nlm.nih.gov/pubmed/9415498.*
Chroic Pain, http://en.wikipedia.org/wiki/Chronic_pain (2010).*
Gunthorpe et al., The Journal of Pharmacology and Experimental Therapeutics, 321, 2007, 1183-1192.*
Alzheimer's Disease Treatment Phases, http://www.alzheimerstreatment.org/treatment/disease-treatment.htm (2009).*
Alzheimer's Drugs, Consumer Reports Best Buy Drugs (p. 1-5) (2009).*
CriticalReviewControlledClinicalTrials, http://www.ncbi.nlm.nih.gov/pubmed/9415498 (2009).*
Yiangou, Y.; Facer, P.; Dyer, N. H.; Chan, C. L.; Knowles, C.: Williams, N. S.; Anand, P. Lancet 2001, 357, 1338-1339.
McVey, D. C.; Schmid, P. C.; Schmid, H. H. O.; Vigna, S. R. J. Pharmacol. Exp. Ther. 2003, 304, 713-722.
Kimball, E. S.; Wallace, N. H.; Schneider, C. R.; D'Andrea, M. R.; Hornby, P. J. Neurogasteroenterology 2004, 16, 811-818.
Walker, K. M.; Urban, L.; Medhurst, S. J.; Patel, S.; Panesar, M.; Fox, A. J.; McIntyre, P. J. Pharmacol. Exp. Ther. 2003, 304, 56-62.
Pomonis, J. D.; Harrison, J. E.; Mark, L.; Bristol, D. R.; Valenzano, K. J.; Walker, K. J. Pharmacol. Exp. Ther. 2003, 306, 387-393.
Lida, T.; Shimizu, I.; Nealen, M. L.; Campbell, A.; Caterina, M. Neurosci. Lett. 2005, 378, 28-33.
Ohnluki, K.; Haramizu, S.; Watanabe, T.; Yazawa, S.; Fushiki, T. J. Nutr. Sci. Vitaminol. (Tokyo) 2001, 47, 295-298.
Woods, A. J.; Stock, M. J.; Gupta, A. N.; Wong, T. T. L.; Andews, P. L. R. Eur. J. Pharmacol. 1994, 264, 125-133.
Romanovsky, A. A. Frontiers in Bioscience 2004, 9, 494-504.
Nault, M. A.; Vincent, S. G.; Fisher, J. T. J. Physiol. 1999, 515, 567-578.
Jia, Y.; McLeod, R. L.; Wang, X.; Parra, L. E.; Egan, R. W.; Hey, J. A. Brit. J. Pharmacol. 2002, 137, 831-836.
Bianco, E. D.; Geppetti, P.; Zippi, P.; Isolani, D.; Magini, B.; Cappugi, P. Brit J of Clin Pharmacol 1996, 41, 1-6.
Kissin, I.; Bright, C. A.; Bradley, E. L., Jr. Anesth Analg 2002, 94, 1253-1258.
Ellison, N., Loprinzi, C. L., Kugler, J., Hatfield, A.K., Miser, A., Sloan, J.A., Wender, D.B., Rowland, K.M., Molina, R., Cascino, T.L., Vukov, A.M., Dhaliwal, H.S. and Ghosh, C.J. Clin. Oncol. 15:2974-2980, 1997.
Berger, A., Henderson, M., Naadoolman, W., Duffy, V., Cooper, D., Saberski, L., and Bartoshuk, L. J. Pain Sympt. Mgmt 10:243-248, 1995.
Avelino, A.; Cruz, F.; Coimbra, A. Eur. J Pharmacol. 1999, 378, 17-22.
Chancellor, M. B.; De Groat, W. C. J. Urol. (Baltimore) 1999, 162, 3-11.
Komiyama, I.; Igawa, Y.; Ishizuka, O.; Nishizawa, O.; Andersson, K.-E. J. Urol. (Baltimore) 1999, 161, 314-319.
de Seze, M; Wiart, L.; de Seze, M.-P.; Soyeur, L.; Dosque, J.-P; Blajezewski, S.; Moore, N.; Brochet, B.; Mazaux, J.-M.; Barat, M.; Joseph, P.-A. Journal of Urology (Hagerstown, MD, United States) 2003, 171, 251-255.
Li, J.; Kaminski, N. E.; Wang, D. H. Hypertension 2003, 41, 747-762.
Yamamoto, H.; Horie, S.; Uchida, M.; Tsuchiya, S.; Murayama, T.; Watanabe. K. Eur. J. Pharmacol. 2001, 432, 203-210.

(Continued)

Primary Examiner — Sun Jae Y Loewe
(74) Attorney, Agent, or Firm — Thomas J. Dodd

(57) ABSTRACT

The invention is directed to compounds of Formula (I):

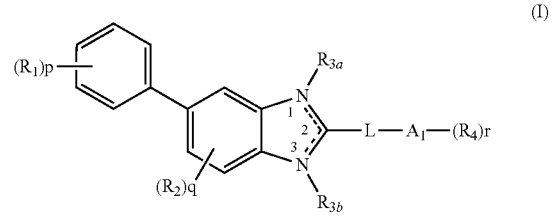

to pharmaceutical compositions containing such compounds and to methods of treatment using them.

17 Claims, No Drawings

OTHER PUBLICATIONS

Kasckow, J.W.; Muchahey, J.J; Geracioti, T.D. Jr. Progress in Neuro-Psychopharmacol. and Biological Psychiatry 2004, 28, 291-295.
Prieto, M. et al., *J. Org. Chem.* 2004, 69: 6812-6820.
Burger, A. et al. *J. Med. Chem.* 1970, 13, 33-35.
Mitsunobu, O., *Synthesis*, 1981, 1-28.
Mattson, R. J. et al. *J. Org. Chem.*, 1990, 55, 2552-2554.
McElvain, S. M. et al. *J. Am. Chem. Soc.* 1942, 64, 1825.
Komoriya et al. *Bioorg. Med. Chem.*, 2004, 12, 2099-2114.
Evans, D.A.; Woerpel, K.A.; Hinman, M.M.; Faul, M.M. *J. Am. Chem. Soc.* 1991, 113, 726-728.
Brennan. T.J. et al., *Pain*,1996, 64: 493-501.

* cited by examiner

BENZIMIDAZOLE MODULATORS OF VR1

CROSS REFERENCE TO RELATED APPLICATIONS

This present application claims benefit of U.S. Provisional Patent Application Ser. No. 60/797,504, filed May 3, 2006, which is incorporated herein by reference in its entirety and for all purposes.

BACKGROUND OF THE INVENTION

Noxious chemical, thermal and mechanical stimuli excite peripheral nerve endings of small diameter sensory neurons (nociceptors) deriving from sensory ganglia (e.g., dorsal root, nodose and trigeminal ganglia) and initiate signals that are perceived as pain. Such nociceptive neurons (i.e., nociceptors) are crucial for the detection of harmful or potentially harmful stimuli (e.g., noxious thermal, chemical, and/or mechanical) that arise from changes in the extracellular environment during inflammatory, ischemic or otherwise traumatic conditions and that cause or have the potential to cause tissue damage (Wall, P. D., and Melzack, R., Textbook of Pain, 1994, New York: Churchill Livingstone).

Nociceptors transduce noxious stimuli into membrane depolarization that leads to an action potential, its subsequent conduction to the CNS, and ultimately to the perception of pain, discomfort, etc. as well as to certain responses thereto. At the molecular level, nociception is carried out by ion channels and/or receptors. Plant-derived vanilloid compounds (e.g., capsaicin and resiniferatoxin) are known to selectively depolarize nociceptors and elicit sensations of burning pain: the sensation that is typically evoked by capsaicin-containing hot chili peppers. Therefore, capsaicin mimics the action of physiological/endogenous stimuli that activate the "nociceptive pathway". Recent advances in pain biology have identified a receptor, called VR1 (a.k.a. capsaicin receptor or TRPV1) for vanilloids, protons and noxious heat. Because nociceptors are drivers of unwanted pain and inflammatory conditions in human beings and animals, modulation of their function is a validated strategy for palliative and other analgesic therapies.

Compounds that are modulators (competitive and non-competitive agonists or antagonists [with respect to capsaicin and/or its recognition site] and allosteric modulators) at VR1 have broad therapeutic potential, as demonstrated by the clinical usefulness of marketed, VR1-targeted pharmaceutical agents or the efficacy of VR1 modulators in animal models of disease. Furthermore, it is recognized that agonist modulators of VR1 may possess clinical utility deriving from their agonist properties, per se, and/or from their ability to produce an agonist-mediated desensitization, which would indirectly manifest as a functional antagonism. Similarly, antagonist modulators could exhibit direct antagonist (competitive or non-competitive) properties and/or indirect antagonist properties via the aforementioned desensitization mechanism. It is further recognized that positive and negative allosteric modulators may produce any or all of the aforementioned functional consequences and, as such, may also have clinical utility. Accordingly, this invention is directed to each of these types of modulators.

The effective use of VR1 agonists has been demonstrated in inflammatory, neuropathic, and visceral pain states. In an experimental human pain model, dermal capsaicin pretreatment reduced the pain caused by intradermal injection of an acidic solution (Bianco, E. D.; Geppetti, P.; Zippi, P.; Isolani, D.; Magini, B.; Cappugi, P. Brit J of Clin Pharmacol 1996, 41, 1-6), suggesting the benefit of VR1 agonists in the treatment of inflammatory pain. A particular role for VR1 agonists has been shown in inflammation and inflammatory pain: for example, resiniferatoxin prevented inflammatory hypersensitivity and edema induction by carrageenan (Kissin, I.; Bright, C. A.; Bradley, E. L., Jr. Anesth Analg 2002, 94, 1253-1258).

Additionally, capsaicin-containing creams (for example, Axcain® and Lidocare®) are marketed for dermal relief of pain related to diabetic neuropathy and postherpetic neuralgia, indicative of the usefulness of VR1 agonists in the treatment of neuropathic pain states. Furthermore, such creams have been shown to reduce postsurgical neuropathic pain (Ellison, N., Loprinzi, C. L., Kugler, J., Hatfield, A. K., Miser, A., Sloan, J. A., Wender, D. B., Rowland, K. M., Molina, R., Cascino, T. L., Vukov, A. M., Dhaliwal, H. S. and Ghosh, C. J. Clin. Oncol. 15:2974-2980, 1997). In cancer patients, capsaicin contained in a taffy vehicle, was shown to substantially reduce oral mucositis pain caused by chemotherapy and radiation therapy (Berger, A., Henderson, M., Naadoolman, W., Duffy, V., Cooper, D., Saberski, L. and Bartoshuk, L. J. Pain Sympt. Mgmt 10:243-248, 1995.

VR1 also plays a role in the physiology of bladder emptying. VR1 is expressed by bladder sensory neurons, where it modulates bladder responsivity to liquid filling. The VR1 agonist resiniferatoxin desensitized bladder afferents in a dose-dependent manner (Avelino, A.; Cruz, F.; Coimbra, A. Eur. J Pharmacol. 1999, 378, 17-22), supporting its usefulness for the treatment of overactive bladder (Chancellor, M. B.; De Groat, W. C. J. Urol. (Baltimore) 1999, 162, 3-11). Indeed, intravesicular administration of capsaicin or resiniferatoxin inhibited bladder contraction in both normal and spinal cord injured rats (Komiyama, I.; Igawa, Y.; Ishizuka, O.; Nishizawa, O.; Andersson, K.-E. J. Urol. (Baltimore) 1999, 161, 314-319), indicative of the usefulness of VR1 agonists in nerve-injured incontinent patients. The effectiveness of capsaicin or resiniferatoxin treatment on incontinence in spinal cord injured patients was confirmed in a clinical study (de Seze, M.; Wiart, L.; de Seze, M.-P.; Soyeur, L.; Dosque, J.-P.; Blajezewski, S.; Moore, N.; Brochet, B.; Mazaux, J.-M.; Barat, M.; Joseph, P.-A. Journal of Urology (Hagerstown, Md., United States) 2003, 171, 251-255).

The effectiveness of VR1 agonists in the reduction of elevated blood pressure is suggested by capsaicin reduction in blood pressure in SHR and WKY rats (Li, J.; Kaminski, N. E.; Wang, D. H. Hypertension 2003, 41, 757-762.). Capsaicin was also gastroprotective with respect to gastric antral ulcers (Yamamoto, H.; Horie, S.; Uchida, M.; Tsuchiya, S.; Murayama, T.; Watanabe, K. Eur. J. Pharmacol. 2001, 432, 203-210).

VR1 antagonists also may be useful in the treatment of inflammatory, neuropathic and visceral pain. For example, the therapeutic utility of VR1 antagonists has been demonstrated in visceral inflammatory conditions. VR1 is elevated in colonic nerve fibers in patients with inflammatory bowel disease, and VR1 antagonists relieved pain and dysmotility (Yiangou, Y.; Facer, P.; Dyer, N. H.; Chan, C. L.; Knowles, C.; Williams, N. S.; Anand, P. Lancet 2001, 357, 1338-1339). Intestinal inflammation induced by toxin A or dextran sulfate sodium in rodents was attenuated by VR1 antagonists (McVey, D. C.; Schmid, P. C.; Schmid, H. H. O.; Vigna, S. R. J. Pharmacol. Exp. Ther. 2003, 304, 713-722). In addition, a synthetic VR1 antagonist reduced colitis disease scores at several important endpoints, including macroscopic damage, microscopic epithelial damage, myeloperoxidase levels, and diarrhea scores, strongly supporting the therapeutic use of VR1 antagonists in inflammatory bowel diseases (Kimball, E. S.; Wallace, N. H.; Schneider, C. R.; D'Andrea, M. R.; Hornby, P. J. Neurogasteroenterology 2004, 16, 811-818). The VR1 antagonists capsazepine and BCTC reversed mechanical hyperalgesia in models of inflammatory and neuropathic pain in guinea pigs (Walker, K. M.; Urban, L.; Medhurst, S. J.; Patel, S.; Panesar, M.; Fox, A. J.; McIntyre, P. J. Pharmacol. Exp. Ther. 2003, 304, 56-62) and rats (Pomonis, J. D.; Harrison, J. E.; Mark, L.; Bristol, D. R.; Valenzano, K. J.; Walker, K. J. Pharmacol. Exp. Ther. 2003, 306, 387-393).

LPS-induced fever was attenuated in VR1 knock out mice (Lida, T.; Shimizu, I.; Nealen, M. L.; Campbell, A.; Caterina, M. Neurosci. Lett. 2005, 378, 28-33). VR1 agonist-induced rises in core body temperature were suppressed by capsazepine, indicative of the usefulness of VR1 antagonists in the treatment of pyresis (Ohnluki, K.; Haramizu, S.; Watanabe, T.; Yazawa, S.; Fushiki, T. J. Nutr. Sci. Vitaminol. (Tokyo) 2001, 47, 295-298).

VR1 agonists also modulate body temperature and fever. In ferret, rat and mouse, administration of resiniferatoxin-induced hypothermia (Woods, A. J.; Stock, M. J.; Gupta, A. N.; Wong, T. T. L.; Andrews, P. L. R. Eur. J. Pharmacol. 1994, 264, 125-133). Additionally, phase I of LPS (lipopolysaccharide)-induced fever did not occur in animals desensitized with low intraperitoneal doses of capsaicin (Romanovsky, A. A. Frontiers in Bioscience 2004, 9, 494-504).

The therapeutic potential of VR1 antagonists in inflammatory bronchial conditions is demonstrated by the finding that they antagonize capsaicin- and acid-induced bronchoconstriction (Nault, M. A.; Vincent, S. G.; Fisher, J. T. J. Physiol. 1999, 515, 567-578). Related findings demonstrate that the VR1 antagonist capsazepine attenuates anandamide-induced cough in guinea pigs (Jia, Y.; McLeod, R. L.; Wang, X.; Parra, L. E.; Egan, R. W.; Hey, J. A. Brit. J. Pharmacol. 2002, 137, 831-836).

The VR1 antagonist capsazepine was demonstrated to significantly reduce anxiety-like behaviors in rats using the elevated plus maze (Kasckow, J. W.; Mulchahey, J. J.; Geracioti, T. D. Jr. Progress in Neuro-Psychopharmacol. and Biological Psychiatry 2004, 28, 291-295). Thus, VR1 antagonists may have utility in the treatment of anxiety, panic disorders, phobias or other non-adaptive stress responses.

U.S. Pat. No. 6,299,796B1 discloses electroluminescent elements comprising units of the formula:

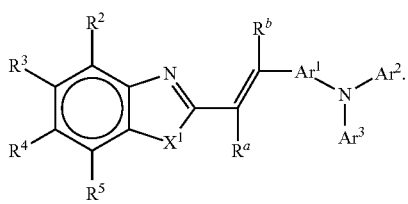

Thus, there is a need for potent modulators of VR1, and in particular, for novel benzimidazole compounds that exhibit potent binding affinity for the human and rat VR1 ion channel. There is also a need for novel benzimidazole compounds that act as potent functional antagonists and/or agonists of the human and rat VR1 ion channel. Finally, there is a need for novel benzimidazoles that bind with high affinity to VR1 and also act as potent functional antagonists of the human and rat VR1 ion channel.

SUMMARY OF THE INVENTION

The present invention is directed to a compound of Formula (I):

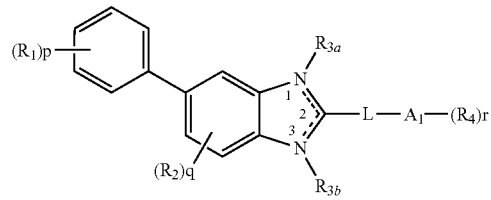

and a form thereof, wherein $R_1$, $R_2$, $R_{3a}$, $R_{3b}$, $R_4$, p, q, r, L and $A_1$ are as defined herein, and their use as potent modulators of VR1.

The present invention is also directed to a method for treating a VR1 ion channel mediated disease in a subject in need thereof comprising administering to the subject an effective amount of a compound of Formula (I). The present invention is further directed to a process for making a compound of Formula (I) and salts thereof.

DETAILED DESCRIPTION OF THE INVENTION

The present invention is directed to compounds of Formula (I):

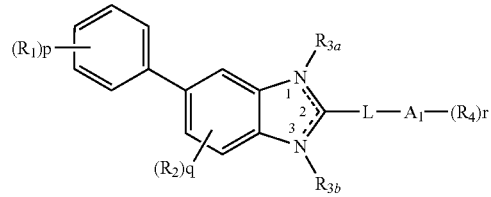

and a form thereof, wherein:

the dashed lines between positions 1, 2 and 3 in Formula (I) indicate the positions of a tautomeric double bond, wherein when a double bond is formed between positions 1 and 2, then $R_{3b}$ is present, and wherein, when a double bond is formed between positions 2 and 3, then $R_{3a}$ is present;

p is 1 or 2;
q is 0 or 1;
r is 0, 1, 2 or 3;
L is $C_{1-3}$alkyl, $C_{2-3}$alkenyl, $C_{2-3}$alkynyl or cyclopropyl;
$A_1$ is selected from the group consisting of phenyl, biphenyl, naphthyl, pyridinyl, quinolinyl and indole;
$R_1$ is each selected from the group consisting of hydroxy, cyano, halogen, formyl, carboxy, $C_{1-6}$alkyl, halo$C_{1-6}$alkyl, $C_{1-6}$alkoxy, halo$C_{1-6}$alkoxy, $C_{1-6}$alkylcarbonyl, $C_{1-6}$alkoxycarbonyl, $C_{1-6}$alkylthio, $C_{1-6}$alkylsulfonyl, $C_{3-8}$cycloalkyl, $C_{3-8}$cycloalkyl-$C_{1-4}$alkyl, $C_{3-8}$cycloalkyl-$C_{1-4}$alkoxy, $C_{3-8}$cycloalkyl-oxy, amino, ($C_{1-6}$alkyl)$_{1-2}$amino, ($C_{3-8}$cycloalkyl)$_{1-2}$amino, ($C_{3-8}$cycloalkyl-$C_{1-4}$alkyl)$_{1-2}$amino, aminocarbonyl, ($C_{1-6}$alkyl)$_{1-2}$aminocarbonyl, $C_{1-6}$alkylcarbonylamino, $C_{1-6}$alkoxycarbonylamino, aminocarbonylamino, ($C_{1-6}$alkyl)$_{1-2}$aminocarbonylamino, $C_{1-6}$alkylsulfonylamino, $C_{1-6}$alkylsulfinylamino, aminosulfonyl, ($C_{1-4}$alkyl)$_{1-2}$aminosulfonyl, aminosulfonylamino and ($C_{1-6}$alkyl)$_{1-2}$aminosulfonylamino, wherein alkyl is optionally substituted with $C_{1-8}$alkoxy, amino, ($C_{1-4}$alkyl)$_{1-2}$amino, $C_{1-6}$alkylcarbonylamino, $C_{1-6}$alkoxycarbonylamino, aminocarbonylamino, ($C_{1-6}$ alkyl)$_{1-2}$aminocarbonylamino, C$_{1-6}$alkylsulfonylamino, aminosulfonylamino, (C$_{1-6}$alkyl)$_{1-2}$aminosulfonylamino hydroxy and phenyl, wherein phenyl is optionally substituted with one, two or three substituents independently selected from the group consisting of halogen, cyano, nitro, C$_{1-6}$alkyl, C$_{1-6}$alkoxy, C$_{1-6}$alkylthio and C$_{1-6}$alkylsulfonyl, and wherein, each instance of alkyl and alkoxy is optionally perfluorinated;

R$_2$ is selected from the group consisting of halogen, C$_{1-4}$alkyl, C$_{1-4}$alkoxy, C$_{1-4}$alkylsulfonyl, nitro, amino, (C$_{1-4}$alkyl)$_{1-2}$amino and cyano, wherein each instance of alkyl and alkoxy is optionally perfluorinated;

R$_{3a}$ and R$_{3b}$ are each selected from the group consisting of hydrogen and optionally perfluorinated C$_{1-4}$alkyl; and R$_4$ is each selected from the group consisting of halogen, nitro, cyano, carboxy, C$_{1-6}$alkyl, C$_{1-6}$alkoxy, haloC$_{1-6}$alkyl, haloC$_{1-6}$alkoxy, C$_{1-6}$alkoxy-C$_{1-6}$alkyl, C$_{1-6}$alkylcarbonyl, C$_{1-6}$alkylthio, haloC$_{1-6}$alkylthio, C$_{1-6}$alkylsulfonyl, haloC$_{1-6}$alkylsulfonyl, C$_{3-8}$cycloalkyl, C$_{3-8}$cycloalkyl-C$_{1-4}$alkyl, C$_{3-8}$cycloalkyl-C$_{1-4}$alkoxy, C$_{3-8}$cycloalkyl-oxy, amino, (C$_{1-6}$alkyl)$_{1-2}$amino, (C$_{3-8}$cycloalkyl)$_{1-2}$amino, (C$_{3-8}$cycloalkyl-C$_{1-4}$alkyl)$_{1-2}$amino, (C$_{1-6}$alkyl)$_{1-2}$aminocarbonyl, C$_{1-6}$alkylcarbonylamino, C$_{1-6}$alkoxycarbonylamino, aminocarbonylamino, (C$_{1-6}$alkyl)$_{1-2}$aminocarbonylamino, C$_{1-6}$alkylsulfonylamino, haloC$_{1-6}$alkylsulfonylamino, C$_{1-6}$alkylsulfinylamino, aminosulfonyl and (C$_{1-4}$alkyl)$_{1-2}$aminosulfonyl, wherein each instance of alkyl is optionally substituted with one, two or three substituents independently selected from the group consisting of C$_{1-8}$alkoxy, amino, (C$_{1-4}$alkyl)$_{1-2}$ amino, C$_{1-6}$alkylcarbonylamino, C$_{1-6}$alkoxycarbonylamino, aminocarbonylamino, (C$_{1-6}$alkyl)$_{1-2}$aminocarbonylamino, C$_{1-6}$alkylsulfonylamino, oxo and hydroxy, and wherein, each instance of alkyl and alkoxy is optionally perfluorinated.

An example of the present invention includes a compound of Formula (I) or a form thereof, wherein q is 0.

An example of the present invention includes a compound of Formula (I) or a form thereof, wherein A$_1$ is selected from the group consisting of phenyl, biphenyl, naphthyl, quinolinyl and indole.

An example of the present invention includes a compound of Formula (I) or a form thereof, wherein R$_1$ is each selected from the group consisting of hydroxy, halogen, formyl, C$_{1-6}$alkyl, haloC$_{1-6}$alkyl, haloC$_{1-6}$alkoxy, C$_{1-6}$alkylcarbonyl, C$_{1-6}$alkoxycarbonyl, C$_{1-6}$alkylthio, C$_{1-6}$alkylsulfonyl, amino, aminocarbonyl, C$_{1-6}$alkylcarbonylamino, C$_{1-6}$alkoxycarbonylamino, C$_{1-6}$alkylsulfonylamino, aminosulfonyl, (C$_{1-4}$alkyl)$_{1-2}$aminosulfonyl and aminosulfonylamino, wherein alkyl is optionally substituted with amino, (C$_{1-4}$alkyl)$_{1-2}$amino, aminosulfonylamino or hydroxy, and wherein, alkyl is optionally perfluorinated.

An example of the present invention includes a compound of Formula (I) or a form thereof, wherein R$_2$ is selected from the group consisting of halogen and C$_{1-4}$alkyl, wherein alkyl is optionally perfluorinated.

An example of the present invention includes a compound of Formula (I) or a form thereof, wherein R$_{3a}$ and R$_{3b}$ are each selected from the group consisting of hydrogen and C$_{1-4}$alkyl.

An example of the present invention includes a compound of Formula (I) or a form thereof, wherein R$_4$ is each selected from the group consisting of halogen, carboxy, C$_{1-6}$alkyl, C$_{1-6}$alkoxy, haloC$_{1-6}$alkyl, haloC$_{1-6}$alkoxy, C$_{1-6}$alkylcarbonyl, haloC$_{1-6}$alkylthio, C$_{1-6}$alkylsulfonyl, haloC$_{1-6}$alkylsulfonyl, (C$_{1-6}$alkyl)$_{1-2}$amino, (C$_{1-6}$alkyl)$_{1-2}$aminocarbonyl, C$_{1-6}$alkylcarbonylamino, C$_{1-6}$alkylsulfonylamino and haloC$_{1-6}$alkylsulfonylamino, wherein alkyl and alkoxy are optionally perfluorinated.

An example of the present invention includes a compound of Formula (I) or a form thereof, wherein p is 1 or 2;
q is 0;
r is 0, 1, 2 or 3;
L is C$_{1-3}$alkyl, C$_{2-3}$alkenyl, C$_{2-3}$alkynyl or cyclopropyl;
A$_1$ is selected from the group consisting of phenyl, biphenyl, naphthyl, quinolinyl and indole;

R$_1$ is each selected from the group consisting of hydroxy, halogen, formyl, C$_{1-6}$alkyl, haloC$_{1-6}$alkyl, haloC$_{1-6}$alkoxy, C$_{1-6}$alkylcarbonyl, C$_{1-6}$alkoxycarbonyl, C$_{1-6}$alkylthio, C$_{1-6}$alkylsulfonyl, amino, aminocarbonyl, C$_{1-6}$alkylcarbonylamino, C$_{1-6}$alkoxycarbonylamino, C$_{1-6}$alkylsulfonylamino, aminosulfonyl, (C$_{1-4}$alkyl)$_{1-2}$aminosulfonyl and aminosulfonylamino, wherein alkyl is optionally substituted with amino, (C$_{1-4}$alkyl)$_{1-2}$amino, aminosulfonylamino or hydroxy, and wherein, alkyl is optionally perfluorinated;

R$_2$ is selected from the group consisting of halogen and C$_{1-4}$alkyl, wherein alkyl is optionally perfluorinated;

R$_{3a}$ and R$_{3b}$ are each selected from the group consisting of hydrogen and C$_{1-4}$alkyl; and R$_4$ is each selected from the group consisting of halogen, carboxy, C$_{1-6}$alkyl, C$_{1-6}$alkoxy, haloC$_{1-6}$alkyl, haloC$_{1-6}$alkoxy, C$_{1-6}$alkylcarbonyl, haloC$_{1-6}$alkylthio, C$_{1-6}$alkylsulfonyl, haloC$_{1-6}$alkylsulfonyl, (C$_{1-6}$alkyl)$_{1-2}$amino, (C$_{1-6}$alkyl)$_{1-2}$aminocarbonyl, C$_{1-6}$alkylcarbonylamino, C$_{1-6}$alkylsulfonylamino and haloC$_{1-6}$alkylsulfonylamino, wherein alkyl and alkoxy are optionally perfluorinated.

The present invention is further directed to compounds of Formula Ia or Ib:

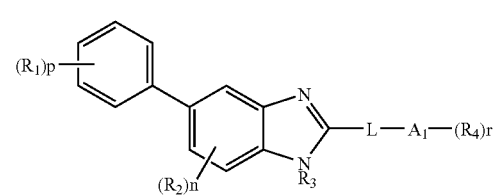

Ia

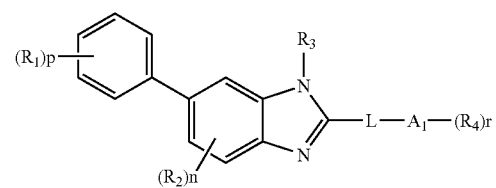

Ib wherein:

R$_1$ is independently hydroxyl; halogen, C$_{1-6}$alkanyl; fluorinated C$_{1-6}$alkanyl; C$_{1-6}$alkanyloxy; fluorinated C$_{1-6}$alkanyloxy; $C_{1-6}$alkanylthio; fluorinated $C_{1-6}$alkanylthio; $C_{1-6}$alkanylsulfonyl; fluorinated $C_{1-6}$alkanylsulfonyl; $C_{3-8}$cycloalkanyl; $C_{3-8}$cycloalkanyl; $C_{1-4}$alkanyl; $C_{3-8}$cycloalkanyloxy; $C_{3-8}$cycloalkanyl; $C_{1-4}$alkanyloxy; amino; $(C_{1-6}$alkanyl$)_{1-2}$amino; $(C_{3-8}$cycloalkanyl$)_{1-2}$amino; $(C_{3-8}$cycloalkanyl; $C_{1-4}$alkanyl$)_{1-2}$amino; cyano; aminocarbonyl; $(C_{1-6}$alkanyl$)_{1-2}$aminocarbonyl; $C_{1-6}$alkanylcarbonylamino; fluorinated $C_{1-6}$alkanylcarbonylamino; $C_{1-6}$alkanyloxycarbonylamino; $C_{0-6}$alkanylaminocarbonylamino; $C_{1-6}$alkanylsulfonylamino; fluorinated $C_{1-6}$alkanylsulfonylamino; aminosulfonyl; $(C_{1-8}$alkanyl$)_{1-2}$aminosulfonyl; fluorinated $(C_{1-8}$alkanyl$)_{1-2}$aminosulfonyl; wherein the alkanyl in any alkanyl-containing substituent of $R_1$ is optionally substituted with 1 to 3 substituents independently selected from the group consisting of amino, $(C_{1-8}$alkanyl$)_{1-2}$amino, $C_{1-6}$alkanylcarbonylamino; fluorinated $C_{1-6}$alkanylcarbonylamino; $C_{1-6}$alkanyloxycarbonylamino; $C_{0-6}$alkanylaminocarbonylamino; $C_{1-6}$alkanylsulfonylamino; fluorinated $C_{1-6}$alkanylsulfonylamino; halogen, oxo, hydroxyl, fluorinated alkanyl, and $C_{1-8}$alkanyloxy;

p is 1 or 2;

$R_2$ is independently selected from the group consisting of halogen; $C_{1-4}$alkanyl; fluorinated $C_{1-4}$alkanyl; $C_{1-4}$alkanyloxy; fluorinated $C_{1-6}$alkanyloxy; $C_{1-4}$alkanylsulfonyl; fluorinated $C_{1-4}$alkanylsulfonyl; nitro; $(C_{1-4}$alkanyl$)_{1-2}$amino; cyano;

n is 0, or 1;

$R_3$ is independently selected from the group consisting of hydrogen, $C_{1-4}$alkanyl, and fluorinated $C_{1-4}$alkanyl;

L is $C_{2-3}$alkyldiyl, $A_1$ is selected from the group consisting of phenyl and naphthyl;

$R_4$ is independently halogen, $C_{1-6}$alkanyl; fluorinated $C_{1-6}$alkanyl; $C_{1-6}$alkanyloxy; fluorinated $C_{1-6}$alkanyloxy; $C_{1-6}$alkanylthio; fluorinated $C_{1-6}$alkanylthio; $C_{1-6}$alkanylsulfonyl; fluorinated $C_{1-6}$alkanylsulfonyl; $C_{3-8}$cycloalkanyl; $C_{3-8}$cycloalkanyl; $C_{1-4}$alkanyl; $C_{3-8}$cycloalkanyloxy; $C_{3-8}$cycloalkanyl; $C_{1-4}$alkanyloxy; amino; $(C_{1-6}$alkanyl$)_{1-2}$amino; $(C_{3-8}$cycloalkanyl$)_{1-2}$amino; $(C_{3-8}$cycloalkanyl; $C_{1-4}$alkanyl$)_{1-2}$amino; cyano; aminocarbonyl; $(C_{1-6}$alkanyl$)_{1-2}$aminocarbonyl; $C_{0-6}$alkanylcarbonylamino; fluorinated $C_{1-6}$alkanylcarbonylamino; $C_{1-6}$alkanyloxycarbonylamino; $C_{0-6}$alkanylaminocarbonylamino; $C_{1-6}$alkanylsulfonylamino; fluorinated $C_{1-6}$alkanylsulfonylamino; aminosulfonyl; $(C_{1-8}$alkanyl$)_{1-2}$aminosulfonyl; fluorinated $(C_{1-8}$alkanyl$)_{1-2}$aminosulfonyl; wherein the alkanyl in any alkanyl-containing substituent of R1 is optionally substituted with 1 to 3 substituents independently selected from the group consisting of halogen, oxo, hydroxyl, fluorinated alkanyl, and $C_{1-8}$alkanyloxy; phenyl optionally substituted with 1 to 3 substituents independently selected from the group consisting of halogen; $C_{1-4}$alkanyl; fluorinated $C_{1-4}$alkanyl; $C_{1-4}$alkanyloxy; fluorinated $C_{1-4}$alkanyloxy; $C_{1-4}$alkanylsulfonyl; fluorinated $C_{1-4}$alkanylsulfonyl; nitro; cyano;

r is 0, 1 or 2; and enantiomers, diastereomers, tautomers, solvates, and pharmaceutically acceptable salts thereof.

An example of the present invention includes compounds and enantiomers, diastereomers, tautomers, solvates, and pharmaceutically acceptable salts thereof selected from the group consisting of:

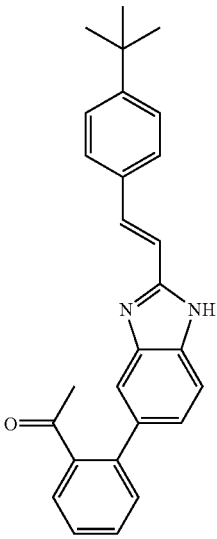

Cpd 1

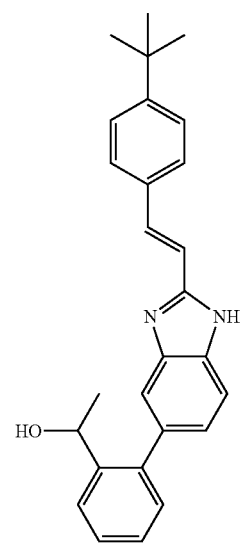

Cpd 2

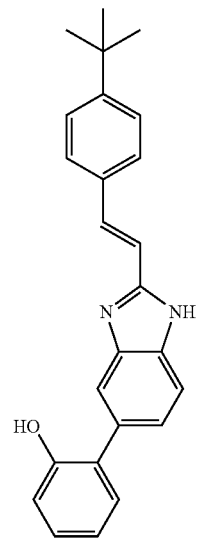

Cpd 3

Cpd 4
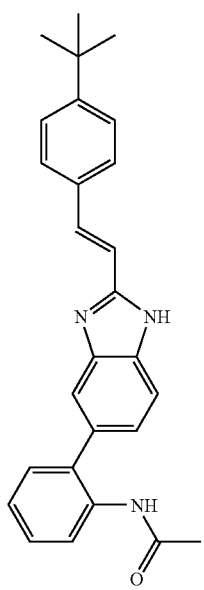
Cpd 6
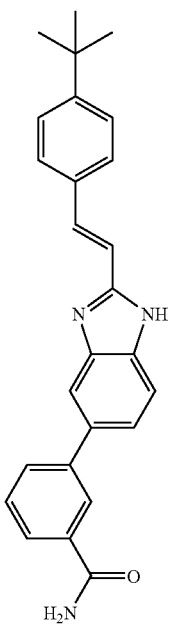
Cpd 5
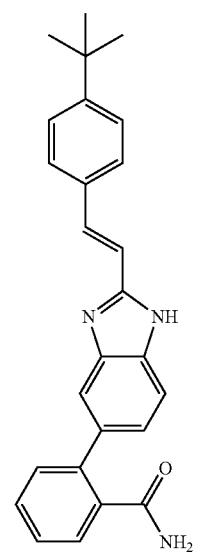
Cpd 7
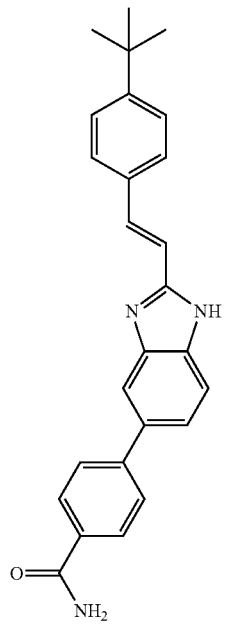

Cpd 8
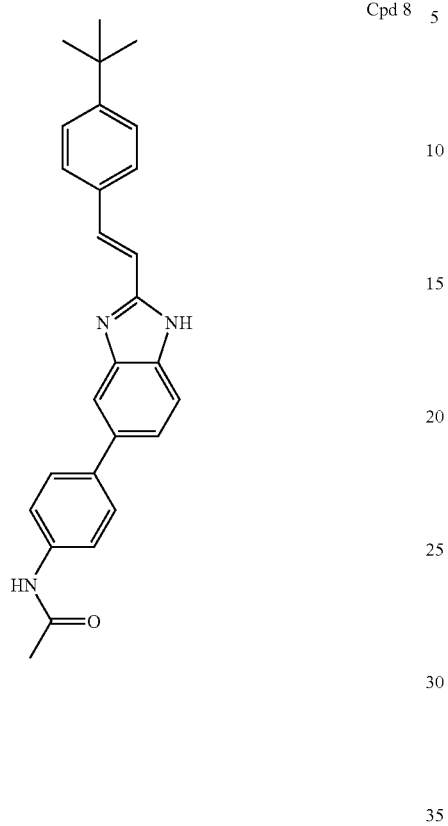
Cpd 9
Cpd 10
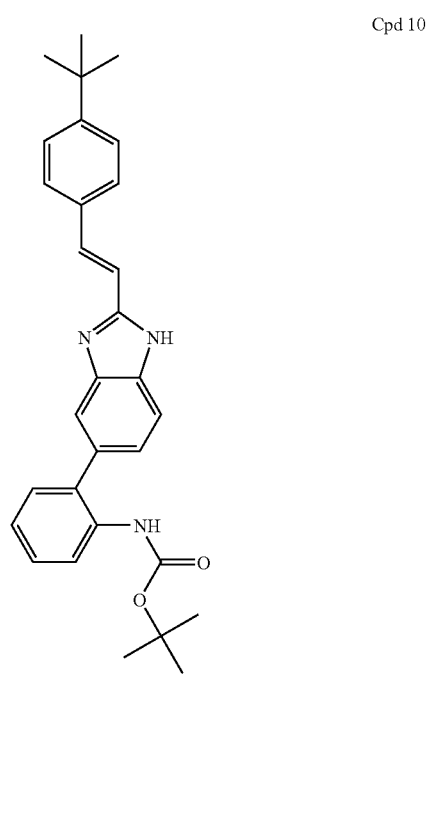
Cpd 11
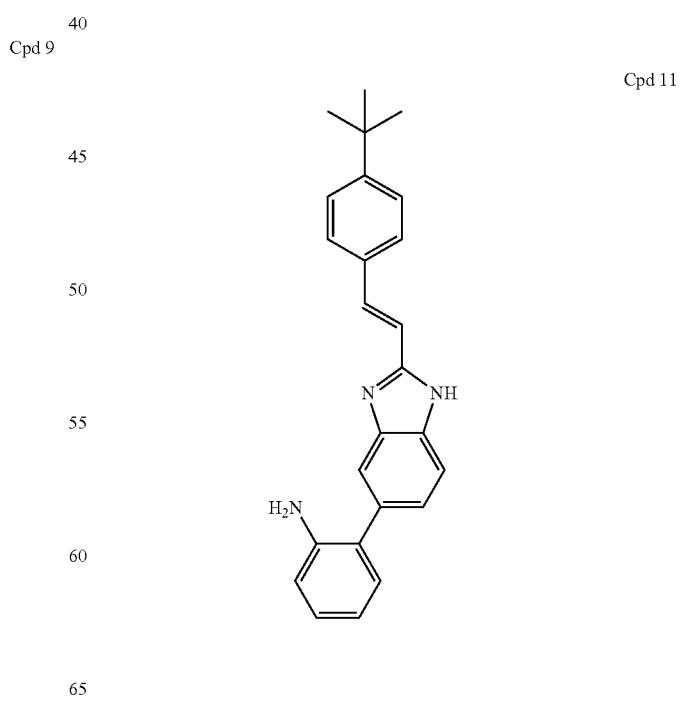

Cpd 12
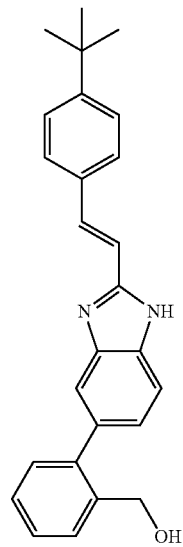
Cpd 15
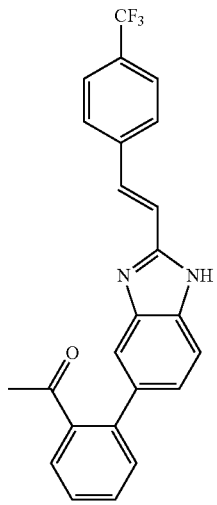
Cpd 13
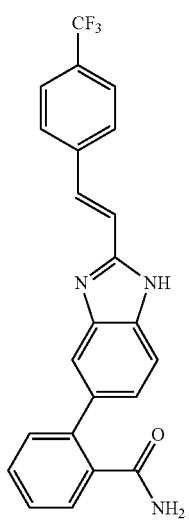
Cpd 16
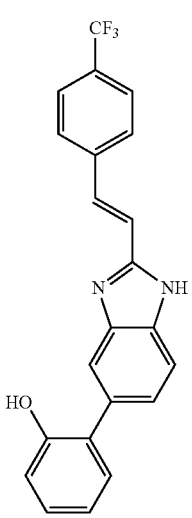
Cpd 14
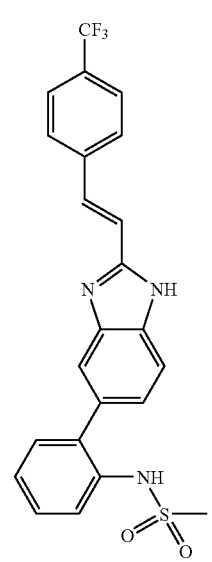
Cpd 17

Cpd 18
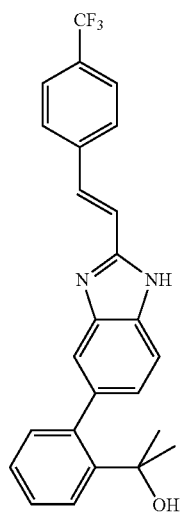
Cpd 19
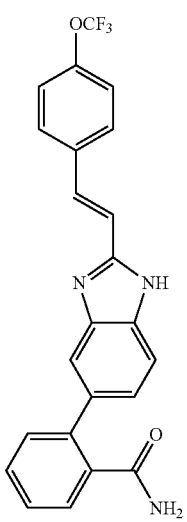
Cpd 20
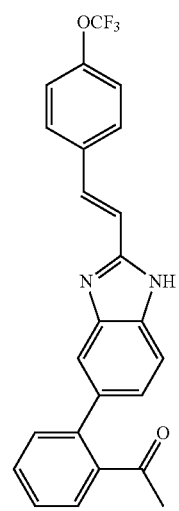
Cpd 21
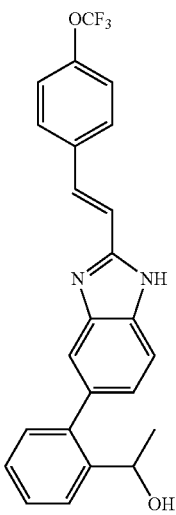
Cpd 22
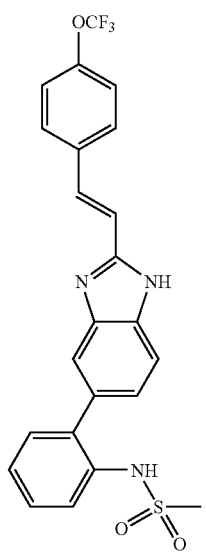
Cpd 23
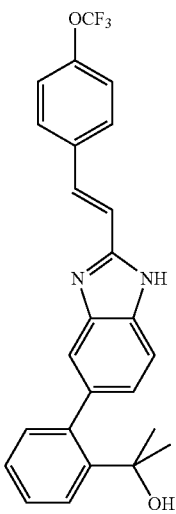

17
-continued
Cpd 24
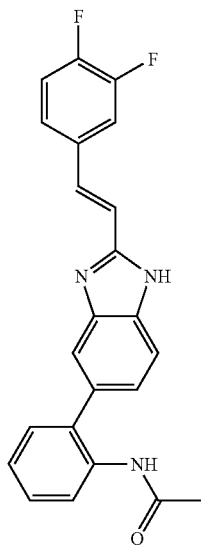
Cpd 25
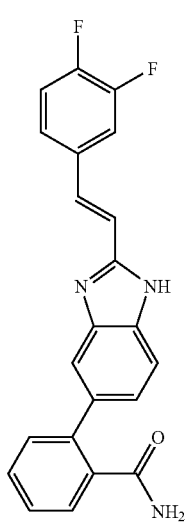
Cpd 26
18
-continued
Cpd 27
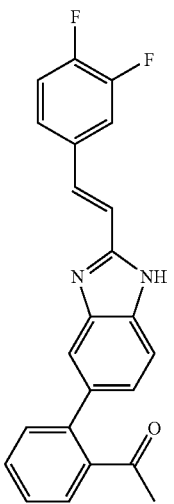
Cpd 28
Cpd 29
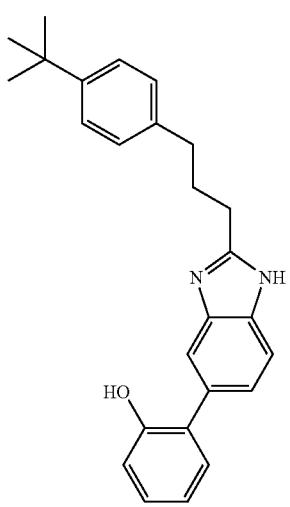

Cpd 30
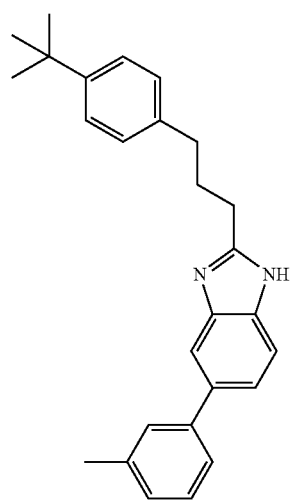
Cpd 33
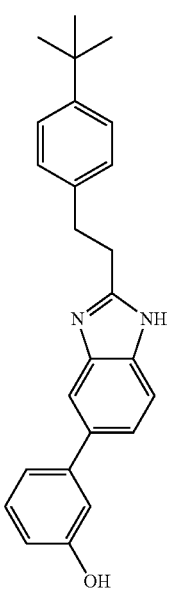
Cpd 31
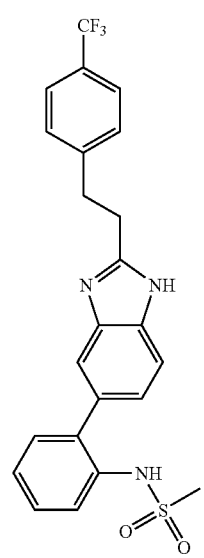
Cpd 32
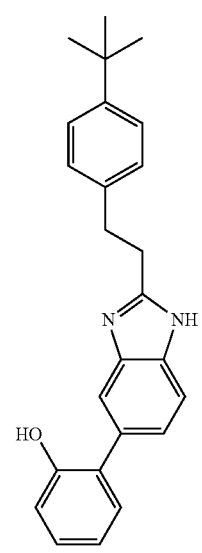
Cpd 34
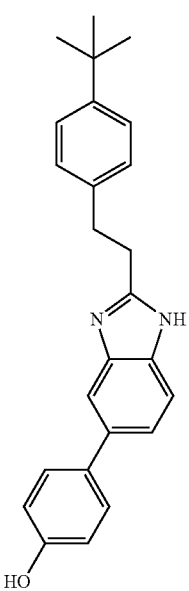

-continued
Cpd 35
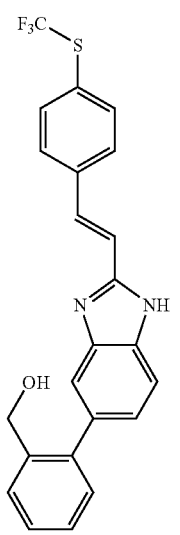
Cpd 36
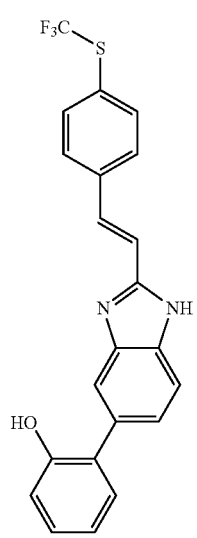
Cpd 37
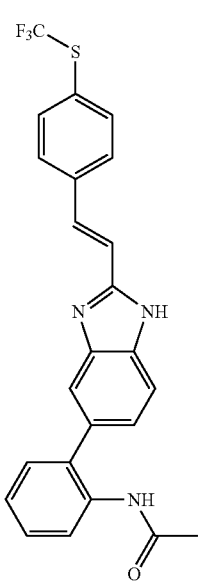
Cpd 38
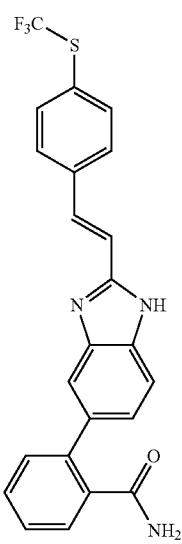
Cpd 39
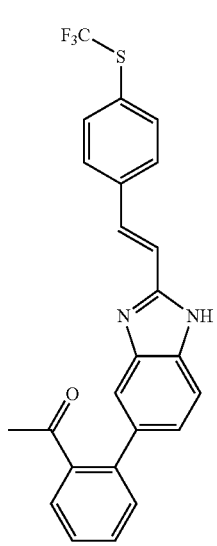
Cpd 40
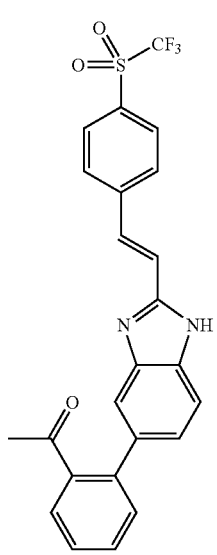

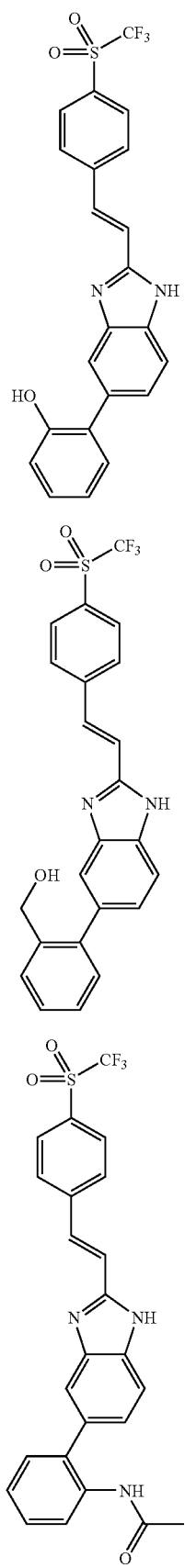
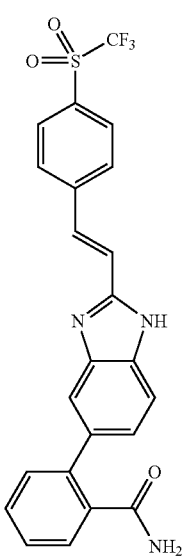
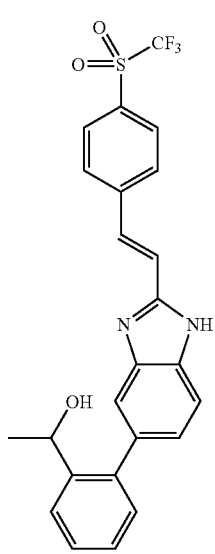
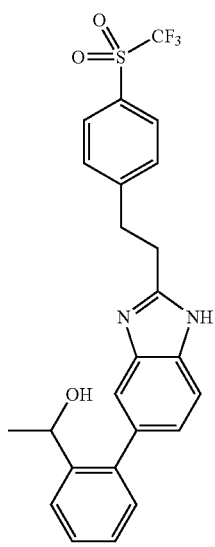
Cpd 41
Cpd 42
Cpd 43
Cpd 44
Cpd 45
Cpd 46

Cpd 47
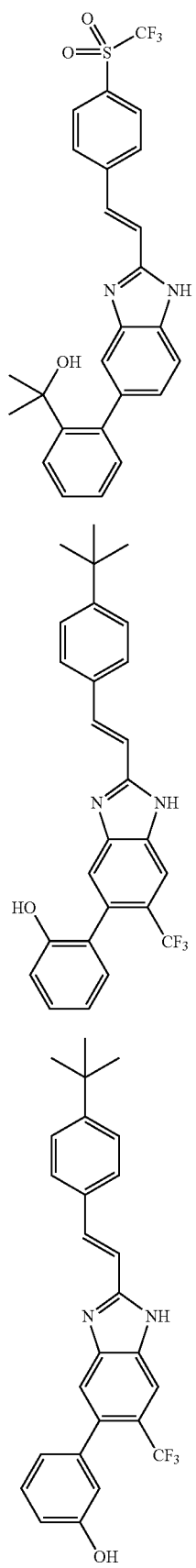
Cpd 48
Cpd 49
Cpd 50
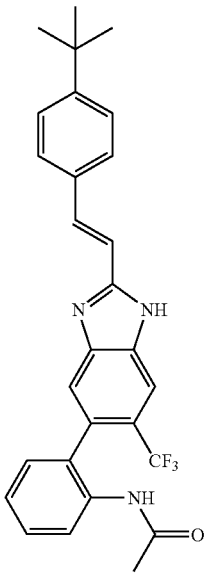
Cpd 51
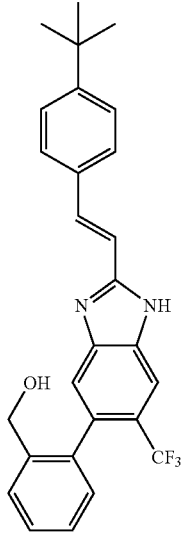
Cpd 52
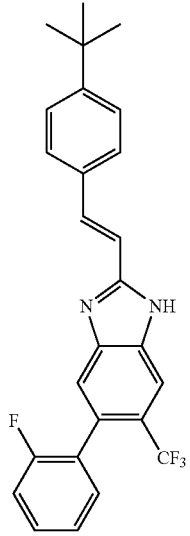

Cpd 53
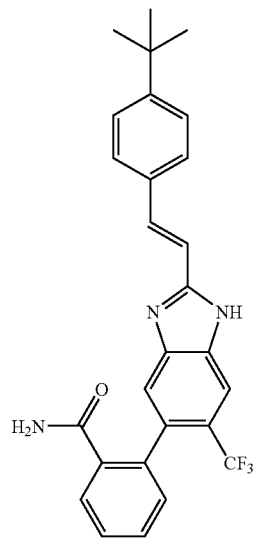
Cpd 54
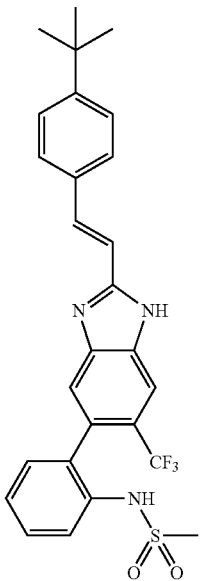
Cpd 55
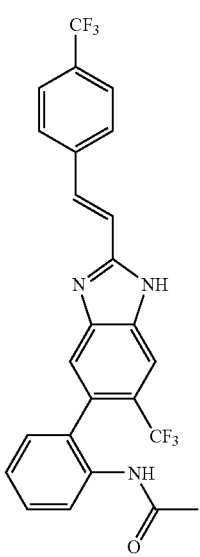
Cpd 56
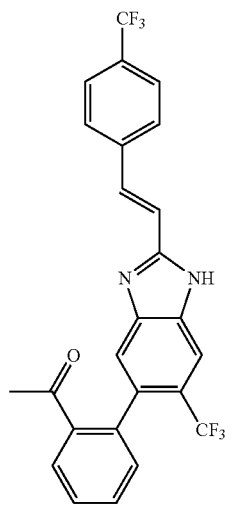
Cpd 57

-continued
Cpd 58
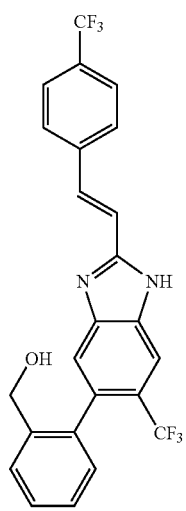
Cpd 59
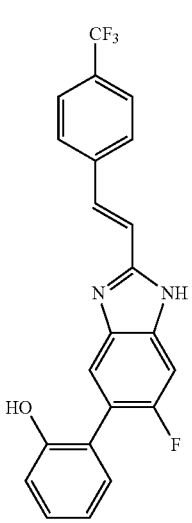
Cpd 60
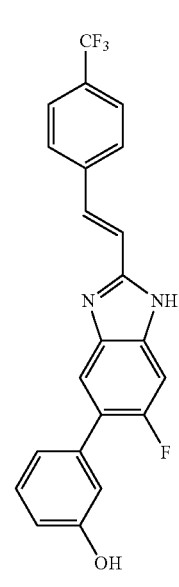
-continued
Cpd 61
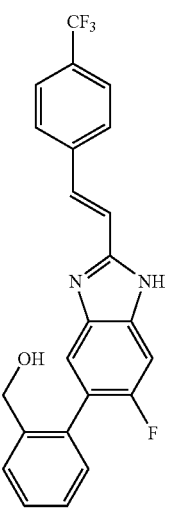
Cpd 62
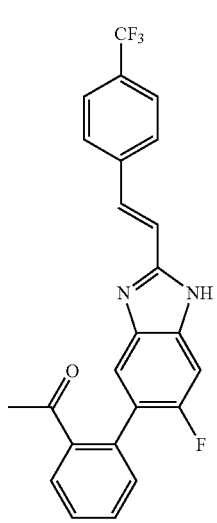
Cpd 63
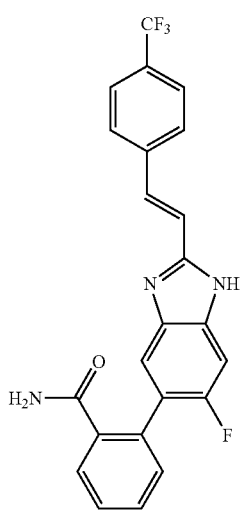

-continued
Cpd 64
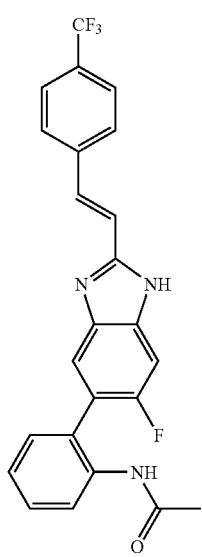
Cpd 65
Cpd 66
-continued
Cpd 67
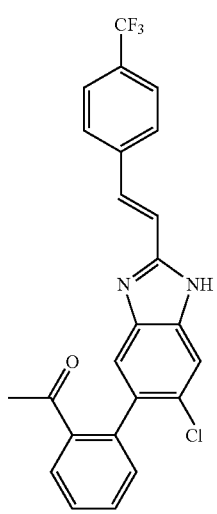
Cpd 68
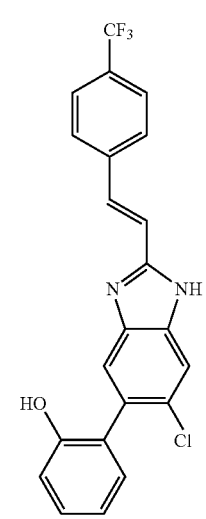
Cpd 69
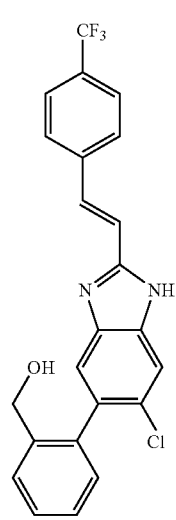
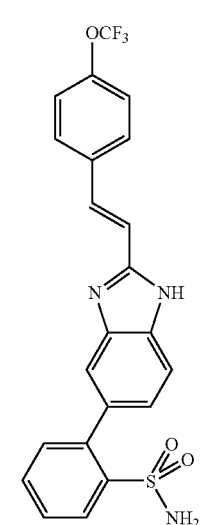

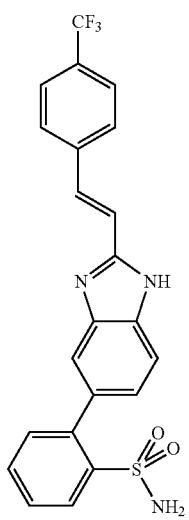
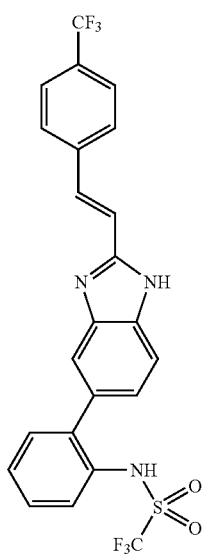

Cpd 76
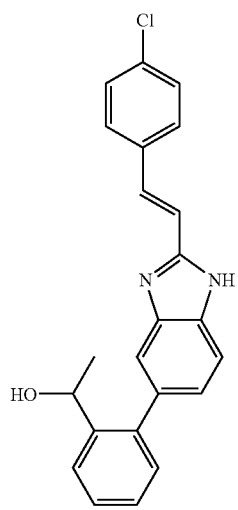
Cpd 77
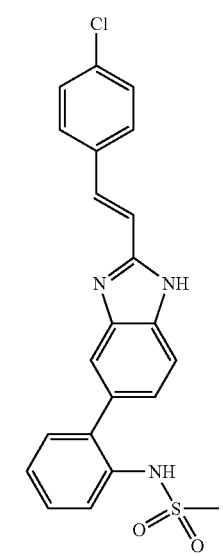
Cpd 78
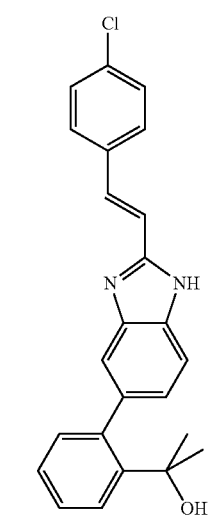
Cpd 79
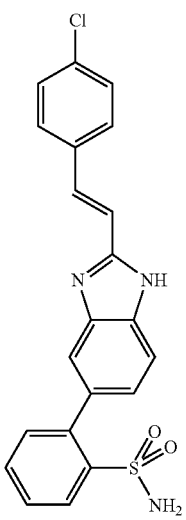
Cpd 80
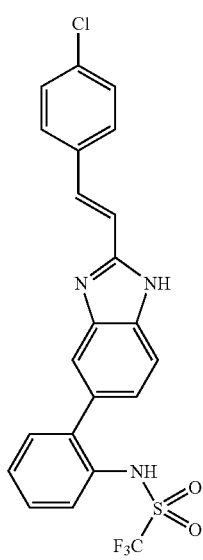
Cpd 81
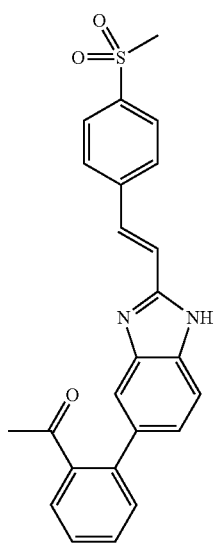

Cpd 82
Cpd 83
Cpd 84
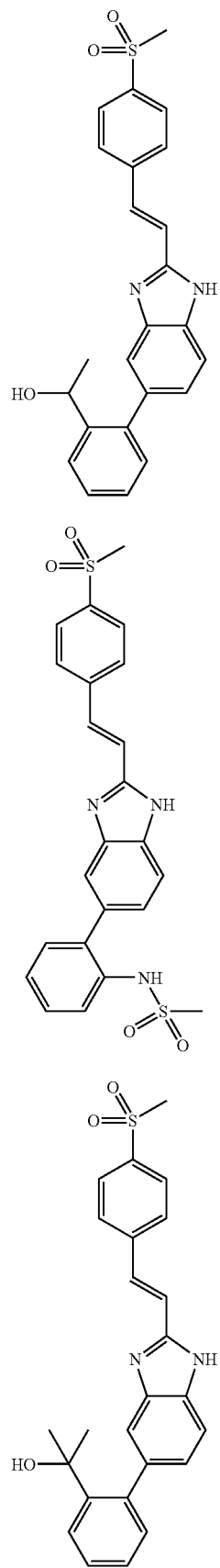
Cpd 85
Cpd 86

Cpd 87
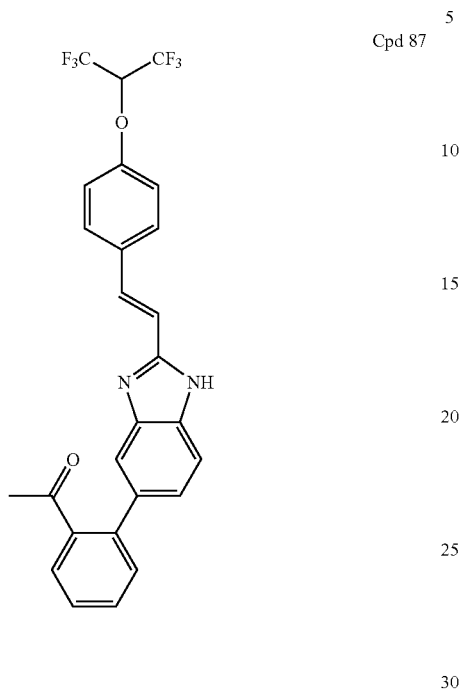
Cpd 89
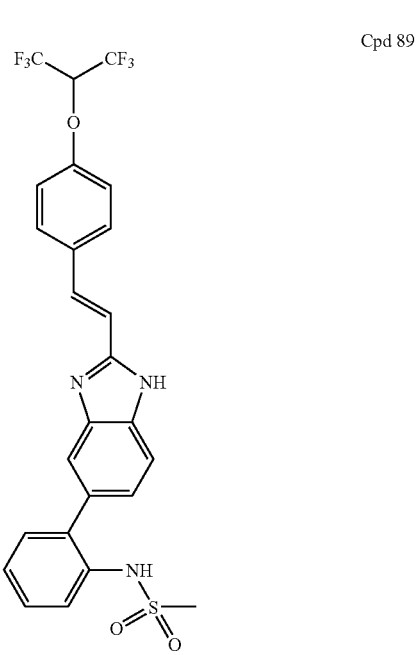
Cpd 88
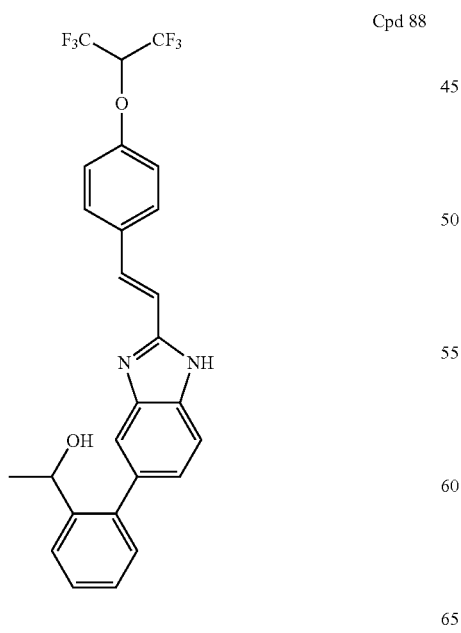
Cpd 90
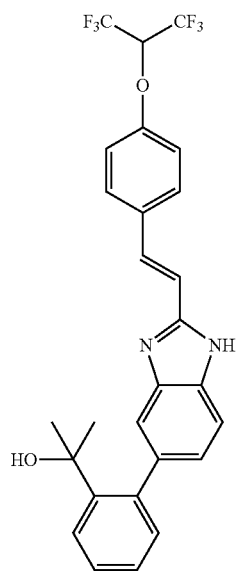

Cpd 91
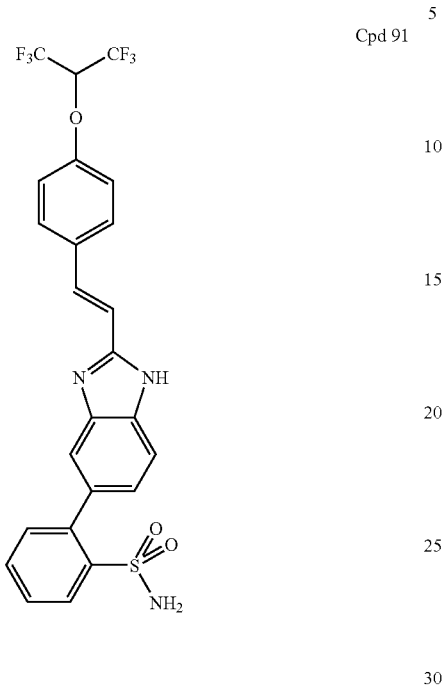
Cpd 93
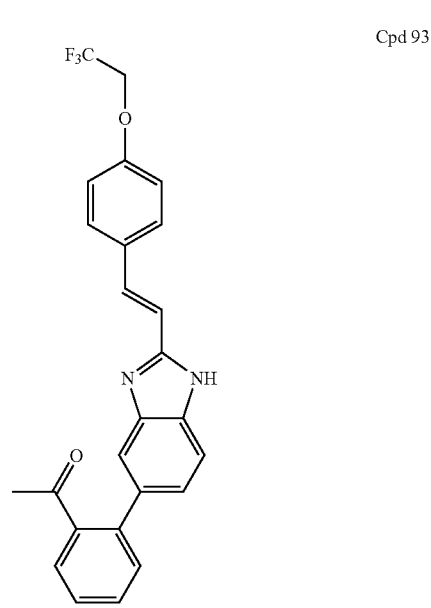
Cpd 92
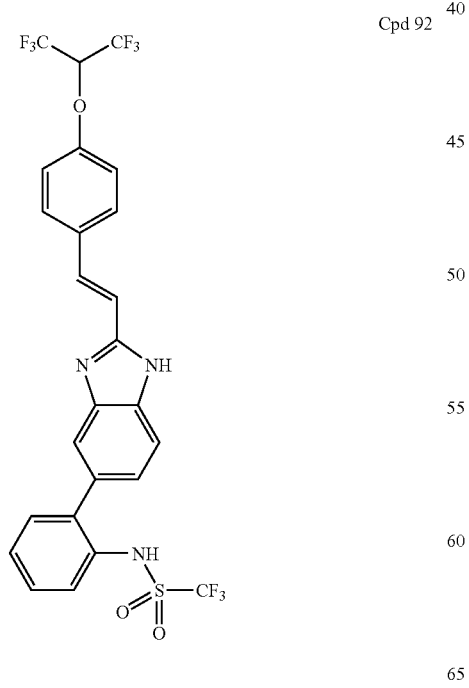
Cpd 94
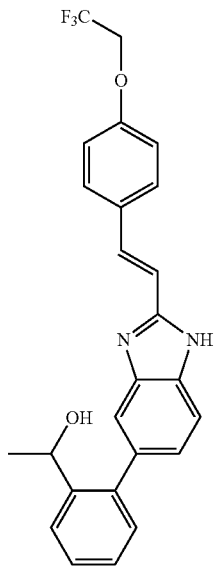

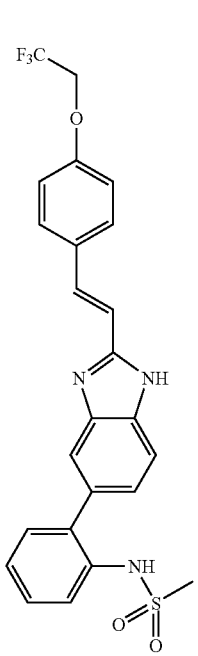 Cpd 95
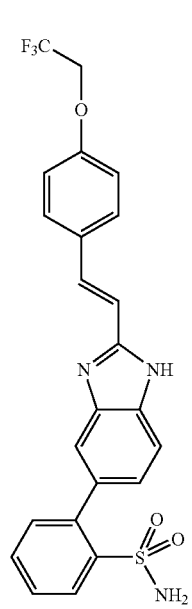 Cpd 97
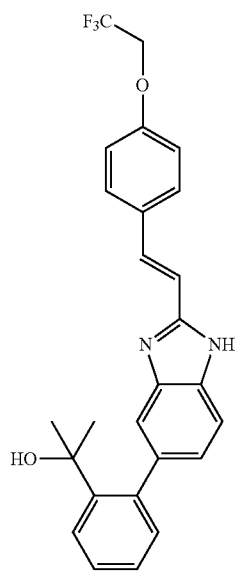 Cpd 96
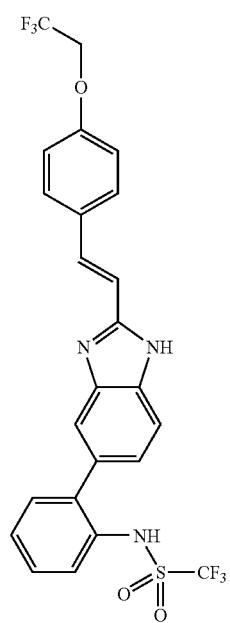 Cpd 98

Cpd 99
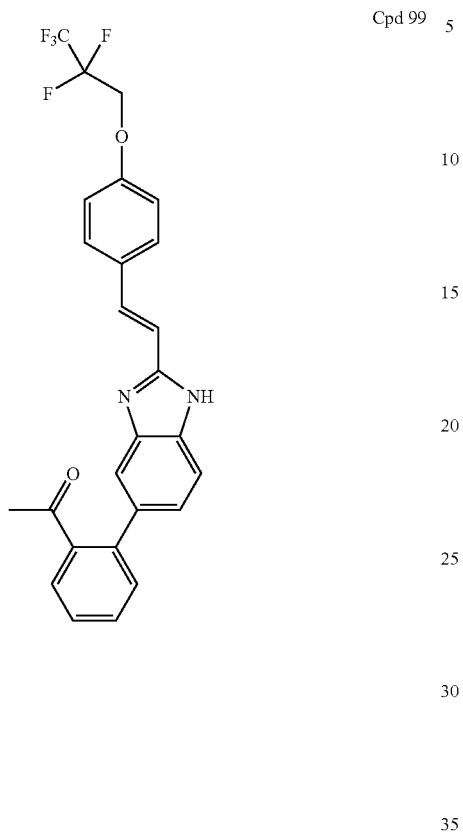
Cpd 100
Cpd 101
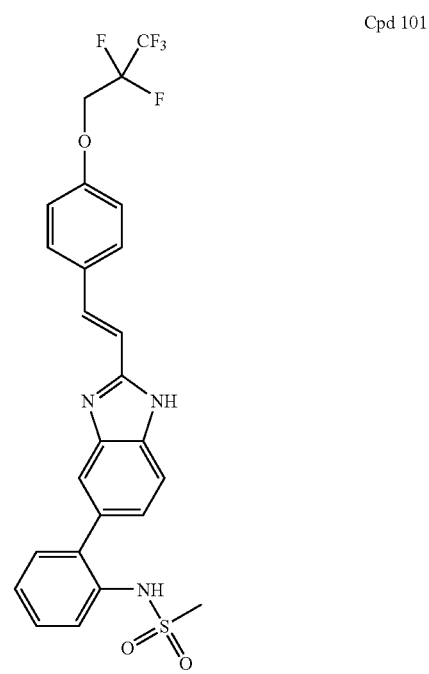
Cpd 102
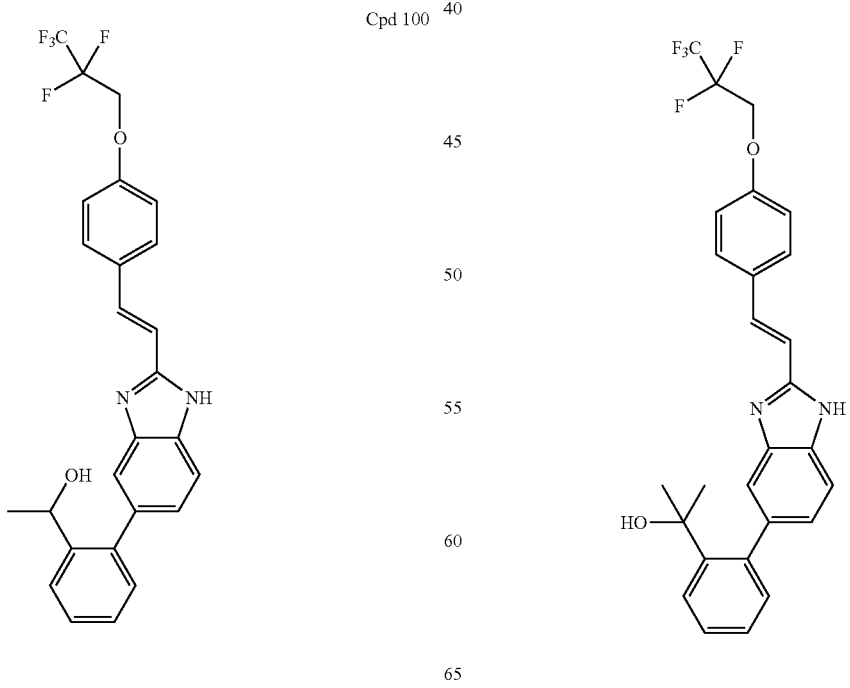

Cpd 103
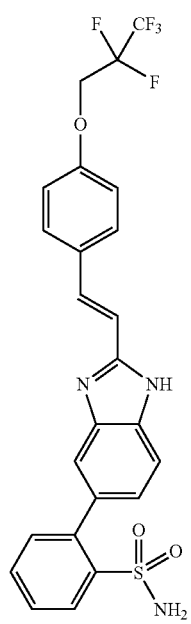
Cpd 105
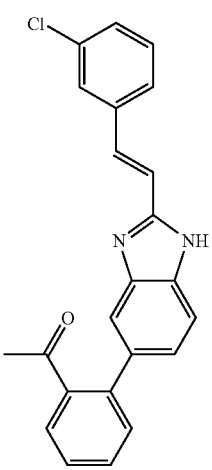
Cpd 106
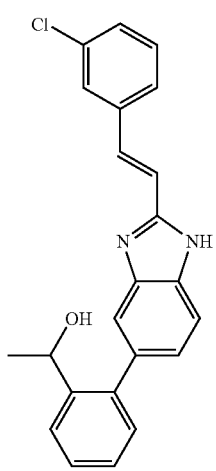
Cpd 104
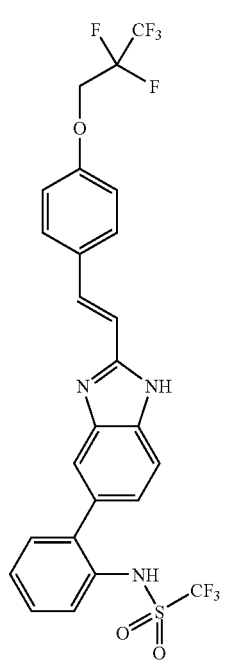
Cpd 107
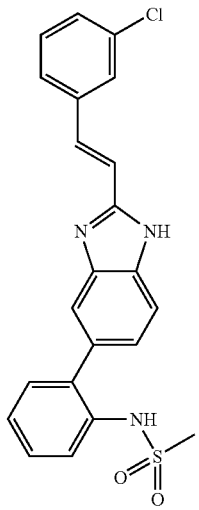

Cpd 108
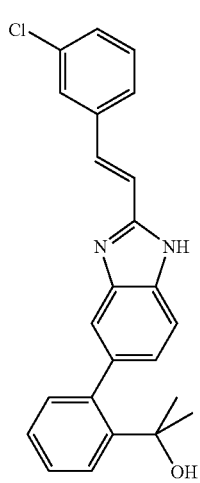
Cpd 109
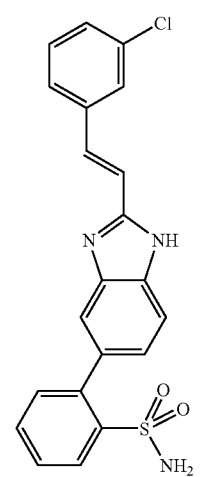
Cpd 110
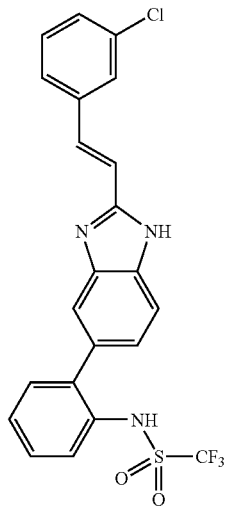
Cpd 111
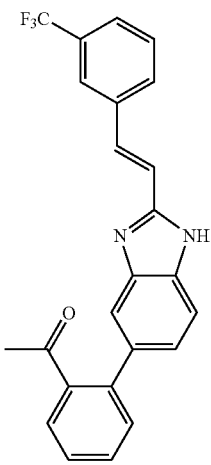
Cpd 112
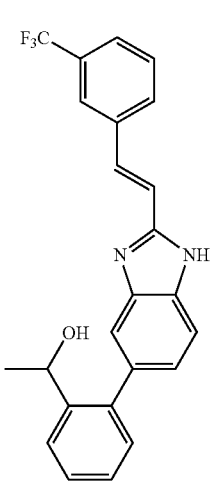
Cpd 113
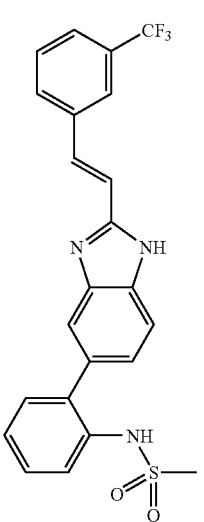

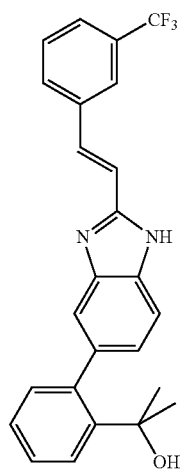 Cpd 114
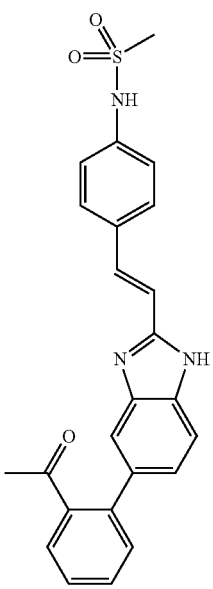 Cpd 117
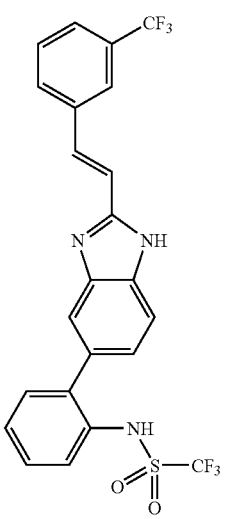 Cpd 115
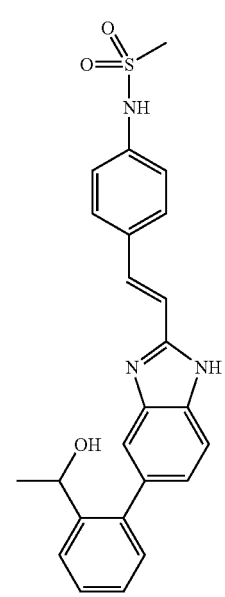 Cpd 118
Cpd 116

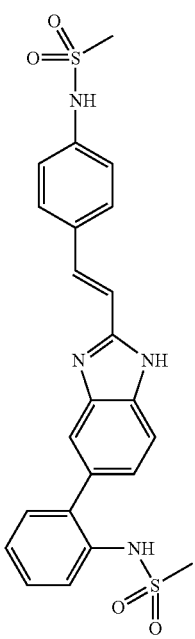
Cpd 119
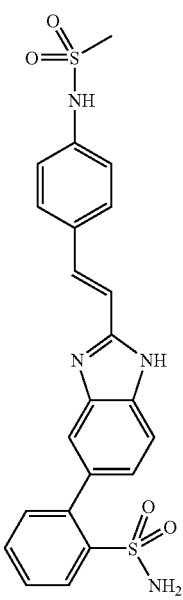
Cpd 121
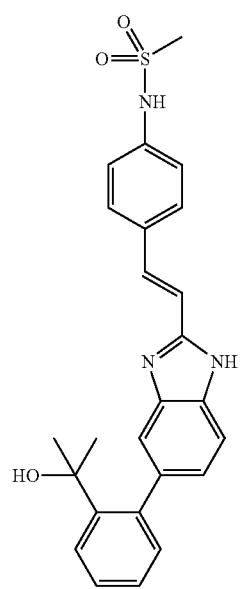
Cpd 120
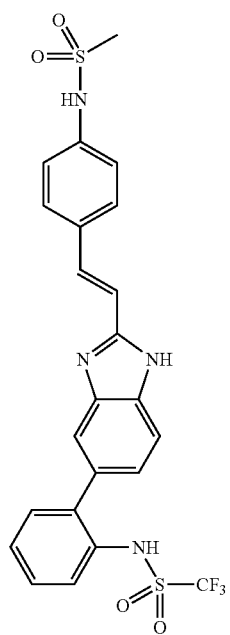
Cpd 122

Cpd 123
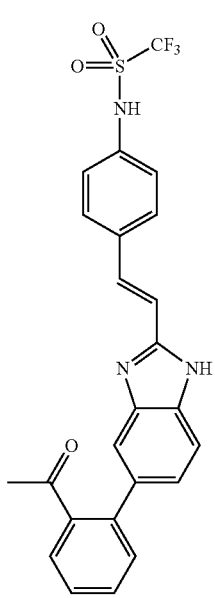
Cpd 125
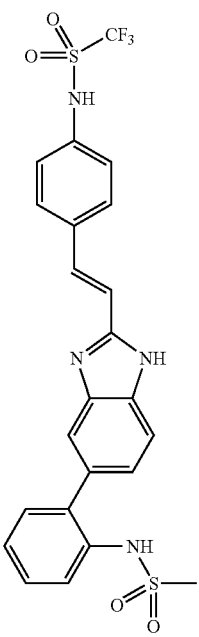
Cpd 124
Cpd 126
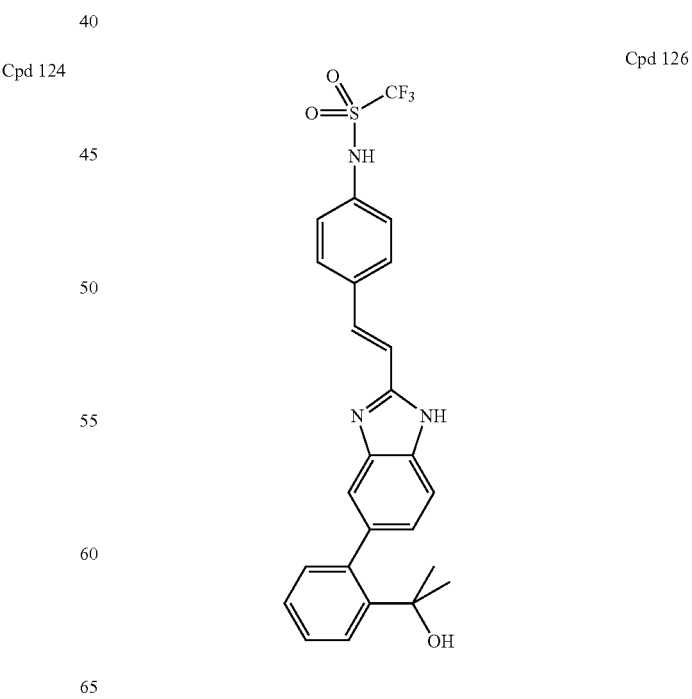

Cpd 127
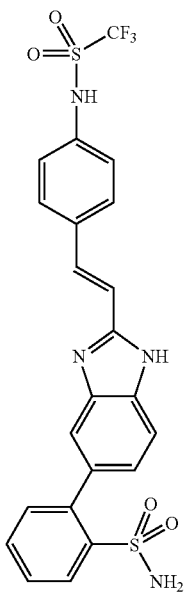
Cpd 128
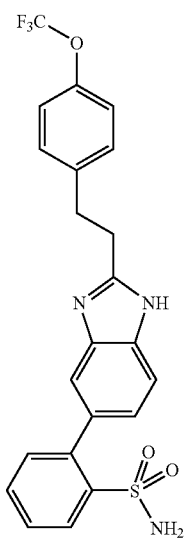
Cpd 129
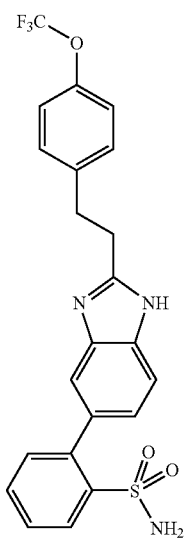
Cpd 130
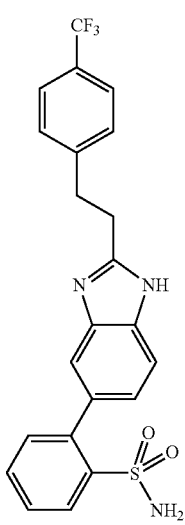
Cpd 131
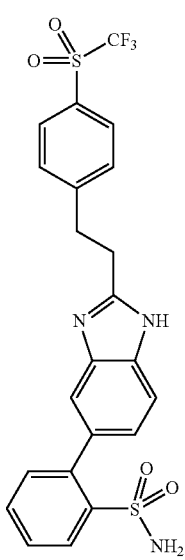

Cpd 132
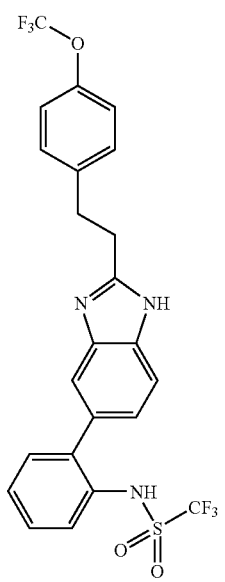
Cpd 134
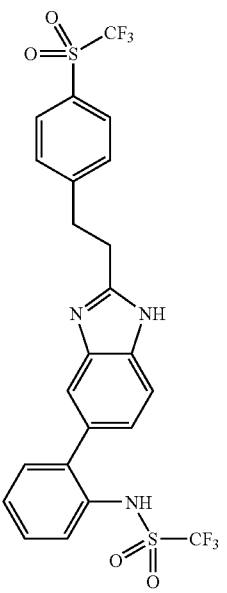
Cpd 135
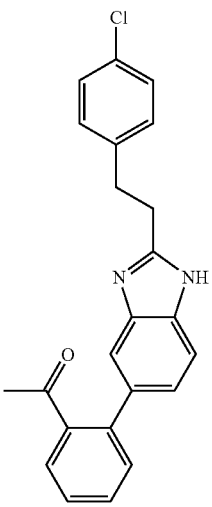
Cpd 133
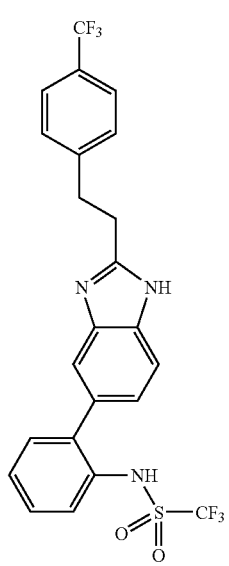
Cpd 136
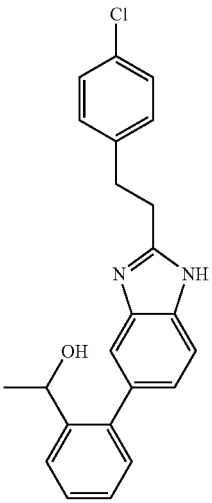

-continued
Cpd 137
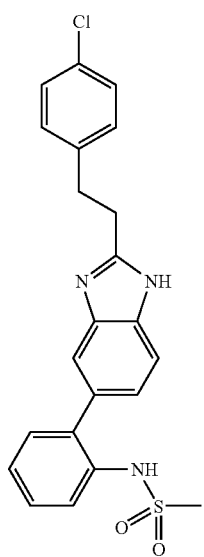
Cpd 138
Cpd 139
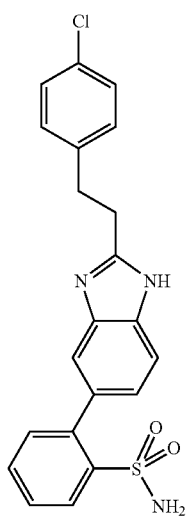
-continued
Cpd 140
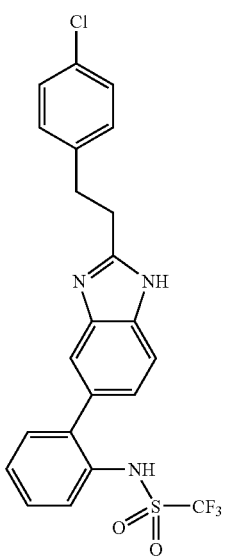
Cpd 141
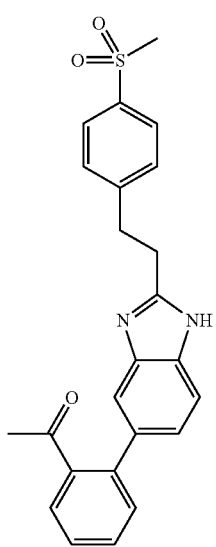
Cpd 142

Cpd 143
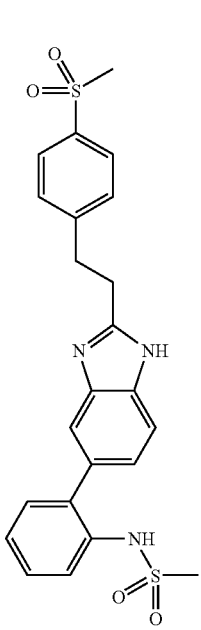
Cpd 145
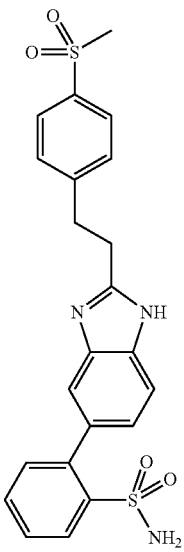
Cpd 144
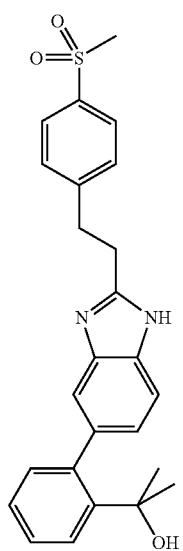
Cpd 146
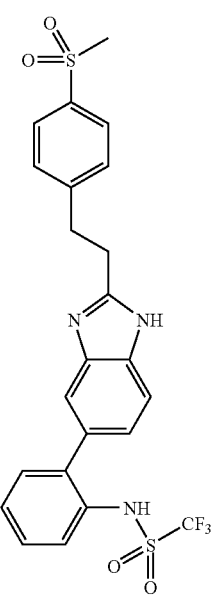

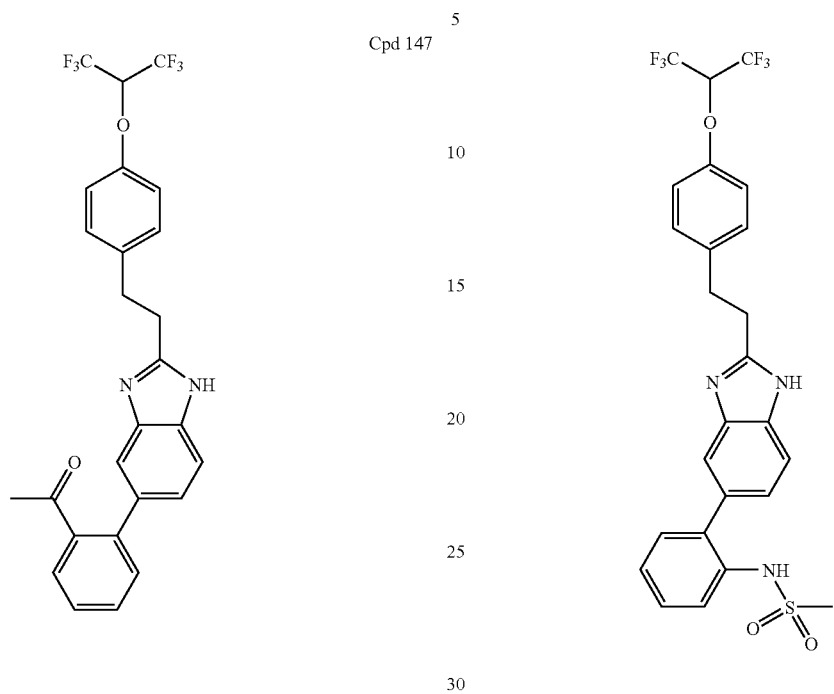
Cpd 147
Cpd 149
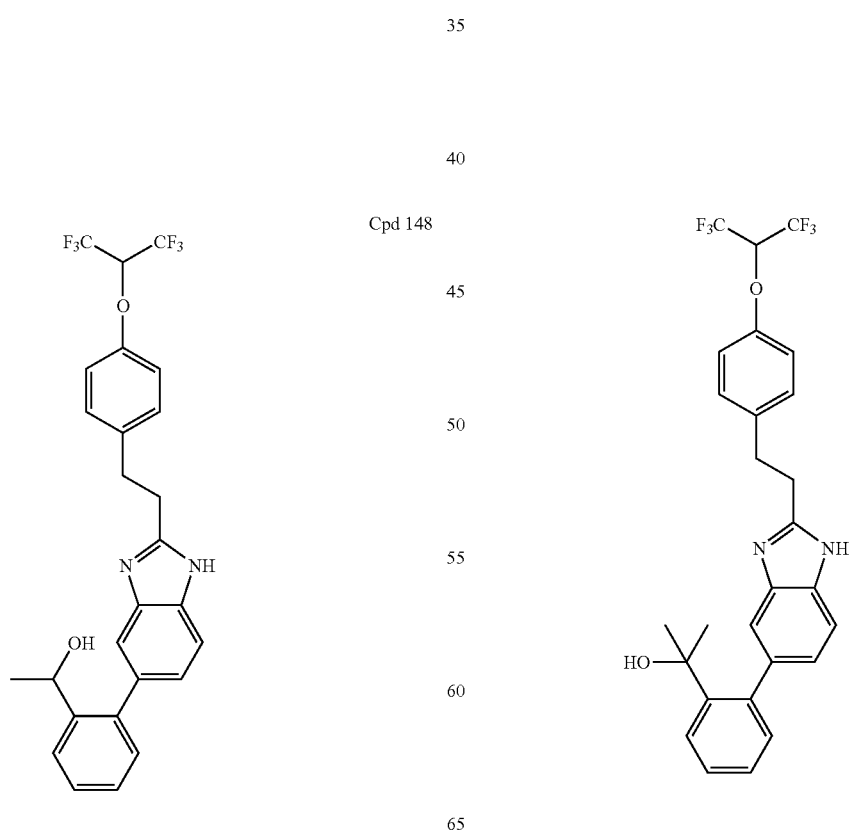
Cpd 148
Cpd 150

Cpd 151
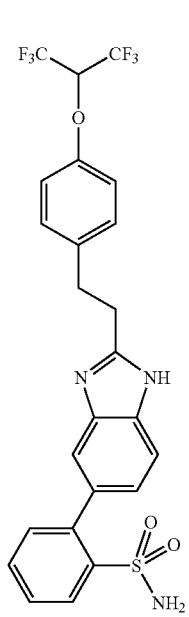
Cpd 153
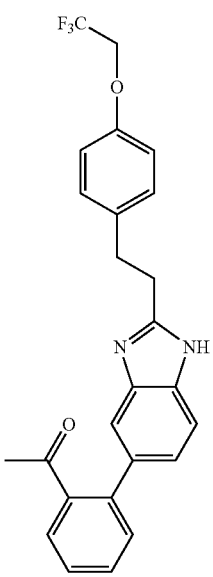
Cpd 152
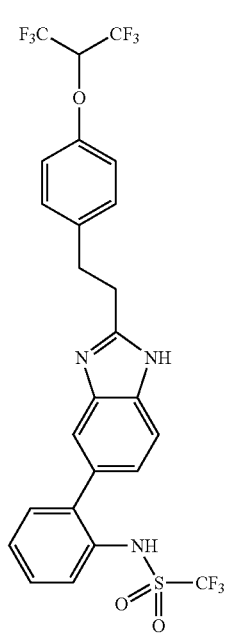
Cpd 154
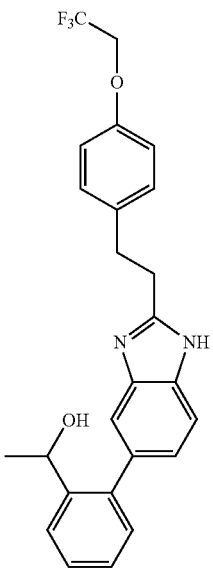

Cpd 155
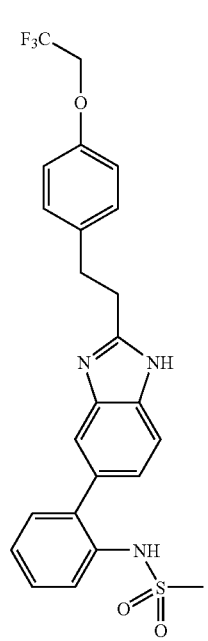
Cpd 157
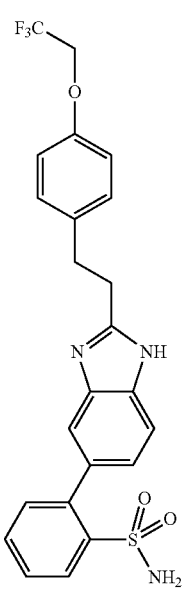
Cpd 156
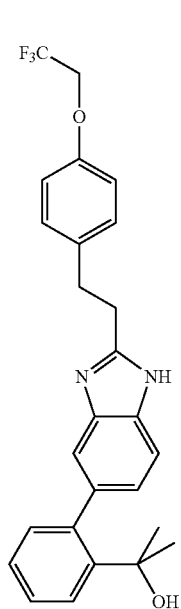
Cpd 158
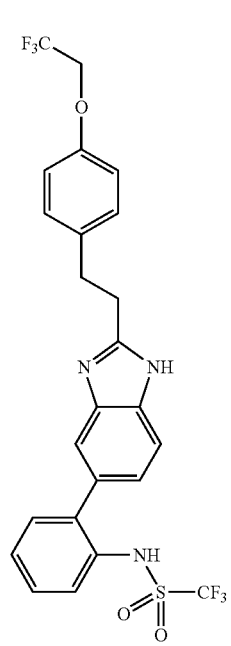

Cpd 159
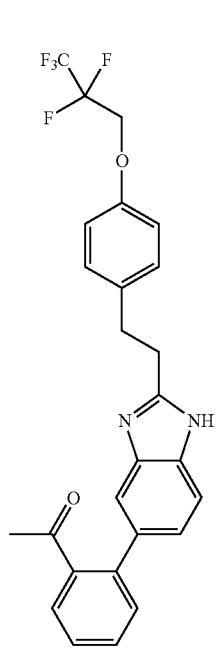
Cpd 160
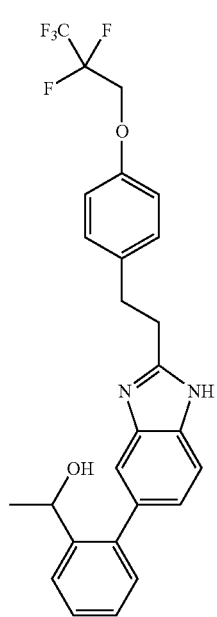
Cpd 161
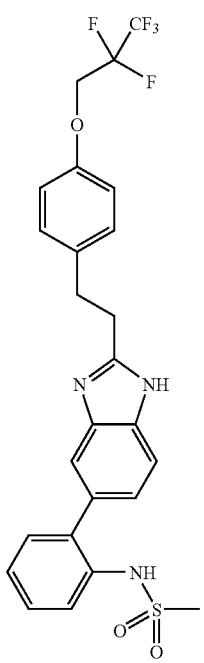
Cpd 162
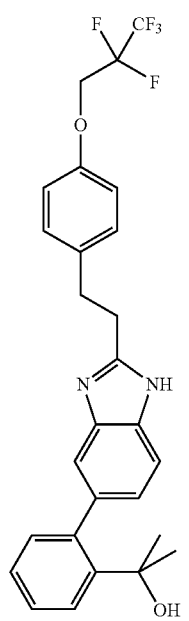

Cpd 163
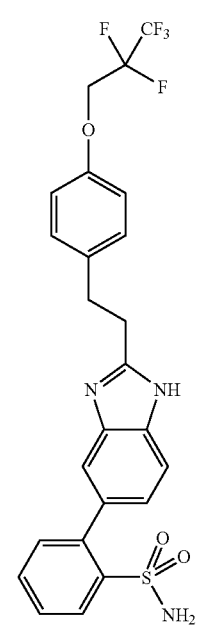
Cpd 164
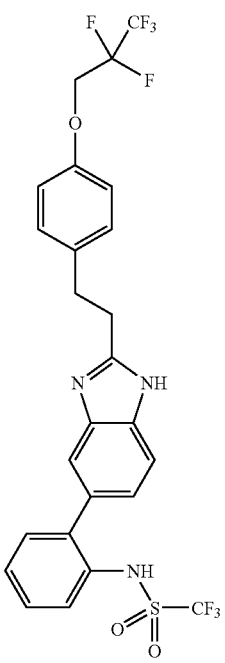
Cpd 165
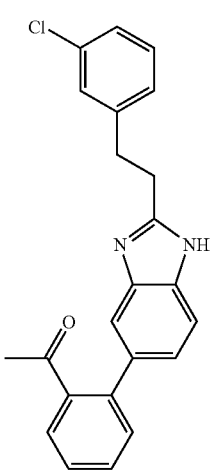
Cpd 166
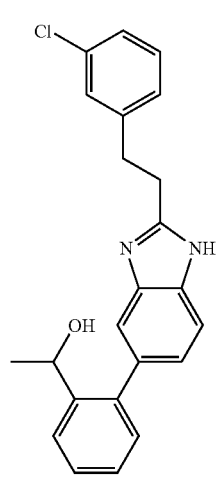
Cpd 167
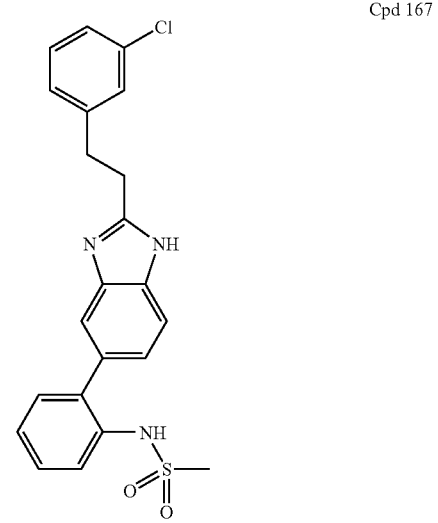

Cpd 168
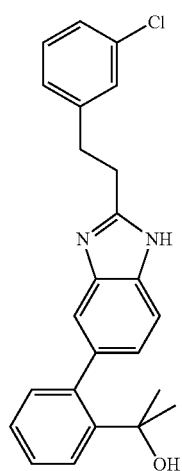
Cpd 169
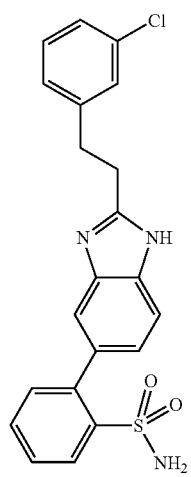
Cpd 170
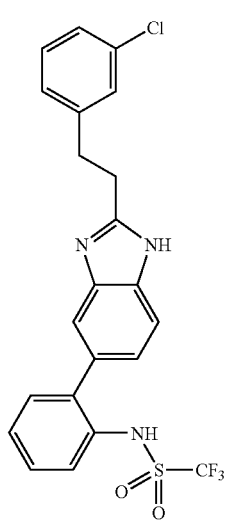
Cpd 171
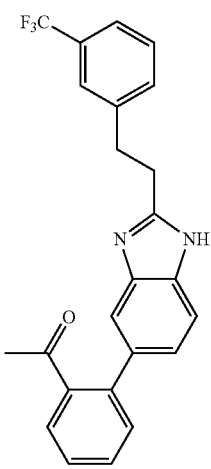
Cpd 172
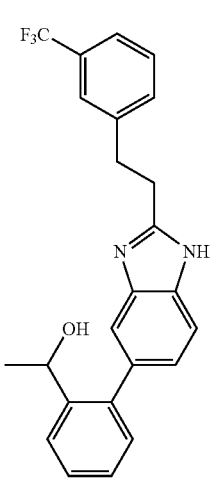
Cpd 173
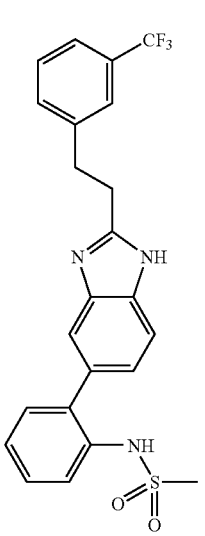

-continued
Cpd 174
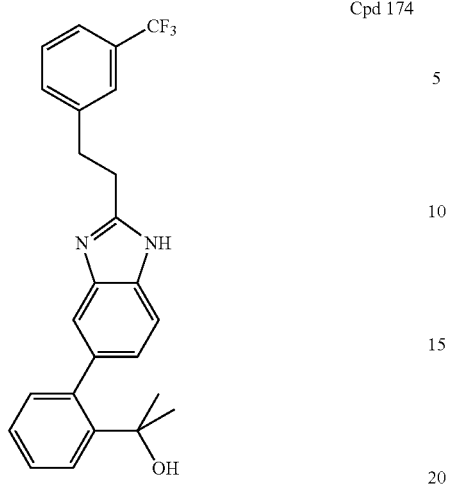
Cpd 175
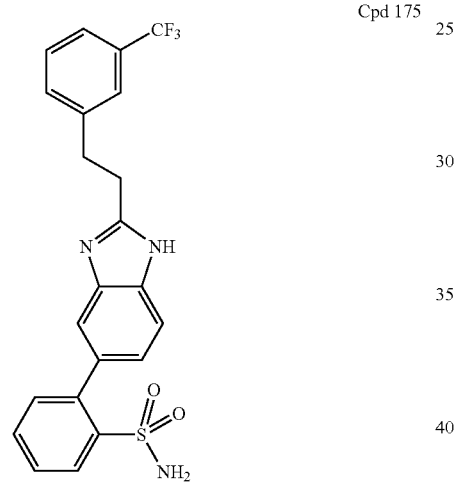
Cpd 176
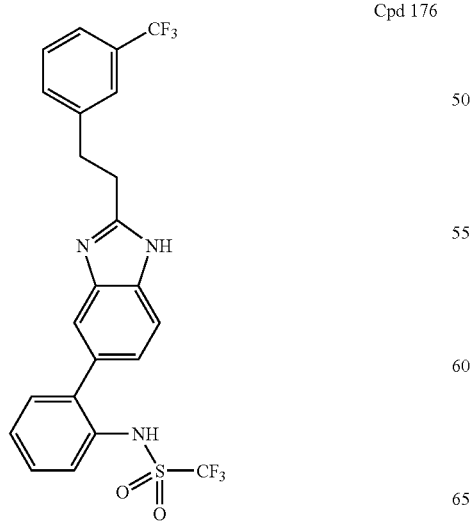
-continued
Cpd 177
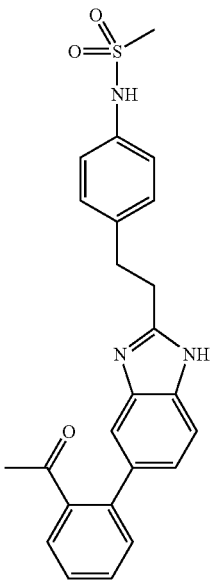
Cpd 178
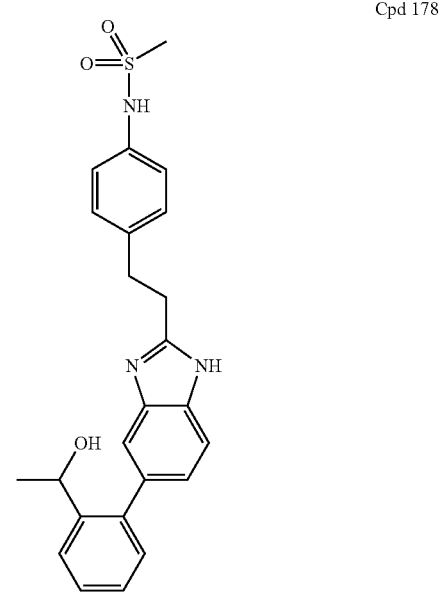

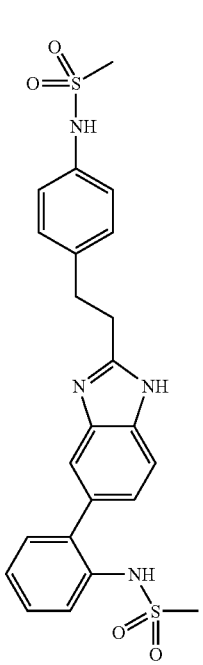 Cpd 179
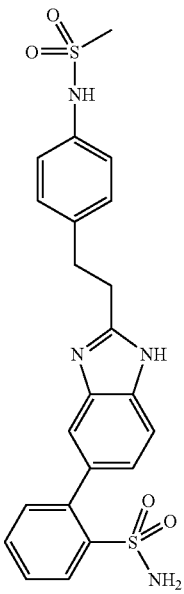 Cpd 181
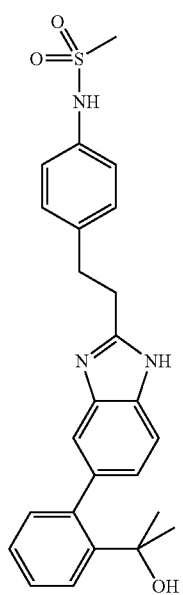 Cpd 180
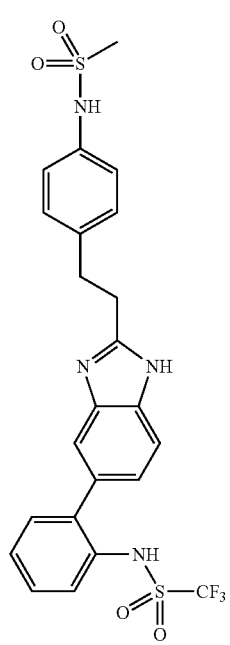 Cpd 182

Cpd 183
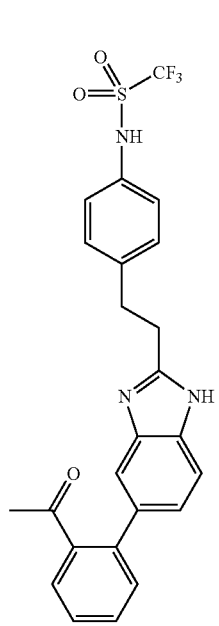
Cpd 184
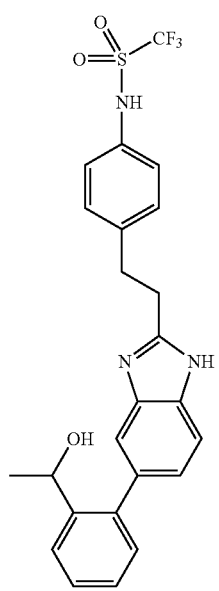
Cpd 185
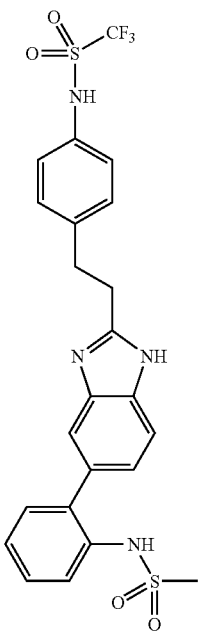
Cpd 186
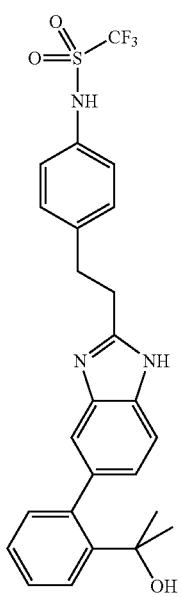

Cpd 187
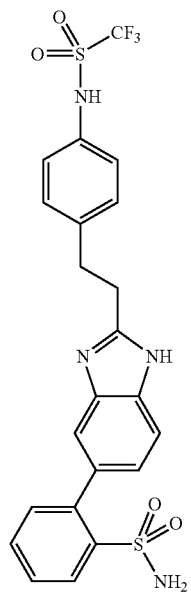
Cpd 188
Cpd 189
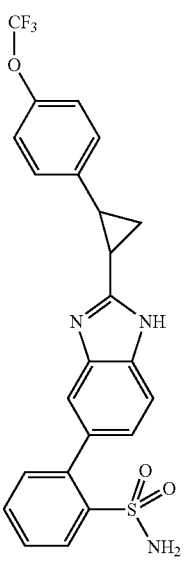
Cpd 190
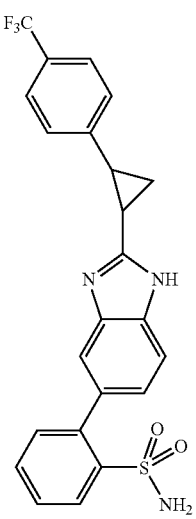
Cpd 191
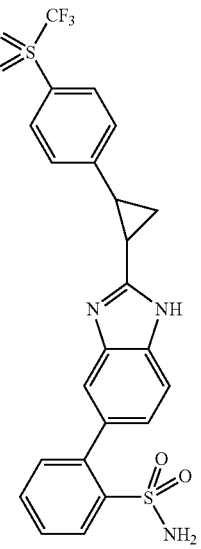

Cpd 192 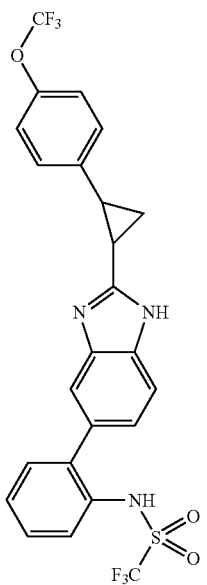
Cpd 193 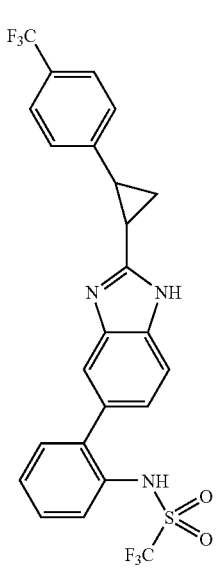
Cpd 194 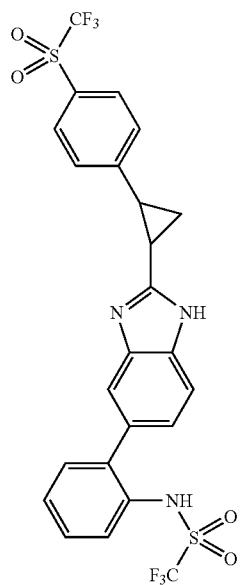
Cpd 195 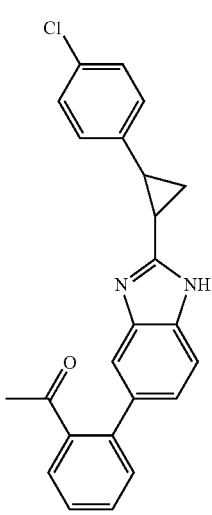
Cpd 196 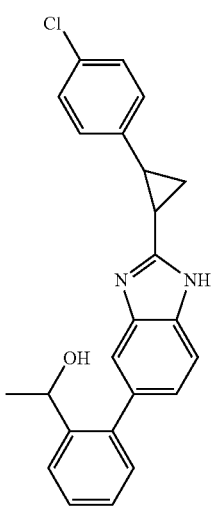

Cpd 197
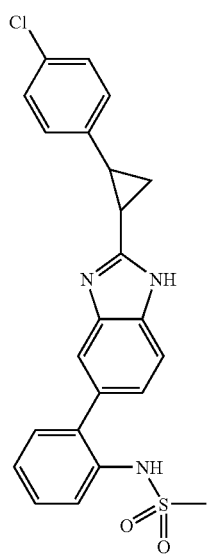
Cpd 200
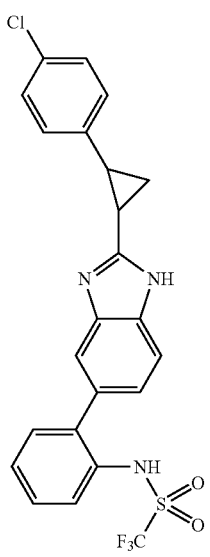
Cpd 201
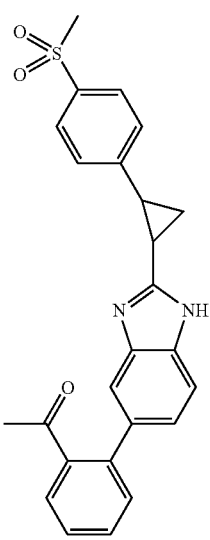
Cpd 198
Cpd 199
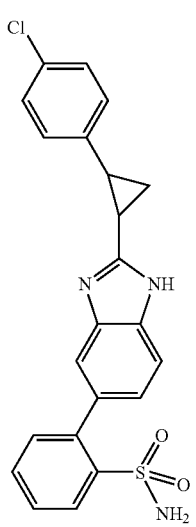
Cpd 202

Cpd 203
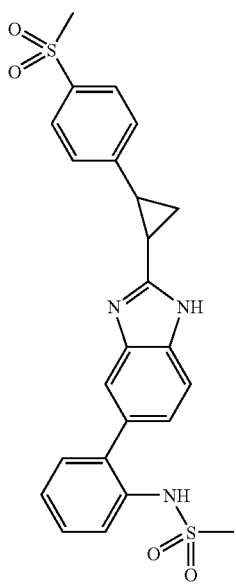
Cpd 204
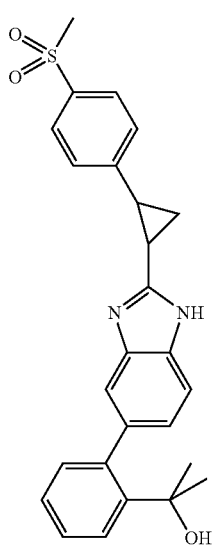
Cpd 205
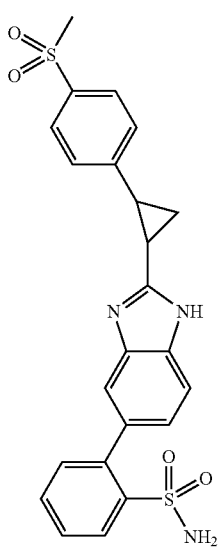
Cpd 206
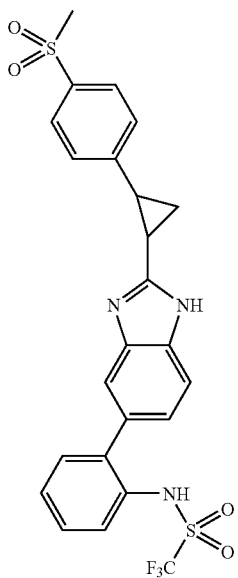
Cpd 207
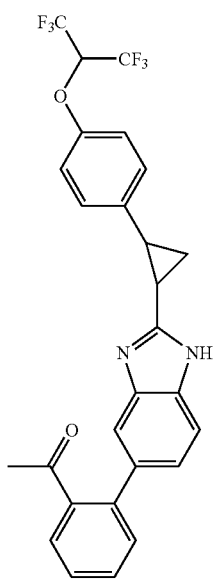

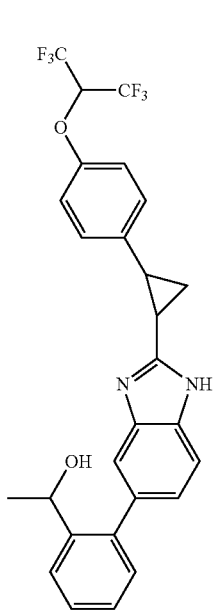
Cpd 208
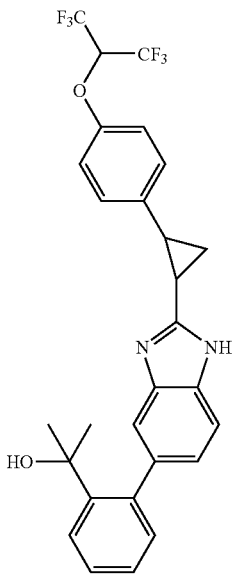
Cpd 210
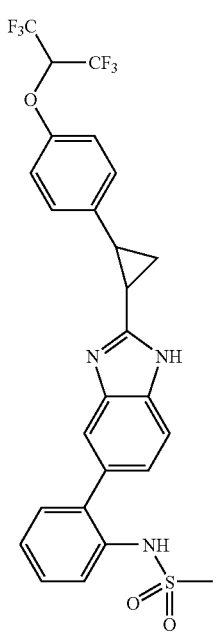
Cpd 209
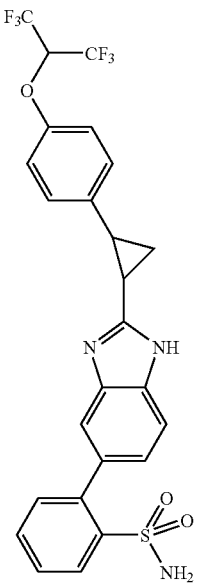
Cpd 211

Cpd 212
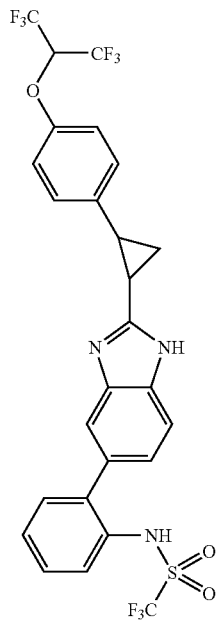
Cpd 213
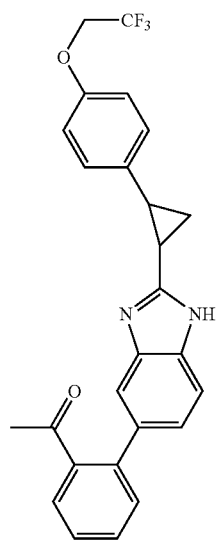
Cpd 214
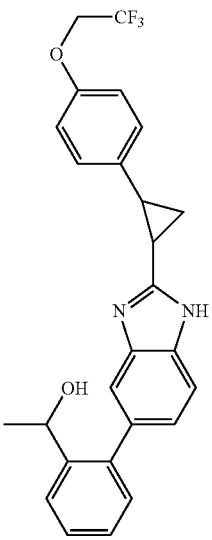
Cpd 215
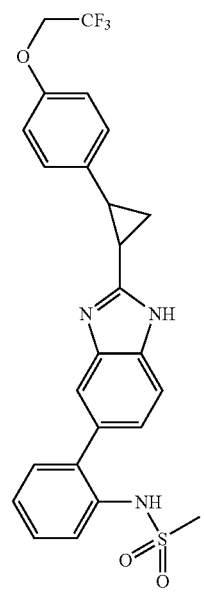
Cpd 216
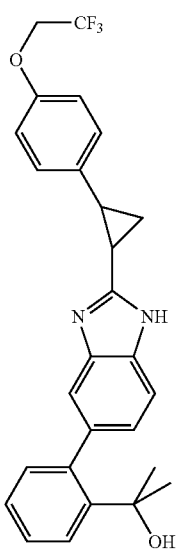

Cpd 217
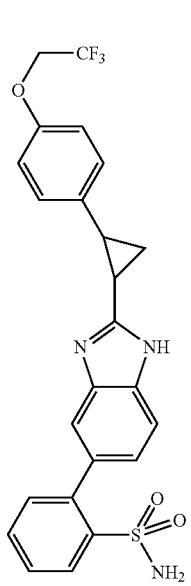
Cpd 219
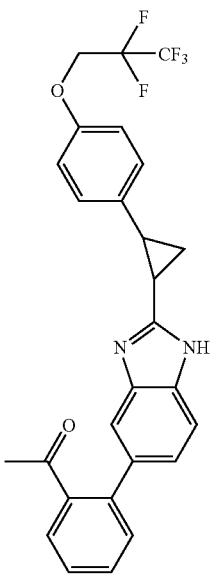
Cpd 218
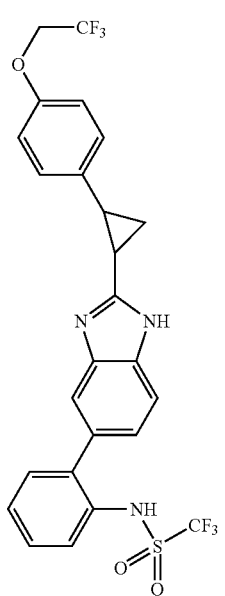
Cpd 220
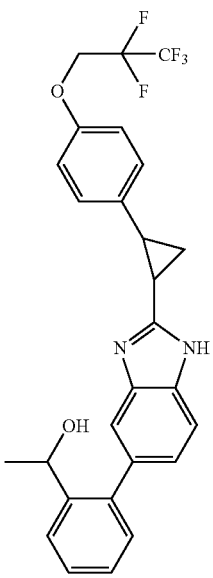

Cpd 221
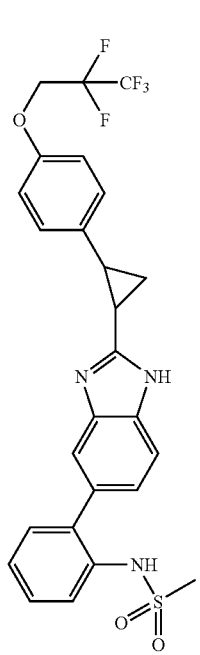
Cpd 223
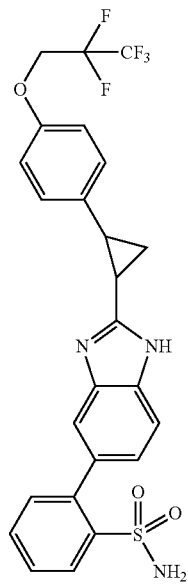
Cpd 222
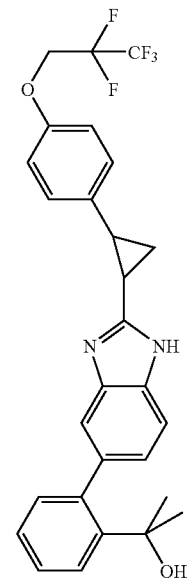
Cpd 224
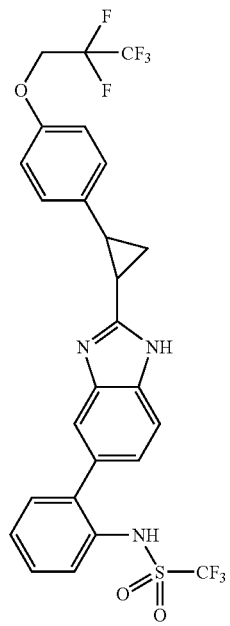

Cpd 225
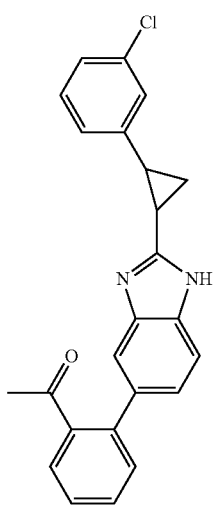
Cpd 226
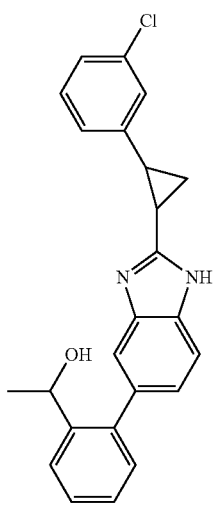
Cpd 227
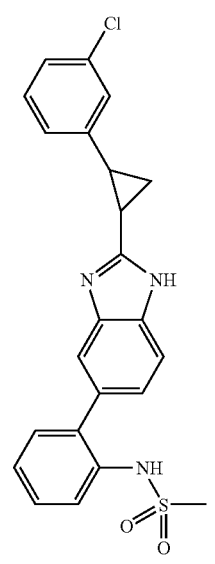
Cpd 228
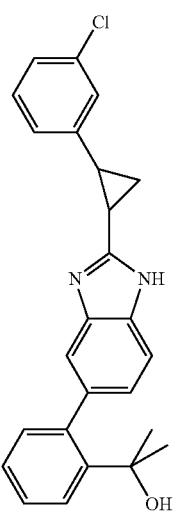
Cpd 229
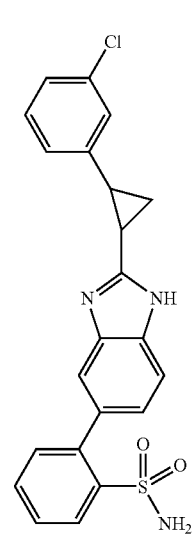
Cpd 230
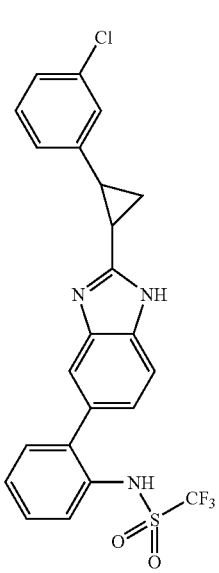

Cpd 231 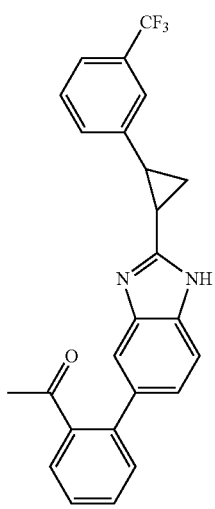
Cpd 234 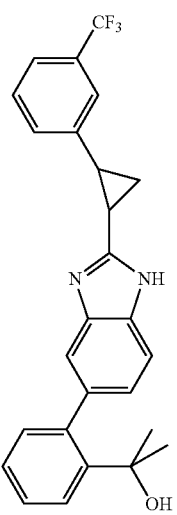
Cpd 232 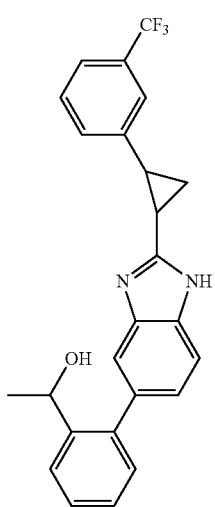
Cpd 235 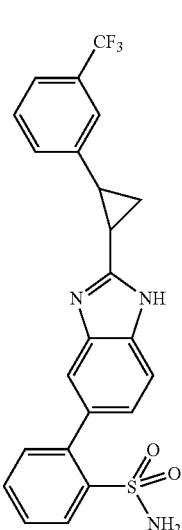
Cpd 233 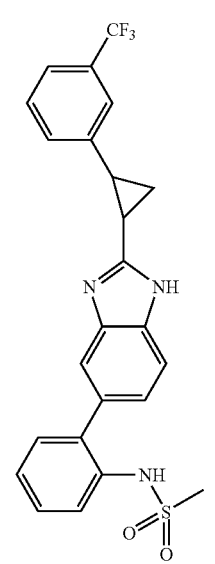
Cpd 236 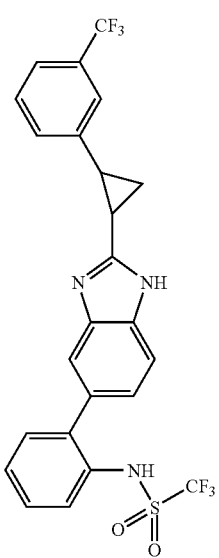

Cpd 237
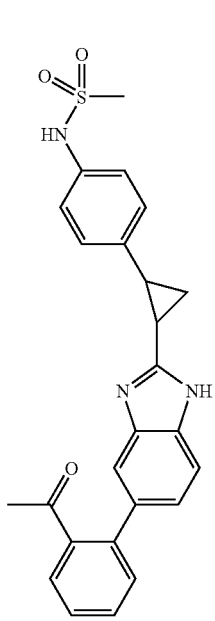
Cpd 239
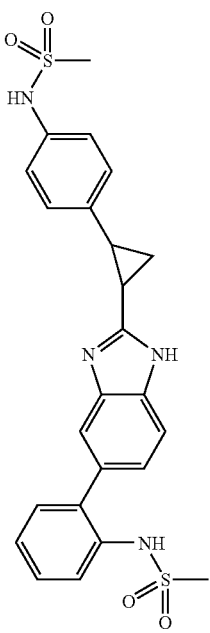
Cpd 238
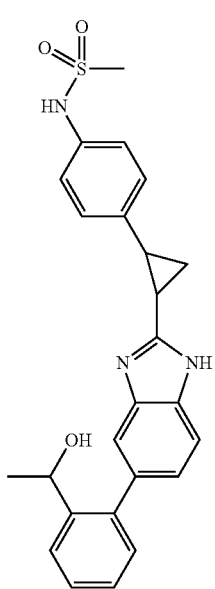
Cpd 240
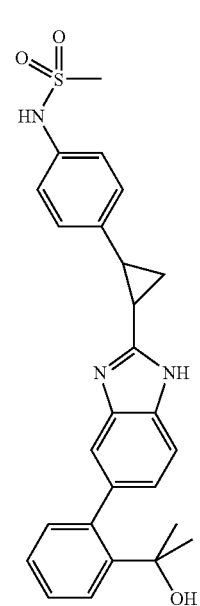

Cpd 241
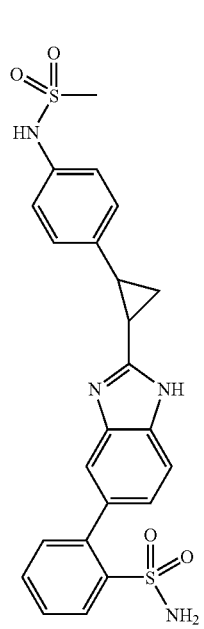
Cpd 243
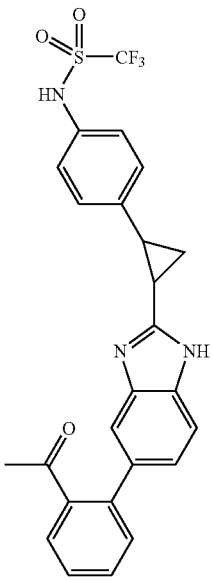
Cpd 242
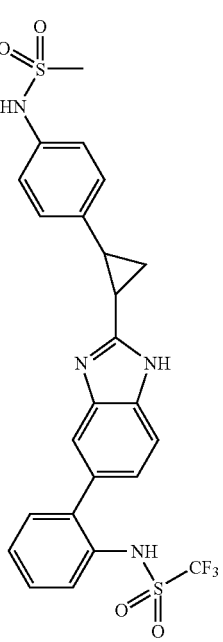
Cpd 244
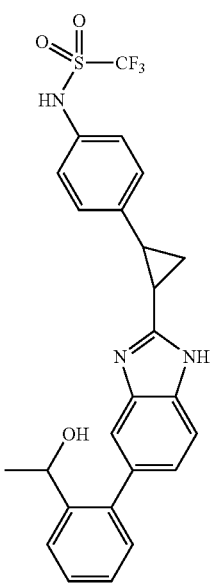

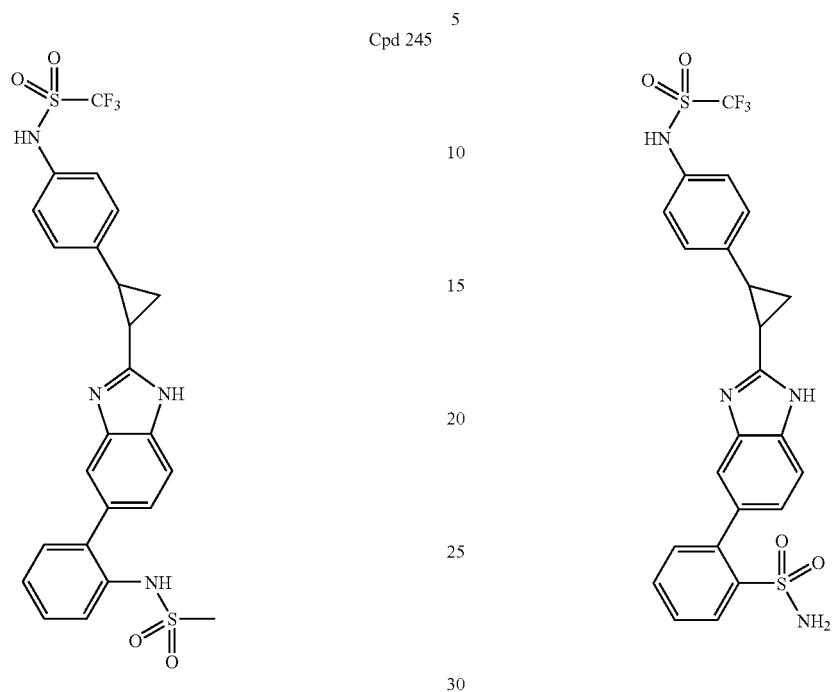
Cpd 245
Cpd 247
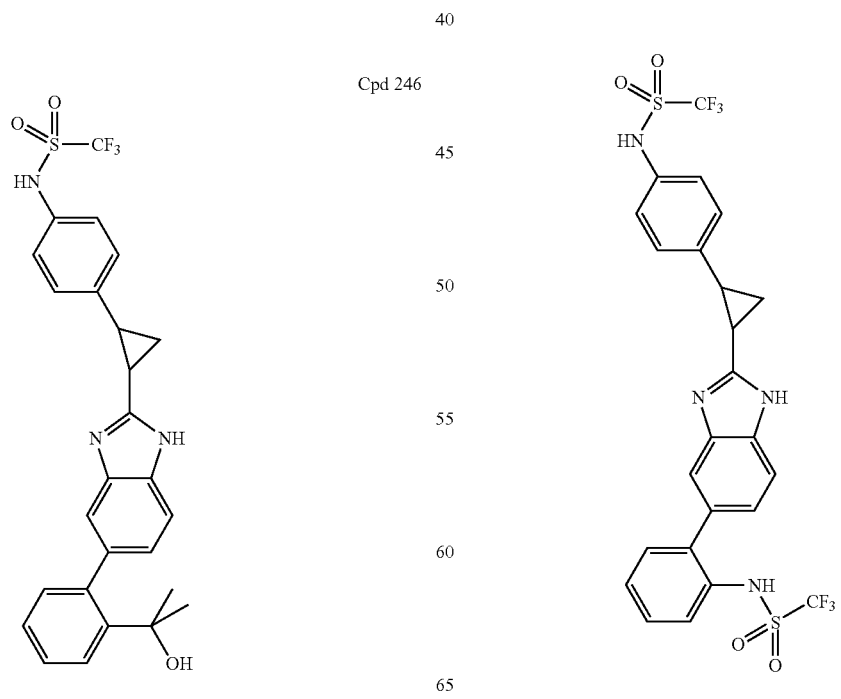
Cpd 246
Cpd 248

Cpd 249
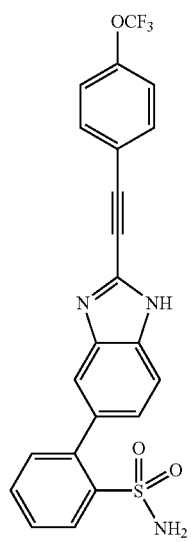
Cpd 250
Cpd 251
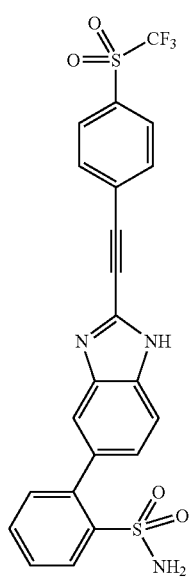
Cpd 252
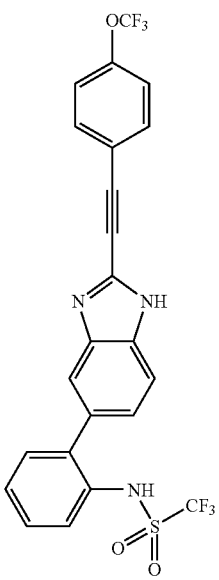
Cpd 253

Cpd 254
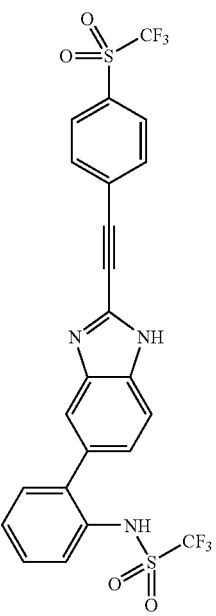
Cpd 255
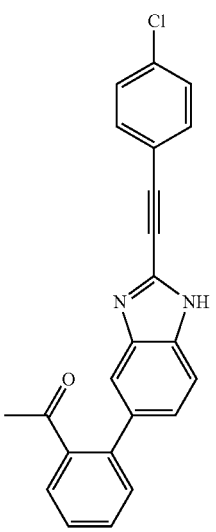
Cpd 256
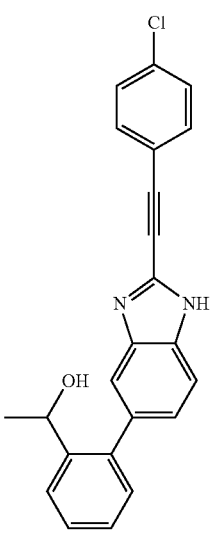
Cpd 257
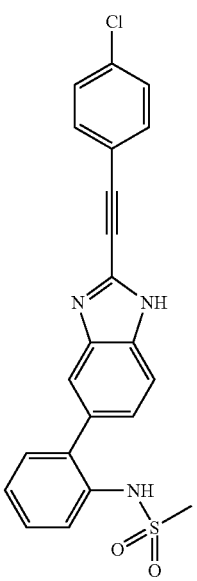
Cpd 258
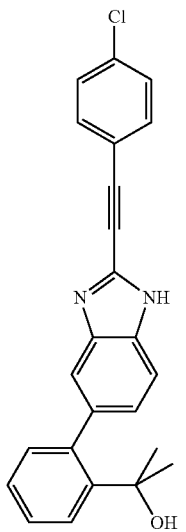
Cpd 259
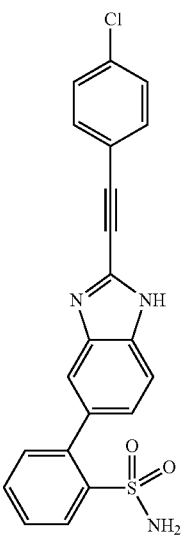

Cpd 260
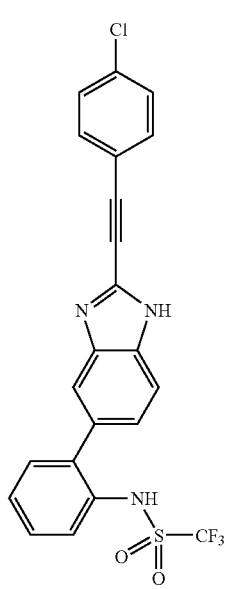
Cpd 262
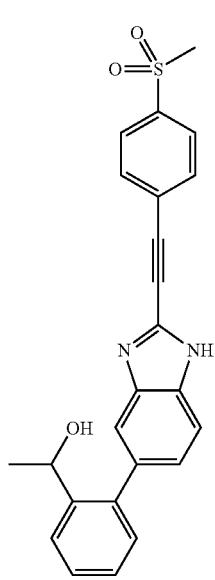
Cpd 261
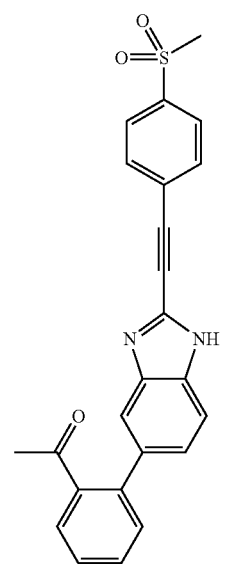
Cpd 263
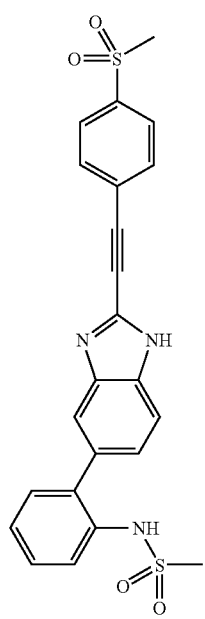

Cpd 264
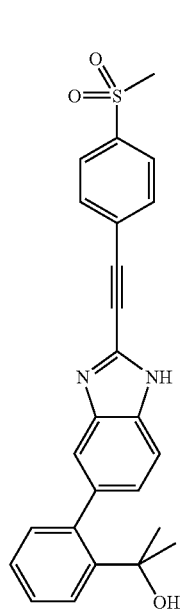
Cpd 266
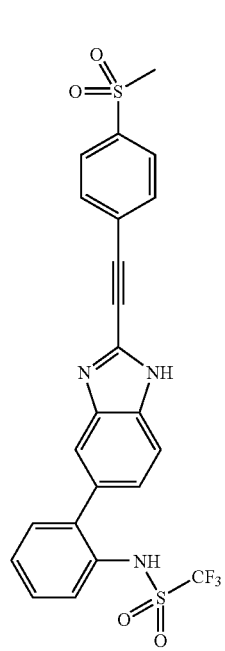
Cpd 265
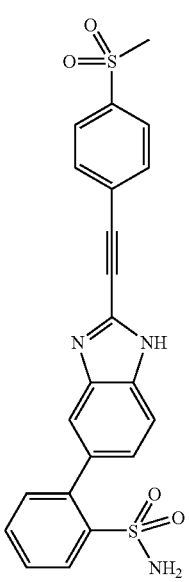
Cpd 267
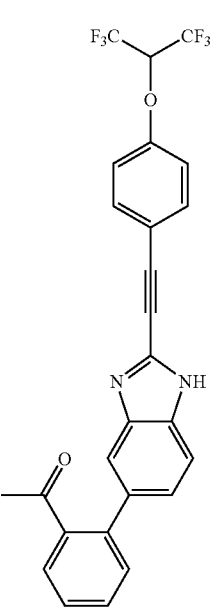

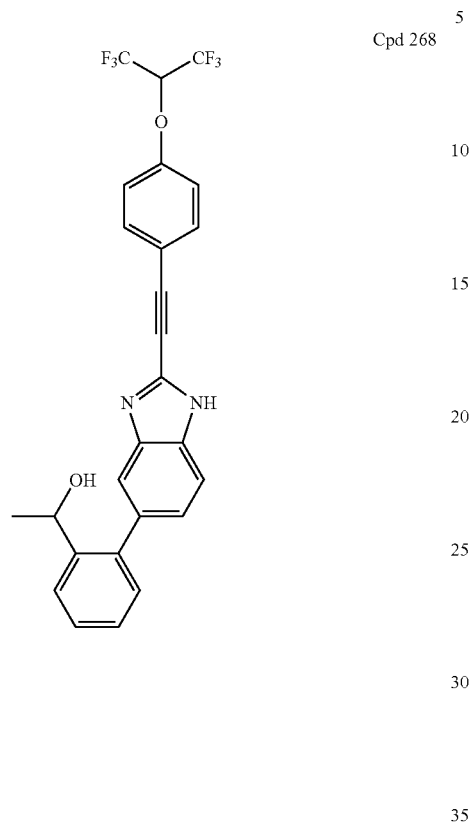
Cpd 268
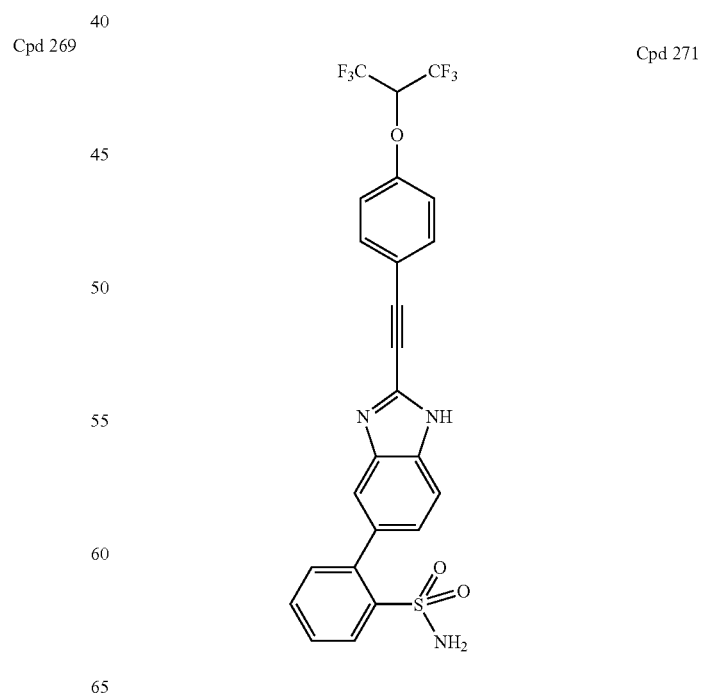
Cpd 270
Cpd 269
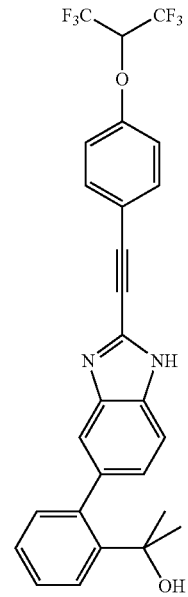
Cpd 271
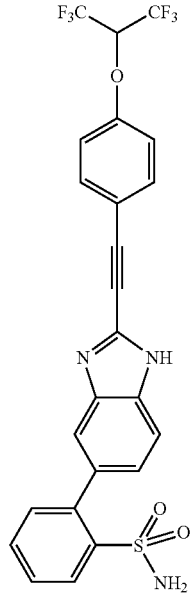

Cpd 272
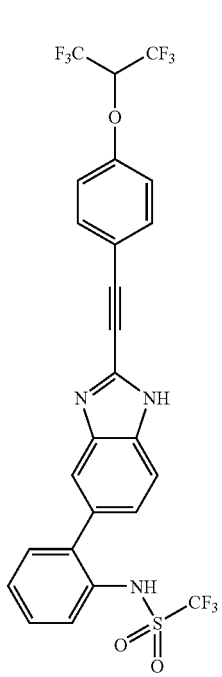
Cpd 274
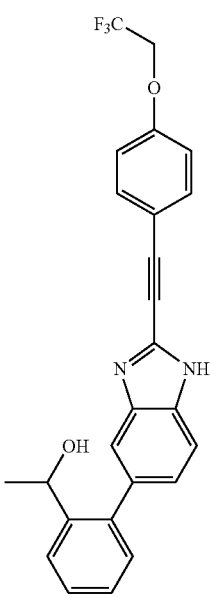
Cpd 273
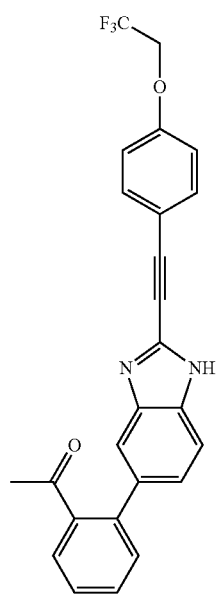
Cpd 275
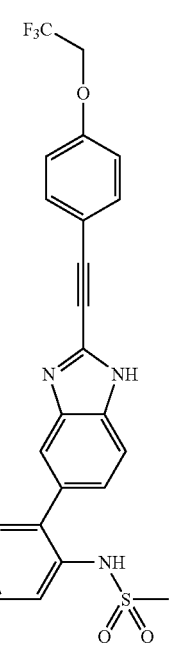

Cpd 276
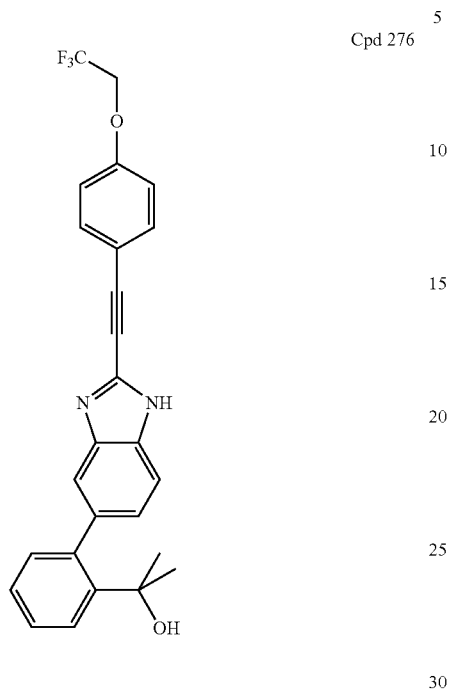
Cpd 277
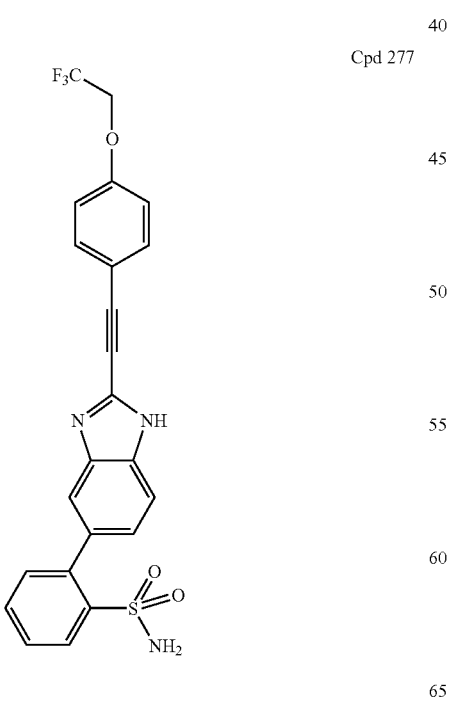
Cpd 278
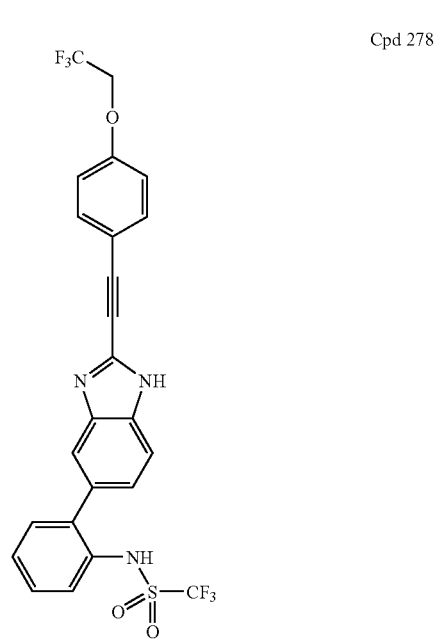
Cpd 279
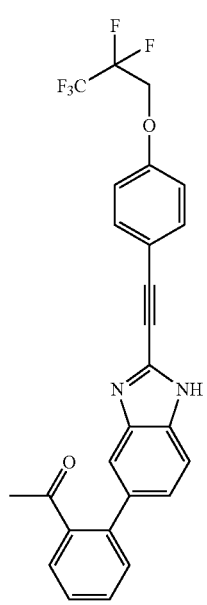

-continued
Cpd 280
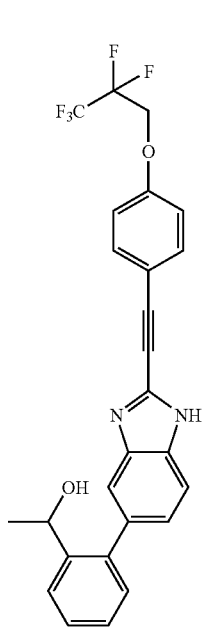
Cpd 281
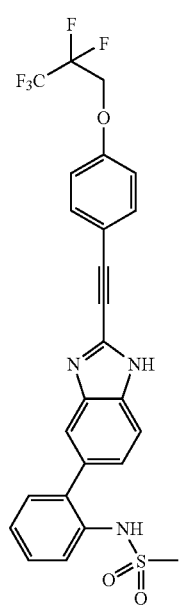
-continued
Cpd 282
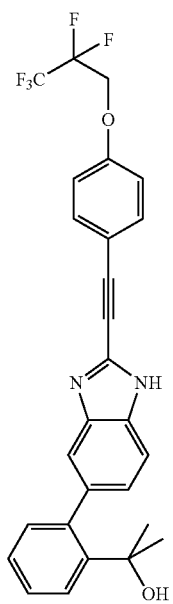
Cpd 283
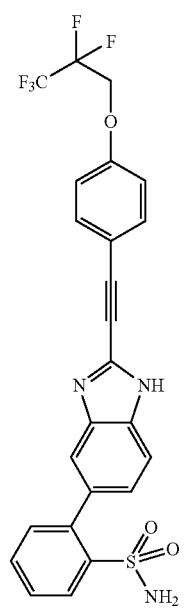

Cpd 284
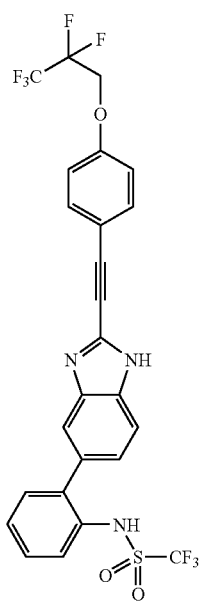
Cpd 285
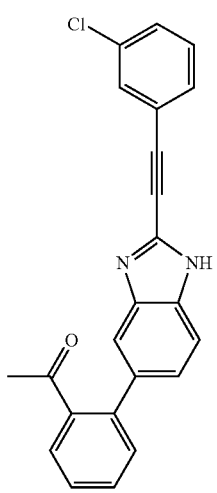
Cpd 286
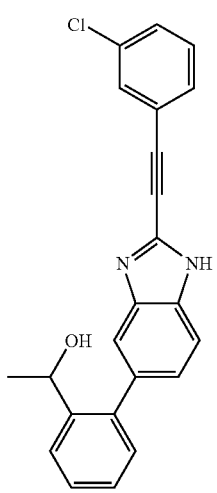
Cpd 287
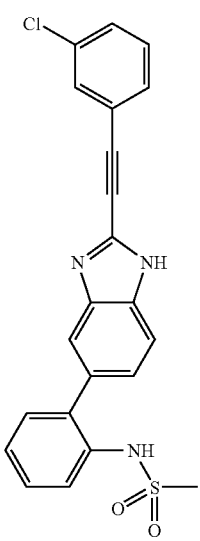
Cpd 288
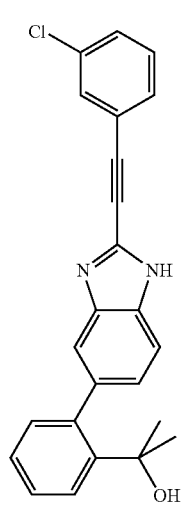
Cpd 289
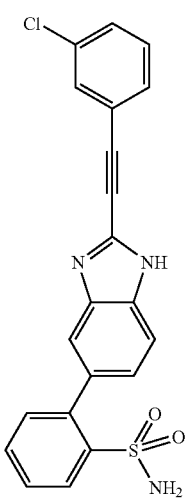

-continued
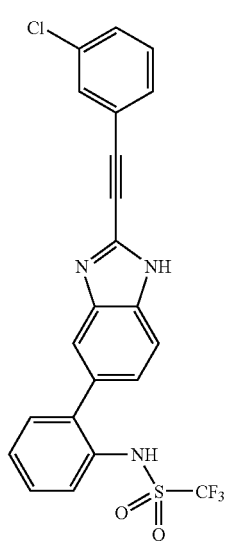
Cpd 290
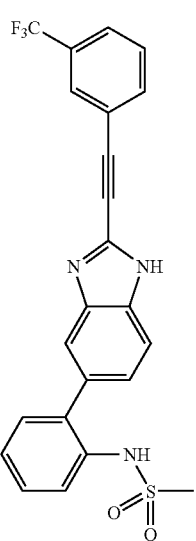
Cpd 293
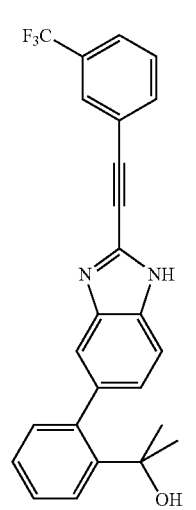
Cpd 294
Cpd 291
Cpd 292
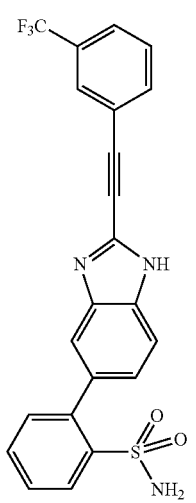
Cpd 295

Cpd 296
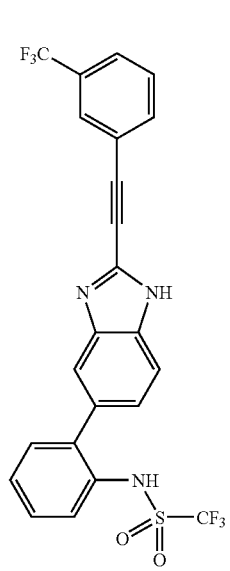
Cpd 298
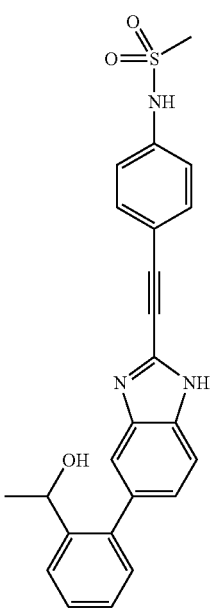
Cpd 297
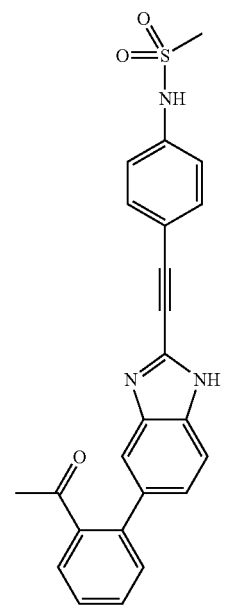
Cpd 299
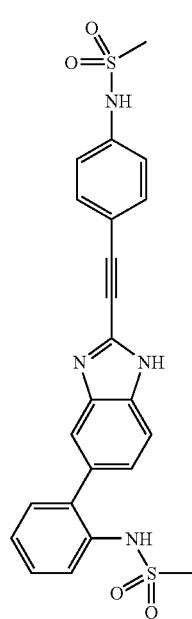

Cpd 300
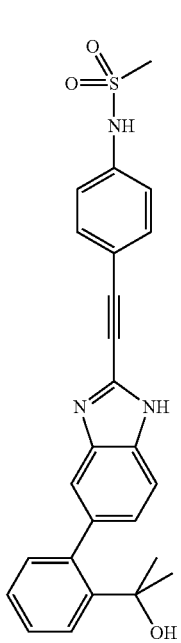
Cpd 302
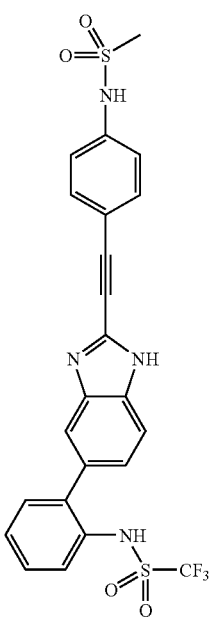
Cpd 301
Cpd 303
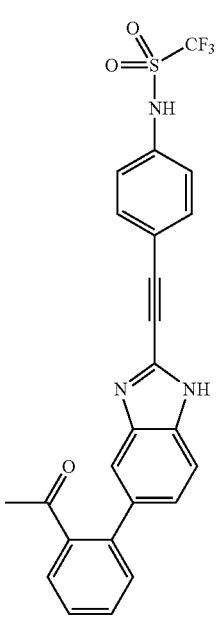

-continued
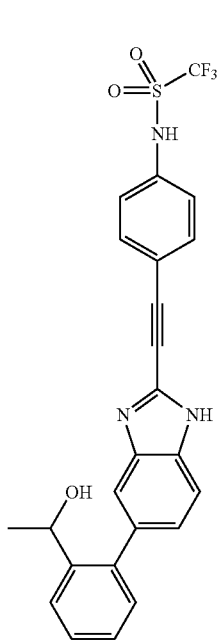
Cpd 304
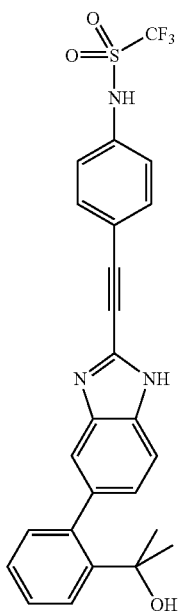
Cpd 306
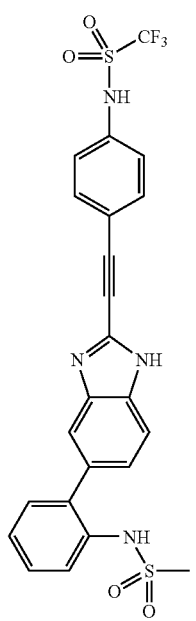
Cpd 305
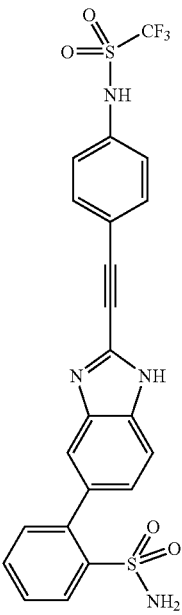
Cpd 307

Cpd 308
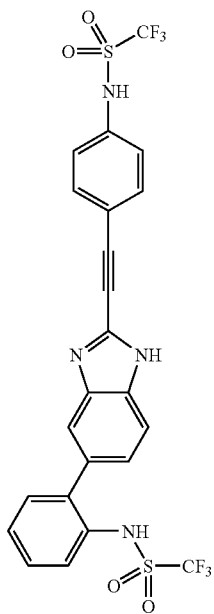
Cpd 309
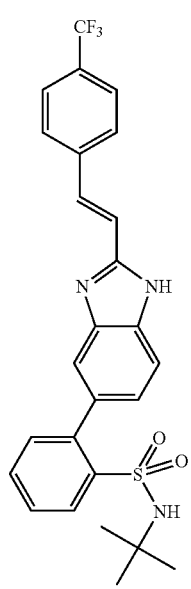
Cpd 310
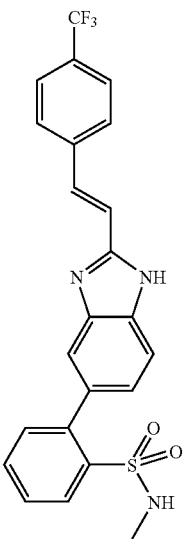
Cpd 311
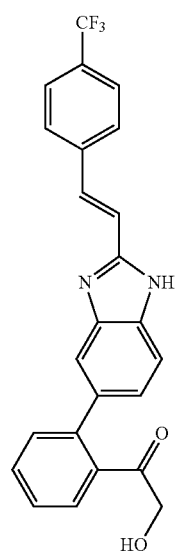
Cpd 312
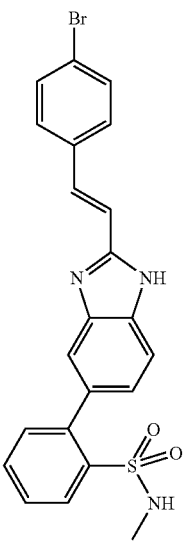

Cpd 314
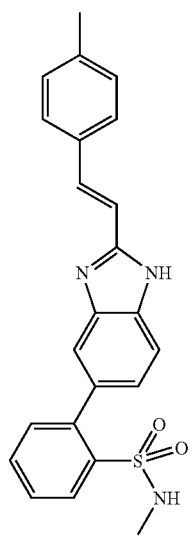
Cpd 315
Cpd 316
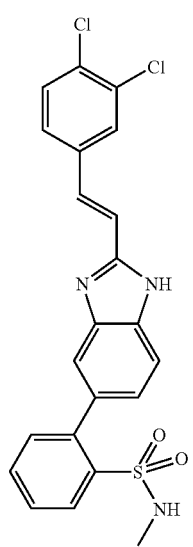
Cpd 317
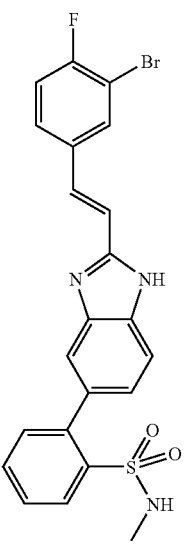
Cpd 318
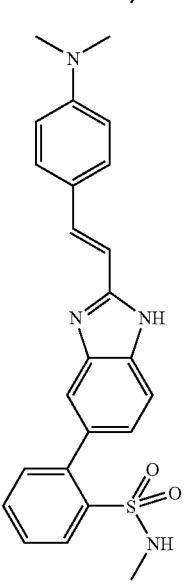
Cpd 319
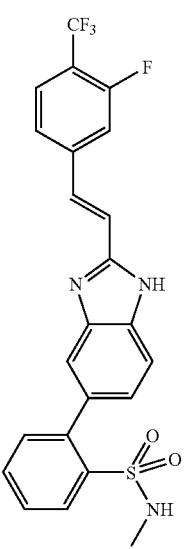

-continued
Cpd 320
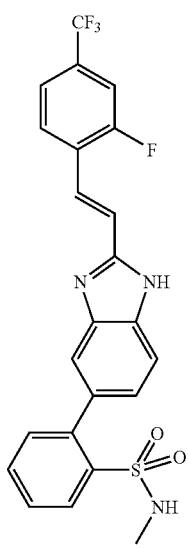
Cpd 321
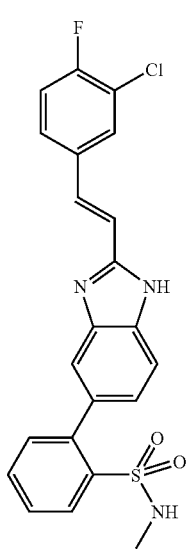
Cpd 322
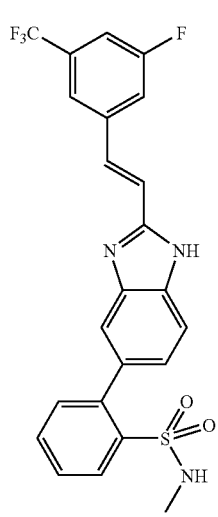
-continued
Cpd 323
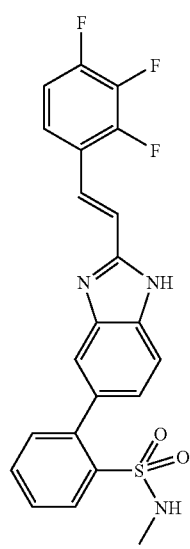
Cpd 324
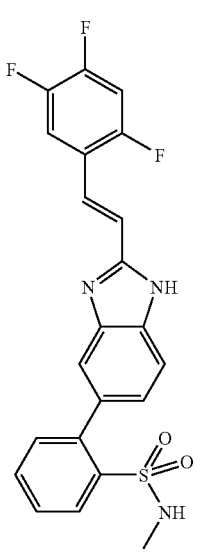
Cpd 325
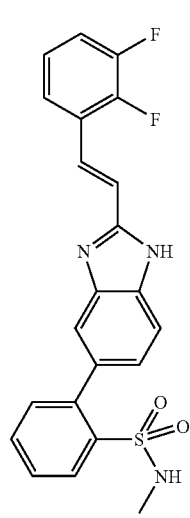

-continued
Cpd 326
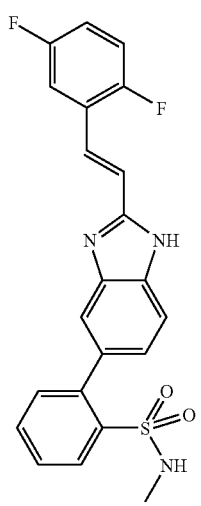
Cpd 327
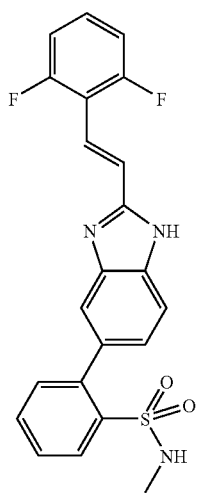
Cpd 328
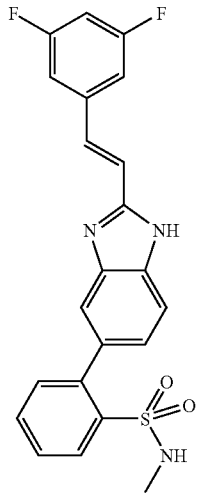
-continued
Cpd 329
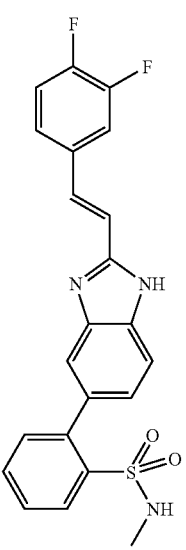
Cpd 330
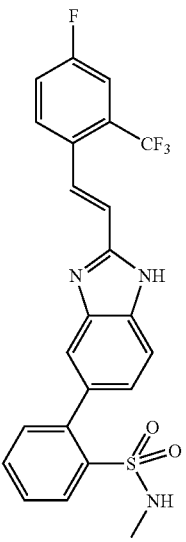
Cpd 331
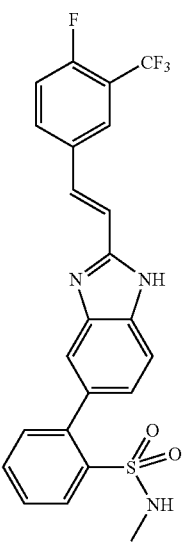

-continued
Cpd 332
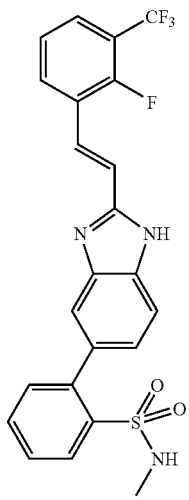
Cpd 333
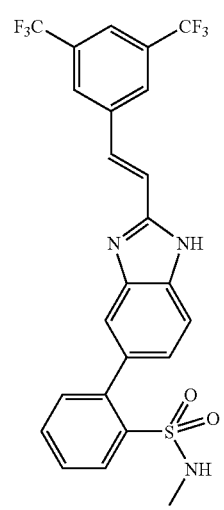
Cpd 334
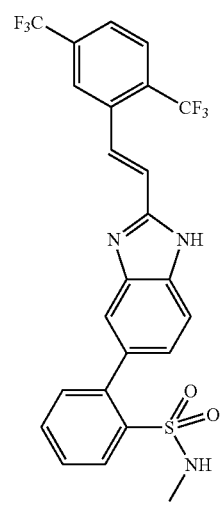
-continued
Cpd 335
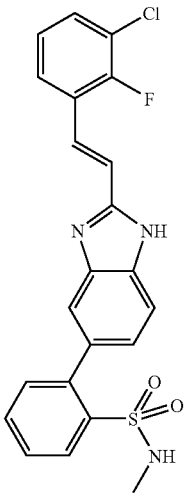
Cpd 336
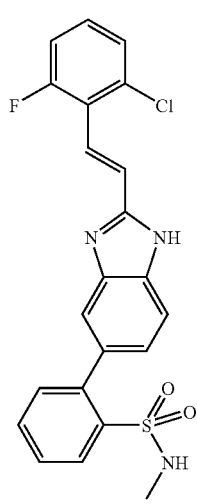
Cpd 337
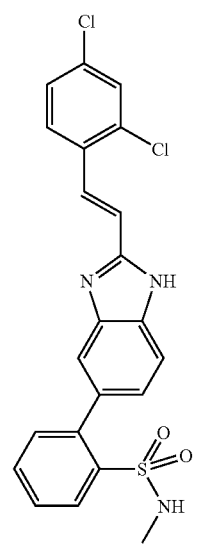

-continued
Cpd 338
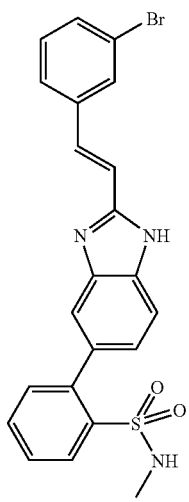
Cpd 339
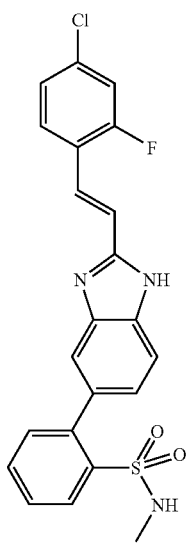
Cpd 340
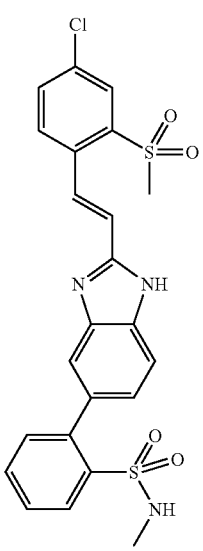
-continued
Cpd 341
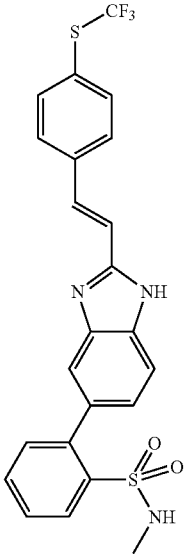
Cpd 342
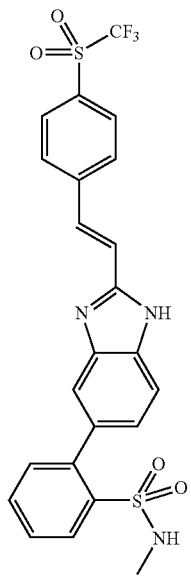
Cpd 343
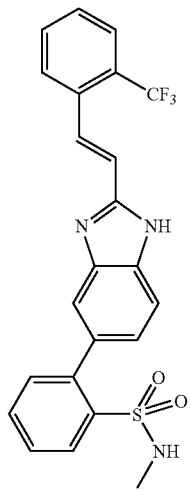

Cpd 344
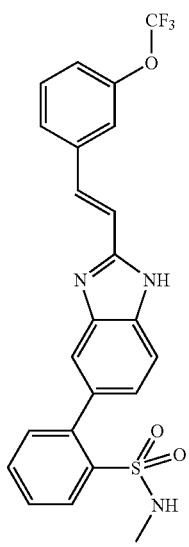
Cpd 345
Cpd 346
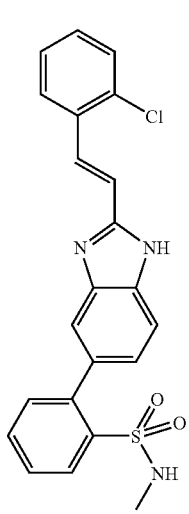
Cpd 347
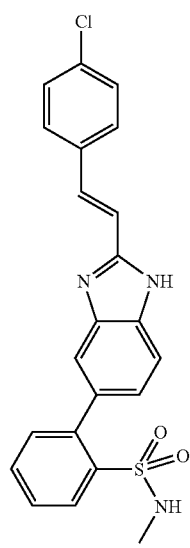
Cpd 348
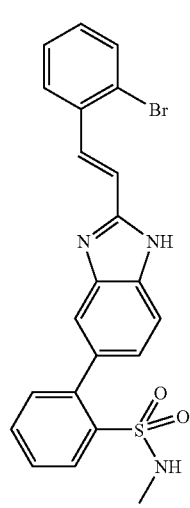
Cpd 349
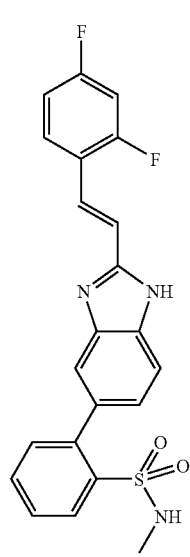

-continued
Cpd 350
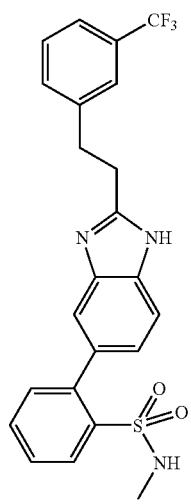
Cpd 351
Cpd 357
-continued
Cpd 358
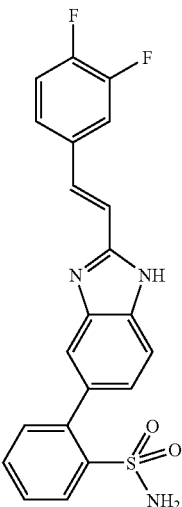
Cpd 359
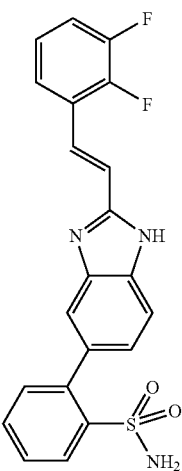
Cpd 360
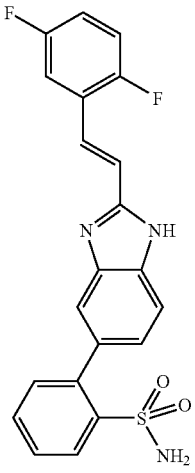

Cpd 361
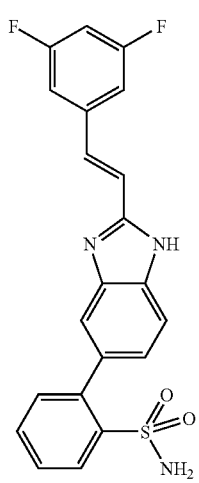
Cpd 362
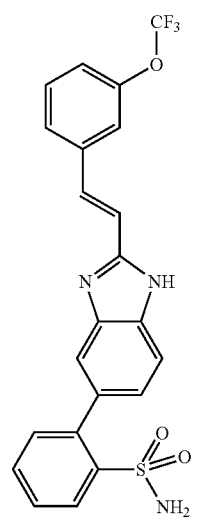
Cpd 363
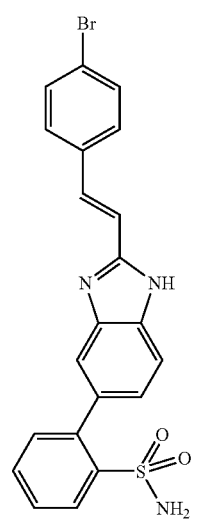
Cpd 364
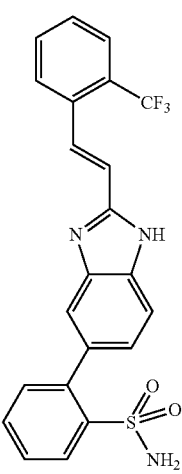
Cpd 365
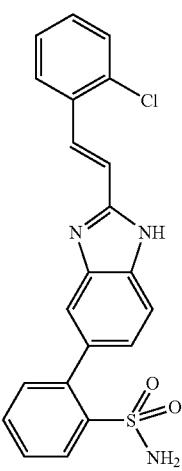
Cpd 366

Cpd 367

Cpd 368

Cpd 369

Cpd 370

Cpd 371

Cpd 372

Cpd 373
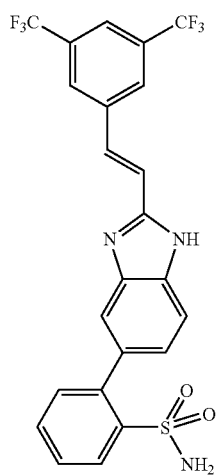
Cpd 374
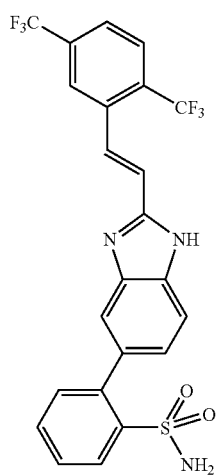
Cpd 375
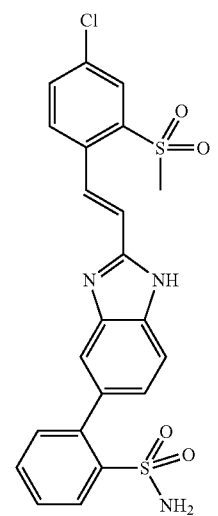
Cpd 376
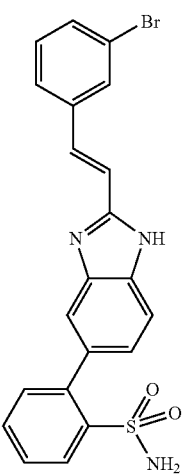
Cpd 378
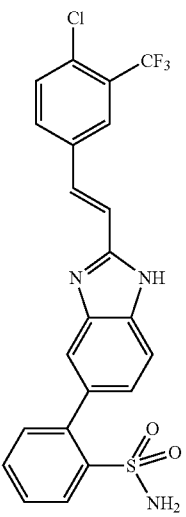
Cpd 379
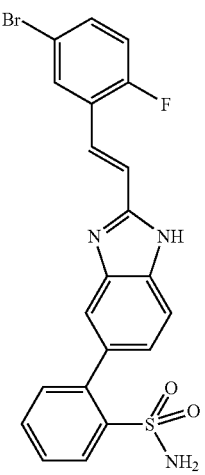

-continued
Cpd 380
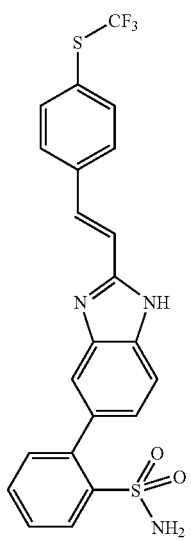
Cpd 383
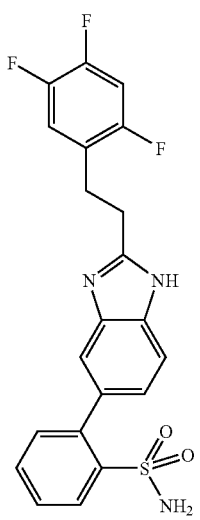
Cpd 384
-continued
Cpd 385
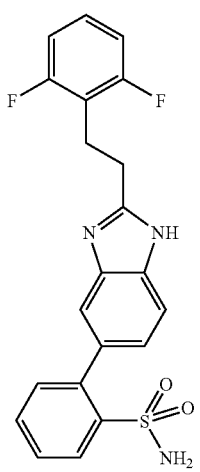
Cpd 386
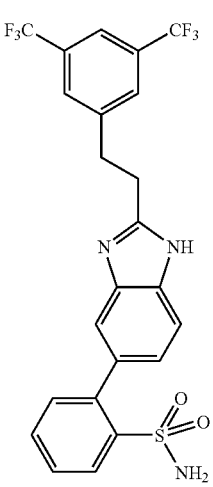
Cpd 387

-continued
Cpd 388
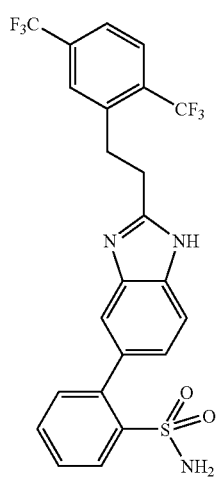
Cpd 389
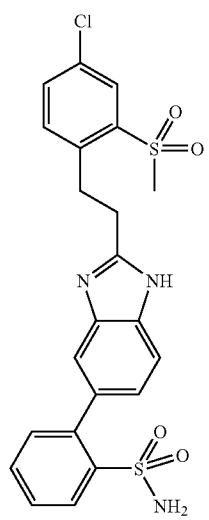
Cpd 390
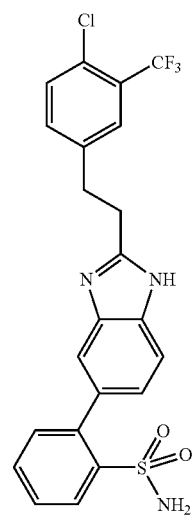
-continued
Cpd 391
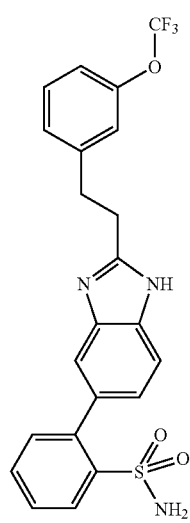
Cpd 392
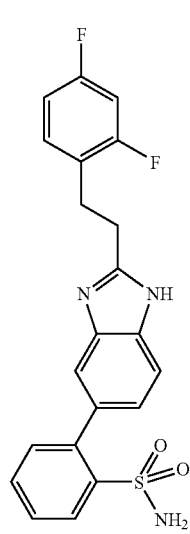
Cpd 393
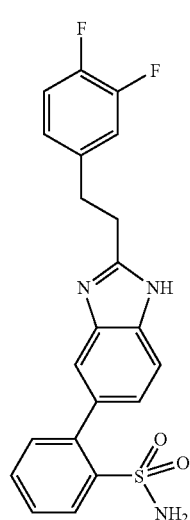

161
-continued
Cpd 394
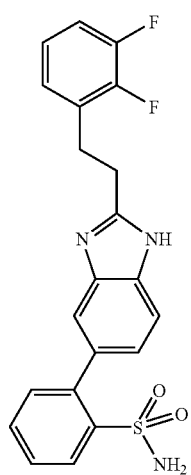
Cpd 395
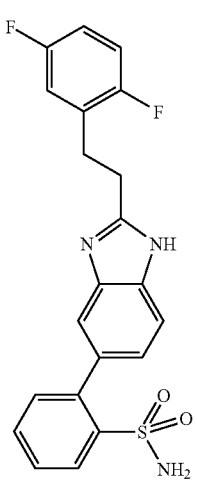
Cpd 396
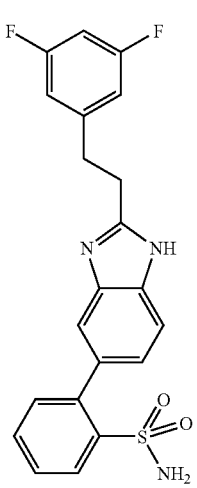
162
-continued
Cpd 397
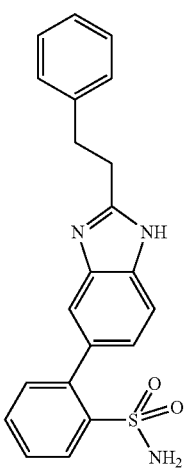
Cpd 398
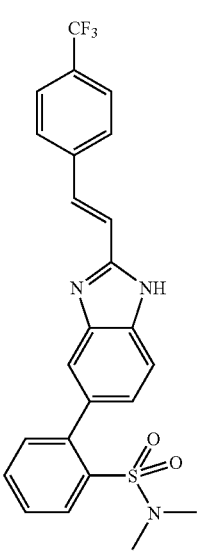
Cpd 399
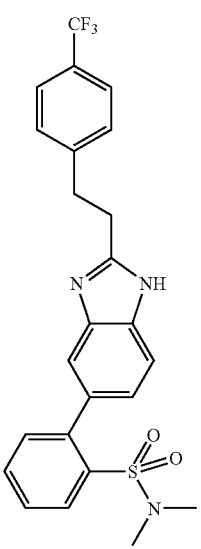

Cpd 400
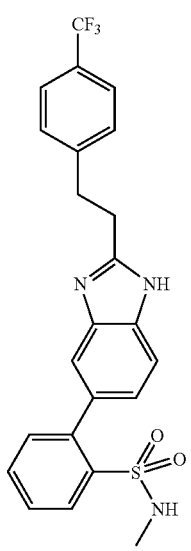
Cpd 405
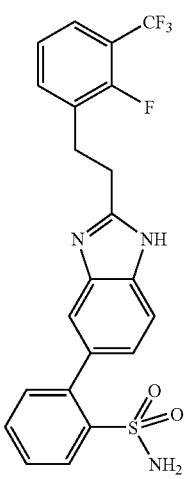
Cpd 402
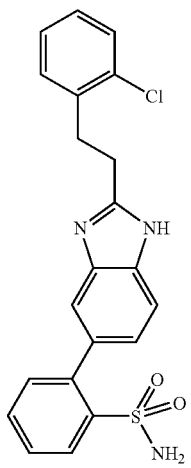
Cpd 406
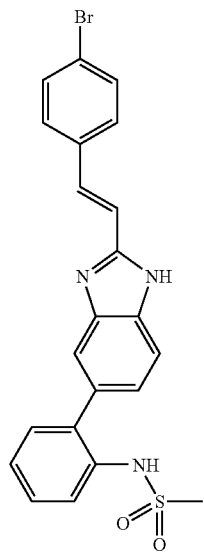
Cpd 404
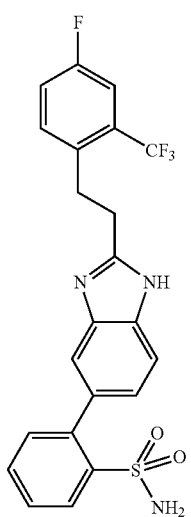
Cpd 407
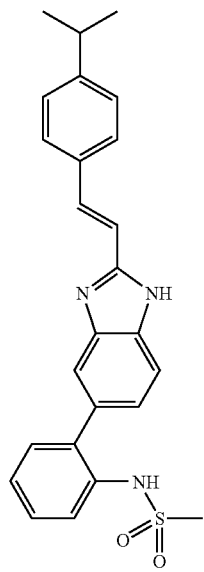

Cpd 408
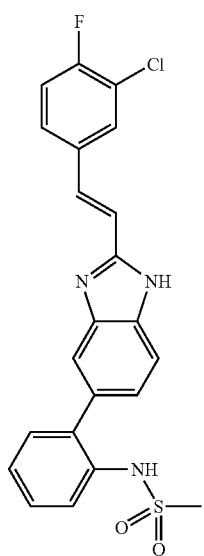
Cpd 409
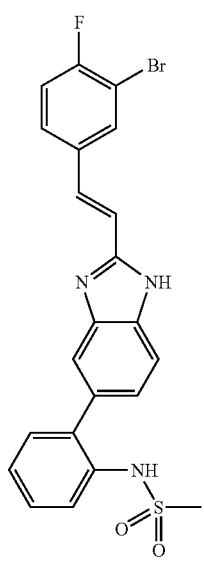
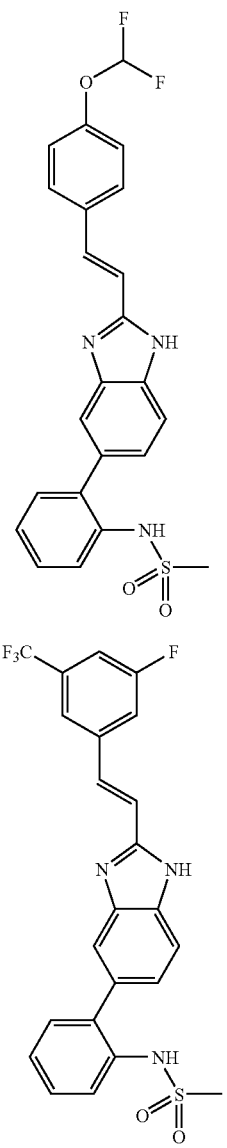
Cpd 410
Cpd 411
Cpd 412

Cpd 413
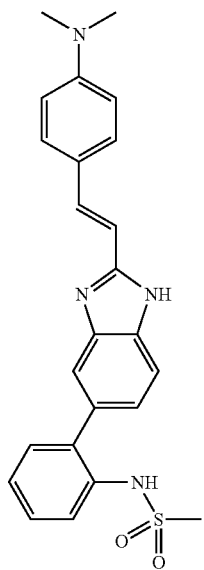
Cpd 414
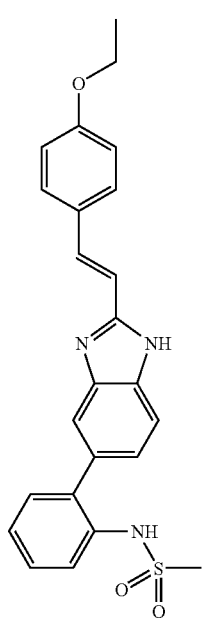
Cpd 415
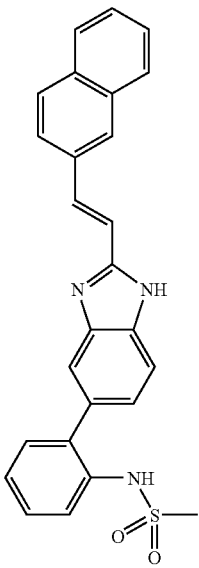
Cpd 416
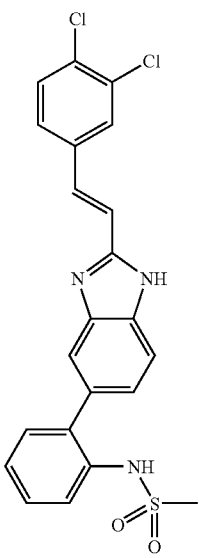
Cpd 417
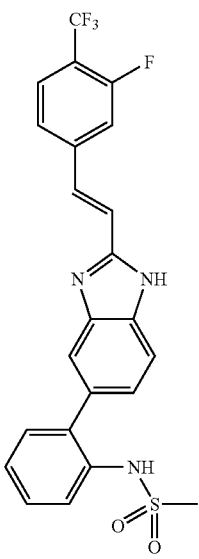

Cpd 418
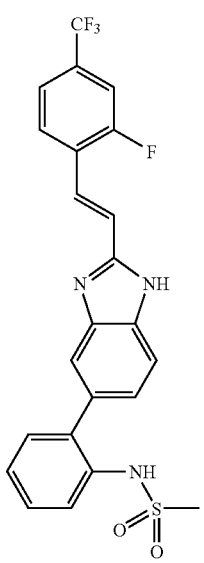
Cpd 419
Cpd 420
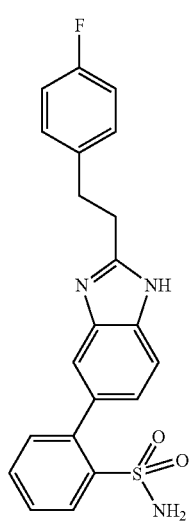
Cpd 421
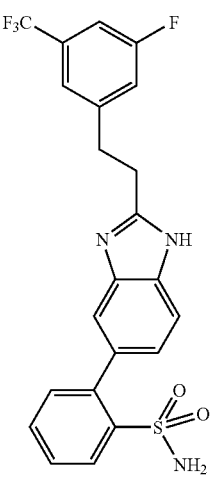
Cpd 422
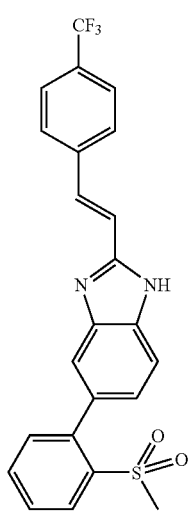
Cpd 423

Cpd 424
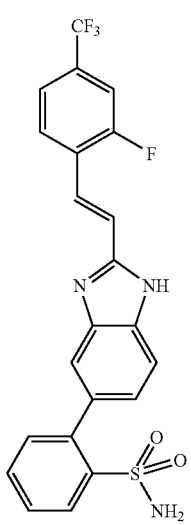
Cpd 425
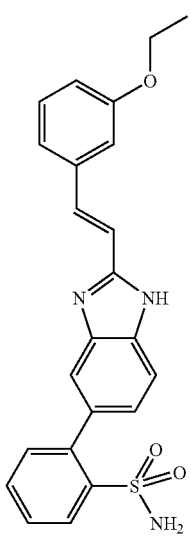
Cpd 426
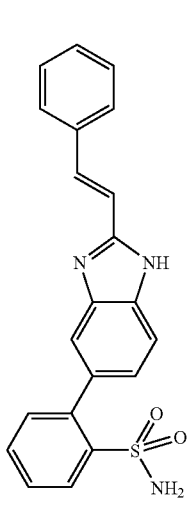
Cpd 427
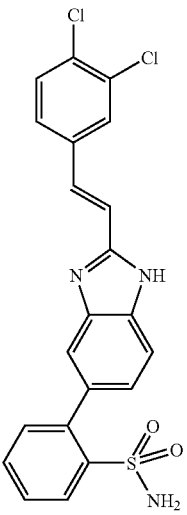
Cpd 428
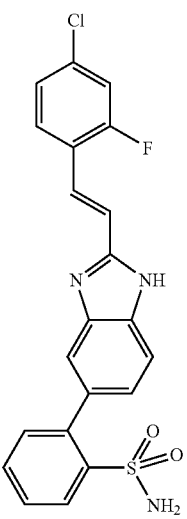
Cpd 429
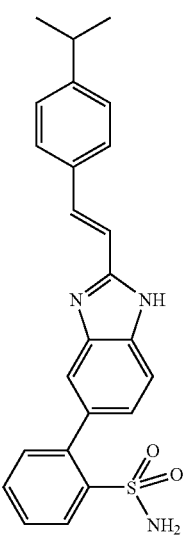

-continued
Cpd 430
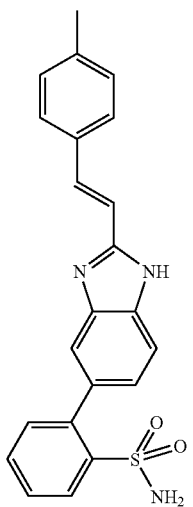
Cpd 431
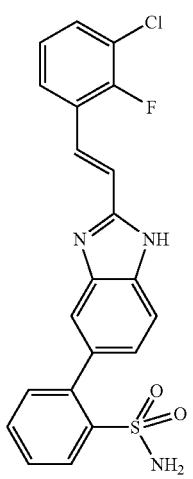
Cpd 432
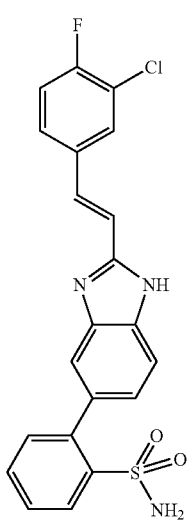
Cpd 433
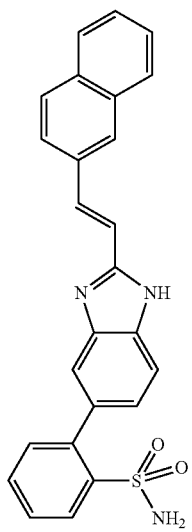
Cpd 434
Cpd 435

Cpd 436
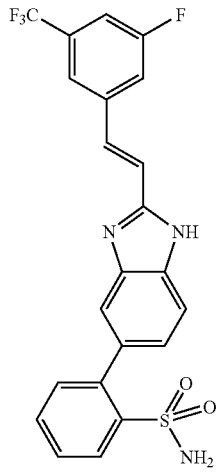
Cpd 437
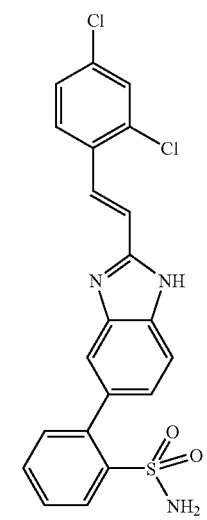
Cpd 438
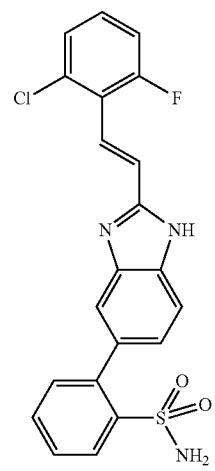
Cpd 439
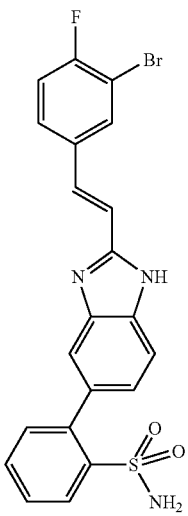
Cpd 440
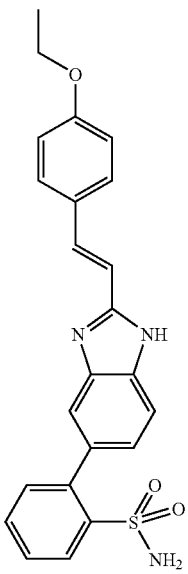
Cpd 441
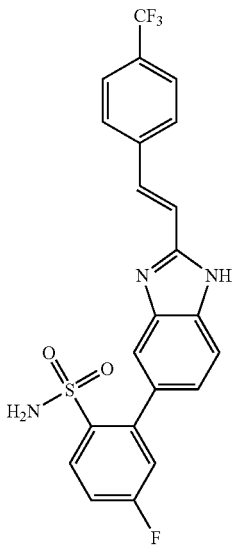

Cpd 442
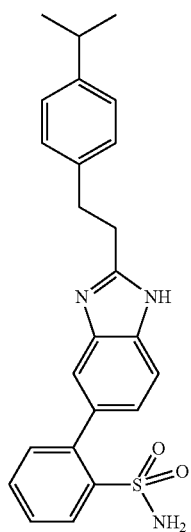
Cpd 443
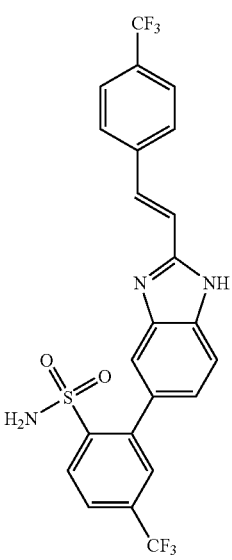
Cpd 444
Cpd 445
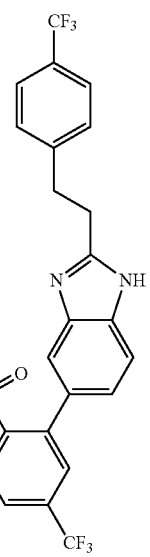
Cpd 446
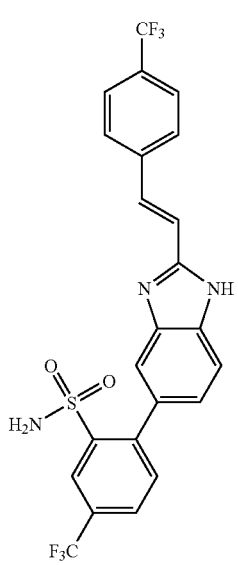
Cpd 447
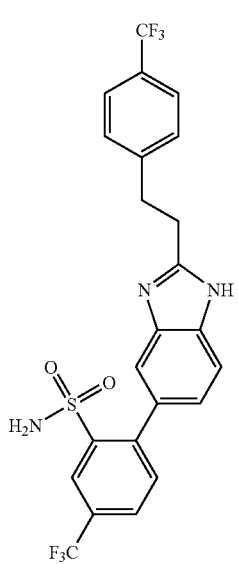

Cpd 448
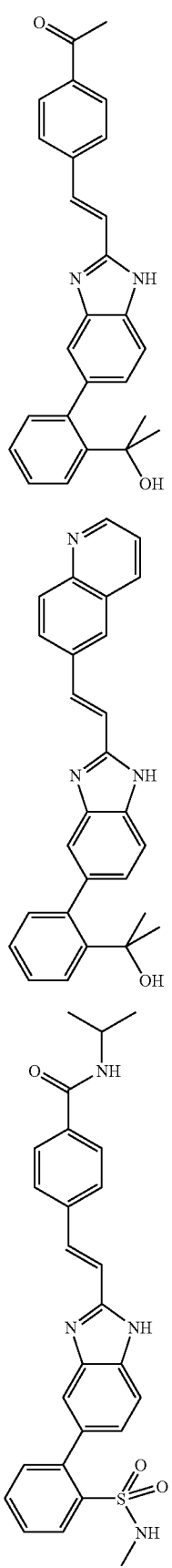
Cpd 449
Cpd 450
Cpd 451
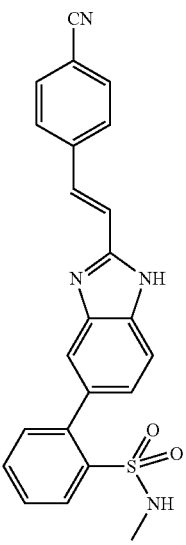
Cpd 452
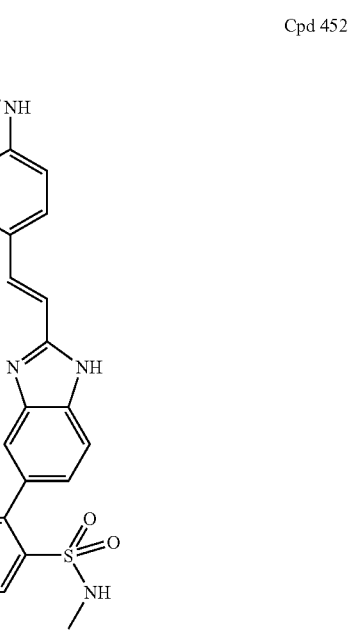

-continued
Cpd 453
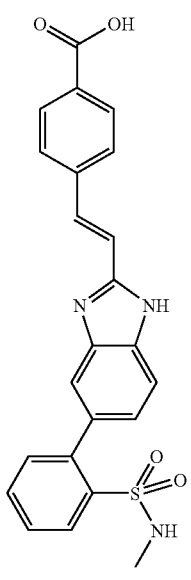
Cpd 454
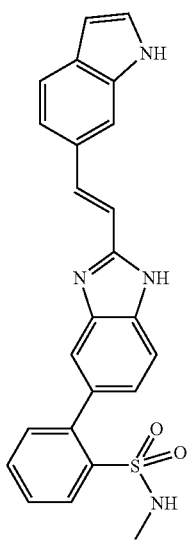
Cpd 455
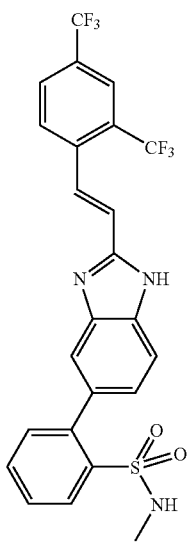
-continued
Cpd 456
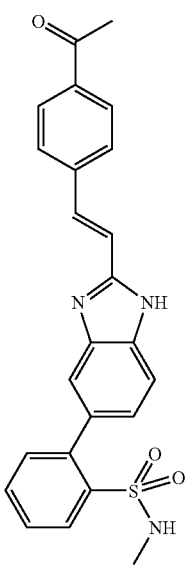
Cpd 457
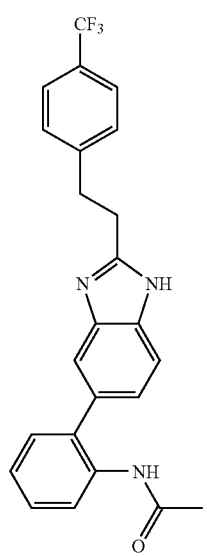
Cpd 458
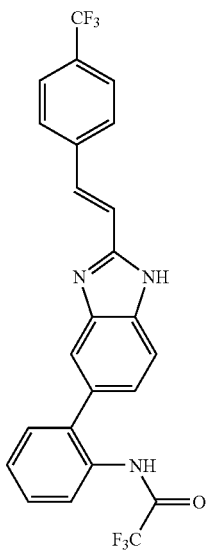

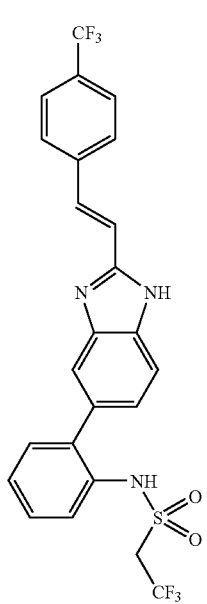
Cpd 459
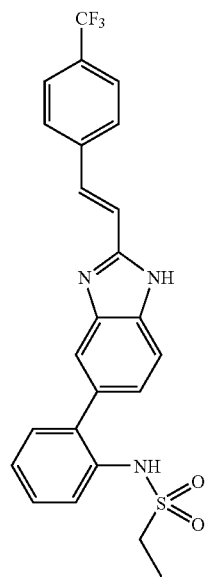
Cpd 461
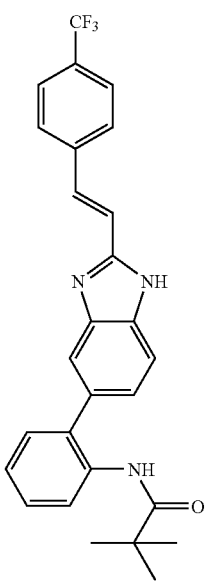
Cpd 460
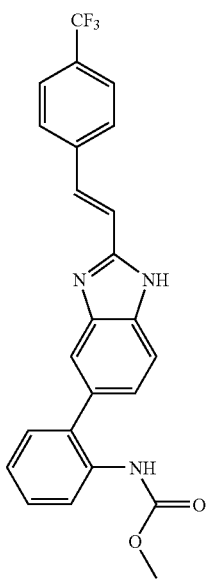
Cpd 462

Cpd 463
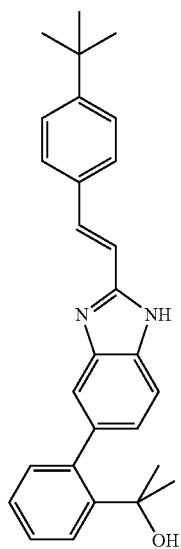
Cpd 464
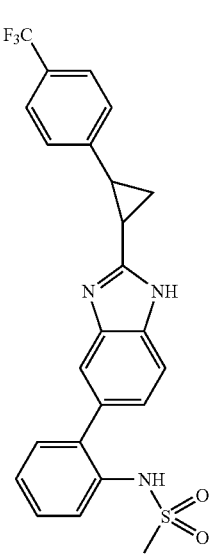
Cpd 465
Cpd 466
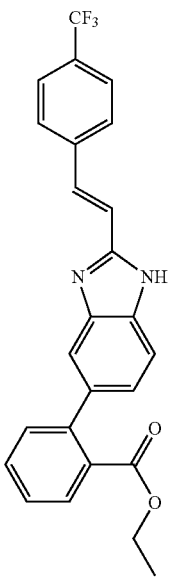
Cpd 467
Cpd 468
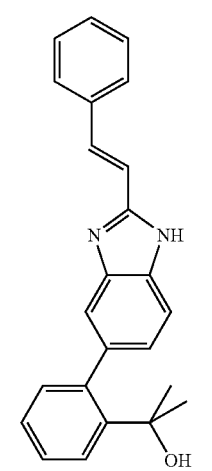

-continued
Cpd 469
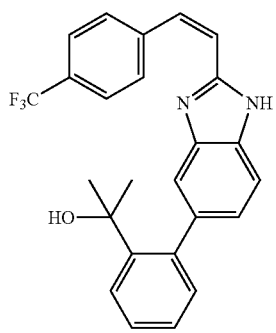
Cpd 470
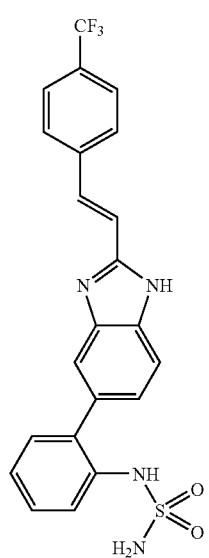
Cpd 471
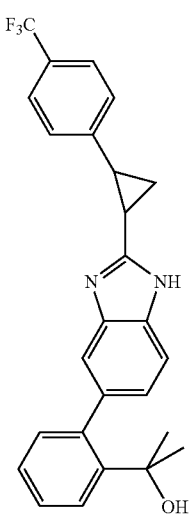
-continued
Cpd 472
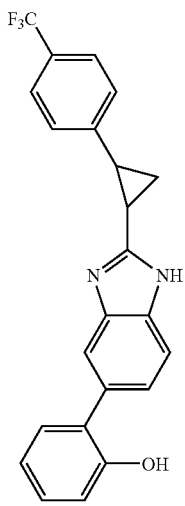
Cpd 473
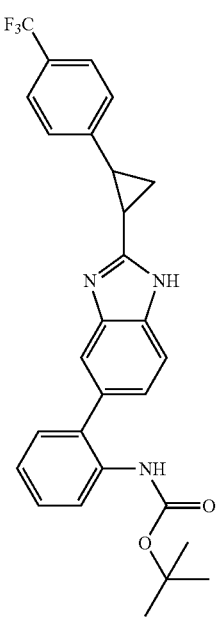
Cpd 474

Cpd 475
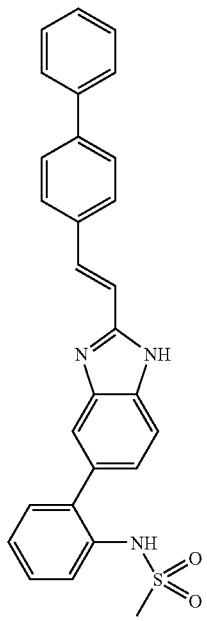
Cpd 476
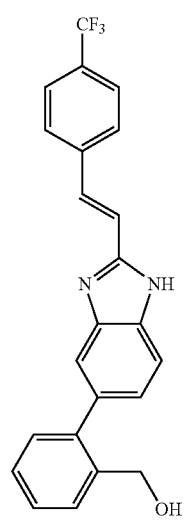
Cpd 477
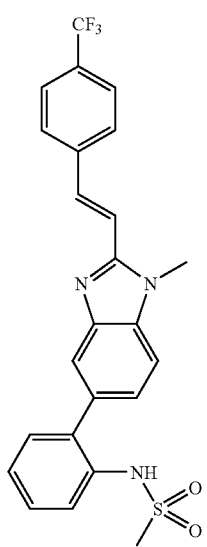
Cpd 478
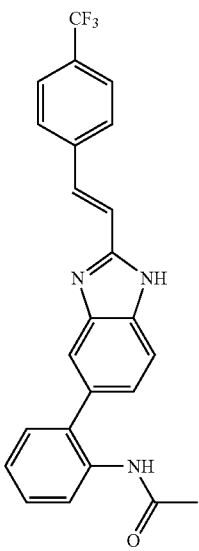
Cpd 479
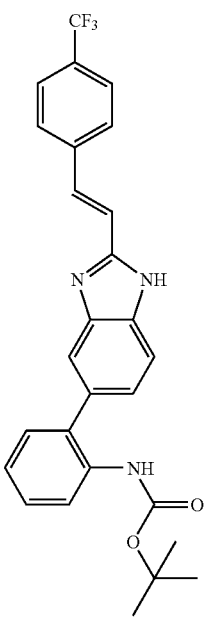
Cpd 480
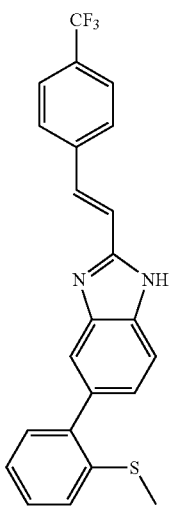

Cpd 481
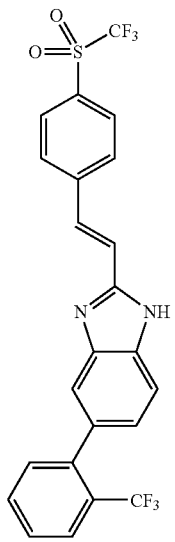
Cpd 482
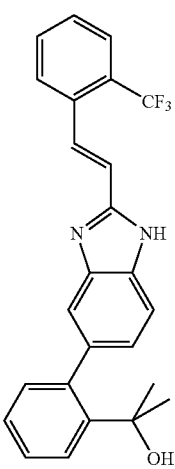
Cpd 483
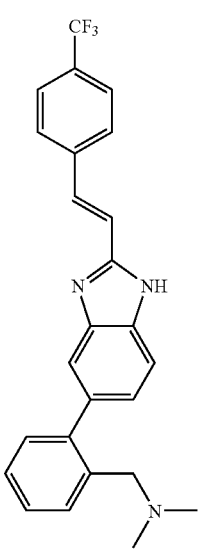
Cpd 484
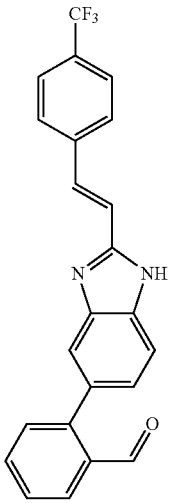
Cpd 485
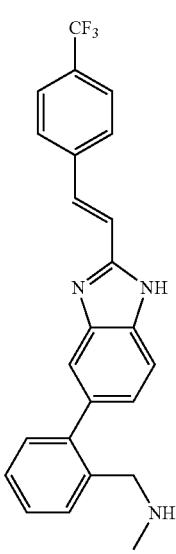
Cpd 486
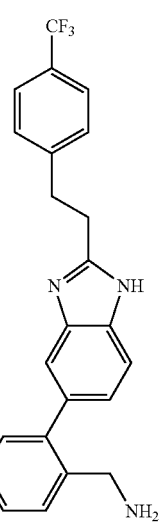

Cpd 487
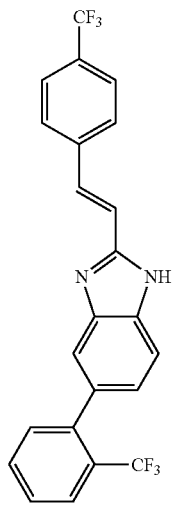
Cpd 488
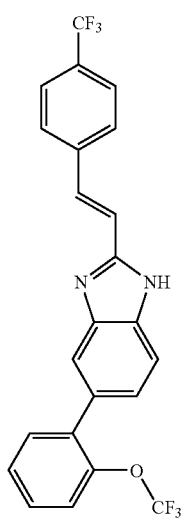
Cpd 489
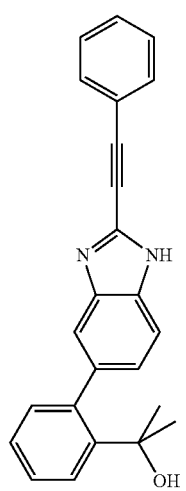
Cpd 490
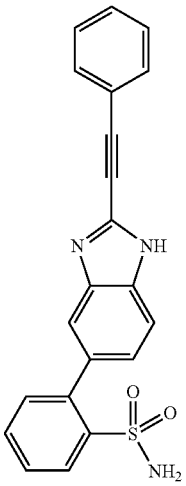
Cpd 491
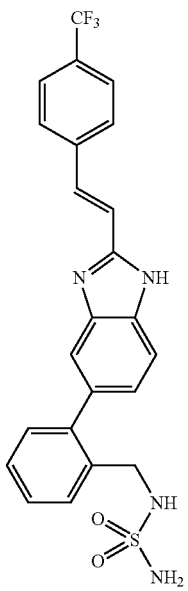
Cpd 492
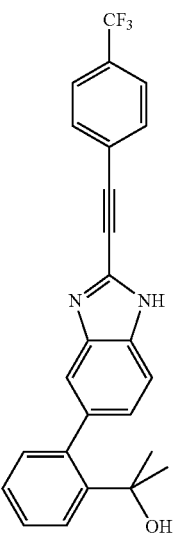

Cpd 494
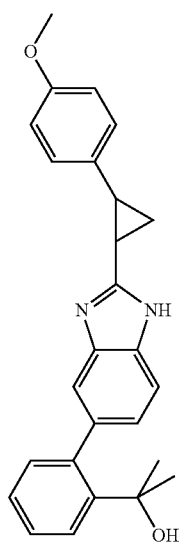
Cpd 497
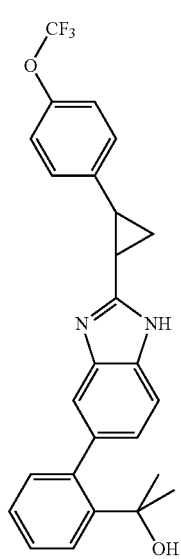
cpd 498
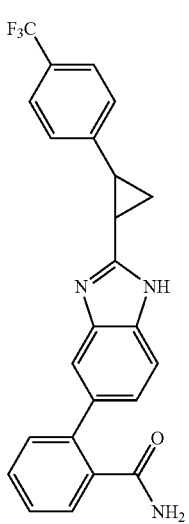
Cpd 499
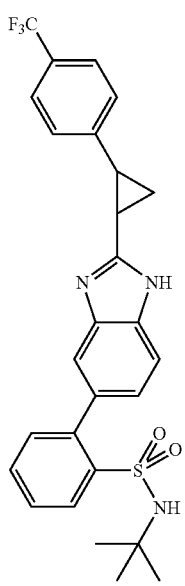
Cpd 500
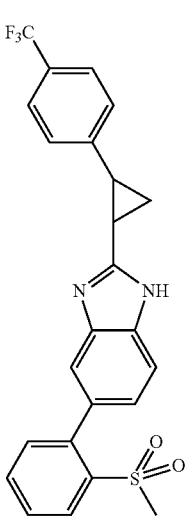
Cpd 501
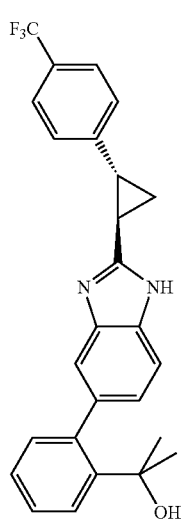

-continued
Cpd 502
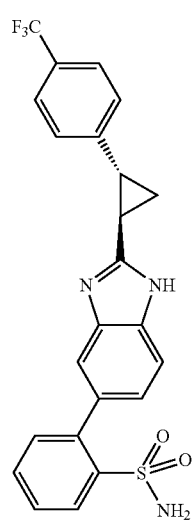
Cpd 503
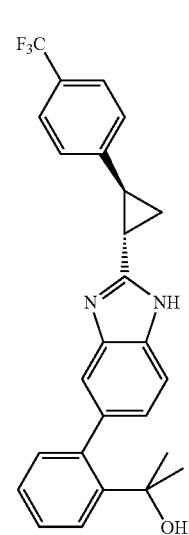
Cpd 504
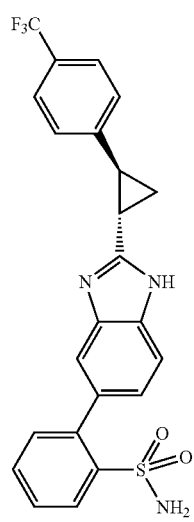
Cpd 505
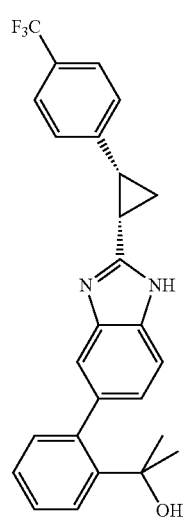
Cpd 506
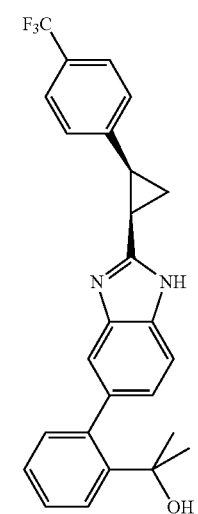
Cpd 507

-continued

Cpd 508

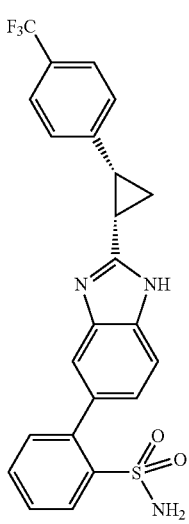

As modulators of the vanilloid VR1 ion channel, the compounds of Formula (I) are useful in methods for treating a VR1 ion channel mediated disease in a subject which disease is affected by the modulation of one or more vanilloid receptors.

Accordingly, the present invention is directed to a method of treating a VR1 ion channel mediated disease in a subject in need thereof comprising administering to the subject an effective amount of a compound of Formula (I) or a salt or solvate thereof.

Compound Forms

The term "form" means, in reference to compounds of the present invention, such may exist as, without limitation, a salt, stereoisomer, tautomer, crystalline, polymorph, amorphous, solvate, hydrate, ester, prodrug or metabolite form. The present invention encompasses all such compound forms and mixtures thereof.

The term "isolated form" means, in reference to compounds of the present invention, that such may exist in an essentially pure state such as, without limitation, an enantiomer, a racemic mixture, a geometric isomer (such as a cis or trans stereoisomer), a mixture of geometric isomers, and the like. The present invention encompasses all such isolated forms and mixtures thereof.

Certain compounds of Formula (I) may exist in various stereoisomeric or tautomeric forms and mixtures thereof. The invention encompasses all such compounds and mixtures thereof.

The compounds of the present invention may be present in the form of pharmaceutically acceptable salts. For use in medicines, the "pharmaceutically acceptable salts" of the compounds of this invention refer to non-toxic acidic/anionic or basic/cationic salt forms.

Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid.

Furthermore when the compounds of the present invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

Thus, representative pharmaceutically acceptable salts include the following: acetate, adipate, benzenesulfonate, benzoate, bicarbonate, bisulfate, bitartrate, borate, bromide, calcium, camsylate (or camphosulphonate), carbonate, chloride, choline, clavulanate, citrate, dihydrochloride, disodium, edetate, fumarate, gluconate, glutamate, hydrabamine, hydrobromine, hydrochloride, iodide, isothionate, lactate, malate, maleate, mandelate, mesylate, nitrate, oleate, pamoate, palmitate, phosphate/diphosphate, salicylate, sodium, stearate, sulfate, succinate, tartrate, tromethane, tosylate, trichloroacetate, trifluoroacetate and the like.

An example of the present invention includes compounds of Formula (I) and a salt form thereof wherein the salt is selected from the group consisting of disodium, hydrochloride and sodium.

The invention includes compounds of various isomers and mixtures thereof. The term "isomer" refers to compounds that have the same composition and molecular weight but differ in physical and/or chemical properties. Such substances have the same number and kind of atoms but differ in structure. The structural difference may be in constitution (geometric isomers) or in an ability to rotate the plane of polarized light (stereoisomers).

The term "optical isomer" means isomers of identical constitution that differ only in the spatial arrangement of their groups. Optical isomers rotate the plane of polarized light in different directions. The term "optical activity" means the degree to which an optical isomer rotates the plane of polarized light.

The term "racemate" or "racemic mixture" means an equimolar mixture of two enantiomeric species, wherein each of the isolated species rotates the plane of polarized light in the opposite direction such that the mixture is devoid of optical activity.

The term "enantiomer" means an isomer having a nonsuperimposable mirror image. The term "diastereomer" means stereoisomers that are not enantiomers.

The term "chiral" means a molecule, which in a given configuration, cannot be superimposed on its mirror image. This is in contrast to achiral molecules, which can be superimposed on their mirror images.

The invention is considered to include the tautomeric forms of all compounds of Formula (I). In addition, for chiral embodiments of the invention, the invention is considered to include pure enantiomers, racemic mixtures, as well as mixtures of enantiomers having 0.001% to 99.99% enantiomeric excess. In addition, some of the compounds represented by Formula (I) may be prodrugs, i.e., derivatives of a drug that possess superior delivery capabilities and therapeutic value as compared to the active drug. Prodrugs are transformed into active drugs by in vivo enzymatic or chemical processes.

The two distinct mirror image versions of the chiral molecule are also known as levo (left-handed), abbreviated L, or dextro (right handed), abbreviated D, depending on which way they rotate polarized light. The symbols "R" and "S" represent the configuration of groups around a stereogenic carbon atom(s).

An example of an enantiomerically enriched form isolated from a racemic mixture includes a dextrorotatory enantiomer, wherein the mixture is substantially free of the levorotatory isomer. In this context, substantially free means the levorotatory isomer may, in a range, comprise less than 25% of the mixture, less than 10%, less than 5%, less than 2% or less than 1% of the mixture according to the formula:

$$\% \text{ levorotatory} = \frac{(\text{mass levorotatory})}{(\text{mass dextrorotatory}) + (\text{mass levorotatory})} \times 100$$

Similarly, an example of an enantiomerically enriched form isolated from a racemic mixture includes a levorotatory enantiomer, wherein the mixture is substantially free of the dextrorotatory isomer. In this context, substantially free means the dextrorotatory isomer may, in a range, comprise less than 25% of the mixture, less than 10%, less than 5%, less than 2% or less than 1% of the mixture according to the formula:

$$\% \text{ dextrorotatory} = \frac{(\text{mass dextrorotatory})}{(\text{mass dextrorotatory}) + (\text{mass levorotatory})} \times 100$$

"Geometric isomer" means isomers that differ in the orientation of substituent atoms in relationship to a carbon-carbon double bond, to a cycloalkyl ring, or to a bridged bicyclic system. Substituent atoms (other than hydrogen) on each side of a carbon-carbon double bond may be in an E or Z configuration. In the "E" configuration, the substituents are on opposite sides in relationship to the carbon-carbon double bond. In the "Z" configuration, the substituents are oriented on the same side in relationship to the carbon-carbon double bond. The scope of the present invention is intended to include all such "E" and "Z" isomers.

Substituent atoms (other than hydrogen) attached to a ring system may be in a cis or trans configuration. In the "cis" configuration, the substituents are on the same side in relationship to the plane of the ring; in the "trans" configuration, the substituents are on opposite sides in relationship to the plane of the ring. Compounds having a mixture of "cis" and "trans" species are designated "cis/trans". The scope of the present invention is intended to include all such "cis" and "trans" isomers.

The isomeric descriptors ("R," "S," "E," and "Z") indicate atom configurations relative to a core molecule and are intended to be used as defined in the literature.

Furthermore, compounds of the present invention may have at least one crystalline, polymorph or amorphous form. The plurality of such forms is included in the scope of the invention. In addition, some of the compounds may form solvates with water (i.e., hydrates) or common organic solvents (e.g., organic esters such as ethanolate and the like). The plurality of such solvates is also intended to be encompassed within the scope of this invention.

Chemical Nomenclature and Definitions

Bond lines drawn into a ring system from a substituent variable indicate that the substituent may be attached to any of the substitutable ring atoms.

As used herein, the following terms are intended to have the following meanings (additional definitions are provided where prophetic throughout the Specification). The definitions herein may specify that a chemical term has an indicated formula. The particular formula provided is not intended to limit the scope of the invention, but is provided as an illustration of the term and is intended to include the plurality of variations expected to be included by one of ordinary skill in the art.

Definitions

The term "$C_{1-6}$alkyl" or "alkyl" means a straight or branched chain hydrocarbon alkyl radical, comprising from 1 to 6 carbon atoms. Non-limiting examples include methyl, ethyl, 1-propyl, 2-propyl, 1-butyl, 2-butyl, tertiary butyl (also referred to as t-butyl or tert-butyl), 1-pentyl, 2-pentyl, 3-pentyl, 1-hexyl, 2-hexyl, 3-hexyl and the like. The term further includes alkyl groups in any combination thereof (e.g. $C_{1-2}$, $C_{1-3}$, $C_{1-4}$ and the like). An alkyl radical may be attached to a core molecule where allowed by available valences.

The terms "$C_{2-3}$alkenyl" and "$C_{2-3}$alkynyl" mean straight or branched carbon chains having 2 to 3 carbon atoms, wherein a $C_{2-3}$alkenyl chain has at least one double bond in the chain and a $C_{2-3}$alkynyl chain has at least one triple bond in the chain. An alkenyl and alkynyl radical may be attached to a core molecule where allowed by available valences.

The term "$C_{1-6}$alkoxy" or "alkoxy" means a straight or branched chain hydrocarbon alkyl radical or alkyldiyl linking group of the formula —O—$C_{1-6}$alkyl, comprising from 1 to 6 carbon atoms. Examples include methoxy, ethoxy, propoxy, isopropoxy, butoxy and the like. The term further includes alkoxy groups in any combination thereof (e.g. $C_{1-2}$, $C_{1-3}$, $C_{1-4}$ and the like). An alkoxy radical may be attached to a core molecule where allowed by available valences.

The term "cycloalkyl" refers to a saturated or partially unsaturated, monocyclic, polycyclic or benzofused hydrocarbon ring system composed of from 3 to 14 carbon atoms. Except when specified, the term includes a $C_{3-8}$cycloalkyl, $C_{3-10}$cycloalkyl, $C_{5-6}$cycloalkyl, $C_{5-8}$cycloalkyl, $C_{5-12}$cycloalkyl, $C_{8-10}$cycloalkyl, $C_{9-13}$cycloalkyl, $C_{3-14}$cycloalkyl or benzofused $C_{3-14}$cycloalkyl ring system. Examples include cyclopropyl, cyclobutyl, cyclopentyl, cyclohexyl, cyclohexenyl, cycloheptyl, cyclooctyl, 1H-indenyl, indanyl, adamantanyl, 9H-fluorenyl, 1,2,3,4-tetrahydro-naphthalenyl, acenaphthenyl, bicyclo[2.2.1]heptenyl and the like. $C_{3-14}$cycloalkyl radicals may be attached to a core molecule and further substituted on any atom when allowed by available valences.

The term "benzofused," used as a prefix for a ring system, means a radical formed by any ring system radical fused with a benzene ring. The benzofused radical may be attached to a core molecule via either ring of the bicyclic system and further substituted on any atom where allowed by available valences.

The term "aryl" refers to monocyclic or bicyclic aromatic ring systems containing from 6 to 12 carbons in the ring. Examples include phenyl, biphenyl, naphthalene, azulenyl, anthracenyl and the like. Aryl radicals may be attached to a core molecule and further substituted on any atom when allowed by available valences.

The term "aromatic" refers to a cycloalkylic hydrocarbon ring system having an unsaturated, conjugated π electron system.

The term "hetero," used as a prefix for a ring system, refers to the replacement of at least one ring carbon atom with one or more heteroatoms independently selected from a nitrogen, oxygen or sulfur atom, wherein the nitrogen and sulfur atoms can exist in any allowed oxidation state. Examples include rings wherein 1, 2, 3 or 4 ring members are a nitrogen atom; or, 0, 1, 2 or 3 ring members are nitrogen atoms and 1 member is an oxygen or sulfur atom. When allowed by available valences, up to two adjacent ring members may be heteroatoms; wherein one heteroatom is nitrogen and the other is one heteroatom selected from N, S or O.

The term "heterocyclyl" refers to a nonaromatic (i.e. saturated or partially unsaturated) monocyclic, polycyclic or benzofused ring system radical. Heteroatom ring members are selected from at least one of N, O, S, S(O) or $SO_2$, wherein the nitrogen and sulfur atoms can exist in any allowed oxidation state. Examples include 2H-pyrrole, 2-pyrrolinyl, 3-pyrrolinyl, pyrrolidinyl, 2-imidazolinyl (also referred to as 4,5-dihydro-1H-imidazolyl), imidazolidinyl, 2-pyrazolinyl, pyrazolidinyl, oxazolidinyl, tetrazolinyl, tetrazolidinyl, piperidinyl, morpholinyl, 1,4-dithianyl, thiomorpholinyl, piperazinyl, azetidinyl, azepanyl, dihydro-pyranyl, tetrahydro-furanyl, tetrahydro-thienyl, tetrahydro-pyranyl, tetrahydro-pyridazinyl, hexahydro-1,4-diazepinyl, hexahydro-1,4-oxazepanyl, 1,3-dioxolanyl, 1,4-dioxanyl, 1,3-benzodioxolyl (also referred to as benzo[1,3]dioxolyl), 2,3-dihydro-1,4-benzodioxinyl (also referred to as 2,3-dihydro-benzo[1,4]dioxinyl) and the like. Heterocyclyl radicals may be attached to a core molecule and further substituted on any atom when allowed by available valences.

The term "heteroaryl" means an aromatic monocyclic, polycyclic or benzofused ring system radical. Heteroatom ring members are selected from at least one of N, O, S, S(O) or $SO_2$, wherein the nitrogen and sulfur atoms can exist in any allowed oxidation state.

Examples include furanyl, thienyl, pyrrolyl, pyrazolyl, 1H-imidazolyl, isothiazolyl, isoxazolyl, oxazolyl, thiazolyl, oxadiazolyl, triazolyl, thiadiazolyl, 1H-tetrazolyl, 2H-tetrazolyl, 1H-[1,2,3]triazolyl, 2H-[1,2,3]triazolyl, 4H-[1,2,4]triazolyl, indazolyl, azaindazolyl, isoindolyl, benzofuranyl, benzothienyl, benzimidazolyl, benzothiazolyl, benzoxazolyl, benzoisoxazolyl, benzothiadiazolyl, benzotriazolyl, purinyl, 4H-quinolizinyl, quinolinyl, isoquinolinyl, cinnolinyl, phthalzinyl, quinazolinyl, quinoxalinyl, 1,8-naphthyridinyl, pteridinyl and the like. Heteroaryl radicals may be attached to a core molecule and further substituted on any atom when allowed by available valences.

The term "$C_{1-6}$alkoxy-$C_{1-6}$alkyl" means a radical of the formula: —$C_{1-6}$alkyl-O—$C_{1-6}$alkyl.

The term "$C_{1-6}$alkoxycarbonyl" means a radical of the formula: —C(O)—O—$C_{1-6}$alkyl. Examples include $C_{1-4}$alkoxycarbonyl.

The term "$C_{1-6}$alkoxycarbonylamino" means a radical of the formula: —NH—C(O)—O—$C_{1-6}$alkyl. Examples include $C_{1-4}$alkylcarbonylamino.

The term "($C_{1-6}$alkyl)$_{1-2}$amino" means a radical of the formula: —NH—$C_{1-6}$alkyl or —N($C_{1-6}$alkyl)$_2$. Examples include ($C_{1-4}$alkyl)$_{1-2}$amino.

The term "($C_{1-6}$alkyl)$_{1-2}$amino-$C_{1-6}$alkyl" means a radical of the formula: —$C_{1-6}$alkyl-NH—$C_{1-6}$alkyl or —$C_{1-6}$alkyl-N($C_{1-6}$alkyl)$_2$. Examples include ($C_{1-4}$alkyl)$_{1-2}$amino-$C_{1-6}$alkyl.

The term "($C_{1-6}$alkyl)$_{1-2}$aminocarbonyl" means a radical of the formula: —C(O)—NH—$C_{1-6}$alkyl or —C(O)—N($C_{1-6}$alkyl)$_2$. Examples include ($C_{1-4}$alkyl)$_{1-2}$aminocarbonyl.

The term "($C_{1-6}$alkyl)$_{1-2}$aminocarbonylamino" means a radical of the formula: —NH—C(O)—NH—$C_{1-6}$alkyl or —NH—C(O)—N($C_{1-6}$alkyl)$_2$. Examples include ($C_{1-4}$alkyl)$_{1-2}$aminocarbonylamino.

The term "($C_{1-4}$alkyl)$_{1-2}$aminosulfonyl" means a radical of the formula: —$SO_2$—NH—$C_{1-4}$alkyl or —$SO_2$—N($C_{1-4}$alkyl)$_2$.

The term "$C_{1-6}$alkylcarbonyl" means a radical of the formula: —C(O)—$C_{1-6}$alkyl. Examples include $C_{1-4}$alkylcarbonyl.

The term "$C_{1-6}$alkylcarbonylamino" means a radical of the formula: —NH—C(O)—$C_{1-6}$alkyl. Examples include $C_{1-4}$alkylcarbonylamino.

The term "$C_{1-6}$alkylsulfonyl" means a radical of the formula: —$SO_2$—$C_{1-6}$alkyl. Examples include $C_{1-4}$alkylsulfonyl.

The term "$C_{1-6}$alkylsulfinylamino" means a radical of the formula: —NH—S(O)—$C_{1-6}$alkyl.

The term "$C_{1-6}$alkylsulfonylamino" means a radical of the formula: —NH—$SO_2$—$C_{1-6}$alkyl.

The term "$C_{1-6}$alkylthio" means a radical of the formula: —S—$C_{1-6}$alkyl. Examples include $C_{1-4}$alkylthio.

The term "amino" means a radical of the formula: —$NH_2$.

The term "amino-$C_{1-6}$alkyl" means a radical of the formula: —$C_{1-6}$alkyl-$NH_2$.

The term "aminocarbonyl" means a radical of the formula: —C(O)—$NH_2$.

The term "aminocarbonylamino" means a radical of the formula: —NH—C(O)—$NH_2$.

The term "aminosulfonyl" means a radical of the formula: —$SO_2$—$NH_2$.

The term "aminosulfonylamino" means a radical of the formula: —NH—$SO_2$—$NH_2$.

The term "($C_{1-6}$alkyl)$_{1-2}$aminosulfonylamino" means a radical of the formula: —NH—$SO_2$—NH—$C_{1-6}$alkyl or —NH—$SO_2$—N($C_{1-6}$alkyl)$_2$. Examples include ($C_{1-4}$alkyl)$_{1-2}$aminosulfonylamino.

The term "aminosulfonylamino-$C_{1-6}$alkyl" means a radical of the formula: —$C_{1-6}$alkyl-NH—$SO_2$—$NH_2$.

The term "($C_{1-6}$alkyl)$_{1-2}$aminosulfonylamino-$C_{1-6}$alkyl" means a radical of the formula: —$C_{1-6}$alkyl-NH—$SO_2$—NH—$C_{1-6}$alkyl or —$C_{1-6}$alkyl-NH—$SO_2$—N($C_{1-6}$alkyl)$_2$.

The term "carboxy" means a radical of the formula: —C(O)OH.

The term "$C_{3-8}$cycloalkyl-$C_{1-6}$alkyl" means a radical of the formula: —$C_{1-6}$alkyl-$C_{3-8}$cycloalkyl. Examples include $C_{3-8}$cycloalkyl-$C_{1-4}$alkyl.

The term "$C_{3-8}$cycloalkyl-$C_{1-6}$alkoxy" means a radical of the formula: —O—$C_{1-6}$alkyl-$C_{3-8}$cycloalkyl. Examples include $C_{3-8}$cycloalkyl-$C_{1-4}$alkoxy.

The term "$C_{3-8}$cycloalkyl-oxy" means a radical of the formula: —O—$C_{3-8}$cycloalkyl.

The term "($C_{3-8}$cycloalkyl)$_{1-2}$amino" means a radical of the formula: —NH—($C_{3-8}$cycloalkyl) or —N($C_{3-8}$cycloalkyl)$_2$.

The term "($C_{3-8}$cycloalkyl-$C_{1-4}$alkyl)$_{1-2}$amino" means a radical of the formula: —NH—$C_{1-4}$alkyl-$C_{3-8}$cycloalkyl or —N($C_{1-4}$alkyl-$C_{3-8}$cycloalkyl)$_2$.

The term "formyl" means a radical of the formula: —C(O)H.

The term "oxo" means a radical of the formula: =O.

The term "halogen" or "halo" means the group chloro, bromo, fluoro or iodo.

The term "halo$C_{1-6}$alkyl" means a radical of the formula: —$C_{1-6}$alkyl(halo)n, wherein "n" represents that amount of available valences on $C_{1-6}$alkyl, which may be substituted with one or more halogen atoms while remaining stable. Examples include difluoromethyl, trifluoromethyl, trifluoroethyl, chloromethyl and the like.

The term "halo$C_{1-6}$alkoxy" means a radical of the formula: —O—$C_{1-6}$alkyl(halo)$_n$, wherein "n" represents that amount of available valences on $C_{1-6}$alkoxy, which may be substituted with one or more halogen atoms while remaining stable. Examples include difluoromethoxy, trifluoromethoxy, trifluoroethoxy, chloromethoxy and the like.

The term "haloC$_{1-6}$alkylsulfonyl" means a radical of the formula: —SO$_2$—C$_{1-6}$alkyl(halo)n, wherein "n" represents that amount of available valences on C$_{1-6}$alkyl, which may be substituted with one or more halogen atoms while remaining stable. Examples include trifluoromethylsulfonyl and the like.

The term "haloC$_{1-6}$alkylsulfonylamino" means a radical of the formula: —NH—SO$_2$—C$_{1-6}$alkyl(halo)n, wherein "n" represents that amount of available valences on C$_{1-6}$alkyl, which may be substituted with one or more halogen atoms while remaining stable. Examples include trifluoromethylsulfonyl and the like.

The term "haloC$_{1-6}$alkylthio" means a radical of the formula: —S—C$_{1-6}$alkyl(halo)n, wherein "n" represents that amount of available valences on C$_{1-6}$alkyl, which may be substituted with one or more halogen atoms while remaining stable. Examples include trifluoromethylsulfonyl and the like.

The term "perfluorinated" means a radical that is substituted with fluoro atoms to the extent allowed by available valences while remaining stable.

The term "substituted," refers to a core molecule on which one or more hydrogen atoms have been replaced with one or more functional radical moieties. The number that is allowed by available valences limits the amount of substituents. Substitution is not limited to the core molecule, but may also occur on a substituent radical, whereby the substituent radical becomes a linking group.

Therapeutic Use

As modulators of the vanilloid VR1 ion channel, the compounds of Formula (I) are useful in methods for treating a VR1 ion channel mediated disease in a subject which disease is affected by the modulation of one or more vanilloid receptors.

Accordingly, the present invention is directed to a method of treating a VR1 ion channel mediated disease in a subject in need thereof comprising administering to the subject an effective amount of a compound of Formula (I) or a salt or solvate thereof.

The term "VR1 ion channel mediated disease" refers to chronic or acute pain due to disease that causes inflammatory pain, burning pain or post-operative pain.

An example of a use of the compound of Formula (I) or a salt or solvate thereof includes use in the manufacture of a medicament for treating a VR1 ion channel mediated disease, wherein the VR1 ion channel mediated disease is chronic or acute pain due to disease that causes inflammatory pain, burning pain or post-operative pain.

An example of a use of the compound of Formula (I) or a salt or solvate thereof includes use as a medicine for treating a VR1 ion channel mediated disease, wherein the VR1 ion channel mediated disease is chronic or acute pain due to disease that causes inflammatory pain, burning pain or post-operative pain.

The term "prodrug" means a compound of Formula (I) or a form thereof that is converted in vivo into a functional derivative form that may contribute to therapeutic biological activity, wherein the converted form may be: 1) a relatively active form; 2) a relatively inactive form; 3) a relatively less active form; or, 4) any form which results, directly or indirectly, from such in vivo conversions.

Prodrugs are useful when said compound may be either too toxic to administer systemically, absorbed poorly by the digestive tract or broken down by the body before it reaches its target. Conventional procedures for the selection and preparation of suitable prodrug derivatives are described in, for example, "*Design of Prodrugs*", ed. H. Bundgaard, Elsevier, 1985.

The term "metabolite" means a form of a compound of Formula (I) or a form thereof converted by in vivo metabolism or a metabolic process to a derivative of said compound.

The term "subject" as used herein, refers to a patient, such as an animal, a mammal or a human, who has been the object of treatment, observation or experiment and is at risk of (or susceptible to) developing a disease that has or will result in VR1 ion channel mediated chronic or acute pain, wherein the pain caused by the disease is inflammatory pain, burning pain or post-operative pain.

The term "effective amount" refers to that amount of a compound of Formula (I) or a form, pharmaceutical composition, medicine or medicament thereof that elicits the biological or medicinal response (such as inhibiting, preventing or ameliorating VR1 ion channel mediated chronic or acute pain) in a tissue system, animal or human, that is being sought by a researcher, veterinarian, medical doctor, or other clinician, which includes alleviation of the symptoms of the inflammatory pain, burning pain or post-operative pain being treated.

The effective amount of a compound of Formula (I) or a form thereof is from about 0.001 mg/kg/day to about 300 mg/kg/day.

The term "pharmaceutical composition" refers to a product containing a compound of Formula (I) or a form thereof, such as a product comprising the specified ingredients in the specified amounts, as well as any product that results, directly or indirectly, from such combinations of the specified ingredients in the specified amounts.

The term "medicament" or "medicine" refers to a product containing a compound of Formula (I) or a form thereof. The present invention includes use of such a medicament for treating VR1 ion channel mediated chronic or acute pain.

The term "pharmaceutically acceptable" refers to molecular entities and compositions that are of sufficient purity and quality for use in the formulation of a pharmaceutical composition, medicine or medicament of the present invention. Since both human use (clinical and over-the-counter) and veterinary use are equally included within the scope of the present invention, a pharmaceutically acceptable formulation would include a pharmaceutical composition, medicine or medicament for either human or veterinary use.

The term "treating" refers, without limitation, inhibiting, ameliorating, facilitating the eradication of, inhibiting the progression of or promoting the stasis of VR1 ion channel mediated chronic or acute pain.

For oral administration, the pharmaceutical composition, medicine or medicament is preferably in the form of a tablet containing, e.g., 0.01, 0.05, 0.1, 0.5, 1.0, 2.5, 5.0, 10.0, 15.0, 25.0, 50.0, 100, 150, 200, 250 and 500 milligrams of a compound of formula (I) or a form thereof for the symptomatic adjustment of the dosage to the patient to be treated. Optimal dosages will vary depending on factors associated with the particular patient being treated (e.g., age, weight, diet and time of administration), the severity of the condition being treated, the particular compound being used, the mode of administration and the strength of the preparation. The use of either daily administration or post-periodic dosing may be employed.

A representative compound of Formula (I) or a form thereof includes a compound selected from the group consisting of:

| Cpd | Name |
|---|---|
| 1 | (E)-1-(2-{2-[2-(4-tert-butyl-phenyl)-vinyl]-1H-benzimidazol-5-yl}-phenyl)-ethanone, |
| 2 | (E)-1-(2-{2-[2-(4-tert-butyl-phenyl)-vinyl]-1H-benzimidazol-5-yl}-phenyl)-ethanol, |
| 3 | (E)-2-{2-[2-(4-tert-butyl-phenyl)-vinyl]-1H-benzimidazol-5-yl}-phenol, |
| 4 | (E)-N-(2-{2-[2-(4-tert-butyl-phenyl)-vinyl]-1H-benzimidazol-5-yl}-phenyl)-acetamide, |
| 5 | (E)-2-{2-[2-(4-tert-butyl-phenyl)-vinyl]-1H-benzimidazol-5-yl}-benzamide, |
| 6 | (E)-3-{2-[2-(4-tert-butyl-phenyl)-vinyl]-1H-benzimidazol-5-yl}-benzamide, |
| 7 | (E)-4-{2-[2-(4-tert-butyl-phenyl)-vinyl]-1H-benzimidazol-5-yl}-benzamide, |
| 8 | (E)-N-(4-{2-[2-(4-tert-butyl-phenyl)-vinyl]-1H-benzimidazol-5-yl}-phenyl)-acetamide, |
| 9 | (E)-N-(2-{2-[2-(4-tert-butyl-phenyl)-vinyl]-1H-benzimidazol-5-yl}-phenyl)-methanesulfonamide, |
| 10 | (E)-(2-{2-[2-(4-tert-butyl-phenyl)-vinyl]-1H-benzimidazol-5-yl}-phenyl)-carbamic acid tert-butyl ester, |
| 11 | (E)-2-{2-[2-(4-tert-butyl-phenyl)-vinyl]-1H-benzimidazol-5-yl}-phenylamine, |
| 12 | (E)-(2-{2-[2-(4-tert-butyl-phenyl)-vinyl]-1H-benzimidazol-5-yl}-phenyl)-methanol, |
| 13 | (E)-2-{2-[2-(4-trifluoromethyl-phenyl)-vinyl]-1H-benzimidazol-5-yl}-benzamide, |
| 14 | (E)-2-{2-[2-(4-trifluoromethyl-phenyl)-vinyl]-1H-benzimidazol-5-yl}-phenol, |
| 15 | (E)-1-(2-{2-[2-(4-trifluoromethyl-phenyl)-vinyl]-1H-benzimidazol-5-yl}-phenyl)-ethanone, |
| 16 | (E)-1-(2-{2-[2-(4-trifluoromethyl-phenyl)-vinyl]-1H-benzimidazol-5-yl}-phenyl)-ethanol, |
| 17 | (E)-N-(2-{2-[2-(4-trifluoromethyl-phenyl)-vinyl]-1H-benzimidazol-5-yl}-phenyl)-methanesulfonamide, |
| 18 | (E)-2-(2-{2-[2-(4-trifluoromethyl-phenyl)-vinyl]-1H-benzimidazol-5-yl}-phenyl)-propan-2-ol, |
| 19 | (E)-2-{2-[2-(4-trifluoromethoxy-phenyl)-vinyl]-1H-benzimidazol-5-yl}-benzamide, |
| 20 | (E)-1-(2-{2-[2-(4-trifluoromethoxy-phenyl)-vinyl]-1H-benzimidazol-5-yl}-phenyl)-ethanone, |
| 21 | (E)-1-(2-{2-[2-(4-trifluoromethoxy-phenyl)-vinyl]-1H-benzimidazol-5-yl}-phenyl)-ethanol, |
| 22 | (E)-N-(2-{2-[2-(4-trifluoromethoxy-phenyl)-vinyl]-1H-benzimidazol-5-yl}-phenyl)-methanesulfonamide, |
| 23 | (E)-2-(2-{2-[2-(4-trifluoromethoxy-phenyl)-vinyl]-1H-benzimidazol-5-yl}-phenyl)-propan-2-ol, |
| 24 | (E)-N-(2-{2-[2-(3,4-difluoro-phenyl)-vinyl]-1H-benzimidazol-5-yl}-phenyl)-acetamide, |
| 25 | (E)-N-(3-{2-[2-(3,4-difluoro-phenyl)-vinyl]-1H-benzimidazol-5-yl}-phenyl)-acetamide, |
| 26 | (E)-2-{2-[2-(3,4-difluoro-phenyl)-vinyl]-1H-benzimidazol-5-yl}-benzamide, |
| 27 | (E)-1-(2-{2-[2-(3,4-difluoro-phenyl)-vinyl]-1H-benzimidazol-5-yl}-phenyl)-ethanone, |
| 28 | (E)-N-(2-{2-[2-(3,4-difluoro-phenyl)-vinyl]-1H-benzimidazol-5-yl}-phenyl)-methanesulfonamide, |
| 29 | 2-{2-[3-(4-tert-butyl-phenyl)-propyl]-1H-benzimidazol-5-yl}-phenol, |
| 30 | 2-[3-(4-tert-butyl-phenyl)-propyl]-5-m-tolyl-1H-benzimidazole, |
| 31 | N-(2-{2-[2-(4-trifluoromethyl-phenyl)-ethyl]-1H-benzimidazol-5-yl}-phenyl)-methanesulfonamide, |
| 32 | 2-{2-[2-(4-tert-butyl-phenyl)-ethyl]-1H-benzimidazol-5-yl}-phenol, |
| 33 | 3-{2-[2-(4-tert-butyl-phenyl)-ethyl]-1H-benzimidazol-5-yl}-phenol, |
| 34 | 4-{2-[2-(4-tert-butyl-phenyl)-ethyl]-1H-benzimidazol-5-yl}-phenol, |
| 35 | (E)-(2-{2-[2-(4-trifluoromethylsulfanyl-phenyl)-vinyl]-1H-benzimidazol-5-yl}-phenyl)-methanol, |
| 36 | (E)-2-{2-[2-(4-trifluoromethylsulfanyl-phenyl)-vinyl]-1H-benzimidazol-5-yl}-phenol, |
| 37 | (E)-N-(2-{2-[2-(4-trifluoromethylsulfanyl-phenyl)-vinyl]-1H-benzimidazol-5-yl}-phenyl)-acetamide, |
| 38 | (E)-2-{2-[2-(4-trifluoromethylsulfanyl-phenyl)-vinyl]-1H-benzimidazol-5-yl}-benzamide, |
| 39 | (E)-1-(2-{2-[2-(4-trifluoromethylsulfanyl-phenyl)-vinyl]-1H-benzimidazol-5-yl}-phenyl)-ethanone, |
| 40 | (E)-1-(2-{2-[2-(4-trifluoromethanesulfonyl-phenyl)-vinyl]-1H-benzimidazol-5-yl}-phenyl)-ethanone, |
| 41 | (E)-2-{2-[2-(4-trifluoromethanesulfonyl-phenyl)-vinyl]-1H-benzimidazol-5-yl}-phenol, |
| 42 | (E)-(2-{2-[2-(4-trifluoromethanesulfonyl-phenyl)-vinyl]-1H-benzimidazol-5-yl}-phenyl)-methanol, |
| 43 | (E)-N-(2-{2-[2-(4-trifluoromethanesulfonyl-phenyl)-vinyl]-1H-benzimidazol-5-yl}-phenyl)-acetamide, |
| 44 | (E)-2-{2-[2-(4-trifluoromethanesulfonyl-phenyl)-vinyl]-1H-benzimidazol-5-yl}-benzamide, |
| 45 | (E)-1-(2-{2-[2-(4-trifluoromethanesulfonyl-phenyl)-vinyl]-1H-benzimidazol-5-yl}-phenyl)-ethanol, |

-continued

| Cpd | Name |
|---|---|
| 46 | 1-(2-{2-[2-(4-trifluoromethanesulfonyl-phenyl)-ethyl]-1H-benzimidazol-5-yl}-phenyl)-ethanol, |
| 47 | (E)-2-(2-{2-[2-(4-trifluoromethanesulfonyl-phenyl)-vinyl]-1H-benzimidazol-5-yl}-phenyl)-propan-2-ol, |
| 48 | (E)-2-{2-[2-(4-tert-butyl-phenyl)-vinyl]-6-trifluoromethyl-1H-benzimidazol-5-yl}-phenol, |
| 49 | (E)-3-{2-[2-(4-tert-butyl-phenyl)-vinyl]-6-trifluoromethyl-1H-benzimidazol-5-yl}-phenol, |
| 50 | (E)-N-(2-{2-[2-(4-tert-butyl-phenyl)-vinyl]-6-trifluoromethyl-1H-benzimidazol-5-yl}-phenyl)-acetamide, |
| 51 | (E)-(2-{2-[2-(4-tert-butyl-phenyl)-vinyl]-6-trifluoromethyl-1H-benzimidazol-5-yl}-phenyl)-methanol, |
| 52 | (E)-2-[2-(4-tert-butyl-phenyl)-vinyl]-5-(2-fluoro-phenyl)-6-trifluoromethyl-1H-benzimidazole, |
| 53 | (E)-2-{2-[2-(4-tert-butyl-phenyl)-vinyl]-6-trifluoromethyl-1H-benzimidazol-5-yl}-benzamide, |
| 54 | (E)-(2-{2-[2-(4-tert-butyl-phenyl)-vinyl]-6-trifluoromethyl-1H-benzimidazol-5-yl}-phenyl)-carbamic acid tert-butyl ester, |
| 55 | (E)-N-(2-{2-[2-(4-tert-butyl-phenyl)-vinyl]-6-trifluoromethyl-1H-benzimidazol-5-yl}-phenyl)-methanesulfonamide, |
| 56 | (E)-N-(2-{6-trifluoromethyl-2-[2-(4-trifluoromethyl-phenyl)-vinyl]-1H-benzimidazol-5-yl}-phenyl)-acetamide, |
| 57 | (E)-1-(2-{6-trifluoromethyl-2-[2-(4-trifluoromethyl-phenyl)-vinyl]-1H-benzimidazol-5-yl}-phenyl)-ethanone, |
| 58 | (E)-(2-{6-trifluoromethyl-2-[2-(4-trifluoromethyl-phenyl)-vinyl]-1H-benzimidazol-5-yl}-phenyl)-methanol, |
| 59 | (E)-2-{6-fluoro-2-[2-(4-trifluoromethyl-phenyl)-vinyl]-1H-benzimidazol-5-yl}-phenol, |
| 60 | (E)-3-{6-fluoro-2-[2-(4-trifluoromethyl-phenyl)-vinyl]-1H-benzimidazol-5-yl}-phenol, |
| 61 | (E)-(2-{6-fluoro-2-[2-(4-trifluoromethyl-phenyl)-vinyl]-1H-benzimidazol-5-yl}-phenyl)-methanol, |
| 62 | (E)-1-(2-{6-fluoro-2-[2-(4-trifluoromethyl-phenyl)-vinyl]-1H-benzimidazol-5-yl}-phenyl)-ethanone, |
| 63 | (E)-2-{6-fluoro-2-[2-(4-trifluoromethyl-phenyl)-vinyl]-1H-benzimidazol-5-yl}-benzamide, |
| 64 | (E)-N-(2-{6-fluoro-2-[2-(4-trifluoromethyl-phenyl)-vinyl]-1H-benzimidazol-5-yl}-phenyl)-acetamide, |
| 65 | (E)-N-(2-{6-fluoro-2-[2-(4-trifluoromethyl-phenyl)-vinyl]-1H-benzimidazol-5-yl}-phenyl)-methanesulfonamide, |
| 66 | (E)-(2-{6-chloro-2-[2-(4-trifluoromethyl-phenyl)-vinyl]-1H-benzimidazol-5-yl}-phenyl)-methanol, |
| 67 | (E)-1-(2-{6-chloro-2-[2-(4-trifluoromethyl-phenyl)-vinyl]-1H-benzimidazol-5-yl}-phenyl)-ethanone, |
| 68 | (E)-2-{6-chloro-2-[2-(4-trifluoromethyl-phenyl)-vinyl]-1H-benzimidazol-5-yl}-phenol, |
| 69 | (E)-2-{2-[2-(4-trifluoromethoxy-phenyl)-vinyl]-1H-benzimidazol-5-yl}-benzenesulfonamide, |
| 70 | (E)-2-{2-[2-(4-trifluoromethyl-phenyl)-vinyl]-1H-benzimidazol-5-yl}-benzenesulfonamide, |
| 71 | (E)-2-{2-[2-(4-trifluoromethanesulfonyl-phenyl)-vinyl]-1H-benzimidazol-5-yl}-benzenesulfonamide, |
| 72 | (E)-C,C,C-trifluoro-N-(2-{2-[2-(4-trifluoromethoxy-phenyl)-vinyl]-1H-benzimidazol-5-yl}-phenyl)-methanesulfonamide, |
| 73 | (E)-C,C,C-trifluoro-N-(2-{2-[2-(4-trifluoromethyl-phenyl)-vinyl]-1H-benzimidazol-5-yl}-phenyl)-methanesulfonamide, |
| 74 | (E)-C,C,C-trifluoro-N-(2-{2-[2-(4-trifluoromethanesulfonyl-phenyl)-vinyl]-1H-benzimidazol-5-yl}-phenyl)-methanesulfonamide, |
| 75 | (E)-1-(2-{2-[2-(4-chloro-phenyl)-vinyl]-1H-benzimidazol-5-yl}-phenyl)-ethanone, |
| 76 | (E)-1-(2-{2-[2-(4-chloro-phenyl)-vinyl]-1H-benzimidazol-5-yl}-phenyl)-ethanol, |
| 77 | (E)-N-(2-{2-[2-(4-chloro-phenyl)-vinyl]-1H-benzimidazol-5-yl}-phenyl)-methanesulfonamide, |
| 78 | (E)-2-(2-{2-[2-(4-chloro-phenyl)-vinyl]-1H-benzimidazol-5-yl}-phenyl)-propan-2-ol, |
| 79 | (E)-2-{2-[2-(4-chloro-phenyl)-vinyl]-1H-benzimidazol-5-yl}-benzenesulfonamide, |
| 80 | (E)-N-(2-{2-[2-(4-chloro-phenyl)-vinyl]-1H-benzimidazol-5-yl}-phenyl)-C,C,C-trifluoro-methanesulfonamide, |
| 81 | (E)-1-(2-{2-[2-(4-methanesulfonyl-phenyl)-vinyl]-1H-benzimidazol-5-yl}-phenyl)-ethanone, |
| 82 | (E)-1-(2-{2-[2-(4-methanesulfonyl-phenyl)-vinyl]-1H-benzimidazol-5-yl}-phenyl)-ethanol, |
| 83 | (E)-N-(2-{2-[2-(4-methanesulfonyl-phenyl)-vinyl]-1H-benzimidazol-5-yl}-phenyl)-methanesulfonamide, |
| 84 | (E)-2-(2-{2-[2-(4-methanesulfonyl-phenyl)-vinyl]-1H-benzimidazol-5-yl}-phenyl)-propan-2-ol, |

-continued

| Cpd | Name |
|---|---|
| 85 | (E)-2-{2-[2-(4-methanesulfonyl-phenyl)-vinyl]-1H-benzimidazol-5-yl}-benzenesulfonamide, |
| 86 | (E)-C,C,C-trifluoro-N-(2-{2-[2-(4-methanesulfonyl-phenyl)-vinyl]-1H-benzimidazol-5-yl}-phenyl)-methanesulfonamide, |
| 87 | (E)-1-[2-(2-{2-[4-(2,2,2-trifluoro-1-trifluoromethyl-ethoxy)-phenyl]-vinyl}-1H-benzimidazol-5-yl)-phenyl]-ethanone, |
| 88 | (E)-1-[2-(2-{2-[4-(2,2,2-trifluoro-1-trifluoromethyl-ethoxy)-phenyl]-vinyl}-1H-benzimidazol-5-yl)-phenyl]-ethanol, |
| 89 | (E)-N-[2-(2-{2-[4-(2,2,2-trifluoro-1-trifluoromethyl-ethoxy)-phenyl]-vinyl}-1H-benzimidazol-5-yl)-phenyl]-methanesulfonamide, |
| 90 | (E)-2-[2-(2-{2-[4-(2,2,2-trifluoro-1-trifluoromethyl-ethoxy)-phenyl]-vinyl}-1H-benzimidazol-5-yl)-phenyl]-propan-2-ol, |
| 91 | (E)-2-(2-{2-[4-(2,2,2-trifluoro-1-trifluoromethyl-ethoxy)-phenyl]-vinyl}-1H-benzimidazol-5-yl)-benzenesulfonamide, |
| 92 | (E)-C,C,C-trifluoro-N-[2-(2-{2-[4-(2,2,2-trifluoro-1-trifluoromethyl-ethoxy)-phenyl]-vinyl}-1H-benzimidazol-5-yl)-phenyl]-methanesulfonamide, |
| 93 | (E)-1-[2-(2-{2-[4-(2,2,2-trifluoro-ethoxy)-phenyl]-vinyl}-1H-benzimidazol-5-yl)-phenyl]-ethanone, |
| 94 | (E)-1-[2-(2-{2-[4-(2,2,2-trifluoro-ethoxy)-phenyl]-vinyl}-1H-benzimidazol-5-yl)-phenyl]-ethanol, |
| 95 | (E)-N-[2-(2-{2-[4-(2,2,2-trifluoro-ethoxy)-phenyl]-vinyl}-1H-benzimidazol-5-yl)-phenyl]-methanesulfonamide, |
| 96 | (E)-2-[2-(2-{2-[4-(2,2,2-trifluoro-ethoxy)-phenyl]-vinyl}-1H-benzimidazol-5-yl)-phenyl]-propan-2-ol, |
| 97 | (E)-2-(2-{2-[4-(2,2,2-trifluoro-ethoxy)-phenyl]-vinyl}-1H-benzimidazol-5-yl)-benzenesulfonamide, |
| 98 | (E)-C,C,C-trifluoro-N-[2-(2-{2-[4-(2,2,2-trifluoro-ethoxy)-phenyl]-vinyl}-1H-benzimidazol-5-yl)-phenyl]-methanesulfonamide, |
| 99 | (E)-1-[2-(2-{2-[4-(2,2,3,3,3-pentafluoro-propoxy)-phenyl]-vinyl}-1H-benzimidazol-5-yl)-phenyl]-ethanone, |
| 100 | (E)-1-[2-(2-{2-[4-(2,2,3,3,3-pentafluoro-propoxy)-phenyl]-vinyl}-1H-benzimidazol-5-yl)-phenyl]-ethanol, |
| 101 | (E)-N-[2-(2-{2-[4-(2,2,3,3,3-pentafluoro-propoxy)-phenyl]-vinyl}-1H-benzimidazol-5-yl)-phenyl]-methanesulfonamide, |
| 102 | (E)-2-[2-(2-{2-[4-(2,2,3,3,3-pentafluoro-propoxy)-phenyl]-vinyl}-1H-benzimidazol-5-yl)-phenyl]-propan-2-ol, |
| 103 | (E)-2-(2-{2-[4-(2,2,3,3,3-pentafluoro-propoxy)-phenyl]-vinyl}-1H-benzimidazol-5-yl)-benzenesulfonamide, |
| 104 | (E)-C,C,C-trifluoro-N-[2-(2-{2-[4-(2,2,3,3,3-pentafluoro-propoxy)-phenyl]-vinyl}-1H-benzimidazol-5-yl)-phenyl]-methanesulfonamide, |
| 105 | (E)-1-(2-{2-[2-(3-chloro-phenyl)-vinyl]-1H-benzimidazol-5-yl}-phenyl)-ethanone, |
| 106 | (E)-1-(2-{2-[2-(3-chloro-phenyl)-vinyl]-1H-benzimidazol-5-yl}-phenyl)-ethanol, |
| 107 | (E)-N-(2-{2-[2-(3-chloro-phenyl)-vinyl]-1H-benzimidazol-5-yl}-phenyl)-methanesulfonamide, |
| 108 | (E)-2-(2-{2-[2-(3-chloro-phenyl)-vinyl]-1H-benzimidazol-5-yl}-phenyl)-propan-2-ol, |
| 109 | (E)-2-{2-[2-(3-chloro-phenyl)-vinyl]-1H-benzimidazol-5-yl}-benzenesulfonamide, |
| 110 | (E)-N-(2-{2-[2-(3-chloro-phenyl)-vinyl]-1H-benzimidazol-5-yl}-phenyl)-C,C,C-trifluoro-methanesulfonamide, |
| 111 | (E)-1-(2-{2-[2-(3-trifluoromethyl-phenyl)-vinyl]-1H-benzimidazol-5-yl}-phenyl)-ethanone, |
| 112 | (E)-1-(2-{2-[2-(3-trifluoromethyl-phenyl)-vinyl]-1H-benzimidazol-5-yl}-phenyl)-ethanol, |
| 113 | (E)-N-(2-{2-[2-(3-trifluoromethyl-phenyl)-vinyl]-1H-benzimidazol-5-yl}-phenyl)-methanesulfonamide, |
| 114 | (E)-2-(2-{2-[2-(3-trifluoromethyl-phenyl)-vinyl]-1H-benzimidazol-5-yl}-phenyl)-propan-2-ol, |
| 115 | (E)-2-{2-[2-(3-trifluoromethyl-phenyl)-vinyl]-1H-benzimidazol-5-yl}-benzenesulfonamide, |
| 116 | (E)-C,C,C-trifluoro-N-(2-{2-[2-(3-trifluoromethyl-phenyl)-vinyl]-1H-benzimidazol-5-yl}-phenyl)-methanesulfonamide, |
| 117 | (E)-N-(4-{2-[5-(2-acetyl-phenyl)-1H-benzimidazol-2-yl]-vinyl}-phenyl)-methanesulfonamide, |
| 118 | (E)-N-[4-(2-{5-[2-(1-hydroxy-ethyl)-phenyl]-1H-benzimidazol-2-yl}-vinyl)-phenyl]-methanesulfonamide, |
| 119 | (E)-N-(2-{2-[2-(4-methanesulfonylamino-phenyl)-vinyl]-1H-benzimidazol-5-yl}-phenyl)-methanesulfonamide, |
| 120 | (E)-N-[4-(2-{5-[2-(1-hydroxy-1-methyl-ethyl)-phenyl]-1H-benzimidazol-2-yl}-vinyl)-phenyl]-methanesulfonamide, |
| 121 | (E)-2-{2-[2-(4-methanesulfonylamino-phenyl)-vinyl]-1H-benzimidazol-5-yl}-benzenesulfonamide, |
| 122 | (E)-C,C,C-trifluoro-N-(2-{2-[2-(4-methanesulfonylamino-phenyl)-vinyl]-1H-benzimidazol-5-yl}-phenyl)-methanesulfonamide, |
| 123 | (E)-N-(4-{2-[5-(2-acetyl-phenyl)-1H-benzimidazol-2-yl]-vinyl}-phenyl)-C,C,C-trifluoro-methanesulfonamide, |

-continued

| Cpd | Name |
|---|---|
| 124 | (E)-C,C,C-trifluoro-N-[4-(2-{5-[2-(1-hydroxy-ethyl)-phenyl]-1H-benzimidazol-2-yl}-vinyl)-phenyl]-methanesulfonamide, |
| 125 | (E)-C,C,C-trifluoro-N-(4-{2-[5-(2-methanesulfonylamino-phenyl)-1H-benzimidazol-2-yl]-vinyl}-phenyl)-methanesulfonamide, |
| 126 | (E)-C,C,C-trifluoro-N-[4-(2-{5-[2-(1-hydroxy-1-methyl-ethyl)-phenyl]-1H-benzimidazol-2-yl}-vinyl)-phenyl]-methanesulfonamide, |
| 127 | (E)-2-{2-[2-(4-trifluoromethanesulfonylamino-phenyl)-vinyl]-1H-benzimidazol-5-yl}-benzenesulfonamide, |
| 128 | (E)-C,C,C-trifluoro-N-(4-{2-[5-(2-trifluoromethanesulfonylamino-phenyl)-1H-benzimidazol-2-yl]-vinyl}-phenyl)-methanesulfonamide, |
| 129 | 2-{2-[2-(4-trifluoromethoxy-phenyl)-ethyl]-1H-benzimidazol-5-yl}-benzenesulfonamide, |
| 130 | 2-{2-[2-(4-trifluoromethyl-phenyl)-ethyl]-1H-benzimidazol-5-yl}-benzenesulfonamide, |
| 131 | 2-{2-[2-(4-trifluoromethanesulfonyl-phenyl)-ethyl]-1H-benzimidazol-5-yl}-benzenesulfonamide, |
| 132 | C,C,C-trifluoro-N-(2-{2-[2-(4-trifluoromethoxy-phenyl)-ethyl]-1H-benzimidazol-5-yl}-phenyl)-methanesulfonamide, |
| 133 | C,C,C-trifluoro-N-(2-{2-[2-(4-trifluoromethyl-phenyl)-ethyl]-1H-benzimidazol-5-yl}-phenyl)-methanesulfonamide, |
| 134 | C,C,C-trifluoro-N-(2-{2-[2-(4-trifluoromethanesulfonyl-phenyl)-ethyl]-1H-benzimidazol-5-yl}-phenyl)-methanesulfonamide, |
| 135 | 1-(2-{2-[2-(4-chloro-phenyl)-ethyl]-1H-benzimidazol-5-yl}-phenyl)-ethanone, |
| 136 | 1-(2-{2-[2-(4-chloro-phenyl)-ethyl]-1H-benzimidazol-5-yl}-phenyl)-ethanol, |
| 137 | N-(2-{2-[2-(4-chloro-phenyl)-ethyl]-1H-benzimidazol-5-yl}-phenyl)-methanesulfonamide, |
| 138 | 2-(2-{2-[2-(4-chloro-phenyl)-ethyl]-1H-benzimidazol-5-yl}-phenyl)-propan-2-ol, |
| 139 | 2-{2-[2-(4-chloro-phenyl)-ethyl]-1H-benzimidazol-5-yl}-benzenesulfonamide, |
| 140 | N-(2-{2-[2-(4-chloro-phenyl)-ethyl]-1H-benzimidazol-5-yl}-phenyl)-C,C,C-trifluoro-methanesulfonamide, |
| 141 | 1-(2-{2-[2-(4-methanesulfonyl-phenyl)-ethyl]-1H-benzimidazol-5-yl}-phenyl)-ethanone, |
| 142 | 1-(2-{2-[2-(4-methanesulfonyl-phenyl)-ethyl]-1H-benzimidazol-5-yl}-phenyl)-ethanol, |
| 143 | N-(2-{2-[2-(4-methanesulfonyl-phenyl)-ethyl]-1H-benzimidazol-5-yl}-phenyl)-methanesulfonamide, |
| 144 | 2-(2-{2-[2-(4-methanesulfonyl-phenyl)-ethyl]-1H-benzimidazol-5-yl}-phenyl)-propan-2-ol, |
| 145 | 2-{2-[2-(4-methanesulfonyl-phenyl)-ethyl]-1H-benzimidazol-5-yl}-benzenesulfonamide, |
| 146 | C,C,C-trifluoro-N-(2-{2-[2-(4-methanesulfonyl-phenyl)-ethyl]-1H-benzimidazol-5-yl}-phenyl)-methanesulfonamide, |
| 147 | 1-[2-(2-{2-[4-(2,2,2-trifluoro-1-trifluoromethyl-ethoxy)-phenyl]-ethyl}-1H-benzimidazol-5-yl)-phenyl]-ethanone, |
| 148 | 1-[2-(2-{2-[4-(2,2,2-trifluoro-1-trifluoromethyl-ethoxy)-phenyl]-ethyl}-1H-benzimidazol-5-yl)-phenyl]-ethanol, |
| 149 | N-[2-(2-{2-[4-(2,2,2-trifluoro-1-trifluoromethyl-ethoxy)-phenyl]-ethyl}-1H-benzimidazol-5-yl)-phenyl]-methanesulfonamide, |
| 150 | 2-[2-(2-{2-[4-(2,2,2-trifluoro-1-trifluoromethyl-ethoxy)-phenyl]-ethyl}-1H-benzimidazol-5-yl)-phenyl]-propan-2-ol, |
| 151 | 2-(2-{2-[4-(2,2,2-trifluoro-1-trifluoromethyl-ethoxy)-phenyl]-ethyl}-1H-benzimidazol-5-yl)-benzenesulfonamide, |
| 152 | C,C,C-trifluoro-N-[2-(2-{2-[4-(2,2,2-trifluoro-1-trifluoromethyl-ethoxy)-phenyl]-ethyl}-1H-benzimidazol-5-yl)-phenyl]-methanesulfonamide, |
| 153 | 1-[2-(2-{2-[4-(2,2,2-trifluoro-ethoxy)-phenyl]-ethyl}-1H-benzimidazol-5-yl)-phenyl]-ethanone, |
| 154 | 1-[2-(2-{2-[4-(2,2,2-trifluoro-ethoxy)-phenyl]-ethyl}-1H-benzimidazol-5-yl)-phenyl]-ethanol, |
| 155 | N-[2-(2-{2-[4-(2,2,2-trifluoro-ethoxy)-phenyl]-ethyl}-1H-benzimidazol-5-yl)-phenyl]-methanesulfonamide, |
| 156 | 2-[2-(2-{2-[4-(2,2,2-trifluoro-ethoxy)-phenyl]-ethyl}-1H-benzimidazol-5-yl)-phenyl]-propan-2-ol, |
| 157 | 2-(2-{2-[4-(2,2,2-trifluoro-ethoxy)-phenyl]-ethyl}-1H-benzimidazol-5-yl)-benzenesulfonamide, |
| 158 | C,C,C-trifluoro-N-[2-(2-{2-[4-(2,2,2-trifluoro-ethoxy)-phenyl]-ethyl}-1H-benzimidazol-5-yl)-phenyl]-methanesulfonamide, |
| 159 | 1-[2-(2-{2-[4-(2,2,3,3,3-pentafluoro-propoxy)-phenyl]-ethyl}-1H-benzimidazol-5-yl)-phenyl]-ethanone, |
| 160 | 1-[2-(2-{2-[4-(2,2,3,3,3-pentafluoro-propoxy)-phenyl]-ethyl}-1H-benzimidazol-5-yl)-phenyl]-ethanol, |
| 161 | N-[2-(2-{2-[4-(2,2,3,3,3-pentafluoro-propoxy)-phenyl]-ethyl}-1H-benzimidazol-5-yl)-phenyl]-methanesulfonamide, |
| 162 | 2-[2-(2-{2-[4-(2,2,3,3,3-pentafluoro-propoxy)-phenyl]-ethyl}-1H-benzimidazol-5-yl)-phenyl]-propan-2-ol, |

| Cpd | Name |
|---|---|
| 163 | 2-(2-{2-[4-(2,2,3,3,3-pentafluoro-propoxy)-phenyl]-ethyl}-1H-benzimidazol-5-yl)-benzenesulfonamide, |
| 164 | C,C,C-trifluoro-N-[2-(2-{2-[4-(2,2,3,3,3-pentafluoro-propoxy)-phenyl]-ethyl}-1H-benzimidazol-5-yl)-phenyl]-methanesulfonamide, |
| 165 | 1-(2-{2-[2-(3-chloro-phenyl)-ethyl]-1H-benzimidazol-5-yl}-phenyl)-ethanone, |
| 166 | 1-(2-{2-[2-(3-chloro-phenyl)-ethyl]-1H-benzimidazol-5-yl}-phenyl)-ethanol, |
| 167 | N-(2-{2-[2-(3-chloro-phenyl)-ethyl]-1H-benzimidazol-5-yl}-phenyl)-methanesulfonamide, |
| 168 | 2-(2-{2-[2-(3-chloro-phenyl)-ethyl]-1H-benzimidazol-5-yl}-phenyl)-propan-2-ol, |
| 169 | 2-{2-[2-(3-chloro-phenyl)-ethyl]-1H-benzimidazol-5-yl}-benzenesulfonamide, |
| 170 | N-(2-{2-[2-(3-chloro-phenyl)-ethyl]-1H-benzimidazol-5-yl}-phenyl)-C,C,C-trifluoro-methanesulfonamide, |
| 171 | 1-(2-{2-[2-(3-trifluoromethyl-phenyl)-ethyl]-1H-benzimidazol-5-yl}-phenyl)-ethanone, |
| 172 | 1-(2-{2-[2-(3-trifluoromethyl-phenyl)-ethyl]-1H-benzimidazol-5-yl}-phenyl)-ethanol, |
| 173 | N-(2-{2-[2-(3-trifluoromethyl-phenyl)-ethyl]-1H-benzimidazol-5-yl}-phenyl)-methanesulfonamide, |
| 174 | 2-(2-{2-[2-(3-trifluoromethyl-phenyl)-ethyl]-1H-benzimidazol-5-yl}-phenyl)-propan-2-ol, |
| 175 | 2-{2-[2-(3-trifluoromethyl-phenyl)-ethyl]-1H-benzimidazol-5-yl}-benzenesulfonamide, |
| 176 | C,C,C-trifluoro-N-(2-{2-[2-(3-trifluoromethyl-phenyl)-ethyl]-1H-benzimidazol-5-yl}-phenyl)-methanesulfonamide, |
| 177 | N-(4-{2-[5-(2-acetyl-phenyl)-1H-benzimidazol-2-yl]-ethyl}-phenyl)-methanesulfonamide, |
| 178 | N-[4-(2-{5-[2-(1-hydroxy-ethyl)-phenyl]-1H-benzimidazol-2-yl}-ethyl)-phenyl]-methanesulfonamide, |
| 179 | N-(2-{2-[2-(4-methanesulfonylamino-phenyl)-ethyl]-1H-benzimidazol-5-yl}-phenyl)-methanesulfonamide, |
| 180 | N-[4-(2-{5-[2-(1-hydroxy-1-methyl-ethyl)-phenyl]-1H-benzimidazol-2-yl}-ethyl)-phenyl]-methanesulfonamide, |
| 181 | 2-{2-[2-(4-methanesulfonylamino-phenyl)-ethyl]-1H-benzimidazol-5-yl}-benzenesulfonamide, |
| 182 | C,C,C-trifluoro-N-(2-{2-[2-(4-methanesulfonylamino-phenyl)-ethyl]-1H-benzimidazol-5-yl}-phenyl)-methanesulfonamide, |
| 183 | N-(4-{2-[5-(2-acetyl-phenyl)-1H-benzimidazol-2-yl]-ethyl}-phenyl)-C,C,C-trifluoro-methanesulfonamide, |
| 184 | C,C,C-trifluoro-N-[4-(2-{5-[2-(1-hydroxy-ethyl)-phenyl]-1H-benzimidazol-2-yl}-ethyl)-phenyl]-methanesulfonamide, |
| 185 | C,C,C-trifluoro-N-(4-{2-[5-(2-methanesulfonylamino-phenyl)-1H-benzimidazol-2-yl]-ethyl}-phenyl)-methanesulfonamide, |
| 186 | C,C,C-trifluoro-N-[4-(2-{5-[2-(1-hydroxy-1-methyl-ethyl)-phenyl]-1H-benzimidazol-2-yl}-ethyl)-phenyl]-methanesulfonamide, |
| 187 | 2-{2-[2-(4-trifluoromethanesulfonylamino-phenyl)-ethyl]-1H-benzimidazol-5-yl}-benzenesulfonamide, |
| 188 | C,C,C-trifluoro-N-(2-{2-[2-(4-trifluoromethanesulfonylamino-phenyl)-ethyl]-1H-benzimidazol-5-yl}-phenyl)-methanesulfonamide, |
| 189 | 2-{2-[2-(4-trifluoromethoxy-phenyl)-cyclopropyl]-1H-benzimidazol-5-yl}-benzenesulfonamide, |
| 190 | 2-{2-[2-(4-trifluoromethyl-phenyl)-cyclopropyl]-1H-benzimidazol-5-yl}-benzenesulfonamide, |
| 191 | 2-{2-[2-(4-trifluoromethanesulfonyl-phenyl)-cyclopropyl]-1H-benzimidazol-5-yl}-benzenesulfonamide, |
| 192 | C,C,C-trifluoro-N-(2-{2-[2-(4-trifluoromethoxy-phenyl)-cyclopropyl]-1H-benzimidazol-5-yl}-phenyl)-methanesulfonamide, |
| 193 | C,C,C-trifluoro-N-(2-{2-[2-(4-trifluoromethyl-phenyl)-cyclopropyl]-1H-benzimidazol-5-yl}-phenyl)-methanesulfonamide, |
| 194 | C,C,C-trifluoro-N-(2-{2-[2-(4-trifluoromethanesulfonyl-phenyl)-cyclopropyl]-1H-benzimidazol-5-yl}-phenyl)-methanesulfonamide, |
| 195 | 1-(2-{2-[2-(4-chloro-phenyl)-cyclopropyl]-1H-benzimidazol-5-yl}-phenyl)-ethanone, |
| 196 | 1-(2-{2-[2-(4-chloro-phenyl)-cyclopropyl]-1H-benzimidazol-5-yl}-phenyl)-ethanol, |
| 197 | N-(2-{2-[2-(4-chloro-phenyl)-cyclopropyl]-1H-benzimidazol-5-yl}-phenyl)-methanesulfonamide, |
| 198 | 2-(2-{2-[2-(4-chloro-phenyl)-cyclopropyl]-1H-benzimidazol-5-yl}-phenyl)-propan-2-ol, |
| 199 | 2-{2-[2-(4-chloro-phenyl)-cyclopropyl]-1H-benzimidazol-5-yl}-benzenesulfonamide, |
| 200 | N-(2-{2-[2-(4-chloro-phenyl)-cyclopropyl]-1H-benzimidazol-5-yl}-phenyl)-C,C,C-trifluoro-methanesulfonamide, |
| 201 | 1-(2-{2-[2-(4-methanesulfonyl-phenyl)-cyclopropyl]-1H-benzimidazol-5-yl}-phenyl)-ethanone, |

| Cpd | Name |
|---|---|
| 202 | 1-(2-{2-[2-(4-methanesulfonyl-phenyl)-cyclopropyl]-1H-benzimidazol-5-yl}-phenyl)-ethanol, |
| 203 | N-(2-{2-[2-(4-methanesulfonyl-phenyl)-cyclopropyl]-1H-benzimidazol-5-yl}-phenyl)-methanesulfonamide, |
| 204 | 2-(2-{2-[2-(4-methanesulfonyl-phenyl)-cyclopropyl]-1H-benzimidazol-5-yl}-phenyl)-propan-2-ol, |
| 205 | 2-{2-[2-(4-methanesulfonyl-phenyl)-cyclopropyl]-1H-benzimidazol-5-yl}-benzenesulfonamide, |
| 206 | C,C,C-trifluoro-N-(2-{2-[2-(4-methanesulfonyl-phenyl)-cyclopropyl]-1H-benzimidazol-5-yl}-phenyl)-methanesulfonamide, |
| 207 | 1-[2-(2-{2-[4-(2,2,2-trifluoro-1-trifluoromethyl-ethoxy)-phenyl]-cyclopropyl}-1H-benzimidazol-5-yl)-phenyl]-ethanone, |
| 208 | 1-[2-(2-{2-[4-(2,2,2-trifluoro-1-trifluoromethyl-ethoxy)-phenyl]-cyclopropyl}-1H-benzimidazol-5-yl)-phenyl]-ethanol, |
| 209 | N-[2-(2-{2-[4-(2,2,2-trifluoro-1-trifluoromethyl-ethoxy)-phenyl]-cyclopropyl}-1H-benzimidazol-5-yl)-phenyl]-methanesulfonamide, |
| 210 | 2-[2-(2-{2-[4-(2,2,2-trifluoro-1-trifluoromethyl-ethoxy)-phenyl]-cyclopropyl}-1H-benzimidazol-5-yl)-phenyl]-propan-2-ol, |
| 211 | 2-(2-{2-[4-(2,2,2-trifluoro-1-trifluoromethyl-ethoxy)-phenyl]-cyclopropyl}-1H-benzimidazol-5-yl)-benzenesulfonamide, |
| 212 | C,C,C-trifluoro-N-[2-(2-{2-[4-(2,2,2-trifluoro-1-trifluoromethyl-ethoxy)-phenyl]-cyclopropyl}-1H-benzimidazol-5-yl)-phenyl]-methanesulfonamide, |
| 213 | 1-[2-(2-{2-[4-(2,2,2-trifluoro-ethoxy)-phenyl]-cyclopropyl}-1H-benzimidazol-5-yl)-phenyl]-ethanone, |
| 214 | 1-[2-(2-{2-[4-(2,2,2-trifluoro-ethoxy)-phenyl]-cyclopropyl}-1H-benzimidazol-5-yl)-phenyl]-ethanol, |
| 215 | N-[2-(2-{2-[4-(2,2,2-trifluoro-ethoxy)-phenyl]-cyclopropyl}-1H-benzimidazol-5-yl)-phenyl]-methanesulfonamide, |
| 216 | 2-[2-(2-{2-[4-(2,2,2-trifluoro-ethoxy)-phenyl]-cyclopropyl}-1H-benzimidazol-5-yl)-phenyl]-propan-2-ol, |
| 217 | 2-(2-{2-[4-(2,2,2-trifluoro-ethoxy)-phenyl]-cyclopropyl}-1H-benzimidazol-5-yl)-benzenesulfonamide, |
| 218 | C,C,C-trifluoro-N-[2-(2-{2-[4-(2,2,2-trifluoro-ethoxy)-phenyl]-cyclopropyl}-1H-benzimidazol-5-yl)-phenyl]-methanesulfonamide, |
| 219 | 1-[2-(2-{2-[4-(2,2,3,3,3-pentafluoro-propoxy)-phenyl]-cyclopropyl}-1H-benzimidazol-5-yl)-phenyl]-ethanone, |
| 220 | 1-[2-(2-{2-[4-(2,2,3,3,3-pentafluoro-propoxy)-phenyl]-cyclopropyl}-1H-benzimidazol-5-yl)-phenyl]-ethanol, |
| 221 | N-[2-(2-{2-[4-(2,2,3,3,3-pentafluoro-propoxy)-phenyl]-cyclopropyl}-1H-benzimidazol-5-yl)-phenyl]-methanesulfonamide, |
| 222 | 2-[2-(2-{2-[4-(2,2,3,3,3-pentafluoro-propoxy)-phenyl]-cyclopropyl}-1H-benzimidazol-5-yl)-phenyl]-propan-2-ol, |
| 223 | 2-(2-{2-[4-(2,2,3,3,3-pentafluoro-propoxy)-phenyl]-cyclopropyl}-1H-benzimidazol-5-yl)-benzenesulfonamide, |
| 224 | C,C,C-trifluoro-N-[2-(2-{2-[4-(2,2,3,3,3-pentafluoro-propoxy)-phenyl]-cyclopropyl}-1H-benzimidazol-5-yl)-phenyl]-methanesulfonamide, |
| 225 | 1-(2-{2-[2-(3-chloro-phenyl)-cyclopropyl]-1H-benzimidazol-5-yl}-phenyl)-ethanone, |
| 226 | 1-(2-{2-[2-(3-chloro-phenyl)-cyclopropyl]-1H-benzimidazol-5-yl}-phenyl)-ethanol, |
| 227 | N-(2-{2-[2-(3-chloro-phenyl)-cyclopropyl]-1H-benzimidazol-5-yl}-phenyl)-methanesulfonamide, |
| 228 | 2-(2-{2-[2-(3-chloro-phenyl)-cyclopropyl]-1H-benzimidazol-5-yl}-phenyl)-propan-2-ol, |
| 229 | 2-{2-[2-(3-chloro-phenyl)-cyclopropyl]-1H-benzimidazol-5-yl}-benzenesulfonamide, |
| 230 | N-(2-{2-[2-(3-chloro-phenyl)-cyclopropyl]-1H-benzimidazol-5-yl}-phenyl)-C,C,C-trifluoro-methanesulfonamide, |
| 231 | 1-(2-{2-[2-(3-trifluoromethyl-phenyl)-cyclopropyl]-1H-benzimidazol-5-yl}-phenyl)-ethanone, |
| 232 | 1-(2-{2-[2-(3-trifluoromethyl-phenyl)-cyclopropyl]-1H-benzimidazol-5-yl}-phenyl)-ethanol, |
| 233 | N-(2-{2-[2-(3-trifluoromethyl-phenyl)-cyclopropyl]-1H-benzimidazol-5-yl}-phenyl)-methanesulfonamide, |
| 234 | 2-(2-{2-[2-(3-trifluoromethyl-phenyl)-cyclopropyl]-1H-benzimidazol-5-yl}-phenyl)-propan-2-ol, |
| 235 | 2-{2-[2-(3-trifluoromethyl-phenyl)-cyclopropyl]-1H-benzimidazol-5-yl}-benzenesulfonamide, |
| 236 | C,C,C-trifluoro-N-(2-{2-[2-(3-trifluoromethyl-phenyl)-cyclopropyl]-1H-benzimidazol-5-yl}-phenyl)-methanesulfonamide, |
| 237 | N-(4-{2-[5-(2-acetyl-phenyl)-1H-benzimidazol-2-yl]-cyclopropyl}-phenyl)-methanesulfonamide, |
| 238 | N-[4-(2-{5-[2-(1-hydroxy-ethyl)-phenyl]-1H-benzimidazol-2-yl}-cyclopropyl)-phenyl]-methanesulfonamide, |
| 239 | N-(2-{2-[2-(4-methanesulfonylamino-phenyl)-cyclopropyl]-1H-benzimidazol-5-yl}-phenyl)-methanesulfonamide, |
| 240 | N-[4-(2-{5-[2-(1-hydroxy-1-methyl-ethyl)-phenyl]-1H-benzimidazol-2-yl}-cyclopropyl)-phenyl]-methanesulfonamide, |

-continued

| Cpd | Name |
|---|---|
| 241 | 2-{2-[2-(4-methanesulfonylamino-phenyl)-cyclopropyl]-1H-benzimidazol-5-yl}-benzenesulfonamide, |
| 242 | C,C,C-trifluoro-N-(2-{2-[2-(4-methanesulfonylamino-phenyl)-cyclopropyl]-1H-benzimidazol-5-yl}-phenyl)-methanesulfonamide, |
| 243 | N-(4-{2-[5-(2-acetyl-phenyl)-1H-benzimidazol-2-yl]-cyclopropyl}-phenyl)-C,C,C-trifluoro-methanesulfonamide, |
| 244 | C,C,C-trifluoro-N-[4-(2-{5-[2-(1-hydroxy-ethyl)-phenyl]-1H-benzimidazol-2-yl}-cyclopropyl)-phenyl]-methanesulfonamide, |
| 245 | C,C,C-trifluoro-N-(4-{2-[5-(2-methanesulfonylamino-phenyl)-1H-benzimidazol-2-yl]-cyclopropyl}-phenyl)-methanesulfonamide, |
| 246 | C,C,C-trifluoro-N-[4-(2-{5-[2-(1-hydroxy-1-methyl-ethyl)-phenyl]-1H-benzimidazol-2-yl}-cyclopropyl)-phenyl]-methanesulfonamide, |
| 247 | 2-{2-[2-(4-trifluoromethanesulfonylamino-phenyl)-cyclopropyl]-1H-benzimidazol-5-yl}-benzenesulfonamide, |
| 248 | C,C,C-trifluoro-N-(2-{2-[2-(4-trifluoromethanesulfonylamino-phenyl)-cyclopropyl]-1H-benzimidazol-5-yl}-phenyl)-methanesulfonamide, |
| 249 | 2-[2-(4-trifluoromethoxy-phenylethynyl)-1H-benzimidazol-5-yl]-benzenesulfonamide, |
| 250 | 2-[2-(4-trifluoromethyl-phenylethynyl)-1H-benzimidazol-5-yl]-benzenesulfonamide, |
| 251 | 2-[2-(4-trifluoromethanesulfonyl-phenylethynyl)-1H-benzimidazol-5-yl]-benzenesulfonamide, |
| 252 | C,C,C-trifluoro-N-{2-[2-(4-trifluoromethoxy-phenylethynyl)-1H-benzimidazol-5-yl]-phenyl}-methanesulfonamide, |
| 253 | C,C,C-trifluoro-N-{2-[2-(4-trifluoromethyl-phenylethynyl)-1H-benzimidazol-5-yl]-phenyl}-methanesulfonamide, |
| 254 | C,C,C-trifluoro-N-{2-[2-(4-trifluoromethanesulfonyl-phenylethynyl)-1H-benzimidazol-5-yl]-phenyl}-methanesulfonamide, |
| 255 | 1-{2-[2-(4-chloro-phenylethynyl)-1H-benzimidazol-5-yl]-phenyl}-ethanone, |
| 256 | 1-{2-[2-(4-chloro-phenylethynyl)-1H-benzimidazol-5-yl]-phenyl}-ethanol, |
| 257 | N-{2-[2-(4-chloro-phenylethynyl)-1H-benzimidazol-5-yl]-phenyl}-methanesulfonamide, |
| 258 | 2-{2-[2-(4-chloro-phenylethynyl)-1H-benzimidazol-5-yl]-phenyl}-propan-2-ol, |
| 259 | 2-[2-(4-chloro-phenylethynyl)-1H-benzimidazol-5-yl]-benzenesulfonamide, |
| 260 | N-{2-[2-(4-chloro-phenylethynyl)-1H-benzimidazol-5-yl]-phenyl}-C,C,C-trifluoro-methanesulfonamide, |
| 261 | 1-{2-[2-(4-methanesulfonyl-phenylethynyl)-1H-benzimidazol-5-yl]-phenyl}-ethanone, |
| 262 | 1-{2-[2-(4-methanesulfonyl-phenylethynyl)-1H-benzimidazol-5-yl]-phenyl}-ethanol, |
| 263 | N-{2-[2-(4-methanesulfonyl-phenylethynyl)-1H-benzimidazol-5-yl]-phenyl}-methanesulfonamide, |
| 264 | 2-{2-[2-(4-methanesulfonyl-phenylethynyl)-1H-benzimidazol-5-yl]-phenyl}-propan-2-ol, |
| 265 | 2-[2-(4-methanesulfonyl-phenylethynyl)-1H-benzimidazol-5-yl]-benzenesulfonamide, |
| 266 | C,C,C-trifluoro-N-{2-[2-(4-methanesulfonyl-phenylethynyl)-1H-benzimidazol-5-yl]-phenyl}-methanesulfonamide, |
| 267 | 1-(2-{2-[4-(2,2,2-trifluoro-1-trifluoromethyl-ethoxy)-phenylethynyl]-1H-benzimidazol-5-yl}-phenyl)-ethanone, |
| 268 | 1-(2-{2-[4-(2,2,2-trifluoro-1-trifluoromethyl-ethoxy)-phenylethynyl]-1H-benzimidazol-5-yl}-phenyl)-ethanol, |
| 269 | N-(2-{2-[4-(2,2,2-trifluoro-1-trifluoromethyl-ethoxy)-phenylethynyl]-1H-benzimidazol-5-yl}-phenyl)-methanesulfonamide, |
| 270 | 2-(2-{2-[4-(2,2,2-trifluoro-1-trifluoromethyl-ethoxy)-phenylethynyl]-1H-benzimidazol-5-yl}-phenyl)-propan-2-ol, |
| 271 | 2-{2-[4-(2,2,2-trifluoro-1-trifluoromethyl-ethoxy)-phenylethynyl]-1H-benzimidazol-5-yl}-benzenesulfonamide, |
| 272 | C,C,C-trifluoro-N-(2-{2-[4-(2,2,2-trifluoro-1-trifluoromethyl-ethoxy)-phenylethynyl]-1H-benzimidazol-5-yl}-phenyl)-methanesulfonamide, |
| 273 | 1-(2-{2-[4-(2,2,2-trifluoro-ethoxy)-phenylethynyl]-1H-benzimidazol-5-yl}-phenyl)-ethanone, |
| 274 | 1-(2-{2-[4-(2,2,2-trifluoro-ethoxy)-phenylethynyl]-1H-benzimidazol-5-yl}-phenyl)-ethanol, |
| 275 | N-(2-{2-[4-(2,2,2-trifluoro-ethoxy)-phenylethynyl]-1H-benzimidazol-5-yl}-phenyl)-methanesulfonamide, |
| 276 | 2-(2-{2-[4-(2,2,2-trifluoro-ethoxy)-phenylethynyl]-1H-benzimidazol-5-yl}-phenyl)-propan-2-ol, |
| 277 | 2-{2-[4-(2,2,2-trifluoro-ethoxy)-phenylethynyl]-1H-benzimidazol-5-yl}-benzenesulfonamide, |
| 278 | C,C,C-trifluoro-N-(2-{2-[4-(2,2,2-trifluoro-ethoxy)-phenylethynyl]-1H-benzimidazol-5-yl}-phenyl)-methanesulfonamide, |
| 279 | 1-(2-{2-[4-(2,2,3,3,3-pentafluoro-propoxy)-phenylethynyl]-1H-benzimidazol-5-yl}-phenyl)-ethanone, |
| 280 | 1-(2-{2-[4-(2,2,3,3,3-pentafluoro-propoxy)-phenylethynyl]-1H-benzimidazol-5-yl}-phenyl)-ethanol, |

-continued

| Cpd | Name |
|---|---|
| 281 | N-(2-{2-[4-(2,2,3,3,3-pentafluoro-propoxy)-phenylethynyl]-1H-benzimidazol-5-yl}-phenyl)-methanesulfonamide, |
| 282 | 2-(2-{2-[4-(2,2,3,3,3-pentafluoro-propoxy)-phenylethynyl]-1H-benzimidazol-5-yl}-phenyl)-propan-2-ol, |
| 283 | 2-{2-[4-(2,2,3,3,3-pentafluoro-propoxy)-phenylethynyl]-1H-benzimidazol-5-yl}-benzenesulfonamide, |
| 284 | C,C,C-trifluoro-N-(2-{2-[4-(2,2,3,3,3-pentafluoro-propoxy)-phenylethynyl]-1H-benzimidazol-5-yl}-phenyl)-methanesulfonamide, |
| 285 | 1-{2-[2-(3-chloro-phenylethynyl)-1H-benzimidazol-5-yl]-phenyl}-ethanone, |
| 286 | 2-{2-[2-(3-chloro-phenylethynyl)-1H-benzimidazol-5-yl]-phenyl}-propan-2-ol, |
| 287 | N-{2-[2-(3-chloro-phenylethynyl)-1H-benzimidazol-5-yl]-phenyl}-methanesulfonamide, |
| 288 | 1-{2-[2-(3-chloro-phenylethynyl)-1H-benzimidazol-5-yl]-phenyl}-ethanol, |
| 289 | 2-[2-(3-chloro-phenylethynyl)-1H-benzimidazol-5-yl]-benzenesulfonamide, |
| 290 | N-{2-[2-(3-chloro-phenylethynyl)-1H-benzimidazol-5-yl]-phenyl}-C,C,C-trifluoro-methanesulfonamide, |
| 291 | 1-{2-[2-(3-trifluoromethyl-phenylethynyl)-1H-benzimidazol-5-yl]-phenyl}-ethanone, |
| 292 | 1-{2-[2-(3-trifluoromethyl-phenylethynyl)-1H-benzimidazol-5-yl]-phenyl}-ethanol, |
| 293 | N-{2-[2-(3-trifluoromethyl-phenylethynyl)-1H-benzimidazol-5-yl]-phenyl}-methanesulfonamide, |
| 294 | 2-{2-[2-(3-trifluoromethyl-phenylethynyl)-1H-benzimidazol-5-yl]-phenyl}-propan-2-ol, |
| 295 | 2-[2-(3-trifluoromethyl-phenylethynyl)-1H-benzimidazol-5-yl]-benzenesulfonamide, |
| 296 | C,C,C-trifluoro-N-{2-[2-(3-trifluoromethyl-phenylethynyl)-1H-benzimidazol-5-yl]-phenyl}-methanesulfonamide, |
| 297 | N-{4-[5-(2-acetyl-phenyl)-1H-benzimidazol-2-yl-ethynyl]-phenyl}-methanesulfonamide, |
| 298 | N-(4-{5-[2-(1-hydroxy-ethyl)-phenyl]-1H-benzimidazol-2-yl-ethynyl}-phenyl)-methanesulfonamide, |
| 299 | N-{2-[2-(4-methanesulfonylamino-phenylethynyl)-1H-benzimidazol-5-yl]-phenyl}-methanesulfonamide, |
| 300 | N-(4-{5-[2-(1-hydroxy-1-methyl-ethyl)-phenyl]-1H-benzimidazol-2-yl-ethynyl}-phenyl)-methanesulfonamide, |
| 301 | 2-[2-(4-methanesulfonylamino-phenylethynyl)-1H-benzimidazol-5-yl]-benzenesulfonamide, |
| 302 | C,C,C-trifluoro-N-{2-[2-(4-methanesulfonylamino-phenylethynyl)-1H-benzimidazol-5-yl]-phenyl}-methanesulfonamide, |
| 303 | N-{4-[5-(2-acetyl-phenyl)-1H-benzimidazol-2-yl-ethynyl]-phenyl}-C,C,C-trifluoro-methanesulfonamide, |
| 304 | C,C,C-trifluoro-N-(4-{5-[2-(1-hydroxy-ethyl)-phenyl]-1H-benzimidazol-2-yl-ethynyl}-phenyl)-methanesulfonamide, |
| 305 | C,C,C-trifluoro-N-{4-[5-(2-methanesulfonylamino-phenyl)-1H-benzimidazol-2-yl-ethynyl]-phenyl}-methanesulfonamide, |
| 306 | C,C,C-trifluoro-N-(4-{5-[2-(1-hydroxy-1-methyl-ethyl)-phenyl]-1H-benzimidazol-2-yl-ethynyl}-phenyl)-methanesulfonamide, |
| 307 | 2-[2-(4-trifluoromethanesulfonylamino-phenylethynyl)-1H-benzimidazol-5-yl]-benzenesulfonamide, |
| 308 | C,C,C-trifluoro-N-{2-[2-(4-trifluoromethanesulfonylamino-phenylethynyl)-1H-benzimidazol-5-yl]-phenyl}-methanesulfonamide, |
| 309 | (E)-N-tert-butyl-2-{2-[2-(4-trifluoromethyl-phenyl)-vinyl]-1H-benzimidazol-5-yl}-benzenesulfonamide, |
| 310 | (E)-N-methyl-2-{2-[2-(4-trifluoromethyl-phenyl)-vinyl]-1H-benzimidazol-5-yl}-benzenesulfonamide, |
| 311 | (E)-2-hydroxy-1-(2-{2-[2-(4-trifluoromethyl-phenyl)-vinyl]-1H-benzimidazol-5-yl}-phenyl)-ethanone, |
| 312 | (E)-2-{2-[2-(4-bromo-phenyl)-vinyl]-1H-benzimidazol-5-yl}-N-methyl-benzenesulfonamide, |
| 314 | (E)-N-methyl-2-[2-(2-p-tolyl-vinyl)-1H-benzimidazol-5-yl]-benzenesulfonamide, |
| 315 | (E)-2-{2-[2-(4-fluoro-phenyl)-vinyl]-1H-benzimidazol-5-yl}-N-methyl-benzenesulfonamide, |
| 316 | (E)-2-{2-[2-(3,4-dichloro-phenyl)-vinyl]-1H-benzimidazol-5-yl}-N-methyl-benzenesulfonamide, |
| 317 | (E)-2-{2-[2-(3-bromo-4-fluoro-phenyl)-vinyl]-1H-benzimidazol-5-yl}-N-methyl-benzenesulfonamide, |
| 318 | (E)-2-{2-[2-(4-dimethylamino-phenyl)-vinyl]-1H-benzimidazol-5-yl}-N-methyl-benzenesulfonamide, |
| 319 | (E)-2-{2-[2-(3-fluoro-4-trifluoromethyl-phenyl)-vinyl]-1H-benzimidazol-5-yl}-N-methyl-benzenesulfonamide, |
| 320 | (E)-2-{2-[2-(2-fluoro-4-trifluoromethyl-phenyl)-vinyl]-1H-benzimidazol-5-yl}-N-methyl-benzenesulfonamide, |
| 321 | (E)-2-{2-[2-(3-chloro-4-fluoro-phenyl)-vinyl]-1H-benzimidazol-5-yl}-N-methyl-benzenesulfonamide, |

| Cpd | Name |
|---|---|
| 322 | (E)-2-{2-[2-(3-fluoro-5-trifluoromethyl-phenyl)-vinyl]-1H-benzimidazol-5-yl}-N-methyl-benzenesulfonamide, |
| 323 | (E)-N-methyl-2-{2-[2-(2,3,4-trifluoro-phenyl)-vinyl]-1H-benzimidazol-5-yl}-benzenesulfonamide, |
| 324 | (E)-N-methyl-2-{2-[2-(2,4,5-trifluoro-phenyl)-vinyl]-1H-benzimidazol-5-yl}-benzenesulfonamide, |
| 325 | (E)-2-{2-[2-(2,3-difluoro-phenyl)-vinyl]-1H-benzimidazol-5-yl}-N-methyl-benzenesulfonamide, |
| 326 | (E)-2-{2-[2-(2,5-difluoro-phenyl)-vinyl]-1H-benzimidazol-5-yl}-N-methyl-benzenesulfonamide, |
| 327 | (E)-2-{2-[2-(2,6-difluoro-phenyl)-vinyl]-1H-benzimidazol-5-yl}-N-methyl-benzenesulfonamide, |
| 328 | (E)-2-{2-[2-(3,5-difluoro-phenyl)-vinyl]-1H-benzimidazol-5-yl}-N-methyl-benzenesulfonamide, |
| 329 | (E)-2-{2-[2-(3,4-difluoro-phenyl)-vinyl]-1H-benzimidazol-5-yl}-N-methyl-benzenesulfonamide, |
| 330 | (E)-2-{2-[2-(4-fluoro-2-trifluoromethyl-phenyl)-vinyl]-1H-benzimidazol-5-yl}-N-methyl-benzenesulfonamide, |
| 331 | (E)-2-{2-[2-(4-fluoro-3-trifluoromethyl-phenyl)-vinyl]-1H-benzimidazol-5-yl}-N-methyl-benzenesulfonamide, |
| 332 | (E)-2-{2-[2-(2-fluoro-3-trifluoromethyl-phenyl)-vinyl]-1H-benzimidazol-5-yl}-N-methyl-benzenesulfonamide, |
| 333 | (E)-2-{2-[2-(3,5-bis-trifluoromethyl-phenyl)-vinyl]-1H-benzimidazol-5-yl}-N-methyl-benzenesulfonamide, |
| 334 | (E)-2-{2-[2-(2,5-bis-trifluoromethyl-phenyl)-vinyl]-1H-benzimidazol-5-yl}-N-methyl-benzenesulfonamide, |
| 335 | (E)-2-{2-[2-(3-chloro-2-fluoro-phenyl)-vinyl]-1H-benzimidazol-5-yl}-N-methyl-benzenesulfonamide, |
| 336 | (E)-2-{2-[2-(2-chloro-6-fluoro-phenyl)-vinyl]-1H-benzimidazol-5-yl}-N-methyl-benzenesulfonamide, |
| 337 | (E)-2-{2-[2-(2,4-dichloro-phenyl)-vinyl]-1H-benzimidazol-5-yl}-N-methyl-benzenesulfonamide, |
| 338 | (E)-2-{2-[2-(3-bromo-phenyl)-vinyl]-1H-benzimidazol-5-yl}-N-methyl-benzenesulfonamide, |
| 339 | (E)-2-{2-[2-(4-chloro-2-fluoro-phenyl)-vinyl]-1H-benzimidazol-5-yl}-N-methyl-benzenesulfonamide, |
| 340 | (E)-2-{2-[2-(4-chloro-2-methanesulfonyl-phenyl)-vinyl]-1H-benzimidazol-5-yl}-N-methyl-benzenesulfonamide, |
| 341 | (E)-N-methyl-2-{2-[2-(4-trifluoromethylsulfanyl-phenyl)-vinyl]-1H-benzimidazol-5-yl}-benzenesulfonamide, |
| 342 | (E)-N-methyl-2-{2-[2-(4-trifluoromethanesulfonyl-phenyl)-vinyl]-1H-benzimidazol-5-yl}-benzenesulfonamide, |
| 343 | (E)-N-methyl-2-{2-[2-(2-trifluoromethyl-phenyl)-vinyl]-1H-benzimidazol-5-yl}-benzenesulfonamide, |
| 344 | (E)-N-methyl-2-{2-[2-(3-trifluoromethoxy-phenyl)-vinyl]-1H-benzimidazol-5-yl}-benzenesulfonamide, |
| 345 | (E)-N-methyl-2-{2-[2-(4-trifluoromethoxy-phenyl)-vinyl]-1H-benzimidazol-5-yl}-benzenesulfonamide, |
| 346 | (E)-2-{2-[2-(2-chloro-phenyl)-vinyl]-1H-benzimidazol-5-yl}-N-methyl-benzenesulfonamide, |
| 347 | (E)-2-{2-[2-(4-chloro-phenyl)-vinyl]-1H-benzimidazol-5-yl}-N-methyl-benzenesulfonamide, |
| 348 | (E)-2-{2-[2-(2-bromo-phenyl)-vinyl]-1H-benzimidazol-5-yl}-N-methyl-benzenesulfonamide, |
| 349 | (E)-2-{2-[2-(2,4-difluoro-phenyl)-vinyl]-1H-benzimidazol-5-yl}-N-methyl-benzenesulfonamide, |
| 350 | N-methyl-2-{2-[2-(3-trifluoromethyl-phenyl)-ethyl]-1H-benzimidazol-5-yl}-benzenesulfonamide, |
| 351 | (E)-2-{2-[2-(4-methanesulfonyl-phenyl)-vinyl]-1H-benzimidazol-5-yl}-N-methyl-benzenesulfonamide, |
| 357 | (E)-2-{2-[2-(2,4-difluoro-phenyl)-vinyl]-1H-benzimidazol-5-yl}-benzenesulfonamide, |
| 358 | (E)-2-{2-[2-(3,4-difluoro-phenyl)-vinyl]-1H-benzimidazol-5-yl}-benzenesulfonamide, |
| 359 | (E)-2-{2-[2-(2,3-difluoro-phenyl)-vinyl]-1H-benzimidazol-5-yl}-benzenesulfonamide, |
| 360 | (E)-2-{2-[2-(2,5-difluoro-phenyl)-vinyl]-1H-benzimidazol-5-yl}-benzenesulfonamide, |
| 361 | (E)-2-{2-[2-(3,5-difluoro-phenyl)-vinyl]-1H-benzimidazol-5-yl}-benzenesulfonamide, |
| 362 | (E)-2-{2-[2-(3-trifluoromethoxy-phenyl)-vinyl]-1H-benzimidazol-5-yl}-benzenesulfonamide, |
| 363 | (E)-2-{2-[2-(4-bromo-phenyl)-vinyl]-1H-benzimidazol-5-yl}-benzenesulfonamide, |
| 364 | (E)-2-{2-[2-(2-trifluoromethyl-phenyl)-vinyl]-1H-benzimidazol-5-yl}-benzenesulfonamide, |
| 365 | (E)-2-{2-[2-(2-chloro-phenyl)-vinyl]-1H-benzimidazol-5-yl}-benzenesulfonamide, |

| Cpd | Name |
|---|---|
| 366 | (E)-2-{2-[2-(2-bromo-phenyl)-vinyl]-1H-benzimidazol-5-yl}-benzenesulfonamide, |
| 367 | (E)-2-{2-[2-(4-fluoro-2-trifluoromethyl-phenyl)-vinyl]-1H-benzimidazol-5-yl}-benzenesulfonamide, |
| 368 | (E)-2-{2-[2-(2-fluoro-3-trifluoromethyl-phenyl)-vinyl]-1H-benzimidazol-5-yl}-benzenesulfonamide, |
| 369 | (E)-2-{2-[2-(4-fluoro-3-trifluoromethyl-phenyl)-vinyl]-1H-benzimidazol-5-yl}-benzenesulfonamide, |
| 370 | (E)-2-{2-[2-(2,3,4-trifluoro-phenyl)-vinyl]-1H-benzimidazol-5-yl}-benzenesulfonamide, |
| 371 | (E)-2-{2-[2-(2,4,5-trifluoro-phenyl)-vinyl]-1H-benzimidazol-5-yl}-benzenesulfonamide, |
| 372 | (E)-2-{2-[2-(2,6-difluoro-phenyl)-vinyl]-1H-benzimidazol-5-yl}-benzenesulfonamide, |
| 373 | (E)-2-{2-[2-(3,5-bis-trifluoromethyl-phenyl)-vinyl]-1H-benzimidazol-5-yl}-benzenesulfonamide, |
| 374 | (E)-2-{2-[2-(2,5-bis-trifluoromethyl-phenyl)-vinyl]-1H-benzimidazol-5-yl}-benzenesulfonamide, |
| 375 | (E)-2-{2-[2-(4-chloro-2-methanesulfonyl-phenyl)-vinyl]-1H-benzimidazol-5-yl}-benzenesulfonamide, |
| 376 | (E)-2-{2-[2-(3-bromo-phenyl)-vinyl]-1H-benzimidazol-5-yl}-benzenesulfonamide, |
| 378 | (E)-2-{2-[2-(4-chloro-3-trifluoromethyl-phenyl)-vinyl]-1H-benzimidazol-5-yl}-benzenesulfonamide, |
| 379 | (E)-2-{2-[2-(5-bromo-2-fluoro-phenyl)-vinyl]-1H-benzimidazol-5-yl}-benzenesulfonamide, |
| 380 | (E)-2-{2-[2-(4-trifluoromethylsulfanyl-phenyl)-vinyl]-1H-benzimidazol-5-yl}-benzenesulfonamide, |
| 383 | 2-{2-[2-(4-fluoro-3-trifluoromethyl-phenyl)-ethyl]-1H-benzimidazol-5-yl}-benzenesulfonamide, |
| 384 | 2-{2-[2-(2,3,4-trifluoro-phenyl)-ethyl]-1H-benzimidazol-5-yl}-benzenesulfonamide, |
| 385 | 2-{2-[2-(2,4,5-trifluoro-phenyl)-ethyl]-1H-benzimidazol-5-yl}-benzenesulfonamide, |
| 386 | 2-{2-[2-(2,6-difluoro-phenyl)-ethyl]-1H-benzimidazol-5-yl}-benzenesulfonamide, |
| 387 | 2-{2-[2-(3,5-bis-trifluoromethyl-phenyl)-ethyl]-1H-benzimidazol-5-yl}-benzenesulfonamide, |
| 388 | 2-{2-[2-(2,5-bis-trifluoromethyl-phenyl)-ethyl]-1H-benzimidazol-5-yl}-benzenesulfonamide, |
| 389 | 2-{2-[2-(4-chloro-2-methanesulfonyl-phenyl)-ethyl]-1H-benzimidazol-5-yl}-benzenesulfonamide, |
| 390 | 2-{2-[2-(4-chloro-3-trifluoromethyl-phenyl)-ethyl]-1H-benzimidazol-5-yl}-benzenesulfonamide, |
| 391 | 2-{2-[2-(3-trifluoromethoxy-phenyl)-ethyl]-1H-benzimidazol-5-yl}-benzenesulfonamide, |
| 392 | 2-{2-[2-(2,4-difluoro-phenyl)-ethyl]-1H-benzimidazol-5-yl}-benzenesulfonamide, |
| 393 | 2-{2-[2-(3,4-difluoro-phenyl)-ethyl]-1H-benzimidazol-5-yl}-benzenesulfonamide, |
| 394 | 2-{2-[2-(2,3-difluoro-phenyl)-ethyl]-1H-benzimidazol-5-yl}-benzenesulfonamide, |
| 395 | 2-{2-[2-(2,5-difluoro-phenyl)-ethyl]-1H-benzimidazol-5-yl}-benzenesulfonamide, |
| 396 | 2-{2-[2-(3,5-difluoro-phenyl)-ethyl]-1H-benzimidazol-5-yl}-benzenesulfonamide, |
| 397 | 2-(2-phenethyl-1H-benzimidazol-5-yl)-benzenesulfonamide, |
| 398 | (E)-N,N-dimethyl-2-{2-[2-(4-trifluoromethyl-phenyl)-vinyl]-1H-benzimidazol-5-yl}-benzenesulfonamide, |
| 399 | N,N-dimethyl-2-{2-[2-(4-trifluoromethyl-phenyl)-ethyl]-1H-benzimidazol-5-yl}-benzenesulfonamide, |
| 400 | N-methyl-2-{2-[2-(4-trifluoromethyl-phenyl)-ethyl]-1H-benzimidazol-5-yl}-benzenesulfonamide, |
| 402 | 2-{2-[2-(2-chloro-phenyl)-ethyl]-1H-benzimidazol-5-yl}-benzenesulfonamide, |
| 404 | 2-{2-[2-(4-fluoro-2-trifluoromethyl-phenyl)-ethyl]-1H-benzimidazol-5-yl}-benzenesulfonamide, |
| 405 | 2-{2-[2-(2-fluoro-3-trifluoromethyl-phenyl)-ethyl]-1H-benzimidazol-5-yl}-benzenesulfonamide, |
| 406 | (E)-N-(2-{2-[2-(4-bromo-phenyl)-vinyl]-1H-benzimidazol-5-yl}-phenyl)-methanesulfonamide, |
| 407 | (E)-N-(2-{2-[2-(4-isopropyl-phenyl)-vinyl]-1H-benzimidazol-5-yl}-phenyl)-methanesulfonamide, |
| 408 | (E)-N-(2-{2-[2-(3-chloro-4-fluoro-phenyl)-vinyl]-1H-benzimidazol-5-yl}-phenyl)-methanesulfonamide, |
| 409 | (E)-N-(2-{2-[2-(3-bromo-4-fluoro-phenyl)-vinyl]-1H-benzimidazol-5-yl}-phenyl)-methanesulfonamide, |

| Cpd | Name |
|---|---|
| 410 | (E)-N-(2-{2-[2-(4-difluoromethoxy-phenyl)-vinyl]-1H-benzimidazol-5-yl}-phenyl)-methanesulfonamide, |
| 411 | (E)-N-(2-{2-[2-(3-fluoro-5-trifluoromethyl-phenyl)-vinyl]-1H-benzimidazol-5-yl}-phenyl)-methanesulfonamide, |
| 412 | (E)-N-{2-[2-(2-p-tolyl-vinyl)-1H-benzimidazol-5-yl]-phenyl}-methanesulfonamide, |
| 413 | (E)-N-(2-{2-[2-(4-dimethylamino-phenyl)-vinyl]-1H-benzimidazol-5-yl}-phenyl)-methanesulfonamide, |
| 414 | (E)-N-(2-{2-[2-(4-ethoxy-phenyl)-vinyl]-1H-benzimidazol-5-yl}-phenyl)-methanesulfonamide, |
| 415 | (E)-N-{2-[2-(2-naphthalen-2-yl-vinyl)-1H-benzimidazol-5-yl]-phenyl}-methanesulfonamide, |
| 416 | (E)-N-(2-{2-[2-(3,4-dichloro-phenyl)-vinyl]-1H-benzimidazol-5-yl}-phenyl)-methanesulfonamide, |
| 417 | (E)-N-(2-{2-[2-(3-fluoro-4-trifluoromethyl-phenyl)-vinyl]-1H-benzimidazol-5-yl}-phenyl)-methanesulfonamide, |
| 418 | (E)-N-(2-{2-[2-(2-fluoro-4-trifluoromethyl-phenyl)-vinyl]-1H-benzimidazol-5-yl}-phenyl)-methanesulfonamide, |
| 419 | 2-{2-[2-(2-fluoro-phenyl)-ethyl]-1H-benzimidazol-5-yl}-benzenesulfonamide, |
| 420 | 2-{2-[2-(4-fluoro-phenyl)-ethyl]-1H-benzimidazol-5-yl}-benzenesulfonamide, |
| 421 | 2-{2-[2-(3-fluoro-5-trifluoromethyl-phenyl)-ethyl]-1H-benzimidazol-5-yl}-benzenesulfonamide, |
| 422 | (E)-5-(2-methanesulfonyl-phenyl)-2-[2-(4-trifluoromethyl-phenyl)-vinyl]-1H-benzimidazole, |
| 423 | (E)-2-{2-[2-(3-fluoro-4-trifluoromethyl-phenyl)-vinyl]-1H-benzimidazol-5-yl}-benzenesulfonamide, |
| 424 | (E)-2-{2-[2-(2-fluoro-4-trifluoromethyl-phenyl)-vinyl]-1H-benzimidazol-5-yl}-benzenesulfonamide, |
| 425 | (E)-2-{2-[2-(3-ethoxy-phenyl)-vinyl]-1H-benzimidazol-5-yl}-benzenesulfonamide, |
| 426 | (E)-2-(2-styryl-1H-benzimidazol-5-yl)-benzenesulfonamide, |
| 427 | (E)-2-{2-[2-(3,4-dichloro-phenyl)-vinyl]-1H-benzimidazol-5-yl}-benzenesulfonamide, |
| 428 | (E)-2-{2-[2-(4-chloro-2-fluoro-phenyl)-vinyl]-1H-benzimidazol-5-yl}-benzenesulfonamide, |
| 429 | (E)-2-{2-[2-(4-isopropyl-phenyl)-vinyl]-1H-benzimidazol-5-yl}-benzenesulfonamide, |
| 430 | (E)-2-[2-(2-p-tolyl-vinyl)-1H-benzimidazol-5-yl]-benzenesulfonamide, |
| 431 | (E)-2-{2-[2-(3-chloro-2-fluoro-phenyl)-vinyl]-1H-benzimidazol-5-yl}-benzenesulfonamide, |
| 432 | (E)-2-{2-[2-(3-chloro-4-fluoro-phenyl)-vinyl]-1H-benzimidazol-5-yl}-benzenesulfonamide, |
| 433 | (E)-2-[2-(2-naphthalen-2-yl-vinyl)-1H-benzimidazol-5-yl]-benzenesulfonamide, |
| 434 | (E)-2-{2-[2-(4-fluoro-phenyl)-vinyl]-1H-benzimidazol-5-yl}-benzenesulfonamide, |
| 435 | (E)-2-{2-[2-(4-difluoromethyl-phenyl)-vinyl]-1H-benzimidazol-5-yl}-benzenesulfonamide, |
| 436 | (E)-2-{2-[2-(3-fluoro-5-trifluoromethyl-phenyl)-vinyl]-1H-benzimidazol-5-yl}-benzenesulfonamide, |
| 437 | (E)-2-{2-[2-(2,4-dichloro-phenyl)-vinyl]-1H-benzimidazol-5-yl}-benzenesulfonamide, |
| 438 | (E)-2-{2-[2-(2-chloro-6-fluoro-phenyl)-vinyl]-1H-benzimidazol-5-yl}-benzenesulfonamide, |
| 439 | (E)-2-{2-[2-(3-bromo-4-fluoro-phenyl)-vinyl]-1H-benzimidazol-5-yl}-benzenesulfonamide, |
| 440 | (E)-2-{2-[2-(4-ethoxy-phenyl)-vinyl]-1H-benzimidazol-5-yl}-benzenesulfonamide, |
| 441 | (E)-4-fluoro-2-{2-[2-(4-trifluoromethyl-phenyl)-vinyl]-1H-benzimidazol-5-yl}-benzenesulfonamide, |
| 442 | 2-{2-[2-(4-isopropyl-phenyl)-ethyl]-1H-benzimidazol-5-yl}-benzenesulfonamide, |
| 443 | (E)-N-(2-{3-methyl-2-[2-(4-trifluoromethyl-phenyl)-vinyl]-3H-benzimidazol-5-yl}-phenyl)-methanesulfonamide, |
| 444 | (E)-4-trifluoromethyl-2-{2-[2-(4-trifluoromethyl-phenyl)-vinyl]-1H-benzimidazol-5-yl}-benzenesulfonamide, |
| 445 | 4-trifluoromethyl-2-{2-[2-(4-trifluoromethyl-phenyl)-ethyl]-1H-benzimidazol-5-yl}-benzenesulfonamide, |
| 446 | (E)-5-trifluoromethyl-2-{2-[2-(4-trifluoromethyl-phenyl)-vinyl]-1H-benzimidazol-5-yl}-benzenesulfonamide, |
| 447 | 5-trifluoromethyl-2-{2-[2-(4-trifluoromethyl-phenyl)-ethyl]-1H-benzimidazol-5-yl}-benzenesulfonamide, |
| 448 | (E)-1-[4-(2-{5-[2-(1-hydroxy-1-methyl-ethyl)-phenyl]-1H-benzimidazol-2-yl}-vinyl)-phenyl]-ethanone, |
| 449 | (E)-2-{2-[2-(2-quinolin-6-yl-vinyl)-1H-benzimidazol-5-yl]-phenyl}-propan-2-ol, |

| Cpd | Name |
|---|---|
| 450 | (E)-N-isopropyl-4-{2-[5-(2-methylsulfamoyl-phenyl)-1H-benzimidazol-2-yl]-vinyl}-benzamide, |
| 451 | (E)-2-{2-[2-(4-cyano-phenyl)-vinyl]-1H-benzimidazol-5-yl}-N-methyl-benzenesulfonamide, |
| 452 | (E)-N-(4-{2-[5-(2-methylsulfamoyl-phenyl)-1H-benzimidazol-2-yl]-vinyl}-phenyl)-acetamide, |
| 453 | (E)-4-{2-[5-(2-methylsulfamoyl-phenyl)-1H-benzimidazol-2-yl]-vinyl}-benzoic acid, |
| 454 | (E)-2-{2-[2-(1H-indol-6-yl)-vinyl]-1H-benzimidazol-5-yl}-N-methyl-benzenesulfonamide, |
| 455 | (E)-2-{2-[2-(2,4-bis-trifluoromethyl-phenyl)-vinyl]-1H-benzimidazol-5-yl}-N-methyl-benzenesulfonamide, |
| 456 | (E)-2-{2-[2-(4-acetyl-phenyl)-vinyl]-1H-benzimidazol-5-yl}-N-methyl-benzenesulfonamide, |
| 457 | N-(2-{2-[2-(4-trifluoromethyl-phenyl)-ethyl]-1H-benzimidazol-5-yl}-phenyl)-acetamide, |
| 458 | (E)-2,2,2-trifluoro-N-(2-{2-[2-(4-trifluoromethyl-phenyl)-vinyl]-1H-benzimidazol-5-yl}-phenyl)-acetamide, |
| 459 | (E)-2,2,2-trifluoro-ethanesulfonic acid (2-{2-[2-(4-trifluoromethyl-phenyl)-vinyl]-1H-benzimidazol-5-yl}-phenyl)-amide, |
| 460 | (E)-2,2-dimethyl-N-(2-{2-[2-(4-trifluoromethyl-phenyl)-vinyl]-1H-benzimidazol-5-yl}-phenyl)-propionamide, |
| 461 | (E)-ethanesulfonic acid (2-{2-[2-(4-trifluoromethyl-phenyl)-vinyl]-1H-benzimidazol-5-yl}-phenyl)-amide, |
| 462 | (E)-(2-{2-[2-(4-trifluoromethyl-phenyl)-vinyl]-1H-benzimidazol-5-yl}-phenyl)-carbamic acid methyl ester, |
| 463 | (E)-2-(2-{2-[2-(4-tert-butyl-phenyl)-vinyl]-1H-benzimidazol-5-yl}-phenyl)-propan-2-ol, |
| 464 | 2-(2-{2-[2-(4-trifluoromethyl-phenyl)-ethyl]-1H-benzimidazol-5-yl}-phenyl)-propan-2-ol, |
| 465 | (E)-2-{2-[2-(4-trifluoromethyl-phenyl)-vinyl]-1H-benzimidazol-5-yl}-phenylamine, |
| 466 | (E)-2-{2-[2-(4-trifluoromethyl-phenyl)-vinyl]-1H-benzimidazol-5-yl}-benzoic acid ethyl ester, |
| 467 | N-(2-{2-[2-(4-trifluoromethyl-phenyl)-cyclopropyl]-1H-benzimidazol-5-yl}-phenyl)-methanesulfonamide, |
| 468 | (E)-2-[2-(2-styryl-1H-benzimidazol-5-yl)-phenyl]-propan-2-ol, |
| 469 | (Z)-2-(2-{2-[2-(4-trifluoromethyl-phenyl)-vinyl]-1H-benzimidazol-5-yl}-phenyl)-propan-2-ol, |
| 470 | (E)-5-(2-aminosulfonylamino-phenyl)-2-[2-(4-trifluoromethyl-phenyl)-vinyl]-1H-benzimidazole, |
| 471 | 2-(2-{2-[2-(4-trifluoromethyl-phenyl)-cyclopropyl]-1H-benzimidazol-5-yl}-phenyl)-propan-2-ol, |
| 472 | 2-{2-[2-(4-trifluoromethyl-phenyl)-cyclopropyl]-1H-benzimidazol-5-yl}-phenol, |
| 473 | (2-{2-[2-(4-trifluoromethyl-phenyl)-cyclopropyl]-1H-benzimidazol-5-yl}-phenyl)-carbamic acid tert-butyl ester, |
| 474 | (2-{2-[2-(4-trifluoromethyl-phenyl)-cyclopropyl]-1H-benzimidazol-5-yl}-phenyl)-methanol, |
| 475 | (E)-N-{2-[2-(2-biphenyl-4-yl-vinyl)-1H-benzimidazol-5-yl]-phenyl}-methanesulfonamide, |
| 476 | (E)-(2-{2-[2-(4-trifluoromethyl-phenyl)-vinyl]-1H-benzimidazol-5-yl}-phenyl)-methanol, |
| 477 | (E)-N-(2-{1-methyl-2-[2-(4-trifluoromethyl-phenyl)-vinyl]-1H-benzimidazol-5-yl}-phenyl)-methanesulfonamide, |
| 478 | (E)-N-(2-{2-[2-(4-trifluoromethyl-phenyl)-vinyl]-1H-benzimidazol-5-yl}-phenyl)-acetamide, |
| 479 | (E)-(2-{2-[2-(4-trifluoromethyl-phenyl)-vinyl]-1H-benzimidazol-5-yl}-phenyl)-carbamic acid tert-butyl ester, |
| 480 | (E)-5-(2-methylsulfanyl-phenyl)-2-[2-(4-trifluoromethyl-phenyl)-vinyl]-1H-benzimidazole, |
| 481 | (E)-2-[2-(4-trifluoromethanesulfonyl-phenyl)-vinyl]-5-(2-trifluoromethyl-phenyl)-1H-benzimidazole, |
| 482 | (E)-2-(2-{2-[2-(2-trifluoromethyl-phenyl)-vinyl]-1H-benzimidazol-5-yl}-phenyl)-propan-2-ol, |
| 483 | (E)-dimethyl-(2-{2-[2-(4-trifluoromethyl-phenyl)-vinyl]-1H-benzimidazol-5-yl}-benzyl)-amine, |
| 484 | (E)-2-{2-[2-(4-trifluoromethyl-phenyl)-vinyl]-1H-benzimidazol-5-yl}-benzaldehyde, |
| 485 | (E)-methyl-(2-{2-[2-(4-trifluoromethyl-phenyl)-vinyl]-1H-benzimidazol-5-yl}-benzyl)-amine, |
| 486 | 2-{2-[2-(4-trifluoromethyl-phenyl)-ethyl]-1H-benzimidazol-5-yl}-benzylamine, |
| 487 | (E)-5-(2-trifluoromethyl-phenyl)-2-[2-(4-trifluoromethyl-phenyl)-vinyl]-1H-benzimidazole, |
| 488 | (E)-5-(2-trifluoromethoxy-phenyl)-2-[2-(4-trifluoromethyl-phenyl)-vinyl]-1H-benzimidazole, |
| 489 | 2-[2-(2-phenylethynyl-1H-benzimidazol-5-yl)-phenyl]-propan-2-ol, |

| Cpd | Name |
|---|---|
| 490 | 2-(2-phenylethynyl-1H-benzimidazol-5-yl)-benzenesulfonamide, |
| 491 | (E)-5-(2-aminosulfonylamino-methylphenyl)-2-[2-(4-trifluoromethyl-phenyl)-vinyl]-1H-benzimidazole, |
| 492 | 2-{2-[2-(4-trifluoromethyl-phenylethynyl)-1H-benzimidazol-5-yl]-phenyl}-propan-2-ol, |
| 494 | 2-(2-{2-[2-(4-methoxy-phenyl)-cyclopropyl]-1H-benzimidazol-5-yl}-phenyl)-propan-2-ol, |
| 497 | 2-(2-{2-[2-(4-trifluoromethoxy-phenyl)-cyclopropyl]-1H-benzimidazol-5-yl}-phenyl)-propan-2-ol, |
| 498 | 2-{2-[2-(4-trifluoromethyl-phenyl)-cyclopropyl]-1H-benzimidazol-5-yl}-benzamide, |
| 499 | N-tert-butyl-2-{2-[2-(4-trifluoromethyl-phenyl)-cyclopropyl]-1H-benzimidazol-5-yl}-benzenesulfonamide, |
| 500 | 5-(2-methanesulfonyl-phenyl)-2-[2-(4-trifluoromethyl-phenyl)-cyclopropyl]-1H-benzimidazole, |
| 501 | 2-(2-{2-[(1R,2R)-2-(4-trifluoromethyl-phenyl)-cyclopropyl]-1H-benzimidazol-5-yl}-phenyl)-propan-2-ol, |
| 502 | 2-{2-[(1R,2R)-2-(4-trifluoromethyl-phenyl)-cyclopropyl]-1H-benzimidazol-5-yl}-benzenesulfonamide, |
| 503 | 2-(2-{2-[(1S,2S)-2-(4-trifluoromethyl-phenyl)-cyclopropyl]-1H-benzimidazol-5-yl}-phenyl)-propan-2-ol, |
| 504 | 2-{2-[(1S,2S)-2-(4-trifluoromethyl-phenyl)-cyclopropyl]-1H-benzimidazol-5-yl}-benzenesulfonamide, |
| 505 | 2-(2-{2-[(1S,2R)-2-(4-trifluoromethyl-phenyl)-cyclopropyl]-1H-benzimidazol-5-yl}-phenyl)-propan-2-ol, |
| 506 | 2-{2-[(1R,2S)-2-(4-trifluoromethyl-phenyl)-cyclopropyl]-1H-benzimidazol-5-yl}-benzenesulfonamide, |
| 507 | 2-(2-{2-[(1R,2S)-2-(4-trifluoromethyl-phenyl)-cyclopropyl]-1H-benzimidazol-5-yl}-phenyl)-propan-2-ol, and |
| 508 | 2-{2-[(1S,2R)-2-(4-trifluoromethyl-phenyl)-cyclopropyl]-1H-benzimidazol-5-yl}-benzenesulfonamide. |

A representative compound of Formula (I) or a form thereof includes a compound selected from the group consisting of:

| Cpd | Name |
|---|---|
| 1 | (E)-1-(2-{2-[2-(4-tert-butyl-phenyl)-vinyl]-1H-benzimidazol-5-yl}-phenyl)-ethanone, |
| 2 | (E)-1-(2-{2-[2-(4-tert-butyl-phenyl)-vinyl]-1H-benzimidazol-5-yl}-phenyl)-ethanol, |
| 3 | (E)-2-{2-[2-(4-tert-butyl-phenyl)-vinyl]-1H-benzimidazol-5-yl}-phenol, |
| 4 | (E)-N-(2-{2-[2-(4-tert-butyl-phenyl)-vinyl]-1H-benzimidazol-5-yl}-phenyl)-acetamide, |
| 5 | (E)-2-{2-[2-(4-tert-butyl-phenyl)-vinyl]-1H-benzimidazol-5-yl}-benzamide, |
| 6 | (E)-3-{2-[2-(4-tert-butyl-phenyl)-vinyl]-1H-benzimidazol-5-yl}-benzamide, |
| 7 | (E)-4-{2-[2-(4-tert-butyl-phenyl)-vinyl]-1H-benzimidazol-5-yl}-benzamide, |
| 8 | (E)-N-(4-{2-[2-(4-tert-butyl-phenyl)-vinyl]-1H-benzimidazol-5-yl}-phenyl)-acetamide, |
| 9 | (E)-N-(2-{2-[2-(4-tert-butyl-phenyl)-vinyl]-1H-benzimidazol-5-yl}-phenyl)-methanesulfonamide, |
| 10 | (E)-(2-{2-[2-(4-tert-butyl-phenyl)-vinyl]-1H-benzimidazol-5-yl}-phenyl)-carbamic acid tert-butyl ester, |
| 11 | (E)-2-{2-[2-(4-tert-butyl-phenyl)-vinyl]-1H-benzimidazol-5-yl}-phenylamine, |
| 12 | (E)-(2-{2-[2-(4-tert-butyl-phenyl)-vinyl]-1H-benzimidazol-5-yl}-phenyl)-methanol, |
| 13 | (E)-2-{2-[2-(4-trifluoromethyl-phenyl)-vinyl]-1H-benzimidazol-5-yl}-benzamide, |
| 14 | (E)-2-{2-[2-(4-trifluoromethyl-phenyl)-vinyl]-1H-benzimidazol-5-yl}-phenol, |
| 15 | (E)-1-(2-{2-[2-(4-trifluoromethyl-phenyl)-vinyl]-1H-benzimidazol-5-yl}-phenyl)-ethanone, |
| 16 | (E)-1-(2-{2-[2-(4-trifluoromethyl-phenyl)-vinyl]-1H-benzimidazol-5-yl}-phenyl)-ethanol, |
| 17 | (E)-N-(2-{2-[2-(4-trifluoromethyl-phenyl)-vinyl]-1H-benzimidazol-5-yl}-phenyl)-methanesulfonamide, |
| 18 | (E)-2-(2-{2-[2-(4-trifluoromethyl-phenyl)-vinyl]-1H-benzimidazol-5-yl}-phenyl)-propan-2-ol, |
| 19 | (E)-2-{2-[2-(4-trifluoromethoxy-phenyl)-vinyl]-1H-benzimidazol-5-yl}-benzamide, |
| 20 | (E)-1-(2-{2-[2-(4-trifluoromethoxy-phenyl)-vinyl]-1H-benzimidazol-5-yl}-phenyl)-ethanone, |

| Cpd | Name |
|---|---|
| 21 | (E)-1-(2-{2-[2-(4-trifluoromethoxy-phenyl)-vinyl]-1H-benzimidazol-5-yl}-phenyl)-ethanol, |
| 22 | (E)-N-(2-{2-[2-(4-trifluoromethoxy-phenyl)-vinyl]-1H-benzimidazol-5-yl}-phenyl)-methanesulfonamide, |
| 23 | (E)-2-(2-{2-[2-(4-trifluoromethoxy-phenyl)-vinyl]-1H-benzimidazol-5-yl}-phenyl)-propan-2-ol, |
| 24 | (E)-N-(2-{2-[2-(3,4-difluoro-phenyl)-vinyl]-1H-benzimidazol-5-yl}-phenyl)-acetamide, |
| 25 | (E)-N-(3-{2-[2-(3,4-difluoro-phenyl)-vinyl]-1H-benzimidazol-5-yl}-phenyl)-acetamide, |
| 26 | (E)-2-{2-[2-(3,4-difluoro-phenyl)-vinyl]-1H-benzimidazol-5-yl}-benzamide, |
| 27 | (E)-1-(2-{2-[2-(3,4-difluoro-phenyl)-vinyl]-1H-benzimidazol-5-yl}-phenyl)-ethanone, |
| 28 | (E)-N-(2-{2-[2-(3,4-difluoro-phenyl)-vinyl]-1H-benzimidazol-5-yl}-phenyl)-methanesulfonamide, |
| 29 | 2-{2-[3-(4-tert-butyl-phenyl)-propyl]-1H-benzimidazol-5-yl}-phenol, |
| 30 | 2-[3-(4-tert-butyl-phenyl)-propyl]-5-m-tolyl-1H-benzimidazole, |
| 31 | N-(2-{2-[2-(4-trifluoromethyl-phenyl)-ethyl]-1H-benzimidazol-5-yl}-phenyl)-methanesulfonamide, |
| 32 | 2-{2-[2-(4-tert-butyl-phenyl)-ethyl]-1H-benzimidazol-5-yl}-phenol, |
| 33 | 3-{2-[2-(4-tert-butyl-phenyl)-ethyl]-1H-benzimidazol-5-yl}-phenol, |
| 34 | 4-{2-[2-(4-tert-butyl-phenyl)-ethyl]-1H-benzimidazol-5-yl}-phenol, |
| 35 | (E)-(2-{2-[2-(4-trifluoromethylsulfanyl-phenyl)-vinyl]-1H-benzimidazol-5-yl}-phenyl)-methanol, |
| 36 | (E)-2-{2-[2-(4-trifluoromethylsulfanyl-phenyl)-vinyl]-1H-benzimidazol-5-yl}-phenol, |
| 37 | (E)-N-(2-{2-[2-(4-trifluoromethylsulfanyl-phenyl)-vinyl]-1H-benzimidazol-5-yl}-phenyl)-acetamide, |
| 38 | (E)-2-{2-[2-(4-trifluoromethylsulfanyl-phenyl)-vinyl]-1H-benzimidazol-5-yl}-benzamide, |
| 39 | (E)-1-(2-{2-[2-(4-trifluoromethylsulfanyl-phenyl)-vinyl]-1H-benzimidazol-5-yl}-phenyl)-ethanone, |
| 40 | (E)-1-(2-{2-[2-(4-trifluoromethanesulfonyl-phenyl)-vinyl]-1H-benzimidazol-5-yl}-phenyl)-ethanone, |
| 41 | (E)-2-{2-[2-(4-trifluoromethanesulfonyl-phenyl)-vinyl]-1H-benzimidazol-5-yl}-phenol, |
| 42 | (E)-(2-{2-[2-(4-trifluoromethanesulfonyl-phenyl)-vinyl]-1H-benzimidazol-5-yl}-phenyl)-methanol, |
| 43 | (E)-N-(2-{2-[2-(4-trifluoromethanesulfonyl-phenyl)-vinyl]-1H-benzimidazol-5-yl}-phenyl)-acetamide, |
| 44 | (E)-2-{2-[2-(4-trifluoromethanesulfonyl-phenyl)-vinyl]-1H-benzimidazol-5-yl}-benzamide, |
| 45 | (E)-1-(2-{2-[2-(4-trifluoromethanesulfonyl-phenyl)-vinyl]-1H-benzimidazol-5-yl}-phenyl)-ethanol, |
| 46 | 1-(2-{2-[2-(4-trifluoromethanesulfonyl-phenyl)-ethyl]-1H-benzimidazol-5-yl}-phenyl)-ethanol, |
| 47 | (E)-2-(2-{2-[2-(4-trifluoromethanesulfonyl-phenyl)-vinyl]-1H-benzimidazol-5-yl}-phenyl)-propan-2-ol, |
| 48 | (E)-2-{2-[2-(4-tert-butyl-phenyl)-vinyl]-6-trifluoromethyl-1H-benzimidazol-5-yl}-phenol, |
| 49 | (E)-3-{2-[2-(4-tert-butyl-phenyl)-vinyl]-6-trifluoromethyl-1H-benzimidazol-5-yl}-phenol, |
| 50 | (E)-N-(2-{2-[2-(4-tert-butyl-phenyl)-vinyl]-6-trifluoromethyl-1H-benzimidazol-5-yl}-phenyl)-acetamide, |
| 51 | (E)-(2-{2-[2-(4-tert-butyl-phenyl)-vinyl]-6-trifluoromethyl-1H-benzimidazol-5-yl}-phenyl)-methanol, |
| 52 | (E)-2-[2-(4-tert-butyl-phenyl)-vinyl]-5-(2-fluoro-phenyl)-6-trifluoromethyl-1H-benzimidazole, |
| 53 | (E)-2-{2-[2-(4-tert-butyl-phenyl)-vinyl]-6-trifluoromethyl-1H-benzimidazol-5-yl}-benzamide, |
| 54 | (E)-(2-{2-[2-(4-tert-butyl-phenyl)-vinyl]-6-trifluoromethyl-1H-benzimidazol-5-yl}-phenyl)-carbamic acid tert-butyl ester, |
| 55 | (E)-N-(2-{2-[2-(4-tert-butyl-phenyl)-vinyl]-6-trifluoromethyl-1H-benzimidazol-5-yl}-phenyl)-methanesulfonamide, |
| 56 | (E)-N-(2-{6-trifluoromethyl-2-[2-(4-trifluoromethyl-phenyl)-vinyl]-1H-benzimidazol-5-yl}-phenyl)-acetamide, |
| 57 | (E)-1-(2-{6-trifluoromethyl-2-[2-(4-trifluoromethyl-phenyl)-vinyl]-1H-benzimidazol-5-yl}-phenyl)-ethanone, |
| 58 | (E)-(2-{6-trifluoromethyl-2-[2-(4-trifluoromethyl-phenyl)-vinyl]-1H-benzimidazol-5-yl}-phenyl)-methanol, |
| 59 | (E)-2-{6-fluoro-2-[2-(4-trifluoromethyl-phenyl)-vinyl]-1H-benzimidazol-5-yl}-phenol, |
| 60 | (E)-3-{6-fluoro-2-[2-(4-trifluoromethyl-phenyl)-vinyl]-1H-benzimidazol-5-yl}-phenol, |
| 61 | (E)-(2-{6-fluoro-2-[2-(4-trifluoromethyl-phenyl)-vinyl]-1H-benzimidazol-5-yl}-phenyl)-methanol, |
| 62 | (E)-1-(2-{6-fluoro-2-[2-(4-trifluoromethyl-phenyl)-vinyl]-1H-benzimidazol-5-yl}-phenyl)-ethanone, |

| Cpd | Name |
|---|---|
| 63 | (E)-2-{6-fluoro-2-[2-(4-trifluoromethyl-phenyl)-vinyl]-1H-benzimidazol-5-yl}-benzamide, |
| 64 | (E)-N-(2-{6-fluoro-2-[2-(4-trifluoromethyl-phenyl)-vinyl]-1H-benzimidazol-5-yl}-phenyl)-acetamide, |
| 65 | (E)-N-(2-{6-fluoro-2-[2-(4-trifluoromethyl-phenyl)-vinyl]-1H-benzimidazol-5-yl}-phenyl)-methanesulfonamide, |
| 66 | (E)-(2-{6-chloro-2-[2-(4-trifluoromethyl-phenyl)-vinyl]-1H-benzimidazol-5-yl}-phenyl)-methanol, |
| 67 | (E)-1-(2-{6-chloro-2-[2-(4-trifluoromethyl-phenyl)-vinyl]-1H-benzimidazol-5-yl}-phenyl)-ethanone, |
| 68 | (E)-2-{6-chloro-2-[2-(4-trifluoromethyl-phenyl)-vinyl]-1H-benzimidazol-5-yl}-phenol, |
| 69 | (E)-2-{2-[2-(4-trifluoromethoxy-phenyl)-vinyl]-1H-benzimidazol-5-yl}-benzenesulfonamide, |
| 70 | (E)-2-{2-[2-(4-trifluoromethyl-phenyl)-vinyl]-1H-benzimidazol-5-yl}-benzenesulfonamide, |
| 71 | (E)-2-{2-[2-(4-trifluoromethanesulfonyl-phenyl)-vinyl]-1H-benzimidazol-5-yl}-benzenesulfonamide, |
| 77 | (E)-N-(2-{2-[2-(4-chloro-phenyl)-vinyl]-1H-benzimidazol-5-yl}-phenyl)-methanesulfonamide, |
| 78 | (E)-2-(2-{2-[2-(4-chloro-phenyl)-vinyl]-1H-benzimidazol-5-yl}-phenyl)-propan-2-ol, |
| 79 | (E)-2-{2-[2-(4-chloro-phenyl)-vinyl]-1H-benzimidazol-5-yl}-benzenesulfonamide, |
| 83 | (E)-N-(2-{2-[2-(4-methanesulfonyl-phenyl)-vinyl]-1H-benzimidazol-5-yl}-phenyl)-methanesulfonamide, |
| 84 | (E)-2-(2-{2-[2-(4-methanesulfonyl-phenyl)-vinyl]-1H-benzimidazol-5-yl}-phenyl)-propan-2-ol, |
| 85 | (E)-2-{2-[2-(4-methanesulfonyl-phenyl)-vinyl]-1H-benzimidazol-5-yl}-benzenesulfonamide, |
| 95 | (E)-N-[2-(2-{2-[4-(2,2,2-trifluoro-ethoxy)-phenyl]-vinyl}-1H-benzimidazol-5-yl)-phenyl]-methanesulfonamide, |
| 101 | (E)-N-[2-(2-{2-[4-(2,2,3,3,3-pentafluoro-propoxy)-phenyl]-vinyl}-1H-benzimidazol-5-yl)-phenyl]-methanesulfonamide, |
| 113 | (E)-N-(2-{2-[2-(3-trifluoromethyl-phenyl)-vinyl]-1H-benzimidazol-5-yl}-phenyl)-methanesulfonamide, |
| 114 | (E)-2-(2-{2-[2-(3-trifluoromethyl-phenyl)-vinyl]-1H-benzimidazol-5-yl}-phenyl)-propan-2-ol, |
| 129 | 2-{2-[2-(4-trifluoromethoxy-phenyl)-ethyl]-1H-benzimidazol-5-yl}-benzenesulfonamide, |
| 130 | 2-{2-[2-(4-trifluoromethyl-phenyl)-ethyl]-1H-benzimidazol-5-yl}-benzenesulfonamide, |
| 131 | 2-{2-[2-(4-trifluoromethanesulfonyl-phenyl)-ethyl]-1H-benzimidazol-5-yl}-benzenesulfonamide, |
| 139 | 2-{2-[2-(4-chloro-phenyl)-ethyl]-1H-benzimidazol-5-yl}-benzenesulfonamide, |
| 145 | 2-{2-[2-(4-methanesulfonyl-phenyl)-ethyl]-1H-benzimidazol-5-yl}-benzenesulfonamide, |
| 175 | 2-{2-[2-(3-trifluoromethyl-phenyl)-ethyl]-1H-benzimidazol-5-yl}-benzenesulfonamide, |
| 190 | 2-{2-[2-(4-trifluoromethyl-phenyl)-cyclopropyl]-1H-benzimidazol-5-yl}-benzenesulfonamide, |
| 198 | 2-(2-{2-[2-(4-chloro-phenyl)-cyclopropyl]-1H-benzimidazol-5-yl}-phenyl)-propan-2-ol, |
| 234 | 2-(2-{2-[2-(3-trifluoromethyl-phenyl)-cyclopropyl]-1H-benzimidazol-5-yl}-phenyl)-propan-2-ol, |
| 250 | 2-[2-(4-trifluoromethyl-phenylethynyl)-1H-benzimidazol-5-yl]-benzenesulfonamide, |
| 294 | 2-{2-[2-(3-trifluoromethyl-phenylethynyl)-1H-benzimidazol-5-yl]-phenyl}-propan-2-ol, |
| 295 | 2-[2-(3-trifluoromethyl-phenylethynyl)-1H-benzimidazol-5-yl]-benzenesulfonamide, |
| 309 | (E)-N-tert-butyl-2-{2-[2-(4-trifluoromethyl-phenyl)-vinyl]-1H-benzimidazol-5-yl}-benzenesulfonamide, |
| 310 | (E)-N-methyl-2-{2-[2-(4-trifluoromethyl-phenyl)-vinyl]-1H-benzimidazol-5-yl}-benzenesulfonamide, |
| 311 | (E)-2-hydroxy-1-(2-{2-[2-(4-trifluoromethyl-phenyl)-vinyl]-1H-benzimidazol-5-yl}-phenyl)-ethanone, |
| 312 | (E)-2-{2-[2-(4-bromo-phenyl)-vinyl]-1H-benzimidazol-5-yl}-N-methyl-benzenesulfonamide, |
| 314 | (E)-N-methyl-2-[2-(2-p-tolyl-vinyl)-1H-benzimidazol-5-yl]-benzenesulfonamide, |
| 315 | (E)-2-{2-[2-(4-fluoro-phenyl)-vinyl]-1H-benzimidazol-5-yl}-N-methyl-benzenesulfonamide, |
| 316 | (E)-2-{2-[2-(3,4-dichloro-phenyl)-vinyl]-1H-benzimidazol-5-yl}-N-methyl-benzenesulfonamide, |
| 317 | (E)-2-{2-[2-(3-bromo-4-fluoro-phenyl)-vinyl]-1H-benzimidazol-5-yl}-N-methyl-benzenesulfonamide, |

| Cpd | Name |
|---|---|
| 318 | (E)-2-{2-[2-(4-dimethylamino-phenyl)-vinyl]-1H-benzimidazol-5-yl}-N-methyl-benzenesulfonamide, |
| 319 | (E)-2-{2-[2-(3-fluoro-4-trifluoromethyl-phenyl)-vinyl]-1H-benzimidazol-5-yl}-N-methyl-benzenesulfonamide, |
| 320 | (E)-2-{2-[2-(2-fluoro-4-trifluoromethyl-phenyl)-vinyl]-1H-benzimidazol-5-yl}-N-methyl-benzenesulfonamide, |
| 321 | (E)-2-{2-[2-(3-chloro-4-fluoro-phenyl)-vinyl]-1H-benzimidazol-5-yl}-N-methyl-benzenesulfonamide, |
| 322 | (E)-2-{2-[2-(3-fluoro-5-trifluoromethyl-phenyl)-vinyl]-1H-benzimidazol-5-yl}-N-methyl-benzenesulfonamide, |
| 323 | (E)-N-methyl-2-{2-[2-(2,3,4-trifluoro-phenyl)-vinyl]-1H-benzimidazol-5-yl}-benzenesulfonamide, |
| 324 | (E)-N-methyl-2-{2-[2-(2,4,5-trifluoro-phenyl)-vinyl]-1H-benzimidazol-5-yl}-benzenesulfonamide, |
| 325 | (E)-2-{2-[2-(2,3-difluoro-phenyl)-vinyl]-1H-benzimidazol-5-yl}-N-methyl-benzenesulfonamide, |
| 326 | (E)-2-{2-[2-(2,5-difluoro-phenyl)-vinyl]-1H-benzimidazol-5-yl}-N-methyl-benzenesulfonamide, |
| 327 | (E)-2-{2-[2-(2,6-difluoro-phenyl)-vinyl]-1H-benzimidazol-5-yl}-N-methyl-benzenesulfonamide, |
| 328 | (E)-2-{2-[2-(3,5-difluoro-phenyl)-vinyl]-1H-benzimidazol-5-yl}-N-methyl-benzenesulfonamide, |
| 329 | (E)-2-{2-[2-(3,4-difluoro-phenyl)-vinyl]-1H-benzimidazol-5-yl}-N-methyl-benzenesulfonamide, |
| 330 | (E)-2-{2-[2-(4-fluoro-2-trifluoromethyl-phenyl)-vinyl]-1H-benzimidazol-5-yl}-N-methyl-benzenesulfonamide, |
| 331 | (E)-2-{2-[2-(4-fluoro-3-trifluoromethyl-phenyl)-vinyl]-1H-benzimidazol-5-yl}-N-methyl-benzenesulfonamide, |
| 332 | (E)-2-{2-[2-(2-fluoro-3-trifluoromethyl-phenyl)-vinyl]-1H-benzimidazol-5-yl}-N-methyl-benzenesulfonamide, |
| 333 | (E)-2-{2-[2-(3,5-bis-trifluoromethyl-phenyl)-vinyl]-1H-benzimidazol-5-yl}-N-methyl-benzenesulfonamide, |
| 334 | (E)-2-{2-[2-(2,5-bis-trifluoromethyl-phenyl)-vinyl]-1H-benzimidazol-5-yl}-N-methyl-benzenesulfonamide, |
| 335 | (E)-2-{2-[2-(3-chloro-2-fluoro-phenyl)-vinyl]-1H-benzimidazol-5-yl}-N-methyl-benzenesulfonamide, |
| 336 | (E)-2-{2-[2-(2-chloro-6-fluoro-phenyl)-vinyl]-1H-benzimidazol-5-yl}-N-methyl-benzenesulfonamide, |
| 337 | (E)-2-{2-[2-(2,4-dichloro-phenyl)-vinyl]-1H-benzimidazol-5-yl}-N-methyl-benzenesulfonamide, |
| 338 | (E)-2-{2-[2-(3-bromo-phenyl)-vinyl]-1H-benzimidazol-5-yl}-N-methyl-benzenesulfonamide, |
| 339 | (E)-2-{2-[2-(4-chloro-2-fluoro-phenyl)-vinyl]-1H-benzimidazol-5-yl}-N-methyl-benzenesulfonamide, |
| 340 | (E)-2-{2-[2-(4-chloro-2-methanesulfonyl-phenyl)-vinyl]-1H-benzimidazol-5-yl}-N-methyl-benzenesulfonamide, |
| 341 | (E)-N-methyl-2-{2-[2-(4-trifluoromethylsulfanyl-phenyl)-vinyl]-1H-benzimidazol-5-yl}-benzenesulfonamide, |
| 342 | (E)-N-methyl-2-{2-[2-(4-trifluoromethanesulfonyl-phenyl)-vinyl]-1H-benzimidazol-5-yl}-benzenesulfonamide, |
| 343 | (E)-N-methyl-2-{2-[2-(2-trifluoromethyl-phenyl)-vinyl]-1H-benzimidazol-5-yl}-benzenesulfonamide, |
| 344 | (E)-N-methyl-2-{2-[2-(3-trifluoromethoxy-phenyl)-vinyl]-1H-benzimidazol-5-yl}-benzenesulfonamide |
| 345 | (E)-N-methyl-2-{2-[2-(4-trifluoromethoxy-phenyl)-vinyl]-1H-benzimidazol-5-yl}-benzenesulfonamide, |
| 346 | (E)-2-{2-[2-(2-chloro-phenyl)-vinyl]-1H-benzimidazol-5-yl}-N-methyl-benzenesulfonamide, |
| 347 | (E)-2-{2-[2-(4-chloro-phenyl)-vinyl]-1H-benzimidazol-5-yl}-N-methyl-benzenesulfonamide, |
| 348 | (E)-2-{2-[2-(2-bromo-phenyl)-vinyl]-1H-benzimidazol-5-yl}-N-methyl-benzenesulfonamide, |
| 349 | (E)-2-{2-[2-(2,4-difluoro-phenyl)-vinyl]-1H-benzimidazol-5-yl}-N-methyl-benzenesulfonamide, |
| 350 | N-methyl-2-{2-[2-(3-trifluoromethyl-phenyl)-ethyl]-1H-benzimidazol-5-yl}-benzenesulfonamide, |
| 351 | (E)-2-{2-[2-(4-methanesulfonyl-phenyl)-vinyl]-1H-benzimidazol-5-yl}-N-methyl-benzenesulfonamide, |
| 357 | (E)-2-{2-[2-(2,4-difluoro-phenyl)-vinyl]-1H-benzimidazol-5-yl}-benzenesulfonamide, |
| 358 | (E)-2-{2-[2-(3,4-difluoro-phenyl)-vinyl]-1H-benzimidazol-5-yl}-benzenesulfonamide, |
| 359 | (E)-2-{2-[2-(2,3-difluoro-phenyl)-vinyl]-1H-benzimidazol-5-yl}-benzenesulfonamide, |
| 360 | (E)-2-{2-[2-(2,5-difluoro-phenyl)-vinyl]-1H-benzimidazol-5-yl}-benzenesulfonamide, |
| 361 | (E)-2-{2-[2-(3,5-difluoro-phenyl)-vinyl]-1H-benzimidazol-5-yl}-benzenesulfonamide, |

| Cpd | Name |
|---|---|
| 362 | (E)-2-{2-[2-(3-trifluoromethoxy-phenyl)-vinyl]-1H-benzimidazol-5-yl}-benzenesulfonamide, |
| 363 | (E)-2-{2-[2-(4-bromo-phenyl)-vinyl]-1H-benzimidazol-5-yl}-benzenesulfonamide, |
| 364 | (E)-2-{2-[2-(2-trifluoromethyl-phenyl)-vinyl]-1H-benzimidazol-5-yl}-benzenesulfonamide, |
| 365 | (E)-2-{2-[2-(2-chloro-phenyl)-vinyl]-1H-benzimidazol-5-yl}-benzenesulfonamide, |
| 366 | (E)-2-{2-[2-(2-bromo-phenyl)-vinyl]-1H-benzimidazol-5-yl}-benzenesulfonamide, |
| 367 | (E)-2-{2-[2-(4-fluoro-2-trifluoromethyl-phenyl)-vinyl]-1H-benzimidazol-5-yl}-benzenesulfonamide, |
| 368 | (E)-2-{2-[2-(2-fluoro-3-trifluoromethyl-phenyl)-vinyl]-1H-benzimidazol-5-yl}-benzenesulfonamide, |
| 369 | (E)-2-{2-[2-(4-fluoro-3-trifluoromethyl-phenyl)-vinyl]-1H-benzimidazol-5-yl}-benzenesulfonamide, |
| 370 | (E)-2-{2-[2-(2,3,4-trifluoro-phenyl)-vinyl]-1H-benzimidazol-5-yl}-benzenesulfonamide, |
| 371 | (E)-2-{2-[2-(2,4,5-trifluoro-phenyl)-vinyl]-1H-benzimidazol-5-yl}-benzenesulfonamide, |
| 372 | (E)-2-{2-[2-(2,6-difluoro-phenyl)-vinyl]-1H-benzimidazol-5-yl}-benzenesulfonamide, |
| 373 | (E)-2-{2-[2-(3,5-bis-trifluoromethyl-phenyl)-vinyl]-1H-benzimidazol-5-yl}-benzenesulfonamide, |
| 374 | (E)-2-{2-[2-(2,5-bis-trifluoromethyl-phenyl)-vinyl]-1H-benzimidazol-5-yl}-benzenesulfonamide, |
| 375 | (E)-2-{2-[2-(4-chloro-2-methanesulfonyl-phenyl)-vinyl]-1H-benzimidazol-5-yl}-benzenesulfonamide, |
| 376 | (E)-2-{2-[2-(3-bromo-phenyl)-vinyl]-1H-benzimidazol-5-yl}-benzenesulfonamide, |
| 378 | (E)-2-{2-[2-(4-chloro-3-trifluoromethyl-phenyl)-vinyl]-1H-benzimidazol-5-yl}-benzenesulfonamide, |
| 379 | (E)-2-{2-[2-(5-bromo-2-fluoro-phenyl)-vinyl]-1H-benzimidazol-5-yl}-benzenesulfonamide, |
| 380 | (E)-2-{2-[2-(4-trifluoromethylsulfanyl-phenyl)-vinyl]-1H-benzimidazol-5-yl}-benzenesulfonamide, |
| 383 | 2-{2-[2-(4-fluoro-3-trifluoromethyl-phenyl)-ethyl]-1H-benzimidazol-5-yl}-benzenesulfonamide, |
| 384 | 2-{2-[2-(2,3,4-trifluoro-phenyl)-ethyl]-1H-benzimidazol-5-yl}-benzenesulfonamide, |
| 385 | 2-{2-[2-(2,4,5-trifluoro-phenyl)-ethyl]-1H-benzimidazol-5-yl}-benzenesulfonamide, |
| 386 | 2-{2-[2-(2,6-difluoro-phenyl)-ethyl]-1H-benzimidazol-5-yl}-benzenesulfonamide, |
| 387 | 2-{2-[2-(3,5-bis-trifluoromethyl-phenyl)-ethyl]-1H-benzimidazol-5-yl}-benzenesulfonamide, |
| 388 | 2-{2-[2-(2,5-bis-trifluoromethyl-phenyl)-ethyl]-1H-benzimidazol-5-yl}-benzenesulfonamide, |
| 389 | 2-{2-[2-(4-chloro-2-methanesulfonyl-phenyl)-ethyl]-1H-benzimidazol-5-yl}-benzenesulfonamide, |
| 390 | 2-{2-[2-(4-chloro-3-trifluoromethyl-phenyl)-ethyl]-1H-benzimidazol-5-yl}-benzenesulfonamide, |
| 391 | 2-{2-[2-(3-trifluoromethoxy-phenyl)-ethyl]-1H-benzimidazol-5-yl}-benzenesulfonamide, |
| 392 | 2-{2-[2-(2,4-difluoro-phenyl)-ethyl]-1H-benzimidazol-5-yl}-benzenesulfonamide, |
| 393 | 2-{2-[2-(3,4-difluoro-phenyl)-ethyl]-1H-benzimidazol-5-yl}-benzenesulfonamide, |
| 394 | 2-{2-[2-(2,3-difluoro-phenyl)-ethyl]-1H-benzimidazol-5-yl}-benzenesulfonamide, |
| 395 | 2-{2-[2-(2,5-difluoro-phenyl)-ethyl]-1H-benzimidazol-5-yl}-benzenesulfonamide, |
| 396 | 2-{2-[2-(3,5-difluoro-phenyl)-ethyl]-1H-benzimidazol-5-yl}-benzenesulfonamide, |
| 397 | 2-(2-phenethyl-1H-benzimidazol-5-yl)-benzenesulfonamide, |
| 398 | (E)-N,N-dimethyl-2-{2-[2-(4-trifluoromethyl-phenyl)-vinyl]-1H-benzimidazol-5-yl}-benzenesulfonamide, |
| 399 | N,N-dimethyl-2-{2-[2-(4-trifluoromethyl-phenyl)-ethyl]-1H-benzimidazol-5-yl}-benzenesulfonamide, |
| 400 | N-methyl-2-{2-[2-(4-trifluoromethyl-phenyl)-ethyl]-1H-benzimidazol-5-yl}-benzenesulfonamide, |
| 402 | 2-{2-[2-(2-chloro-phenyl)-ethyl]-1H-benzimidazol-5-yl}-benzenesulfonamide, |
| 404 | 2-{2-[2-(4-fluoro-2-trifluoromethyl-phenyl)-ethyl]-1H-benzimidazol-5-yl}-benzenesulfonamide, |
| 405 | 2-{2-[2-(2-fluoro-3-trifluoromethyl-phenyl)-ethyl]-1H-benzimidazol-5-yl}-benzenesulfonamide, |

-continued

| Cpd | Name |
|---|---|
| 406 | (E)-N-(2-{2-[2-(4-bromo-phenyl)-vinyl]-1H-benzimidazol-5-yl}-phenyl)-methanesulfonamide, |
| 407 | (E)-N-(2-{2-[2-(4-isopropyl-phenyl)-vinyl]-1H-benzimidazol-5-yl}-phenyl)-methanesulfonamide, |
| 408 | (E)-N-(2-{2-[2-(3-chloro-4-fluoro-phenyl)-vinyl]-1H-benzimidazol-5-yl}-phenyl)-methanesulfonamide, |
| 409 | (E)-N-(2-{2-[2-(3-bromo-4-fluoro-phenyl)-vinyl]-1H-benzimidazol-5-yl}-phenyl)-methanesulfonamide, |
| 410 | (E)-N-(2-{2-[2-(4-difluoromethoxy-phenyl)-vinyl]-1H-benzimidazol-5-yl}-phenyl)-methanesulfonamide, |
| 411 | (E)-N-(2-{2-[2-(3-fluoro-5-trifluoromethyl-phenyl)-vinyl]-1H-benzimidazol-5-yl}-phenyl)-methanesulfonamide, |
| 412 | (E)-N-{2-[2-(2-p-tolyl-vinyl)-1H-benzimidazol-5-yl]-phenyl}-methanesulfonamide, |
| 413 | (E)-N-(2-{2-[2-(4-dimethylamino-phenyl)-vinyl]-1H-benzimidazol-5-yl}-phenyl)-methanesulfonamide, |
| 414 | (E)-N-(2-{2-[2-(4-ethoxy-phenyl)-vinyl]-1H-benzimidazol-5-yl}-phenyl)-methanesulfonamide, |
| 415 | (E)-N-{2-[2-(2-naphthalen-2-yl-vinyl)-1H-benzimidazol-5-yl]-phenyl}-methanesulfonamide, |
| 416 | (E)-N-(2-{2-[2-(3,4-dichloro-phenyl)-vinyl]-1H-benzimidazol-5-yl}-phenyl)-methanesulfonamide, |
| 417 | (E)-N-(2-{2-[2-(3-fluoro-4-trifluoromethyl-phenyl)-vinyl]-1H-benzimidazol-5-yl}-phenyl)-methanesulfonamide, |
| 418 | (E)-N-(2-{2-[2-(2-fluoro-4-trifluoromethyl-phenyl)-vinyl]-1H-benzimidazol-5-yl}-phenyl)-methanesulfonamide, |
| 419 | 2-{2-[2-(2-fluoro-phenyl)-ethyl]-1H-benzimidazol-5-yl}-benzenesulfonamide, |
| 420 | 2-{2-[2-(4-fluoro-phenyl)-ethyl]-1H-benzimidazol-5-yl}-benzenesulfonamide, |
| 421 | 2-{2-[2-(3-fluoro-5-trifluoromethyl-phenyl)-ethyl]-1H-benzimidazol-5-yl}-benzenesulfonamide, |
| 422 | (E)-5-(2-methanesulfonyl-phenyl)-2-[2-(4-trifluoromethyl-phenyl)-vinyl]-1H-benzimidazole, |
| 423 | (E)-2-{2-[2-(3-fluoro-4-trifluoromethyl-phenyl)-vinyl]-1H-benzimidazol-5-yl}-benzenesulfonamide, |
| 424 | (E)-2-{2-[2-(2-fluoro-4-trifluoromethyl-phenyl)-vinyl]-1H-benzimidazol-5-yl}-benzenesulfonamide, |
| 425 | (E)-2-{2-[2-(3-ethoxy-phenyl)-vinyl]-1H-benzimidazol-5-yl}-benzenesulfonamide, |
| 426 | (E)-2-(2-styryl-1H-benzimidazol-5-yl)-benzenesulfonamide, |
| 427 | (E)-2-{2-[2-(3,4-dichloro-phenyl)-vinyl]-1H-benzimidazol-5-yl}-benzenesulfonamide, |
| 428 | (E)-2-{2-[2-(4-chloro-2-fluoro-phenyl)-vinyl]-1H-benzimidazol-5-yl}-benzenesulfonamide, |
| 429 | (E)-2-{2-[2-(4-isopropyl-phenyl)-vinyl]-1H-benzimidazol-5-yl}-benzenesulfonamide, |
| 430 | (E)-2-[2-(2-p-tolyl-vinyl)-1H-benzimidazol-5-yl]-benzenesulfonamide, |
| 431 | (E)-2-{2-[2-(3-chloro-2-fluoro-phenyl)-vinyl]-1H-benzimidazol-5-yl}-benzenesulfonamide, |
| 432 | (E)-2-{2-[2-(3-chloro-4-fluoro-phenyl)-vinyl]-1H-benzimidazol-5-yl}-benzenesulfonamide, |
| 433 | (E)-2-[2-(2-naphthalen-2-yl-vinyl)-1H-benzimidazol-5-yl]-benzenesulfonamide, |
| 434 | (E)-2-{2-[2-(4-fluoro-phenyl)-vinyl]-1H-benzimidazol-5-yl}-benzenesulfonamide, |
| 435 | (E)-2-{2-[2-(4-difluoromethyl-phenyl)-vinyl]-1H-benzimidazol-5-yl}-benzenesulfonamide, |
| 436 | (E)-2-{2-[2-(3-fluoro-5-trifluoromethyl-phenyl)-vinyl]-1H-benzimidazol-5-yl}-benzenesulfonamide, |
| 437 | (E)-2-{2-[2-(2,4-dichloro-phenyl)-vinyl]-1H-benzimidazol-5-yl}-benzenesulfonamide, |
| 438 | (E)-2-{2-[2-(2-chloro-6-fluoro-phenyl)-vinyl]-1H-benzimidazol-5-yl}-benzenesulfonamide, |
| 439 | (E)-2-{2-[2-(3-bromo-4-fluoro-phenyl)-vinyl]-1H-benzimidazol-5-yl}-benzenesulfonamide, |
| 440 | (E)-2-{2-[2-(4-ethoxy-phenyl)-vinyl]-1H-benzimidazol-5-yl}-benzenesulfonamide, |
| 441 | (E)-4-fluoro-2-{2-[2-(4-trifluoromethyl-phenyl)-vinyl]-1H-benzimidazol-5-yl}-benzenesulfonamide, |
| 442 | 2-{2-[2-(4-isopropyl-phenyl)-ethyl]-1H-benzimidazol-5-yl}-benzenesulfonamide, |
| 443 | (E)-N-(2-{3-methyl-2-[2-(4-trifluoromethyl-phenyl)-vinyl]-3H-benzimidazol-5-yl}-phenyl)-methanesulfonamide, |
| 444 | (E)-4-trifluoromethyl-2-{2-[2-(4-trifluoromethyl-phenyl)-vinyl]-1H-benzimidazol-5-yl}-benzenesulfonamide, |
| 445 | 4-trifluoromethyl-2-{2-[2-(4-trifluoromethyl-phenyl)-ethyl]-1H-benzimidazol-5-yl}-benzenesulfonamide, |

| Cpd | Name |
|---|---|
| 446 | (E)-5-trifluoromethyl-2-{2-[2-(4-trifluoromethyl-phenyl)-vinyl]-1H-benzimidazol-5-yl}-benzenesulfonamide, |
| 447 | 5-trifluoromethyl-2-{2-[2-(4-trifluoromethyl-phenyl)-ethyl]-1H-benzimidazol-5-yl}-benzenesulfonamide, |
| 448 | (E)-1-[4-(2-{5-[2-(1-hydroxy-1-methyl-ethyl)-phenyl]-1H-benzimidazol-2-yl}-vinyl)-phenyl]-ethanone, |
| 449 | (E)-2-{2-[2-(2-quinolin-6-yl-vinyl)-1H-benzimidazol-5-yl]-phenyl}-propan-2-ol, |
| 450 | (E)-N-isopropyl-4-{2-[5-(2-methylsulfamoyl-phenyl)-1H-benzimidazol-2-yl]-vinyl}-benzamide, |
| 451 | (E)-2-{2-[2-(4-cyano-phenyl)-vinyl]-1H-benzimidazol-5-yl}-N-methyl-benzenesulfonamide, |
| 452 | (E)-N-(4-{2-[5-(2-methylsulfamoyl-phenyl)-1H-benzimidazol-2-yl]-vinyl}-phenyl)-acetamide, |
| 453 | (E)-4-{2-[5-(2-methylsulfamoyl-phenyl)-1H-benzimidazol-2-yl]-vinyl}-benzoic acid, |
| 454 | (E)-2-{2-[2-(1H-indol-6-yl)-vinyl]-1H-benzimidazol-5-yl}-N-methyl-benzenesulfonamide, |
| 455 | (E)-2-{2-[2-(2,4-bis-trifluoromethyl-phenyl)-vinyl]-1H-benzimidazol-5-yl}-N-methyl-benzenesulfonamide, |
| 456 | (E)-2-{2-[2-(4-acetyl-phenyl)-vinyl]-1H-benzimidazol-5-yl}-N-methyl-benzenesulfonamide, |
| 457 | N-(2-{2-[2-(4-trifluoromethyl-phenyl)-ethyl]-1H-benzimidazol-5-yl}-phenyl)-acetamide, |
| 458 | (E)-2,2,2-trifluoro-N-(2-{2-[2-(4-trifluoromethyl-phenyl)-vinyl]-1H-benzimidazol-5-yl}-phenyl)-acetamide, |
| 459 | (E)-2,2,2-trifluoro-ethanesulfonic acid (2-{2-[2-(4-trifluoromethyl-phenyl)-vinyl]-1H-benzimidazol-5-yl}-phenyl)-amide, |
| 460 | (E)-2,2-dimethyl-N-(2-{2-[2-(4-trifluoromethyl-phenyl)-vinyl]-1H-benzimidazol-5-yl}-phenyl)-propionamide, |
| 461 | (E)-ethanesulfonic acid (2-{2-[2-(4-trifluoromethyl-phenyl)-vinyl]-1H-benzimidazol-5-yl}-phenyl)-amide, |
| 462 | (E)-(2-{2-[2-(4-trifluoromethyl-phenyl)-vinyl]-1H-benzimidazol-5-yl}-phenyl)-carbamic acid methyl ester, |
| 463 | (E)-2-(2-{2-[2-(4-tert-butyl-phenyl)-vinyl]-1H-benzimidazol-5-yl]-phenyl)-propan-2-ol, |
| 464 | 2-(2-{2-[2-(4-trifluoromethyl-phenyl)-ethyl]-1H-benzimidazol-5-yl}-phenyl)-propan-2-ol, |
| 465 | (E)-2-{2-[2-(4-trifluoromethyl-phenyl)-vinyl]-1H-benzimidazol-5-yl}-phenylamine, |
| 466 | (E)-2-{2-[2-(4-trifluoromethyl-phenyl)-vinyl]-1H-benzimidazol-5-yl}-benzoic acid ethyl ester, |
| 467 | N-(2-{2-[2-(4-trifluoromethyl-phenyl)-cyclopropyl]-1H-benzimidazol-5-yl}-phenyl)-methanesulfonamide, |
| 468 | (E)-2-[2-(2-styryl-1H-benzimidazol-5-yl)-phenyl]-propan-2-ol, |
| 469 | (Z)-2-(2-{2-[2-(4-trifluoromethyl-phenyl)-vinyl]-1H-benzimidazol-5-yl}-phenyl)-propan-2-ol, |
| 470 | (E)-5-(2-aminosulfonylamino-phenyl)-2-[2-(4-trifluoromethyl-phenyl)-vinyl]-1H-benzimidazole, |
| 471 | 2-(2-{2-[2-(4-trifluoromethyl-phenyl)-cyclopropyl]-1H-benzimidazol-5-yl}-phenyl)-propan-2-ol, |
| 472 | 2-{2-[2-(4-trifluoromethyl-phenyl)-cyclopropyl]-1H-benzimidazol-5-yl}-phenol, |
| 473 | (2-{2-[2-(4-trifluoromethyl-phenyl)-cyclopropyl]-1H-benzimidazol-5-yl}-phenyl)-carbamic acid tert-butyl ester, |
| 474 | (2-{2-[2-(4-trifluoromethyl-phenyl)-cyclopropyl]-1H-benzimidazol-5-yl}-phenyl)-methanol, |
| 475 | (E)-N-{2-[2-(2-biphenyl-4-yl-vinyl)-1H-benzimidazol-5-yl]-phenyl}-methanesulfonamide, |
| 476 | (E)-(2-{2-[2-(4-trifluoromethyl-phenyl)-vinyl]-1H-benzimidazol-5-yl}-phenyl)-methanol, |
| 477 | (E)-N-(2-{1-methyl-2-[2-(4-trifluoromethyl-phenyl)-vinyl]-1H-benzimidazol-5-yl}-phenyl)-methanesulfonamide, |
| 478 | (E)-N-(2-{2-[2-(4-trifluoromethyl-phenyl)-vinyl]-1H-benzimidazol-5-yl}-phenyl)-acetamide, |
| 479 | (E)-(2-{2-[2-(4-trifluoromethyl-phenyl)-vinyl]-1H-benzimidazol-5-yl}-phenyl)-carbamic acid tert-butyl ester, |
| 480 | (E)-5-(2-methylsulfanyl-phenyl)-2-[2-(4-trifluoromethyl-phenyl)-vinyl]-1H-benzimidazole, |
| 481 | (E)-2-[2-(4-trifluoromethanesulfonyl-phenyl)-vinyl]-5-(2-trifluoromethyl-phenyl)-1H-benzimidazole, |
| 482 | (E)-2-(2-{2-[2-(2-trifluoromethyl-phenyl)-vinyl]-1H-benzimidazol-5-yl}-phenyl)-propan-2-ol, |
| 483 | (E)-dimethyl-(2-{2-[2-(4-trifluoromethyl-phenyl)-vinyl]-1H-benzimidazol-5-yl}-benzyl)-amine, |
| 484 | (E)-2-{2-[2-(4-trifluoromethyl-phenyl)-vinyl]-1H-benzimidazol-5-yl}-benzaldehyde, |

-continued

| Cpd | Name |
|---|---|
| 485 | (E)-methyl-(2-{2-[2-(4-trifluoromethyl-phenyl)-vinyl]-1H-benzimidazol-5-yl}-benzyl)-amine, |
| 486 | 2-{2-[2-(4-trifluoromethyl-phenyl)-ethyl]-1H-benzimidazol-5-yl}-benzylamine, |
| 487 | (E)-5-(2-trifluoromethyl-phenyl)-2-[2-(4-trifluoromethyl-phenyl)-vinyl]-1H-benzimidazole, |
| 488 | (E)-5-(2-trifluoromethoxy-phenyl)-2-[2-(4-trifluoromethyl-phenyl)-vinyl]-1H-benzimidazole, |
| 489 | 2-[2-(2-phenylethynyl-1H-benzimidazol-5-yl)-phenyl]-propan-2-ol, |
| 490 | 2-(2-phenylethynyl-1H-benzimidazol-5-yl)-benzenesulfonamide, |
| 491 | (E)-5-(2-aminosulfonylamino-methylphenyl)-2-[2-(4-trifluoromethyl-phenyl)-vinyl]-1H-benzimidazole, |
| 492 | 2-{2-[2-(4-trifluoromethyl-phenylethynyl)-1H-benzimidazol-5-yl]-phenyl}-propan-2-ol, |
| 494 | 2-(2-{2-[2-(4-methoxy-phenyl)-cyclopropyl]-1H-benzimidazol-5-yl}-phenyl)-propan-2-ol, |
| 497 | 2-(2-{2-[2-(4-trifluoromethoxy-phenyl)-cyclopropyl]-1H-benzimidazol-5-yl}-phenyl)-propan-2-ol, |
| 498 | 2-{2-[2-(4-trifluoromethyl-phenyl)-cyclopropyl]-1H-benzimidazol-5-yl}-benzamide, |
| 499 | N-tert-butyl-2-{2-[2-(4-trifluoromethyl-phenyl)-cyclopropyl]-1H-benzimidazol-5-yl}-benzenesulfonamide, |
| 500 | 5-(2-methanesulfonyl-phenyl)-2-[2-(4-trifluoromethyl-phenyl)-cyclopropyl]-1H-benzimidazole, |
| 501 | 2-(2-{2-[(1R,2R)-2-(4-trifluoromethyl-phenyl)-cyclopropyl]-1H-benzimidazol-5-yl}-phenyl)-propan-2-ol, |
| 502 | 2-{2-[(1R,2R)-2-(4-trifluoromethyl-phenyl)-cyclopropyl]-1H-benzimidazol-5-yl}-benzenesulfonamide, |
| 503 | 2-(2-{2-[(1S,2S)-2-(4-trifluoromethyl-phenyl)-cyclopropyl]-1H-benzimidazol-5-yl}-phenyl)-propan-2-ol, |
| 504 | 2-{2-[(1S,2S)-2-(4-trifluoromethyl-phenyl)-cyclopropyl]-1H-benzimidazol-5-yl}-benzenesulfonamide, |
| 505 | 2-(2-{2-[(1S,2R)-2-(4-trifluoromethyl-phenyl)-cyclopropyl]-1H-benzimidazol-5-yl}-phenyl)-propan-2-ol, |
| 506 | 2-{2-[(1R,2S)-2-(4-trifluoromethyl-phenyl)-cyclopropyl]-1H-benzimidazol-5-yl}-benzenesulfonamide, |
| 507 | 2-(2-{2-[(1R,2S)-2-(4-trifluoromethyl-phenyl)-cyclopropyl]-1H-benzimidazol-5-yl}-phenyl)-propan-2-ol, and |
| 508 | 2-{2-[(1S,2R)-2-(4-trifluoromethyl-phenyl)-cyclopropyl]-1H-benzimidazol-5-yl}-benzenesulfonamide. |

A representative compound of Formula (I) or a form thereof includes a compound selected from the group consisting of:

| Cpd | Name |
|---|---|
| 1 | (E)-1-(2-{2-[2-(4-tert-butyl-phenyl)-vinyl]-1H-benzimidazol-5-yl}-phenyl)-ethanone, |
| 2 | (E)-1-(2-{2-[2-(4-tert-butyl-phenyl)-vinyl]-1H-benzimidazol-5-yl}-phenyl)-ethanol, |
| 3 | (E)-2-{2-[2-(4-tert-butyl-phenyl)-vinyl]-1H-benzimidazol-5-yl}-phenol, |
| 4 | (E)-N-(2-{2-[2-(4-tert-butyl-phenyl)-vinyl]-1H-benzimidazol-5-yl}-phenyl)-acetamide, |
| 5 | (E)-2-{2-[2-(4-tert-butyl-phenyl)-vinyl]-1H-benzimidazol-5-yl}-benzamide, |
| 9 | (E)-N-(2-{2-[2-(4-tert-butyl-phenyl)-vinyl]-1H-benzimidazol-5-yl}-phenyl)-methanesulfonamide, |
| 10 | (E)-(2-{2-[2-(4-tert-butyl-phenyl)-vinyl]-1H-benzimidazol-5-yl}-phenyl)-carbamic acid tert-butyl ester, |
| 11 | (E)-2-{2-[2-(4-tert-butyl-phenyl)-vinyl]-1H-benzimidazol-5-yl}-phenylamine, |
| 12 | (E)-(2-{2-[2-(4-tert-butyl-phenyl)-vinyl]-1H-benzimidazol-5-yl}-phenyl)-methanol, |
| 13 | (E)-2-{2-[2-(4-trifluoromethyl-phenyl)-vinyl]-1H-benzimidazol-5-yl}-benzamide, |
| 15 | (E)-1-(2-{2-[2-(4-trifluoromethyl-phenyl)-vinyl]-1H-benzimidazol-5-yl}-phenyl)-ethanone, |
| 16 | (E)-1-(2-{2-[2-(4-trifluoromethyl-phenyl)-vinyl]-1H-benzimidazol-5-yl}-phenyl)-ethanol, |
| 17 | (E)-N-(2-{2-[2-(4-trifluoromethyl-phenyl)-vinyl]-1H-benzimidazol-5-yl}-phenyl)-methanesulfonamide, |
| 18 | (E)-2-(2-{2-[2-(4-trifluoromethyl-phenyl)-vinyl]-1H-benzimidazol-5-yl}-phenyl)-propan-2-ol, |

-continued

| Cpd | Name |
|---|---|
| 22 | (E)-N-(2-{2-[2-(4-trifluoromethoxy-phenyl)-vinyl]-1H-benzimidazol-5-yl}-phenyl)-methanesulfonamide, |
| 27 | (E)-1-(2-{2-[2-(3,4-difluoro-phenyl)-vinyl]-1H-benzimidazol-5-yl}-phenyl)-ethanone, |
| 28 | (E)-N-(2-{2-[2-(3,4-difluoro-phenyl)-vinyl]-1H-benzimidazol-5-yl}-phenyl)-methanesulfonamide, |
| 31 | N-(2-{2-[2-(4-trifluoromethyl-phenyl)-ethyl]-1H-benzimidazol-5-yl}-phenyl)-methanesulfonamide, |
| 32 | 2-{2-[2-(4-tert-butyl-phenyl)-ethyl]-1H-benzimidazol-5-yl}-phenol, |
| 34 | 4-{2-[2-(4-tert-butyl-phenyl)-ethyl]-1H-benzimidazol-5-yl}-phenol, |
| 35 | (E)-(2-{2-[2-(4-trifluoromethylsulfanyl-phenyl)-vinyl]-1H-benzimidazol-5-yl}-phenyl)-methanol, |
| 38 | (E)-2-{2-[2-(4-trifluoromethylsulfanyl-phenyl)-vinyl]-1H-benzimidazol-5-yl}-benzamide, |
| 39 | (E)-1-(2-{2-[2-(4-trifluoromethylsulfanyl-phenyl)-vinyl]-1H-benzimidazol-5-yl}-phenyl)-ethanone, |
| 40 | (E)-1-(2-{2-[2-(4-trifluoromethanesulfonyl-phenyl)-vinyl]-1H-benzimidazol-5-yl}-phenyl)-ethanone, |
| 41 | (E)-2-{2-[2-(4-trifluoromethanesulfonyl-phenyl)-vinyl]-1H-benzimidazol-5-yl}-phenol, |
| 42 | (E)-(2-{2-[2-(4-trifluoromethanesulfonyl-phenyl)-vinyl]-1H-benzimidazol-5-yl}-phenyl)-methanol, |
| 44 | (E)-2-{2-[2-(4-trifluoromethanesulfonyl-phenyl)-vinyl]-1H-benzimidazol-5-yl}-benzamide, |
| 45 | (E)-1-(2-{2-[2-(4-trifluoromethanesulfonyl-phenyl)-vinyl]-1H-benzimidazol-5-yl}-phenyl)-ethanol, |
| 46 | 1-(2-{2-[2-(4-trifluoromethanesulfonyl-phenyl)-ethyl]-1H-benzimidazol-5-yl}-phenyl)-ethanol, |
| 47 | (E)-2-(2-{2-[2-(4-trifluoromethanesulfonyl-phenyl)-vinyl]-1H-benzimidazol-5-yl}-phenyl)-propan-2-ol, |
| 50 | (E)-N-(2-{2-[2-(4-tert-butyl-phenyl)-vinyl]-6-trifluoromethyl-1H-benzimidazol-5-yl}-phenyl)-acetamide, |
| 51 | (E)-(2-{2-[2-(4-tert-butyl-phenyl)-vinyl]-6-trifluoromethyl-1H-benzimidazol-5-yl}-phenyl)-methanol, |
| 53 | (E)-2-{2-[2-(4-tert-butyl-phenyl)-vinyl]-6-trifluoromethyl-1H-benzimidazol-5-yl}-benzamide, |
| 56 | (E)-N-(2-{6-trifluoromethyl-2-[2-(4-trifluoromethyl-phenyl)-vinyl]-1H-benzimidazol-5-yl}-phenyl)-acetamide, |
| 58 | (E)-(2-{6-trifluoromethyl-2-[2-(4-trifluoromethyl-phenyl)-vinyl]-1H-benzimidazol-5-yl}-phenyl)-methanol, |
| 59 | (E)-2-{6-fluoro-2-[2-(4-trifluoromethyl-phenyl)-vinyl]-1H-benzimidazol-5-yl}-phenol, |
| 61 | (E)-(2-{6-fluoro-2-[2-(4-trifluoromethyl-phenyl)-vinyl]-1H-benzimidazol-5-yl}-phenyl)-methanol, |
| 62 | (E)-1-(2-{6-fluoro-2-[2-(4-trifluoromethyl-phenyl)-vinyl]-1H-benzimidazol-5-yl}-phenyl)-ethanone, |
| 63 | (E)-2-{6-fluoro-2-[2-(4-trifluoromethyl-phenyl)-vinyl]-1H-benzimidazol-5-yl}-benzamide, |
| 66 | (E)-(2-{6-chloro-2-[2-(4-trifluoromethyl-phenyl)-vinyl]-1H-benzimidazol-5-yl}-phenyl)-methanol, |
| 67 | (E)-1-(2-{6-chloro-2-[2-(4-trifluoromethyl-phenyl)-vinyl]-1H-benzimidazol-5-yl}-phenyl)-ethanone, |
| 68 | (E)-2-{6-chloro-2-[2-(4-trifluoromethyl-phenyl)-vinyl]-1H-benzimidazol-5-yl}-phenol, |
| 69 | (E)-2-{2-[2-(4-trifluoromethoxy-phenyl)-vinyl]-1H-benzimidazol-5-yl}-benzenesulfonamide, |
| 70 | (E)-2-{2-[2-(4-trifluoromethyl-phenyl)-vinyl]-1H-benzimidazol-5-yl}-benzenesulfonamide, |
| 71 | (E)-2-{2-[2-(4-trifluoromethanesulfonyl-phenyl)-vinyl]-1H-benzimidazol-5-yl}-benzenesulfonamide, |
| 77 | (E)-N-(2-{2-[2-(4-chloro-phenyl)-vinyl]-1H-benzimidazol-5-yl}-phenyl)-methanesulfonamide, |
| 78 | (E)-2-(2-{2-[2-(4-chloro-phenyl)-vinyl]-1H-benzimidazol-5-yl}-phenyl)-propan-2-ol, |
| 79 | (E)-2-{2-[2-(4-chloro-phenyl)-vinyl]-1H-benzimidazol-5-yl}-benzenesulfonamide, |
| 84 | (E)-2-(2-{2-[2-(4-methanesulfonyl-phenyl)-vinyl]-1H-benzimidazol-5-yl}-phenyl)-propan-2-ol, |
| 95 | (E)-N-[2-(2-{2-[4-(2,2,2-trifluoro-ethoxy)-phenyl]-vinyl}-1H-benzimidazol-5-yl)-phenyl]-methanesulfonamide, |
| 114 | (E)-2-(2-{2-[2-(3-trifluoromethyl-phenyl)-vinyl]-1H-benzimidazol-5-yl}-phenyl)-propan-2-ol, |
| 129 | 2-{2-[2-(4-trifluoromethoxy-phenyl)-ethyl]-1H-benzimidazol-5-yl}-benzenesulfonamide, |
| 130 | 2-{2-[2-(4-trifluoromethyl-phenyl)-ethyl]-1H-benzimidazol-5-yl}-benzenesulfonamide, |
| 131 | 2-{2-[2-(4-trifluoromethanesulfonyl-phenyl)-ethyl]-1H-benzimidazol-5-yl}-benzenesulfonamide, |

| Cpd | Name |
|---|---|
| 139 | 2-{2-[2-(4-chloro-phenyl)-ethyl]-1H-benzimidazol-5-yl}-benzenesulfonamide, |
| 175 | 2-{2-[2-(3-trifluoromethyl-phenyl)-ethyl]-1H-benzimidazol-5-yl}-benzenesulfonamide, |
| 190 | 2-{2-[2-(4-trifluoromethyl-phenyl)-cyclopropyl]-1H-benzimidazol-5-yl}-benzenesulfonamide, |
| 198 | 2-(2-{2-[2-(4-chloro-phenyl)-cyclopropyl]-1H-benzimidazol-5-yl}-phenyl)-propan-2-ol, |
| 250 | 2-[2-(4-trifluoromethyl-phenylethynyl)-1H-benzimidazol-5-yl]-benzenesulfonamide, |
| 294 | 2-{2-[2-(3-trifluoromethyl-phenylethynyl)-1H-benzimidazol-5-yl]-phenyl}-propan-2-ol, |
| 295 | 2-[2-(3-trifluoromethyl-phenylethynyl)-1H-benzimidazol-5-yl]-benzenesulfonamide, |
| 309 | (E)-N-tert-butyl-2-{2-[2-(4-trifluoromethyl-phenyl)-vinyl]-1H-benzimidazol-5-yl}-benzenesulfonamide, |
| 310 | (E)-N-methyl-2-{2-[2-(4-trifluoromethyl-phenyl)-vinyl]-1H-benzimidazol-5-yl}-benzenesulfonamide, |
| 311 | (E)-2-hydroxy-1-(2-{2-[2-(4-trifluoromethyl-phenyl)-vinyl]-1H-benzimidazol-5-yl}-phenyl)-ethanone, |
| 312 | (E)-2-{2-[2-(4-bromo-phenyl)-vinyl]-1H-benzimidazol-5-yl}-N-methyl-benzenesulfonamide, |
| 314 | (E)-N-methyl-2-[2-(2-p-tolyl-vinyl)-1H-benzimidazol-5-yl]-benzenesulfonamide, |
| 315 | (E)-2-{2-[2-(4-fluoro-phenyl)-vinyl]-1H-benzimidazol-5-yl}-N-methyl-benzenesulfonamide, |
| 316 | (E)-2-{2-[2-(3,4-dichloro-phenyl)-vinyl]-1H-benzimidazol-5-yl}-N-methyl-benzenesulfonamide, |
| 317 | (E)-2-{2-[2-(3-bromo-4-fluoro-phenyl)-vinyl]-1H-benzimidazol-5-yl}-N-methyl-benzenesulfonamide, |
| 318 | (E)-2-{2-[2-(4-dimethylamino-phenyl)-vinyl]-1H-benzimidazol-5-yl}-N-methyl-benzenesulfonamide, |
| 319 | (E)-2-{2-[2-(3-fluoro-4-trifluoromethyl-phenyl)-vinyl]-1H-benzimidazol-5-yl}-N-methyl-benzenesulfonamide, |
| 320 | (E)-2-{2-[2-(2-fluoro-4-trifluoromethyl-phenyl)-vinyl]-1H-benzimidazol-5-yl}-N-methyl-benzenesulfonamide, |
| 321 | (E)-2-{2-[2-(3-chloro-4-fluoro-phenyl)-vinyl]-1H-benzimidazol-5-yl}-N-methyl-benzenesulfonamide, |
| 322 | (E)-2-{2-[2-(3-fluoro-5-trifluoromethyl-phenyl)-vinyl]-1H-benzimidazol-5-yl}-N-methyl-benzenesulfonamide, |
| 323 | (E)-N-methyl-2-{2-[2-(2,3,4-trifluoro-phenyl)-vinyl]-1H-benzimidazol-5-yl}-benzenesulfonamide, |
| 324 | (E)-N-methyl-2-{2-[2-(2,4,5-trifluoro-phenyl)-vinyl]-1H-benzimidazol-5-yl}-benzenesulfonamide, |
| 325 | (E)-2-{2-[2-(2,3-difluoro-phenyl)-vinyl]-1H-benzimidazol-5-yl}-N-methyl-benzenesulfonamide, |
| 326 | (E)-2-{2-[2-(2,5-difluoro-phenyl)-vinyl]-1H-benzimidazol-5-yl}-N-methyl-benzenesulfonamide, |
| 327 | (E)-2-{2-[2-(2,6-difluoro-phenyl)-vinyl]-1H-benzimidazol-5-yl}-N-methyl-benzenesulfonamide, |
| 328 | (E)-2-{2-[2-(3,5-difluoro-phenyl)-vinyl]-1H-benzimidazol-5-yl}-N-methyl-benzenesulfonamide, |
| 329 | (E)-2-{2-[2-(3,4-difluoro-phenyl)-vinyl]-1H-benzimidazol-5-yl}-N-methyl-benzenesulfonamide, |
| 330 | (E)-2-{2-[2-(4-fluoro-2-trifluoromethyl-phenyl)-vinyl]-1H-benzimidazol-5-yl}-N-methyl-benzenesulfonamide, |
| 331 | (E)-2-{2-[2-(4-fluoro-3-trifluoromethyl-phenyl)-vinyl]-1H-benzimidazol-5-yl}-N-methyl-benzenesulfonamide, |
| 332 | (E)-2-{2-[2-(2-fluoro-3-trifluoromethyl-phenyl)-vinyl]-1H-benzimidazol-5-yl}-N-methyl-benzenesulfonamide, |
| 333 | (E)-2-{2-[2-(3,5-bis-trifluoromethyl-phenyl)-vinyl]-1H-benzimidazol-5-yl}-N-methyl-benzenesulfonamide, |
| 334 | (E)-2-{2-[2-(2,5-bis-trifluoromethyl-phenyl)-vinyl]-1H-benzimidazol-5-yl}-N-methyl-benzenesulfonamide, |
| 335 | (E)-2-{2-[2-(3-chloro-2-fluoro-phenyl)-vinyl]-1H-benzimidazol-5-yl}-N-methyl-benzenesulfonamide, |
| 336 | (E)-2-{2-[2-(2-chloro-6-fluoro-phenyl)-vinyl]-1H-benzimidazol-5-yl}-N-methyl-benzenesulfonamide, |
| 337 | (E)-2-{2-[2-(2,4-dichloro-phenyl)-vinyl]-1H-benzimidazol-5-yl}-N-methyl-benzenesulfonamide, |
| 338 | (E)-2-{2-[2-(3-bromo-phenyl)-vinyl]-1H-benzimidazol-5-yl}-N-methyl-benzenesulfonamide, |
| 339 | (E)-2-{2-[2-(4-chloro-2-fluoro-phenyl)-vinyl]-1H-benzimidazol-5-yl}-N-methyl-benzenesulfonamide, |
| 340 | (E)-2-{2-[2-(4-chloro-2-methanesulfonyl-phenyl)-vinyl]-1H-benzimidazol-5-yl}-N-methyl-benzenesulfonamide, |
| 341 | (E)-N-methyl-2-{2-[2-(4-trifluoromethylsulfanyl-phenyl)-vinyl]-1H-benzimidazol-5-yl}-benzenesulfonamide, |

| Cpd | Name |
| --- | --- |
| 342 | (E)-N-methyl-2-{2-[2-(4-trifluoromethanesulfonyl-phenyl)-vinyl]-1H-benzimidazol-5-yl}-benzenesulfonamide, |
| 343 | (E)-N-methyl-2-{2-[2-(2-trifluoromethyl-phenyl)-vinyl]-1H-benzimidazol-5-yl}-benzenesulfonamide, |
| 344 | (E)-N-methyl-2-{2-[2-(3-trifluoromethoxy-phenyl)-vinyl]-1H-benzimidazol-5-yl}-benzenesulfonamide, |
| 345 | (E)-N-methyl-2-{2-[2-(4-trifluoromethoxy-phenyl)-vinyl]-1H-benzimidazol-5-yl}-benzenesulfonamide, |
| 346 | (E)-2-{2-[2-(2-chloro-phenyl)-vinyl]-1H-benzimidazol-5-yl}-N-methyl-benzenesulfonamide, |
| 347 | (E)-2-{2-[2-(4-chloro-phenyl)-vinyl]-1H-benzimidazol-5-yl}-N-methyl-benzenesulfonamide, |
| 348 | (E)-2-{2-[2-(2-bromo-phenyl)-vinyl]-1H-benzimidazol-5-yl}-N-methyl-benzenesulfonamide, |
| 349 | (E)-2-{2-[2-(2,4-difluoro-phenyl)-vinyl]-1H-benzimidazol-5-yl}-N-methyl-benzenesulfonamide, |
| 350 | N-methyl-2-{2-[2-(3-trifluoromethyl-phenyl)-ethyl]-1H-benzimidazol-5-yl}-benzenesulfonamide, |
| 357 | (E)-2-{2-[2-(2,4-difluoro-phenyl)-vinyl]-1H-benzimidazol-5-yl}-benzenesulfonamide, |
| 358 | (E)-2-{2-[2-(3,4-difluoro-phenyl)-vinyl]-1H-benzimidazol-5-yl}-benzenesulfonamide, |
| 359 | (E)-2-{2-[2-(2,3-difluoro-phenyl)-vinyl]-1H-benzimidazol-5-yl}-benzenesulfonamide, |
| 360 | (E)-2-{2-[2-(2,5-difluoro-phenyl)-vinyl]-1H-benzimidazol-5-yl}-benzenesulfonamide, |
| 361 | (E)-2-{2-[2-(3,5-difluoro-phenyl)-vinyl]-1H-benzimidazol-5-yl}-benzenesulfonamide, |
| 362 | (E)-2-{2-[2-(3-trifluoromethoxy-phenyl)-vinyl]-1H-benzimidazol-5-yl}-benzenesulfonamide, |
| 363 | (E)-2-{2-[2-(4-bromo-phenyl)-vinyl]-1H-benzimidazol-5-yl}-benzenesulfonamide, |
| 364 | (E)-2-{2-[2-(2-trifluoromethyl-phenyl)-vinyl]-1H-benzimidazol-5-yl}-benzenesulfonamide, |
| 365 | (E)-2-{2-[2-(2-chloro-phenyl)-vinyl]-1H-benzimidazol-5-yl}-benzenesulfonamide, |
| 366 | (E)-2-{2-[2-(2-bromo-phenyl)-vinyl]-1H-benzimidazol-5-yl}-benzenesulfonamide, |
| 367 | (E)-2-{2-[2-(4-fluoro-2-trifluoromethyl-phenyl)-vinyl]-1H-benzimidazol-5-yl}-benzenesulfonamide, |
| 368 | (E)-2-{2-[2-(2-fluoro-3-trifluoromethyl-phenyl)-vinyl]-1H-benzimidazol-5-yl}-benzenesulfonamide, |
| 369 | (E)-2-{2-[2-(4-fluoro-3-trifluoromethyl-phenyl)-vinyl]-1H-benzimidazol-5-yl}-benzenesulfonamide, |
| 370 | (E)-2-{2-[2-(2,3,4-trifluoro-phenyl)-vinyl]-1H-benzimidazol-5-yl}-benzenesulfonamide, |
| 371 | (E)-2-{2-[2-(2,4,5-trifluoro-phenyl)-vinyl]-1H-benzimidazol-5-yl}-benzenesulfonamide, |
| 372 | (E)-2-{2-[2-(2,6-difluoro-phenyl)-vinyl]-1H-benzimidazol-5-yl}-benzenesulfonamide, |
| 373 | (E)-2-{2-[2-(3,5-bis-trifluoromethyl-phenyl)-vinyl]-1H-benzimidazol-5-yl}-benzenesulfonamide, |
| 374 | (E)-2-{2-[2-(2,5-bis-trifluoromethyl-phenyl)-vinyl]-1H-benzimidazol-5-yl}-benzenesulfonamide, |
| 375 | (E)-2-{2-[2-(4-chloro-2-methanesulfonyl-phenyl)-vinyl]-1H-benzimidazol-5-yl}-benzenesulfonamide, |
| 376 | (E)-2-{2-[2-(3-bromo-phenyl)-vinyl]-1H-benzimidazol-5-yl}-benzenesulfonamide, |
| 378 | (E)-2-{2-[2-(4-chloro-3-trifluoromethyl-phenyl)-vinyl]-1H-benzimidazol-5-yl}-benzenesulfonamide, |
| 379 | (E)-2-{2-[2-(5-bromo-2-fluoro-phenyl)-vinyl]-1H-benzimidazol-5-yl}-benzenesulfonamide, |
| 380 | (E)-2-{2-[2-(4-trifluoromethylsulfanyl-phenyl)-vinyl]-1H-benzimidazol-5-yl}-benzenesulfonamide, |
| 383 | 2-{2-[2-(4-fluoro-3-trifluoromethyl-phenyl)-ethyl]-1H-benzimidazol-5-yl}-benzenesulfonamide, |
| 384 | 2-{2-[2-(2,3,4-trifluoro-phenyl)-ethyl]-1H-benzimidazol-5-yl}-benzenesulfonamide, |
| 385 | 2-{2-[2-(2,4,5-trifluoro-phenyl)-ethyl]-1H-benzimidazol-5-yl}-benzenesulfonamide, |
| 386 | 2-{2-[2-(2,6-difluoro-phenyl)-ethyl]-1H-benzimidazol-5-yl}-benzenesulfonamide, |
| 387 | 2-{2-[2-(3,5-bis-trifluoromethyl-phenyl)-ethyl]-1H-benzimidazol-5-yl}-benzenesulfonamide, |
| 388 | 2-{2-[2-(2,5-bis-trifluoromethyl-phenyl)-ethyl]-1H-benzimidazol-5-yl}-benzenesulfonamide, |
| 390 | 2-{2-[2-(4-chloro-3-trifluoromethyl-phenyl)-ethyl]-1H-benzimidazol-5-yl}-benzenesulfonamide, |

| Cpd | Name |
|---|---|
| 391 | 2-{2-[2-(3-trifluoromethoxy-phenyl)-ethyl]-1H-benzimidazol-5-yl}-benzenesulfonamide, |
| 392 | 2-{2-[2-(2,4-difluoro-phenyl)-ethyl]-1H-benzimidazol-5-yl}-benzenesulfonamide, |
| 393 | 2-{2-[2-(3,4-difluoro-phenyl)-ethyl]-1H-benzimidazol-5-yl}-benzenesulfonamide, |
| 394 | 2-{2-[2-(2,3-difluoro-phenyl)-ethyl]-1H-benzimidazol-5-yl}-benzenesulfonamide, |
| 395 | 2-{2-[2-(2,5-difluoro-phenyl)-ethyl]-1H-benzimidazol-5-yl}-benzenesulfonamide, |
| 396 | 2-{2-[2-(3,5-difluoro-phenyl)-ethyl]-1H-benzimidazol-5-yl}-benzenesulfonamide, |
| 397 | 2-(2-phenethyl-1H-benzimidazol-5-yl)-benzenesulfonamide, |
| 398 | (E)-N,N-dimethyl-2-{2-[2-(4-trifluoromethyl-phenyl)-vinyl]-1H-benzimidazol-5-yl}-benzenesulfonamide, |
| 399 | N,N-dimethyl-2-{2-[2-(4-trifluoromethyl-phenyl)-ethyl]-1H-benzimidazol-5-yl}-benzenesulfonamide, |
| 402 | 2-{2-[2-(2-chloro-phenyl)-ethyl]-1H-benzimidazol-5-yl}-benzenesulfonamide, |
| 404 | 2-{2-[2-(4-fluoro-2-trifluoromethyl-phenyl)-ethyl]-1H-benzimidazol-5-yl}-benzenesulfonamide, |
| 405 | 2-{2-[2-(2-fluoro-3-trifluoromethyl-phenyl)-ethyl]-1H-benzimidazol-5-yl}-benzenesulfonamide, |
| 406 | (E)-N-(2-{2-[2-(4-bromo-phenyl)-vinyl]-1H-benzimidazol-5-yl}-phenyl)-methanesulfonamide, |
| 407 | (E)-N-(2-{2-[2-(4-isopropyl-phenyl)-vinyl]-1H-benzimidazol-5-yl}-phenyl)-methanesulfonamide, |
| 410 | (E)-N-(2-{2-[2-(4-difluoromethoxy-phenyl)-vinyl]-1H-benzimidazol-5-yl}-phenyl)-methanesulfonamide, |
| 411 | (E)-N-(2-{2-[2-(3-fluoro-5-trifluoromethyl-phenyl)-vinyl]-1H-benzimidazol-5-yl}-phenyl)-methanesulfonamide, |
| 412 | (E)-N-{2-[2-(2-p-tolyl-vinyl)-1H-benzimidazol-5-yl]-phenyl}-methanesulfonamide, |
| 413 | (E)-N-(2-{2-[2-(4-dimethylamino-phenyl)-vinyl]-1H-benzimidazol-5-yl}-phenyl)-methanesulfonamide, |
| 414 | (E)-N-(2-{2-[2-(4-ethoxy-phenyl)-vinyl]-1H-benzimidazol-5-yl}-phenyl)-methanesulfonamide, |
| 415 | (E)-N-{2-[2-(2-naphthalen-2-yl-vinyl)-1H-benzimidazol-5-yl]-phenyl}-methanesulfonamide, |
| 416 | (E)-N-(2-{2-[2-(3,4-dichloro-phenyl)-vinyl]-1H-benzimidazol-5-yl}-phenyl)-methanesulfonamide, |
| 417 | (E)-N-(2-{2-[2-(3-fluoro-4-trifluoromethyl-phenyl)-vinyl]-1H-benzimidazol-5-yl}-phenyl)-methanesulfonamide, |
| 418 | (E)-N-(2-{2-[2-(2-fluoro-4-trifluoromethyl-phenyl)-vinyl]-1H-benzimidazol-5-yl}-phenyl)-methanesulfonamide, |
| 419 | 2-{2-[2-(2-fluoro-phenyl)-ethyl]-1H-benzimidazol-5-yl}-benzenesulfonamide, |
| 420 | 2-{2-[2-(4-fluoro-phenyl)-ethyl]-1H-benzimidazol-5-yl}-benzenesulfonamide, |
| 421 | 2-{2-[2-(3-fluoro-5-trifluoromethyl-phenyl)-ethyl]-1H-benzimidazol-5-yl}-benzenesulfonamide, |
| 422 | (E)-5-(2-methanesulfonyl-phenyl)-2-[2-(4-trifluoromethyl-phenyl)-vinyl]-1H-benzimidazole, |
| 423 | (E)-2-{2-[2-(3-fluoro-4-trifluoromethyl-phenyl)-vinyl]-1H-benzimidazol-5-yl}-benzenesulfonamide, |
| 424 | (E)-2-{2-[2-(2-fluoro-4-trifluoromethyl-phenyl)-vinyl]-1H-benzimidazol-5-yl}-benzenesulfonamide, |
| 426 | (E)-2-(2-styryl-1H-benzimidazol-5-yl)-benzenesulfonamide, |
| 427 | (E)-2-{2-[2-(3,4-dichloro-phenyl)-vinyl]-1H-benzimidazol-5-yl}-benzenesulfonamide, |
| 428 | (E)-2-{2-[2-(4-chloro-2-fluoro-phenyl)-vinyl]-1H-benzimidazol-5-yl}-benzenesulfonamide, |
| 429 | (E)-2-{2-[2-(4-isopropyl-phenyl)-vinyl]-1H-benzimidazol-5-yl}-benzenesulfonamide, |
| 430 | (E)-2-[2-(2-p-tolyl-vinyl)-1H-benzimidazol-5-yl]-benzenesulfonamide, |
| 431 | (E)-2-{2-[2-(3-chloro-2-fluoro-phenyl)-vinyl]-1H-benzimidazol-5-yl}-benzenesulfonamide, |
| 432 | (E)-2-{2-[2-(3-chloro-4-fluoro-phenyl)-vinyl]-1H-benzimidazol-5-yl}-benzenesulfonamide, |
| 433 | (E)-2-[2-(2-naphthalen-2-yl-vinyl)-1H-benzimidazol-5-yl]-benzenesulfonamide, |
| 434 | (E)-2-{2-[2-(4-fluoro-phenyl)-vinyl]-1H-benzimidazol-5-yl}-benzenesulfonamide, |
| 435 | (E)-2-{2-[2-(4-difluoromethyl-phenyl)-vinyl]-1H-benzimidazol-5-yl}-benzenesulfonamide, |
| 436 | (E)-2-{2-[2-(3-fluoro-5-trifluoromethyl-phenyl)-vinyl]-1H-benzimidazol-5-yl}-benzenesulfonamide, |

| Cpd | Name |
|---|---|
| 437 | (E)-2-{2-[2-(2,4-dichloro-phenyl)-vinyl]-1H-benzimidazol-5-yl}-benzenesulfonamide, |
| 438 | (E)-2-{2-[2-(2-chloro-6-fluoro-phenyl)-vinyl]-1H-benzimidazol-5-yl}-benzenesulfonamide, |
| 439 | (E)-2-{2-[2-(3-bromo-4-fluoro-phenyl)-vinyl]-1H-benzimidazol-5-yl}-benzenesulfonamide, |
| 440 | (E)-2-{2-[2-(4-ethoxy-phenyl)-vinyl]-1H-benzimidazol-5-yl}-benzenesulfonamide, |
| 442 | 2-{2-[2-(4-isopropyl-phenyl)-ethyl]-1H-benzimidazol-5-yl}-benzenesulfonamide, |
| 444 | (E)-4-trifluoromethyl-2-{2-[2-(4-trifluoromethyl-phenyl)-vinyl]-1H-benzimidazol-5-yl}-benzenesulfonamide, |
| 445 | 4-trifluoromethyl-2-{2-[2-(4-trifluoromethyl-phenyl)-ethyl]-1H-benzimidazol-5-yl}-benzenesulfonamide, |
| 446 | (E)-5-trifluoromethyl-2-{2-[2-(4-trifluoromethyl-phenyl)-vinyl]-1H-benzimidazol-5-yl}-benzenesulfonamide, |
| 447 | 5-trifluoromethyl-2-{2-[2-(4-trifluoromethyl-phenyl)-ethyl]-1H-benzimidazol-5-yl}-benzenesulfonamide, |
| 448 | (E)-1-[4-(2-{5-[2-(1-hydroxy-1-methyl-ethyl)-phenyl]-1H-benzimidazol-2-yl}-vinyl)-phenyl]-ethanone, |
| 449 | (E)-2-{2-[2-(2-quinolin-6-yl-vinyl)-1H-benzimidazol-5-yl]-phenyl}-propan-2-ol, |
| 451 | (E)-2-{2-[2-(4-cyano-phenyl)-vinyl]-1H-benzimidazol-5-yl}-N-methyl-benzenesulfonamide, |
| 455 | (E)-2-{2-[2-(2,4-bis-trifluoromethyl-phenyl)-vinyl]-1H-benzimidazol-5-yl}-N-methyl-benzenesulfonamide, |
| 456 | (E)-2-{2-[2-(4-acetyl-phenyl)-vinyl]-1H-benzimidazol-5-yl}-N-methyl-benzenesulfonamide, |
| 461 | (E)-ethanesulfonic acid (2-{2-[2-(4-trifluoromethyl-phenyl)-vinyl]-1H-benzimidazol-5-yl}-phenyl)-amide, |
| 462 | (E)-(2-{2-[2-(4-trifluoromethyl-phenyl)-vinyl]-1H-benzimidazol-5-yl}-phenyl)-carbamic acid methyl ester, |
| 463 | (E)-2-(2-{2-[2-(4-tert-butyl-phenyl)-vinyl]-1H-benzimidazol-5-yl}-phenyl)-propan-2-ol, |
| 464 | 2-(2-{2-[2-(4-trifluoromethyl-phenyl)-ethyl]-1H-benzimidazol-5-yl}-phenyl)-propan-2-ol, |
| 465 | (E)-2-{2-[2-(4-trifluoromethyl-phenyl)-vinyl]-1H-benzimidazol-5-yl}-phenylamine, |
| 466 | (E)-2-{2-[2-(4-trifluoromethyl-phenyl)-vinyl]-1H-benzimidazol-5-yl}-benzoic acid ethyl ester, |
| 467 | N-(2-{2-[2-(4-trifluoromethyl-phenyl)-cyclopropyl]-1H-benzimidazol-5-yl}-phenyl)-methanesulfonamide, |
| 468 | (E)-2-[2-(2-styryl-1H-benzimidazol-5-yl)-phenyl]-propan-2-ol, |
| 469 | (Z)-2-(2-{2-[2-(4-trifluoromethyl-phenyl)-vinyl]-1H-benzimidazol-5-yl}-phenyl)-propan-2-ol, |
| 470 | (E)-5-(2-aminosulfonylamino-phenyl)-2-[2-(4-trifluoromethyl-phenyl)-vinyl]-1H-benzimidazole, |
| 471 | 2-(2-{2-[2-(4-trifluoromethyl-phenyl)-cyclopropyl]-1H-benzimidazol-5-yl}-phenyl)-propan-2-ol, |
| 475 | (E)-N-{2-[2-(2-biphenyl-4-yl-vinyl)-1H-benzimidazol-5-yl]-phenyl}-methanesulfonamide, |
| 476 | (E)-(2-{2-[2-(4-trifluoromethyl-phenyl)-vinyl]-1H-benzimidazol-5-yl}-phenyl)-methanol, |
| 482 | (E)-2-(2-{2-[2-(2-trifluoromethyl-phenyl)-vinyl]-1H-benzimidazol-5-yl}-phenyl)-propan-2-ol, |
| 489 | 2-[2-(2-phenylethynyl-1H-benzimidazol-5-yl)-phenyl]-propan-2-ol, |
| 490 | 2-(2-phenylethynyl-1H-benzimidazol-5-yl)-benzenesulfonamide, |
| 491 | (E)-5-(2-aminosulfonylamino-methylphenyl)-2-[2-(4-trifluoromethyl-phenyl)-vinyl]-1H-benzimidazole, |
| 492 | 2-{2-[2-(4-trifluoromethyl-phenylethynyl)-1H-benzimidazol-5-yl]-phenyl}-propan-2-ol, |
| 494 | 2-(2-{2-[2-(4-methoxy-phenyl)-cyclopropyl]-1H-benzimidazol-5-yl}-phenyl)-propan-2-ol, |
| 497 | 2-(2-{2-[2-(4-trifluoromethoxy-phenyl)-cyclopropyl]-1H-benzimidazol-5-yl}-phenyl)-propan-2-ol, |
| 498 | 2-{2-[2-(4-trifluoromethyl-phenyl)-cyclopropyl]-1H-benzimidazol-5-yl}-benzamide, |
| 500 | 5-(2-methanesulfonyl-phenyl)-2-[2-(4-trifluoromethyl-phenyl)-cyclopropyl]-1H-benzimidazole, |
| 501 | 2-(2-{2-[(1R,2R)-2-(4-trifluoromethyl-phenyl)-cyclopropyl]-1H-benzimidazol-5-yl}-phenyl)-propan-2-ol, |
| 502 | 2-{2-[(1R,2R)-2-(4-trifluoromethyl-phenyl)-cyclopropyl]-1H-benzimidazol-5-yl}-benzenesulfonamide, |
| 503 | 2-(2-{2-[(1S,2S)-2-(4-trifluoromethyl-phenyl)-cyclopropyl]-1H-benzimidazol-5-yl}-phenyl)-propan-2-ol, and |
| 504 | 2-{2-[(1S,2S)-2-(4-trifluoromethyl-phenyl)-cyclopropyl]-1H-benzimidazol-5-yl}-benzenesulfonamide. |

A representative compound of Formula (I) or a form thereof includes a compound selected from the group consisting of:

| Cpd | Name |
|---|---|
| 1 | (E)-1-(2-{2-[2-(4-tert-butyl-phenyl)-vinyl]-1H-benzimidazol-5-yl}-phenyl)-ethanone, |
| 2 | (E)-1-(2-{2-[2-(4-tert-butyl-phenyl)-vinyl]-1H-benzimidazol-5-yl}-phenyl)-ethanol, |
| 5 | (E)-2-{2-[2-(4-tert-butyl-phenyl)-vinyl]-1H-benzimidazol-5-yl}-benzamide, |
| 9 | (E)-N-(2-{2-[2-(4-tert-butyl-phenyl)-vinyl]-1H-benzimidazol-5-yl}-phenyl)-methanesulfonamide, |
| 12 | (E)-(2-{2-[2-(4-tert-butyl-phenyl)-vinyl]-1H-benzimidazol-5-yl}-phenyl)-methanol, |
| 16 | (E)-1-(2-{2-[2-(4-trifluoromethyl-phenyl)-vinyl]-1H-benzimidazol-5-yl}-phenyl)-ethanol, |
| 17 | (E)-N-(2-{2-[2-(4-trifluoromethyl-phenyl)-vinyl]-1H-benzimidazol-5-yl}-phenyl)-methanesulfonamide, |
| 18 | (E)-2-(2-{2-[2-(4-trifluoromethyl-phenyl)-vinyl]-1H-benzimidazol-5-yl}-phenyl)-propan-2-ol, |
| 22 | (E)-N-(2-{2-[2-(4-trifluoromethoxy-phenyl)-vinyl]-1H-benzimidazol-5-yl}-phenyl)-methanesulfonamide, |
| 31 | N-(2-{2-[2-(4-trifluoromethyl-phenyl)-ethyl]-1H-benzimidazol-5-yl}-phenyl)-methanesulfonamide, |
| 35 | (E)-(2-{2-[2-(4-trifluoromethylsulfanyl-phenyl)-vinyl]-1H-benzimidazol-5-yl}-phenyl)-methanol, |
| 40 | (E)-1-(2-{2-[2-(4-trifluoromethanesulfonyl-phenyl)-vinyl]-1H-benzimidazol-5-yl}-phenyl)-ethanone, |
| 42 | (E)-(2-{2-[2-(4-trifluoromethanesulfonyl-phenyl)-vinyl]-1H-benzimidazol-5-yl}-phenyl)-methanol, |
| 45 | (E)-1-(2-{2-[2-(4-trifluoromethanesulfonyl-phenyl)-vinyl]-1H-benzimidazol-5-yl}-phenyl)-ethanol, |
| 46 | 1-(2-{2-[2-(4-trifluoromethanesulfonyl-phenyl)-ethyl]-1H-benzimidazol-5-yl}-phenyl)-ethanol, |
| 47 | (E)-2-(2-{2-[2-(4-trifluoromethanesulfonyl-phenyl)-vinyl]-1H-benzimidazol-5-yl}-phenyl)-propan-2-ol, |
| 51 | (E)-(2-{2-[2-(4-tert-butyl-phenyl)-vinyl]-6-trifluoromethyl-1H-benzimidazol-5-yl}-phenyl)-methanol, |
| 53 | (E)-2-{2-[2-(4-tert-butyl-phenyl)-vinyl]-6-trifluoromethyl-1H-benzimidazol-5-yl}-benzamide, |
| 58 | (E)-(2-{6-trifluoromethyl-2-[2-(4-trifluoromethyl-phenyl)-vinyl]-1H-benzimidazol-5-yl}-phenyl)-methanol, |
| 61 | (E)-(2-{6-fluoro-2-[2-(4-trifluoromethyl-phenyl)-vinyl]-1H-benzimidazol-5-yl}-phenyl)-methanol, |
| 66 | (E)-(2-{6-chloro-2-[2-(4-trifluoromethyl-phenyl)-vinyl]-1H-benzimidazol-5-yl}-phenyl)-methanol, |
| 69 | (E)-2-{2-[2-(4-trifluoromethoxy-phenyl)-vinyl]-1H-benzimidazol-5-yl}-benzenesulfonamide, |
| 70 | (E)-2-{2-[2-(4-trifluoromethyl-phenyl)-vinyl]-1H-benzimidazol-5-yl}-benzenesulfonamide, |
| 71 | (E)-2-{2-[2-(4-trifluoromethanesulfonyl-phenyl)-vinyl]-1H-benzimidazol-5-yl}-benzenesulfonamide, |
| 77 | (E)-N-(2-{2-[2-(4-chloro-phenyl)-vinyl]-1H-benzimidazol-5-yl}-phenyl)-methanesulfonamide, |
| 78 | (E)-2-(2-{2-[2-(4-chloro-phenyl)-vinyl]-1H-benzimidazol-5-yl}-phenyl)-propan-2-ol, |
| 79 | (E)-2-{2-[2-(4-chloro-phenyl)-vinyl]-1H-benzimidazol-5-yl}-benzenesulfonamide, |
| 84 | (E)-2-(2-{2-[2-(4-methanesulfonyl-phenyl)-vinyl]-1H-benzimidazol-5-yl}-phenyl)-propan-2-ol, |
| 114 | (E)-2-(2-{2-[2-(3-trifluoromethyl-phenyl)-vinyl]-1H-benzimidazol-5-yl}-phenyl)-propan-2-ol, |
| 129 | 2-{2-[2-(4-trifluoromethoxy-phenyl)-ethyl]-1H-benzimidazol-5-yl}-benzenesulfonamide, |
| 130 | 2-{2-[2-(4-trifluoromethyl-phenyl)-ethyl]-1H-benzimidazol-5-yl}-benzenesulfonamide, |
| 131 | 2-{2-[2-(4-trifluoromethanesulfonyl-phenyl)-ethyl]-1H-benzimidazol-5-yl}-benzenesulfonamide, |
| 139 | 2-{2-[2-(4-chloro-phenyl)-ethyl]-1H-benzimidazol-5-yl}-benzenesulfonamide, |
| 175 | 2-{2-[2-(3-trifluoromethyl-phenyl)-ethyl]-1H-benzimidazol-5-yl}-benzenesulfonamide, |
| 190 | 2-{2-[2-(4-trifluoromethyl-phenyl)-cyclopropyl]-1H-benzimidazol-5-yl}-benzenesulfonamide, |
| 198 | 2-(2-{2-[2-(4-chloro-phenyl)-cyclopropyl]-1H-benzimidazol-5-yl}-phenyl)-propan-2-ol, |
| 250 | 2-[2-(4-trifluoromethyl-phenylethynyl)-1H-benzimidazol-5-yl]-benzenesulfonamide, |

-continued

| Cpd | Name |
|---|---|
| 294 | 2-{2-[2-(3-trifluoromethyl-phenylethynyl)-1H-benzimidazol-5-yl]-phenyl}-propan-2-ol, |
| 295 | 2-[2-(3-trifluoromethyl-phenylethynyl)-1H-benzimidazol-5-yl]-benzenesulfonamide, |
| 310 | (E)-N-methyl-2-{2-[2-(4-trifluoromethyl-phenyl)-vinyl]-1H-benzimidazol-5-yl}-benzenesulfonamide, |
| 311 | (E)-2-hydroxy-1-(2-{2-[2-(4-trifluoromethyl-phenyl)-vinyl]-1H-benzimidazol-5-yl}-phenyl)-ethanone, |
| 312 | (E)-2-{2-[2-(4-bromo-phenyl)-vinyl]-1H-benzimidazol-5-yl}-N-methyl-benzenesulfonamide, |
| 314 | (E)-N-methyl-2-[2-(2-p-tolyl-vinyl)-1H-benzimidazol-5-yl]-benzenesulfonamide, |
| 315 | (E)-2-{2-[2-(4-fluoro-phenyl)-vinyl]-1H-benzimidazol-5-yl}-N-methyl-benzenesulfonamide, |
| 316 | (E)-2-{2-[2-(3,4-dichloro-phenyl)-vinyl]-1H-benzimidazol-5-yl}-N-methyl-benzenesulfonamide, |
| 317 | (E)-2-{2-[2-(3-bromo-4-fluoro-phenyl)-vinyl]-1H-benzimidazol-5-yl}-N-methyl-benzenesulfonamide, |
| 318 | (E)-2-{2-[2-(4-dimethylamino-phenyl)-vinyl]-1H-benzimidazol-5-yl}-N-methyl-benzenesulfonamide, |
| 319 | (E)-2-{2-[2-(3-fluoro-4-trifluoromethyl-phenyl)-vinyl]-1H-benzimidazol-5-yl}-N-methyl-benzenesulfonamide, |
| 320 | (E)-2-{2-[2-(2-fluoro-4-trifluoromethyl-phenyl)-vinyl]-1H-benzimidazol-5-yl}-N-methyl-benzenesulfonamide, |
| 321 | (E)-2-{2-[2-(3-chloro-4-fluoro-phenyl)-vinyl]-1H-benzimidazol-5-yl}-N-methyl-benzenesulfonamide, |
| 322 | (E)-2-{2-[2-(3-fluoro-5-trifluoromethyl-phenyl)-vinyl]-1H-benzimidazol-5-yl}-N-methyl-benzenesulfonamide, |
| 323 | (E)-N-methyl-2-{2-[2-(2,3,4-trifluoro-phenyl)-vinyl]-1H-benzimidazol-5-yl}-benzenesulfonamide, |
| 324 | (E)-N-methyl-2-{2-[2-(2,4,5-trifluoro-phenyl)-vinyl]-1H-benzimidazol-5-yl}-benzenesulfonamide, |
| 328 | (E)-2-{2-[2-(3,5-difluoro-phenyl)-vinyl]-1H-benzimidazol-5-yl}-N-methyl-benzenesulfonamide, |
| 329 | (E)-2-{2-[2-(3,4-difluoro-phenyl)-vinyl]-1H-benzimidazol-5-yl}-N-methyl-benzenesulfonamide, |
| 331 | (E)-2-{2-[2-(4-fluoro-3-trifluoromethyl-phenyl)-vinyl]-1H-benzimidazol-5-yl}-N-methyl-benzenesulfonamide, |
| 332 | (E)-2-{2-[2-(2-fluoro-3-trifluoromethyl-phenyl)-vinyl]-1H-benzimidazol-5-yl}-N-methyl-benzenesulfonamide, |
| 333 | (E)-2-{2-[2-(3,5-bis-trifluoromethyl-phenyl)-vinyl]-1H-benzimidazol-5-yl}-N-methyl-benzenesulfonamide, |
| 335 | (E)-2-{2-[2-(3-chloro-2-fluoro-phenyl)-vinyl]-1H-benzimidazol-5-yl}-N-methyl-benzenesulfonamide, |
| 337 | (E)-2-{2-[2-(2,4-dichloro-phenyl)-vinyl]-1H-benzimidazol-5-yl}-N-methyl-benzenesulfonamide, |
| 339 | (E)-2-{2-[2-(4-chloro-2-fluoro-phenyl)-vinyl]-1H-benzimidazol-5-yl}-N-methyl-benzenesulfonamide, |
| 340 | (E)-2-{2-[2-(4-chloro-2-methanesulfonyl-phenyl)-vinyl]-1H-benzimidazol-5-yl}-N-methyl-benzenesulfonamide, |
| 341 | (E)-N-methyl-2-{2-[2-(4-trifluoromethylsulfanyl-phenyl)-vinyl]-1H-benzimidazol-5-yl}-benzenesulfonamide, |
| 342 | (E)-N-methyl-2-{2-[2-(4-trifluoromethanesulfonyl-phenyl)-vinyl]-1H-benzimidazol-5-yl}-benzenesulfonamide, |
| 344 | (E)-N-methyl-2-{2-[2-(3-trifluoromethoxy-phenyl)-vinyl]-1H-benzimidazol-5-yl}-benzenesulfonamide, |
| 345 | (E)-N-methyl-2-{2-[2-(4-trifluoromethoxy-phenyl)-vinyl]-1H-benzimidazol-5-yl}-benzenesulfonamide, |
| 347 | (E)-2-{2-[2-(4-chloro-phenyl)-vinyl]-1H-benzimidazol-5-yl}-N-methyl-benzenesulfonamide, |
| 349 | (E)-2-{2-[2-(2,4-difluoro-phenyl)-vinyl]-1H-benzimidazol-5-yl}-N-methyl-benzenesulfonamide, |
| 350 | N-methyl-2-{2-[2-(3-trifluoromethyl-phenyl)-ethyl]-1H-benzimidazol-5-yl}-benzenesulfonamide, |
| 357 | (E)-2-{2-[2-(2,4-difluoro-phenyl)-vinyl]-1H-benzimidazol-5-yl}-benzenesulfonamide, |
| 358 | (E)-2-{2-[2-(3,4-difluoro-phenyl)-vinyl]-1H-benzimidazol-5-yl}-benzenesulfonamide, |
| 359 | (E)-2-{2-[2-(2,3-difluoro-phenyl)-vinyl]-1H-benzimidazol-5-yl}-benzenesulfonamide, |
| 360 | (E)-2-{2-[2-(2,5-difluoro-phenyl)-vinyl]-1H-benzimidazol-5-yl}-benzenesulfonamide, |
| 361 | (E)-2-{2-[2-(3,5-difluoro-phenyl)-vinyl]-1H-benzimidazol-5-yl}-benzenesulfonamide, |
| 362 | (E)-2-{2-[2-(3-trifluoromethoxy-phenyl)-vinyl]-1H-benzimidazol-5-yl}-benzenesulfonamide, |
| 363 | (E)-2-{2-[2-(4-bromo-phenyl)-vinyl]-1H-benzimidazol-5-yl}-benzenesulfonamide, |

| Cpd | Name |
|---|---|
| 364 | (E)-2-{2-[2-(2-trifluoromethyl-phenyl)-vinyl]-1H-benzimidazol-5-yl}-benzenesulfonamide, |
| 365 | (E)-2-{2-[2-(2-chloro-phenyl)-vinyl]-1H-benzimidazol-5-yl}-benzenesulfonamide, |
| 366 | (E)-2-{2-[2-(2-bromo-phenyl)-vinyl]-1H-benzimidazol-5-yl}-benzenesulfonamide, |
| 367 | (E)-2-{2-[2-(4-fluoro-2-trifluoromethyl-phenyl)-vinyl]-1H-benzimidazol-5-yl}-benzenesulfonamide, |
| 368 | (E)-2-{2-[2-(2-fluoro-3-trifluoromethyl-phenyl)-vinyl]-1H-benzimidazol-5-yl}-benzenesulfonamide, |
| 369 | (E)-2-{2-[2-(4-fluoro-3-trifluoromethyl-phenyl)-vinyl]-1H-benzimidazol-5-yl}-benzenesulfonamide, |
| 370 | (E)-2-{2-[2-(2,3,4-trifluoro-phenyl)-vinyl]-1H-benzimidazol-5-yl}-benzenesulfonamide, |
| 371 | (E)-2-{2-[2-(2,4,5-trifluoro-phenyl)-vinyl]-1H-benzimidazol-5-yl}-benzenesulfonamide, |
| 372 | (E)-2-{2-[2-(2,6-difluoro-phenyl)-vinyl]-1H-benzimidazol-5-yl}-benzenesulfonamide, |
| 373 | (E)-2-{2-[2-(3,5-bis-trifluoromethyl-phenyl)-vinyl]-1H-benzimidazol-5-yl}-benzenesulfonamide, |
| 374 | (E)-2-{2-[2-(2,5-bis-trifluoromethyl-phenyl)-vinyl]-1H-benzimidazol-5-yl}-benzenesulfonamide, |
| 376 | (E)-2-{2-[2-(3-bromo-phenyl)-vinyl]-1H-benzimidazol-5-yl}-benzenesulfonamide, |
| 378 | (E)-2-{2-[2-(4-chloro-3-trifluoromethyl-phenyl)-vinyl]-1H-benzimidazol-5-yl}-benzenesulfonamide, |
| 379 | (E)-2-{2-[2-(5-bromo-2-fluoro-phenyl)-vinyl]-1H-benzimidazol-5-yl}-benzenesulfonamide, |
| 380 | (E)-2-{2-[2-(4-trifluoromethylsulfanyl-phenyl)-vinyl]-1H-benzimidazol-5-yl}-benzenesulfonamide, |
| 383 | 2-{2-[2-(4-fluoro-3-trifluoromethyl-phenyl)-ethyl]-1H-benzimidazol-5-yl}-benzenesulfonamide, |
| 384 | 2-{2-[2-(2,3,4-trifluoro-phenyl)-ethyl]-1H-benzimidazol-5-yl}-benzenesulfonamide, |
| 385 | 2-{2-[2-(2,4,5-trifluoro-phenyl)-ethyl]-1H-benzimidazol-5-yl}-benzenesulfonamide, |
| 386 | 2-{2-[2-(2,6-difluoro-phenyl)-ethyl]-1H-benzimidazol-5-yl}-benzenesulfonamide, |
| 387 | 2-{2-[2-(3,5-bis-trifluoromethyl-phenyl)-ethyl]-1H-benzimidazol-5-yl}-benzenesulfonamide, |
| 388 | 2-{2-[2-(2,5-bis-trifluoromethyl-phenyl)-ethyl]-1H-benzimidazol-5-yl}-benzenesulfonamide, |
| 390 | 2-{2-[2-(4-chloro-3-trifluoromethyl-phenyl)-ethyl]-1H-benzimidazol-5-yl}-benzenesulfonamide, |
| 391 | 2-{2-[2-(3-trifluoromethoxy-phenyl)-ethyl]-1H-benzimidazol-5-yl}-benzenesulfonamide, |
| 392 | 2-{2-[2-(2,4-difluoro-phenyl)-ethyl]-1H-benzimidazol-5-yl}-benzenesulfonamide, |
| 393 | 2-{2-[2-(3,4-difluoro-phenyl)-ethyl]-1H-benzimidazol-5-yl}-benzenesulfonamide, |
| 394 | 2-{2-[2-(2,3-difluoro-phenyl)-ethyl]-1H-benzimidazol-5-yl}-benzenesulfonamide, |
| 395 | 2-{2-[2-(2,5-difluoro-phenyl)-ethyl]-1H-benzimidazol-5-yl}-benzenesulfonamide, |
| 396 | 2-{2-[2-(3,5-difluoro-phenyl)-ethyl]-1H-benzimidazol-5-yl}-benzenesulfonamide, |
| 397 | 2-(2-phenethyl-1H-benzimidazol-5-yl)-benzenesulfonamide, |
| 398 | (E)-N,N-dimethyl-2-{2-[2-(4-trifluoromethyl-phenyl)-vinyl]-1H-benzimidazol-5-yl}-benzenesulfonamide, |
| 399 | N,N-dimethyl-2-{2-[2-(4-trifluoromethyl-phenyl)-ethyl]-1H-benzimidazol-5-yl}-benzenesulfonamide, |
| 402 | 2-{2-[2-(2-chloro-phenyl)-ethyl]-1H-benzimidazol-5-yl}-benzenesulfonamide, |
| 404 | 2-{2-[2-(4-fluoro-2-trifluoromethyl-phenyl)-ethyl]-1H-benzimidazol-5-yl}-benzenesulfonamide, |
| 405 | 2-{2-[2-(2-fluoro-3-trifluoromethyl-phenyl)-ethyl]-1H-benzimidazol-5-yl}-benzenesulfonamide, |
| 407 | (E)-N-(2-{2-[2-(4-isopropyl-phenyl)-vinyl]-1H-benzimidazol-5-yl}-phenyl)-methanesulfonamide, |
| 417 | (E)-N-(2-{2-[2-(3-fluoro-4-trifluoromethyl-phenyl)-vinyl]-1H-benzimidazol-5-yl}-phenyl)-methanesulfonamide, |
| 418 | (E)-N-(2-{2-[2-(2-fluoro-4-trifluoromethyl-phenyl)-vinyl]-1H-benzimidazol-5-yl}-phenyl)-methanesulfonamide, |
| 419 | 2-{2-[2-(2-fluoro-phenyl)-ethyl]-1H-benzimidazol-5-yl}-benzenesulfonamide, |
| 420 | 2-{2-[2-(4-fluoro-phenyl)-ethyl]-1H-benzimidazol-5-yl}-benzenesulfonamide, |

-continued

| Cpd | Name |
|---|---|
| 421 | 2-{2-[2-(3-fluoro-5-trifluoromethyl-phenyl)-ethyl]-1H-benzimidazol-5-yl}-benzenesulfonamide, |
| 422 | (E)-5-(2-methanesulfonyl-phenyl)-2-[2-(4-trifluoromethyl-phenyl)-vinyl]-1H-benzimidazole, |
| 423 | (E)-2-{2-[2-(3-fluoro-4-trifluoromethyl-phenyl)-vinyl]-1H-benzimidazol-5-yl}-benzenesulfonamide, |
| 424 | (E)-2-{2-[2-(2-fluoro-4-trifluoromethyl-phenyl)-vinyl]-1H-benzimidazol-5-yl}-benzenesulfonamide, |
| 426 | (E)-2-(2-styryl-1H-benzimidazol-5-yl)-benzenesulfonamide, |
| 427 | (E)-2-{2-[2-(3,4-dichloro-phenyl)-vinyl]-1H-benzimidazol-5-yl}-benzenesulfonamide, |
| 428 | (E)-2-{2-[2-(4-chloro-2-fluoro-phenyl)-vinyl]-1H-benzimidazol-5-yl}-benzenesulfonamide, |
| 429 | (E)-2-{2-[2-(4-isopropyl-phenyl)-vinyl]-1H-benzimidazol-5-yl}-benzenesulfonamide, |
| 430 | (E)-2-[2-(2-p-tolyl-vinyl)-1H-benzimidazol-5-yl]-benzenesulfonamide, |
| 431 | (E)-2-{2-[2-(3-chloro-2-fluoro-phenyl)-vinyl]-1H-benzimidazol-5-yl}-benzenesulfonamide, |
| 432 | (E)-2-{2-[2-(3-chloro-4-fluoro-phenyl)-vinyl]-1H-benzimidazol-5-yl}-benzenesulfonamide, |
| 433 | (E)-2-[2-(2-naphthalen-2-yl-vinyl)-1H-benzimidazol-5-yl]-benzenesulfonamide, |
| 434 | (E)-2-{2-[2-(4-fluoro-phenyl)-vinyl]-1H-benzimidazol-5-yl}-benzenesulfonamide, |
| 435 | (E)-2-{2-[2-(4-difluoromethyl-phenyl)-vinyl]-1H-benzimidazol-5-yl}-benzenesulfonamide, |
| 436 | (E)-2-{2-[2-(3-fluoro-5-trifluoromethyl-phenyl)-vinyl]-1H-benzimidazol-5-yl}-benzenesulfonamide, |
| 437 | (E)-2-{2-[2-(2,4-dichloro-phenyl)-vinyl]-1H-benzimidazol-5-yl}-benzenesulfonamide, |
| 438 | (E)-2-{2-[2-(2-chloro-6-fluoro-phenyl)-vinyl]-1H-benzimidazol-5-yl}-benzenesulfonamide, |
| 439 | (E)-2-{2-[2-(3-bromo-4-fluoro-phenyl)-vinyl]-1H-benzimidazol-5-yl}-benzenesulfonamide, |
| 440 | (E)-2-{2-[2-(4-ethoxy-phenyl)-vinyl]-1H-benzimidazol-5-yl}-benzenesulfonamide, |
| 442 | 2-{2-[2-(4-isopropyl-phenyl)-ethyl]-1H-benzimidazol-5-yl}-benzenesulfonamide, |
| 444 | (E)-4-trifluoromethyl-2-{2-[2-(4-trifluoromethyl-phenyl)-vinyl]-1H-benzimidazol-5-yl}-benzenesulfonamide, |
| 445 | 4-trifluoromethyl-2-{2-[2-(4-trifluoromethyl-phenyl)-ethyl]-1H-benzimidazol-5-yl}-benzenesulfonamide, |
| 446 | (E)-5-trifluoromethyl-2-{2-[2-(4-trifluoromethyl-phenyl)-vinyl]-1H-benzimidazol-5-yl}-benzenesulfonamide, |
| 447 | 5-trifluoromethyl-2-{2-[2-(4-trifluoromethyl-phenyl)-ethyl]-1H-benzimidazol-5-yl}-benzenesulfonamide, |
| 448 | (E)-1-[4-(2-{5-[2-(1-hydroxy-1-methyl-ethyl)-phenyl]-1H-benzimidazol-2-yl}-vinyl)-phenyl]-ethanone, |
| 449 | (E)-2-{2-[2-(2-quinolin-6-yl-vinyl)-1H-benzimidazol-5-yl]-phenyl}-propan-2-ol, |
| 451 | (E)-2-{2-[2-(4-cyano-phenyl)-vinyl]-1H-benzimidazol-5-yl}-N-methyl-benzenesulfonamide, |
| 455 | (E)-2-{2-[2-(2,4-bis-trifluoromethyl-phenyl)-vinyl]-1H-benzimidazol-5-yl}-N-methyl-benzenesulfonamide, |
| 456 | (E)-2-{2-[2-(4-acetyl-phenyl)-vinyl]-1H-benzimidazol-5-yl}-N-methyl-benzenesulfonamide, |
| 461 | (E)-ethanesulfonic acid (2-{2-[2-(4-trifluoromethyl-phenyl)-vinyl]-1H-benzimidazol-5-yl}-phenyl)-amide, |
| 462 | (E)-(2-{2-[2-(4-trifluoromethyl-phenyl)-vinyl]-1H-benzimidazol-5-yl}-phenyl)-carbamic acid methyl ester, |
| 463 | (E)-2-(2-{2-[2-(4-tert-butyl-phenyl)-vinyl]-1H-benzimidazol-5-yl}-phenyl)-propan-2-ol, |
| 464 | 2-(2-{2-[2-(4-trifluoromethyl-phenyl)-ethyl]-1H-benzimidazol-5-yl}-phenyl)-propan-2-ol, |
| 466 | (E)-2-{2-[2-(4-trifluoromethyl-phenyl)-vinyl]-1H-benzimidazol-5-yl}-benzoic acid ethyl ester, |
| 468 | (E)-2-[2-(2-styryl-1H-benzimidazol-5-yl)-phenyl]-propan-2-ol, |
| 469 | (Z)-2-(2-{2-[2-(4-trifluoromethyl-phenyl)-vinyl]-1H-benzimidazol-5-yl}-phenyl)-propan-2-ol, |
| 470 | (E)-5-(2-aminosulfonylamino-phenyl)-2-[2-(4-trifluoromethyl-phenyl)-vinyl]-1H-benzimidazole, |
| 471 | 2-(2-{2-[2-(4-trifluoromethyl-phenyl)-cyclopropyl]-1H-benzimidazol-5-yl}-phenyl)-propan-2-ol, |
| 475 | (E)-N-{2-[2-(2-biphenyl-4-yl-vinyl)-1H-benzimidazol-5-yl]-phenyl}-methanesulfonamide, |
| 476 | (E)-(2-{2-[2-(4-trifluoromethyl-phenyl)-vinyl]-1H-benzimidazol-5-yl}-phenyl)-methanol, |

-continued

| Cpd | Name |
|---|---|
| 482 | (E)-2-(2-{2-[2-(2-trifluoromethyl-phenyl)-vinyl]-1H-benzimidazol-5-yl}-phenyl)-propan-2-ol, |
| 489 | 2-[2-(2-phenylethynyl-1H-benzimidazol-5-yl)-phenyl]-propan-2-ol, |
| 490 | 2-(2-phenylethynyl-1H-benzimidazol-5-yl)-benzenesulfonamide, |
| 491 | (E)-5-(2-aminosulfonylamino-methylphenyl)-2-[2-(4-trifluoromethyl-phenyl)-vinyl]-1H-benzimidazole, |
| 492 | 2-{2-[2-(4-trifluoromethyl-phenylethynyl)-1H-benzimidazol-5-yl]-phenyl}-propan-2-ol, |
| 494 | 2-(2-{2-[2-(4-methoxy-phenyl)-cyclopropyl]-1H-benzimidazol-5-yl}-phenyl)-propan-2-ol, |
| 497 | 2-(2-{2-[2-(4-trifluoromethoxy-phenyl)-cyclopropyl]-1H-benzimidazol-5-yl}-phenyl)-propan-2-ol, |
| 498 | 2-{2-[2-(4-trifluoromethyl-phenyl)-cyclopropyl]-1H-benzimidazol-5-yl}-benzamide, |
| 500 | 5-(2-methanesulfonyl-phenyl)-2-[2-(4-trifluoromethyl-phenyl)-cyclopropyl]-1H-benzimidazole, |
| 501 | 2-(2-{2-[(1R,2R)-2-(4-trifluoromethyl-phenyl)-cyclopropyl]-1H-benzimidazol-5-yl}-phenyl)-propan-2-ol, |
| 503 | 2-(2-{2-[(1S,2S)-2-(4-trifluoromethyl-phenyl)-cyclopropyl]-1H-benzimidazol-5-yl}-phenyl)-propan-2-ol, and |
| 504 | 2-{2-[(1S,2S)-2-(4-trifluoromethyl-phenyl)-cyclopropyl]-1H-benzimidazol-5-yl}-benzenesulfonamide. |

A representative compound of Formula (I) or a form thereof includes a compound selected from the group consisting of:

| Cpd | Name |
|---|---|
| 9 | (E)-N-(2-{2-[2-(4-tert-butyl-phenyl)-vinyl]-1H-benzimidazol-5-yl}-phenyl)-methanesulfonamide, |
| 12 | (E)-(2-{2-[2-(4-tert-butyl-phenyl)-vinyl]-1H-benzimidazol-5-yl}-phenyl)-methanol, |
| 17 | (E)-N-(2-{2-[2-(4-trifluoromethyl-phenyl)-vinyl]-1H-benzimidazol-5-yl}-phenyl)-methanesulfonamide, |
| 18 | (E)-2-(2-{2-[2-(4-trifluoromethyl-phenyl)-vinyl]-1H-benzimidazol-5-yl}-phenyl)-propan-2-ol, |
| 69 | (E)-2-{2-[2-(4-trifluoromethoxy-phenyl)-vinyl]-1H-benzimidazol-5-yl}-benzenesulfonamide, |
| 70 | (E)-2-{2-[2-(4-trifluoromethyl-phenyl)-vinyl]-1H-benzimidazol-5-yl}-benzenesulfonamide, |
| 78 | (E)-2-(2-{2-[2-(4-chloro-phenyl)-vinyl]-1H-benzimidazol-5-yl}-phenyl)-propan-2-ol, |
| 79 | (E)-2-{2-[2-(4-chloro-phenyl)-vinyl]-1H-benzimidazol-5-yl}-benzenesulfonamide, |
| 114 | (E)-2-(2-{2-[2-(3-trifluoromethyl-phenyl)-vinyl]-1H-benzimidazol-5-yl}-phenyl)-propan-2-ol, |
| 130 | 2-{2-[2-(4-trifluoromethyl-phenyl)-ethyl]-1H-benzimidazol-5-yl}-benzenesulfonamide, |
| 310 | (E)-N-methyl-2-{2-[2-(4-trifluoromethyl-phenyl)-vinyl]-1H-benzimidazol-5-yl}-benzenesulfonamide, |
| 312 | (E)-2-{2-[2-(4-bromo-phenyl)-vinyl]-1H-benzimidazol-5-yl}-N-methyl-benzenesulfonamide, |
| 319 | (E)-2-{2-[2-(3-fluoro-4-trifluoromethyl-phenyl)-vinyl]-1H-benzimidazol-5-yl}-N-methyl-benzenesulfonamide, |
| 341 | (E)-N-methyl-2-{2-[2-(4-trifluoromethylsulfanyl-phenyl)-vinyl]-1H-benzimidazol-5-yl}-benzenesulfonamide, |
| 357 | (E)-2-{2-[2-(2,4-difluoro-phenyl)-vinyl]-1H-benzimidazol-5-yl}-benzenesulfonamide, |
| 358 | (E)-2-{2-[2-(3,4-difluoro-phenyl)-vinyl]-1H-benzimidazol-5-yl}-benzenesulfonamide, |
| 362 | (E)-2-{2-[2-(3-trifluoromethoxy-phenyl)-vinyl]-1H-benzimidazol-5-yl}-benzenesulfonamide, |
| 369 | (E)-2-{2-[2-(4-fluoro-3-trifluoromethyl-phenyl)-vinyl]-1H-benzimidazol-5-yl}-benzenesulfonamide, |
| 384 | 2-{2-[2-(2,3,4-trifluoro-phenyl)-ethyl]-1H-benzimidazol-5-yl}-benzenesulfonamide, |
| 390 | 2-{2-[2-(4-chloro-3-trifluoromethyl-phenyl)-ethyl]-1H-benzimidazol-5-yl}-benzenesulfonamide, |
| 391 | 2-{2-[2-(3-trifluoromethoxy-phenyl)-ethyl]-1H-benzimidazol-5-yl}-benzenesulfonamide, |
| 394 | 2-{2-[2-(2,3-difluoro-phenyl)-ethyl]-1H-benzimidazol-5-yl}-benzenesulfonamide, |

| Cpd | Name |
|---|---|
| 398 | (E)-N,N-dimethyl-2-{2-[2-(4-trifluoromethyl-phenyl)-vinyl]-1H-benzimidazol-5-yl}-benzenesulfonamide, |
| 399 | N,N-dimethyl-2-{2-[2-(4-trifluoromethyl-phenyl)-ethyl]-1H-benzimidazol-5-yl}-benzenesulfonamide, |
| 407 | (E)-N-(2-{2-[2-(4-isopropyl-phenyl)-vinyl]-1H-benzimidazol-5-yl}-phenyl)-methanesulfonamide, |
| 421 | 2-{2-[2-(3-fluoro-5-trifluoromethyl-phenyl)-ethyl]-1H-benzimidazol-5-yl}-benzenesulfonamide, |
| 422 | (E)-5-(2-methanesulfonyl-phenyl)-2-[2-(4-trifluoromethyl-phenyl)-vinyl]-1H-benzimidazole, |
| 428 | (E)-2-{2-[2-(4-chloro-2-fluoro-phenyl)-vinyl]-1H-benzimidazol-5-yl}-benzenesulfonamide, |
| 429 | (E)-2-{2-[2-(4-isopropyl-phenyl)-vinyl]-1H-benzimidazol-5-yl}-benzenesulfonamide, |
| 430 | (E)-2-[2-(2-p-tolyl-vinyl)-1H-benzimidazol-5-yl]-benzenesulfonamide, |
| 434 | (E)-2-{2-[2-(4-fluoro-phenyl)-vinyl]-1H-benzimidazol-5-yl}-benzenesulfonamide, |
| 442 | 2-{2-[2-(4-isopropyl-phenyl)-ethyl]-1H-benzimidazol-5-yl}-benzenesulfonamide, |
| 449 | (E)-2-{2-[2-(2-quinolin-6-yl-vinyl)-1H-benzimidazol-5-yl]-phenyl}-propan-2-ol, |
| 461 | (E)-ethanesulfonic acid (2-{2-[2-(4-trifluoromethyl-phenyl)-vinyl]-1H-benzimidazol-5-yl}-phenyl)-amide, |
| 464 | 2-(2-{2-[2-(4-trifluoromethyl-phenyl)-ethyl]-1H-benzimidazol-5-yl}-phenyl)-propan-2-ol, |
| 468 | (E)-2-[2-(2-styryl-1H-benzimidazol-5-yl)-phenyl]-propan-2-ol, |
| 469 | (Z)-2-(2-{2-[2-(4-trifluoromethyl-phenyl)-vinyl]-1H-benzimidazol-5-yl}-phenyl)-propan-2-ol, |
| 471 | 2-(2-{2-[2-(4-trifluoromethyl-phenyl)-cyclopropyl]-1H-benzimidazol-5-yl}-phenyl)-propan-2-ol, |
| 489 | 2-[2-(2-phenylethynyl-1H-benzimidazol-5-yl)-phenyl]-propan-2-ol, |
| 492 | 2-{2-[2-(4-trifluoromethyl-phenylethynyl)-1H-benzimidazol-5-yl]-phenyl}-propan-2-ol, and |
| 503 | 2-(2-{2-[(1S,2S)-2-(4-trifluoromethyl-phenyl)-cyclopropyl]-1H-benzimidazol-5-yl}-phenyl)-propan-2-ol. |

A representative prophetic compound of Formula (I) or a form thereof includes a compound selected from the group consisting of:

| Cpd | Name |
|---|---|
| 72 | (E)-C,C,C-trifluoro-N-(2-{2-[2-(4-trifluoromethoxy-phenyl)-vinyl]-1H-benzimidazol-5-yl}-phenyl)-methanesulfonamide, |
| 73 | (E)-C,C,C-trifluoro-N-(2-{2-[2-(4-trifluoromethyl-phenyl)-vinyl]-1H-benzimidazol-5-yl}-phenyl)-methanesulfonamide, |
| 74 | (E)-C,C,C-trifluoro-N-(2-{2-[2-(4-trifluoromethanesulfonyl-phenyl)-vinyl]-1H-benzimidazol-5-yl}-phenyl)-methanesulfonamide, |
| 75 | (E)-1-(2-{2-[2-(4-chloro-phenyl)-vinyl]-1H-benzimidazol-5-yl}-phenyl)-ethanone, |
| 76 | (E)-1-{2-[2-(4-chloro-phenyl)-vinyl]-1H-benzimidazol-5-yl}-phenyl)-ethanol, |
| 80 | (E)-N-(2-{2-[2-(4-chloro-phenyl)-vinyl]-1H-benzimidazol-5-yl}-phenyl)-C,C,C-trifluoro-methanesulfonamide, |
| 81 | (E)-1-(2-{2-[2-(4-methanesulfonyl-phenyl)-vinyl]-1H-benzimidazol-5-yl}-phenyl)-ethanone, |
| 82 | (E)-1-(2-{2-[2-(4-methanesulfonyl-phenyl)-vinyl]-1H-benzimidazol-5-yl}-phenyl)-ethanol, |
| 86 | (E)-C,C,C-trifluoro-N-(2-{2-[2-(4-methanesulfonyl-phenyl)-vinyl]-1H-benzimidazol-5-yl}-phenyl)-methanesulfonamide, |
| 87 | (E)-1-[2-(2-{2-[4-(2,2,2-trifluoro-1-trifluoromethyl-ethoxy)-phenyl]-vinyl}-1H-benzimidazol-5-yl)-phenyl]-ethanone, |
| 88 | (E)-1-[2-(2-{2-[4-(2,2,2-trifluoro-1-trifluoromethyl-ethoxy)-phenyl]-vinyl}-1H-benzimidazol-5-yl)-phenyl]-ethanol, |
| 89 | (E)-N-[2-(2-{2-[4-(2,2,2-trifluoro-1-trifluoromethyl-ethoxy)-phenyl]-vinyl}-1H-benzimidazol-5-yl)-phenyl]-methanesulfonamide, |
| 90 | (E)-2-[2-(2-{2-[4-(2,2,2-trifluoro-1-trifluoromethyl-ethoxy)-phenyl]-vinyl}-1H-benzimidazol-5-yl)-phenyl]-propan-2-ol, |
| 91 | (E)-2-(2-{2-[4-(2,2,2-trifluoro-1-trifluoromethyl-ethoxy)-phenyl]-vinyl}-1H-benzimidazol-5-yl)-benzenesulfonamide, |
| 92 | (E)-C,C,C-trifluoro-N-[2-(2-{2-[4-(2,2,2-trifluoro-1-trifluoromethyl-ethoxy)-phenyl]-vinyl}-1H-benzimidazol-5-yl)-phenyl]-methanesulfonamide, |

| Cpd | Name |
|---|---|
| 93 | (E)-1-[2-(2-{2-[4-(2,2,2-trifluoro-ethoxy)-phenyl]-vinyl}-1H-benzimidazol-5-yl)-phenyl]-ethanone, |
| 94 | (E)-1-[2-(2-{2-[4-(2,2,2-trifluoro-ethoxy)-phenyl]-vinyl}-1H-benzimidazol-5-yl)-phenyl]-ethanol, |
| 96 | (E)-2-[2-(2-{2-[4-(2,2,2-trifluoro-ethoxy)-phenyl]-vinyl}-1H-benzimidazol-5-yl)-phenyl]-propan-2-ol, |
| 97 | (E)-2-(2-{2-[4-(2,2,2-trifluoro-ethoxy)-phenyl]-vinyl}-1H-benzimidazol-5-yl)-benzenesulfonamide, |
| 98 | (E)-C,C,C-trifluoro-N-[2-(2-{2-[4-(2,2,2-trifluoro-ethoxy)-phenyl]-vinyl}-1H-benzimidazol-5-yl)-phenyl]-methanesulfonamide, |
| 99 | (E)-1-[2-(2-{2-[4-(2,2,3,3,3-pentafluoro-propoxy)-phenyl]-vinyl}-1H-benzimidazol-5-yl)-phenyl]-ethanone, |
| 100 | (E)-1-[2-(2-{2-[4-(2,2,3,3,3-pentafluoro-propoxy)-phenyl]-vinyl}-1H-benzimidazol-5-yl)-phenyl]-ethanol, |
| 102 | (E)-2-[2-(2-{2-[4-(2,2,3,3,3-pentafluoro-propoxy)-phenyl]-vinyl}-1H-benzimidazol-5-yl)-phenyl]-propan-2-ol, |
| 103 | (E)-2-(2-{2-[4-(2,2,3,3,3-pentafluoro-propoxy)-phenyl]-vinyl}-1H-benzimidazol-5-yl)-benzenesulfonamide, |
| 104 | (E)-C,C,C-trifluoro-N-[2-(2-{2-[4-(2,2,3,3,3-pentafluoro-propoxy)-phenyl]-vinyl}-1H-benzimidazol-5-yl)-phenyl]-methanesulfonamide, |
| 105 | (E)-1-(2-{2-[2-(3-chloro-phenyl)-vinyl]-1H-benzimidazol-5-yl}-phenyl)-ethanone, |
| 106 | (E)-1-(2-{2-[2-(3-chloro-phenyl)-vinyl]-1H-benzimidazol-5-yl}-phenyl)-ethanol, |
| 107 | (E)-N-(2-{2-[2-(3-chloro-phenyl)-vinyl]-1H-benzimidazol-5-yl}-phenyl)-methanesulfonamide, |
| 108 | (E)-2-(2-{2-[2-(3-chloro-phenyl)-vinyl]-1H-benzimidazol-5-yl}-phenyl)-propan-2-ol, |
| 109 | (E)-2-{2-[2-(3-chloro-phenyl)-vinyl]-1H-benzimidazol-5-yl}-benzenesulfonamide, |
| 110 | (E)-N-(2-{2-[2-(3-chloro-phenyl)-vinyl]-1H-benzimidazol-5-yl}-phenyl)-C,C,C-trifluoro-methanesulfonamide, |
| 111 | (E)-1-(2-{2-[2-(3-trifluoromethyl-phenyl)-vinyl]-1H-benzimidazol-5-yl}-phenyl)-ethanone, |
| 112 | (E)-1-(2-{2-[2-(3-trifluoromethyl-phenyl)-vinyl]-1H-benzimidazol-5-yl}-phenyl)-ethanol, |
| 115 | (E)-2-{2-[2-(3-trifluoromethyl-phenyl)-vinyl]-1H-benzimidazol-5-yl}-benzenesulfonamide, |
| 116 | (E)-C,C,C-trifluoro-N-(2-{2-[2-(3-trifluoromethyl-phenyl)-vinyl]-1H-benzimidazol-5-yl}-phenyl)-methanesulfonamide, |
| 117 | (E)-N-(4-{2-[5-(2-acetyl-phenyl)-1H-benzimidazol-2-yl]-vinyl}-phenyl)-methanesulfonamide, |
| 118 | (E)-N-[4-(2-{5-[2-(1-hydroxy-ethyl)-phenyl]-1H-benzimidazol-2-yl}-vinyl)-phenyl]-methanesulfonamide, |
| 119 | (E)-N-(2-{2-[2-(4-methanesulfonylamino-phenyl)-vinyl]-1H-benzimidazol-5-yl}-phenyl)-methanesulfonamide, |
| 120 | (E)-N-[4-(2-{5-[2-(1-hydroxy-1-methyl-ethyl)-phenyl]-1H-benzimidazol-2-yl}-vinyl)-phenyl]-methanesulfonamide, |
| 121 | (E)-2-{2-[2-(4-methanesulfonylamino-phenyl)-vinyl]-1H-benzimidazol-5-yl}-benzenesulfonamide, |
| 122 | (E)-C,C,C-trifluoro-N-(2-{2-[2-(4-methanesulfonylamino-phenyl)-vinyl]-1H-benzimidazol-5-yl}-phenyl)-methanesulfonamide, |
| 123 | (E)-N-(4-{2-[5-(2-acetyl-phenyl)-1H-benzimidazol-2-yl]-vinyl}-phenyl)-C,C,C-trifluoro-methanesulfonamide, |
| 124 | (E)-C,C,C-trifluoro-N-[4-(2-{5-[2-(1-hydroxy-ethyl)-phenyl]-1H-benzimidazol-2-yl}-vinyl)-phenyl]-methanesulfonamide, |
| 125 | (E)-C,C,C-trifluoro-N-(4-{2-[5-(2-methanesulfonylamino-phenyl)-1H-benzimidazol-2-yl]-vinyl}-phenyl)-methanesulfonamide, |
| 126 | (E)-C,C,C-trifluoro-N-[4-(2-{5-[2-(1-hydroxy-1-methyl-ethyl)-phenyl]-1H-benzimidazol-2-yl}-vinyl)-phenyl]-methanesulfonamide, |
| 127 | (E)-2-{2-[2-(4-trifluoromethanesulfonylamino-phenyl)-vinyl]-1H-benzimidazol-5-yl}-benzenesulfonamide, |
| 128 | (E)-C,C,C-trifluoro-N-(4-{2-[5-(2-trifluoromethanesulfonylamino-phenyl)-1H-benzimidazol-2-yl]-vinyl}-phenyl)-methanesulfonamide, |
| 132 | C,C,C-trifluoro-N-(2-{2-[2-(4-trifluoromethoxy-phenyl)-ethyl]-1H-benzimidazol-5-yl}-phenyl)-methanesulfonamide, |
| 133 | C,C,C-trifluoro-N-(2-{2-[2-(4-trifluoromethyl-phenyl)-ethyl]-1H-benzimidazol-5-yl}-phenyl)-methanesulfonamide, |
| 134 | C,C,C-trifluoro-N-(2-{2-[2-(4-trifluoromethanesulfonyl-phenyl)-ethyl]-1H-benzimidazol-5-yl}-phenyl)-methanesulfonamide, |
| 135 | 1-(2-{2-[2-(4-chloro-phenyl)-ethyl]-1H-benzimidazol-5-yl}-phenyl)-ethanone, |
| 136 | 1-(2-{2-[2-(4-chloro-phenyl)-ethyl]-1H-benzimidazol-5-yl}-phenyl)-ethanol, |
| 137 | N-(2-{2-[2-(4-chloro-phenyl)-ethyl]-1H-benzimidazol-5-yl}-phenyl)-methanesulfonamide, |
| 138 | 2-(2-{2-[2-(4-chloro-phenyl)-ethyl]-1H-benzimidazol-5-yl}-phenyl)-propan-2-ol, |

| Cpd | Name |
|---|---|
| 140 | N-(2-{2-[2-(4-chloro-phenyl)-ethyl]-1H-benzimidazol-5-yl}-phenyl)-C,C,C-trifluoro-methanesulfonamide, |
| 141 | 1-(2-{2-[2-(4-methanesulfonyl-phenyl)-ethyl]-1H-benzimidazol-5-yl}-phenyl)-ethanone, |
| 142 | 1-(2-{2-[2-(4-methanesulfonyl-phenyl)-ethyl]-1H-benzimidazol-5-yl}-phenyl)-ethanol, |
| 143 | N-(2-{2-[2-(4-methanesulfonyl-phenyl)-ethyl]-1H-benzimidazol-5-yl}-phenyl)-methanesulfonamide, |
| 144 | 2-(2-{2-[2-(4-methanesulfonyl-phenyl)-ethyl]-1H-benzimidazol-5-yl}-phenyl)-propan-2-ol, |
| 146 | C,C,C-trifluoro-N-(2-{2-[2-(4-methanesulfonyl-phenyl)-ethyl]-1H-benzimidazol-5-yl}-phenyl)-methanesulfonamide, |
| 147 | 1-[2-(2-{2-[4-(2,2,2-trifluoro-1-trifluoromethyl-ethoxy)-phenyl]-ethyl}-1H-benzimidazol-5-yl)-phenyl]-ethanone, |
| 148 | 1-(2-(2-{2-[4-(2,2,2-trifluoro-1-trifluoromethyl-ethoxy)-phenyl]-ethyl}-1H-benzimidazol-5-yl)-phenyl]-ethanol, |
| 149 | N-[2-(2-{2-[4-(2,2,2-trifluoro-1-trifluoromethyl-ethoxy)-phenyl]-ethyl}-1H-benzimidazol-5-yl)-phenyl]-methanesulfonamide, |
| 150 | 2-[2-(2-{2-[4-(2,2,2-trifluoro-1-trifluoromethyl-ethoxy)-phenyl]-ethyl}-1H-benzimidazol-5-yl)-phenyl]-propan-2-ol, |
| 151 | 2-(2-{2-[4-(2,2,2-trifluoro-1-trifluoromethyl-ethoxy)-phenyl]-ethyl}-1H-benzimidazol-5-yl)-benzenesulfonamide, |
| 152 | C,C,C-trifluoro-N-[2-(2-{2-[4-(2,2,2-trifluoro-1-trifluoromethyl-ethoxy)-phenyl]-ethyl}-1H-benzimidazol-5-yl)-phenyl]-methanesulfonamide, |
| 153 | 1-[2-(2-{2-[4-(2,2,2-trifluoro-ethoxy)-phenyl]-ethyl}-1H-benzimidazol-5-yl)-phenyl]-ethanone, |
| 154 | 1-[2-(2-{2-[4-(2,2,2-trifluoro-ethoxy)-phenyl]-ethyl}-1H-benzimidazol-5-yl)-phenyl]-ethanol, |
| 155 | N-[2-(2-{2-[4-(2,2,2-trifluoro-ethoxy)-phenyl]-ethyl}-1H-benzimidazol-5-yl)-phenyl]-methanesulfonamide, |
| 156 | 2-[2-(2-{2-[4-(2,2,2-trifluoro-ethoxy)-phenyl]-ethyl}-1H-benzimidazol-5-yl)-phenyl]-propan-2-ol, |
| 157 | 2-(2-{2-[4-(2,2,2-trifluoro-ethoxy)-phenyl]-ethyl}-1H-benzimidazol-5-yl)-benzenesulfonamide, |
| 158 | C,C,C-trifluoro-N-[2-(2-{2-[4-(2,2,2-trifluoro-ethoxy)-phenyl]-ethyl}-1H-benzimidazol-5-yl)-phenyl]-methanesulfonamide, |
| 159 | 1-[2-(2-{2-[4-(2,2,3,3,3-pentafluoro-propoxy)-phenyl]-ethyl}-1H-benzimidazol-5-yl)-phenyl]-ethanone, |
| 160 | 1-[2-(2-{2-[4-(2,2,3,3,3-pentafluoro-propoxy)-phenyl]-ethyl}-1H-benzimidazol-5-yl)-phenyl]-ethanol, |
| 161 | N-[2-(2-{2-[4-(2,2,3,3,3-pentafluoro-propoxy)-phenyl]-ethyl}-1H-benzimidazol-5-yl)-phenyl]-methanesulfonamide, |
| 162 | 2-[2-(2-{2-[4-(2,2,3,3,3-pentafluoro-propoxy)-phenyl]-ethyl}-1H-benzimidazol-5-yl)-phenyl]-propan-2-ol, |
| 163 | 2-(2-{2-[4-(2,2,3,3,3-pentafluoro-propoxy)-phenyl]-ethyl}-1H-benzimidazol-5-yl)-benzenesulfonamide, |
| 164 | C,C,C-trifluoro-N-[2-(2-{2-[4-(2,2,3,3,3-pentafluoro-propoxy)-phenyl]-ethyl}-1H-benzimidazol-5-yl)-phenyl]-methanesulfonamide, |
| 165 | 1-(2-{2-[2-(3-chloro-phenyl)-ethyl]-1H-benzimidazol-5-yl}-phenyl)-ethanone, |
| 166 | 1-(2-{2-[2-(3-chloro-phenyl)-ethyl]-1H-benzimidazol-5-yl}-phenyl)-ethanol, |
| 167 | N-(2-{2-[2-(3-chloro-phenyl)-ethyl]-1H-benzimidazol-5-yl}-phenyl)-methanesulfonamide, |
| 168 | 2-(2-{2-[2-(3-chloro-phenyl)-ethyl]-1H-benzimidazol-5-yl}-phenyl)-propan-2-ol, |
| 169 | 2-{2-[2-(3-chloro-phenyl)-ethyl]-1H-benzimidazol-5-yl}-benzenesulfonamide, |
| 170 | N-(2-{2-[2-(3-chloro-phenyl)-ethyl]-1H-benzimidazol-5-yl}-phenyl)-C,C,C-trifluoro-methanesulfonamide, |
| 171 | 1-(2-{2-[2-(3-trifluoromethyl-phenyl)-ethyl]-1H-benzimidazol-5-yl}-phenyl)-ethanone, |
| 172 | 1-(2-{2-[2-(3-trifluoromethyl-phenyl)-ethyl]-1H-benzimidazol-5-yl}-phenyl)-ethanol, |
| 173 | N-(2-{2-[2-(3-trifluoromethyl-phenyl)-ethyl]-1H-benzimidazol-5-yl}-phenyl)-methanesulfonamide, |
| 174 | 2-(2-{2-[2-(3-trifluoromethyl-phenyl)-ethyl]-1H-benzimidazol-5-yl}-phenyl)-propan-2-ol, |
| 176 | C,C,C-trifluoro-N-(2-{2-[2-(3-trifluoromethyl-phenyl)-ethyl]-1H-benzimidazol-5-yl}-phenyl)-methanesulfonamide, |
| 177 | N-(4-{2-[5-(2-acetyl-phenyl)-1H-benzimidazol-2-yl]-ethyl}-phenyl)-methanesulfonamide, |
| 178 | N-[4-(2-{5-[2-(1-hydroxy-ethyl)-phenyl]-1H-benzimidazol-2-yl}-ethyl)-phenyl]-methanesulfonamide, |
| 179 | N-(2-{2-[2-(4-methanesulfonylamino-phenyl)-ethyl]-1H-benzimidazol-5-yl}-phenyl)-methanesulfonamide, |
| 180 | N-[4-(2-{5-[2-(1-hydroxy-1-methyl-ethyl)-phenyl]-1H-benzimidazol-2-yl}-ethyl)-phenyl]-methanesulfonamide, |

-continued

| Cpd | Name |
|---|---|
| 181 | 2-{2-[2-(4-methanesulfonylamino-phenyl)-ethyl]-1H-benzimidazol-5-yl}-benzenesulfonamide, |
| 182 | C,C,C-trifluoro-N-(2-{2-[2-(4-methanesulfonylamino-phenyl)-ethyl]-1H-benzimidazol-5-yl}-phenyl)-methanesulfonamide, |
| 183 | N-(4-{2-[5-(2-acetyl-phenyl)-1H-benzimidazol-2-yl]-ethyl}-phenyl)-C,C,C-trifluoro-methanesulfonamide, |
| 184 | C,C,C-trifluoro-N-[4-(2-{5-[2-(1-hydroxy-ethyl)-phenyl]-1H-benzimidazol-2-yl}-ethyl)-phenyl]-methanesulfonamide, |
| 185 | C,C,C-trifluoro-N-(4-{2-[5-(2-methanesulfonylamino-phenyl)-1H-benzimidazol-2-yl]-ethyl}-phenyl)-methanesulfonamide, |
| 186 | C,C,C-trifluoro-N-[4-(2-{5-[2-(1-hydroxy-1-methyl-ethyl)-phenyl]-1H-benzimidazol-2-yl}-ethyl)-phenyl]-methanesulfonamide, |
| 187 | 2-{2-[2-(4-trifluoromethanesulfonylamino-phenyl)-ethyl]-1H-benzimidazol-5-yl}-benzenesulfonamide, |
| 188 | C,C,C-trifluoro-N-(2-{2-[2-(4-trifluoromethanesulfonylamino-phenyl)-ethyl]-1H-benzimidazol-5-yl}-phenyl)-methanesulfonamide, |
| 189 | 2-{2-[2-(4-trifluoromethoxy-phenyl)-cyclopropyl]-1H-benzimidazol-5-yl}-benzenesulfonamide, |
| 191 | 2-{2-[2-(4-trifluoromethanesulfonyl-phenyl)-cyclopropyl]-1H-benzimidazol-5-yl}-benzenesulfonamide, |
| 192 | C,C,C-trifluoro-N-(2-{2-[2-(4-trifluoromethoxy-phenyl)-cyclopropyl]-1H-benzimidazol-5-yl}-phenyl)-methanesulfonamide, |
| 193 | C,C,C-trifluoro-N-(2-{2-[2-(4-trifluoromethyl-phenyl)-cyclopropyl]-1H-benzimidazol-5-yl}-phenyl)-methanesulfonamide, |
| 194 | C,C,C-trifluoro-N-(2-{2-[2-(4-trifluoromethanesulfonyl-phenyl)-cyclopropyl]-1H-benzimidazol-5-yl}-phenyl)-methanesulfonamide, |
| 195 | 1-(2-{2-[2-(4-chloro-phenyl)-cyclopropyl]-1H-benzimidazol-5-yl}-phenyl)-ethanone, |
| 196 | 1-(2-{2-[2-(4-chloro-phenyl)-cyclopropyl]-1H-benzimidazol-5-yl}-phenyl)-ethanol, |
| 197 | N-(2-{2-[2-(4-chloro-phenyl)-cyclopropyl]-1H-benzimidazol-5-yl}-phenyl)-methanesulfonamide, |
| 199 | 2-{2-[2-(4-chloro-phenyl)-cyclopropyl]-1H-benzimidazol-5-yl}-benzenesulfonamide, |
| 200 | N-(2-{2-[2-(4-chloro-phenyl)-cyclopropyl]-1H-benzimidazol-5-yl}-phenyl)-C,C,C-trifluoro-methanesulfonamide, |
| 201 | 1-(2-{2-[2-(4-methanesulfonyl-phenyl)-cyclopropyl]-1H-benzimidazol-5-yl}-phenyl)-ethanone, |
| 202 | 1-(2-{2-[2-(4-methanesulfonyl-phenyl)-cyclopropyl]-1H-benzimidazol-5-yl}-phenyl)-ethanol, |
| 203 | N-(2-{2-[2-(4-methanesulfonyl-phenyl)-cyclopropyl]-1H-benzimidazol-5-yl}-phenyl)-methanesulfonamide, |
| 204 | 2-(2-{2-[2-(4-methanesulfonyl-phenyl)-cyclopropyl]-1H-benzimidazol-5-yl}-phenyl)-propan-2-ol, |
| 205 | 2-{2-[2-(4-methanesulfonyl-phenyl)-cyclopropyl]-1H-benzimidazol-5-yl}-benzenesulfonamide, |
| 206 | C,C,C-trifluoro-N-(2-{2-[2-(4-methanesulfonyl-phenyl)-cyclopropyl]-1H-benzimidazol-5-yl}-phenyl)-methanesulfonamide, |
| 207 | 1-[2-(2-{2-[4-(2,2,2-trifluoro-1-trifluoromethyl-ethoxy)-phenyl]-cyclopropyl}-1H-benzimidazol-5-yl)-phenyl]-ethanone, |
| 208 | 1-[2-(2-{2-[4-(2,2,2-trifluoro-1-trifluoromethyl-ethoxy)-phenyl]-cyclopropyl}-1H-benzimidazol-5-yl)-phenyl]-ethanol, |
| 209 | N-[2-(2-{2-[4-(2,2,2-trifluoro-1-trifluoromethyl-ethoxy)-phenyl]-cyclopropyl}-1H-benzimidazol-5-yl)-phenyl]-methanesulfonamide, |
| 210 | 2-[2-(2-{2-[4-(2,2,2-trifluoro-1-trifluoromethyl-ethoxy)-phenyl]-cyclopropyl}-1H-benzimidazol-5-yl)-phenyl]-propan-2-ol, |
| 211 | 2-(2-{2-[4-(2,2,2-trifluoro-1-trifluoromethyl-ethoxy)-phenyl]-cyclopropyl}-1H-benzimidazol-5-yl)-benzenesulfonamide, |
| 212 | C,C,C-trifluoro-N-[2-(2-{2-[4-(2,2,2-trifluoro-1-trifluoromethyl-ethoxy)-phenyl]-cyclopropyl}-1H-benzimidazol-5-yl)-phenyl]-methanesulfonamide, |
| 213 | 1-[2-(2-{2-[4-(2,2,2-trifluoro-ethoxy)-phenyl]-cyclopropyl}-1H-benzimidazol-5-yl)-phenyl]-ethanone, |
| 214 | 1-[2-(2-{2-[4-(2,2,2-trifluoro-ethoxy)-phenyl]-cyclopropyl}-1H-benzimidazol-5-yl)-phenyl]-ethanol, |
| 215 | N-[2-(2-{2-[4-(2,2,2-trifluoro-ethoxy)-phenyl]-cyclopropyl}-1H-benzimidazol-5-yl)-phenyl]-methanesulfonamide, |
| 216 | 2-[2-(2-{2-[4-(2,2,2-trifluoro-ethoxy)-phenyl]-cyclopropyl}-1H-benzimidazol-5-yl)-phenyl]-propan-2-ol, |
| 217 | 2-(2-{2-[4-(2,2,2-trifluoro-ethoxy)-phenyl]-cyclopropyl}-1H-benzimidazol-5-yl)-benzenesulfonamide, |
| 218 | C,C,C-trifluoro-N-[2-(2-{2-[4-(2,2,2-trifluoro-ethoxy)-phenyl]-cyclopropyl}-1H-benzimidazol-5-yl)-phenyl]-methanesulfonamide, |
| 219 | 1-[2-(2-{2-[4-(2,2,3,3,3-pentafluoro-propoxy)-phenyl]-cyclopropyl}-1H-benzimidazol-5-yl)-phenyl]-ethanone, |
| 220 | 1-[2-(2-{2-[4-(2,2,3,3,3-pentafluoro-propoxy)-phenyl]-cyclopropyl}-1H-benzimidazol-5-yl)-phenyl]-ethanol, |
| 221 | N-[2-(2-{2-[4-(2,2,3,3,3-pentafluoro-propoxy)-phenyl]-cyclopropyl}-1H-benzimidazol-5-yl)-phenyl]-methanesulfonamide, |

| Cpd | Name |
|---|---|
| 222 | 2-[2-(2-{2-[4-(2,2,3,3,3-pentafluoro-propoxy)-phenyl]-cyclopropyl}-1H-benzimidazol-5-yl)-phenyl]-propan-2-ol, |
| 223 | 2-(2-{2-[4-(2,2,3,3,3-pentafluoro-propoxy)-phenyl]-cyclopropyl}-1H-benzimidazol-5-yl)-benzenesulfonamide, |
| 224 | C,C,C-trifluoro-N-[2-(2-{2-[4-(2,2,3,3,3-pentafluoro-propoxy)-phenyl]-cyclopropyl}-1H-benzimidazol-5-yl)-phenyl]-methanesulfonamide, |
| 225 | 1-(2-{2-[2-(3-chloro-phenyl)-cyclopropyl]-1H-benzimidazol-5-yl}-phenyl)-ethanone, |
| 226 | 1-(2-{2-[2-(3-chloro-phenyl)-cyclopropyl]-1H-benzimidazol-5-yl}-phenyl)-ethanol, |
| 227 | N-(2-{2-[2-(3-chloro-phenyl)-cyclopropyl]-1H-benzimidazol-5-yl}-phenyl)-methanesulfonamide, |
| 228 | 2-(2-{2-[2-(3-chloro-phenyl)-cyclopropyl]-1H-benzimidazol-5-yl}-phenyl)-propan-2-ol, |
| 229 | 2-{2-[2-(3-chloro-phenyl)-cyclopropyl]-1H-benzimidazol-5-yl}-benzenesulfonamide, |
| 230 | N-(2-{2-[2-(3-chloro-phenyl)-cyclopropyl]-1H-benzimidazol-5-yl}-phenyl)-C,C,C-trifluoro-methanesulfonamide, |
| 231 | 1-(2-{2-[2-(3-trifluoromethyl-phenyl)-cyclopropyl]-1H-benzimidazol-5-yl}-phenyl)-ethanone, |
| 232 | 1-(2-{2-[2-(3-trifluoromethyl-phenyl)-cyclopropyl]-1H-benzimidazol-5-yl}-phenyl)-ethanol, |
| 233 | N-(2-{2-[2-(3-trifluoromethyl-phenyl)-cyclopropyl]-1H-benzimidazol-5-yl}-phenyl)-methanesulfonamide, |
| 235 | 2-{2-[2-(3-trifluoromethyl-phenyl)-cyclopropyl]-1H-benzimidazol-5-yl}-benzenesulfonamide, |
| 236 | C,C,C-trifluoro-N-(2-{2-[2-(3-trifluoromethyl-phenyl)-cyclopropyl]-1H-benzimidazol-5-yl}-phenyl)-methanesulfonamide, |
| 237 | N-(4-{2-[5-(2-acetyl-phenyl)-1H-benzimidazol-2-yl]-cyclopropyl}-phenyl)-methanesulfonamide, |
| 238 | N-[4-(2-{5-[2-(1-hydroxy-ethyl)-phenyl]-1H-benzimidazol-2-yl}-cyclopropyl)-phenyl]-methanesulfonamide, |
| 239 | N-(2-{2-[2-(4-methanesulfonylamino-phenyl)-cyclopropyl]-1H-benzimidazol-5-yl}-phenyl)-methanesulfonamide, |
| 240 | N-[4-(2-{5-[2-(1-hydroxy-1-methyl-ethyl)-phenyl]-1H-benzimidazol-2-yl}-cyclopropyl)-phenyl]-methanesulfonamide, |
| 241 | 2-{2-[2-(4-methanesulfonylamino-phenyl)-cyclopropyl]-1H-benzimidazol-5-yl}-benzenesulfonamide, |
| 242 | C,C,C-trifluoro-N-(2-{2-[2-(4-methanesulfonylamino-phenyl)-cyclopropyl]-1H-benzimidazol-5-yl}-phenyl)-methanesulfonamide, |
| 243 | N-(4-{2-[5-(2-acetyl-phenyl)-1H-benzimidazol-2-yl]-cyclopropyl}-phenyl)-C,C,C-trifluoro-methanesulfonamide, |
| 244 | C,C,C-trifluoro-N-[4-(2-{5-[2-(1-hydroxy-ethyl)-phenyl]-1H-benzimidazol-2-yl}-cyclopropyl)-phenyl]-methanesulfonamide, |
| 245 | C,C,C-trifluoro-N-(4-{2-[5-(2-methanesulfonylamino-phenyl)-1H-benzimidazol-2-yl]-cyclopropyl}-phenyl)-methanesulfonamide, |
| 246 | C,C,C-trifluoro-N-[4-(2-{5-[2-(1-hydroxy-1-methyl-ethyl)-phenyl]-1H-benzimidazol-2-yl}-cyclopropyl)-phenyl]-methanesulfonamide, |
| 247 | 2-{2-[2-(4-trifluoromethanesulfonylamino-phenyl)-cyclopropyl]-1H-benzimidazol-5-yl}-benzenesulfonamide, |
| 248 | C,C,C-trifluoro-N-(2-{2-[2-(4-trifluoromethanesulfonylamino-phenyl)-cyclopropyl]-1H-benzimidazol-5-yl}-phenyl)-methanesulfonamide, |
| 249 | 2-[2-(4-trifluoromethoxy-phenylethynyl)-1H-benzimidazol-5-yl]-benzenesulfonamide, |
| 251 | 2-[2-(4-trifluoromethanesulfonyl-phenylethynyl)-1H-benzimidazol-5-yl]-benzenesulfonamide, |
| 252 | C,C,C-trifluoro-N-{2-[2-(4-trifluoromethoxy-phenylethynyl)-1H-benzimidazol-5-yl]-phenyl}-methanesulfonamide, |
| 253 | C,C,C-trifluoro-N-{2-[2-(4-trifluoromethyl-phenylethynyl)-1H-benzimidazol-5-yl]-phenyl}-methanesulfonamide, |
| 254 | C,C,C-trifluoro-N-{2-[2-(4-trifluoromethanesulfonyl-phenylethynyl)-1H-benzimidazol-5-yl]-phenyl}-methanesulfonamide, |
| 255 | 1-{2-[2-(4-chloro-phenylethynyl)-1H-benzimidazol-5-yl]-phenyl}-ethanone, |
| 256 | 1-{2-[2-(4-chloro-phenylethynyl)-1H-benzimidazol-5-yl]-phenyl}-ethanol, |
| 257 | N-{2-[2-(4-chloro-phenylethynyl)-1H-benzimidazol-5-yl]-phenyl}-methanesulfonamide, |
| 258 | 2-{2-[2-(4-chloro-phenylethynyl)-1H-benzimidazol-5-yl]-phenyl}-propan-2-ol, |
| 259 | 2-[2-(4-chloro-phenylethynyl)-1H-benzimidazol-5-yl]-benzenesulfonamide, |
| 260 | N-{2-[2-(4-chloro-phenylethynyl)-1H-benzimidazol-5-yl]-phenyl}-C,C,C-trifluoro-methanesulfonamide, |
| 261 | 1-{2-[2-(4-methanesulfonyl-phenylethynyl)-1H-benzimidazol-5-yl]-phenyl}-ethanone, |
| 262 | 1-{2-[2-(4-methanesulfonyl-phenylethynyl)-1H-benzimidazol-5-yl]-phenyl}-ethanol, |
| 263 | N-{2-[2-(4-methanesulfonyl-phenylethynyl)-1H-benzimidazol-5-yl]-phenyl}-methanesulfonamide, |

| Cpd | Name |
|---|---|
| 264 | 2-{2-[2-(4-methanesulfonyl-phenylethynyl)-1H-benzimidazol-5-yl]-phenyl}-propan-2-ol, |
| 265 | 2-[2-(4-methanesulfonyl-phenylethynyl)-1H-benzimidazol-5-yl]-benzenesulfonamide, |
| 266 | C,C,C-trifluoro-N-{2-[2-(4-methanesulfonyl-phenylethynyl)-1H-benzimidazol-5-yl]-phenyl}-methanesulfonamide, |
| 267 | 1-(2-{2-[4-(2,2,2-trifluoro-1-trifluoromethyl-ethoxy)-phenylethynyl]-1H-benzimidazol-5-yl}-phenyl)-ethanone, |
| 268 | 1-(2-{2-[4-(2,2,2-trifluoro-1-trifluoromethyl-ethoxy)-phenylethynyl]-1H-benzimidazol-5-yl}-phenyl)-ethanol, |
| 269 | N-(2-{2-[4-(2,2,2-trifluoro-1-trifluoromethyl-ethoxy)-phenylethynyl]-1H-benzimidazol-5-yl}-phenyl)-methanesulfonamide, |
| 270 | 2-(2-{2-[4-(2,2,2-trifluoro-1-trifluoromethyl-ethoxy)-phenylethynyl]-1H-benzimidazol-5-yl}-phenyl)-propan-2-ol, |
| 271 | 2-{2-[4-(2,2,2-trifluoro-1-trifluoromethyl-ethoxy)-phenylethynyl]-1H-benzimidazol-5-yl}-benzenesulfonamide, |
| 272 | C,C,C-trifluoro-N-(2-{2-[4-(2,2,2-trifluoro-1-trifluoromethyl-ethoxy)-phenylethynyl]-1H-benzimidazol-5-yl}-phenyl)-methanesulfonamide, |
| 273 | 1-(2-{2-[4-(2,2,2-trifluoro-ethoxy)-phenylethynyl]-1H-benzimidazol-5-yl}-phenyl)-ethanone, |
| 274 | 1-(2-{2-[4-(2,2,2-trifluoro-ethoxy)-phenylethynyl]-1H-benzimidazol-5-yl}-phenyl)-ethanol, |
| 275 | N-(2-{2-[4-(2,2,2-trifluoro-ethoxy)-phenylethynyl]-1H-benzimidazol-5-yl}-phenyl)-methanesulfonamide, |
| 276 | 2-(2-{2-[4-(2,2,2-trifluoro-ethoxy)-phenylethynyl]-1H-benzimidazol-5-yl}-phenyl)-propan-2-ol, |
| 277 | 2-{2-[4-(2,2,2-trifluoro-ethoxy)-phenylethynyl]-1H-benzimidazol-5-yl}-benzenesulfonamide, |
| 278 | C,C,C-trifluoro-N-(2-{2-[4-(2,2,2-trifluoro-ethoxy)-phenylethynyl]-1H-benzimidazol-5-yl}-phenyl)-methanesulfonamide, |
| 279 | 1-(2-{2-[4-(2,2,3,3,3-pentafluoro-propoxy)-phenylethynyl]-1H-benzimidazol-5-yl}-phenyl)-ethanone, |
| 280 | 1-(2-{2-[4-(2,2,3,3,3-pentafluoro-propoxy)-phenylethynyl]-1H-benzimidazol-5-yl}-phenyl)-ethanol, |
| 281 | N-(2-{2-[4-(2,2,3,3,3-pentafluoro-propoxy)-phenylethynyl]-1H-benzimidazol-5-yl}-phenyl)-methanesulfonamide, |
| 282 | 2-(2-{2-[4-(2,2,3,3,3-pentafluoro-propoxy)-phenylethynyl]-1H-benzimidazol-5-yl}-phenyl)-propan-2-ol, |
| 283 | 2-{2-[4-(2,2,3,3,3-pentafluoro-propoxy)-phenylethynyl]-1H-benzimidazol-5-yl}-benzenesulfonamide, |
| 284 | C,C,C-trifluoro-N-(2-{2-[4-(2,2,3,3,3-pentafluoro-propoxy)-phenylethynyl]-1H-benzimidazol-5-yl}-phenyl)-methanesulfonamide, |
| 285 | 1-{2-[2-(3-chloro-phenylethynyl)-1H-benzimidazol-5-yl]-phenyl}-ethanone, |
| 286 | 2-{2-[2-(3-chloro-phenylethynyl)-1H-benzimidazol-5-yl]-phenyl}-propan-2-ol, |
| 287 | N-{2-[2-(3-chloro-phenylethynyl)-1H-benzimidazol-5-yl]-phenyl}-methanesulfonamide, |
| 288 | 1-{2-[2-(3-chloro-phenylethynyl)-1H-benzimidazol-5-yl]-phenyl}-ethanol, |
| 289 | 2-[2-(3-chloro-phenylethynyl)-1H-benzimidazol-5-yl]-benzenesulfonamide, |
| 290 | N-{2-[2-(3-chloro-phenylethynyl)-1H-benzimidazol-5-yl]-phenyl}-C,C,C-trifluoro-methanesulfonamide, |
| 291 | 1-{2-[2-(3-trifluoromethyl-phenylethynyl)-1H-benzimidazol-5-yl]-phenyl}-ethanone, |
| 292 | 1-{2-[2-(3-trifluoromethyl-phenylethynyl)-1H-benzimidazol-5-yl]-phenyl}-ethanol, |
| 293 | N-{2-[2-(3-trifluoromethyl-phenylethynyl)-1H-benzimidazol-5-yl]-phenyl}-methanesulfonamide, |
| 296 | C,C,C-trifluoro-N-{2-[2-(3-trifluoromethyl-phenylethynyl)-1H-benzimidazol-5-yl]-phenyl}-methanesulfonamide, |
| 297 | N-{4-[5-(2-acetyl-phenyl)-1H-benzimidazol-2-yl-ethynyl]-phenyl}-methanesulfonamide, |
| 298 | N-(4-{5-[2-(1-hydroxy-ethyl)-phenyl]-1H-benzimidazol-2-yl-ethynyl}-phenyl)-methanesulfonamide, |
| 299 | N-{2-[2-(4-methanesulfonylamino-phenylethynyl)-1H-benzimidazol-5-yl]-phenyl}-methanesulfonamide, |
| 300 | N-(4-{5-[2-(1-hydroxy-1-methyl-ethyl)-phenyl]-1H-benzimidazol-2-yl-ethynyl}-phenyl)-methanesulfonamide, |
| 301 | 2-[2-(4-methanesulfonylamino-phenylethynyl)-1H-benzimidazol-5-yl]-benzenesulfonamide, |
| 302 | C,C,C-trifluoro-N-{2-[2-(4-methanesulfonylamino-phenylethynyl)-1H-benzimidazol-5-yl]-phenyl}-methanesulfonamide, |
| 303 | N-{4-[5-(2-acetyl-phenyl)-1H-benzimidazol-2-yl-ethynyl]-phenyl}-C,C,C-trifluoro-methanesulfonamide, |
| 304 | C,C,C-trifluoro-N-(4-{5-[2-(1-hydroxy-ethyl)-phenyl]-1H-benzimidazol-2-yl-ethynyl}-phenyl)-methanesulfonamide, |
| 305 | C,C,C-trifluoro-N-{4-[5-(2-methanesulfonylamino-phenyl)-1H-benzimidazol-2-yl-ethynyl]-phenyl}-methanesulfonamide, |

-continued

| Cpd | Name |
|---|---|
| 306 | C,C,C-trifluoro-N-(4-{5-[2-(1-hydroxy-1-methyl-ethyl)-phenyl]-1H-benzimidazol-2-yl-ethynyl}-phenyl)-methanesulfonamide, |
| 307 | 2-[2-(4-trifluoromethanesulfonylamino-phenylethynyl)-1H-benzimidazol-5-yl]-benzenesulfonamide, and |
| 308 | C,C,C-trifluoro-N-{2-[2-(4-trifluoromethanesulfonylamino-phenylethynyl)-1H-benzimidazol-5-yl]-phenyl}-methanesulfonamide. |

General Synthetic Methods

Representative compounds of the present invention can be synthesized in accordance with the general synthetic methods described below and are illustrated in the schemes that follows. Since the schemes are an illustration, the invention should not be construed as being limited by the chemical reactions and conditions expressed. The preparation of the various starting materials used in the schemes is well within the skill of persons versed in the art.

Compounds of the present invention can be synthesized using the methods described in the schemes that follow.

The terms used in describing the invention are commonly used and known to those skilled in the art. As used herein, the following abbreviations and formulas have the indicated meanings:

| Abbreviation | Meaning |
|---|---|
| Boc | tert-butoxycarbonyl |
| BOP | benzotriazol-1-yloxy-tris(dimethylamino)phosphonium hexafluorophosphate |
| AcOH | acetic acid |
| Cpd | compound |
| DBU | 1,8-diazabicyclo[5.4.0]undec-7-ene |
| DCM | dichloromethane |
| DIEA | N,N-diisopropyl ethyl amine |
| DME | ethylene glycol dimethyl ether |
| DMF | N,N-dimethylformamide |
| DMSO | dimethyl sulfoxide |
| EtOAc | ethyl acetate |
| EtOH | ethanol |
| HPLC | high performance liquid chromatography |
| LiOH | lithium hydroxide |
| min | minute(s) |
| n-BuLi | n-butyl lithium |
| h/hr/hrs | hour(s) |
| mCPBA | m-chloroperbenzoic acid |
| MeOH | methanol |
| MTBE | methyl-t-butyl ether |
| PdCl$_2$(dppf) or Pd(dppf)Cl$_2$CH$_2$Cl$_2$ | [1,1'-bis-(diphenylphosphino)ferroceno] dichloropalladium (II) dichloromethane complex |
| Pd(PPh$_3$)$_4$ | palladium tetrakistriphenylphosphine |
| RT or rt | room temperature |
| TBAB | tetrabutylammonium bromide |
| TBSOTf | t-butyldimethylsilyl trifluoromethane sulfonate |
| Et$_3$N | triethylamine |
| TFA | trifluoroacetic acid |
| THF | tetrahydrofuran |
| TLC | thin layer chromatography |

Reaction Scheme AA

Scheme AA illustrates a general synthesis of benzimidazoles of formula AA5, representative of a compound of Formula (I).

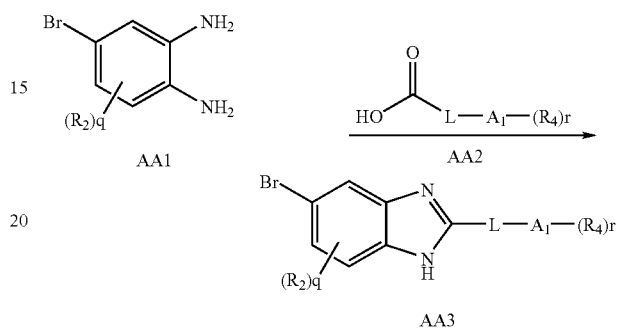

Typically, a solution of 4-bromobenzene-1,2-diamine AA1 and a suitable carboxylic acid AA2 in phosphorous oxychloride (POCl$_3$) is heated at reflux to obtain bromobenzimidazole AA3.

Alternatively, the acid can be converted to an acid chloride using oxalyl chloride and a catalytic amount of DMF in a solvent such as methylene chloride.

The acid chloride AA2 is heated with 4-bromobenzene-1, 2-diamine AA1 in acetic acid to give AA3. A suitably substituted phenyl group can be appended to AA3 by a variety of coupling reactions (Suzuki, Stille) that are well known to those versed in the art. A particularly useful substitution method employs a palladium catalyzed cross-coupling Suzuki reaction (Huff, B. et. al. *Org. Syn.* 1997, 75: 53-60; and, Goodson, F. E. et. al. *Org. Synth.* 1997, 75: 61-68).

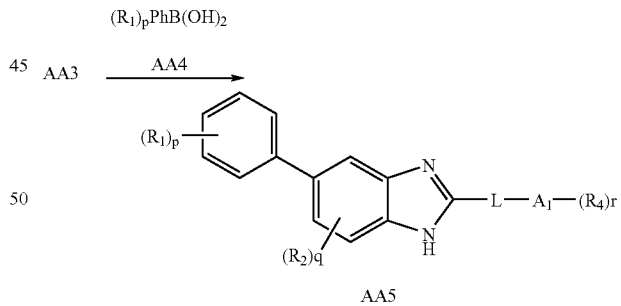

As an example, a mixture of bromobenzimidazole AA3 is reacted with a suitable phenyl boronic acid AA4 in the presence of a reagent such as cesium carbonate and a catalytic amount of a palladium catalyst such as PdCl$_2$dppf in a solvent such as a mixture of dioxane and ethanol at elevated temperatures to give AA5. The reaction times can be reduced by carrying out this procedure at similar (about 100° C.) or lower temperatures in a microwave synthesizer. Other palladium catalysts suitable for this type of reaction include Pd(PPh$_3$)$_4$.

Reaction Scheme BB

Cinnamic acids, as required, can be synthesized via procedures described in reaction Scheme BB.

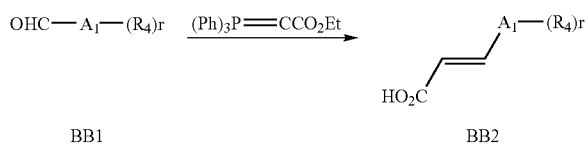

A solution of arylaldehyde BB1 and (carbethoxymethylene)triphenyl phosphorane in a solvent such as toluene or benzene in the presence of a base such as NaOH is stirred usually at elevated temperatures to give the corresponding cinnamate ester. The ester is hydrolyzed under standard conditions to provide the corresponding cinnamic acid BB2.

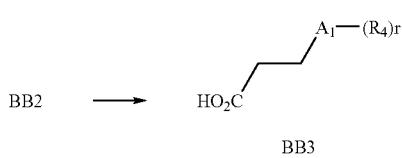

Phenylpropionic acid BB3, as required, can be synthesized from cinnamic acid BB2 by hydrogenation using a variety of standard procedures. As shown above, a mixture of BB2 in ethanol with a catalytic amount of palladium on carbon (10%) is stirred at room temperature in an atmosphere of hydrogen (50 psi) to provide acid BB3.

Reaction Scheme BB'

Reaction Scheme BB' is a variation of Reaction Scheme BB.

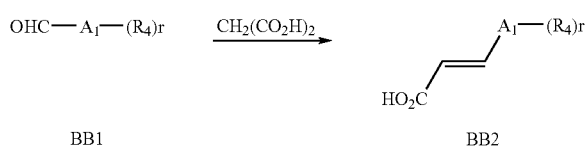

Reaction of aldehyde BB1 with malonic acid and a catalytic amount of piperidine in pyridine at elevated temperatures produces cinnamic acid BB2 in high yield.

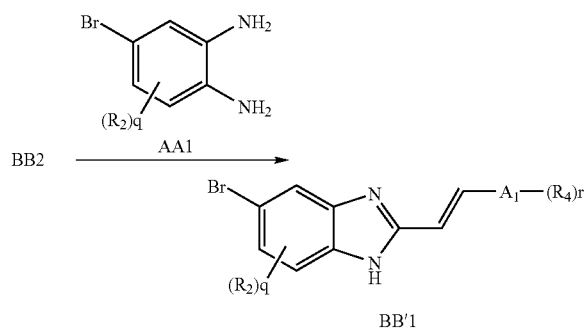

Acid BB2 is converted to the acid chloride by reaction with oxalyl chloride and a catalytic amount of DMF in a solvent such as methylene chloride. The acid chloride is then heated with AA1 in acetic acid to give BB'1, which is further elaborated in place of AA3 as described in reaction Scheme AA.

Reaction Scheme CC

Reaction Scheme CC provides a method to prepare substituted 4-bromobenzene-1,2-diamine intermediates.

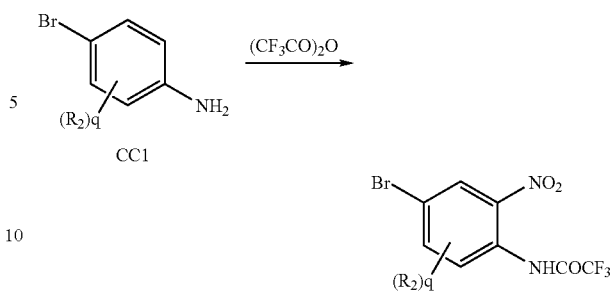

As an example, to a solution of a suitably substituted 4-bromoaniline CC1 in trifluoroacetic anhydride is added $KNO_3$ portionwise at a suitable temperature. The reaction mixture may then be warmed to room temperature for optimal conversion to nitroamide CC2.

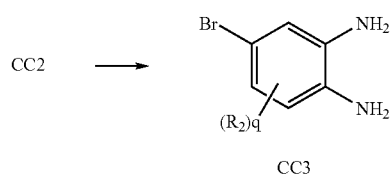

Sequentially, using standard procedures, the amide is hydrolyzed and the nitro group is reduced to give bromodiamine CC3. Intermediate CC3 is further elaborated as described in reaction Scheme AA.

Reaction Scheme DD

An alternative synthetic sequence to produce compounds of the present invention is described in reaction Scheme DD.

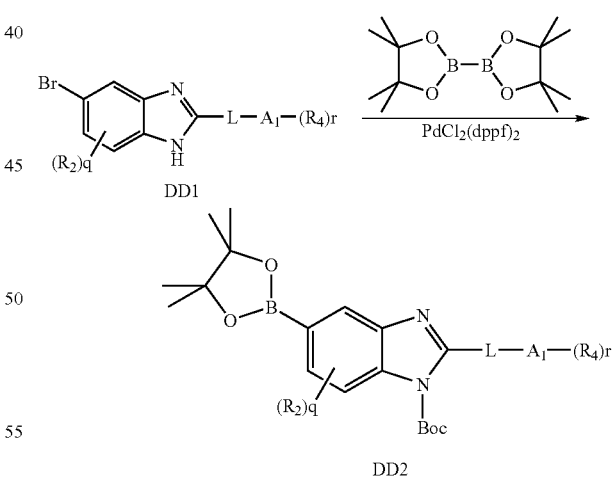

A substituted bromobenzimidazole DD1 (representative of AA3 in Scheme AA) is protected (using a protecting group such as Boc), then converted to a pinicolboronate ester DD2 under standard Suzuki coupling conditions (Prieto, M. et. al., *J. Org. Chem.* 2004, 69: 6812-6820; McDonald, D. et. al., *Bioorg. Med. Chem. Lett.* 2005,15: 5241-5246; and, Poon, S. F. et. al. *Bioorg. Med. Chem. Lett.* 2004, 14, 5477-5480).

In a typical procedure, a mixture of bromo-benzimidazole DD1, bis-(pinacolato)diboron, potassium carbonate and a catalytic amount of a palladium catalyst such as PdCl$_2$dppf in DMF is heated at elevated temperatures to give boronate ester DD2. Frequently, the reaction durations can be reduced by carrying out this procedure at similar or lower temperatures in a microwave irradiation apparatus.

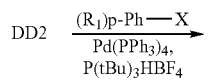

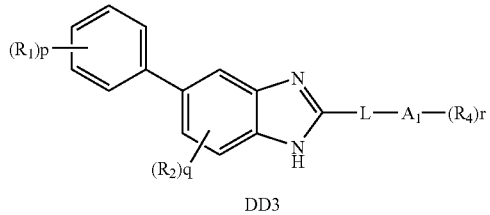

Boronate ester DD2 can be converted to compounds of the present invention (Boc protected DD3) by Suzuki coupling with a phenyl halide, mesylate or triflate (R$_1$)$_p$Ph-X. In this instance, borane DD2 is reacted with a suitable aryl halide, tetrakis (triphenylphosphine) palladium (0) and tri-tert-butylphosphonium tetrafluoroborate in 2M aqueous potassium carbonate in toluene at 100° C. to give the protected form of DD3. Deprotection with an acid such as TFA gives DD3.

Reaction Scheme EE

Reaction Scheme EE describes methods to prepare representative compounds of the present invention.

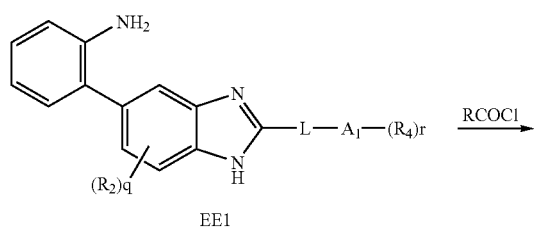

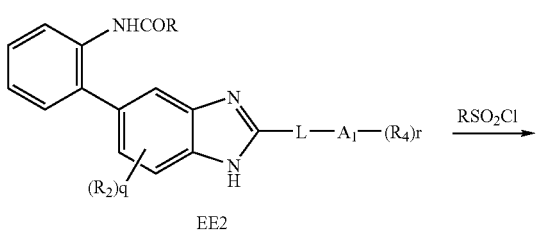

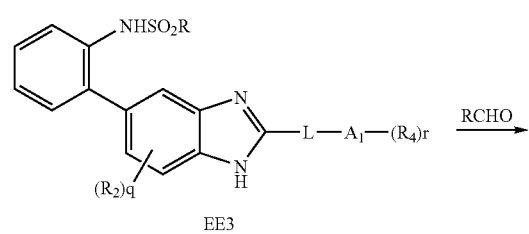

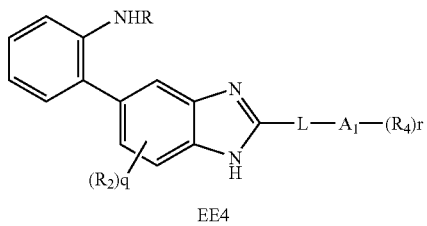

Aniline EE1 can be converted to a variety of amides, carbamates or ureas EE2 by utilizing any number of acylation methods that are commonly used by persons versed in the art. As an example, reaction of EE1 in a solvent such as THF with a substituted acid chloride and a base such as triethylamine gives the corresponding amide of EE2. As a further example, reaction of EE1 in THF with a substituted chloroformate and triethylamine gives the corresponding substituted carbamate of EE2.

EE1 can be converted to sulfonamides by utilizing various sulfonylation conditions. For instance, reaction of EE1 in a solvent such as THF with an alkylsulfonyl chloride and triethylamine gives the alkylsulfonamide EE3. EE1 can be selectively, and successively substituted to give EE3. An efficient method of achieving this is via reductive alkylation with aldehydes or ketones (see Mattson, R. J. et. al. *J. Org. Chem.* 1990, 55, 2552-2554) and references cited therein]. In this procedure, equal amounts of EE1 and an aldehyde or ketone are stirred with titanium (IV) isopropoxide, followed the addition of sodium cyanoborohydride in a solvent such as ethanol to give substituted amine EE3.

Reaction Scheme FF

A synthetic sequence to produce compounds of the present invention wherein L is cyclopropyl is described in reaction Scheme FF.

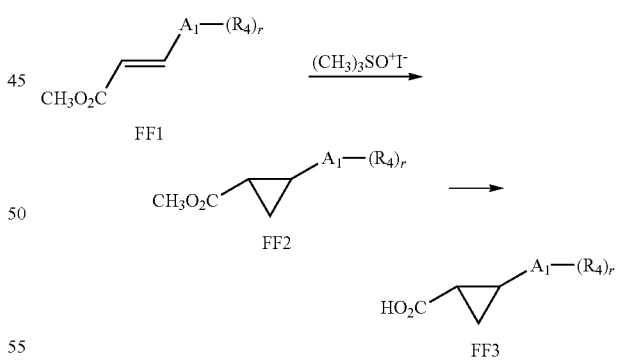

Reaction of cinnamate ester FF1, in this case a methyl ester, with trimethylsulfonium iodide methylide in a solvent such as DMSO and sodium hydride (as exemplified by Burger, A. et. al. *J. Med. Chem.* 1970, 13, 33-35), gives cyclopropyl ester FF2. Hydrolysis of FF2 gives acid FF3, which is further elaborated into the benzimidazoles described in Scheme AA.

Reaction Scheme GG

Reaction Scheme GG describes an alternative method to prepare cyclopropyl acid intermediates.

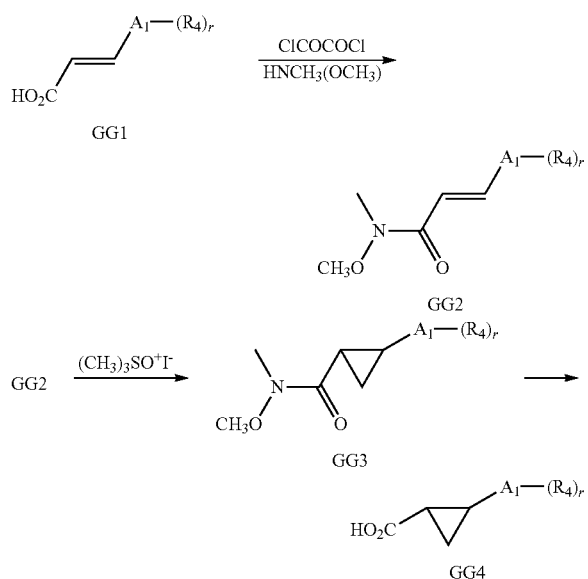

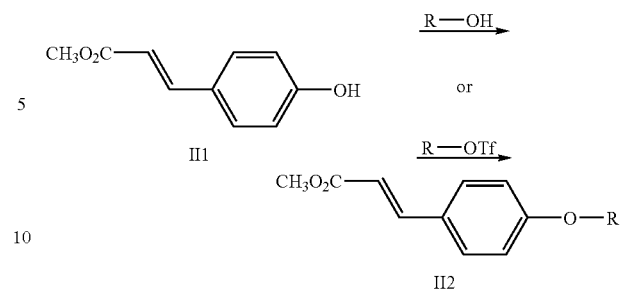

An ester of commercially available 4-hydroxycinnamic acid II1 can be converted to ether analogs by a number of routes including the Williamson reaction. In this well-known procedure, II1 and an alkyl halide is reacted with a base such as cesium carbonate in a solvent such as acetonitrile to give the product II2.

More effective electrophiles can be derivatives of alcohols such as mesylates, p-toluene sulfonates or trifluoromethanesulfonates (triflates). An effective alternative method is the conversion of II1 to ether analogs II2 via the Mitsunobu reaction (as reviewed by Mitsunobu, O., *Synthesis*, 1981, 1-28).

Cinnamic acids are converted to the corresponding Weinreb amide, by conversion to the acid chloride as described in Reaction Scheme AA and BB'. The acid chloride is reacted with N,N-dimethylhydroxylamine hydrochloride and a base such as triethylamine in methylene chloride to give amide GG2.

Amide GG2 is converted to cyclopropyl amide GG3 as described in Scheme FF. The amide GG3 is then hydrolyzed to give acid GG4, typically by reaction with potassium tertiary butoxide in THF.

Reaction Scheme HH

A synthetic sequence to produce compounds of the present invention wherein $R_1Ar$ is benzenesulfonamide is described in reaction Scheme HH.

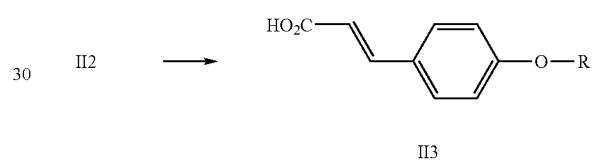

Ether analogs II2 can be further reduced to acid II3 using standard techniques.

Reaction Scheme JJ

Reaction Scheme JJ describes methods to prepare cinnamic acids that contain substituted amino groups.

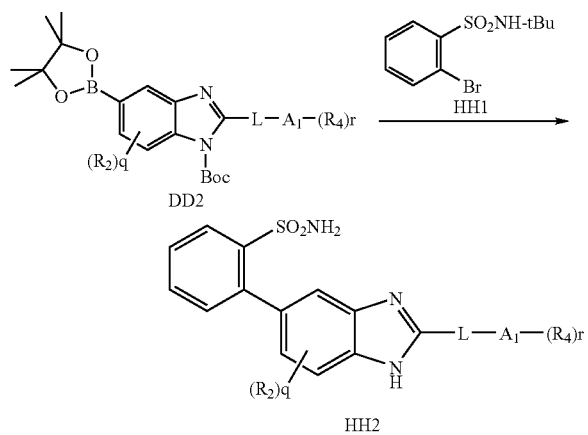

Coupling by Suzuki reaction of boronate ester DD2 from reaction Scheme DD and bromobenzene-t-butylsulfonamide HH1 followed by deprotection with TFA gives the product HH2.

Reaction Scheme II

A synthetic sequence to produce compounds of the present invention wherein R is an ether group is described in reaction Scheme II.

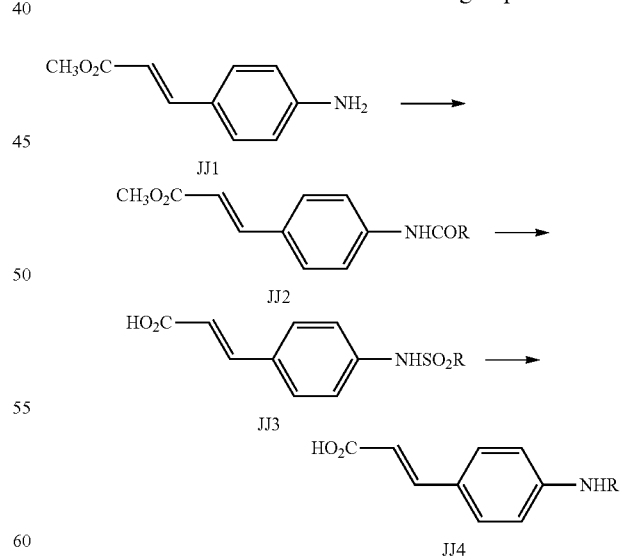

Cinnamate ester JJ1 can be converted to a variety of amides, carbamates or ureas JJ2 by utilizing any number of acylation methods that are commonly used by persons versed in the art. As an example, reaction of JJ1 in a solvent such as THF with a substituted acid chloride and a base such as triethylamine gives the corresponding amide of JJ2. As a further example, reaction of JJ1 in THF with a substituted chloroformate and triethylamine gives the corresponding substituted carbamate of JJ2. JJ1 can be converted to sulfonamides by utilizing various sulfonylation conditions.

For instance, reaction of JJ1 in a solvent such as THF with an alkylsulfonyl chloride and triethylamine gives the alkylsulfonamide JJ3. JJ1 can be selectively, and successively substituted to give JJ4. An efficient method of substitution is via reductive alkylation with aldehydes or ketones (see Mattson, R. J. et. al. *J. Org. Chem.*, 1990, 55, 2552-2554 and references cited therein). In this procedure, equal amounts of JJ1 and an aldehyde or ketone are stirred with titanium (IV) isopropoxide, followed the addition of sodium cyanoborohydride in a solvent such as ethanol to give substituted amine JJ4.

Reaction Scheme KK

A synthetic sequence to prepare compounds of the present invention wherein L is acetylene is described in Reaction Scheme KK.

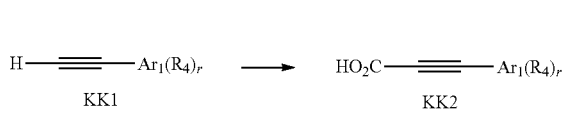

When not commercially available, propiolic acids KK2 are prepared by reaction of acetylenes KK1 with n-butyl lithium in THF at −78° C. warming to 0° C. for 30 min. The mixture is cooled to −78° C., and transferred to a saturated solution of carbon dioxide in THF at −78° C. The reaction is slowly warmed to rt to give the corresponding propiolic acid KK2.

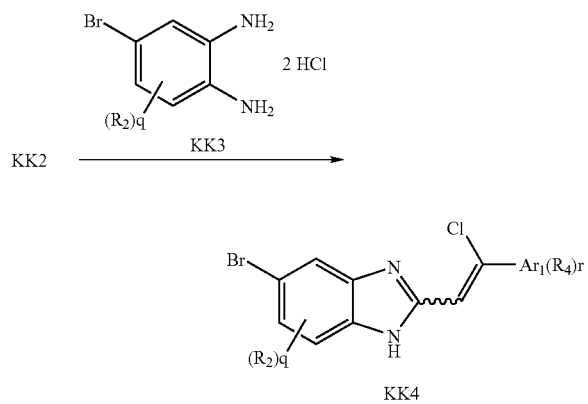

Reaction of the propiolic acid KK2 with 4-bromobenzene-1,2-diamine dihydrochloride KK3 in refluxing ethylene glycol gives chlorovinylbenzimidazole KK4.

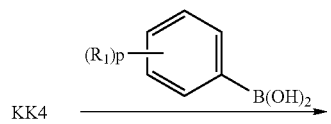

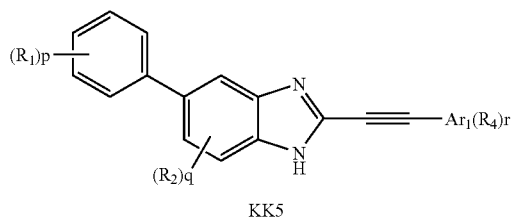

Reaction of KK3 with a phenyl boronic acid under Suzuki conditions in a microwave synthesizer and thermal conditions as described in Reaction Scheme AA gives acetylene compounds KK4.

Reaction Scheme LL

An alternative synthetic sequence to produce compounds of the present invention is described in reaction Scheme LL.

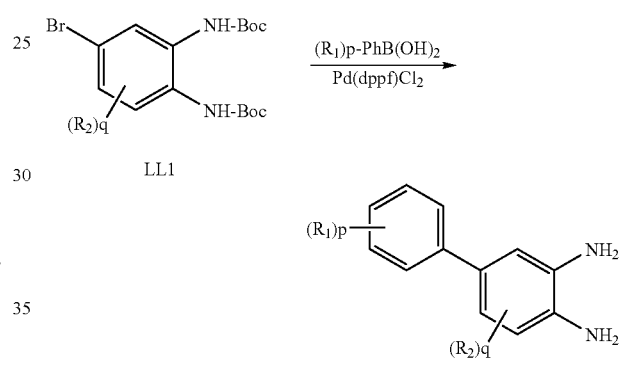

Protected bromodiamine LL1 is coupled with a suitable boronic acid via Suzuki coupling as described in previous reaction schemes to give the diamine LL2.

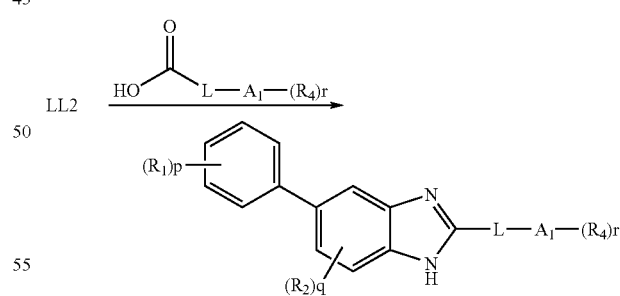

LL2 is then reacted with an acid or acid chloride to give LL3 (as described in reaction Schemes AA or BB').

Reaction Scheme MM

A synthetic sequence to produce compounds of the present invention wherein L is vinyl or ethyl that may be used as an alternative to Scheme BB' is described in reaction Scheme MM.

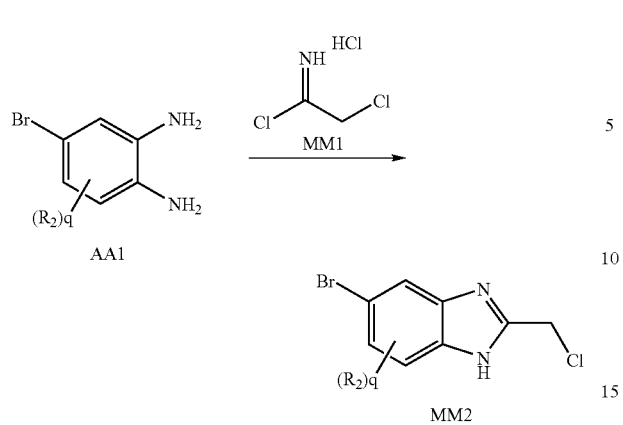

A solution of AA1 and dichloroimine MM1 (as described in McElvain, S. M. et. al. *J Am. Chem. Soc.* 1942, 64, 1825) in ethanol is heated to give chloromethyl benzimidazole MM2 (as described in Komoriya et. al. *Bioorg. Med. Chem.*, 2004, 12, 2099-2114).

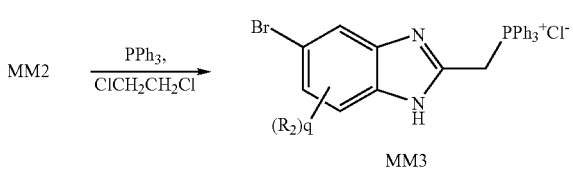

Heating in dichloroethane with triphenylphosphine converts MM2 to the phosphonium salt MM3.

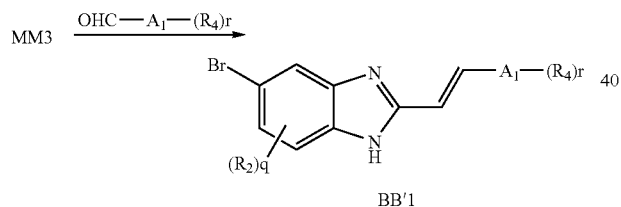

Reaction of MM3 with various aldehydes or ketones in a solution of anhydrous THF and EtOH with a base such as DBU (1,8-diazabicyclo[4.5.0]undec-7-ene) gives bromobenzimidazole BB'1, which is further elaborated as described in reaction Scheme AA.

Reaction Scheme NN

An alternative synthetic sequence to produce compounds of the present invention is described in reaction Scheme NN.

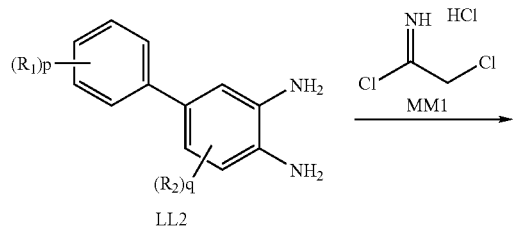

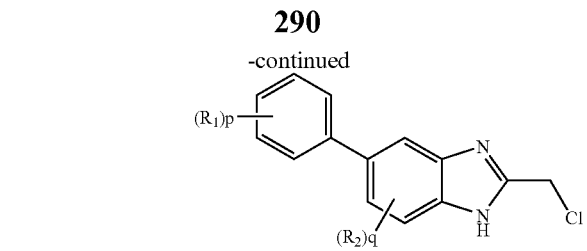

The biaryldiamine LL2 is reacted with dichloroimine MM1 as described in reaction Scheme MM to give NN1.

NN1 ⟶

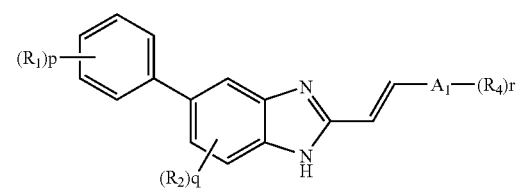

As described in reaction Scheme MM, NN1 is carried forward to give NN2.

Reaction Scheme OO

Compounds of the present invention wherein L is ethylene can be prepared by the alternate route described in Reaction Scheme OO.

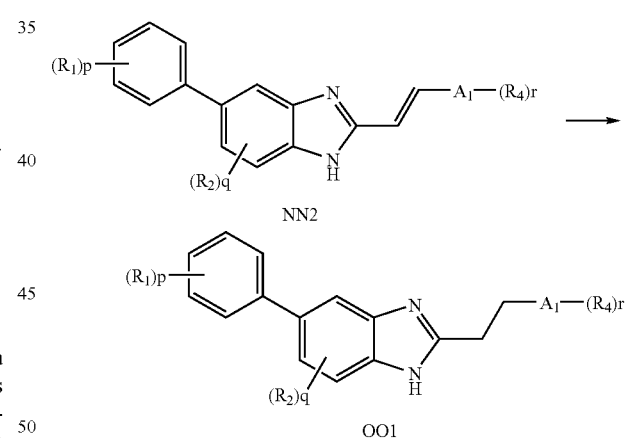

Compounds of the present invention such as NN3, wherein L is vinyl, are dissolved in a solvent such as methanol, and are hydrogenated using a catalyst such as 10% Pd on carbon to give OO1.

Reaction Scheme PP

A synthetic sequence to produce compounds of the present invention wherein L is cyclopropyl is described in reaction Scheme PP.

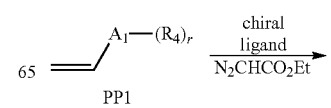

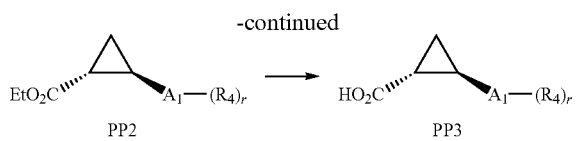

Reaction of olefin PP1 with an alkyl diazoacetate, such as ethyl diazoacetate, in the presence of a catalyst, such as copper(I)trifluoromethane sulfonate and Evans' chiral ligand (Evans, D. A.; Woerpel, K. A.; Hinman, M. M.; Faul, M. M. *J.Am. Chem. Soc.* 1991, 113, 726-728) in a solvent such as chloroform, gives a cyclopropyl ester enantiomer PP2.

The (R,R)-cyclopropyl ester PP2 enantiomer is obtained when a chiral ligand such as 2,2-bis-[2-((4S)-(1,1-dimethylethyl)-1,3-oxazolinyl)]propane Compound 38b is used. The (S,S)-cyclopropyl ester enantiomer is obtained when the chiral ligand 2,2-bis-[2-((4R)-(1,1-dimethylethyl)-1,3-oxazolinyl)]propane Compound 38a is used. The configurations of the cyclopropyl moiety were predicted based on Evans' *J.Am. Chem. Soc.* 1991 report. Hydrolysis of the ester PP2 gives acid PP3, which is further elaborated into the benzimidazoles of Scheme AA.

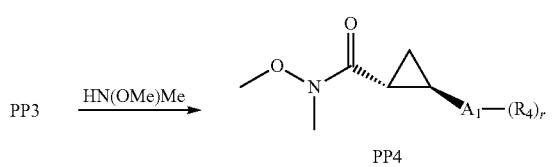

To determine the enantiomeric excess of the asymmetric cyclopropanation products PP2, acid PP3 is reacted with N,O-dimethylhydroxyl amine in the presence of a base such as diisopropylethylamine, and an amide coupling reagent such as BOP, in a solvent such as DMF to produce the methoxy methyl amide PP4.

The resulting $^1$H NMR of amide PP4 in the presence of an appropriate amount of chiral shifting agent, such as (R)-(−)-2,2,2-trifluoro-1-(9-anthryl)ethanol, gives base line resolution of the resulting methoxy singlets. The ratio of the integration of the methoxy singlets gives the ee value. Thus, the NMR showed methoxy singlets around 3.47 and 3.45 ppm. The integration of the singlets was 1 and 99, respectively; thus providing an ee value of 99%.

Reaction Scheme QQ

A synthetic sequence to produce compounds of the present invention wherein $R_1$ is an alcohol is described in reaction Scheme QQ.

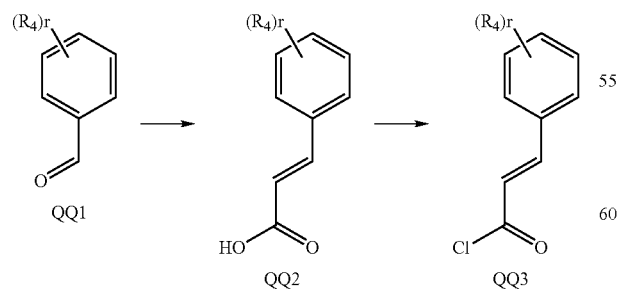

As elaborated in Scheme BB', the aldehyde QQ1 is reacted with malonic acid and a catalytic amount of piperidine in pyridine at elevated temperatures to provide an acid QQ2.

Acid QQ2 is converted to an acid chloride QQ3 by reaction with oxalyl chloride and a catalytic amount of DMF in a solvent such as methylene chloride.

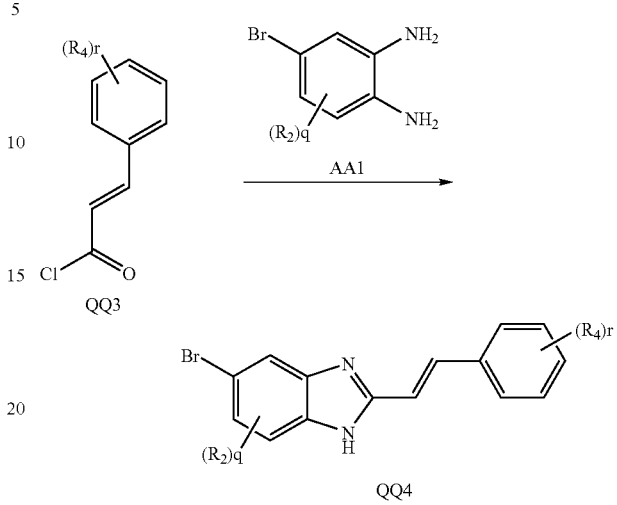

As elaborated in Scheme AA, the acid chloride QQ3 is heated with 4-bromobenzene-1,2-diamine AA1 in acetic acid to give a bromobenzimidazole QQ4.

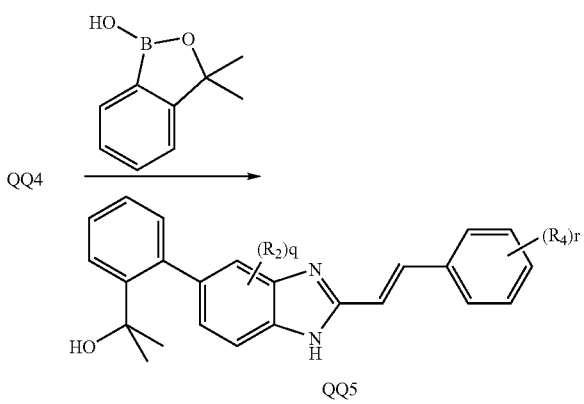

As elaborated in Scheme AA, a suitably substituted phenyl boronic acid is reacted with benzimidazole QQ4 in the presence of a reagent and a catalytic amount of a palladium catalyst in a solvent to give an alcohol substituted benzimidazole QQ5, representative of a compound of Formula (I).

EXAMPLE 1

(E)-1-(2-{2-[2-(4-tert-butyl-phenyl)-vinyl]-1H-benzimidazol-5-yl}-phenyl)-ethanone (Cpd 1)

Step A. (E)-5-bromo-2-[2-(4-tert-butyl-phenyl)-vinyl]-1H-benzimidazole

To a solution of 3-(4-tert-butyl-phenyl)-acrylic acid (12 g, 58.7 mmol) in POCl$_3$ (200 mL), was slowly added 4-bromobenzene-1,2-diamine (10 g, 53.4 mmol). The solution was heated at reflux for 18 h. The solution was concentrated, and the residual POCl$_3$ was azeotropically removed with toluene. The residue was partitioned between EtOAc and 10% Na$_2$CO$_3$. The organic layer was washed with brine, dried over Na$_2$SO$_4$, filtered, and the filtrate was concentrated. The residue was purified by chromatography (silica, EtOAc: hexanes, 3:7) to give the title Compound 1a (7.1 g, 31% yield). $^1$H-NMR (400 MHz, CDCl$_3$) δ (ppm): 7.64 (d, 1H, J=13.9 Hz) 7.62 (s, 1H) 7.41 (d, 2H, J=8.4 Hz) 7.36 (d, 1H, J=8.5 Hz) 7.33 (d, 2H, J=8.4 Hz) 7.28 (s, 1H) 7.22 (dd, 1H, J=1.8 Hz, J=8.5 Hz) 7.02 (d, 1H, J=16.5 Hz) 1.25 (s, 9H).

Step B. (E)-1-(2-{2-[2-(4-tert-butyl-phenyl)-vinyl]-1H-benzimidazol-5-yl}-phenyl)-ethanone A solution of Compound 1a (0.106 g, 0.30 mmol), 2-acetylbenzeneboronic acid (136 mg; 0.76 mmol), PdCl$_2$dppf (0.06 mmol) and Cs$_2$CO$_3$ (0.244 g, 0.75 mmol) in 1,4-dioxane:EtOH 5:1 was heated to 115° C. After 18 h, the solution was cooled and concentrated. The residue was purified using preactive TLC plates (silica gel, 20×20 cm, 2000 microns, EtOAc:hexanes 3:7) to give the title Compound 1 (0.0146 g). $^1$H-NMR (400 MHz, CD$_3$OD) δ (ppm): 7.54 (m, 11H) 7.23 (dd, 1H, J=1.6 Hz, J=8.3 Hz) 7.15 (d, 1H, J=16.5 Hz) 2.02 (s, 3H) 1.36 (s, 9H). MS (ESI, pos. ion) m/z: 395.3 (M+1).

Using the procedures described in Example 1 and reagents, starting materials and conditions known to those skilled in the art, the following compounds representative of the present invention were prepared:

| Cpd | Name and Data |
|---|---|
| 3 | (E)-2-{2-[2-(4-tert-butyl-phenyl)-vinyl]-1H-benzimidazol-5-yl}-phenol<br>The title compound (0.0048 g) was prepared from 2-hydroxybenzeneboronic acid (0.0345 g, 0.25 mmol) and Compound 1a (0.029 g, 0.1 mmol).<br>$^1$H-NMR(400MHz, CDCl$_3$) δ (ppm): 7.56(s, 1H) 7.31(dd, 2H, J=12.2 Hz, J=24.1 Hz) 7.10(m, 8H) 6.86(t, 1H, J=7.3 Hz) 6.78(d, 1H, J=16.4 Hz) 1.19(s, 9H).<br>MS(ESI, pos. ion) m/z: 368.3(M+1). |
| 4 | (E)-N-(2-{2-[2-(4-tert-butyl-phenyl)-vinyl]-1H-benzimidazol-5-yl}-phenyl)-acetamide<br>The title compound (0.001 g) was prepared from 2-N-acetyl-benzeneboronic acid (0.136 g, 0.76 mmol) and Compound 1a (0.106 g, 0.3 mmol).<br>$^1$H-NMR(400MHz, CD$_3$OD) δ (ppm) 7.44(m, 4H) 7.24(m, 6H) 6.91(d, 1H, J=12.4 Hz) 6.47(d, 1H, J=12.4 Hz) 1.86(s, 1H) 1.20(s, 9H). MS(ESI, pos. ion) m/z: 410.2(M+1). |
| 5 | (E)-2-{2-[2-(4-tert-butyl-phenyl)-vinyl]-1H-benzimidazol-5-yl}-benzamide<br>The title compound (0.001 g) was prepared from 2-aminocarbonyl benzeneboronic acid (0.136 g, 0.76 mmol) and Compound 1a (0.106 g, 0.3 mmol).<br>$^1$H-NMR(400MHz, CD$_3$OD) δ (ppm) 7.48(m, 6H) 7.37(m, 5H) 7.26(dd, 1H, J=1.6Hz, J=8.3 Hz) 7.04(d, 1H, J=16.5 Hz) 1.26(s, 9H). MS(ESI, pos. ion) m/z: 396.1(M+1). |
| 6 | (E)-3-{2-[2-(4-tert-butyl-phenyl)-vinyl]-1H-benzimidazol-5-yl}-benzamide<br>The title compound (0.001 g) was prepared from 3-aminocarbonylbenzene boronic acid (0.136 g, 0.76 mmol) and Compound 1a (0.106 g, 0.3 mmol). $^1$H-NMR(400MHz, CD$_3$OD) δ (ppm) 8.22(t, 1H, J=1.7 Hz) 7.88(m, 3H) 7.62(m, 6H) 7.51(m, 2H) 7.17(d, 1H, J=16.5 Hz) 1.38(s, 9H). MS(ESI, pos. ion) m/z: 396.1(M+1). |
| 7 | (E)-4-{2-[2-(4-tert-butyl-phenyl)-vinyl]-1H-benzimidazol-5-yl}-benzamide<br>The title compound (0.002 g) was prepared from 4-aminocarbonylbenzene boronic acid (0.136 g, 0.76 mmol) and Compound 1a (0.106 g, 0.3 mmol). $^1$H-NMR(400MHz, CD$_3$OD) δ (ppm) 7.97(m, 2H) 7.77(m, 4H) 7.60(m, 4H) 7.47(d, 2H, J=8.4 Hz) 7.13(d, 1H, J=16.5 Hz) 1.36(s, 9H). MS(ESI, pos. ion) m/z: 410.2(M+1). |
| 8 | (E)-N-(4-{2-[2-(4-tert-butyl-phenyl)-vinyl]-1H-benzimidazol-5-yl}-phenyl)-acetamide<br>The title compound 0.0038 g) was prepared from 4-N-acetylbenzeneboronic acid (0.136 g, 0.76 mmol) and Compound 1a (0.106 g, 0.3 mmol) to give the title compound (0.0038 g). $^1$H-NMR(400MHz, CD$_3$OD) δ (ppm) 7.73(m, 2H) 7.61(m, 7H) 7.49(m, 3H) 7.12(d, 1H, J=16.5 Hz) 2.17(s, 3H) 1.36(s, 9H). MS(ESI, pos. ion) m/z: 410.2(M+1). |
| 9 | (E)-N-(2-{2-[2-(4-tert-butyl-phenyl)-vinyl]-1H-benzimidazol-5-yl}-phenyl)-methanesulfonamide<br>The title compound (0.0045 g) was prepared from 2-methanesulfonamide benzeneboronic acid (0.163 g, 0.76 mmol) and Compound 1a (0.106 g, 0.3 mmol).<br>$^1$H-NMR(400MHz, CD$_3$OD) δ (ppm) 7.62(m, 6H) 7.50(d, 2H, J=8.5 Hz) 7.41(m, 2H) 7.34(m, 2H) 7.17(d, 1H, J=16.5 Hz) 2.75(s, 3H) 1.37(s, 9H). MS(ESI, pos. ion) m/z: 446.2(M+1). |
| 10 | (E)-(2-{2-[2-(4-tert-butyl-phenyl)-vinyl]-1H-benzimidazol-5-yl}-phenyl)-carbamic acid tert-butyl ester<br>The title compound (0.0016 g) was prepared from 2-N-Boc-benzeneboronic acid (0.180 g, 0.76 mmol) and (E)-5-bromo-2-[2-(4-tert-butyl-phenyl)-vinyl]-1H-aminobenzimidazole Compound 1b (0.106 g, 0.3 mmol). $^1$H-NMR(400MHz, CD$_3$OD) δ (ppm) 7.62(m, 5H) 7.50(m, 2H) 7.33(dd, 1H, J=1.6 Hz, J=8.3 Hz) 7.14(m, 3H) 6.83(m, 2H) 3.37(s, 9H) 1.37(s, 9H). MS(ESI, pos. ion) m/z: 468.1(M+1). |
| 11 | (E)-2-{2-[2-(4-tert-butyl-phenyl)-vinyl]-1H-benzimidazol-5-yl}-phenylamine<br>A solution of (E)-(2-{2-[2-(4-tert-butyl-phenyl)-vinyl]-1H-benzimidazol-5-yl}-phenyl)-carbamic acid tert-butyl ester (0.005 g, 0.01 mmol) in methylene chloride (1 mL) was treated with trifluoroacetic acid (0.5 mL). The solution was stirred at room temperature for 4 h, then concentrated to give the title compound (0.003 g). $^1$H-NMR(400MHz, CD$_3$OD) δ (ppm) 8.03(d, 1H, J=16.5 Hz) 7.90(d, |

| Cpd | Name and Data |
|---|---|
| | 1H, J=8.5 Hz) 7.85(s, 1H) 7.74(d, 2H, J=8.4 Hz) 7.65(dd, 1H, J=1.5 Hz, J=8.5Hz) 7.59(d, 2H, J=8.4 Hz) 7.43(m, 5H) 1.39(s, 9H). MS(ESI, pos. ion) m/z: 368.1(M+1). |
| 12 | (E)-(2-{2-[2-(4-tert-butyl-phenyl)-vinyl]-1H-benzimidazol-5-yl}-phenyl)-methanol<br>The title compound (0.0046 g) was prepared from 2-hydroxymethylbenzene boronic acid (0.102 g, 0.76 mmol) and Compound 1a (0.106 g, 0.3 mmol). $^1$H-NMR(400MHz, CD$_3$OD) δ (ppm) 7.59(m, 5H) 7.49(d, 2H, J=8.4 Hz) 7.40(m, 2H) 7.34(m, 2H) 7.27(dd, 1H, J=1.6 Hz, J=8.3 Hz) 7.16(d, 1H, J=16.6 Hz) 4.58(s, 2H) 1.37(s, 9H). MS(ESI, pos. ion) m/z: 383.2(M+1). |
| 24 | (E)-N-(2-{2-[2-(3,4-difluoro-phenyl)-vinyl]-1H-benzimidazol-5-yl}-phenyl)-acetamide<br>Using the procedure of Example 1, Step B, the title compound (0.001 g) was prepared from 2-N-acetylbenzeneboronic acid (0.136 g, 0.76 mmol) and (E)-5-bromo-2-[2-(3,4-difluoro-phenyl)-vinyl]-1H-benzimidazole Compound 1c (0.10 g, 0.30 mmol). $^1$H-NMR(400MHz, CD$_3$OD) δ (ppm) 7.61(m, 5H) 7.39(m, 6H) 7.18(d, 1H, J=16.5 Hz) 1.99(s, 3H). MS(ESI, pos. ion) m/z: 390.2(M+1). |
| 25 | (E)-N-(3-{2-[2-(3,4-difluoro-phenyl)-vinyl]-1H-benzimidazol-5-yl}-phenyl)-acetamide<br>The title compound (0.0102 g) was prepared from 3-N-acetylbenzeneboronic acid (0.136 g, 0.76 mmol) and Compound 1c (0.10 g, 0.30 mmol). $^1$H-NMR(400MHz, CD$_3$OD) δ (ppm) 7.78(d, 1H, J=0.9 Hz) 7.63(s, 1H) 7.44(m, 5H) 7.26(m, 4H) 7.01(d, 1H, J=16.5 Hz) 2.06(s, 3H). MS(ESI, pos. ion) m/z: 390.1(M+1). |
| 26 | (E)-2-{2-[2-(3,4-difluoro-phenyl)-vinyl]-1H-benzimidazol-5-yl}-benzamide<br>The title compound (0.0031 g) was prepared from 2-aminocarbonylbenzene boronic acid (0.125 g, 0.76 mmol) and Compound 1c (0.10 g, 0.30 mmol). $^1$H-NMR(400MHz, CDCl$_3$+CD$_3$OD) δ (ppm) 7.62(s, 1H) 7.40(m, 9H) 7.18(td, 1H, J=8.4 Hz, J=10.1 Hz) 7.01(d, 1H, J=16.5 Hz). MS(ESI, pos. ion) m/z: 376.2(M+1). |
| 27 | (E)-1-(2-{2-[2-(3,4-difluoro-phenyl)-vinyl]-1H-benzimidazol-5-yl}-phenyl)-ethanone<br>The title compound (0.001 g) was prepared from 2-acetylbenzeneboronic acid (0.125 g, 0.76 mmol) and Compound 1c (0.10 g, 0.30 mmol). $^1$H-NMR(400MHz, CD$_3$OD) δ (ppm) 7.49(m, 5H) 7.37(m, 4H) 7.23(td, 1H, J=8.4 Hz, J=10.3 Hz) 7.14(dd, 1H, J=1.7 Hz, J=8.3 Hz) 7.06(d, 1H, J=16.5 Hz) 1.91(s, 3H). MS(ESI, pos. ion) m/z: 375.2(M+1). |
| 28 | (E)-N-(2-{2-[2-(3,4-difluoro-phenyl)-vinyl]-1H-benzimidazol-5-yl}-phenyl)-methanesulfonamide<br>The title compound (0.0021 g) was prepared from 2-methylsulfonylamino benzeneboronic acid (0.163 g, 0.76 mmol) and Compound 1c (0.10 g, 0.30 mmol). $^1$H-NMR(400MHz, CD$_3$OD) δ (ppm) 7.50(m, 5H) 7.36(m, 1H) 7.26(m, 5H) 7.07(d, 1H, J=16.5 Hz) 2.64(s, 3H). MS(ESI, pos. ion) m/z: 426.1(M+1). |
| 30 | (E)-2-[3-(4-tert-butyl-phenyl)-propyl]-5-m-tolyl-1H-benzimidazole<br>The title compound (0.0182 g) was prepared from 3-methylphenylbenzene boronic acid (0.052 g, 0.38 mmol) and 5-bromo-2-[3-(4-tert-butyl-phenyl)-propyl]-1H-benzimidazole Compound 5a (0.055 g, 0.15 mmol). $^1$H-NMR(400MHz, CDCl$_3$) δ (ppm) 7.33(m, 3H) 7.18(m, 5H) 7.03(d, 1H, J=7.4Hz) 6.95(d, 2H, J=8.3 Hz) 2.85(m, 2H) 2.57(t, 2H, J=7.5 Hz) 2.30(s, 3H) 2.06(m, 2H) 1.17(s, 9H). MS(ESI, pos. ion) m/z: 383.2(M+1). |

EXAMPLE 2

(E)-1-(2-{2-[2-(4-tert-butyl-phenyl)-vinyl]-1H-benzimidazol-5-yl}-phenyl)-ethanol (Cpd 2)

A solution of (E)-1-(2-{2-[2-(4-tert-butyl-phenyl)-vinyl]-1H-benzimidazol-5-yl}-phenyl)-ethanone Cpd 1 (0.005 g, 0.01 mmol) in ethanol (0.5 mL) was treated with NaBH$_4$ (0.003 g, 0.08 mmol). After 3 h, the reaction mixture was applied to a preative TLC plate (2000 microns, silica gel, 20×20) and developed using EtOAc:hexanes, 1:1. The desired band was extracted and concentrated to give the title compound (0.002 g). $^1$H-NMR (400 MHz, CD$_3$OD) δ (ppm) 7.69 (m, 1H) 7.62 (m, 3H) 7.50 (m, 3H) 7.41 (ddd, 2H, J=2.5 Hz, J=10.1 Hz, J=14.1 Hz) 7.32 (dt, 1H, J=1.4 Hz, J=7.5 Hz) 7.23 (m, 2H) 7.17 (d, 1H, J=16.5 Hz) 4.99 (q, 1H, J=6.3 Hz) 1.38 (s, 9H) 1.35 (d, 1.5H, J=6.1 Hz) 1.33 (d, 1.5H, J=6.1 Hz). MS (ESI, pos. ion) m/z: 397.2 (M+1).

EXAMPLE 3

(E)-2-{2-[2-(4-trifluoromethyl-phenyl)-vinyl]-1H-benzimidazol-5-yl}-benzamide (Cpd 13)

Step A. (E)-5-bromo-2-[2-(4-trifluoromethyl-phenyl)-vinyl]-1H-benzimidazole

Using the procedure of Example 1, Step A, the title Compound 10c (0.910 g) was prepared from 3-(4-trifluoromethyl-phenyl)-acrylic acid Compound 10a (1.5 g, 6.9 mmol) and 4-bromo-benzene-1,2-diamine (1.3 g, 6.9 mmol). $^1$H-NMR (400 MHz, CDCl$_3$+DMSO(d6)) δ(ppm) 7.78 (d, 1H, J=16.5 Hz) 7.73 (d, 1H, J=1.7 Hz) 7.66 (m, 4H) 7.48 (d, 2H, J=8.0 Hz) 7.33 (dd, 1H, J=1.8 Hz, J=8.5 Hz) 7.23 (d, 1H, J=16.5 Hz).

Step B. (E)-2-{2-[2-(4-trifluoromethyl-phenyl)-vinyl]-1H-benzimidazol-5-yl}-benzamide Using the procedure of Example 1, Step B, the title compound (0.001 g) was prepared from 2-carboxamidophenylbenzeneboronic acid (0.120 g, 0.76 mmol) and Compound 10c (0.110 g, 0.30 mmol). $^1$H-NMR (400 MHz, CD$_3$OD) δ (ppm) 7.74 (d, 2H, J=8.2 Hz) 7.63 (m, 3H) 7.57 (s, 1H) 7.40 (m, 6H) 7.22 (d, 1H, J=16.5 Hz). MS (ESI, pos. ion) m/z: 408.1 (M+1).

Using the procedures described in Example 3 and reagents, starting materials and conditions known to those skilled in the art, the following compounds representative of the present invention were prepared:

| Cpd | Name and Data |
|---|---|
| 14 | (E)-2-{2-[2-(4-trifluoromethyl-phenyl)-vinyl]-1H-benzimidazol-5-yl}-phenol<br>The title compound (0.001g) was prepared from 2-hydroxybenzeneboronic acid (0.105g, 0.38mmol) and Compound 10c (0.110g, 0.30mmol). $^1$H-NMR(400MHz, CD$_3$OD) δ (ppm) 7.74(d, 2H, J=8.3Hz) 7.63(dd, 3H, J=8.7Hz, J=17.1 Hz) 7.56(s, 1H) 7.50(d, 1H, J=8.3 Hz) 7.38(dd, 1H, J=1.5 Hz, J=8.4 Hz) 7.22(m, 2H) 7.06(m, 1H) 6.82(m, 2H). MS(ESI, pos. ion) m/z: 381.3(M+1). |
| 15 | (E)-1-(2-{2-[2-(4-trifluoromethyl-phenyl)-vinyl]-1H-benzimidazol-5-yl}-phenyl)-ethanone<br>The title compound (0.001g) was prepared from 2-acetylbenzeneboronic acid (0.125g, 0.76mmol) and Compound 10c (0.110g, 0.30mmol). $^1$H-NMR(400MHz, CD$_3$OD) δ (ppm) 7.75(d, 2H, J=8.2 Hz) 7.60(m, 4H) 7.48(m, 2H) 7.38(m, 3H) 7.23(d, 1H, J=16.6 Hz) 7.16(dd, 1H, J=1.7 Hz, J=8.3 Hz) 1.92(s, 3H). MS(ESI, pos. ion) m/z: 407.3(M+1). |
| 16 | (E)-1-(2-{2-[2-(4-trifluoromethyl-phenyl)-vinyl]-1H-benzimidazol-5-yl}-phenyl)-ethanol<br>A solution of (E)-1-(2-{2-[2-(4-trifluoromethyl-phenyl)-vinyl]-1H-benzimidazol-5-yl}-phenyl)-ethanone Compound 15 (0.005g, 0.01mmol) in ethanol (0.5mL) was treated with NaBH$_4$ (0.003g, 0.08mmol). After 3h, the solution was applied to a preparative TLC plate (2000 microns, silica gel, 20×20) and developed using EtOAc: hexanes, 1:1. The desired band was extracted and concentrated to give the title compound (0.001g). $^1$H-NMR(400MHz, CD$_3$OD) δ (ppm) 7.87(d, 1H, J=8.2 Hz) 7.76(d, 1H, J=8.0 Hz) 7.67(m, 1H) 7.51(s, 1H) 7.42(m, 1H) 7.32(m, 1H) 7.25(m, 1H) 4.98(q, 1H, J=6.4Hz) 1.35(d, 1H, J=6.4 Hz). MS(ESI, pos. ion) m/z: 409.2(M+1). |
| 17 | (E)-N-(2-{2-[2-(4-trifluoromethyl-phenyl)-vinyl]-1H-benzimidazol-5-yl}-phenyl)-methanesulfonamide<br>The title compound (0094g) was prepared from 2-methylsulfonyl aminobenzeneboronic acid (0.163g, 0.76mmol) and Compound 10c (0.110g, 0.30mmol). $^1$H-NMR(400MHz, DMSO(d6)) δ (ppm) 12.82(s, 1H) 8.89(s, 1H) 7.91(d, 2H, J=8.1 Hz) 7.80(m, 2H) 7.75(s, 1H) 7.70(m, 1H) 7.58(d, 1H, J=6.9 Hz) 7.37(m, 6H) 2.73(d, 3H, J=28.8 Hz). MS(ESI, pos. ion) m/z: 458.2(M+1). |
| 31 | N-(2-{2-[2-(4-trifluoromethyl-phenyl)-ethyl]-1H-benzimidazol-5-yl}-phenyl)-methanesulfonamide<br>Using the procedure of Example 1, Step A., 5-bromo-2-[2-(4-trifluoroethyl-phenyl)-ethyl]-1H-benzimidazole Compound 3b was prepared from 3-(4-trifluoromethyl-phenyl)-propionic acid (1.04g, 5.04mmol) and 4-bromo-benzene-1,2-diamine (0.946g, 5.06mmol).<br>Using the procedure of Example 1, Step B., the title compound was prepared from 2-methylsulfonylaminobenzeneboronic acid (0.367g, 1.7mmol) and Compound 3b (0.188g, 0.51mmol). $^1$H-NMR(400MHz, (CD$_3$OD) δ (ppm) 7.64-7.50(m, 5H), 7.47-7.34(m, 4H), 7.34-7.27(m, 2H), 3.27(s, 4H), 2.71(s, 3H). MS(ESI, pos. ion) m/z: 460.16(M+1). |

EXAMPLE 4

(E)-2-{2-[2-(4-trifluoromethoxy-phenyl)-vinyl]-1H-benzimidazol-5-yl}-benzamide (Cpd 19)

Step A. 3-(4-trifluoromethoxy-phenyl)-acrylic acid

A solution of 4-trifluoromethoxybenzaldehyde (26.3 mmol), malonic acid (5.6 g, 53.8 mmol) and piperidine (0.265 mL, 2.7 mmol) in pyridine (15 mL) was heated to 70° C. for 18 h. Water (200 mL) was added to the reaction solution. The mixture was acidified to pH 4 using concentrated hydrochloric acid. The solution was filtered. The solid was washed with water. The solid was dried in vacuo to give the title Compound 4a (1.2 g). $^1$H-NMR (d6-DMSO) δ (ppm): 6.80 (d, J=16.02 Hz, 1H), 6.72 (m, 2H), 6.38 (m, 2H), 5.55 (d, J=16.00 Hz, 1H).

Step B. 3-(4-trifluoromethoxy-phenyl)-acryloyl chloride

A solution of Compound 4a (1.2 g, 5.2 mmol) in methylene chloride (20 mL) was treated with oxalyl chloride (7.8 mL, 3.6 mmol). To the solution was added DMF (0.02 mL). The reaction solution was stirred at room temperature for 2 h. The reaction solution was concentrated. The residue was dried in vacuo to provide Compound 4b, which was used without further purification in the next step.

Step C. (E)-5-bromo-2-[2-(4-trifluoromethoxy-phenyl)-vinyl]-1H-benzimidazole A solution of Compound 4b (1 g, 4 mmol) in acetic acid (10 mL) was added slowly to a solution of 4-bromo-benzene-1,2-diamine (0.744 g, 4 mmol) in acetic acid (10 mL). The solution was heated to 100° C. for 18 h. The solution was cooled to room temperature. To the solution was added ethyl acetate:hexanes 3:7 (100 mL). The solution was filtered. The solid was dried in vacuo to give the title Compound 4c (1.1 g). $^1$H-NMR (400 MHz, DMSO d6) ppm 8.12 (d, J=16.60 Hz, 1H), 7.98 (m, 1H), 7.87 (m, 2H), 7.82-7.68 (m, 1H), 7.67-7.37 (m, 4H), 7.34 (d, J=16.58 Hz, 1H). MS (ESI pos. ion) m/z: 383.2 and 385.2.

Step D. (E)-2-{2-[2-(4-trifluoromethoxy-phenyl)-vinyl]-1H-benzimidazol-5-yl}-benzamide Using the procedure of Example 1, Step B, the title Compound 19 was prepared from 2-carboxamido-phenylbenzene boronic acid and Compound 4c.

Using the procedures described in Example 4 and reagents, starting materials and conditions known to those skilled in the art, the following compounds representative of the present invention were prepared:

| Cpd | Name and Data |
|---|---|
| 20 | (E)-1-(2-{2-[2-(4-trifluoromethoxy-phenyl)-vinyl]-1H-benzimidazol-5-yl}-phenyl)-ethanone<br>The title compound (0.001g) was prepared from 2-acetylbenzeneboronic acid (0.280g, 1.7mmol) and Compound 4c (0.195g, 0.51mmol). $^1$H-NMR(400MHz, CD$_3$OD) δ (ppm) 7.66(d, J=8.72 Hz, 2H), 7.61-7.43(m, 4H), 7.43-7.32(m, 3H), 7.24(d, J=8.19 Hz, 2H), 7.19-7.06(m, 2H), 1.96-1.86(m, 3H). MS (ESI, pos. ion) m/z: 423.14(M+1). |
| 21 | (E)-1-(2-{2-[2-(4-trifluoromethoxy-phenyl)-vinyl]-1H-benzimidazol-5-yl}-phenyl)-ethanol<br>Using the procedure of Example 2, the title compound was prepared from Compound 20. $^1$H-NMR(400MHz, CD$_3$OD) δ (ppm) 7.76-7.80(d, J=8.84 Hz, 2H) 7.60-7.70(m, 3H) 7.50(bs, 1H) 7.40-7.44(ddd, J=1.26, 7.32Hz, 1H) 7.29-7.37(m, 3H) 7.20-7.25(m, 3H) 4.96-5.02(q, J=6.57 Hz, 1H) 1.34-1.36(d, J=6.32 Hz, 3H). MS(ESI, pos. ion) m/z: 425.2(M+1). |
| 22 | (E)-N-(2-{2-[2-(4-trifluoromethoxy-phenyl)-vinyl]-1H-benzimidazol-5-yl}-phenyl)-methanesulfonamide<br>The title compound (0.05g) was prepared from 2-methylsulfonyl aminobenzeneboronic acid (0.521g, 2.4mmol) and Compound 4c (0.463g, 1.2mmol). $^1$H-NMR(400MHz, DMSO(d6)) δ (ppm) 12.76(d, J=5.43 Hz, 1H), 8.90(d, J=4.68 Hz, 1H), 7.83(d, J=8.72 Hz, 2H), 7.65(m, 1H), 7.50-7.22(m, 8H), 2.76(s, 1.5H), 2.69(s, 1.5H). MS(ESI, pos. ion) m/z: 474.2(M+1). |

EXAMPLE 5

2-{2-[3-(4-tert-butyl-phenyl)-propyl]-1H-benzimidazol-5-yl}-phenyl (Cpd 29)

Step A. 5-bromo-2-[3-(4-tert-butyl-phenyl)-propyl]-1H-benzimidazole

Using the procedure of Example 1, Step A, the title Compound 5a (0.512 g) was prepared from 4-(4-tert-butyl-phenyl)-butyric acid (2.0 g, 10.7 mmol) and 4-bromo-benzene-1,2-diamine (2.0 g, 10.7 mmol). $^1$H-NMR (400 MHz, CDCl$_3$) δ(ppm) 7.73 (d, 1H, J=1.6 Hz) 7.45 (d, 1H, J=8.5 Hz) 7.38 (dd, 1H, J=1.8 Hz, J=8.5 Hz) 7.32 (m, 3H) 7.12 (d, 2H, J=8.3 Hz) 2.97 (m, 2H) 2.73 (t, 2H, J=7.4 Hz) 2.23 (m, 2H) 1.33 (s, 9H).

Step B. 2-{2-[3-(4-tert-butyl-phenyl)-propyl]-1H-benzimidazol-5-yl}-phenol

Using the procedure outlined in Example 1, Step B, the title Compound 29 (0.0083 g) was prepared from 2-hydroxybenzeneboronic acid (0.07 g, 0.5 mmol) and Compound 5a (0.074 g, 0.2 mmol). $^1$H-NMR (400 MHz,CDCl$_3$) δ (ppm) 7.51 (s, 1H) 7.39 (d, 1H, J=8.1 Hz) 7.16 (m, 6H) 6.95 (d, 3H, J=8.2 Hz) 6.88 (t, 1H, J=7.4 Hz) 2.73 (t, 2H, J=7.5 Hz) 2.52 (t, 2H, J=7.3 Hz) 2.00 (m, 2H) 1.20 (s, 9H). MS (ESI, pos. ion) m/z: 385.3 (M+1).

EXAMPLE 6

2-{2-[2-(4-tert-butyl-phenyl)-ethyl]-1H-benzimidazol-5-yl}-phenyl (Cpd 32)

Step A. 3-(4-tert-butyl-phenyl)-propionic acid

A mixture of 3-(4-tert-butyl-phenyl)-acrylic acid (12.28 g, 60.1 mmol) and 10% palladium on carbon (0.6 g) in ethanol was hydrogenated at 50 psi hydrogen for 2 hours. The reaction mixture was filtered over a pad of celite, a nylon disk, and the solvents were removed in vacuo to yield the title Compound 6a (12.36 g, 59.9 mmol) as a white crystalline powder. $^1$H-NMR (d6-DMSO) δ (ppm): 12.10 (s, 1H), 7.29 (d, 2H), 7.12 (d, 2H), 2.88 (t, 2H), 2.50 (t, 2H), 1.25 (s, 9H). MS (ESI pos. ion) m/z: 228.9 (M+Na$^+$).

Step B. 5-bromo-2-[2-(4-tert-butyl-phenyl)-ethyl]-1H-benzimidazole

To a solution of Compound 6a (1.04 g, 5.04 mmol), in 25 mL of POCl$_3$ was added 4-bromo-benzene-1,2-diamine (0.946 g, 5.06 mmol). The reaction mixture was refluxed under a nitrogen atmosphere for 2.5 h then concentrated in vacuo. The residue was treated with 25 mL benzene and evaporated in vacuo. The residue was partitioned between 50 mL EtOAc and 50 mL saturated NaHCO$_3$. The organic fractions were washed with 50 mL of saturated NaHCO$_3$ and with 50 mL brine. The organic fraction was dried with Na$_2$SO$_4$, filtered and the filtrate was concentrated in vacuo. The residue was purified by chromatography (silica gel, EtOAc:Heptane, 2:8-4:6)) to yield the title Compound 6b (0.726 g, 2.03 mmol) as a tan powder. $^1$H-NMR (d6-DMSO) δ (ppm): 12.48-12.32 (m, 1H), 7.74-7.58 (m, 1H), 7.51-7.38 (m, 1H), 7.33-7.22 (m, 3H), 7.17 (d, 2H), 3.10 (m, 4H), 1.27 (s, 9H). MS (ESI pos. ion) m/z: 357.1/359.1 (M+H$^+$).

Step C. 2-{2-[2-(4-tert-butyl-phenyl)-ethyl]-1H-benzimidazol-5-yl}-phenol

A mixture of Compound 6b, (0.036 g, 0.10 mmol), 2-hydroxy phenyl boronic acid (0.022 g, 0.16 mmol), Cs$_2$CO$_3$ (0.074 g, 0.23 mmol), and PdCl$_2$(dppf) (0.008 g, 0.01 mmol)

in 2 mL 5:1 dioxane/EtOH in a sealed tube was heated at 100° C. for 15 minutes in a microwave synthesizer. More 2-hydroxy phenyl boronic acid (0.024 g, 0.17 mmol) and more PdCl$_2$(dppf) (0.010 g, 0.01 mmol) were added and the reaction was heated at 120° C. for 20 minutes. The reaction mixture was partitioned between 20 mL EtOAc, 20 mL water, and 2 mL brine. The organic fraction was evaporated, and the residue was purified by chromatography. (reverse-phase, acetonitrile:water+0.1% TFA, 25:75-95:5). The relevant fractions were frozen and lyophilized to give the product Compound 32 (0.013 g, 0.04 mmol) as a tan powder. $^1$H-NMR (d6-DMSO) δ (ppm): 14.55 (br s, 1H), 9.69 (s, 1H), 7.87 (s, 1H), 7.77 (d, 1H), 7.65 (d, 1H), 7.36-7.30 (m, 3H), 7.24-7.15 (m, 3H), 6.98 (d, 1H), 6.92 (t, 1H), 3.40 (t, 2H), 3.17 (t, 2H), 1.25 (s, 9H). MS (ESI pos. ion) m/z: 371.2 (M+H$^+$).

Using the procedures described in Example 6 and reagents, starting materials and conditions known to those skilled in the art, the following compounds representative of the present invention were prepared:

| Cpd | Name and Data |
|---|---|
| 33 | 3-{2-[2-(4-tert-butyl-phenyl)-ethyl]-1H-benzimidazol-5-yl}-phenol<br>The title compound (0.016g) was prepared from 3-hydroxy phenyl boronic acid (0.037g) and Compound 6b (0.036g). $^1$H-NMR(d6-DMSO) δ (ppm): 14.62(br s, 1H), 9.62(s, 1H), 7.88(s, 1H), 7.81(d, 1H), 7.71(dd, 1H), 7.36-7.27(m, 3H), 7.18(d, 2H), 7.13(d, 1H), 7.08(t, 1H), 6.82(dd, 1H), 3.40(t, 2H), 3.16(t, 2H), 1.25(s, 9H). MS(ESI pos. ion): 371.2(M+H$^+$). |
| 34 | 4-{2-[2-(4-tert-butyl-phenyl)-ethyl]-1H-benzimidazol-5-yl}-phenol<br>The title compound (0.022g) was prepared from 4-hydroxy phenyl boronic acid (0.032g) and Compound 6b (0.036g). $^1$H-NMR(d6-DMSO) δ (ppm): 14.61(br s, 1H), 9.65(s, 1H), 7.85(s, 1H), 7.78(d, 1H), 7.71(dd, 1H), 7.56(d, 2H), 7.33(d, 2H), 7.18(d, 2H), 6.89(d, 2H), 3.39(t, 2H), 3.16(t, 2H), 1.25(s, 9H). MS (ESI pos. ion) m/z: 371.2(M+H$^+$). |

EXAMPLE 7

(E)-(2-{2-[2-(4-trifluoromethylsulfanyl-phenyl)-vinyl]-1H-benzimidazol-5-yl}-phenyl)-methanol
(Cpd 35)

Step A.
(E)-3-(4-trifluoromethylsulfanyl-phenyl)-acrylic acid ethyl ester

To a solution of 4-trifluoromethylsulfanyl-benzaldehyde (15.46 g, 75.0 mmol) in 350 mL of benzene was added (carbethoxymethylene)triphenyl-phosphorane (26.14 g, 75.0 mmol). The reaction mixture was refluxed under a nitrogen atmosphere for 6 hours. The solvents were removed in vacuo and the resulting material was triturated with 350 mL of diethyl ether and filtered. The filtrate was concentrated in vacuo and triturated once more with 50 mL diethyl ether and filtered. The filtrate was evaporated in vacuo and purified by chromatography (silica, EtOAc:heptane, 0:10-1:9) to obtain the title Compound 7a (15.8 g, 57.3 mmol) as a white solid. $^1$H-NMR (400 MHz, d6-DMSO) δ (ppm): 7.89 (d, 2H), 7.75 (d, 2H), 7.70 (d, 1H), 6.77 (d, 1H), 4.21 (q, 2H), 1.27 (t, 3H). MS (ESI pos. ion) m/z: 277.0 (M+H$^+$).

Step B.
(E)-3-(4-trifluoromethylsulfanyl-phenyl)-acrylic acid

To a solution of Compound 7a (10.31 g, 37.3 mmol), in 300 mL of ethanol was added 3N aqueous NaOH solution (13.0 mL, 39.0 mmol). The reaction mixture was stirred for 21 hours, then evaporated in vacuo. The residue was dissolved in 250 mL water, and to it was added 1N aqueous HCl (45 mL, 45 mmol). The resulting precipitate was filtered, rinsed with water and dried under a stream of air to yield the title Compound 7b (8.967 g, 36.1 mmol) as a white powder. $^1$H-NMR (400M Hz, d6-DMSO) δ (ppm): 12.58 (s, 1H), 7.85 (d, 2H), 7.74 (d, 2H), 7.63 (d, 1H), 6.66 (d, 1H).

Step C. (E)-5-bromo-2-[2-(4-trifluoromethylsulfanyl-phenyl)-vinyl]-1H-benzimidazole To a suspension of Compound 7b (1.240 g, 5.00 mmol) in 100 mL of CH$_3$CN was added POCl$_3$ (2.3 mL, 25.1 mmol) and 4-bromo-benzene-1,2-diamine (0.938 g, 5.01 mmol). The reaction mixture was heated at reflux under a nitrogen atmosphere for 18 hours, cooled slightly then additional 4-bromo-benzene-1,2-diamine (0.468 g, 2.50 mmol) was added. Refluxing was continued for 6 hours, then a final amount of 4-bromo-benzene-1,2-diamine (0.468 g, 2.50 mmol) was added. After heating for an additional 15 hours, the reaction mixture was concentrated in vacuo. The residue was purified by chromatography (silica, NH$_3$ in MeOH (2M): CH$_2$Cl$_2$, 1:99-5:95) then a second time (EtOAc:heptane, 1:9-1:1)) to afford the title Compound 7c (1.255 g, 3.14 mmol) as a tan powder. $^1$H-NMR (400 MHz, d6-DMSO) δ (ppm): 12.96-12.83 (br d, 1H), 7.87-7.68 (m, 6H), 7.60-7.45 (m, 1H), 7.39-7.29 (m, 2H). MS (ESI pos. ion) m/z: 398.9/400.9 (M+H$^+$).

Step D. (E)-2-{2-[2-(4-trifluoromethylsulfanyl-phenyl)-vinyl]-1H-benzimidazol-5-yl}-phenyl)-methanol To a solution of Compound 7c (0.040 g, 0.10 mmol) and 2-hydroxymethyl phenyl boronic acid (0.029 g, 0.19 mmol) in 3 mL dioxane in a small pressure tube was added aqueous Na$_2$CO$_3$ solution (0.13 mL, 2M, 0.26 mmol) followed by PdCl$_2$(dppf) (0.008 g, 0.01 mmol). The vessel was flushed with argon, capped and heated in an oil bath at 120° C. for 1 hour. The reaction mixture was partitioned between 20 mL EtOAc, 20 mL water, and 2 mL brine. The organic fractions were dried with Na$_2$SO$_4$, filtered and the filtrate was evaporated. The residue was purified by chromatography (reverse-phase, acetonitrile:water+0.1% TFA, 1:3-95.5). The relevant fractions were mixed with poly(vinylpyridine), filtered, frozen and lyophilized to give the title Compound 35 (0.027 g, 0.063 mmol) as a yellow powder. $^1$H-NMR (400 MHz, d6-DMSO) δ (ppm): 7.89-7.78 (m, 5H), 7.71-7.57 (m, 3H), 7.44-7.28 (m, 5H), 4.44 (s, 2H). MS (ESI pos. ion) m/z: 426.7 (M+H$^+$).

Using the procedures described in Example 7 and reagents, starting materials and conditions known to those skilled in the art, the following compounds representative of the present invention were prepared:

| Cpd | Name and Data |
|---|---|
| 36 | (E)-2-{2-[2-(4-trifluoromethylsulfanyl-phenyl)-vinyl]-1H-benzimidazol-5-yl}-phenol<br>The title compound (0.029g) was prepared from 2-hydroxy phenyl boronic acid (0.028g) and Compound 7c (0.040g). $^1$H-NMR(400MHz, d6-DMSO) δ (ppm): 9.61(s, 1H), 7.90-7.79(m, 6H), 7.70(d, 1H), 7.54(d, 1H), 7.42(d, 1H), 7.33(dd, 1H), 7.19(dt, 1H), 6.98(d, 1H), 6.91(dt, 1H). MS(ESI pos. ion) m/z: 412.8(M+H$^+$). |
| 37 | (E)-N-(2-{2-[2-(4-trifluoromethylsulfanyl-phenyl)-vinyl]-1H-benzimidazol-5-yl}-phenyl)-acetamide<br>The title compound (0.016g) was prepared from N-[2-(4,4,5,5-tetramethyl-[1,3,2]dioxaborolan-2-yl)-phenyl]-acetamide (0.052g) and Compound 7c (0.040g). $^1$H-NMR(400MHz, d6-DMSO) δ (ppm): 9.24(s, 1H), 7.86(d, 2H), 7.82-7.75(m, 3H), 7.67(d, 1H), 7.57(s, 1H), 7.51(d, 1H), 7.44-7.24(m, 5H), 1.89(s, 3H). MS(ESI pos. ion) m/z: 453.8(M+H$^+$). |
| 38 | (E)-2-{2-[2-(4-trifluoromethylsulfanyl-phenyl)-vinyl]-1H-benzimidazol-5-yl}-benzamide<br>The title compound (0.031g) was prepared from 2-benzamido boronic acid (0.034g) and Compound 7c (0.040g). $^1$H-NMR(400MHz, d6-DMSO) δ (ppm): 7.91-7.79(m, 5H), 7.73-7.66(m, 3H), 7.54-7.38(m, 6H), 7.31(s, 1H). MS(ESI pos. ion) m/z: 439.8(M+H$^+$). |
| 39 | (E)-1-(2-{2-[2-(4-trifluoromethylsulfanyl-phenyl)-vinyl]-1H-benzimidazol-5-yl}-phenyl)-ethanone<br>The title compound (0.027g) was prepared from 2-acetyl phenyl boronic acid (0.034g) and Compound 7c (0.040g). $^1$H-NMR(400MHz, d6-DMSO) δ (ppm): 7.87(d, 2H), 7.84-7.77(m, 3H), 7.69(d, 1H), 7.55-7.47(m, 2H), 7.64-7.58(m, 3H), 7.40(d, 1H), 7.21(dd, 1H), 2.09(s, 3H). MS(ESI pos. ion) m/z: 438.7(M+H$^+$). |

EXAMPLE 8

(E)-1-(2-{2-[2-(4-trifluoromethanesulfonyl-phenyl)-vinyl]-1H-benzimidazol-5-yl}-phenyl)-ethanone (Cpd 40)

Step A.
(E)-3-(4-trifluoromethanesulfonyl-phenyl)-acrylic acid

To a suspension of Compound 7b (2.483 g, 10.01 mmol), in 50 mL of TFA was added 30% H$_2$O$_2$ solution (8 mL, 83 mmol). The reaction mixture was stirred for 21 h, then poured into 250 mL of ice water. The resulting precipitate was filtered off, rinsed with water and dried under vacuum at 50° C. to yield the title Compound 8a (2.281 g, 8.14 mmol) as a white powder. $^1$H-NMR (400 MHz, d6-DMSO) δ (ppm): 12.80 (s, 1H), 8.15 (s, 4H), 7.73 (d, 1H), 6.83 (d, 1H). MS (ESI pos. ion) m/z: 278.9 (M–H$^+$).

Step B. (E)-5-bromo-2-[2-(4-trifluoromethanesulfonyl-phenyl)-vinyl]-1H-benzimidazole To a suspension of Compound 8a (1.405 g, 5.01 mmol) in 100 mL of acetonitrile was added POCl$_3$ (2.3 mL, 25.1 mmol). The reaction mixture was refluxed under a nitrogen atmosphere for 30 minutes, then cooled slightly. To this reaction mixture was added 4-bromo-benzene-1,2-diamine (0.946 g, 5.06 mmol) and the reaction was refluxed for 2 h before additional 4-bromo-benzene-1,2-diamine (0.942 g, 5.04 mmol) was added. After an hour of heating, the reaction mixture was cooled and filtered over a pad of celite. The filter cake was rinsed with acetonitrile, ethyl acetate, and methanol. The filtrate was stirred with aqueous NaHCO$_3$/EtOAc. The organic fraction was evaporated, and partitioned between 100 mL EtOAc and 100 mL saturated NaHCO$_3$. The organic fraction was dried with Na$_2$SO$_4$, filtered, and the filtrate was evaporated. The residue was purified by chromatography (silica gel, EtOAc:heptane, 1:4-1:1)) to yield the title Compound 8b (1.595 g, 3.70 mmol) as a tan powder. $^1$H-NMR (400 MHz, d6-DMSO) δ (ppm): 13.00 (d, 1H), 8.14 (q, 4H), 7.87-7.73 (m, 2H), 7.63-7.50 (m, 2H), 7.40-7.33 (m, 1H). MS (ESI pos. ion) m/z: 430.8/432.8 (M+H$^+$).

Step C. (E)-1-(2-{2-[2-(4-trifluoromethanesulfonyl-phenyl)-vinyl]-1H-benzimidazol-5-yl}-phenyl)-ethanone A solution of Compound 8b (0.043 g, 0.10 mmol), and 2-acetyl phenyl boronic acid (0.035 g, 0.21 mmol) in 3 mL dioxane was stirred in a small pressure tube. Aqueous Na$_2$CO$_3$ solution (0.13 mL, 2M, 0.26 mmol) was added followed by PdCl$_2$(dppf) (0.007 g, 0.01 mmol). The vessel was flushed with argon, capped and heated in an oil bath at 120° C. for 1 h. The reaction mixture was partitioned between 20 mL EtOAc, 20 mL water, and 2 mL brine. The organic fraction was dried with Na$_2$SO$_4$, filtered, and the filtrate was evaporated. The residue was flushed over a plug of silica gel with 100% EtOAc then evaporated. The crude material was purified by chromatography (reverse-phase, acetonitrile/water+ 0.1% TFA, 1:3-95:5). The appropriate fractions were mixed with poly(vinylpyridine), filtered, frozen and lyophilized to give the title Compound 40 (0.022 g, 0.047 mmol) as a yellow powder. $^1$H-NMR (400 MHz, d6-DMSO) δ (ppm): 8.16 (q, 4H), 7.87 (d, 1H), 7.70 (d, 1H), 7.64-7.56 (m, 3H), 7.55-7.47 (m, 3H), 7.21 (d, 1H), 2.09 (s, 3H). MS (ESI pos. ion): 471.0 (M+H$^+$).

Using the procedures described in Example 8 and reagents, starting materials and conditions known to those skilled in the art, the following compounds representative of the present invention were prepared:

| Cpd | Name and Data |
|---|---|
| 41 | (E)-2-{2-[2-(4-trifluoromethanesulfonyl-phenyl)-vinyl]-1H-benzimidazol-5-yl}-phenol<br>The title compound (0.024g) was prepared from 2-hydroxy phenyl boronic acid (0.029g) and Compound 8b (0.043g). $^1$H-NMR(400MHz, d6-DMSO) δ (ppm): 9.53(s, 1H), 8.16(q, 4H), 7.85(d, 1H), 7.77(s, 1H), 7.65(d, 1H), 7.58(d, 1H), 7.47(d, 1H), 7.33(d, 1H), 7.17(dt, 1H), 6.97(d, 1H), 6.90(dt, 1H). MS(ESI pos. ion) m/z: 445.0(M+H$^+$). |
| 42 | (E)-(2-{2-[2-(4-trifluoromethanesulfonyl-phenyl)-vinyl]-1H-benzimidazol-5-yl}-phenyl)-methanol<br>The title compound (0.030g) was prepared from 2-hydroxymethyl phenyl boronic acid (0.027g) and Compound 8b (0.043g). $^1$H-NMR(400MHz, d6-DMSO) δ (ppm): 8.16(q, 4H), 7.89(d, 1H), 7.69(d, 1H), 7.62(d, 2H), 7.58(d, 1H), 7.43-7.33(m, 2H), 7.30(dd, 2H), 4.44(s, 2H). MS(ESI pos. ion) m/z: 459.0(M+H$^+$). |
| 43 | (E)-N-(2-{2-[2-(4-trifluoromethanesulfonyl-phenyl)-vinyl]-1H-benzimidazol-5-yl}-phenyl)-acetamide<br>The title compound (0.011g) was prepared from N-[2-(4,4,5,5-tetramethyl-[1,3,2]dioxaborolan-2-yl)-phenyl]-acetamide (0.053g) and Compound 8b (0.043g). $^1$H-NMR(400MHz, d6-DMSO) δ (ppm): 9.23(s, 1H), 8.15(q, 4H), 7.85(d, 1H), 7.67(d, 1H), 7.62-7.55(m, 2H), 7.51(d, 1H), 7.42-7.23(m, 4H), 1.89(s, 3H). MS(ESI pos. ion) m/z: 486.1(M+H$^+$). |
| 44 | (E)-2-{2-[2-(4-trifluoromethanesulfonyl-phenyl)-vinyl]-1H-benzimidazol-5-yl}-benzamide<br>The title compound (0.018g) was prepared from 2-benzamido boronic acid (0.034g) and Compound 8b (0.043g). $^1$H-NMR(400MHz, d6-DMSO) δ (ppm): 8.16(q, 4H), 7.88(d, 1H), 7.70-7.64(m, 3H), 7.59(d, 1H), 7.54-7.39(m, 4H), 7.36(dd, 1H), 7.30(s, 1H). MS(ESI pos. ion) m/z: 472.0(M+H$^+$). |

EXAMPLE 9

(E)-1-(2-{2-[2-(4-trifluoromethanesulfonyl-phenyl)-vinyl]-1H-benzimidazol-5-yl}-phenyl)-ethanol
(Cpd 45)

1-(2-{2-[2-(4-trifluoromethanesulfonyl-phenyl)-ethyl]-1H-benzimidazol-5-yl}-phenyl)-ethanol
(Cpd 46)

To a solution of Compound 40 (0.047 g, 0.10 mmol) in 5 mL EtOH was added NaBH$_4$ (0.028 g, 0.74 mmol). After 1 h, an additional amount of NaBH$_4$ (0.024 g, 0.63 mmol) was added. After an additional 4.5 h, the reaction was diluted into 25 mL EtOAc and washed twice with 25 mL water/brine. The organic fractions were dried with Na$_2$SO$_4$, filtered and the filtrate was evaporated. The residue was purified by chromatography (reverse-phase (acetonitrile/water with 0.1% TFA, 1:3-95:5). The two products were isolated, frozen and lyophilized to give the products Compound 45 (0.024 g, 0.051 mmol) as a yellow powder and Compound 46 (0.020 g, 0.042 mmol) as a white powder.

Compound 45: $^1$H-NMR (400 MHz, d6-DMSO) δ (ppm): 8.18 (dd, 4H), 7.93 (d, 1H), 7.74 (d, 1H), 7.67 (d, 1H), 7.64-7.57 (m, 2H), 7.43 (dt, 1H), 7.35-7.27 (m, 2H), 7.21 (dd, 1H), 4.80 (q, 1H), 1.22 (d, 3H). MS (ESI pos. ion) m/z: 472.8 (M+H$^+$).

Compound 46: $^1$H-NMR (400 MHz, d6-DMSO) δ (ppm): 8.12 (d, 2H), 7.82-7.74 (m, 3H), 7.70-7.63 (m, 2H), 7.47-7.37 (m, 2H), 7.32 (dt, 1H), 7.18 (dd, 1H), 4.72 (q, 1H), 3.47 (t, 2H), 3.40 (t, 2H), 1.19 (d, 3H). MS (ESI pos. ion) m/z: 474.8 (M+H$^+$).

EXAMPLE 10

(E)-2-(2-{2-[2-(4-trifluoromethyl-phenyl)-vinyl]-1H-benzimidazol-5-yl}-phenyl)-propan-2-ol(Cpd 18)

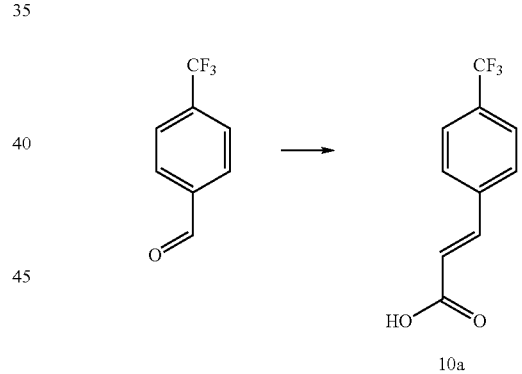

Step A. 3-(4-trifluoromethyl-phenyl)-acrylic acid

A solution of 4-trifluoromethylbenzaldehyde (7.7 mL, 57.7 mmol), malonic acid (12.0 g, 115.4 mmol), 0.567 µL piperidine (5.75 mmol) in 30 mL of pyridine was stirred at 70° C. for 18 h. The reaction solution was cooled to room temperature. Water (300 mL) was added and the resulting mixture was acidified to pH 4 (litmus) using concentrated hydrochloric acid to give a precipitate. The solid was filtered, and washed with water until the filtrate was neutral. The solid product was dried in vacuo to give the title Compound 10a as a white powder (11.2 g, 90%). $^1$HNMR (400 MHz, DMSO-d$_6$) δ (ppm): 12.60 (bs, 1H), 7.92 (d, 2H, J=8.2 Hz), 7.77 (d, 2H, J=8.2 Hz), 7.66 (d, 1H, J=16.0 Hz), 6.70 (d, 1H, J=16.0 Hz).

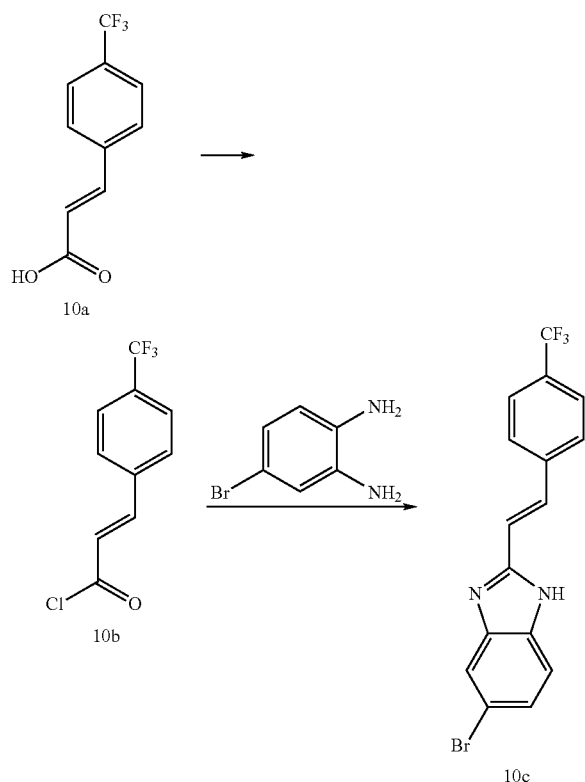

Step B. (E)-5-bromo-2-[2-(4-trifluoromethyl-phenyl)-vinyl]-1H-benzimidazole

A solution of Compound 10a (20.6 g, 95.4 mmol) in anhydrous methylene chloride (200 mL) was treated with oxalyl chloride (16.6 mL, 190 mmol) and "3 drops" of anhydrous dimethylformamide. The resulting solution was stirred at room temperature under an argon atmosphere for 18 h. The solvent was concentrated to give 3-(4-trifluoromethyl-phenyl)-acryloyl chloride Compound 10b as a solid, which was used without further purification in the next step.

To a solution of 4-bromo-benzene-1,2-diamine (16.1 g, 86.7 mmol) in acetic acid (100 mL) was added dropwise a solution of Compound 10b (assumed 95.4 mmol) in acetic acid (100 mL). The reaction mixture was stirred at 100° C. for 18 h. The reaction mixture was cooled to room temperature, and a mixture of ethyl acetate and hexanes 3:7 (500 mL) was added. The mixture was triturated at room temperature for 3 h to give a precipitate. The solid was filtered, and dried in vacuo to give the title Compound 10c (23.2 g, 73%). ¹H NMR (400 MHz, DMSO-d₆/CDCl₃) δ (ppm): 8.45 (d, 1H, J=16.7 Hz), 7.84-7.90 (m, 1H), 7.74 (d, 2H, J=8.3 Hz), 7.56-7.62 (m, 3H), 7.50-7.52 (m, 1H), 7.34 (d, 1H, 16.7 Hz).

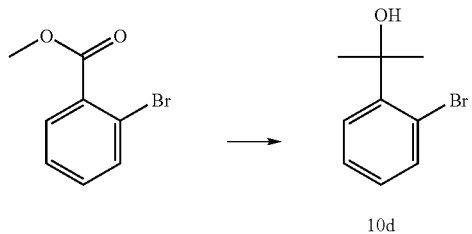

Step C. 2-(2-bromo-phenyl)-propan-2-ol

To a solution of methyl 2-bromobenzoate (20.76 g, 96 mmol) in 120 mL of anhydrous ether under Argon at 0° C. was slowly added methylmagnesium bromide (77 mL, 3.26 M) at a rate that the internal temperature of the mixture was below 20° C. A white suspension resulted, and the mixture was stirred at room temperature for 2 h. The mixture was cooled in an ice-water bath. To the reaction mixture was very slowly added hydrochloric acid (400 mL, 0.5 M). The pH of the final mixture was adjusted to less than about 6 with few drops of 2M hydrochloric acid. The layers were separated, and the aqueous layer was extracted twice with ether. The organic layers were combined and dried over magnesium sulfate. The organic fraction was filtered, and the filtrate was concentrated to yield the title compound as a pale yellow liquid, which was distilled under vacuum to afford the title Compound 10d as a colorless liquid (16.9 g, 82%, b.p. about 65-70° C./0.3 mmHg). ¹H NMR (400 MHz, CDCl₃) δ (ppm): 7.67 (dd, 1H, J=1.7, 7.9 Hz), 7.58 (dd, 1H, J=1.3, 7.9 Hz), 7.30 (ddd, 1H, J=1.4, 7.4, 7.9 Hz), 7.10 (ddd, 1H, J=1.7, 7.4, 7.8 Hz), 2.77 (br s, 1H), 1.76 (s, 6H).

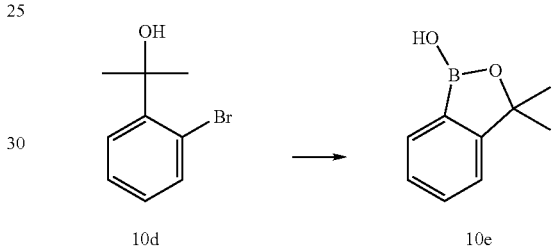

Step D. 3,3-dimethyl-3H-benzo[c][1,2]oxaborol-1-ol

To a solution of n-BuLi (166 mL, 2.6 M, 432 mmol) in 200 mL of THF at −78° C. under argon was slowly added a solution of Compound 10d (42.2 g, 196 mmol) in 60 mL of THF at a rate that the internal temperature remained below −70° C. The mixture was stirred at −75° C. for 2 h. To the reaction mixture was then added triisopropylborate (59 mL, 255 mmol) in three portions. The mixture was allowed to warm slowly to room temperature overnight. The mixture was then cooled to 0° C., and was carefully quenched with dilute hydrochloric acid (250 mL, 2N). The mixture was then stirred at room temperature for 1 h. The pH of the mixture was checked and adjusted to acidic using additional 2N HCl if prophetic. The two layers were separated, and the aqueous layer was extracted twice with ether. The organic layers were combined, and dried with magnesium sulfate and filtered. The filtrate was concentrated under reduced pressure to yield a pale yellow oil. The residue was then diluted with ethyl acetate (400 mL) and, washed with 1N sodium hydroxide solution (150 mL×3). The basic aqueous layers were combined and acidified with 2N HCl. The clear solution turned cloudy when the acid was added. The mixture was extracted with ether (150 mL×3). The organic layers were combined and dried with magnesium sulfate. The solution was filtered, and the filtrate was concentrated under reduced pressure to yield the title Compound 10e as a colorless oil (26.2 g, 82%) which was used without further purification in the next step. ¹H NMR (400 MHz, DMSO-d₆) δ (ppm): 9.00 (s, 1H), 7.66 (dm, 1H, J=7.3 Hz), 7.45 (dt, 1H, J=1.1, 7.7 Hz), 7.40 (dm, 1H, J=7.6 Hz), 7.31 (dt, 1H, J=1.2, 7.1 Hz), 1.44 (s, 6H).

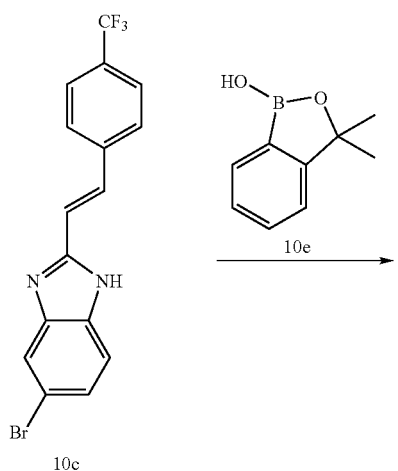

10c

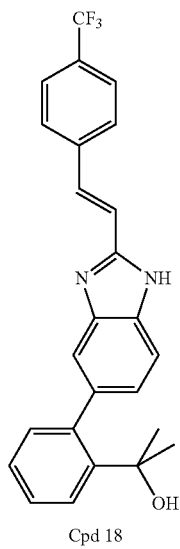

Cpd 18

Step E. (E)-2-(2-{2-[2-(4-trifluoromethyl-phenyl)-vinyl]-1H-benzimidazol-5-yl}-phenyl)-propan-2-ol To a mixture of Compound 10e (11.7 g, 71 mmol), Compound 10c (19.9 g, 54 mmol), sodium carbonate (46 g, 435 mmol) and PdCl$_2$(dppf).CH$_2$Cl$_2$ (8.9 g, 11 mmol) in a 1 L round bottom flask equipped with water condenser was added 400 mL of anhydrous DME and 200 mL of water. The mixture was evacuated and filled with Argon three times. The mixture was heated to 100° C. for 20 h. The mixture was then cooled to room temperature. The biphasic system was transferred to a 1 L separatory funnel and the two layers were separated. The organic layer was washed with brine (2×300 mL). The aqueous layers were combined and extracted with ethyl acetate once (about 300 mL). The organic layers were combined, dried with sodium sulfate, and filtered. The volume of the filtrate was reduced to about 170 mL under reduced pressure. The mixture was then filtered through a pad of silica gel and the pad was washed with ethyl acetate until the filtrate did not contain any product. After concentration, a light pink/beige solid was obtained. The solid was triturated with 50 mL ethyl acetate, and the mixture was heated to 85° C. for 5 min. The mixture was slowly cooled to r.t., then cooled at 0° C. for 0.5 h. The mixture was filtered, and the solid was washed with cold ethyl acetate twice, and dried under vacuum at 40° C. to yield the title Compound 18 as a light beige solid (7.58 g, 33%). RP-HPLC 95% pure. $^1$H NMR (400 MHz, DMSO-d$_6$) δ (ppm): 12.73 (m, 1H,), 7.90 (d, 2H, J=8.2 Hz), 7.85 (dd, 1H, J=8.0, 0.6 Hz), 7.78 (d, 2H, J=8.4 Hz), 7.74 (d,1 H, J=16.8 Hz), 7.59-7.47 (m, 1H), 7.41 (s, 1H), 7.37-7.32 (m, 2H), 7.21 (dt, 1H, J=1.2, 7.4 Hz), 7.06 (s, 1H), 7.02 (d, 1H, J=7.4 Hz), 4.85 (s, 1H), 1.21 (s, 6H). Mass Spectrum (LCMS, APCI pos.) Calcd. For $C_{25}H_{21}F_3N_2O$: 423.2 (M+H), Found 423.3. m.p. (uncorr.) 250-251° C.

Using the procedures described in Example 10 and corresponding reagents, starting materials and conditions known to those skilled in the art, the following compounds representative of the present invention were prepared:

| Cpd | Name and Data |
|---|---|
| 23 | (E)-2-(2-{2-[2-(4-trifluoromethoxy-phenyl)-vinyl]-1H-benzimidazol-5-yl}-phenyl)-propan-2-ol<br>$^1$H-NMR(400MHz, DMSO d6) δ (ppm) 7.84(dd, J=1.26, 8.084 Hz, 1H) 7.75-7.85(m, 2H) 7.66(d, J=16.4 Hz) 7.53-7.58(m, 1H) 7.45(bs, 1H) 7.34-7.38(m, 3H) 7.17-7.26(m, 3H) 7.09(dd, J=1.58, 7.58 Hz, 1H) 1.36(s, 6H). MS(ESI, pos. ion) m/z: 439.2(M+1). |
| 47 | (E)-2-(2-{2-[2-(4-trifluoromethanesulfonyl-phenyl)-vinyl]-1H-benzimidazol-5-yl}-phenyl)-propan-2-ol<br>$^1$H NMR(400MHz, CD$_3$OD) δ (ppm): 8.07(d, 2H, J=8.6 Hz), 7.98(d, 2H, J=8.6 Hz), 7.78(dd, 1H, J=1.1, 8.1Hz), 7.69(d, 1H, J=16.5 Hz), 7.54(d, 1H, J=8.2 Hz), 7.44(d, 1H, J=16.5 Hz), 7.42(brs, 1H), 7.31(ddd, 1H, J=1.5, 7.8, 8.1 Hz), 7.18(dt, 1H, J=1.3, 7.4 Hz), 7.16(dd, 1H, J=1.5, 8.3 Hz), 7.03(dd, 1H, J=1.4, 7.5Hz), 1.31(s, 6H). Mass Spectrum(LCMS, APCI pos.) Calcd. For $C_{25}H_{21}F_3N_2O_3S$: 487.1(M+H), Found 487.1. |
| 78 | (E)-2-(2-{2-[2-(4-chloro-phenyl)-vinyl]-1H-benzimidazol-5-yl}-phenyl)-propan-2-ol<br>$^1$H NMR(400MHz, CD$_3$OD) δ (ppm): 7.79(dd, 1H, J=8.1, 1.1 Hz), 7.63-7.54(m, 3H), 7.51(br d, 1H, J=9.7, 7.4Hz), 7.40-7.38(m, 3H), 7.31(m, 1H), 7.19(dt, 1H, J=1.4, 7.4 Hz), 7.15(d, 1H, J=16.5 Hz), 7.13(dd, 1H, J=7.9, 1.8 Hz), 7.04(dd, 1H, J=7.5, 1.4 Hz), 1.30(s, 6H). Mass Spectrum(LCMS, APCI pos.) Calcd. For $C_{24}H_{21}ClN_2O$: 389.1(M+H), Found 389.3. |
| 84 | (E)-2-(2-{2-[2-(4-methanesulfonyl-phenyl)-vinyl]-1H-benzimidazol-5-yl}-phenyl)-propan-2-ol<br>$^1$H-NMR(400MHz, CD$_3$OD) δ (ppm): 8.00(d, J=8Hz, 2H), 7.91(d, J=8 Hz, 2H), 7.82(dd, J=1.6, 8Hz, 1H), 7.70(d, J=16.4Hz, 2H), 7.41(s, 1H), 7.36(dt, J=1.6, 8Hz, 1H), 7.34(s, 1H), 7.23(dt, J=1.6, 8 Hz, 1H), 7.19(dd, J=1.6, 8 Hz, 1H), |

-continued

| Cpd | Name and Data |
|---|---|
| | 7.07(dd, J=1.6, 8 Hz, 1H), 3.16(s, 3H), 1.26(s, 6H). Mass Spectrum(LCMS, ESI pos.) Calcd. For $C_{25}H_{24}N_2O_3S$: 433.1(M+H), Found 433.4. |
| 114 | (E)-2-(2-{2-[2-(3-trifluoromethyl-phenyl)-vinyl]-1H-benzimidazol-5-yl}-phenyl)-propan-2-ol<br>$^1$H NMR(400MHz, CD$_3$OD) δ (ppm): 7.89-7.87(m, 2H), 7.79(dd, 1H, J=8.1, 1.1Hz), 7.67-7.56(m, 3H), 7.52(m, 1H), 7.40(br s, 1H), 7.31(m, 1H), 7.27(d, 1H, J=16.6 Hz), 7.18(dt, 1H, J=1.3, 7.4 Hz), 7.14(dd, 1H, J=8.3, 1.4 Hz), 7.04(dd, 1H, J=7.52, 1.38 Hz), 1.31(s, 6H). Mass Spectrum(LCMS, APCI pos.) Calcd. For $C_{25}H_{21}F_3N_2O$: 423.2(M+H), Found 423.3. |
| 458 | (E)-2,2,2-trifluoro-N-(2-{2-[2-(4-trifluoromethyl-phenyl)-vinyl]-1H-benzimidazol-5-yl}-phenyl)-acetamide.<br>The title compound (0.0195g) was prepared from Compound 465 (0.10g, 0.26mmol) and trifluoroacetylimidazolide (0.047g, 0.29mmol). $^1$H-NMR(400MHz, DMSO d6) δ (ppm): 12.7-12.9(bs, 1H) 11.0(s, 1H) 7.90-7.94(d, J=8.59 Hz, 2H)) 7.78-7.81(d, J=8.59 Hz, 2H) 7.37-7.76(m, 7H) 7.20(d, J=9.34 Hz, 1H) MS(ESI, pos. ion) m/z: 476.2(M+1). |
| 459 | (E)-2,2,2-trifluoro-ethanesulfonic acid (2-{2-[2-(4-trifluoromethyl-phenyl)-vinyl]-1H-benzimidazol-5-yl}-phenyl)-amide<br>The title compound (0.0015g) was prepared from Compound 465 (0.034g, 0.09mmol) and trifluoromethylsulfonylchloride (0.018g, 0.10mmol). $^1$H-NMR(400MHz, DMSO d6) δ (ppm) 12.75-12.82(bs, 1H) 9.70-9.80(bs, 1H) 7.90-7.96(d, J=8.08 Hz, 2H) 7.78-7.84(m, 3H) 7.54-7.77(m, 2H) 7.40-7.50(m, 2H) 7.24-7.40(m, 6H) 4.0(bs, 2H) MS(ESI, pos. ion) m/z: 526.1(M+1). |
| 460 | (E)-2,2-dimethyl-N-(2-{2-[2-(4-trifluoromethyl-phenyl)-vinyl]-1H-benzimidazol-5-yl}-phenyl)-propionamide<br>The title compound (0.0014g) was prepared from Compound 465 (0.034g, 0.09mmol) and trimethylacetylchloride (0.012mL, 0.036mmol). $^1$H-NMR(400MHz, CD$_3$OD) δ (ppm) 7.80-7.84(m, 3H) 7.58-7.78(m, 6H) 7.38-7.42(m, 2H) 7.24-7.35(m, 3H) 1.20(s, 9H) MS(ESI, pos. ion) m/z: 464.3(M+1). |
| 461 | (E)-ethanesulfonic acid (2-{2-[2-(4-trifluoromethyl-phenyl)-vinyl]-1H-benzimidazol-5-yl}-phenyl)-amide<br>The title compound (0.0018g) was prepared from Compound 465 (0.10g, 0.26mmol) and ethylsulfonyl chloride (0.027mL, 0.29mmol). $^1$H-NMR(400MHz, DMSO d6) δ (ppm) 12.88(d, J=9.1 Hz, 1H) 8.92(d, J=7.3 Hz, 1H) 7.78(d, J=8.08 Hz, 2H)) 7.85(d, J=8.08 Hz, 2H) 7.72-7.82(m, 3H) 7.63-7.68(m, 1H) 7.30-7.53(m, 6H) 2.78-2.92(qq, J=7.33 Hz, 2H) 1.00(tt, J=7.33 Hz, 3H). MS (ESI, pos. ion) m/z: 472.1(M+1). |
| 462 | (E)-(2-{2-[2-(4-trifluoromethyl-phenyl)-vinyl]-1H-benzimidazol-5-yl}-phenyl)-carbamic acid methyl ester<br>The title compound (0.0056g) was prepared from Compound 465 (0.10g, 0.26mmol) and chloromethylformate (0.022mL, 0.29mmol). $^1$H-NMR(400MHz, DMSO d6) δ (ppm) 7.82-7.84(d, J=8.59 Hz, 2H) 7.76-7.78(d, J=8.59 Hz, 2H) 7.62-7.70(m, 3H) 7.59(bs, 1H) 7.36-7.41(m, 3H) 7.24-7.34(m, 3H). MS(ESI, pos. ion) m/z: 438.4(M+1). |
| 463 | (E)-2-(2-{2-[2-(4-tert-butyl-phenyl)-vinyl]-1H-benzimidazol-5-yl}-phenyl)-propan-2-ol<br>$^1$H-NMR(400MHz, DMSO d6) δ (ppm) 7.82-7.84(m, 1H) 7.35-7.64(m, 8H) 7.10-7.30(m, 4H) 1.38(s, 15H). MS(ESI, pos. ion) m/z: 411.3(M+1). |
| 465 | (E)-2-{2-[2-(4-trifluoromethyl-phenyl)-vinyl]-1H-benzimidazol-5-yl}-phenylamine<br>The title compound was prepared from Compound 479 by stirring in TFA with heating.<br>$^1$H-NMR(400MHz, DMSO d6) δ (ppm): 12.78(s, 0.5H) 12.75(s, 0.5H) 7.91(d, J=8.08 Hz, 2H) 7.78-7.81(m, 3H) 7.74(d, J=4.55 Hz, 1H) 7.68(d, J=8.08 Hz, 1H) 7.56-7.62(m, 1H) 7.52(bs, 1H) 7.41(d, J=16.4 Hz, 1H) 7.20-7.29(m, 1H) 7.05(t, J=7.6 Hz, 2H) 6.78(d, J=8.34 Hz, 1H) 6.65(t, J=6.8 Hz, 1H) 4.81(s, 1H) 4.74(s, 1H) MS(ESI, pos. ion) m/z: 526.1(M+1). |
| 466 | (E)-2-{2-[2-(4-trifluoromethyl-phenyl)-vinyl]-1H-benzimidazol-5-yl}-benzoic acid ethyl ester<br>$^1$H-NMR(400MHz, DMSO d6) δ (ppm) 7.82-7.84(d, J=8.59 Hz, 2H) 7.76-7.78(d, J=8.59 Hz, 2H) 7.62-7.70(m, 3H) 7.59(bs, 1H) 7.36-7.41(m, 3H) 7.24-7.34(m, 3H). MS(ESI, pos. ion) m/z: 438.4(M+1). |
| 468 | (E)-2-[2-(2-styryl-1H-benzimidazol-5-yl)-phenyl]-propan-2-ol<br>$^1$H-NMR(400MHz, CD$_3$OD) δ (ppm) 8.18(bs, 2H) 7.70(m, 3H) 7.44(m, 3H) 7.30(m, 3H) 7.22(m, 2H) 7.19(m, 1H) 1.28(s, 9H). MS(ESI, pos. ion) m/z: 412.2(M+1). |
| 470 | (E)-N-(2-{2-[2-(4-trifluoromethyl-phenyl)-vinyl]-1H-benzimidazol-5-yl}-phenyl)sulfamide<br>The title compound (0.0023g) was prepared from Compound 465 (0.0175g, 0.046mmol) and sulfamide (0.5g, 5.2mmol). $^1$H-NMR(400MHz, DMSO d6) δ (ppm) 7.86(d, J=8.61Hz, 2H) 7.62-7.78(m, 6H) 7.31-7.41(m, 4H) 7.21-7.25(m, 1H). MS(ESI, pos. ion) m/z: 459.2(M+1). |
| 476 | (E)-(2-{2-[2-(4-trifluoromethyl-phenyl)-vinyl]-1H-benzimidazol-5-yl}-phenyl)-methanol<br>$^1$H-NMR(400MHz, CD$_3$OD) δ (ppm) 7.83(d, J=8.59 Hz, 2H) 7.77(d, J=8.34 Hz, 2H)7.56-7.74(m, 5H)7.24-7.42(m, 5H) 4.56(s, 2H) MS(ESI, pos. ion) m/z: 395.1(M+1). |

| Cpd | Name and Data |
|---|---|
| 478 | (E)-N-(2-{2-[2-(4-trifluoromethyl-phenyl)-vinyl]-1H-benzimidazol-5-yl}-phenyl)-acetamide<br>$^1$H-NMR(400MHz, CD$_3$OD) δ (ppm) 7.80-7.84(m, 3H) 7.56-7.78(m, 5H) 7.30-7.44(m, 5H) 1.97(s, 3H). MS(ESI, pos. ion) m/z: 422.3(M+1). |
| 479 | (E)-(2-{2-[2-(4-trifluoromethyl-phenyl)-vinyl]-1H-benzimidazol-5-yl}-phenyl)-carbamic acid tert-butyl ester<br>$^1$H-NMR(400MHz, CD$_3$OD) δ (ppm) 7.76-8.00(d, J=8.1 Hz, 2H) 7.82-7.90(d, J=8.8 Hz, 2H) 7.68-7.79(m, 4H) 7.36-7.48(5H) 1.44(s, 9H). MS(ESI, pos. ion) m/z: 480.2(M+1). |
| 480 | (E)-5-(2-methylsulfanyl-phenyl)-2-[2-(4-trifluoromethyl-phenyl)-vinyl]-1H-benzimidazole<br>$^1$H-NMR(400MHz, CD$_3$OD) δ (ppm) 7.84-7.87(d, J=8.1 Hz, 2H) 7.56-7.78(m, 5H) 7.20-7.40(m, 6H). MS(ESI, pos. ion) m/z: 411.2(M+1). |
| 481 | (E)-2-[2-(4-trifluoromethanesulfonyl-phenyl)-vinyl]-5-(2-trifluoromethyl-phenyl)-1H-benzimidazole<br>$^1$H NMR(400MHz, CD$_3$OD) δ (ppm): 8.10(d, 2H, J=8.5 Hz, 1H), 8.02(d, 2H, J=8.5 Hz), 7.77(d, 1H, J=7.8 Hz, 1H), 7.73(d, 1H, J=16.5 Hz), 7.64(d, 1H, J=7.4 Hz), 7.60(d, 1H, J=8.4 Hz), 7.54(d, 1H, J=7.7 Hz), 7.50(s, 1H), 7.46(d, 1H, J=16.5 Hz), 7.42(d, 1H, J=7.6 Hz), 7.22(dd, 1H, J=8.4, 1.0 Hz). Mass Spectrum(LCMS, APCI pos.) Calcd. For C$_{23}$H$_{14}$F$_6$N$_2$O$_2$S: 497.1(M+H), Found 497.1. |
| 482 | (E)-2-(2-{2-[2-(2-trifluoromethyl-phenyl)-vinyl]-1H-benzimidazol-5-yl}-phenyl)-propan-2-ol<br>$^1$H NMR(400MHz, CD$_3$OD) δ (ppm): 8.00-7.94(m, 2H), 7.79(dd, 1H, J=8.1, 1.1Hz), 7.73(d, 1H, J=7.9 Hz), 7.66(t, 1H, J=7.7 Hz), 7.53(br s, 1H), 7.50(t, 1H, J=7.67, 7.67 Hz), 7.41(br s, 1H), 7.31(m, 1H), 7.21-7.13(m, 3H), 7.04(dd, 1H, J=7.5, 1.4 Hz), 1.31(s, 6H). Mass Spectrum(LCMS, APCI pos.) Calcd. For C$_{25}$H$_{21}$F$_3$N$_2$O: 423.2(M+H), Found 423.3. |
| 483 | (E)-dimethyl-(2-{2-[2-(4-trifluoromethyl-phenyl)-vinyl]-1H-benzimidazol-5-yl}-benzyl)-amine<br>To a solution of Compound 484 (20.7mg, 0.053mmol) in DMF (10mL) was added dimethylamine 2.0 M in THF (66μL, 0.132mmol). The mixture was stirred for 45 min and sodium triacetoxyborohydride (17mg, 0.080mmol) was added. The mixture was stirred at rt for 2.5 d and then concentrated under reduced pressure. The residue was purified using preparative TLC plates (silica gel, 20×20cm, 2000 microns, EtOAc:hexanes:methanol 5:5:1) to give the title compound (18.2mg, 81%). $^1$H NMR(400MHz, CD$_3$OD) δ (ppm): 7.81(d, 2H, J=8.2 Hz), 7.70(d, 2H, J=8.0 Hz), 7.67(d, 1H, J=16.3 Hz), 7.60(d, 1H, J=8.2 Hz), 7.55-7.47(m, 2H), 7.40-7.26(m, 4H), 7.19(dd, 1H, J=8.3, 1.5 Hz), 3.58(s, 2H), 2.14(s, 6H). Mass Spectrum(LCMS, APCI pos.) Calcd. For C$_{25}$H$_{22}$F$_3$N$_3$: 422.2(M+H), Found 422.1. |
| 484 | (E)-2-{2-[2-(4-trifluoromethyl-phenyl)-vinyl]-1H-benzimidazol-5-yl}-benzaldehyde<br>$^1$H NMR(400MHz, DMSO-d6) δ (ppm): 12.93(d, 1H, J=12.5 Hz), 9.93(s, 1H), 7.93(d, 3H, J=8.4 Hz), 7.82-7.56(m, 8H), 7.44(d, 1H, J=16.5 Hz), 7.28(dd, 1H, J=10.1, 9.3 Hz). Mass Spectrum(LCMS, APCI pos.) Calcd. For C$_{23}$H$_{15}$F$_3$N$_2$O: 393.1(M+H), Found 393.3. |
| 485 | (E)-methyl-(2-{2-[2-(4-trifluoromethyl-phenyl)-vinyl]-1H-benzimidazol-5-yl}-benzyl)-amine<br>The title compound was prepared according to the procedure used for Compound 483, with the exception that methylamine was used. $^1$H NMR(400MHz, CD$_3$OD) δ (ppm): 7.82(d, 2H, J=8.3Hz, 1H), 7.71(d, 2H, J=8.3 Hz), 7.69(d, 1H, J=16.6 Hz), 7.63(d, 1H, J=8.1 Hz), 7.52-7.47(m, 2H), 7.39(tdd, 2H, J=9.1, 7.2, 3.6, 3.6 Hz), 7.35-7.29(m, 2H), 7.23(dd, 1H, J=8.3, 1.6 Hz), 3.86(s, 2H), 2.30(s, 3H). Mass Spectrum(LCMS, APCI pos.) Calcd. For C$_{24}$H$_{20}$F$_3$N$_3$: 408.2(M+H), Found 408.1. |
| 487 | (E)-5-(2-trifluoromethyl-phenyl)-2-[2-(4-trifluoromethyl-phenyl)-vinyl]-1H-benzimidazole<br>$^1$H NMR(400MHz, CD$_3$OD) δ (ppm): 7.80(d, 2H, J=8.2 Hz), 7.76(d, 1H, J=7.9 Hz), 7.70-7.60(m, 4H), 7.57(d, 1H, J=8.3 Hz), 7.52(t, 1H, J=7.7 Hz), 7.47(s, 1H), 7.40(d, 1H, J=7.6 Hz), 7.29(d, 1H, J=16.6 Hz), 7.19(dd, 1H, J=8.3, 1.0Hz). Mass Spectrum(LCMS, APCI pos.) Calcd. For C$_{23}$H$_{14}$F$_6$N$_2$: 433.1(M+H), Found 433.3. |
| 488 | (E)-5-(2-trifluoromethoxy-phenyl)-2-[2-(4-trifluoromethyl-phenyl)-vinyl]-1H-benzimidazole<br>$^1$H NMR(400MHz, CD$_3$OD) δ (ppm): 7.78(d, 2H, J=8.3 Hz), 7.68-7.66(m, 3H), 7.63-7.58(m, 2H), 7.50(m, 1H), 7.43-7.35(m, 3H), 7.33(dd, 1H, J=8.4, 1.6 Hz), 7.27(d, 1H, J=16.6 Hz). Mass Spectrum(LCMS, APCI pos.) Calcd. For C$_{23}$H$_{14}$F$_6$N$_2$O: 449.1(M+H), Found 449.3. |

EXAMPLE 10.1

Scale Up Preparation of (E)-2-(2-{2-[2-(4-trifluoromethyl-phenyl)-vinyl]-1H-benzimidazol-5-yl}-phenyl)-propan-2-ol (Cpd 18)

Step A. 3-(4-trifluoromethyl-phenyl)-acrylic acid

A 2-L 4-neck round bottom flask equipped with an air condenser/argon inlet, mechanical stirrer, thermocouple and a stopper was charged with 4-(trifluoromethyl)benzaldehyde (250 g, 196.2 mL, 1.44 mol), malonic acid (302.6 g, 2.87 mol), and pyridine (750 mL). An exotherm developed (about 38-40° C.), which was maintained for 30 min. Piperidine (14.202 mL, 143.58 mmol) was then added to the reaction and a second exotherm developed ($T_{max}$ about 42° C. after about 10 min.). The reaction was stirred for 30 min and then heated to 60° C. for 18 h (overnight). The reaction appeared to be complete by TLC, and was cooled to about 40° C., diluted into water (2 L; done to prevent reaction freezing), cooled to room temperature, and further diluted with water (4 L, 6 L total). The slurry was acidified to pH=2.0-3.0 with concentrated hydrochloric acid (about 675-700 mL). The material was stirred for 30 min., and a white solid was collected by filtration. The filter cake was washed with water until the filtrate was neutral (pH about 5.5-6, 2.5 L), air-dried in a Buchner funnel for 2 h, and then further dried in a vacuum oven at 60° C. overnight to provide 300.5 g (96%) of the title Compound 10a as a white solid.

Step B. (E)-5-bromo-2-[2-(4-trifluoromethyl-phenyl)-vinyl]-1H-benzimidazole

To a 5-L 4-neck round bottom flask equipped with a magnetic stirrer, argon inlet-argon outlet to a carbonate scrub, two stoppers, and a room temperature water bath was charged with 4-(trifluoromethyl)cinnamic acid (315 g, 1.46 mol) and dichloromethane (3.15 L) to give a slurry. To the slurry was added oxalyl chloride (151.71 mL, 1.75 mol) and DMF (1.13 mL, 14.57 mmol). Upon addition of DMF, gas evolution commenced, and the reaction was continued for about 3 h during which time a solution developed. When the reaction was complete (LC-MS), it was concentrated to dryness to give 342.4 g of 3-(4-trifluoromethyl-phenyl)-acrylol chloride Compound 10b (>100%) as a yellow oily solid.

A 5-L 4-neck round bottom flask equipped with mechanical stirrer, thermocouple, air condenser with argon inlet, and a stopper was charged with 4-bromo-benzene-1,2-diamine (244 g, 1.27 mol) and acetic acid (2.13 L). To this solution was added a solution of Compound 10b (327 g, 1.39 mol) in toluene (237 mL). After this addition, the temperature spiked to 45° C. in about 30 seconds and then subsided. The reaction was then heated to 90° C. for 16 h (overnight). The reaction was cooled to 40° C., and poured into a mixed solution of EtOAc and heptane (about 1:3, 5.75 L) and a precipitate occurred. The resulting slurry was stirred for 3 h, and the solid was collected by filtration, washed with EtOAc: heptane (1:3, 3 L), and then dried in a vacuum oven (60° C.) to give 324.3 g (65%) of the title Compound 10c as a partial acetate salt.

Step C. 2-(2-bromo-phenyl)-propan-2-ol

A 12-Liter 4-neck flask equipped with a thermocouple, condenser, septum, addition funnel and overhead mechanical stirrer under argon was charged with methyl-2-bromobenzoate (226.5 g, 1.05 mol) and THF (1.6 L, 19.66 mol). The mixture was cooled to a temperature between 2 and 5° C. with stirring and held for 30 min. To the solution was slowly added methyl magnesium bromide in diethyl ether (3M, 1.05 L; 3.15 mol) via the addition funnel at a rate to maintain the reaction temperature below 15° C. An exotherm was observed during the addition, the reaction temperature warmed from 3 to 15° C. The addition of 1.05 L Grignard was complete in 4 h (approximate feed rate was 4.17 mL/min). The reaction mixture appeared to be off-white/yellow slurry. The reaction was allowed to warm to room temperature and stirred overnight (15 h). The reaction was sampled by HPLC/TLC and showed no starting material present. The ice bath was again applied to the reaction flask and a 0.5 M HCl solution (4.5 L; 2.25 mol) was slowly added over a period of 2 h. The temperature increased dramatically from 0 to 15° C. After the quench was complete, the reaction was stirred at room temperature for 30 min. Additional 2 N HCl (500 mL; 1.00 mol) was slowly added to maintain a pH less than 6. MTBE (1 L) was added to help with the phase split. The reaction was stirred at room temperature for 1 to 2 h to dissolve the solid material into the aqueous phase (most likely $Mg(OH)_2$ which is very basic). The pH must be checked and adjusted with additional acid when necessary. The phases were separated and the aqueous layer was washed with an additional 1 L MTBE (2×500 mL). The organic phases were combined, washed with $NaHCO_3$ solution (2×300 mL), dried over $MgSO_4$, filtered and the filtrate was concentrated under vacuum to yield the title Compound 10d (220.83 g, 97.48% yield) as a clear yellow oil.

Step D. 3,3-dimethyl-3H-benzo[c][1,2]oxaborol-1-ol

A 12-Liter 4-neck round bottom flask equipped with a thermocouple, condenser, addition funnel and overhead mechanical stirrer under dry Argon was charged with anhydrous THF, (3 L) and chilled to −70 to −78° C. via a dry ice/acetone bath. n-Butyl lithium (2.5N in hexanes, 860 mL, 2.15 mol) was slowly added via addition funnel. An exotherm was observed as the temperature rose from −78 to −70° C. To the addition funnel was added a solution of Compound 10d (220 g, 979.97 mmol) in anhydrous THF (1 L). The 2-(2-bromophenyl)propan-2-ol solution was slowly added to the n-BuLi solution. The addition took 90 min in order to maintain a reaction temperature below −70° C. After the addition was complete, the reaction mixture was stirred at −70 to −75° C. for 30 min. The triethylborate (230 mL, 1.35 mol) was quickly added in 3 portions at −70° C. An exotherm was observed, the batch temperature rose from −70 to −64° C. The reaction was stirred at −70° C. and slowly warmed to room temperature over night. After the reaction was cooled to 0-5° C., the reaction was slowly quenched with 2 M HCl (1 L, 2.00 mol) added via the addition funnel while maintaining the batch temperature 0-5° C. The reaction mixture was stirred for 1 h. The aqueous phase pH was 9-10. The pH was then adjusted to acidic (4-5) with 2 M HCl (200 mL). The two phases were separated and the aqueous layer was extracted with MTBE (2×500 mL). The combined organic phases were dried with anhydrous magnesium sulfate. The solution was filtered and concentrated to yield a yellow oil. The yellow oil was diluted with MTBE (1.5 L) and washed with 1M NaOH (3×500 mL). The product containing basic aqueous phases were combined and acidified with 2 M HCl (800 mL) (the clear solution turns turbid with the addition of acid). After stirring the turbid solution for 15 min (pH=4-5) (Note 1), it was extracted with MTBE (2×500 mL). The organic phases were combined and dried over $MgSO_4$. The solution was filtered and the filtrate was concentrated to yield the title Compound 10e as a clear yellow oil (121.78 grams, 77% yield).

Step E. (E)-2-(2-{2-[2-(4-Trifluoromethyl-phenyl)-vinyl]-1H-benzimidazol-5-yl}-phenyl)-propan-2-ol A 5-L 4-neck flask equipped with a thermocouple controller, condenser, overhead mechanical stirrer, Firestone Valve® and a nitrogen inlet/outlet was charged with dimethoxyethane (2 L), DI water (1 L) and sodium carbonate (230.9 g, 2.18 mol). The solution was degassed and purged with $N_2$ three times. Compound 10e (71.7 g, 0.35 mol) and Compound 10c (100.0 g, 0.27 mol) were added to the degassed solution. The solution was degassed and purged with $N_2$ three times. $PdCl_2$ (dppf) (44.48 g, 54.4 mmol) was added to the solution, and the solution was degassed and purged with $N_2$ three times. The resulting two-phase suspension was heated to reflux for 18 h, and then cooled to room temperature. The reaction mixture was transferred to a 12-L seatory funnel, and the layers were separated. The organic layer was washed with brine (1 L). The two aqueous layers were combined and extracted with EtOAc (1 L). The combined organic layers were dried ($Na_2SO_4$), filtered, and the filtrate was concentrated to an oil. Two seate 100 g coupling reactions were combined and purified by chromatography in 10 successive chromatography runs on an ISCO preparative chromatography system (10×1.5 Kg SiO2, 5 column volumes of EtOAc, 250 mL/min flow rate). The combined fractions were transferred to two 22 L 4-neck round bottom flasks, and Silicycle Si-thiol functionalized silica gel (2 g) was added to each solution. The solutions were warmed to 40° C. and aged for 1 h. The solutions were filtered thru a medium glass funnel and washed with EtOAc (4 L) and combined. The filtrate was evaporated to a semi solid, which was transferred to a 2 L round bottom flask, to which EtOAc (0.4 L) was added. The resulting white precipitate slurry was cooled to −5° C. and stirred for 1 h. The slurry was filtered and washed twice with cold EtOAc (100 mL). The solids were dried in a vacuum oven at 40° C. for 40 h to afford 84.0 g (36.5% yield, 98.8 area % purity) of the title Compound 18 as a white solid. Anal. Calcd for $C_{25}H_{21}N_2OF_3$ 0.04% $H_2O$ 0.15 mol MeOH: C, 70.48; H, 5.14: N, 6.42; F, 13.06 Found: C, 70.54; H, 4.83: N, 6.18; F, 13.33

EXAMPLE 10.2

(E)-2-(2-{2-[2-(4-trifluoromethyl-phenyl)-vinyl]-1H-benzimidazol-5-yl}-phenyl)-propan-2-ol monosodium salt (Cpd 18)

A 5-L 4-neck flask equipped with a thermocouple controller, an overhead mechanical stirrer, and a nitrogen inlet/outlet was charged with (E)-2-(2-{2-[2-(4-trifluoromethyl-phenyl)-vinyl]-1H-benzimidazol-5-yl}-phenyl)-propan-2-ol. Compound 18 (125.0 g, 0.510 mol) and MeOH (1.25 L). A solution of sodium methoxide in methanol (0.5 M, 592 mL, 0.3 mol) was added. The reaction was heated to 65° C. for 30 min and all solids dissolved. The solution was cooled and evaporated to dryness. The foam was collected by scraping it out of the flask. The solids were placed in vacuum oven for 24 h at 40° C. to afford 139 g (about 100% isolated yield) of the title Compound 18 monosodium salt as a yellowish solid. $^1H$ NMR (400 MHz, DMSO-$d_6$) δ 7.80-7.84 (m, 3H), 7.74 (d, 2H, J=8.59 Hz), 7.65 (d, 1H, J=16.4 Hz), 7.40-7.44 (m, 2H), 7.25-7.37 (m, 2H), 7.16-7.20 (m, 1H), 7.01-7.05 (m, 1H), 6.84-6.87 (m, 1H), 1.23 (s, 6H). Mass Spectrum (LCMS, APCl pos.) Calcd. For $C_{25}H_{21}F_3N_2O$: 423.2 (M+H), Found 423.3. m.p. (uncorr.) 258-259° C.

EXAMPLE 10.3

(E)-2-(2-{2-[2-(4-trifluoromethyl-phenyl)-vinyl]-1H-benzimidazol-5-yl}-phenyl)-propan-2-ol hydrochloride salt (Cpd 18)

A 250-mL seatory funnel was charged with (E)-2-(2-{2-[2-(4-trifluoromethyl-phenyl)-vinyl]-1H-benzimidazol-5-yl}-phenyl)-propan-2-ol. Compound 18 (1.0 g, 2.4 mmol) and EtOAc (20 mL). Aqueous HCl (1M, 20 mL) was added to the white slurry, and the seatory funnel was shaken. The solid product quickly dissolved, and a white precipitate started to form. The organic layer was transferred to a 100 mL round bottom flask equipped with a magnetic stir bar, and was stirred for 2 h. The thick slurry was filtered, rinsed with EtOAc (2×5 mL), and put into a vacuum oven at 40° C. for 36 h to afford 0.95 g (87.5%) of the title Compound 18 hydrochloride salt.

EXAMPLE 11

(E)-2-{2-[2-(4-tert-butyl-phenyl)-vinyl]-6-trifluoromethyl-1H-benzimidazol-5-yl}-phenol (Cpd 48)

Step A. N-(4-bromo-2-nitro-5-trifluoromethyl-phenyl)-2,2,2-trifluoro-acetamide 4-bromo-3-trifluoromethyl aniline (4.8 g, 0.02 mol) was added in portions to a stirred ice-cold trifluoroacetic anhydride (50 mL). To the resulting solution was added $KNO_3$ (2.22 g, 0.022 mol, 1.1 eq) in portions. The reaction mixture was stirred at 0° C. for 1 h, and then allowed to warm to room temperature overnight. The reaction mixture was diluted with ice water (150 mL), and the solid was collected by vacuum filtration. The solid was washed with water (50 mL) and dried in vacuo to provide the title Compound 11a as a bright yellow solid (6.4 g). $^1$H-NMR (400 MHz, $CDCl_3$) δ (ppm): 9.19 (S, 1H) 8.64 (s, 1H) MS (ESI, pos. ion) m/z: 381.4 (M+1).

Step B.
4-bromo-2-nitro-5-trifluoromethyl-phenylamine

Compound 11a (5.7 g, 0.015 mol) was dissolved in a mixture of methanol (25 mL) and saturated aqueous $K_2CO_3$ (15 mL). The reaction mixture was then stirred at room temperature for 10 h. The reaction mixture was diluted with water (25 mL) and the product was collected by vacuum filtration to provide the title Compound 11b as a yellow solid (2.99 g). $^1$H-NMR (400 MHz, $CDCl_3$) δ (ppm): 8.44 (s, 1H) 7.21 (s, 1H), 6.21 (bs, 2H). MS (ESI, pos. ion) m/z: 285.0 (M+1).

Step C.
4-bromo-5-trifluoromethyl-benzene-1,2-diamine

Compound 11b (2.85 g, 0.01 mol) was dissolved in 30 mL of ethanol. Zinc powder (5.9 g, 0.09 mol) was added in portions followed by the addition of ammonium chloride (1.07 g, 0.02 mol, 2 eq). The reaction mixture was stirred at room temperature overnight (16 h). The reaction mixture was filtered over a pad of celite and the solvent was evaporated in vacuo. The residue was taken up in ethyl acetate (40 mL), washed with 35 mL of brine, dried over $Na_2SO_4$, and evaporated in vacuo. The residue was purified by chromatography (silica gel, $CH_2Cl_2$:MeOH, 96:4-94:6)) to provide the title Compound 11c as a bright yellow solid (1.53 g), which was used without further purification in the next step. $^1$H-NMR (400 MHz, $CD_3OD$) δ (ppm): 6.99 (s, 1H) 6.92 (s, 1H) MS (ESI, pos. ion) m/z: 254.7 (M+1).

Step D. (E)-5-bromo-2-[2-(4-tert-butyl-phenyl)-vinyl]-6-trifluoromethyl-1H-benzimidazole 4-t-butyl acrylic acid (1.02 g, 0.0055, 1.1 eq) was dissolved in 30 mL of POCl$_3$. To this was added Compound 11c (1.27 g, 0.005 mol), and the reaction mixture was heated at reflux for 6 h. (The reaction mixture was quite dark). The reaction mixture was cooled to room temperature and concentrated in vacuo. The residue was taken up in 50 mL of ethyl acetate, washed with 50 mL of brine, dried over Na$_2$SO$_4$, filtered and the filtrate was concentrated in vacuo. The residue was purified by chromatography (silica gel, hexanes:EtOAc, 1:3-2:3) to provide the title Compound 11d as a light brown solid (0.84 g). $^1$H-NMR (400 MHz, CDCl$_3$) δ (ppm): 7.91 (d, 2H, J=18.5 Hz) 7.69 (d, 1H, J=16.4 Hz), 7.32 (m, 4H) 7.09 (d, 1H, J=16.5 Hz) 1.28 (s, 9H). MS (ESI, pos. ion) m/z: 423.7 (M+1).

Step E. (E)-2-{2-[2-(4-tert-butyl-phenyl)-vinyl]-6-trifluoromethyl-1H-benzimidazol-5-yl}-phenol Compound 11d (0.00026 mol, 0.10 g) was dissolved in 5 mL of dioxane. 2-hydroxyphenyl boronic acid (0.00052 mol, 0.072 g, 2.0 equiv) was added followed by aqueous Na$_2$CO$_3$ (0.00055 mol, 0.28 mL of 2M solution) and dichlorobis(tricyclohexylphosphine)-palladium(II) (0.011 g, 6 mol %). The reaction mixture was heated in a microwave synthesizer at 110° C. for 20 minutes. The reaction mixture was cooled and the solvent was concentrated in vacuo. The residue was taken up in 10 mL of CH$_2$Cl$_2$, and washed sequentially with 10 mL of saturated aqueous NaHCO$_3$ and 10 mL of brine. The organic fractions were dried over Na$_2$SO$_4$, filtered, and the filtrate was concentrated in vacuo. The residue purified by chromatography (silica gel, CH$_2$Cl$_2$:MeOH, 98:2-95:5) to provide the title Compound 48 as a white solid. $^1$H-NMR (400 MHz, CDCl$_3$) δ (ppm): 7.29-7.56 (m, 8H) 7.15 (d, 1H, J=6.7 Hz) 6.89-7.05 (m, 3H)) 1.34 (s, 9H). MS (ESI, pos. ion) m/z: 437.1 (M+1).

Using the procedures described in Example 11 and reagents, starting materials and conditions known to those skilled in the art, the following compounds representative of the present invention were prepared:

| Cpd | Name and Data |
|---|---|
| 49 | (E)-3-{2-[2-(4-tert-butyl-phenyl)-vinyl]-6-trifluoromethyl-1H-benzimidazol-5-yl}-phenol<br>The title compound was prepared from 3-hydroxyphenyl boronic acid (0.00052mol, 0.072g) and Compound 1a (0.00026mol, 0.10g). $^1$H-NMR(400MHz, CDCl$_3$) δ (ppm): 7.25-7.61(m, 8H) 7.19(d, 1H, J=7.0Hz) 6.90-7.11(m, 3H)) 1.28(s, 9H). MS(ESI, pos. ion) m/z: 437.1(M+1). |
| 50 | (E)-N-(2-{2-[2-(4-tert-butyl-phenyl)-vinyl]-6-trifluoromethyl-1H-benzimidazol-5-yl}-phenyl)-acetamide<br>The title compound was prepared from 2-acetamidophenyl boronic acid (0.00052mol, 0.093g) and Compound 1a (0.00026mol, 0.10g) to give the product as an off-white solid. $^1$H-NMR(400MHz, CDCl$_3$) δ (ppm): 8.15(d, 2H, J=8.1 Hz) 7.73-7.76(m, 2H) 7.35-7.52(m, 4H) 7.0-7.14(m, 3H) 6.77(s, 1H) 1.45(s, 9H) 1.35(s, 3H). MS(ESI, pos. ion) m/z: 478.2(M+1). |
| 51 | (E)-(2-{2-[2-(4-tert-butyl-phenyl)-vinyl]-6-trifluoromethyl-1H-benzimidazol-5-yl}-phenyl)-methanol<br>The title compound was prepared from 2-hydroxymethyl phenylboronic acid (0.00052mol, 0.070g) and Compound 1a (0.00026mol, 0.10g) to give the product as a white solid. $^1$H-NMR(400MHz, CDCl$_3$) δ (ppm): 6.9-7.5(m, 12H) 4.39(m, 2H) MS(ESI, pos. ion) m/z: 451.2(M+1). |
| 52 | (E)-2-[2-(4-tert-butyl-phenyl)-vinyl]-5-(2-fluoro-phenyl)-6-trifluoromethyl-1H-benzimidazole<br>The title compound was prepared from 2-fluorophenylboronic acid (0.00052mol, 0.073g) and Compound 1a (0.00026mol, 0.10g) to give the product as a beige solid. $^1$H-NMR(400MHz, CDCl$_3$) δ (ppm): 8.1(m, 2H) 7.72(d, 2H, J=16.5 Hz) 7.42-7.53(m, 4H) 7.05-7.20(m, 4H) 1.34(s, 9H). MS(ESI, pos. ion) m/z: 440.1(M+1). |
| 53 | (E)-2-{2-'-(4-tert-butyl-phenyl)-vinyl]-6-trifluoromethyl-1H-benzimidazol-5-yl}-benzamide<br>The title compound was prepared from 2-aminocarbonyl phenylboronic acid (0.00052 mol, 0.086g) and Compound 1a (0.00026mol, 0.10g) to give the product as a yellow solid. $^1$H-NMR(400MHz, CDCl$_3$) δ (ppm): 7.2-7.8(m, 9H) 6.91(d, 2H, J=5.4 Hz) 6.68(d, 1H, J=19.5 Hz) 1.3(s, 9H). MS(ESI, pos. ion) m/z: 465.25(M+1). |
| 54 | (E)-(2-{2-[2-(4-tert-butyl-phenyl)-vinyl]-6-trifluoromethyl-1H-benzimidazol-5-yl}-phenyl)-carbamic acid tert-butyl ester<br>The title compound was prepared from t-butyl-N-[2-4,4,5,5-tetramethyl-1,3,2-dioxaborolan-2-yl) phenylcarbamate (0.00052mol, 0.166g) and Compound 1a (0.00026mol, 0.10g) to give the product as a beige solid. $^1$H-NMR(400MHz, DMSO-d6) δ (ppm): 8.0(s, 1H), 7.89(s, 1H), 7.62-7.79(m, 4H), 7.42-7.55(m, 3H), 7.36-7.41(m, 2H), 7.15-7.30(m, 2H))) 1.32(s, 18H) MS(ESI, pos. ion) m/z: 536.2(M+1). |
| 55 | (E)-N-(2-{2-[2-(4-tert-butyl-phenyl)-vinyl]-6-trifluoromethyl-1H-benzimidazol-5-yl}-phenyl)-methanesulfonamide<br>The title compound was prepared from 2-methylsulfonylaminophenyl boronic acid (0.00052mol, 0.111g) and Compound 1a (0.00026mol, 0.10g) to give the product as a bright yellow solid. $^1$H-NMR(400MHz, DMSO-d6) δ (ppm): 8.0(s, 1H) 7.79(d, 1H, J=16.5 Hz) 7.65(d, 2H, J=8.4 Hz) 7.5(m, 3H) 7.41(t, 1H, J=7.7 Hz) 7.23-7.28(m, 3H) 7.10(d, 1H, J=12.1 Hz) 2.5(s, 3H) 1.31(s, 9H). MS(ESI, pos. ion) m/z: 514.2(M+1). |

EXAMPLE 12

(E)-N-(2-{6-trifluoromethyl-2-[2-(4-trifluoromethyl-phenyl)-vinyl]-1H-benzimidazol-5-yl}-phenyl)-acetamide (Cpd 56)

Step A. (E)-5-bromo-6-trifluoromethyl-2-[2-(4-trifluoromethyl-phenyl)-vinyl]-1H-benzimidazole Using the procedure of Example 11, Step D, 4-trifluoromethyl acrylic acid (1.19 g, 0.0055, 1.1 eq) was dissolved in 30 mL of $POCl_3$. To this solution was added Compound 11c (1.27 g, 0.005 mol), and the reaction mixture was heated at reflux for 6 h (The reaction mixture was quite dark). The reaction mixture was cooled to room temperature and then concentrated in vacuo. The residue was taken up in 50 mL of ethyl acetate, washed with 50 mL of brine, dried over $Na_2SO_4$, filtered, and the filtrate was concentrated in vacuo. The residue was purified by chromatography (silica gel, hexanes:EtOAc, 3:1-3:2) to provide the title Compound 12a as a light yellow solid (1.02 g). $^1$H-NMR (400 MHz, $CDCl_3$) δ (ppm): 7.92 (d, 2H, J=14.1 Hz) 6.67-7.76 (m, 5H) 7.21 (d, 1H, J=16.5 Hz) MS (ESI, pos. ion) m/z: 368.3 (M+1).

Step B. (E)-N-(2-{6-trifluoromethyl-2-[2-(4-trifluoromethyl-phenyl)-vinyl]-1H-benzimidazol-5-yl}-phenyl)-acetamide Compound 12a (0.00025 mol, 0.10 g) was dissolved in 5 mL of dioxane. 2-acetamidophenyl boronic acid (0.0005 mol, 0.089 g, 2.0 equiv) was added followed by aqueous $Na_2CO_3$ (0.00055 mol, 0.28 mL of 2M solution) and dichlorobis(tricyclohexylphosphine)-palladium(II) (0.011 g, 6 mol %). The reaction mixture was heated in a microwave synthesizer at 110° C. for 20 minutes. The reaction mixture was cooled and the reaction mixture was concentrated in vacuo. The residue was taken up in 10 mL of $CH_2Cl_2$, and washed sequentially with 10 mL of saturated aqueous $NaHCO_3$ and 10 mL of brine. The organic fractions were dried over $Na_2SO_4$, filtered and the filtrate was concentrated in vacuo. The residue was purified by chromatography (silica gel $CH_2Cl_2$:MeOH, 98:2-95:5) to provide the title Compound 56 as a white solid. $^1$H-NMR (400M Hz, DMSO-d6) δ (ppm): 8.68 (s, 1H) 8.03 (s, 1H) 7.80-7.96 (m, 6H) 7.35-7.50 (m, 3H) 7.20 (d, 2, J=4.1 Hz) 1.8 (s, 3H) MS (ESI, pos. ion) m/z: 490.0 (M+1).

Using the procedures described in Example 12 and reagents, starting materials and conditions known to those skilled in the art, the following compounds representative of the present invention were prepared:

EXAMPLE 13

(E)-2-{6-fluoro-2-[2-(4-trifluoromethyl-phenyl)-vinyl]-1H-benzimidazol-5-yl}-phenol (Cpd 59)

Step A. N-(4-bromo-5-fluoro-2-nitro-phenyl)-2,2,2-trifluoro-acetamide 4-bromo-3-fluoromethyl aniline (3.8 g, 0.02 mol) was added in portions to a stirred ice-cold trifluoroacetic anhydride (50 mL). To the solution was added $KNO_3$ (2.22 g, 0.022 mol, 1.1 eq) in portions. The reaction mixture was stirred at 0° C. for 1 h and then allowed to warm to room temperature overnight. The reaction mixture was diluted with ice water (150 mL) and the solid was collected by vacuum filtration. The solid was washed with water (50 mL) and dried in vacuo to provide the title Compound 13a as a bright yellow solid (5.42 g). $^1$H-NMR (400 MHz, $CDCl_3$) δ (ppm): 8.66 (d, 1H, J=10.0 Hz) 8.60 (d, 1H, J=11.3 Hz). MS (ESI, pos. ion) m/z: 402.0 (M+Na).

Step B. 4-bromo-5-fluoro-2-nitro-phenylamine

Compound 13a (5.0 g, 0.015 mol) was dissolved in a mixture of methanol (25 mL) and saturated aqueous $K_2CO_3$ (15 mL) and the mixture was stirred at room temperature for 10 h. The reaction mixture was diluted with water (25 mL) and the product was collected by vacuum filtration to provide the title Compound 13b as a yellow solid (2.5 g). $^1$H-NMR (400 MHz, $CDCl_3$) δ (ppm): 8.39 (d, 1H, J=7.1 Hz) 6.75 (d, 1H, J=9.6 Hz) 6.19 (bs, 2H). MS (ESI, pos. ion) m/z: 236.9 (M+1).

Step C. 4-bromo-5-fluoro-benzene-1,2-diamine

Compound 13b (1.88 g, 0.008 mol) was dissolved in 20 mL of ethanol. Zinc powder (4.71 g, 0.072 mol) was added in portions followed by the addition of the ammonium chloride (0.86 g, 0.016 mol). The reaction mixture was stirred at room temperature overnight (16 h). The reaction mixture was filtered over a pad of celite and the solvent was evaporated in vacuo. The residue was taken up in ethyl acetate (30 mL) and washed with 25 mL of brine. The organic fractions were dried over $Na_2SO_4$, filtered and the filtrate was concentrated in vacuo. The residue was purified by flash chromatography (silica gel, $CH_2Cl_2$:MeOH, 96:4-94:6)) to provide the title Compound 13c as a dark yellow solid (1.02 g) that was used immediately in the next reaction. MS (ESI, pos. ion) m/z: 235.7 (M+1).

| Cpd | Name and Data |
| --- | --- |
| 57 | (E)-1-(2-{6-trifluoromethyl-2-[2-(4-trifluoromethyl-phenyl)-vinyl]-1H-benzimidazol-5-yl}-phenyl)-ethanone<br>The title compound was prepared from 2-acetylphenyl boronic acid (0.0005mol, 0.082g) and Compound 12a (0.00025mol, 0.10g) to give the product as a whitish-yellow solid. $^1$H-NMR(400MHz, DMSO-d6) δ (ppm): 7.81-8.0(m, 8H) 7.42-7.62(m, 3H) 7.30(d, 1H, J=6.8 Hz) 2.49(s, 3H) MS(ESI, pos. ion) m/z: 475.0(M+1). |
| 58 | (E)-(2-{6-trifluoromethyl-2-[2-(4-trifluoromethyl-phenyl)-vinyl]-1H-benzimidazol-5-yl}-phenyl)-methanol<br>The title compound was prepared from 2-hydroxymethyl phenylboronic acid (0.0005mol, 0.067g) and Compound 12a (0.00025mol, 0.10g) to give the product as a light yellow powder. $^1$H-NMR(400MHz, $CDCl_3$) δ (ppm): 8.0(d, 2H, J=8.1 Hz) 7.8(d, 2H, J=8.2 Hz) 7.0-7.59(m, 8H) 4.91-5.07(m, 1H) 4.09-4.22(m, 2H) (s, 9H). MS(ESI, pos. ion) m/z: 463.0(M+1). |

Step D. (E)-5-bromo-6-fluoro-2-[2-(4-trifluoromethyl-phenyl)-vinyl]-1H-benzimidazole 4-trifluoromethyl cinnamic acid (1.2 g, 0.0055, 1.1 eq) was dissolved in 30 mL of $POCl_3$. To the solution was added Compound 13c (1.02 g, 0.005 mol), and the reaction mixture was heated at reflux for 6 h. The reaction mixture was cooled to room temperature and then evaporated in vacuo. The residue was taken up in 50 mL of ethyl acetate, and washed with 50 mL of brine. The organic fractions were dried over $Na_2SO_4$ and concentrated in vacuo. The residue was purified by chromatography (silica gel, hexanes:EtOAc, 3:1-3:2) to provide the title Compound 13d as a light brown solid (0.80 g). $^1$H-NMR (400 MHz, DMSO-d6) δ (ppm): 7.63-8.09 (m, 4H) 7.4 (d, 1H, J=20.7 Hz) 6.69 (d, 1H, J=20.7 Hz) MS (ESI, pos. ion) m/z: 386.0 (M+1).

Step E. (E)-2-{6-fluoro-2-[2-(4-trifluoromethyl-phenyl)-vinyl]-1H-benzimidazol-5-yl}-phenol Compound 13d (0.00025 mol, 0.096 g) was dissolved in 5 mL of dioxane. 2-hydroxyphenyl boronic acid (0.0005 mol, 0.069 g) was added followed by aqueous $Na_2CO_3$ (0.00055 mol, 0.28 mL of 2M solution) and dichlorobis(tricyclohexylphosphine)-palladium(II) (0.011 g, 6 mol %). The reaction mixture was heated in a microwave synthesizer at 110° C. for 20 minutes. The reaction mixture was cooled and the solvent was evaporated in vacuo. The residue was taken up in 10 mL of $CH_2Cl_2$, and washed sequentially with 10 mL of saturated aqueous $NaHCO_3$ and 10 mL of brine. The organic fractions were dried over $Na_2SO_4$, filtered and the filtrate was concentrated in vacuo. The residue was purified by chromatography (silica gel ($CH_2Cl_2$:MeOH, 98:2-95:5) to provide the title Compound 59 as a tan solid. $^1$H-NMR (400 MHz, DMSO-d6) δ (ppm): 7.90 (d, 2H, J=8.0 Hz) 7.79 (d, 2H, J=7.8 Hz) 7.22-7.53 (m, 4H) 6.88-6.96 (m, 4H) MS (ESI, pos. ion) m/z: 399.1 (M+1).

Using the procedures described in Example 13 and reagents, starting materials and conditions known to those skilled in the art, the following compounds representative of the present invention were prepared:

| Cpd | Name and Data |
|---|---|
| 60 | (E)-3-{6-fluoro-2-[2-(4-trifluoromethyl-phenyl)-vinyl]-1H-benzimidazol-5-yl}-phenol<br>The title compound was prepared from 3-hydroxyphenyl boronic acid (0.0005mol, 0.069g) and Compound 13d (0.00025mol, 0.096g) to give the product as an off-white solid. $^1$H-NMR(400MHz, DMSO-d6) δ (ppm): 7.76-8.0(m, 4H) 7.24-7.64(m, 5H) 6.96-7.03(m, 1H) 6.75-6.8(m, 2H) MS(ESI, pos. ion) m/z: 399.3(M+1). |
| 61 | (E)-(2-{6-fluoro-2-[2-(4-trifluoromethyl-phenyl)-vinyl]-1H-benzimidazol-5-yl}-phenyl)-methanol<br>The title compound was prepared from 2-hydroxymethyl phenylboronic acid (0.0005mol, 0.067g) and Compound 13d (0.00025mol, 0.096g) to give the product as a yellowish solid. $^1$H-NMR(400MHz, CD3OD) δ (ppm): 7.83(d, 2H, J=8.2 Hz) 7.70-7.73(m, 2H) 7.64(t, 2H, J=7.9, 7.5 Hz)) 7.55(d, 1H, J=7.2 Hz) 7.25-7.46(m, 4H) 7.10(dd, 1H, J=1.2 Hz) 4.29(d, 2H, J=0.85 Hz) MS (ESI, pos. ion) m/z: 413.1(M+1). |
| 62 | (E)-1-(2-{6-fluoro-2-[2-(4-trifluoromethyl-phenyl)-vinyl]-1H-benzimidazol-5-yl}-phenyl)-ethanone<br>The title compound was prepared from 2-acetylphenyl boronic acid (0.0005mol, 0.082g) and Compound 13d (0.00025mol, 0.096g) to give the product as a bright yellow solid. $^1$H-NMR(400MHz, CD$_3$OD) δ (ppm): 7.75-7.91(m, 5H) 7.55-7.68(m, 4H) 7.41-7.47(m, 3H) 2.46(s, 3H) MS(ESI, pos. ion) m/z: 425.1(M+1). |
| 63 | (E)-2-{6-fluoro-2-[2-(4-trifluoromethyl-phenyl)-vinyl]-1H-benzimidazol-5-yl}-benzamide<br>The title compound was prepared from 2-aminocarbonyl phenylboronic acid (0.0005mol, 0.083g) and Compound 13d (0.00025mol, 0.096g) to give the product as a sticky tan solid. $^1$H-NMR(400MHz, DMSO-d6) δ (ppm): 7.93(d, 2H, J=8.6 Hz) 7.83(d, 2H, J=8.6 Hz) 7.40-7.71(m, 8H) MS(ESI, pos. ion) m/z: 426.0(M+1). |
| 64 | (E)-N-(2-{6-fluoro-2-[2-(4-trifluoromethyl-phenyl)-vinyl]-1H-benzimidazol-5-yl}-phenyl)-acetamide<br>The title compound was prepared from 2-acetamidophenyl boronic acid (0.0005mol, 0.089g) and Compound 13d (0.00025mol, 0.096g) to give the product as an off-white solid. $^1$H-NMR(400MHz, DMSO-d6) δ (ppm): 8.68(s, 1H) 8.03(s, 1H) 7.80-7.96(m, 6H) 7.35-7.50(m, 3H) 7.20(d, 2H, J=4.1 Hz) 1.8(s, 3H) MS (ESI, pos. ion) m/z: 440.1(M+1). |
| 65 | (E)-N-(2-{6-fluoro-2-[2-(4-trifluoromethyl-phenyl)-vinyl]-1H-benzimidazol-5-yl}-phenyl)-methanesulfonamide<br>The title compound was prepared from 2 methylsulfonylaminophenyl boronic acid (0.0005mol, 0.108g) and Compound 13d (0.00025mol, 0.096g) to give the product as an off-white solid. $^1$H-NMR(400MHz, CD$_3$OD) δ (ppm): 7.65(s, 1H) 7.59(d, 1H, J=6.7 Hz) 7.26-7.48(m, 10H) 2.95(s, 3H) MS(ESI, pos. ion) m/z: 476.1(M+1). |

EXAMPLE 14

(E)-(2-{6-chloro-2-[2-(4-trifluoromethyl-phenyl)-vinyl]-1H-benzimidazol-5-yl}-phenyl)-methanol (Cpd 66)

Step A. N-(4-bromo-5-chloro-2-nitro-phenyl)-2,2,2-trifluoro-acetamide

4-Bromo-3-chloromethyl aniline (4.1 g, 0.02 mol) was added in portions to a stirred ice cold trifluoroacetic anhydride (50 mL). To the resulting solution was added $KNO_3$ (2.22 g, 0.022 mol, 1.1 eq) in portions. The reaction mixture was stirred at 0° C. for 1 hour and then allowed to warm to room temperature overnight. The reaction mixture was diluted with ice water (150 mL) and the solid was collected by vacuum filtration. The solid was washed with water (50 mL) and dried in vacuo to provide the title Compound 14a as a pale yellow solid (5.55 g).

Step B. 4-bromo-5-chloro-2-nitro-phenylamine

Compound 14a (5.2 g, 0.015 mol) was dissolved in a mixture of methanol (25 mL) saturated aqueous $K_2CO_3$ (15 mL). The reaction mixture was stirred at room temperature for 10 hours. The reaction mixture was diluted with water (25 mL) and the product was collected by vacuum filtration to provide the title Compound 14b as a yellow solid (2.71 g). $^1$H-NMR (400 MHz, $CDCl_3$) δ (ppm): 8.39 (s, 1H) 6.98 (s, 1H) 6.08 (bs, 2H). MS (ESI, pos. ion) m/z: 250.9 (Br, Cl pattern).

Step C. 4-bromo-5-chloro-benzene-1,2-diamine

Compound 14b (2.0 g, 0.008 mol) was dissolved in 20 mL of ethanol. Zinc powder (4.7 g, 0.072 mol) was added in portions followed by the addition of the ammonium chloride (0.88 g, 0.016 mol, 2 eq). The reaction mixture was stirred at room temperature overnight (16 hours). The reaction mixture was filtered over a pad of celite and the solvent was evaporated in vacuo. The residue was taken up in ethyl acetate (30 mL) and washed with 25 mL of brine. The organic fractions were dried over $Na_2SO_4$, filtered and the filtrate was concentrated in vacuo. The residue was purified by flash chromatography (silica gel, $CH_2Cl_2$:MeOH, 96:4-94:6) to provide the title Compound 14c as a dark yellowish-brown solid (1.08 g) and was used immediately in the next reaction. MS (ESI, pos. ion) m/z: 220.9 (Br, Cl pattern).

Step D. (E)-5-bromo-6-chloro-2-[2-(4-trifluoromethyl-phenyl)-vinyl]-1H-benzimidazole 4-trifluoromethyl cinnamic acid (1.2 g, 0.0055, 1.1 eq) was dissolved in 30 mL of $POCl_3$. To this solution was added Compound 14c (1.08 g, 0.005 mol), and the reaction mixture was heated to reflux for 6 hours (The reaction mixture was quite dark). The reaction mixture was cooled to room temperature and the evaporated in vacuo. The residue was taken up in 50 mL of ethyl acetate, and washed with 50 mL of brine. The organic fractions were dried over $Na_2SO_4$, filtered and the filtrate was evaporated in vacuo. The residue was purified by chromatography (silica gel hexanes:EtOAc, 3:1-3:2) to provide the title Compound 14d as a light brown solid (0.80 g). $^1$H-NMR (400 MHz, DMSO-d6) δ (ppm): 7.57-8.21 (m, 4H) 7.35 (d, 1H, J=19 Hz) 6.72 (d, 1H, J=18.5 Hz). MS (ESI, pos. ion) m/z: 401.0.

Step E. (E)-(2-{6-chloro-2-[2-(4-trifluoromethyl-phenyl)-vinyl]-1H-benzimidazol-5-yl}-phenyl)-methanol Compound 14d (0.00025 mol, 0.100 g) was dissolved in 5 mL of dioxane. 2-hydroxymethyl phenylboronic acid (0.0005 mol, 0.067 g, 2.0 equiv) was added followed by aqueous $Na_2CO_3$ (0.00055 mol, 0.28 mL of 2M solution) and dichlorobis(tricyclohexylphosphine)-palladium(II) (0.011 g, 6 mol %). The reaction mixture was heated in a microwave at 110° C. for 20 minutes. The reaction mixture was cooled and the solvent was evaporated in vacuo. The residue was taken up in 10 mL of $CH_2Cl_2$, and washed sequentially with 10 mL of saturated aqueous $NaHCO_3$ and 10 mL of brine. The organic fractions were dried over $Na_2SO_4$, filtered and the solvent was evaporated in vacuo. The residue was purified by chromatography (silica gel,$CH_2Cl_2$:MeOH, 98:2-95:5) to provide the title Compound 66 as a yellow sticky solid. $^1$H-NMR (400 MHz, $CD_3OD$) δ (ppm): 7.82-7.85 (d, 2H, J=8.4 Hz) 7.72-7.74 (d, 2H, J=8.3 Hz) 7.56-7.66 (m, 3H) 7.26-7.43 (m, 5H) 5.05 (s, 1H) 4.58 (s, 2H). MS (ESI, pos. ion) m/z: 395.3 (—$CH_2OH$).

Using the procedures described in Example 14 and reagents, starting materials and conditions known to those skilled in the art, the following compounds representative of the present invention were prepared:

| Cpd | Name and Data |
|---|---|
| 67 | (E)-1-(2-{6-chloro-2-[2-(4-trifluoromethyl-phenyl)-vinyl]-1H-benzimidazol-5-yl}-phenyl)-ethanone<br>The title compound was prepared from 2-acetylphenyl boronic acid (0.0005mol, 0.082g) and Compound 14d (0.00025mol, 0.100g) to give the product as a pale yellow solid. $^1$H-NMR(400MHz, $CD_3OD$) δ (ppm): 7.80-7.84(m, 2H) 7.70-7.74(m, 2H) 7.67(s, 1H), 7.50-7.7.64(m, 2H) 7.27-7.43(m, 5H), 1.36(s, 9H). MS(ESI, pos. ion) m/z: 441.1(M+1). |
| 68 | (E)-2-{6-chloro-2-[2-(4-trifluoromethyl-phenyl)-vinyl]-1H-benzimidazol-5-yl}-phenol<br>The title compound was prepared from 2-hydroxyphenyl boronic acid (0.0005mol, 0.108g) and Compound 14d (0.00025mol, 0.069g) to give the product as a dark yellow solid. $^1$H-NMR(400MHz, $CD_3OD$) δ (ppm): 6.2-6.6(m, 5H) 5.99-6.05(m, 5H) 5.59-5.66(2H) 7.80-7.84(m, 2H). MS(ESI, pos. ion) m/z: 415.0(M+1). |

EXAMPLE 15

(E)-2-{2-[2-(4-trifluoromethyl-phenyl)-vinyl]-1H-benzimidazol-5-yl}-benzenesulfonamide (Cpd 70)

(E)-N-tert-butyl-2-{2-[2-(4-trifluoromethyl-phenyl)-vinyl]-1H-benzimidazol-5-yl}-benzenesulfonamide (Cpd 309)

Step A. (E)-N-tert-butyl-2-{2-[2-(4-trifluoromethyl-phenyl)-vinyl]-1H-benzimidazol-5-yl}-benzenesulfonamide A mixture of 2-(t-butylamino)sulfonylphenyl boronic acid (12.4 g, 0.048 mol), Compound 10c (13.6 g, 0.037 mol), Pd(dppf)Cl$_2$CH$_2$Cl$_2$ (3.00 g, 3.70 mmol), TBAB (11.9 g, 0.037 mmol), and Na$_2$CO$_3$ (31.4, 0.296 mol) in 750 mL of mixed solvent (DME:water, 4:1) was heated at 90° C. for 12 hours. The reaction mixture was concentrated, and the residue was purified by chromatography (silica gel, hexanes:EtOAc, 1:1) to provide the title Compound 309 as a yellow oil. $^1$H-NMR (400 MHz, CD$_3$OD) δ (ppm): 8.14 (dd, 1H, J=1.6 and 7.6 Hz) 7.84 (d, 2H, J=8.4 Hz) 7.73 (d, 2H, J=8.4 Hz) 7.70-7.62 (m, 4H) 7.54 (dt,1H, J=1.6 and 8.6 Hz) 7.41 (dd, 1H, J=1.2 and 7.6 Hz) 7.37-7.31 (m, 2H) 1.00 (s, 9H) MS (ESI, pos. ion) m/z: 490.3 (M+1).

Step B. (E)-2-{2-[2-(4-trifluoromethyl-phenyl)-vinyl]-1H-benzimidazol-5-yl}-benzenesulfonamide A solution of Compound 309 in 60 mL TFA was heated at 70° C. for 2 hours. The reaction was concentrated, the residue was dissolved in EtOAc, and washed with sat'd NaHCO$_3$. The organic layer was dried over Na$_2$SO$_4$, filtered, and the residue was concentrated. The residue was purified by chromatography (silica gel, hexanes:EtOAc, 1:2) to provide the title Compound 70 as a light brown solid. M.p. 168-170° C. $^1$H-NMR (400 MHz, CD$_3$OD) δ (ppm): 8.16 (dd, 1H, J=1.2 and 8.0 Hz) 7.95-7.91 (m, 3H) 7.82-7.76 (m, 4H) 7.70-7.56 (m, 3H) 7.44 (s, 1H) 7.16 (d, 1H, J=9.6 Hz) MS (ESI, pos. ion) m/z: 444.3 (M+1).

Using the procedures described in Example 15 and reagents, starting materials and conditions known to those skilled in the art, the following compound representative of the present invention was prepared:

| Cpd | Name and Data |
|---|---|
| 71 | (E)-2-{2-[2-(4-trifluoromethanesulfonyl-phenyl)-vinyl]-1H-benzimidazol-5-yl}-benzenesulfonamide<br>$^1$H-NMR(400MHz, CD$_3$OD) δ (ppm): 8.14(dd, 1H, J=1.2 and 7.6 Hz) 8.10(d, 2H, J=8.4 Hz) 8.01(d, 2H, J=8.4 Hz) 7.71-7.53(m, 5H) 7.44(d, 1H, J=16.4 Hz) 7.41(dd, 1H, J=1.2 and 7.6 Hz) 7.35(dd, 1H, J=1.2 and 8.4 Hz) MS(ESI, pos. ion) m/z: 508.3(M+1). |
| 398 | (E)-N,N-dimethyl-2-{2-[2-(4-trifluoromethyl-phenyl)-vinyl]-1H-benzimidazol-5-yl}-benzenesulfonamide<br>The title compound was prepared from 2-N,N-dimethylaminosulfonylphenyl boronic acid and Compound 10c.<br>$^1$H-NMR(400MHz, CD$_3$OD) δ (ppm): 8.08(dd, 1H, J=1.2 and 8.4 Hz) 7.84(d, 2H, J=8.4 Hz) 7.73(d, 2H, J=8.8 Hz) 7.69-7.56(m, 5H) 7.43(dd, 1H, J=1.2 and 7.2 Hz) 7.33(d, 1H, J=16.4 Hz) 7.28(dd, 1H, J=1.6 and 8.4 Hz) 2.34(s, 6H) MS(ESI, pos. ion) m/z: 472.5(M+1). |
| 441 | (E)-4-fluoro-2-{2-[2-(4-trifluoromethyl-phenyl)-vinyl]-1H-benzimidazol-5-yl}-benzenesulfonamide<br>The title compound was prepared from 2-tert-butylaminosulfonyl-5-fluorophenylboronic acid and Compound 10c.<br>$^1$H-NMR(400MHz, CD$_3$OD) δ (ppm): 8.18(dd, J=5.6, 8 Hz, 1H), 7.94(d, J=5.6, 8 Hz, 1H), 7.84(d, J=8 Hz, 2H), 7.73(s, 1H), 7.71-7.69(m, 2H), 7.63(d, J=8 Hz, 1H), 7.35-7.32(m, 1H), 7.28-7.22(m, 2H), 7.14(dd, J=2, 9 Hz, 1H). Mass Spectrum(LCMS, ESI pos) Calcd. For C$_{22}$H$_{15}$F$_4$N$_3$O$_2$S: 462.4(M+H), Found 462.2. |
| 444 | (E)-4-trifluoromethyl-2-{2-[2-(4-trifluoromethyl-phenyl)-vinyl]-1H-benzimidazol-5-yl}-benzenesulfonamide<br>The title compound was prepared from 2-tert-butylaminosulfonyl-5-trifluoromethylphenyl boronic acid and Compound 10c.<br>$^1$H-NMR(400MHz, CD$_3$OD) δ (ppm): 8.33(d, J=8 Hz, 1H), 7.88(s, 1H), 7.85(d, J=8 Hz, 2H), 7.74-7.68(m, 6H), 7.36-7.32(m, 1H), 7.34(d, J=16.4 Hz, 1H). Mass Spectrum(LCMS, ESI pos) Calcd. For C$_{23}$H$_{15}$F$_6$N$_3$O$_2$S: 512.5(M+H), Found 512.3. |
| 446 | (E)-5-trifluoromethyl-2-{2-[2-(4-trifluoromethyl-phenyl)-vinyl]-1H-benzimidazol-5-yl}-benzenesulfonamide<br>The title compound was prepared from 2-tert-butylaminosulfonyl-4-trifluoromethylphenyl boronic acid and Compound 10c.<br>$^1$H-NMR(400MHz, CD$_3$OD) δ (ppm): 8.42(s, 1H), 7.94(d, J=8 Hz, 1H), 7.85(d, J=8 Hz, 2H), 7.73(d, J=8 Hz, 2H), 7.71(d, J=8 Hz, 2H), 7.64(d, J=8 Hz, 2H), 7.34(d, J=16.4Hz, 2H). Mass Spectrum(LCMS, ESI pos) Calcd. For C$_{23}$H$_{15}$F$_6$N$_3$O$_2$S: 512.1(M+H), Found 512.2. |

EXAMPLE 16

(E)-2-{2-[2-(4-trifluoromethoxy-phenyl)-vinyl]-1H-benzimidazol-5-yl}-benzenesulfonamide (Cpd 69)

Step A. (5-bromo-2-tert-butoxycarbonylamino-phenyl)-carbamic acid tert-butyl ester 4-bromo-phenylenediamine (25 g, 0.134 mol) was added portionwise to di-t-butyl dicarbonate (175 g, 0.802 mol) at 25° C., and the reaction mixture was stirred for 10 hours. The mixture was purified by chromatography (silica gel, hexanes to hexanes:EtOAc, 1:1) to provide the title Compound 16a as a light brown solid. $^1$H-NMR (400 MHz, CDCl$_3$) δ (ppm): 7.76 (brs, 1H) 7.32 (brs, 1H) 7.22 (dd, 1H, J=2.0 and 8.8 Hz) 6.72 (brs, 1H) 6.53 (brs, 1H).

Step B. (3-tert-butoxycarbonylamino-2'-tert-butylsulfamoyl-biphenyl-4-yl)-carbamic acid tert-butyl ester A mixture of 2-(t-butylamino)sulfonylphenyl boronic acid (4.7 g, 0.018 mmol), Compound 16a (4.7 g, 0.012 mmol), Pd(dppf)Cl2.CH$_2$Cl$_2$ (0.99 g, 0.0012 mmol), TBAB (3.90 g, 0.012 mmol), and 20 mL of 1 M Na$_2$CO$_3$ (aq) in 100 mL of DME was heated at 100° C. for 12 hours. The reaction mixture was concentrated, and the residue was purified by chromatography (silica gel, hexanes:EtOAc, 2:1) to provide the title Compound 16b as a yellow oil.

Step C. 3',4'-diamino-biphenyl-2-sulfonic acid tert-butylamide

A mixture of Compound 16b in 20 mL of 4M HCl in dioxane was stirred for 3 hours. The reaction mixture was concentrated, diluted with EtOAc and washed with sat'd NaHCO$_3$ (aq), then dried over Na$_2$SO$_4$ and filtered. The filtrate was concentrated to provide the title Compound 16c as a brown oil. $^1$H-NMR (400 MHz, CD$_3$OD) δ (ppm): 8.04 (dd, 1H, J=1.2 and 7.6 Hz) 7.56 (dt, 1H, J=1.2 and 8.2 Hz) 7.44 (dt, 1H, J=1.2 and 8.4 Hz) 7.33 (dd, 1H, J=1.2 and 7.6 Hz) 6.86 (d, 1H, J=1.6 Hz) 6.77 (d, 1H, J=7.6 Hz) 6.73 (dd, 1H, J=2.0 and 8.0 Hz) 0.97 (s, 9H). MS (ESI, pos. ion) m/z: 319.9 (M+1).

Step D. (E)-2-{2-[2-(4-trifluoromethoxy-phenyl)-vinyl]-1H-benzimidazol-5-yl}-benzenesulfonamide A mixture of Compound 16c (0.120 g, 0.376 mmol), trans 4-(trifluoromethoxy)-cinnamic acid (0.105 g, 0.451 mmol), and 0.4 mL of 4N HCl (aq) in 4 mL of ethylene glycol was heated at 180° C. for 1 hour. The reaction mixture was purified directly by HPLC (YMC ODS-A, H$_2$O: MeCN, 90:10 to 40:60, over 10 min) to provide the title Compound 69 as an off-white solid. $^1$H-NMR (400 MHz, CD$_3$OD) δ (ppm): 8.14 (dd, 1H, J=1.2 and 8.0 Hz) 7.75 (d, 2H, J=8.4 Hz) 7.68-7.53 (m, 5H) 7.41 (dd, 1H, J=1.2 and 7.6 Hz) 7.37-7.33 (m, 3H) 7.19 (d, 1H, J=16.8 Hz) MS (ESI, pos. ion) m/z: 460.3 (M+1).

Using the procedures described in Example 16 and reagents, starting materials and conditions known to those skilled in the art, the following compounds representative of the present invention were prepared:

| Cpd | Name and Data |
|---|---|
| 79 | (E)-2-{2-[2-(4-chloro-phenyl)-vinyl]-1H-benzimidazol-5-yl}-benzene sulfonamide<br>$^1$H-NMR(400MHz, CD$_3$OD) δ (ppm): 8.14(dd, 1H, J=1.2 and 7.6 Hz) 7.68-7.54(m, 7H) 7.46-7.40(m, 3H) 7.38(dd, 1H, J=1.2 and 8.4 Hz) 7.19(d, 1H, J=16.8 Hz) MS(ESI, pos. ion) m/z: 410.4(M+1). |
| 85 | (E)-2-{2-[2-(4-methanesulfonyl-phenyl)-vinyl]-1H-benzimidazol-5-yl}-benzenesulfonamide<br>$^1$H-NMR(400MHz, CD$_3$OD) δ (ppm): 8.14(dd, 1H, J=1.2 and 7.6 Hz) 7.99(d, 2H, J=8.4 Hz) 7.89(d, 2H, J=8.4 Hz) 7.71-7.53(m, 5H) 7.41(dd, 1H, J=1.6 and 7.6 Hz) 7.36(d, 1H, J=16.4 Hz) 7.34(dd, 1H, J=1.6 and 8.4 Hz) MS(ESI, pos. ion) m/z: 453.4(M+1). |
| 357 | (E)-2-{2-[2-(2,4-difluoro-phenyl)-vinyl]-1H-benzimidazol-5-yl}-benzenesulfonamide<br>$^1$H-NMR(400MHz, CD$_3$OD) δ (ppm): 8.13(d, 1H, J=8.0 Hz) 7.83-7.75(m, 2H) 7.67-7.53(m, 4H) 7.38(t, 2H, J=9.2 Hz) 7.22(d, 1H, J=16.8 Hz) 7.08-7.03(m, 2H) MS(ESI, pos. ion) m/z: 412.4(M+1). |
| 358 | (E)-2-{2-[2-(3,4-difluoro-phenyl)-vinyl]-1H-benzimidazol-5-yl}-benzenesulfonamide<br>$^1$H-NMR(400MHz, CD$_3$OD) δ (ppm): 8.14(dd, 1H, J=1.2 and 7.6 Hz) 7.72-7.55(m, 6H) 7.48-7.35(m, 4H) 7.20(d, 1H, J=16.4 Hz) MS(ESI, pos. ion) m/z: 412.4(M+1). |
| 359 | (E)-2-{2-[2-(2,3-difluoro-phenyl)-vinyl]-1H-benzimidazol-5-yl}-benzenesulfonamide<br>$^1$H-NMR(400MHz, CD$_3$OD) δ (ppm): 8.14(dd, 1H, J=1.2 and 8.0 Hz) 7.84(d, 1H, J=16.8 Hz) 7.70-7.54(m, 5H) 7.41(dd, 2H, J=1.6 and 8.4 Hz) 7.33(d, 1H, J=16.8 Hz) 7.29-7.23(m, 2H) MS(ESI, pos. ion) m/z: 412.4(M+1). |
| 360 | (E)-2-{2-[2-(2,5-difluoro-phenyl)-vinyl]-1H-benzimidazol-5-yl}-benzenesulfonamide<br>$^1$H-NMR(400MHz, CD$_3$OD) δ (ppm): 8.14(dd, 1H, J=1.2 and 8.0 Hz) 7.81(d, 1H, J=16.8 Hz) 7.69-7.54(m, 5H) 7.46-7.38(m, 2H) 7.33(d, 1H, J=16.8 Hz) 7.26-7.14(m, 2H) MS(ESI, pos. ion) m/z: 412.4(M+1). |
| 361 | (E)-2-{2-[2-(3,5-difluoro-phenyl)-vinyl]-1H-benzimidazol-5-yl}-benzenesulfonamide<br>$^1$H-NMR(400MHz, CD$_3$OD) δ (ppm): 8.14(dd, 1H, J=1.6 and 8.0Hz) 7.71-7.55(m, 5H) 7.42(td, 2H, J=1.4 and 8.4 Hz) 7.34-7.28(m, 3H) 7.04-6.99(m, 1H) MS(ESI, pos. ion) m/z: 412.4(M+1). |
| 362 | (E)-2-{2-[2-(3-trifluoromethoxy-phenyl)-vinyl]-1H-benzimidazol-5-yl}-benzenesulfonamide<br>$^1$H-NMR(400MHz, CD$_3$OD) δ (ppm): 8.14(dd, 1H, J=1.2 and 7.6 Hz) 7.37-7.51(m, 8H) 7.41(dd, 1H, J=1.2 and 8.0 Hz) 7.35(dd, 1H, J=1.6 and 8.0 Hz) 7.29(d, 1H, J=8.8 Hz) 7.25(d, 1H, J=16.8 Hz) 7.34(dd, 1H, J=1.6 and 8.4 Hz) MS(ESI, pos. ion) m/z: 460.4(M+1). |
| 363 | (E)-2-{2-[2-(4-bromo-phenyl)-vinyl]-1H-benzimidazol-5-yl}-benzenesulfonamide<br>$^1$H-NMR(400MHz, CD$_3$OD) δ (ppm): 8.13(dd, 1H, J=1.2 and 7.6 Hz) 7.93(d, 1H, J=1.2 and 7.6 Hz) 7.65-7.47(m, 6H) 7.42-7.29(m, 4H) 7.22(d, 1H, J=16.8 Hz) MS(ESI, pos. ion) m/z: 454.3(M+1). |

| Cpd | Name and Data |
|---|---|
| 364 | (E)-2-{2-[2-(2-trifluoromethyl-phenyl)-vinyl]-1H-benzimidazol-5-yl}-benzenesulfonamide<br>$^1$H-NMR(400MHz, CD$_3$OD) δ (ppm): 8.14(dd, 1H, J=1.2 and 8.0 Hz) 8.10(dd, 1H, J=2.0 and 16.4 Hz) 8.01(d, 1H, J=7.6 Hz) 7.80(d, 1H, J=7.6 Hz) 7.75-7.55(m, 6H) 7.42(dd, 2H, J=1.2 and 8.4 Hz) 7.25(d, 1H, J=16.4 Hz) MS(ESI, pos. ion) m/z: 444.3(M+1). |
| 365 | (E)-2-{2-[2-(2-chloro-phenyl)-vinyl]-1H-benzimidazol-5-yl}-benzenesulfonamide<br>$^1$H-NMR(400MHz, CD$_3$OD) δ (ppm): 8.16(d, 1H, J=7.6 Hz) 8.13(s, 1H) 7.90(d, 1H, J=9.2 Hz) 7.68(d, 1H, J=14.4 Hz) 7.65-7.49(m, 4H) 7.43-7.38(m, 4H) 7.25(d, 1H, J=16.4 Hz) MS(ESI, pos. ion) m/z: 410.3(M+1). |
| 366 | (E)-2-{2-[2-(2-bromo-phenyl)-vinyl]-1H-benzimidazol-5-yl}-benzenesulfonamide<br>$^1$H-NMR(400MHz, CD$_3$OD) δ (ppm): 8.35(d, 1H, J=16.4 Hz) 8.16(dd, 1H, J=1.6 and 8.0Hz) 7.97(dd, 1H, J=1.6 and 7.6 Hz) 7.84(s, 1H) 7.80(d, 1H, J=9.2 Hz) 7.76(dd, 1H, J=1.2 and 8.0 Hz) 7.70-7.60(m, 3H) 7.52(dt, 1H, J=1.2 and 8.2 Hz) 7.45-7.39(m, 2H) 7.32(d, 1H, J=16.4 Hz) MS(ESI, pos. ion) m/z: 454.3(M+1). |
| 367 | (E)-2-{2-[2-(4-fluoro-2-trifluoromethyl-phenyl)-vinyl]-1H-benzimidazol-5-yl}-benzenesulfonamide<br>$^1$H-NMR(400MHz, CD$_3$OD) δ (ppm): 8.15(dd, 1H, J=1.2 and 7.6 Hz) 8.12-8.08(m, 2H) 7.76-7.41(m, 8H) 7.25(d, 1H, J=16.4 Hz) MS(ESI, pos. ion) m/z: 461.4(M+1). |
| 368 | (E)-2-{2-[2-(2-fluoro-3-trifluoromethyl-phenyl)-vinyl]-1H-benzimidazol-5-yl}-benzenesulfonamide<br>$^1$H-NMR(400MHz, CD$_3$OD) δ (ppm): 8.14(dd, 1H, J=1.2 and 7.6 Hz) 8.10(t, 1H, 7.0 Hz) 7.91(d, 1H, J=16.4 Hz) 7.75-7.54(m, 5H) 7.46-7.34(m, 4H) MS(ESI, pos. ion) m/z: 461.4(M+1). |
| 369 | (E)-2-{2-[2-(4-fluoro-3-trifluoromethyl-phenyl)-vinyl]-1H-benzimidazol-5-yl}-benzenesulfonamide<br>$^1$H-NMR(400MHz, CD$_3$OD) δ (ppm): 8.16(dd, 1H, J=1.6 and 8.0 Hz) 8.12-8.10(m, 2H) 7.94(d, 1H, J=16.8 Hz) 7.85(dd, 1H, J=0.8 and 1.6 Hz) 7.80(dd, 1H, J=0.8 and 8.8 Hz) 7.70-7.59(m, 3H) 7.52(t, 1H, J=9.8 Hz) 7.43(dd, 1H, J=1.6 and 7.6 Hz) 7.39(d, 1H, J=16.8 Hz) MS(ESI, pos. ion) m/z: 462.3(M+1). |
| 370 | (E)-2-{2-[2-(2,3,4-trifluoro-phenyl)-vinyl]-1H-benzimidazol-5-yl}-benzenesulfonamide<br>$^1$H-NMR(400MHz, CD$_3$OD) δ (ppm): 8.14(d, 1H, J=8.0 Hz) 7.79(d, 1H, J=16.8 Hz) 7.68(d, 1H, J=16.0 Hz) 7.64-7.55(m, 4H) 7.43-7.40(m, 2H) 7.31(d, 1H, J=16.8 Hz) 7.23(q, 1H, J=8.1 Hz) MS(ESI, pos. ion) m/z: 430.4(M+1). |
| 371 | (E)-2-{2-[2-(2,4,5-trifluoro-phenyl)-vinyl]-1H-benzimidazol-5-yl}-benzenesulfonamide<br>$^1$H-NMR(400MHz, CD$_3$OD) δ (ppm): 8.14(dd, 1H, J=1.2 and 8.0 Hz) 7.84-7.79(m, 1H) 7.75(d, 1H, J=15.6 Hz) 7.68-7.53(m, 4H) 7.41(dd, 1H, J=1.2 and 7.6 Hz) 7.37(dd, 1H, J=1.6 and 8.4 Hz) 7.33-7.25(m, 2H) MS(ESI, pos. ion) m/z: 430.3(M+1). |
| 372 | (E)-2-{2-[2-(2,6-difluoro-phenyl)-vinyl]-1H-benzimidazol-5-yl}-benzenesulfonamide<br>$^1$H-NMR(400MHz, CD$_3$OD) δ (ppm): 8.14(dd, 1H, J=0.8 and 7.6 Hz) 7.85(d, 1H, J=16.8 Hz) 7.70-7.54(m, 4H) 7.49(d, 1H, J=16.8 Hz) 7.46-7.40(m, 3H) 7.10(t, 2H, J=8.8 Hz) MS(ESI, pos. ion) m/z: 412.3(M+1). |
| 373 | (E)-2-{2-[2-(3,5-bis-trifluoromethyl-phenyl)-vinyl]-1H-benzimidazol-5-yl}-benzenesulfonamide<br>$^1$H-NMR(400MHz, CD$_3$OD) δ (ppm): 8.25(s, 2H) 8.14(dd, 1H, J=1.2 and 7.6 Hz) 7.95(s, 1H) 7.71(d, 1H, J=16.8 Hz) 7.68-7.53(m, 4H) 7.44(d, 1H, J=16.8 Hz) 7.42(dd, 1H, J=1.2 and 7.6 Hz) 7.35(dd, 1H, J=1.6 and 8.0 Hz) MS(ESI, pos. ion) m/z: 512.4(M+1). |
| 374 | (E)-2-{2-[2-(2,5-bis-trifluoromethyl-phenyl)-vinyl]-1H-benzimidazol-5-yl}-benzenesulfonamide<br>$^1$H-NMR(400MHz, CD$_3$OD) δ (ppm): 8.36(s, 1H) 8.24(dd, 1H, J=2.0 and 16.4 Hz) 8.16(dd, 1H, J=1.2 and 8.0 Hz) 8.06(d, 1H, J=8.4 Hz) 7.84(d, 1H, J=8.4 Hz) 7.83(s, 1H) 7.79(d, 1H, J=8.8 Hz) 7.69-7.57(m, 3H) 7.48-7.42(m, 2H) MS (ESI, pos. ion) m/z: 512.4(M+1). |
| 375 | (E)-2-{2-[2-(4-chloro-2-methanesulfonyl-phenyl)-vinyl]-1H-benzimidazol-5-yl}-benzenesulfonamide<br>$^1$H-NMR(400MHz, CD$_3$OD) δ (ppm): 8.51(d, 1H, J=16.0 Hz) 8.16-8.10(m, 2H) 8.03(d, 1H, J=8.4 Hz) 7.82(dd, 1H, J=1.6 and 8.0 Hz) 7.75-7.55(m, 4H) 7.49-7.36(m, 2H) 7.28(d, 1H, J=16.4 Hz) MS(ESI, pos. ion) m/z: 488.1(M+1). |
| 376 | (E)-2-{2-[2-(3-bromo-phenyl)-vinyl]-1H-benzimidazol-5-yl}-benzenesulfonamide<br>$^1$H-NMR(400MHz, CD$_3$OD) δ (ppm): 8.15(d, 1H, J=7.6 Hz) 7.89(s, 1H) 7.74-7.58(m, 7H) 7.48-7.37(m, 3H) 7.27(d, 1H, J=16.4 Hz) MS(ESI, pos. ion) m/z: 454.3(M). |
| 378 | (E)-2-{2-[2-(4-chloro-3-trifluoromethyl-phenyl)-vinyl]-1H-benzimidazol-5-yl}-benzenesulfonamide<br>$^1$H-NMR(400MHz, CD$_3$OD) δ (ppm): 8.14(dd, 1H, J=1.6 and 8.0 Hz) 8.04(d, 1H, J=2.0 Hz) 7.93(dd, 1H, J=2.0 and 8.4 Hz) 7.71-7.54(m, 6H) 7.43-7.38(m, 2H) 7.32(d, 1H, J=16.8 Hz) MS(ESI, pos. ion) m/z: 478.4(M+1). |

-continued

| Cpd | Name and Data |
|---|---|
| 379 | (E)-2-{2-[2-(5-bromo-2-fluoro-phenyl)-vinyl]-1H-benzimidazol-5-yl}-benzenesulfonamide
$^1$H-NMR(400MHz, CD$_3$OD) δ (ppm): 8.15(dd, 1H, J=1.2 and 8.0 Hz) 8.00(dd, 1H, J=2.4 and 6.4 Hz) 7.88(d, 1H, J=16.4 Hz) 7.76-7.57(m, 5H) 7.51(dd, 1H, J=1.6 and 8.8 Hz) 7.42(dd, 1H, J=1.2 and 8.0 Hz) 7.38(d, 1H, J=16.4 Hz) 7.20(dd, 1H, J=8.8 and 10.4 Hz) MS(ESI, pos. ion) m/z: 472.3(M+1). |
| 423 | (E)-2-{2-[2-(3-fluoro-4-trifluoromethyl-phenyl)-vinyl]-1H-benzimidazol-5-yl}-benzenesulfonamide
$^1$H-NMR(400MHz, CD$_3$OD) δ (ppm): 8.14(dd, J=1.2, 8.2 Hz, 1H), 7.74-7.62(m, 7H), 7.43-7.34(m, 3H), 6.64(d, J=16.0 Hz, 1H). Mass Spectrum(LCMS, ESI pos.) Calcd. For C$_{22}$H$_{15}$F$_4$N$_3$O$_2$S: 462.1(M+H), Found 462.2. |
| 424 | (E)-2-{2-[2-(2-fluoro-4-trifluoromethyl-phenyl)-vinyl]-1H-benzimidazol-5-yl}-benzenesulfonamide
$^1$H-NMR(400MHz, CD$_3$OD) δ (ppm): 8.13(dd, J=1.6, 8.0 Hz, 1H), 7.99(t, J=7.2 Hz, 1H), 7.83(d, J=16.8 Hz, 1H), 7.67-7.52(m, 4H), 7.45(s, 1H), 7.43-7.40(m, 3H), 7.34(dd, J=1.6, 7.6 Hz, 1H). Mass Spectrum(LCMS, ESI pos.) Calcd. For C$_{22}$H$_{15}$F$_4$N$_3$O$_2$S: 462.1(M+H), Found 462.2. |
| 425 | (E)-2-{2-[2-(3-ethoxy-phenyl)-vinyl]-1H-benzimidazol-5-yl}-benzene sulfonamide
$^1$H-NMR(400MHz, CD$_3$OD) δ (ppm): 8.13(dd, J=1.6, 8.0 Hz, 1H), 7.99(t, J=7.2 Hz, 1H), 7.57(d, J=16 Hz, 1H), 7.67-7.60(m, 2H), 7.45(s, 1H), 7.43-7.40(m, 2H), 7.25(t, J=4 Hz, 1H), 7.11(d, J=8 Hz, 1H), 7.07-7.08(m, 1H), 6.92-6.89(m, 1H), 6.45(d, J=16 Hz, 1H). Mass Spectrum(LCMS, ESI pos.) Calcd. For C$_{23}$H$_{21}$N$_3$O$_3$S: 420.1(M+H), Found 420.2. |
| 426 | (E)-2-(2-styryl-1H-benzimidazol-5-yl)-benzenesulfonamide
1H-NMR(400MHz, CD$_3$OD) δ (ppm): 8.13(dd, J=1.6, 7.8 Hz, 1H), 7.66-7.58(m, 6H), 7.54(dt, J=1.6, 7.6 Hz, 1H), 7.44-7.40(m, 3H), 7.38-7.34(m, 1H), 7.31(dd, J=1.6, 8 Hz, 1H), 7.18(d, J=16.4 Hz, 1H). Mass Spectrum(LCMS, ESI pos.) Calcd. For C$_{21}$H$_{17}$N$_3$O$_2$S: 376.1(M+H), Found 376.3. |
| 427 | (E)-2-{2-[2-(3,4-dichloro-phenyl)-vinyl]-1H-benzimidazol-5-yl}-benzene sulfonamide
$^1$H-NMR(400MHz, CD$_3$OD) δ (ppm): 8.13(dd, J=1.6, 8 Hz, 1H), 7.82(s, 1H), 7.65-7.61(m, 3H), 7.60-7.54(m, 3H), 7.52(s, 1H), 7.41(dd, J=1.6, 8 Hz, 1H), 7.32(dd, J=1.6, 8 Hz, 1H), 7.22(d, J=16.4 Hz, 1H). Mass Spectrum(LCMS, ESI pos.) Calcd. For C$_{21}$H$_{15}$Cl$_2$N$_3$O$_2$S: 444.0(M+H), Found 444.1. |
| 428 | (E)-2-{2-[2-(4-chloro-2-fluoro-phenyl)-vinyl]-1H-benzimidazol-5-yl}-benzenesulfonamide
$^1$H-NMR(400MHz, CD$_3$OD) δ (ppm): 8.13(dd, J=1.6, 8 Hz, 1H), 7.78(d, J=8 Hz, 1H), 7.75(d, J=8 Hz, 1H), 7.72(s, 1H), 7.55-7.54(m, 1H), 7.62(dd, J=1.6, 8 Hz, 1H), 7.54(dt, J=1.6, 8 Hz, 1H), 7.41(dd, J=1.6, 8 Hz, 1H), 7.34-7.26(m, 4H). Mass Spectrum(LCMS, ESI pos.) Calcd. For C$_{21}$H$_{15}$ClFN$_3$O$_2$S: 428.9(M+H), Found 430.2. |
| 429 | (E)-2-{2-[2-(4-isopropyl-phenyl)-vinyl]-1H-benzimidazol-5-yl}-benzenesulfonamide
$^1$H-NMR(400MHz, CD$_3$OD) δ (ppm): 8.13(dd, J=1.6, 8 Hz, 1H), 7.65-7.60(m, 4H), 7.58-7.52(m, 3H), 7.41(dd, J=1.6, 8 Hz, 1H), 7.32-7.29(m, 3H), 7.13(d, J=16.8 Hz, 1H), 2.94(h, J=2.4 Hz, 1H), 1.27(d, J=8 Hz, 6H). Mass Spectrum (LCMS, ESI pos.) Calcd. For C$_{24}$H$_{23}$N$_3$O$_2$S: 418.1(M+H), Found 418.4. |
| 430 | (E)-2-[2-(2-p-tolyl-vinyl)-1H-benzimidazol-5-yl]-benzenesulfonamide
$^1$H-NMR(400MHz, CD$_3$OD) δ (ppm): 8.13(dd, J=1.6, 8 Hz, 1H), 7.65-7.58(m, 5H), 7.53(d, J=7.6 Hz, 2H), 7.41(dd, J=1.6, 8 Hz, 1H), 7.30(dd, J=1.6, 8 Hz, 1H), 7.23(d, J=8 Hz, 2H), 7.11(d, J=16.8 Hz, 1H), 2.36(s, 3H). Mass Spectrum (LCMS, ESI pos.) Calcd. For C$_{22}$H$_{19}$N$_3$O$_2$S: 390.1(M+H), Found 390.5. |
| 431 | (E)-2-{2-[2-(3-chloro-2-fluoro-phenyl)-vinyl]-1H-benzimidazol-5-yl}-benzenesulfonamide
$^1$H-NMR(400MHz, CD$_3$OD) δ (ppm): 8.13(dd, J=1.6, 8 Hz, 1H), 7.80(d, J=16 Hz, 1H), 7.73(t, J=7.2 Hz, 1H), 7.66-7.60(m, 4H), 7.57-7.52(m, 1H), 7.51-7.46(m, 1H), 7.42(dd, J=1.6, 8 Hz, 1H), 7.33(dd, J=1.6, 8 Hz, 1H), 7.22(d, J=16.8 Hz, 1H). Mass Spectrum(LCMS, ESI pos.) Calcd. For C$_{21}$H$_{15}$ClFN$_3$O$_2$S: 428.9(M+H), Found 428.3. |
| 432 | (E)-2-{2-[2-(3-chloro-4-fluoro-phenyl)-vinyl]-1H-benzimidazol-5-yl}-benzenesulfonamide
$^1$H-NMR(400MHz, CD$_3$OD) δ (ppm): 8.13(dd, J=1.6, 8 Hz, 1H), 7.80(dd, J=2, 7.2 Hz, 1H), 7.65-7.52(m, 6H), 7.41(dd, J=1.6, 8 Hz, 1H), 7.33-7.28(m, 2H), 7.16(d, J=16.8 Hz, 1H). Mass Spectrum(LCMS, ESI pos.) Calcd. For C$_{21}$H$_{15}$ClFN$_3$O$_2$S: 428.9(M+H), Found 428.3. |
| 433 | (E)-2-[2-(2-naphthalen-2-yl-vinyl)-1H-benzimidazol-5-yl]-benzene sulfonamide
$^1$H-NMR(400MHz, CD$_3$OD) δ (ppm): 8.13(dd, J=1.6, 8 Hz, 1H), 8.01(s, 1H), 7.91-7.82(m, 4H), 7.80(d, J=16.8 Hz, 1H), 7.66-7.59(m, 3H), 7.55(dd, J=1.6, 8 Hz, 1H), 7.52-7.48(m, 2H), 7.42(dd, J=2, 7.6 Hz, 1H), 7.32(dd, J=1.6, 8 Hz, 1H), 7.30(d, J=16.8 Hz, 1H). Mass Spectrum(LCMS, ESI pos.) Calcd. For C$_{25}$H$_{19}$N$_3$O$_2$S: 426.5(M+H), Found 426.3. |
| 434 | (E)-2-{2-[2-(4-fluoro-phenyl)-vinyl]-1H-benzimidazol-5-yl}-benzene sulfonamide
$^1$H-NMR(400MHz, CD$_3$OD) δ (ppm): 8.13(dd, J=1.6, 8 Hz, 1H), 7.69-7.66(m, 2H), 7.65-7.52(m, 5H), 7.41(dd, J=1.6, 8 Hz, 1H), 7.31(dd, J=1.6, 8 Hz, 1H), |

-continued

| Cpd | Name and Data |
|---|---|
|  | 7.18-7.10(m, 3H). Mass Spectrum(LCMS, ESI pos.) Calcd. For $C_{21}H_{16}FN_3O_2S$: 394.4(M+H), Found 394.3. |
| 435 | (E)-2-{2-[2-(4-difluoromethyl-phenyl)-vinyl]-1H-benzimidazol-5-yl}-benzene sulfonamide<br>$^1$H-NMR(400MHz, CD$_3$OD) δ (ppm): 8.13(dd, J=1.6, 8 Hz, 1H), 7.70(d, J=8 Hz, 2H), 7.66-7.61(m, 4H), 7.54(dt, J=1.6, 8 Hz, 1H), 7.42(dd, J=1.6, 8 Hz, 1H), 7.32(d, J=8 Hz, 1H), 7.20(d, J=8 Hz, 2H), 7.15(d, J=16 Hz, 1H), 6.89(s, 1H). Mass Spectrum(LCMS, ESI pos.) Calcd. For $C_{22}H_{17}F_2N_3O_2S$: 426.5(M+H), Found 426.3. |
| 436 | (E)-2-{2-[2-(3-fluoro-5-trifluoromethyl-phenyl)-vinyl]-1H-benzimidazol-5-yl}-benzenesulfonamide<br>$^1$H-NMR(400MHz, CD$_3$OD) δ (ppm): 8.13(dd, J=1.6, 8 Hz, 1H), 7.78(s, 1H), 7.73(dd, J=1.6, 8 Hz, 1H), 7.66-7.61(m, 4H), 7.54(dt, J=1.6, 8 Hz, 1H), 7.44(d, J=8 Hz, 1H), 7.41(dd, J=1.6, 8 Hz, 1H), 7.33(d, J=8 Hz, 1H), 7.34(d, J=16 Hz, 1H). Mass Spectrum(LCMS, ESI pos.) Calcd. For $C_{22}H_{15}F_4N_3O_2S$: 461.4(M+H), Found 462.2. |
| 437 | (E)-2-{2-[2-(2,4-dichloro-phenyl)-vinyl]-1H-benzimidazol-5-yl}-benzene sulfonamide<br>$^1$H-NMR(400MHz, CD$_3$OD) δ (ppm): 8.13(dd, J=1.6, 8 Hz, 1H), 7.97(d, J=16.8 Hz, 1H), 7.84(d, J=8 Hz, 1H), 7.66-7.51(m, 5H), 7.41-7.37(m, 2H), 7.32(dd, J=1.6, 8Hz, 1H), 7.20(d, J=16 Hz, 1H). Mass Spectrum(LCMS, ESI pos.) Calcd. For $C_{21}H_{15}Cl_2N_3O_2S$: 445.3(M+H), Found 446.1. |
| 438 | (E)-2-{2-[2-(2-chloro-6-fluoro-phenyl)-vinyl]-1H-benzimidazol-5-yl}-benzene sulfonamide<br>$^1$H-NMR(400MHz, CD$_3$OD) δ (ppm): 8.13(dd, J=1.6, 8 Hz, 1H), 7.89(d, J=16.8 Hz, 1H), 7.66-7.60(m, 3H), 7.54(dt, J=1.6, 8 Hz, 1H), 7.45(d, J=16 Hz, 1H), 7.43(s, 1H), 7.41-7.32(m, 3H), 7.24-7.18(m, 1H). Mass Spectrum(LCMS, ESI pos.) Calcd. For $C_{21}H_{15}ClFN_3O_2S$: 428.9(M+H), Found 428.3. |
| 439 | (E)-2-{2-[2-(3-bromo-4-fluoro-phenyl)-vinyl]-1H-benzimidazol-5-yl}-benzenesulfonamide<br>$^1$H-NMR(400MHz, CD$_3$OD) δ (ppm): 8.13(dd, J=1.6, 8 Hz, 1H), 7.94(dd, J=1.6, 8 Hz, 1H), 7.68-7.62(m, 6H), 7.41(dd, J=1.6, 8 Hz, 1H), 7.32(d, J=1.6, 8 Hz, 1H), 7.28(t, J=8 Hz, 1H), 7.16(d, J=16.8 Hz, 1H). Mass Spectrum(LCMS, ESI pos.) Calcd. For $C_{21}H_{15}BrFN_3O_2S$: 473.3(M+H), Found 473.2. |
| 440 | (E)-2-{2-[2-(3-bromo-4-fluoro-phenyl)-vinyl]-1H-benzimidazol-5-yl}-benzenesulfonamide<br>$^1$H-NMR(400MHz, CD$_3$OD) δ (ppm): 8.13(dd, J=1.6, 8 Hz, 1H), 7.94(dd, J=1.6, 8 Hz, 1H), 7.68-7.62(m, 6H), 7.41(dd, J=1.6, 8 Hz, 1H), 7.32(d, J=1.6, 8 Hz, 1H), 7.28(t, J=8 Hz, 1H), 7.16(d, J=16.8 Hz, 1H). Mass Spectrum(LCMS, ESI pos.) Calcd. For $C_{21}H_{15}BrFN_3O_2S$: 473.3(M+H), Found 473.2. |

PROPHETIC EXAMPLE 17

Using the procedures described in Example 15 or 16 and reagents, starting materials and conditions known to those skilled in the art, the following prophetic compounds representative of the present invention may be prepared:

| Cpd | Name and Data |
|---|---|
| 91 | (E)-2-(2-{2-[4-(2,2,2-trifluoro-1-trifluoromethyl-ethoxy)-phenyl]-vinyl}-1H-benzimidazol-5-yl)-benzenesulfonamide, |
| 97 | (E)-2-(2-{2-[4-(2,2,2-trifluoro-ethoxy)-phenyl]-vinyl}-1H-benzimidazol-5-yl)-benzenesulfonamide, |
| 103 | (E)-2-(2-{2-[4-(2,2,3,3,3-pentafluoro-propoxy)-phenyl]-vinyl}-1H-benzimidazol-5-yl)-benzenesulfonamide, |
| 109 | (E)-2-{2-[2-(3-chloro-phenyl)-vinyl]-1H-benzimidazol-5-yl}-benzenesulfonamide, |
| 115 | (E)-2-{2-[2-(3-trifluoromethyl-phenyl)-vinyl]-1H-benzimidazol-5-yl}-benzenesulfonamide, |
| 121 | (E)-2-{2-[2-(4-methanesulfonylamino-phenyl)-vinyl]-1H-benzimidazol-5-yl}-benzenesulfonamide, and |
| 127 | (E)-2-{2-[2-(4-trifluoromethanesulfonylamino-phenyl)-vinyl]-1H-benzimidazol-5-yl}-benzenesulfonamide. |

EXAMPLE 18

(E)-N-Methyl-2-{2-[2-(4-trifluoromethyl-phenyl)-vinyl]-1H-benzimidazol-5-yl}-benzenesulfonamide (Cpd 310)

Step A. N-methylbenzenesulfonamide-2-boronic acid

To a solution of N-methylbenzenesulfonamide (2.00 g, 0.0117 mmol) in 20 mL THF at 0° C. was added dropwise n-butyl lithium (1.6 M in hexanes, 14.6 mL, 0.0234 mmol). After 30 min., triisopropyl borate (3.1 mL, 0.0164 mmol) was added, and the mixture was stirred at 0° C. for 2 hours. The reaction was quenched by addition of 20 mL of 1M HCl (aq). The mixture was extracted with EtOAc, and the organic fractions were washed with brine, dried over Na$_2$SO$_4$, filtered, and the filtrate was concentrated to provide the title Compound 18a as a yellow oil. $^1$H-NMR (400 MHz, CD$_3$OD) δ (ppm): 7.81 (d, 1H) 7.62-7.56 (m, 2H) 2.52 (s, 3H).

Step B. (3-tert-butoxycarbonylamino-2'-methylsulfamoyl-biphenyl-4-yl)-carbamic acid tert-butyl ester A mixture of the freshly prepared Compound 18a (9.3 g, 0.0434 mol), Compound 16a (11.2 g, 0.289 mol), Pd(dppf) Cl$_2$CH$_2$Cl$_2$ (4.7 g, 6.42 mmol), TBAB (9.3 g, 0.0289 mol), in 120 mL of 1M Na$_2$CO$_3$ (aq) and 600 mL DME was heated at 85° C. for 10 hours. The reaction mixture was cooled, and concentrated. The residue was purified by chromatography (silica gel, hexanes:EtOAc, 2:1) to provide the title Compound 18b as a yellow oil. $^1$H-NMR (400 MHz, CDCl3) δ (ppm): 8.12 (d, 1H) 7.86 (d, 1H) 7.62-7.46 (m, 3H) 7.22 (d, 1H) 7.14 (d, 1H) 2.62 (d, 3H) 1.55 (s, 9H) 1.44 (s, 9H).

Step C. 3',4'-diamino-biphenyl-2-sulfonic acid methylamide

A solution of Compound 18b (21.4 g, 0.0995 mol) in 210 mL of 4M HCl in dioxane was stirred for 4 hours. The reaction mixture was concentrated, made basic with 1M NaOH (aq), and extracted with EtOAc. The organic fraction was dried over $Na_2SO_4$, filtered, and the filtrate was concentrated to provide the title Compound 18c as a brown oil. $^1$H-NMR (400 MHz, $CD_3OD$) δ (ppm): 8.00 (dd, 1H, J=1.6 and 8.0 Hz) 7.59 (dt, 1H, J=1.6 and 8.4 Hz) 7.48 (dt, 1H, J=1.2 and 8.4 Hz) 7.33 (dd, 1H, J=1.2 and 8.0 Hz) 6.79 (d, 1H, J=2.0 Hz) 6.75 (d, 1H, J=8.4 Hz) 6.68 (d, 1H, J=2.0 and 7.6 Hz) 2.93 (s, 3H) MS (ESI, pos. ion) m/z: 277.9 (M+1).

Step D. (E)-N-methyl-2-{2-[2-(4-trifluoromethyl-phenyl)-vinyl]-1H-benzimidazol-5-yl}-benzene-sulfonamide A mixture of Compound 18c (0.100 g, 0.361 mmol) and 4-trifluoromethyl cinnamic acid (0.324 mmol) in 2 mL of $POCl_3$ was heated to 100° C. for 14 hours. Evaporation of the reaction mixture provided a residue, which was then purified by HPLC ($H_2O$:MeCN, 90:10 to 30:70, over 15 min) to provide the title Compound 310 as a white solid. $^1$H-NMR (400 MHz, $CD_3OD$) δ (ppm): 8.07 (dd, 1H, J=1.2 and 8.4 Hz) 7.85 (d, 2H, J=8.4 Hz) 7.73 (d, 2H, J=8 Hz) 7.69-7.63 (m, 3H) 7.58 (dt, 2H, J=1.6 and 7.2 Hz) 7.44 (dd, 1H, J=1.2 and 7.2 Hz) 7.34 (d, J=16.4 Hz) 2.37 (s, 3H) MS (ESI, pos. ion) m/z: 499.2 (M+MeCN+1).

Using the procedures described in Example 18 and reagents, starting materials and conditions known to those skilled in the art, the following compounds representative of the present invention were prepared:

| Cpd | Name and Data |
|---|---|
| 312 | (E)-2-{2-[2-(4-bromo-phenyl)-vinyl]-1H-benzimidazol-5-yl}-N-methyl-benzenesulfonamide<br>$^1$H-NMR(400MHz, $CD_3OD$) δ (ppm): 8.06(dd, 1H, J=1.2 and 8.0 Hz) 7.68-7.60(m, 3H) 7.59-7.55(m, 6H) 7.43(dd, 1H, J=1.2 and 7.2 Hz) 7.30(dd, 1H, J=1.6 and 8.0 Hz) 7.21(d, 1H, J=16.4 Hz) 2.38(s, 3H) MS(ESI, pos. ion) m/z: 509.2(M+MeCN). |
| 314 | (E)-N-methyl-2-[2-(2-p-tolyl-vinyl)-1H-benzimidazol-5-yl]-benzene sulfonamide<br>$^1$H-NMR(400MHz, $CD_3OD$) δ (ppm): 8.04(dd, 1H, J=1.2 and 8.0 Hz) 7.77(d, 1H, J=16.4 Hz) 7.70(d, 1H, J=15.2 Hz) 7.66-7.64(m, 2H) 7.61-7.55(m, 3H) 7.46(dd, 1H, J=1.6 and 8.4 Hz) 7.41(dd, 1H, J=1.2 and 7.6 Hz) 7.26(d, 2H, J=7.6 Hz) 7.15(d, 1H, J=16.8 Hz) 2.42(s, 3H) 2.36(s, 3H) MS(ESI, pos. ion) m/z: 404.2(M+1). |
| 315 | (E)-2-{2-[2-(4-fluoro-phenyl)-vinyl]-1H-benzimidazol-5-yl}-N-methyl-benzenesulfonamide<br>$^1$H-NMR(400MHz, $CD_3OD$) δ (ppm): 8.05(dd, 1H, J=1.2 and 7.6 Hz) 7.82-7.73(m, 4H) 7.70-7.66(m, 2H) 7.61(dd, 1H, J=1.2 and 7.6 Hz) 7.45(dd, 1H, J=1.2 and 8.0 Hz) 7.43(dd, 1H, J=1.2 and 7.2 Hz) 7.22(d, 1H, J=8.4 Hz) 7.21(s, 2H) 7.18(d, 1H, J=7.6 Hz) 2.42(s, 3H) MS(ESI, pos. ion) m/z: 408.3(M+1). |
| 316 | (E)-2-{2-[2-(3,4-dichloro-phenyl)-vinyl]-1H-benzimidazol-5-yl}-N-methyl-benzenesulfonamide<br>$^1$H-NMR(400MHz, $CD_3OD$) δ (ppm): 8.05(dd, 1H, J=1.2 and 7.6 Hz) 7.84(s, 1H) 7.70-7.66(m, 2H) 7.64(d, 1H) 7.60(d, 2H, J=7.6 Hz) 7.59(s, 2H) 7.42(dt, 2H, J=1.6 and 9.2 Hz) 7.25(d, 1H, J=16.4 Hz) 2.42(s, 3H) MS(ESI, pos. ion) m/z: 408.3(M+1). |
| 317 | (E)-2-{2-[2-(3-bromo-4-fluoro-phenyl)-vinyl]-1H-benzimidazol-5-yl}-N-methyl-benzenesulfonamide<br>$^1$H-NMR(400MHz, $CD_3OD$) δ (ppm): 8.05(dd, 1H, J=1.2 and 7.6 Hz) 7.96(dd, 1H, J=2 and 5 Hz) 7.69-7.62(m, 4H) 7.61-7.57(m, 2H) 7.43(dd, 1H, J=1.2 and 7.2 Hz) 7.39(dd, 1H, J=1.6 and 8.0 Hz) 7.29(t, 1H, J=8.4 Hz) 7.18(d, 1H, J=16.4 Hz) 2.40(s, 3H) MS(ESI, pos. ion) m/z: 486.2(M). |
| 318 | (E)-2-{2-[2-(4-dimethylamino-phenyl)-vinyl]-1H-benzimidazol-5-yl}-N-methyl-benzenesulfonamide<br>$^1$H-NMR(400MHz, $CD_3OD$) δ (ppm): 8.05(dd, 1H, J=1.6 and 7.6 Hz) 7.96(d, 1H, J=16.4 Hz) 7.73-7.67(m, 3H) 7.63(dd, 1H, J=1.2 and 8.0 Hz) 7.59(d, 2H, J=9.2 Hz) 7.52(dd, 1H, J=1.6 and 8.4 Hz) 7.44(dd, 1H, J=1.6 and 7.6 Hz) 6.90(d, 1H, J=16 Hz) 6.81(d, 2H, J=8.8 Hz) 3.06(s, 6H) 2.45(s, 3H) MS(ESI, pos. ion) m/z: 433.4(M+1). |
| 319 | (E)-2-{2-[2-(3-fluoro-4-trifluoromethyl-phenyl)-vinyl]-1H-benzimidazol-5-yl}-N-methyl-benzenesulfonamide<br>$^1$H-NMR(400MHz, $CD_3OD$) δ (ppm): 8.05(dd, 1H, J=1.6 and 6.4 Hz) 7.77(q, 1H, J=5.3 Hz) 7.73-7.63(m, 5H) 7.60(dt, 1H, J=1.6 and 8.4 Hz) 7.51(dd, 1H, J=1.6 and 6.4 Hz) 7.43(d, 2H, J=8.4 Hz) 7.39(d, 1H, J=16.8 Hz) 2.41(s, 3H) MS(ESI, pos. ion) m/z: 476.3(M+1). |
| 320 | (E)-2-{2-[2-(2-fluoro-4-trifluoromethyl-phenyl)-vinyl]-1H-benzimidazol-5-yl}-N-methyl-benzenesulfonamide<br>$^1$H-NMR(400MHz, $CD_3OD$) δ (ppm): 8.06(dd, 1H, J=1.2 and 6.4 Hz) 8.01(t, 1H, J=7.8 Hz) 7.90(d, 1H, J=16.4 Hz) 7.70-7.65(m, 3H) 7.61-7.56(m, 3H) 7.45(d, 1H, J=16.8 Hz) 7.28(dd, 1H, J=1.2 and 7.2 Hz) 7.40(d, 1H, J=1.2 and 7.2 Hz) 2.40(s, 3H) MS(ESI, pos. ion) m/z: 476.3(M+1). |

-continued

| Cpd | Name and Data |
|---|---|
| 321 | (E)-2-{2-[2-(3-chloro-4-fluoro-phenyl)-vinyl]-1H-benzimidazol-5-yl}-N-methyl-benzenesulfonamide<br>$^1$H-NMR(400MHz, CD$_3$OD) δ (ppm): 8.05(dd, 1H, J=1.6 and 6.0 Hz) 7.86(t, 1H, J=2.0 and 6.2 Hz) 7.73-7.65(m, 5H) 7.61(dd, 1H, J=1.6 and 7.6 Hz) 7.46(dd, 1H, J=1.6 and 8.8 Hz) 7.43(dd, 1H, J=1.2 and 7.2 Hz) 7.34(t, 1H, J=8.8 Hz) 7.22(d, 1H, J=16.4 Hz) 2.42(s, 3H) MS(ESI, pos. ion) m/z: 442.3(M+1). |
| 322 | (E)-2-{2-[2-(3-fluoro-5-trifluoromethyl-phenyl)-vinyl]-1H-benzimidazol-5-yl}-N-methyl-benzenesulfonamide<br>$^1$H-NMR(400MHz, CD$_3$OD) δ (ppm): 8.05(dd, 1H, J=1.6 and 6.0 Hz) 7.86(t, 1H, J=2.0 and 6.2 Hz) 7.73-7.65(m, 5H) 7.61(dd, 1H, J=1.6 and 7.6 Hz) 7.46(dd, 1H, J=1.6 and 8.8 Hz) 7.43(dd, 1H, J=1.2 and 7.2 Hz) 7.34(t, 1H, J=8.8 Hz) 7.22(d, 1H, J=16.4 Hz) 2.42(s, 3H) MS(ESI, pos. ion) m/z: 442.3(M+1). |
| 323 | (E)-N-methyl-2-{2-[2-(2,3,4-trifluoro-phenyl)-vinyl]-1H-benzimidazol-5-yl}-benzenesulfonamide<br>$^1$H-NMR(400MHz, CD$_3$OD) δ (ppm): 8.06(d, 1H, J=7.6 Hz) 7.75(d, 1H, J=16.8 Hz) 7.68-7.56(m, 5H) 7.43(d, 1H, J=3.2 Hz) 7.34(d, 1H, J=1.2 and 8.0 Hz) 7.33(d, 1H, J=4.0 Hz) 7.22(q, 1H, J=8.8 Hz) 2.38(s, 3H) MS(ESI, pos. ion) m/z: 444.4(M+1). |
| 324 | (E)-N-methyl-2-{2-[2-(2,4,5-trifluoro-phenyl)-vinyl]-1H-benzimidazol-5-yl}-benzenesulfonamide<br>$^1$H-NMR(400MHz, CD$_3$OD) δ (ppm): 8.05(dd, 1H, J=1.2 and 8.0 Hz) 7.87-7.82(m, 2H) 7.72-7.58(m, 5H) 7.46-7.42(m, 2H) 7.31(d, 1H, J=16.4 Hz) 2.41(s, 3H) MS(ESI, pos. ion) m/z: 444.4(M+1). |
| 325 | (E)-2-{2-[2-(2,3-difluoro-phenyl)-vinyl]-1H-benzimidazol-5-yl}-N-methyl-benzenesulfonamide<br>$^1$H-NMR(400MHz, CD$_3$OD) δ (ppm): 8.06(dd, 1H, J=1.2 and 7.6 Hz) 7.95(d, 1H, J=16.8 Hz) 7.74-7.66(m, 3H) 7.63-7.59(m, 2H) 7.47(dd, 1H, J=1.6 and 8.0 Hz) 7.44(dd, 1H, J=1.6 and 8.0 Hz) 7.39(d, 1H, J=16.8 Hz) 7.34-7.70(m, 2H) 2.42(s, 3H) MS(ESI, pos. ion) m/z: 426.4(M+1). |
| 326 | (E)-2-{2-[2-(2,5-difluoro-phenyl)-vinyl]-1H-benzimidazol-5-yl}-N-methyl-benzenesulfonamide<br>$^1$H-NMR(400MHz, CD$_3$OD) δ (ppm): 8.06(dd, 1H, J=1.2 and 7.6 Hz) 7.82(d, 1H, J=16.4 Hz) 7.69-7.64(m, 3H) 7.61-7.55(m, 2H) 7.43(dd, 1H, J=1.6 and 7.6 Hz) 7.37(dd, 1H, J=1.6 and 8.8 Hz) 7.33(d, 1H, J=16.8 Hz) 7.26-7.15(m, 2H) 2.39(s, 3H) MS(ESI, pos. ion) m/z: 426.4(M+1). |
| 327 | (E)-2-{2-[2-(2,6-difluoro-phenyl)-vinyl]-1H-benzimidazol-5-yl}-N-methyl-benzenesulfonamide<br>$^1$H-NMR(400MHz, CD$_3$OD) δ (ppm): 8.06(dd, 1H, J=1.2 and 7.6 Hz) 7.90(d, 1H, J=16.8 Hz) 7.71-7.58(m, 4H) 7.51(d, 1H, J=16.8 Hz) 7.46-7.43(m, 3H) 7.12(t, 2H, J=9.0 Hz) 2.41(s, 3H) MS(ESI, pos. ion) m/z: 426.4(M+1). |
| 328 | (E)-2-{2-[2-(3,5-difluoro-phenyl)-vinyl]-1H-benzimidazol-5-yl}-N-methyl-benzenesulfonamide<br>$^1$H-NMR(400MHz, CD$_3$OD) δ (ppm): 8.05(dd, 1H, J=1.2 and 8.0 Hz) 7.68-7.56(m, 5H) 7.43(dd, 1H, J=1.2 and 7.2 Hz) 7.36(dd, 1H, J=1.6 and 8.8 Hz) 7.31-7.25(m, 3H) 6.99-6.96(m, 1H) 2.39(s, 3H) MS(ESI, pos. ion) m/z: 426.3(M+1). |
| 329 | (E)-2-{2-[2-(3,4-difluoro-phenyl)-vinyl]-1H-benzimidazol-5-yl}-N-methyl-benzenesulfonamide<br>$^1$H-NMR(400MHz, CD$_3$OD) δ (ppm): 8.06(dd, 1H, J=1.2 and 7.6 Hz) 7.66-7.56(m, 6H) 7.48-7.42(m, 2H) 7.36-7.32(m, 2H) 7.17(d, 1H, J=16.8 Hz) 2.38(s, 3H) MS(ESI, pos. ion) m/z: 426.4(M+1). |
| 330 | (E)-2-{2-[2-(4-fluoro-2-trifluoromethyl-phenyl)-vinyl]-1H-benzimidazol-5-yl}-N-methyl-benzenesulfonamide<br>$^1$H-NMR(400MHz, CD$_3$OD) δ (ppm): 8.25(dd, 1H, J=1.6 and 16.4 Hz) 8.16(dd, 1H, J=1.2 and 9.2 Hz) 8.06(dd, 1H, J=1.2 and 7.6 Hz) 8.4(d, 1H, J=1.2 Hz) 8.25(dd, 1H, J=0.8 and 8.0 Hz) 7.73-7.56(m, 5H) 7.46(dd, 1H, J=1.6 and 8.0 Hz) 7.65(d, 1H, J=16.4 Hz) 2.46(s, 3H) MS(ESI, pos. ion) m/z: 476.4(M+1). |
| 331 | (E)-2-{2-[2-(4-fluoro-3-trifluoromethyl-phenyl)-vinyl]-1H-benzimidazol-5-yl}-N-methyl-benzenesulfonamide<br>$^1$H-NMR(400MHz, CD$_3$OD) δ (ppm): 8.06(dd, 1H, J=1.2 and 8.0 Hz) 8.02-7.98(m, 2H) 7.18-7.56(m, 4H) 7.45-7.40(m, 2H) 7.38(dd, 1H, J=1.6 and 8.4 Hz) 7.26(d, 1H, J=16.8 Hz) 2.39(s, 3H) MS(ESI, pos. ion) m/z: 476.4(M+1). |
| 332 | (E)-2-{2-[2-(2-fluoro-3-trifluoromethyl-phenyl)-vinyl]-1H-benzimidazol-5-yl}-N-methyl-benzenesulfonamide<br>$^1$H-NMR(400MHz, CD$_3$OD) δ (ppm): 8.10-8.05(m, 2H) 7.84(d, 1H, J=16.8 Hz) 7.71-7.55(m, 5H) 7.43(dd, 1H, J=1.6 and 7.2 Hz) 7.37(d, 1H, J=16.8 Hz) 7.32(dd, 1H, J=1.2 and 8.4 Hz) 2.37(s, 3H) MS(ESI, pos. ion) m/z: 476.5(M+1). |
| 333 | (E)-2-{2-[2-(3,5-bis-trifluoromethyl-phenyl)-vinyl]-1H-benzimidazol-5-yl}-N-methyl-benzenesulfonamide<br>$^1$H-NMR(400MHz, CD$_3$OD) δ (ppm): 8.24(s, 2H) 7.06(dd, 1H, J=1.2 and 8.0 Hz) 7.94(s, 1H) 7.73-7.55(m, 5H) 7.45-7.40(m, 2H) 7.32(dd, 1H, J=1.6 and 8.4 Hz) 2.38(s, 3H) MS(ESI, pos. ion) m/z: 526.4(M+1). |

-continued

| Cpd | Name and Data |
|---|---|
| 334 | (E)-2-{2-[2-(2,5-bis-trifluoromethyl-phenyl)-vinyl]-1H-benzimidazol-5-yl}-N-methyl-benzenesulfonamide<br>$^1$H-NMR(400MHz, CD$_3$OD) δ (ppm): 8.27(s, 1H) 8.08-7.92(m, 3H) 8.87(d, 1H, J=8.4 Hz) 7.69-7.56(m, 4H) 7.44(dd, 1H, J=1.6 and 8.0 Hz) 7.36-7.32(m, 2H) 2.37(s, 3H) MS(ESI, pos. ion) m/z: 526.4(M+1). |
| 335 | (E)-2-{2-[2-(3-chloro-2-fluoro-phenyl)-vinyl]-1H-benzimidazol-5-yl}-N-methyl-benzenesulfonamide<br>$^1$H-NMR(400MHz, CD$_3$OD) δ (ppm): 8.06(d, 1H, J=8.4 Hz) 7.93(d, 1H, J=8.0 Hz) 7.81(d, 1H, J=16.4 Hz) 7.74-7.56(m, 4H) 7.50-7.23(m, 5H) 2.37(s, 3H) MS(ESI, pos. ion) m/z: 442.4(M+1). |
| 336 | (E)-2-{2-[2-(2-chloro-6-fluoro-phenyl)-vinyl]-1H-benzimidazol-5-yl}-N-methyl-benzenesulfonamide<br>$^1$H-NMR(400MHz, CD$_3$OD) δ (ppm): 8.06(dd, 1H, J=1.2 and 8.0 Hz) 7.89(d, 1H, J=16.8 Hz) 7.68-7.55(m, 4H) 7.45(d, 1H, J=16.8 Hz) 7.43(dd, 1H, J=1.2 and 7.6 Hz) 7.38-7.31(m, 3H) 7.23-7.18(m, 1H) 2.37(s, 3H) MS(ESI, pos. ion) m/z: 442.4(M+1). |
| 337 | (E)-2-{2-[2-(2,4-dichloro-phenyl)-vinyl]-1H-benzimidazol-5-yl}-N-methyl-benzenesulfonamide<br>$^1$H-NMR(400MHz, CD$_3$OD) δ (ppm): 8.05(dd, 1H, J=1.2 and 8.0 Hz) 8.51(d, 1H, J=16.8 Hz) 7.88(d, 1H, J=8.0 Hz) 7.68-7.56(m, 5H) 7.45-7.41(m, 2H) 7.32(dd, 1H, J=1.6 and 8.4 Hz) 7.24(d, 1H, J=16.4 Hz) 2.37(s, 3H) MS(ESI, pos. ion) m/z: 458.3(M+1). |
| 338 | (E)-2-{2-[2-(3-bromo-phenyl)-vinyl]-1H-benzimidazol-5-yl}-N-methyl-benzenesulfonamide<br>$^1$H-NMR(400MHz, CD$_3$OD) δ (ppm): 8.06(dd, 1H, J=1.2 and 7.6 Hz) 7.82(t, 1H, J=1.8 Hz) 7.68-7.49(m, 7H) 7.43(dd, 1H, J=1.2 and 7.2 Hz) 7.35(d, 1H, J=7.6 Hz) 7.30(dd, 1H, J=0.8 and 8.0 Hz) 7.21(d, 1H, J=16.4 Hz) 2.37(s, 3H) MS(ESI, pos. ion) m/z: 468.3(M+1). |
| 339 | (E)-2-{2-[2-(4-chloro-2-fluoro-phenyl)-vinyl]-1H-benzimidazol-5-yl}-N-methyl-benzenesulfonamide<br>$^1$H-NMR(400MHz, CD$_3$OD) δ (ppm): 8.40(d, 1H, J=16.4 Hz) 8.08-8.06(m, 2H) 8.01(d, 1H, J=8.4 Hz) 7.89(dd, 1H, J=2.4 and 8.4 Hz) 7.80-7.56(m, 4H) 7.44(dd, 1H, J=1.2 and 7.2 Hz) 7.33(dd, 1H, J=1.6 and 7.2 Hz) 7.26(d, 1H, J=16.4 Hz) 2.37(s, 3H) MS(ESI, pos. ion) m/z: 442.3(M+1). |
| 340 | (E)-2-{2-[2-(4-chloro-2-methanesulfonyl-phenyl)-vinyl]-1H-benzimidazol-5-yl}-N-methyl-benzenesulfonamide<br>$^1$H-NMR(400MHz, CD$_3$OD) δ (ppm): 8.06(dd, 1H, J=1.2 and 7.6 Hz) 7.76-7.72(m, 2H) 7.66-7.54(m, 4H) 7.42(dd, 1H, J=0.8 and 7.2 Hz) 7.32-7.26(m, 4H) 2.37(s, 3H) MS(ESI, pos. ion) m/z: 502.3(M+1). |
| 341 | (E)-N-methyl-2-{2-[2-(4-trifluoromethylthio-phenyl)-vinyl]-1H-benzimidazol-5-yl}-benzenesulfonamide<br>$^1$H-NMR(400MHz, CD$_3$OD) δ (ppm): 8.12(d, 2H, J=8.8 Hz) 8.06(dd, 1H, J=1.2 and 8.4 Hz) 8.06(d, 2H, J=8.8 Hz) 7.75-7.56(m, 5H) 7.47(d, 1H, J=16.4 Hz) 7.44(dd, 1H, J=1.2 and 7.2 Hz) 7.34(dd, 1H, J=1.2 and 8.4 Hz) 2.38(s, 3H) MS(ESI, pos. ion) m/z: 522.3(M+1). |
| 342 | (E)-N-methyl-2-{2-[2-(4-trifluoromethanesulfonyl-phenyl)-vinyl]-1H-benzimidazol-5-yl}-benzenesulfonamide<br>$^1$H-NMR(400MHz, CD$_3$OD) δ (ppm): 8.06(dd, 1H, J=1.2 and 8.4 Hz) 7.75(q, 4H, J=10.6 Hz) 7.44-7.55(m, 5H) 7.43(dd, 1H, J=1.2 and 7.6 Hz) 7.33-7.28(m, 2H) 2.37(s, 3H) MS(ESI, pos. ion) m/z: 490.3(M+1). |
| 343 | (E)-N-methyl-2-{2-[2-(2-trifluoromethyl-phenyl)-vinyl]-1H-benzimidazol-5-yl}-benzenesulfonamide<br>$^1$H-NMR(400MHz, CD$_3$OD) δ (ppm): 8.07(dd, 1H, J=1.2 and 8.0 Hz) 8.02(dd, 1H, J=12.0 and 16.0 Hz) 7.98(d, 1H, J=8.0 Hz) 7.77(d, 1H, J=8.4 Hz) 7.72-7.62(m, 4H) 7.57(dt, 1H, J=1.6 and 8.4 Hz) 7.54(t, 1H, J=7.6 Hz) 7.44(dd, 1H, J=1.2 and 7.2 Hz) 7.32(dd, 1H, J=1.6 and 8.4 Hz) 7.21(d, 1H, J=16.4 Hz) 2.37(s, 3H) MS(ESI, pos. ion) m/z: 458.4(M+1). |
| 344 | (E)-N-methyl-2-{2-[2-(3-trifluoromethoxy-phenyl)-vinyl]-1H-benzimidazol-5-yl}-benzenesulfonamide<br>$^1$H-NMR(400MHz, CD$_3$OD) δ (ppm): 8.06(dd, 1H, J=1.2 and 8.0 Hz) 7.66-7.62(m, 4H) 7.60-7.54(m, 3H) 7.51(d, 1H, J=8.0 Hz) 7.43(dd, 1H, J=1.2 and 7.2 Hz) 7.31(dd, 1H, J=1.2 and 8.0 Hz) 7.28(d, 1H, J=8.4 Hz) 7.25(d, 1H, J=16.8 Hz) 2.37(s, 3H) MS(ESI, pos. ion) m/z: 474.4(M+1). |
| 345 | (E)-N-methyl-2-{2-[2-(4-trifluoromethoxy-phenyl)-vinyl]-1H-benzimidazol-5-yl}-benzenesulfonamide<br>$^1$H-NMR(400MHz, CD$_3$OD) δ (ppm): 8.06(dd, 1H, J=1.2 and 7.6 Hz) 7.75(d, 2H, J=8.4 Hz) 7.69-7.64(m, 3H) 7.61(d, 1H, J=8.0 Hz) 7.57(dt, 1H, J=1.2 and 8.4 Hz) 7.42(dd, 1H, J=1.6 and 8.4 Hz) 7.33(d, 3H, J=10.0 Hz) 7.20(d, 1H, J=16.4 Hz) 2.38(s, 3H) MS(ESI, pos. ion) m/z: 474.4(M+1). |
| 346 | (E)-2-{2-[2-(2-chloro-phenyl)-vinyl]-1H-benzimidazol-5-yl}-N-methyl-benzenesulfonamide<br>$^1$H-NMR(400MHz, CD$_3$OD) δ (ppm): 8.03-8.05(m, 2H) 7.87(dd, 2H, J=1.68 and 7.6 Hz) 7.66-7.55(m, 4H) 7.45(dd, 1H, J=1.6 and 7.6 Hz) 7.43(dd, 1H, J=1.2 and 7.2 Hz) 7.38-7.30(m, 3H) 7.22(d, 1H, J=16.4 Hz) 2.37(s, 3H) MS(ESI, pos. ion) m/z: 425.3(M+1). |
| 347 | (E)-2-{2-[2-(4-chloro-phenyl)-vinyl]-1H-benzimidazol-5-yl}-N-methyl-benzenesulfonamide<br>$^1$H-NMR(400MHz, CD$_3$OD) δ (ppm): 8.06(dd, 1H, J=1.2 and 8.0 Hz) |

-continued

| Cpd | Name and Data |
|---|---|
| | 7.36-7.63(m, 4H) 7.62-7.55(m, 3H) 7.44(d, 3H, J=8.0 Hz) 7.31(dd, 1H, J=1.6 and 8.0 Hz) 7.19(d, 1H, J=16.4 Hz) 2.36(s, 3H) MS(ESI, pos. ion) m/z: 425.3(M+1). |
| 348 | (E)-2-{2-[2-(2-bromo-phenyl)-vinyl]-1H-benzimidazol-5-yl}-N-methyl-benzenesulfonamide<br>$^1$H-NMR(400MHz, CD$_3$OD) δ (ppm): 8.07(dd, 1H, J=1.2 and 8.0 Hz) 8.02(d, 1H, J=16.4 Hz) 7.84(dd, 1H, J=1.6 and 8.4 Hz) 7.68-7.55(m, 5H) 7.44-7.40(m, 2H) 7.31(dd, 1H, J=1.2 and 6.8 Hz) 7.02(dt, 1H, J=1.6 and 8.4 Hz) 7.17(d, 1H, J=16.4 Hz) 2.37(s, 3H) MS(ESI, pos. ion) m/z: 469.5(M+1). |
| 349 | (E)-2-{2-[2-(2,4-difluoro-phenyl)-vinyl]-1H-benzimidazol-5-yl}-N-methyl-benzenesulfonamide<br>$^1$H-NMR(400MHz, CD$_3$OD) δ (ppm): 8.06(dd, 1H, J=1.2 and 8.0 Hz) 7.80(q, 1H, J=8.0 Hz) 7.74(d, 1H, J=16.8 Hz) 7.67-7.54(m, 5H) 7.42(dd, 1H, J=1.2 and 7.6 Hz) 7.30(dd, 1H, J=1.6 and 8.4 Hz) 7.23(d, 1H, J=16.8 Hz) 7.05(t, 1H, J=8.8 Hz) 2.37(s, 3H) MS(ESI, pos. ion) m/z: 426.4(M+1). |
| 351 | (E)-2-{2-[2-(4-methanesulfonyl-phenyl)-vinyl]-1H-benzimidazol-5-yl}-N-methyl-benzenesulfonamide<br>$^1$H-NMR(400MHz, CD$_3$OD) δ (ppm): 8.07(dd, 1H, J=1.2 and 8.0 Hz) 8.01(d, 2H, J=8.4 Hz) 7.90(d, 2H, J=8.8 Hz) 7.72(d, 1H, J=16.4 Hz) 7.67-7.56(m, 4H) 7.44(dd, 1H, J=1.6 and 7.2 Hz) 7.38(d, 1H, J=16.4 Hz) 7.33(dd, 1H, J=1.6 and 8.4 Hz) 3.15(s, 3H) 2.37(s, 3H) MS(ESI, pos. ion) m/z: 468.4(M+1). |

EXAMPLE 19

(E)-N-(2-{2-[2-(4-ethoxy-phenyl)-vinyl]-1 H-benzimidazol-5-yl}-phenyl)-methanesulfonamide (Cpd 414)

Step A. (3-tert-butoxycarbonylamino-2'-methanesulfonylamino-biphenyl-4-yl)-carbamic acid tert-butyl ester To a solution of Compound 16a (2.0 g, 5.1 mmol), 2-methylsulfonylphenyl boronic acid (1.1 g, 5.1 mmol), and K$_2$CO$_3$ (2.1 g, 15.3 mmol) in 1,4-dioxane:water (4:1,120 mL), was added Pd(dppf)Cl$_2$CH$_2$Cl$_2$ (0.42 g, 0.51 mmol) under an argon atmosphere. The mixture was heated at 95° C. for 12 h. The reaction mixture was cooled to room temperature and concentrated under reduced pressure. The residue was purified by chromatography (silica, EtOAc:hexanes, 3:7) to provide the title Compound 19a as a yellow solid (1.7 g, 70% yield). $^1$H NMR (400 MHz, CDCl$_3$) δ (ppm): 7.64 (d, J=8.4 Hz, 1H), 7.57 (d, J=14.4 Hz, 1H), 7.34 (t, J=8.4 Hz, 1H), 7.26-7.15 (m, 3H), 7.07 (s, 1H), 7.04 (d, J=8 Hz, 1H), 6.87 (s, 1H), 6.63 (s, 1H), 2.90 (s, 3H), 1.51 (s, 9H), 1.49 (s, 9H). Mass Spectrum (LCMS, ESI pos.) Calcd. For C$_{23}$H$_{31}$N$_3$O$_6$S: 478.19 (M+H), Found 478.0.

Step B. N-(3',4'-diamino-biphenyl-2-yl)-methanesulfonamide

A solution of Compound 19a (1.0 g, 2.1 mmol) in a mixture of 4M HCl in 1,4-dioxane (10 mL) was heated at 70° C. for 2 h. After concentration of the reaction, the residue was dissolved in dichloromethane (20 mL), and to the solution was added K$_2$CO$_3$ (0.5 g) and the mixture was stirred at room temperature for 20 min. After filtration and removal of solvents, the residue was dried to provide the title Compound 19b as a brown solid (0.58 g, quantitative yield). $^1$H NMR (400MHz, CD$_3$OD) δ (ppm): 7.47 (d, J=8.4 Hz, 1H), 7.40-7.35 (m, 1H), 7.32-7.29 (m, 2H), 7.16-7.09 (m, 3H), 2.80 (s, 3H). Mass Spectrum (LCMS, ESI pos.) Calcd. For C$_{13}$H$_{15}$N$_3$O$_2$S: 278.09 (M+H), Found 278.1.

Step C. (E)-N-(2-{2-[2-(4-ethoxy-phenyl)-vinyl]-1H-benzimidazol-5-yl}-phenyl)-methanesulfonamide A solution of Compound 19b (50 mg, 0.18 mmol) and commercially available 3-(4-ethoxy-phenyl)-acrylic acid (34.6 mg, 0.18 mmol) in POCl$_3$ (1.5 mL) was heated to 100° C. for 12 h. The reaction was cooled, the excess POCl$_3$ was removed under reduced pressure, and the residue was purified by HPLC (Gilson, C-18 column, CH$_3$CN:H$_2$O (gradient of CH$_3$CN:5%-80%)) to provide the title Compound 414 as an off-white solid (25 mg, 32% yield). $^1$H NMR (400 MHz, CD$_3$OD) δ (ppm):7.62-7.59.(m, 4H), 7.54-7.52.(m, 1H), 7.41-7.37 (m, 2H), 7.35-7.30 (m, 2H), 7.03 (d, J=16.8 Hz, 2H), 6.97 (d, J=12 Hz, 2H), 4.09 (q, J=7.2 Hz, 2H), 2.72 (s, 3H), 1.41 (t, J=7.2 Hz, 3H). Mass Spectrum (LCMS, ESI pos.) Calcd. For C$_{24}$H$_{23}$N$_3$O$_3$S: 434.1 (M+H), Found 434.1.

Using the procedures described in Example 19 and reagents, starting materials and conditions known to those skilled in the art, the following compounds representative of the present invention were prepared:

| Cpd | Name and Data |
|---|---|
| 77 | (E)-N-(2-{2-[2-(4-chloro-phenyl)-vinyl]-1H-benzimidazol-5-yl}-phenyl)-methanesulfonamide<br>$^1$H-NMR(400MHz, CD$_3$OD) δ (ppm) 7.40-7.56(m, 6H) 7.24-7.33(m, 4H) 7.19-7.22(m, 2H) 7.05(d, J=16.4Hz, 1H) 2.61(s, 3H). MS(ESI, pos. ion) m/z: 424.1(M+1)., |
| 83 | (E)-N-(2-{2-[2-(4-methanesulfonyl-phenyl)-vinyl]-1H-benzimidazol-5-yl}-phenyl)-methanesulfonamide<br>$^1$H-NMR(400MHz, CD$_3$OD) δ (ppm): 7.99-7.96(m, 2H), 7.89-7.86(m, 4H), 7.78(dd, J=6.4, 15.8 Hz, 2H), 7.60(dd, J=1.2, 8.2 Hz, 1H), 7.46-7.39(m, 2H), 7.33(dt, J=1.6, 8.2 Hz, 2H), 6.99(dd, J=6.4, 15.8 Hz, 2H), 3.10(s, 3H), 3.09(s, 3H). |

| Cpd | Name and Data |
|---|---|
| | Mass Spectrum(LCMS, ESI pos.) Calcd. For $C_{23}H_{21}N_3O_4S_2$: 468.1(M+H), Found 468.0., |
| 95 | (E)-N-[2-(2-{2-[4-(2,2,2-trifluoro-ethoxy)-phenyl]-vinyl}-1H-benzimidazol-5-yl)-phenyl]-methanesulfonamide<br>$^1$H NMR(400MHz, CD$_3$OD) δ (ppm): 7.67-7.62(m, 5H), 7.54-7.52,(m,1H), 7.42-7.33(m, 4H), 7.09(d, J=16.4 Hz, 2H), 7.08(d, J=12 Hz, 1H), 4.60(q, J=8.4 Hz, 2H), 2.74(s, 3H). Mass Spectrum(LCMS, ESI pos.) Calcd. For $C_{24}H_{20}F_3N_3O_3S$: 488.1(M+H), Found 488.3, |
| 101 | (E)-N-[2-(2-{2-[4-(2,2,3,3,3-pentafluoro-propoxy)-phenyl]-vinyl}-1H-benzimidazol-5-yl)-phenyl]-methanesulfonamide<br>$^1$H-NMR(400MHz, CD$_3$OD) δ (ppm): 7.65-7.60(m, 5H), 7.54-7.52(m, 1H), 7.41-7.37(m, 2H), 7.34-7.30(m, 2H), 7.10-7.06(m, 3H), 4.68(t, J=12.8 Hz, 2H), 2.74(s, 3H). Mass Spectrum(LCMS, ESI pos.) Calcd. For $C_{25}H_{20}F_5N_3O_3S$: 538.1(M+H), Found 538.2., |
| 113 | (E)-N-(2-{2-[2-(3-trifluoromethyl-phenyl)-vinyl]-1H-benzimidazol-5-yl}-phenyl)-methanesulfonamide<br>$^1$H-NMR(400MHz, CD3OD) δ (ppm) 7.90-7.96(m, 2H) 7.54-7.76(m, 6H) 7.26-7.42(m, 5H) 2.76(s, 3H). MS(ESI, pos. ion) m/z: 458.1(M+1)., |
| 406 | (E)-N-(2-{2-[2-(4-bromo-phenyl)-vinyl]-1H-benzimidazol-5-yl}-phenyl)-methanesulfonamide<br>$^1$H-NMR(400MHz, CD$_3$OD) δ (ppm): 7.87-7.80(m, 2H), 7.58-7.30(m, 9H), 2.85(s, 3H). Mass Spectrum(LCMS, ESI pos.) Calcd. For $C_{22}H_{18}BrN_3O_2S$: 468.0(M+H), Found 469.1., |
| 407 | (E)-N-(2-{2-[2-(4-isopropyl-phenyl)-vinyl]-1H-benzimidazol-5-yl}-phenyl)-methanesulfonamide<br>$^1$H-NMR(400MHz, CD$_3$OD) δ (ppm): 7.67-7.52)(m, 6H), 7.14(d, J=16.4 Hz, 1H), 3.13-3.12(m, 1H), 2.72(s, 3H), 1.27(d, J=6.8 Hz, 6H). Mass Spectrum (LCMS, ESI pos.) Calcd. For $C_{25}H_{25}N_3O_2S$: 432.2(M+H), Found 432.2., |
| 408 | (E)-N-(2-{2-[2-(4-isopropyl-phenyl)-vinyl]-1H-benzimidazol-5-yl}-phenyl)-methanesulfonamide<br>$^1$H-NMR(400MHz, CD$_3$OD) δ (ppm): 7.82(dd, J=2.4, 7.2Hz, 1H) 7.66-7.60(m, 4H), 7.56-7.52(m, 2H), 7.41-7.39(m, 6H), 7.18(d, J=16.4 Hz, 1H), 2.73(s, 3H). Mass Spectrum(LCMS, ESI pos.) Calcd. For $C_{22}H_{17}ClFN_3O_2S$: 442.1(M+H), Found 442.3., |
| 409 | (E)-N-(2-{2-[2-(3-bromo-4-fluoro-phenyl)-vinyl]-1H-benzimidazol-5-yl}-phenyl)-methanesulfonamide<br>$^1$H-NMR(400MHz, CD$_3$OD) δ (ppm): 7.95(dd, J=2.4, 6.8 Hz, 1H), 7.69-7.68(m, 1H), 7.67-7.63(m, 2H), 7.58(d, J=16.4 Hz, 1H), 7.53-7.51(m, 1H), 7.40-7.26(m, 5H), 7.18(d, J=16.4 Hz, 1H), 2.72(s, 3H). Mass Spectrum(LCMS, ESI pos.) Calcd. For $C_{22}H_{17}BrFN_3O_2S$: 486.0(M+H), Found 486.3., |
| 410 | (E)-N-(2-{2-[2-(4-difluoromethoxy-phenyl)-vinyl]-1H-benzimidazol-5-yl}-phenyl)-methanesulfonamide<br>$^1$H-NMR(400MHz, CD$_3$OD) δ (ppm): 7.73(d, J=12.8 Hz, 2H), 7.54-7.52(m, 1H), 7.48-7.45(m, 1H), 7.41-7.39(m, 2H), 7.34-7.30(m, 2H), 7.21(d, J=8.8 Hz, 2H), 7.16(d, J=17.2 Hz, 1H), 6.90(s, 1H), 2.73(s, 3H). Mass Spectrum (LCMS, ESI pos.) Calcd. For $C_{23}H_{19}F_2N_3O_3S$: 456.1(M+H), Found 456.1., |
| 411 | (E)-N-(2-{2-[2-(3-fluoro-5-trifluoromethyl-phenyl)-vinyl]-1H-benzimidazol-5-yl}-phenyl)-methanesulfonamide<br>$^1$H-NMR(400MHz, CD$_3$OD) δ (ppm): 7.77(s, 1H), 7.75(d, J=12 Hz, 1H), 7.68(s, 1H), 7.67-7.64(m, 2H), 7.52(d, J=12 Hz, 1H), 7.46(d, J=12 Hz, 1H), 7.40-7.25(m, 5H), 2.74(s, 3H). Mass Spectrum(LCMS, ESI pos.) Calcd. For $C_{23}H_{17}F_4N_3O_2S$: 476.1(M+H), Found 476.2, |
| 412 | (E)-N-{2-[2-(2-p-tolyl-vinyl)-1H-benzimidazol-5-yl]-phenyl}-methanesulfonamide<br>$^1$H-NMR(400MHz, CD$_3$OD) δ (ppm): 7.65-7.60(m, 3H), 7.41-7.36(m, 3H), 7.41-7.36(m, 2H), 7.33-7.30(m, 2H), 7.26(d, J=10 Hz, 2H), 7.18(d, J=20 Hz, 1H), 2.74(s, 3H), 2.39(s, 3H). Mass Spectrum(LCMS, ESI pos.) Calcd. For $C_{23}H_{21}N_3O_2S$: 404.1(M+H), Found 404.3, |
| 413 | (E)-N-(2-{2-[2-(4-dimethylamino-phenyl)-vinyl]-1H-benzimidazol-5-yl}-phenyl)-methanesulfonamide<br>$^1$H-NMR(400MHz, CD$_3$OD) δ (ppm): 7.69-7.61(m, 2H) 7.57-7.51(m, 2H), 7.46-7.39(m, 3H), 7.29(d, J=16.2 Hz, 2H), 7.05(d, J=12 Hz, 1H), 6.67(d, J=16.2 Hz, 2H), 6.33(d, J=12 Hz, 1H), 3.01(s, 3H), 2.97(s, 6H). Mass Spectrum(LCMS, ESI pos.) Calcd. For $C_{24}H_{24}N_4O_2S$: 433.2(M+H), Found 433.3, |
| 415 | (E)-N-{2-[2-(2-naphthalen-2-yl-vinyl)-1H-benzimidazol-5-yl]-phenyl}-methanesulfonamide<br>$^1$H-NMR(400MHz, CD$_3$OD) δ (ppm): 8.09(s, 1H), 7.96-7.88, (m, 4H), 7.74-7.72(m, 2H), 7.57-7.52(m, 3H), 7.51-7.33(m, 6H), 2.80(s, 3H). Mass Spectrum (LCMS, ESI pos.) Calcd. For $C_{26}H_{21}N_3O_2S$: 440.1(M+H), Found 440.3, |
| 416 | (E)-N-(2-{2-[2-(3,4-dichloro-phenyl)-vinyl]-1H-benzimidazol-5-yl}-phenyl)-methanesulfonamide<br>$^1$H-NMR(400MHz, CD$_3$OD) δ (ppm): 8.03-8.00(m, 1H), 7.93(s, 1H), 7.77(s, 1H), 7.74(d, J=11.2 Hz, 1H), 7.69(s, 1H), 7.57-7.52(m, 2H), 7.47(d, J=8 Hz, 1H), 7.44(d, J=7.6 Hz, 2H), 7.40-7.36(m, 1H), 7.32(d, J=17.2 Hz, 1H), 2.84(s, 3H). Mass Spectrum(LCMS, ESI pos.) Calcd. For $C_{22}H_{17}Cl_2N_3O_2S$: 458.0(M+H), Found 458.2., |

| Cpd | Name and Data |
|---|---|
| 417 | (E)-N-(2-{2-[2-(3-fluoro-4-trifluoromethyl-phenyl)-vinyl]-1H-benzimidazol-5-yl}-phenyl)-methanesulfonamide<br>$^1$H-NMR(400MHz, CD$_3$OD) δ (ppm): 8.03-8.00(m, 1H), 7.76(t, J=8.0 Hz, 1H), 7.71-7.67(m, 3H), 7.63(d, J=8.4 Hz, 1H), 7.54-7.52(m, 1H), 7.78-7.44(m, 1H), 7.43-7.38(m, 3H), 7.38-7.32(m, 1H), 2.77(s, 3H). Mass Spectrum(LCMS, ESI pos.) Calcd. For C$_{23}$H$_{17}$F$_4$N$_3$O$_2$S: 476.1(M+H), Found 476.2., |
| 418 | (E)-N-(2-{2-[2-(2-fluoro-4-trifluoromethyl-phenyl)-vinyl]-1H-benzimidazol-5-yl}-phenyl)-methanesulfonamide<br>$^1$H-NMR(400MHz, CD$_3$OD) δ (ppm): 8.00(t, J=8.4 Hz, 1H), 7.84(d, J=17.2 Hz, 1H), 7.62-7.58(m, 2H), 7.55-7.52(m, 2H), 7.46(s, 1H), 7.44-7.38(m, 3H), 7.38-7.32(m, 2H), 2.74(s, 3H). Mass Spectrum(LCMS, ESI pos.) Calcd. For C$_{23}$H$_{17}$F$_4$N$_3$O$_2$S: 476.1(M+H), Found 476.2, |
| 475 | (E)-N-{2-[2-(2-biphenyl-4-yl-vinyl)-1H-benzimidazol-5-yl]-phenyl}-methanesulfonamide<br>$^1$H-NMR(400MHz, CDCl$_3$) δ (ppm) 7.44-7.65(m, 10H) 7.22-7.40(m, 5H) 7.10-7.20(m, 3H) 2.76(s, 3H). MS(ESI, pos. ion) m/z: 466.2(M+1)., |

PROPHETIC EXAMPLE 20

Using the procedures described in Example 19, or using the procedures in Example 1 and the corresponding bromobenzimidazole and boronic acid or boronate ester, and reagents, starting materials and conditions known to those skilled in the art, the following prophetic compounds representative of the present invention may be prepared:

| Cpd | Name and Data |
|---|---|
| 89 | (E)-N-[2-(2-{2-[4-(2,2,2-trifluoro-1-trifluoromethyl-ethoxy)-phenyl]-vinyl}-1H-benzimidazol-5-yl)-phenyl]-methanesulfonamide, |
| 107 | (E)-N-(2-{2-[2-(3-chloro-phenyl)-vinyl]-1H-benzimidazol-5-yl}-phenyl)-methanesulfonamide, |
| 119 | (E)-N-(2-{2-[2-(4-methanesulfonylamino-phenyl)-vinyl]-1H-benzimidazol-5-yl}-phenyl)-methanesulfonamide, |
| 125 | (E)-C,C,C-trifluoro-N-(4-{2-[5-(2-methanesulfonylamino-phenyl)-1H-benzimidazol-2-yl]-vinyl}-phenyl)-methanesulfonamide, |

PROPHETIC EXAMPLE 21

Using the procedures described in Example 1 or Example 19 and reagents, starting materials and conditions known to those skilled in the art, the following prophetic compounds representative of the present invention may be prepared:

| Cpd | Name and Data |
|---|---|
| 72 | (E)-C,C,C-trifluoro-N-(2-{2-[2-(4-trifluoromethoxy-phenyl)-vinyl]-1H-benzimidazol-5-yl}-phenyl)-methanesulfonamide, |
| 73 | (E)-C,C,C-trifluoro-N-(2-{2-[2-(4-trifluoromethyl-phenyl)-vinyl]-1H-benzimidazol-5-yl}-phenyl)-methanesulfonamide, |
| 74 | (E)-C,C,C-trifluoro-N-(2-{2-[2-(4-trifluoromethanesulfonyl-phenyl)-vinyl]-1H-benzimidazol-5-yl}-phenyl)-methanesulfonamide, |
| 75 | (E)-1-(2-{2-[2-(4-chloro-phenyl)-vinyl]-1H-benzimidazol-5-yl}-phenyl)-ethanone, |
| 76 | (E)-1-(2-{2-[2-(4-chloro-phenyl)-vinyl]-1H-benzimidazol-5-yl}-phenyl)-ethanol, |
| 80 | (E)-N-(2-{2-[2-(4-chloro-phenyl)-vinyl]-1H-benzimidazol-5-yl}-phenyl)-C,C,C-trifluoro-methanesulfonamide. |
| 81 | (E)-1-(2-{2-[2-(4-methanesulfonyl-phenyl)-vinyl]-1H-benzimidazol-5-yl}-phenyl)-ethanone, |
| 82 | (E)-1-(2-{2-[2-(4-methanesulfonyl-phenyl)-vinyl]-1H-benzimidazol-5-yl}-phenyl)-ethanol, |
| 87 | (E)-1-[2-(2-{2-[4-(2,2,2-trifluoro-1-trifluoromethyl-ethoxy)-phenyl]-vinyl}-1H-benzimidazol-5-yl)-phenyl]-ethanone, |
| 88 | (E)-1-[2-(2-{2-[4-(2,2,2-trifluoro-1-trifluoromethyl-ethoxy)-phenyl]-vinyl}-1H-benzimidazol-5-yl)-phenyl]-ethanol, |
| 90 | (E)-2-[2-(2-{2-[4-(2,2,2-trifluoro-1-trifluoromethyl-ethoxy)-phenyl]-vinyl}-1H-benzimidazol-5-yl)-phenyl]-propan-2-ol, |
| 92 | (E)-C,C,C-trifluoro-N-[2-(2-{2-[4-(2,2,2-trifluoro-1-trifluoromethyl-ethoxy)-phenyl]-vinyl}-1H-benzimidazol-5-yl)-phenyl]-methanesulfonamide, |
| 93 | (E)-1-[2-(2-{2-[4-(2,2,2-trifluoro-ethoxy)-phenyl]-vinyl}-1H-benzimidazol-5-yl)-phenyl]-ethanone, |
| 94 | (E)-1-[2-(2-{2-[4-(2,2,2-trifluoro-ethoxy)-phenyl]-vinyl}-1H-benzimidazol-5-yl)-phenyl]-ethanol, |
| 96 | (E)-2-[2-(2-{2-[4-(2,2,2-trifluoro-ethoxy)-phenyl]-vinyl}-1H-benzimidazol-5-yl)-phenyl]-propan-2-ol, |
| 98 | (E)-C,C,C-trifluoro-N-[2-(2-{2-[4-(2,2,2-trifluoro-ethoxy)-phenyl]-vinyl}-1H-benzimidazol-5-yl)-phenyl]-methanesulfonamide, |

-continued

| Cpd | Name and Data |
|---|---|
| 99 | (E)-1-[2-(2-{2-[4-(2,2,3,3,3-pentafluoro-propoxy)-phenyl]-vinyl}-1H-benzimidazol-5-yl)-phenyl]-ethanone, |
| 100 | (E)-1-[2-(2-{2-[4-(2,2,3,3,3-pentafluoro-propoxy)-phenyl]-vinyl}-1H-benzimidazol-5-yl)-phenyl]-ethanol, |
| 102 | (E)-2-[2-(2-{2-[4-(2,2,3,3,3-pentafluoro-propoxy)-phenyl]-vinyl}-1H-benzimidazol-5-yl)-phenyl]-propan-2-ol, and |
| 104 | (E)-C,C,C-trifluoro-N-[2-(2-{2-[4-(2,2,3,3,3-pentafluoro-propoxy)-phenyl]-vinyl}-1H-benzimidazol-5-yl)-phenyl]-methanesulfonamide. |
| 105 | (E)-1-(2-{2-[2-(3-chloro-phenyl)-vinyl]-1H-benzimidazol-5-yl}-phenyl)-ethanone, |
| 106 | (E)-1-(2-{2-[2-(3-chloro-phenyl)-vinyl]-1H-benzimidazol-5-yl}-phenyl)-ethanol, |
| 108 | (E)-2-(2-{2-[2-(3-chloro-phenyl)-vinyl]-1H-benzimidazol-5-yl}-phenyl)-propan-2-ol, |
| 110 | (E)-N-(2-{2-[2-(3-chloro-phenyl)-vinyl]-1H-benzimidazol-5-yl}-phenyl)-C,C,C-trifluoro-methanesulfonamide, |
| 111 | (E)-1-(2-{2-[2-(3-trifluoromethyl-phenyl)-vinyl]-1H-benzimidazol-5-yl}-phenyl)-ethanone, |
| 112 | (E)-1-(2-{2-[2-(3-trifluoromethyl-phenyl)-vinyl]-1H-benzimidazol-5-yl}-phenyl)-ethanol, |
| 116 | (E)-C,C,C-trifluoro-N-(2-{2-[2-(3-trifluoromethyl-phenyl)-vinyl]-1H-benzimidazol-5-yl}-phenyl)-methanesulfonamide. |
| 117 | (E)-N-(4-{2-[5-(2-acetyl-phenyl)-1H-benzimidazol-2-yl]-vinyl}-phenyl)-methanesulfonamide, |
| 118 | (E)-N-[4-(2-{5-[2-(1-hydroxy-ethyl)-phenyl]-1H-benzimidazol-2-yl}-vinyl)-phenyl]-methanesulfonamide, |
| 120 | (E)-N-[4-(2-{5-[2-(1-hydroxy-1-methyl-ethyl)-phenyl]-1H-benzimidazol-2-yl}-vinyl)-phenyl]-methanesulfonamide, |
| 122 | (E)-C,C,C-trifluoro-N-(2-{2-[2-(4-methanesulfonylamino-phenyl)-vinyl]-1H-benzimidazol-5-yl}-phenyl)-methanesulfonamide, |
| 123 | (E)-N-(4-{2-[5-(2-acetyl-phenyl)-1H-benzimidazol-2-yl]-vinyl}-phenyl)-C,C,C-trifluoro-methanesulfonamide, |
| 124 | (E)-C,C,C-trifluoro-N-[4-(2-{5-[2-(1-hydroxy-ethyl)-phenyl]-1H-benzimidazol-2-yl}-vinyl)-phenyl]-methanesulfonamide, |
| 126 | (E)-C,C,C-trifluoro-N-[4-(2-{5-[2-(1-hydroxy-1-methyl-ethyl)-phenyl]-1H-benzimidazol-2-yl}-vinyl)-phenyl]-methanesulfonamide, and |
| 128 | (E)-C,C,C-trifluoro-N-(4-{2-[5-(2-trifluoromethanesulfonylamino-phenyl)-1H-benzimidazol-2-yl]-vinyl}-phenyl)-methanesulfonamide. |

EXAMPLE 22

2-{2-[2-(2-trifluoromethyl-phenyl)-ethyl]-1H-benzimidazol-5-yl}-benzenesulfonamide (Cpd 401)

A mixture of (E)-2-{2-[2-(2-trifluoromethyl-phenyl)-vinyl]-1H-benzimidazol-5-yl}-benzenesulfonamide Cpd 364 (0.020 g, 0.045 mmol) and 10% palladium on charcoal (0.005 g, 0.0045 mmol) in 2 mL MeOH was hydrogenated under $H_2$ gas (1 atm) for 1 hour. The catalyst was removed by filtration, the filtrate was concentrated to dryness, and the residue was purified by chromatography (silica gel, MeOH:$CH_2Cl_2$=10:1) to give the title compound as a white solid. $^1$H-NMR (400 MHz, $CD_3OD$) δ (ppm): 8.14 (dd, 1H, J=1.2 and 7.6 Hz) 7.74-7.53 (m, 4H) 7.60-7.56 (m, 2H) 7.51-7.40 (m, 4H) 3.41 (m, 4H) MS (ESI, pos. ion) m/z: 446.5 (M+1).

Using the procedures described in Example 22 and reagents, starting materials and conditions known to those skilled in the art, the following compounds representative of the present invention were prepared from the corresponding vinyl derivatives:

| Cpd | Name and Data |
|---|---|
| 129 | 2-{2-[2-(4-trifluoromethoxy-phenyl)-ethyl]-1H-benzimidazol-5-yl}-benzenesulfonamide<br>$^1$H-NMR(400MHz, $CD_3OD$) δ (ppm): 8.14(dd, 1H, 1.2 and 8.0 Hz) 7.65-7.54(m, 4H) 7.44-7.31(m, 4H) 7.20(d, 2H, J=8.8 Hz) 3.26-3.23(m, 4H) MS(ESI, pos. ion) m/z: 462.4(M+1). |
| 130 | 2-{2-[2-(4-trifluoromethyl-phenyl)-ethyl]-1H-benzimidazol-5-yl}-benzenesulfonamide<br>$^1$H-NMR(400MHz, $CD_3OD$) δ (ppm): 8.12(dd, 1H, J=1.2 and 8.4 Hz) 7.64-7.51(m, 6H) 7.42(d, 2H, J=8.0 Hz) 7.39(dd, 1H, J=1.2 and 7.6 Hz) 7.27(dd, 1H, J=1.6 and 8.4 Hz) 3.24(m, 4H) MS(ESI, pos. ion) m/z: 446.4(M+1). |
| 131 | 2-{2-[2-(4-trifluoromethanesulfonyl-phenyl)-ethyl]-1H-benzimidazol-5-yl}-benzenesulfonamide<br>$^1$H-NMR(400MHz, $CD_3OD$) δ (ppm): 8.15(dd, 1H, J=1.2 and 8.0 Hz) 8.02(d, 2H, J=8.8 Hz) 7.70-7.55(m, 7H) 7.42(dd, 1H, J=1.6 and 7.2 Hz) 7.36(dd, 1H, J=1.6 and 8.4 Hz) 3.41-3.48(m, 4H) MS(ESI, pos. ion) m/z: 510.2(M+1). |
| 139 | 2-{2-[2-(4-chloro-phenyl)-ethyl]-1H-benzimidazol-5-yl}-benzenesulfonamide<br>$^1$H-NMR(400MHz, $CD_3OD$) δ (ppm): 8.12(dd, 1H, 1.6 and 8.0 Hz) |

| Cpd | Name and Data |
|---|---|
| | 7.64-7.59(m, 2H) 7.55-7.51(m, 2H) 7.39(dd, 1H, J=0.8 and 7.6 Hz) 7.32-7.14(m, 5H) 3.20-3.13(m, 4H) MS(ESI, pos. ion) m/z: 412.3(M+1). |
| 145 | 2-{2-[2-(4-methanesulfonyl-phenyl)-ethyl]-1H-benzimidazol-5-yl}-benzenesulfonamide<br>$^1$H-NMR(400MHz, CD$_3$OD) δ (ppm): 8.14(dd, 1H, 1.2 and 7.6 Hz) 7.87(d, 2H, J=8.4 Hz) 7.66-7.50(m, 6H) 7.41(dd, 1H, J=1.2 and 8.0 Hz) 7.30(dd, 1H, J=1.6 and 8.4 Hz) 3.10(m, 4H) MS(ESI, pos. ion) m/z: 456.3(M+1). |
| 175 | 2-{2-[2-(3-trifluoromethyl-phenyl)-ethyl]-1H-benzimidazol-5-yl}-benzenesulfonamide<br>$^1$H-NMR(400MHz, CD$_3$OD) δ (ppm): 8.13(dd, 1H, J=1.2 and 7.6 Hz) 7.70-7.48(m, 8H) 7.44(dd, 1H, J=1.6 and 8.0 Hz) 7.39(dd, 1H, J=1.2 and 7.2 Hz) 3.40-3.30(m, 4H) MS(ESI, pos. ion) m/z: 446.4(M+1). |
| 383 | 2-{2-[2-(4-fluoro-3-trifluoromethyl-phenyl)-ethyl]-1H-benzimidazol-5-yl}-benzenesulfonamide<br>$^1$H-NMR(400MHz, CD$_3$OD) δ (ppm): 8.02(dd, 1H, J=1.2 and 8.0 Hz) 7.52-7.49(m, 2H) 7.45-7.41(m, 4H) 7.31-7.26(m, 1H) 7.18(dd, 1H, J=1.2 and 8.0 Hz) 7.13(t, 1H, J=7.2 Hz) 3.20-3.15(m, 4H) MS(ESI, pos. ion) m/z: 446.4(M+1). |
| 384 | 2-{2-[2-(2,3,4-trifluoro-phenyl)-ethyl]-1H-benzimidazol-5-yl}-benzenesulfonamide<br>$^1$H-NMR(400MHz, CD$_3$OD) δ (ppm): 8.14(dd, 1H, J=1.2 and 8.0 Hz) 7.66-7.53(m, 4H) 7.42(dd, 1H, J=1.6 and 7.6 Hz) 7.29(dd, 1H, J=1.6 and 8.4 Hz) 7.04-6.99(m, 2H) 3.24(m, 4H) MS(ESI, pos. ion) m/z: 432.5(M+1). |
| 385 | 2-{2-[2-(2,4,5-trifluoro-phenyl)-ethyl]-1H-benzimidazol-5-yl}-benzenesulfonamide<br>$^1$H-NMR(400MHz, CD$_3$OD) δ (ppm): 8.14(dd, 1H, J=1.2 and 8.4 Hz) 7.67-7.53(m, 4H) 7.42(dd, 1H, J=1.2 and 7.6 Hz) 7.30(dd, 1H, J=1.6 and 8.4 Hz) 7.26-7.10(m, 2H) 3.23-3.20(m, 4H) MS(ESI, pos. ion) m/z: 432.3(M+1). |
| 386 | 2-{2-[2-(2,6-difluoro-phenyl)-ethyl]-1H-benzimidazol-5-yl}-benzenesulfonamide<br>$^1$H-NMR(400MHz, CD$_3$OD) δ (ppm): 8.14(dd, 1H, J=1.2 and 8.0 Hz) 7.67-7.53(m, 4H) 7.42(dd, 1H, J=1.2 and 7.6 Hz) 7.31-7.25(m, 2H) 6.97-6.93(m, 2H) 3.26-3.19(m, 4H) MS(ESI, pos. ion) m/z: 414.3(M+1). |
| 387 | 2-{2-[2-(3,5-bis-trifluoromethyl-phenyl)-ethyl]-1H-benzimidazol-5-yl}-benzenesulfonamide<br>$^1$H-NMR(400MHz, CD$_3$OD) δ (ppm): 8.12(dd, 1H, 1.6 and 8.0 Hz) 7.92(dd, 1H, 1.2 and 8.4 Hz) 7.80(s, 1H) 7.64-7.51(m, 4H) 7.40-7.33(m, 2H) 7.28(dd, 1H, J=1.6 and 8.0 Hz) 3.38-3.25(m, 4H) MS(ESI, pos. ion) m/z: 514.4(M+1). |
| 388 | 2-{2-[2-(2,5-bis-trifluoromethyl-phenyl)-ethyl]-1H-benzimidazol-5-yl}-benzenesulfonamide<br>$^1$H-NMR(400MHz, CD$_3$OD) δ (ppm): 8.15(dd, 1H, J=1.2 and 7.6 Hz) 7.94(d, 1H, J=8.0 Hz) 7.76-7.72(m, 2H) 7.67-7.54(m, 4H) 7.42(dd, 1H, J=1.2 and 7.6Hz) 7.33(dd, 1H, J=1.6 and 8.4 Hz) 3.50-3.45(m, 2H) 3.31-3.26(m, 2H) MS(ESI, pos. ion) m/z: 514.5(M+1). |
| 390 | 2-{2-[2-(4-chloro-3-trifluoromethyl-phenyl)-ethyl]-1H-benzimidazol-5-yl}-benzenesulfonamide<br>$^1$H-NMR(400MHz, CD$_3$OD) δ (ppm): 8.12(dd, 1H, 1.6 and 8.0 Hz) 7.54-7.60(m, 3H) 7.54(dd, 1H, J=1.2 and 8.0 Hz) 7.52-7.48(m, 2H) 7.43(dd, 1H, J=2.0 and 8.4 Hz) 7.39(dd, 1H, J=1.6 and 7.2 Hz) 7.27(d, 1H, J=8.0 Hz) 3.23(m, 4H) MS(ESI, pos. ion) m/z: 480.4(M+1). |
| 391 | 2-{2-[2-(3-trifluoromethoxy-phenyl)-ethyl]-1H-benzimidazol-5-yl}-benzenesulfonamide<br>$^1$H-NMR(400MHz, CD$_3$OD) δ (ppm): 8.15(dd, 1H, J=1.2 and 8.0 Hz) 7.65-7.54(m, 4H) 7.43-7.37(m, 2H) 7.33(dd, 1H, J=2.0 and 8.0 Hz) 7.26(d, 1H, J=8.8 Hz) 7.17(s, 1H) 7.13(d, 1H, J=9.6 Hz) 3.26(m, 4H) MS(ESI, pos. ion) m/z: 462.4(M+1). |
| 392 | 2-{2-[2-(2,4-difluoro-phenyl)-ethyl]-1H-benzimidazol-5-yl}-benzenesulfonamide<br>$^1$H-NMR(400MHz, CD$_3$OD) δ (ppm): 8.15(dd, 1H, 1.6 and 6.4 Hz) 7.67-7.53(m, 4H) 7.42(dd, 1H, 1.6 and 8.0 Hz) 7.30(dd, 1H, J=1.2 and 6.8 Hz) 7.28-7.23(m, 1H) 6.96-6.85(m, 2H) 3.22(m, 4H) MS(ESI, pos. ion) m/z: 414.2(M+1). |
| 393 | 2-{2-[2-(3,4-difluoro-phenyl)-ethyl]-1H-benzimidazol-5-yl}-benzenesulfonamide<br>$^1$H-NMR(400MHz, CD$_3$OD) δ (ppm): 8.15(dd, 1H, 1.2 and 7.6 Hz) 7.65-7.53(m, 4H) 7.42(dd, 1H, 1.2 and 7.2 Hz) 7.32(dd, 1H, J=1.2 and 8.4 Hz) 7.22-7.13(m, 2H) 7.04-7.01(m, 1H) 3.22(m, 4H) MS(ESI, pos. ion) m/z: 414.4(M+1). |
| 394 | 2-{2-[2-(2,3-difluoro-phenyl)-ethyl]-1H-benzimidazol-5-yl}-benzenesulfonamide<br>$^1$H-NMR(400MHz, CD$_3$OD) δ (ppm): 8.14(dd, 1H, 1.6 and 8.0 Hz) 7.68-7.53(m, 4H) 7.42(dd, 1H, 1.6 and 7.6 Hz) 7.32(dd, 1H, J=1.6 and 8.0 Hz) 7.15-7.01(m, 3H) 3.28(m, 4H) MS(ESI, pos. ion) m/z: 414.3(M+1). |
| 395 | 2-{2-[2-(2,5-difluoro-phenyl)-ethyl]-1H-benzimidazol-5-yl}-benzenesulfonamide<br>$^1$H-NMR(400MHz, CD$_3$OD) δ (ppm): 8.15(dd, 1H, 2.4 and 7.6 Hz) 7.67-7.53(m, 4H) 7.43-7.39(m, 1H) 7.33-7.29(m, 1H) 7.12-6.94(m, 3H) 3.26(m, 4H) MS(ESI, pos. ion) m/z: 414.4(M+1). |

-continued

| Cpd | Name and Data |
|---|---|
| 396 | 2-{2-[2-(3,5-difluoro-phenyl)-ethyl]-1H-benzimidazol-5-yl}-benzenesulfonamide<br>$^1$H-NMR(400MHz, CD$_3$OD) δ (ppm): 8.15(dd, 1H, 2.0 and 8.0 Hz)<br>7.67-7.54(m, 4H) 7.42(dd, 1H, 1.6 and 7.6 Hz) 7.36(dd, 1H, 1.6 and 8.4 Hz)<br>6.91-6.77(m, 3H) 3.26-3.20(m, 4H) MS(ESI, pos. ion) m/z: 414.6(M+1). |
| 397 | 2-(2-phenethyl-1H-benzimidazol-5-yl)-benzenesulfonamide<br>$^1$H-NMR(400MHz, CD$_3$OD) δ (ppm): 8.14(dd, 1H, 1.6 and 7.6 Hz)<br>7.67-7.54(m, 4H) 7.42(dd, 1H, 1.6 and 7.6 Hz) 7.30-7.17(m, 7H) 3.25-3.06(m, 4H) MS (ESI, pos. ion) m/z: 378.3(M+1). |
| 399 | N,N-dimethyl-2-{2-[2-(4-trifluoromethyl-phenyl)-ethyl]-1H-benzimidazol-5-yl}-benzenesulfonamide<br>The title compound was prepared by hydrogenation using Compound 398.<br>$^1$H-NMR(400MHz,CD$_3$OD) δ (ppm): 8.07(dd, 1H, J=1.2 and 8.0 Hz) 7.65(dt, 1H, J=1.6 and 8.2 Hz) 7.58-7.53(m, 5H) 7.41-7.38(m, 3H) 7.20(dd, 1H, J=1.6 and 8.4 Hz) 3.25(m, 4H) 2.27(s, 6H) MS(ESI, pos. ion) m/z: 474.4(M+1). |
| 402 | 2-{2-[2-(2-chloro-phenyl)-ethyl]-1H-benzimidazol-5-yl}-benzenesulfonamide<br>$^1$H-NMR(400MHz, CD$_3$OD) δ (ppm): 8.12(d, 1H) 7.64-7.52(m, 4H) 7.41-7.38(m, 2H) 7.26-7.19(m, 4H) 3.22-3.18(m, 4H) MS(ESI, pos. ion) m/z: 412.3(M+1). |
| 404 | 2-{2-[2-(4-fluoro-2-trifluoromethyl-phenyl)-ethyl]-1H-benzimidazol-5-yl}-benzenesulfonamide<br>$^1$H-NMR(400MHz, CD$_3$OD) δ (ppm): 8.12(dd, 1H, J=1.6 and 8.0 Hz) 7.64-7.60(m, 2H) 7.56-7.51(m, 2H) 7.46-7.38(m, 3H) 7.30-7.27(m, 2H) 3.33-3.30(m, 2H) 3.35-3.32(m, 2H) MS(ESI, pos. ion) m/z: 464.4(M+1). |
| 405 | 2-{2-[2-(2-fluoro-3-trifluoromethyl-phenyl)-ethyl]-1H-benzimidazol-5-yl}-benzenesulfonamide<br>$^1$H-NMR(400MHz, CD$_3$OD) δ (ppm): 8.15(dd, 1H, J=1.2 and 8.0 Hz) 7.66-7.62(m, 2H) 7.59-7.50(m, 4H) 7.41(dd, 1H, J=1.2 and 7.6 Hz) 7.31(dd, 1H, J=1.6 and 8.0 Hz) 7.26-7.21(m, 1H) 3.26(m, 4H) MS(ESI, pos. ion) m/z: 464.3(M+1). |
| 419 | 2-{2-[2-(2-fluoro-phenyl)-ethyl]-1H-benzimidazol-5-yl}-benzenesulfonamide<br>$^1$H-NMR(400MHz, CD$_3$OD) δ (ppm): 8.14(d, J=8.0 Hz, 1H), 7.71(s, 1H), 7.68-7.64(m, 2H), 7.60-7.57(m, 1H), 7.40(d, J=8.0 Hz, 1H), 7.48(d, J=8.0 Hz, 1H), 7.29-7.24(m, 2H), 7.12-7.06(m, 2H), 3.41(t, J=8.0 Hz, 2H), 3.28(t, J=8.0 Hz, 2H). Mass Spectrum(LCMS, ESI pos.) Calcd. For C$_{21}$H$_{18}$FN$_3$O$_2$S: 396.1(M+H), Found 396.3. |
| 420 | 2-{2-[2-(4-fluoro-phenyl)-ethyl]-1H-benzimidazol-5-yl}-benzenesulfonamide<br>$^1$H-NMR(400MHz, CD$_3$OD) δ (ppm): 8.14(dd, J=1.6, 8.0 Hz, 1H), 7.73(s, 1H), 7.69(d, J=8.0 Hz, 1H), 7.65(dd, J=1.6, 8.0 Hz, 1H), 7.58(dt, J=1.6, 8.0 Hz, 1H), 7.51(d, J=1.6, 8.0 Hz, 1H), 7.40(dd, J=1.2, 7.2 Hz, 1H), 7.27-7.24(m, 2H), 7.04-7.00(m, 2H), 3.42(t, J=8.0 Hz, 2H), 3.23(t, J=8.0 Hz, 2H). Mass Spectrum(LCMS, ESI pos.) Calcd. For C$_{21}$H$_{18}$FN$_3$O$_2$S: 396.1(M+H), Found 396.3. |
| 421 | 2-{2-[2-(3-fluoro-5-trifluoromethyl-phenyl)-ethyl]-1H-benzimidazol-5-yl}-benzenesulfonamide<br>$^1$H-NMR(400MHz, CD$_3$OD) δ (ppm): 8.12(d, J=8.0 Hz, 1H), 7.64-7.60(m, 2H), 7.56-7.51(m, 2H), 7.40-7.36(m, 2H), 7.32-7.29(m, 3H), 3.27-3.25(m, 4H). Mass Spectrum(LCMS, ESI pos.) Calcd. For C$_{22}$H$_{17}$F$_4$N$_3$O$_2$S: 464.1(M+H), Found 464.3. |
| 442 | 2-{2-[2-(3-fluoro-5-trifluoromethyl-phenyl)-ethyl]-1H-benzimidazol-5-yl}-benzenesulfonamide<br>$^1$H-NMR(400MHz, CD$_3$OD) δ (ppm): 8.12(dd, J=1.6, 8 Hz, 1H), 8.01(d, J=1.6, 8 Hz, 1H), 7.65-7.60(m, 3H), 7.58-7.53(m, 3H), 7.48-7.44(m, 1H), 7.40(dd, J=1.6, 8 Hz, 1H), 7.33(dd, J=1.6, 8 Hz, 1H), 3.13(m, 1H), 2.86(t, J=7.6 Hz, 2H), 2.83(t, J=7.6 Hz, 2H), 1.21(d, J=7.6 Hz, 6H). Mass Spectrum(LCMS, ESI pos.) Calcd. For C$_{24}$H$_{25}$N$_3$O$_2$S: 420.5(M+H), Found 420.4. |
| 445 | 4-trifluoromethyl-2-{2-[2-(4-trifluoromethyl-phenyl)-ethyl]-1H-benzimidazol-5-yl}-benzenesulfonamide<br>The title compound was prepared by hydrogenation using Compound 444.<br>$^1$H-NMR(400MHz, CD$_3$OD) δ (ppm): 8.33(d, J=8 Hz, 1H), 7.83(dd, J=2, 8 Hz, 1H), 7.63(d, J=8 Hz, 2H), 7.58-7.54(m, 3H), 7.42(d, J=8 Hz, 2H), 7.29(dd, J=2, 8 Hz, 1H), 3.28-3.24(m, 4H). Mass Spectrum(LCMS, ESI pos.) Calcd. For C$_{23}$H$_{17}$F$_6$N$_3$O$_2$S: 514.5(M+H), Found 514.3. |
| 447 | 4-trifluoromethyl-2-{2-[2-(4-trifluoromethyl-phenyl)-ethyl]-1H-benzimidazol-5-yl}-benzenesulfonamide<br>The title compound was prepared by hydrogenation using Compound 446.<br>$^1$H-NMR(400MHz, CD$_3$OD) δ (ppm): 8.42(s, 1H), 7.94(d, J=8 Hz, 1H), 7.63-7.56(m, 5H), 7.42(d, J=8 Hz, 2H), 7.29(d, J=1.6, 8 Hz, 1H), 3.27-3.25(m, 4H). Mass Spectrum(LCMS, ESI pos.) Calcd. For C$_{23}$H$_{17}$F$_6$N$_3$O$_2$S: 514.1(M+H), Found 514.2. |

EXAMPLE 23

N-methyl-2-{2-[2-(4-trifluoromethyl-phenyl)-ethyl]-1H-benzimidazol-5-yl}-benzenesulfonamide (Cpd 400)

Using the procedure of Example 18, the title compound was prepared from Compound 18c and 4-trifluoromethylphenyl propionic acid. $^1$H-NMR (400 MHz, CD$_3$OD) δ (ppm): 8.04 (dd, 1H, J=1.2 and 8.0 Hz) 7.66-7.53 (m, 6H) 7.42-7.38 (m, 3H) 7.29 (dd, 1H, J=1.6 and 8.4 Hz) 3.27 (m, 4H) MS (ESI, pos. ion) m/z: 460.4 (M+1).

EXAMPLE 24

N-methyl-2-{2-[2-(3-trifluoromethyl-phenyl)-ethyl]-1H-benzimidazol-5-yl}-benzenesulfonamide (Cpd 350)

Using the procedure of Example 18, the title compound was prepared from Compound 18c and 3-trifluoromethylphenyl propionic acid. $^1$H-NMR (400 MHz, CD$_3$OD) δ (ppm): 8.05 (dd, 1H, J=1.2 and 7.6 Hz) 7.64 (td, 1H, 1.2 and 8.2 Hz) 7.58-7.53 (m, 4H) 7.50-7.44 (m, 3H) 7.40 (dd, 1H, J=1.2 and 7.2 Hz) 7.25 (dd, 1H, J=1.6 and 8.0 Hz) 3.26-3.22 (m, 4H) MS (ESI, pos. ion) m/z: 460.4 (M+1).

EXAMPLE 25

2-(2-{2-[2-(4-trifluoromethyl-phenyl)-ethyl]-1H-benzimidazol-5-yl}-phenyl)-propan-2-ol (Cpd 464)

Using the procedure of Example 10, the title Compound 464 (0.013 g) was prepared from 5-bromo-2-[2-(4-trifluoromethyl-phenyl)-ethyl]-1H-benzimidazole Compound 25a (0.048 g, 0.13 mmol) and Compound 10e (0.032g, 0.20 mmol).

$^1$H-NMR (400 MHz, DMSO d6) δ (ppm) 7.71 (dd, J=1.26, 8.08 Hz, 1H) 7.45 (d, J=7.8 Hz, 2H) 7.37 (d, J=8.34 Hz, 1H) 7.31 (d, J=8.08 Hz, 2H) 7.20-7.26 (m, 2H) 7.10 (ddd, J=1.51, 7.33, 7.58 Hz, 1H) 6.93-7.20 (m, 2H) 3.14 (m, 4H) 1.21 (s, 6H). MS (ESI, pos. ion) m/z: 425.1 (M+1).

Using the procedures described in Example 25 and Compound 25a, and reagents, starting materials and conditions known to those skilled in the art, the following compounds representative of the present invention were prepared from the corresponding vinyl derivatives:

| Cpd | Name and Data |
|---|---|
| 457 | N-(2-{2-[2-(4-trifluoromethyl-phenyl)-ethyl]-1H-benzimidazol-5-yl}-phenyl)-acetamide<br>$^1$H-NMR(400MHz, CD$_3$OD) δ (ppm): 7.50-7.60(m, 5H) 7.32-7.44(m, 5H) 7.22-7.26(d, J=8.6Hz, 1H) 3.24-3.30(s, 4H) 1.96(s, 3H). MS(ESI, pos. ion) m/z: 424.2(M+1). |

PROPHETIC EXAMPLE 26

Using the procedures of Examples 22, 23, 24 or 25, and reagents, starting materials and conditions known to those skilled in the art, the following prophetic compounds representative of the present invention may be prepared.

| Cpd | Name and Data |
|---|---|
| 133 | C,C,C-trifluoro-N-(2-{2-[2-(4-trifluoromethyl-phenyl)-ethyl]-1H-benzimidazol-5-yl}-phenyl)-methanesulfonamide, |
| 134 | C,C,C-trifluoro-N-(2-{2-[2-(4-trifluoromethanesulfonyl-phenyl)-ethyl]-1H-benzimidazol-5-yl}-phenyl)-methanesulfonamide, |
| 135 | 1-(2-{2-[2-(4-chloro-phenyl)-ethyl]-1H-benzimidazol-5-yl}-phenyl)-ethanone, |
| 136 | 1-(2-{2-[2-(4-chloro-phenyl)-ethyl]-1H-benzimidazol-5-yl}-phenyl)-ethanol, |
| 137 | N-(2-{2-[2-(4-chloro-phenyl)-ethyl]-1H-benzimidazol-5-yl}-phenyl)-methanesulfonamide, |
| 138 | 2-(2-{2-[2-(4-chloro-phenyl)-ethyl]-1H-benzimidazol-5-yl}-phenyl)-propan-2-ol, |
| 140 | N-(2-{2-[2-(4-chloro-phenyl)-ethyl]-1H-benzimidazol-5-yl}-phenyl)-C,C,C-trifluoro-methanesulfonamide, |
| 141 | 1-(2-{2-[2-(4-methanesulfonyl-phenyl)-ethyl]-1H-benzimidazol-5-yl}-phenyl)-ethanone, |
| 142 | 1-(2-{2-[2-(4-methanesulfonyl-phenyl)-ethyl]-1H-benzimidazol-5-yl}-phenyl)-ethanol, |
| 143 | N-(2-{2-[2-(4-methanesulfonyl-phenyl)-ethyl]-1H-benzimidazol-5-yl}-phenyl)-methanesulfonamide, |
| 144 | 2-(2-{2-[2-(4-methanesulfonyl-phenyl)-ethyl]-1H-benzimidazol-5-yl}-phenyl)-propan-2-ol, |
| 146 | C,C,C-trifluoro-N-(2-{2-[2-(4-methanesulfonyl-phenyl)-ethyl]-1H-benzimidazol-5-yl}-phenyl)-methanesulfonamide, |
| 147 | 1-[2-(2-{2-[4-(2,2,2-trifluoro-1-trifluoromethyl-ethoxy)-phenyl]-ethyl}-1H-benzimidazol-5-yl)-phenyl]-ethanone, |
| 148 | 1-[2-(2-{2-[4-(2,2,2-trifluoro-1-trifluoromethyl-ethoxy)-phenyl]-ethyl}-1H-benzimidazol-5-yl)-phenyl]-ethanol, |
| 149 | N-[2-(2-{2-[4-(2,2,2-trifluoro-1-trifluoromethyl-ethoxy)-phenyl]-ethyl}-1H-benzimidazol-5-yl)-phenyl]-methanesulfonamide, |
| 150 | 2-[2-(2-{2-[4-(2,2,2-trifluoro-1-trifluoromethyl-ethoxy)-phenyl]-ethyl}-1H-benzimidazol-5-yl)-phenyl]-propan-2-ol, |
| 151 | 2-(2-{2-[4-(2,2,2-trifluoro-1-trifluoromethyl-ethoxy)-phenyl]-ethyl}-1H-benzimidazol-5-yl)-benzenesulfonamide, |
| 152 | C,C,C-trifluoro-N-[2-(2-{2-[4-(2,2,2-trifluoro-1-trifluoromethyl-ethoxy)-phenyl]-ethyl}-1H-benzimidazol-5-yl)-phenyl]-methanesulfonamide, |
| 153 | 1-[2-(2-{2-[4-(2,2,2-trifluoro-ethoxy)-phenyl]-ethyl}-1H-benzimidazol-5-yl)-phenyl]-ethanone, |

| Cpd | Name and Data |
|---|---|
| 154 | 1-[2-(2-{2-[4-(2,2,2-trifluoro-ethoxy)-phenyl]-ethyl}-1H-benzimidazol-5-yl)-phenyl]-ethanol, |
| 155 | N-[2-(2-{2-[4-(2,2,2-trifluoro-ethoxy)-phenyl]-ethyl}-1H-benzimidazol-5-yl)-phenyl]-methanesulfonamide, |
| 156 | 2-[2-(2-{2-[4-(2,2,2-trifluoro-ethoxy)-phenyl]-ethyl}-1H-benzimidazol-5-yl)-phenyl]-propan-2-ol, |
| 157 | 2-(2-{2-[4-(2,2,2-trifluoro-ethoxy)-phenyl]-ethyl}-1H-benzimidazol-5-yl)-benzenesulfonamide, |
| 158 | C,C,C-trifluoro-N-[2-(2-{2-[4-(2,2,2-trifluoro-ethoxy)-phenyl]-ethyl}-1H-benzimidazol-5-yl)-phenyl]-methanesulfonamide, |
| 159 | 1-[2-(2-{2-[4-(2,2,3,3,3-pentafluoro-propoxy)-phenyl]-ethyl}-1H-benzimidazol-5-yl)-phenyl]-ethanone, |
| 160 | 1-[2-(2-{2-[4-(2,2,3,3,3-pentafluoro-propoxy)-phenyl]-ethyl}-1H-benzimidazol-5-yl)-phenyl]-ethanol, |
| 161 | N-[2-(2-{2-[4-(2,2,3,3,3-pentafluoro-propoxy)-phenyl]-ethyl}-1H-benzimidazol-5-yl)-phenyl]-methanesulfonamide, |
| 162 | 2-[2-(2-{2-[4-(2,2,3,3,3-pentafluoro-propoxy)-phenyl]-ethyl}-1H-benzimidazol-5-yl)-phenyl]-propan-2-ol, |
| 163 | 2-(2-{2-[4-(2,2,3,3,3-pentafluoro-propoxy)-phenyl]-ethyl}-1H-benzimidazol-5-yl)-benzenesulfonamide, |
| 164 | C,C,C-trifluoro-N-[2-(2-{2-[4-(2,2,3,3,3-pentafluoro-propoxy)-phenyl]-ethyl}-1H-benzimidazol-5-yl)-phenyl]-methanesulfonamide, |
| 165 | 1-(2-{2-[2-(3-chloro-phenyl)-ethyl]-1H-benzimidazol-5-yl}-phenyl)-ethanone, |
| 166 | 1-(2-{2-[2-(3-chloro-phenyl)-ethyl]-1H-benzimidazol-5-yl}-phenyl)-ethanol, |
| 167 | N-(2-{2-[2-(3-chloro-phenyl)-ethyl]-1H-benzimidazol-5-yl}-phenyl)-methanesulfonamide, |
| 168 | 2-(2-{2-[2-(3-chloro-phenyl)-ethyl]-1H-benzimidazol-5-yl}-phenyl)-propan-2-ol, |
| 169 | 2-{2-[2-(3-chloro-phenyl)-ethyl]-1H-benzimidazol-5-yl}-benzenesulfonamide, |
| 170 | N-(2-{2-[2-(3-chloro-phenyl)-ethyl]-1H-benzimidazol-5-yl}-phenyl)-C,C,C-trifluoro-methanesulfonamide, |
| 171 | 1-(2-{2-[2-(3-trifluoromethyl-phenyl)-ethyl]-1H-benzimidazol-5-yl}-phenyl)-ethanone, |
| 172 | 1-(2-{2-[2-(3-trifluoromethyl-phenyl)-ethyl]-1H-benzimidazol-5-yl}-phenyl)-ethanol, |
| 173 | N-(2-{2-[2-(3-trifluoromethyl-phenyl)-ethyl]-1H-benzimidazol-5-yl}-phenyl)-methanesulfonamide, |
| 174 | 2-(2-{2-[2-(3-trifluoromethyl-phenyl)-ethyl]-1H-benzimidazol-5-yl}-phenyl)-propan-2-ol, |
| 176 | C,C,C-trifluoro-N-(2-{2-[2-(3-trifluoromethyl-phenyl)-ethyl]-1H-benzimidazol-5-yl}-phenyl)-methanesulfonamide, |
| 177 | N-(4-{2-[5-(2-acetyl-phenyl)-1H-benzimidazol-2-yl]-ethyl}-phenyl)-methanesulfonamide, |
| 178 | N-[4-(2-{5-[2-(1-hydroxy-ethyl)-phenyl]-1H-benzimidazol-2-yl}-ethyl)-phenyl]-methanesulfonamide, |
| 179 | N-(2-{2-[2-(4-methanesulfonylamino-phenyl)-ethyl]-1H-benzimidazol-5-yl}-phenyl)-methanesulfonamide, |
| 180 | N-[4-(2-{5-[2-(1-hydroxy-1-methyl-ethyl)-phenyl]-1H-benzimidazol-2-yl}-ethyl)-phenyl]-methanesulfonamide, |
| 181 | 2-{2-[2-(4-methanesulfonylamino-phenyl)-ethyl]-1H-benzimidazol-5-yl}-benzenesulfonamide, |
| 182 | C,C,C-trifluoro-N-(2-{2-[2-(4-methanesulfonylamino-phenyl)-ethyl]-1H-benzimidazol-5-yl}-phenyl)-methanesulfonamide, |
| 183 | N-(4-{2-[5-(2-acetyl-phenyl)-1H-benzimidazol-2-yl]-ethyl}-phenyl)-C,C,C-trifluoro-methanesulfonamide, |
| 184 | C,C,C-trifluoro-N-[4-(2-{5-[2-(1-hydroxy-ethyl)-phenyl]-1H-benzimidazol-2-yl}-ethyl)-phenyl]-methanesulfonamide, |
| 185 | C,C,C-trifluoro-N-(4-{2-[5-(2-methanesulfonylamino-phenyl)-1H-benzimidazol-2-yl]-ethyl}-phenyl)-methanesulfonamide, |
| 186 | C,C,C-trifluoro-N-[4-(2-{5-[2-(1-hydroxy-1-methyl-ethyl)-phenyl]-1H-benzimidazol-2-yl}-ethyl)-phenyl]-methanesulfonamide, |
| 187 | 2-{2-[2-(4-trifluoromethanesulfonylamino-phenyl)-ethyl]-1H-benzimidazol-5-yl}-benzenesulfonamide, and |
| 188 | C,C,C-trifluoro-N-(2-{2-[2-(4-trifluoromethanesulfonylamino-phenyl)-ethyl]-1H-benzimidazol-5-yl}-phenyl)-methanesulfonamide. |

EXAMPLE 27

2-{2-[2-(4-trifluoromethyl-phenyl)-cyclopropyl]-1H-benzimidazol-5-yl}-benzenesulfonamide (Cpd 190)

Step A. 2-(4-trifluoromethyl-phenyl)-cyclopropanecarboxylic acid methyl ester To a solution of trimethylsulfonium iodide (0.53 g, 2.39 mmol) in 8 mL of DMSO was added sodium hydride (0.06 g, 2.39 mmol) at 25° C. After stirring for one hour, a solution of methyl 4-trifluoromethylcinnamate (0.50 g, 2.17 mmol) in 4 mL DMSO was added. The reaction mixture was stirred for six hours, when it was quenched by sat'd $NH_4Cl$ solution. The resulting mixture was extracted with $CH_2Cl_2$, the organic layer was dried over $Na_2SO_4$, filtered and the filtrate was concentrated. The residue was purified by chromatography (silica gel, hexanes:EtOAc, 2:1) to provide the title Compound 27a as a solid.

Step B. 2-(4-trifluoromethyl-phenyl)-cyclopropanecarboxylic acid

A solution of Compound 27a in 10 mL MeOH and 4 mL of 1N LiOH (aq) was heated at 70° C. for 4 h. The mixture was then acidified by 4N HCl (aq) and extracted with EtOAc. The organic layer was washed with brine, dried over $Na_2SO_4$, filtered, and filtrate was concentrated to provide the title Compound 27b.
$^1$H-NMR (400 MHz, $CD_3OD$) δ (ppm): 7.56 (d, 2H) 7.25 (d, 2H) 2.39 (m, 1H) 1.80 (m, 1H) 1.47 (m, 1H) 1.18 (m, 1H).

Step C. 2-{2-[2-(4-trifluoromethyl-phenyl)-cyclopropyl]-1H-benzimidazol-5-yl}-benzenesulfonamide To a solution of Compound 16c (0.140 g, 0.438 mmol) and N-(3-dimethylaminopropyl)-N'-ethylcarbodiimide hydrochloride Compound 27c (0.060 g, 0.313 mmol) in 4 mL acetonitrile at rt was slowly added a solution of Compound 27b (0.072 g, 0.313 mmol) in 2 mL of acetonitrile. After stirring for 2 hours, the mixture was passed through a short column (silica gel, hexanes:EtOAc, 2:1). The collected eluent was concentrated, and the residue was dissolved in AcOH. The reaction was heated at 80° C. for 3 h. The reaction was concentrated and the residue was purified by chromatography (silica gel, hexanes:EtOAc, 2:1). This material was dissolved in TFA, and the mixture was heated at 60° C. for 2 h. The reaction was concentrated, and the residue was purified by chromatography (silica gel, hexanes:EtOAc, 1:1) to provide the title Compound 190 as a solid. $^1$H-NMR (400 MHz, $CD_3OD$) δ (ppm): 8.14 (dd, 1H, J=1.2 and 7.6 Hz) 7.74-7.63 (m, 6H) 7.60-7.47 (m, 5H) 7.40 (dd, 1H, J=1.6 and 7.2 Hz) 2.97-2.92 (m, 1H) 2.76-2.71 (m, 1H) 2.12-2.00 (m, 2H) MS (ESI, pos. ion) m/z: 458.3 (M+1).

EXAMPLE 28

2-(2-{2-[2-(4-trifluoromethyl-phenyl)-cyclopropyl]-1H-benzimidazol-5-yl}-phenyl)-propan-2-ol (Cpd 471)

Step A. N-methoxy-N-methyl-3-(4-trifluoromethyl-phenyl)-acrylamide

To a solution of 4-trifluoromethyl cinnamic acid (3.6 g, 16.7 mmol) in anhydrous methylene chloride (40 mL) was slowly added oxalyl chloride (1.7 mL, 19.5 mmol). To the solution was added anhydrous dimethylformamide (10 μL) and the reaction was stirred at room temperature under an argon atmosphere. After 18 h, the reaction was concentrated. A solution of the residue Compound 10b (16.7 mmol) in methylene chloride (40 mL) was added dropwise to a solution of N,N-dimethylhydroxylamine hydrochloride (1.6 g, 16.7 mmol) and triethylamine (5.8 mL, 41.7 mmol) in methylene chloride (40 mL) at 0° C. The reaction mixture was stirred at 0° C. for 30 min, then warmed to room temperature. After 6 h, the reaction was successively washed with sodium carbonate (10% in water), water and brine. The organic fraction was dried over magnesium sulfate, filtered and the filtrate was concentrated. The compound was purified by chromatography (silica, EtOAc:hexanes, 1:1) to provide the title Compound 28a (2.2 g, 50% over two steps) $^1$H-NMR (400 MHz, DMSO d6) δ (ppm) 7.96 (d, J=8.3 Hz, 2H) 7.78 (d, J=8.08 Hz, 2H) 7.64 (d, J=15.9 Hz, 1H) 7.24 (d, J=15.9 Hz, 1H) 3.77 (s, 3H) 3.23 (s, 3H).

Step B. 2-(4-trifluoromethyl-phenyl)-cyclopropanecarboxylic acid methoxy-methyl-amide Anhydrous dimethylsulfoxide (8 mL) was added dropwise under an argon atmosphere to a mixture of sodium hydride (60% suspension in oil, 0.369 g, 9.2 mmol) and trimethylsulfoxonium iodide (2 g, 9.1 mmol). To the solution was added dropwise Compound 28a (1.2g, 4.6 mmol) in DMSO (8 mL). The reaction mixture was stirred at room temperature for 18 h. The reaction was poured into ethyl ether:water (1:1, 50 mL). The organic layer was seated and washed successively with water and brine. The organic fraction was dried over magnesium sulfate, filtered and the filtrate was concentrated to provide the title Compound 28b (1.9 g, 90%). $^1$H-NMR (400 MHz, $CDCl_3$) δ (ppm) 7.55 (d, J=8.08 Hz, 2H) 7.25 (d, J=8.3 Hz, 2H) 3.72 (s, 3H) 3.26 (s, 3H) 2.54-2.59 (m, 1H) 2.43-2.52 (m, 1H) 1.68-1.74 (m, 1H) 1.33-1.38 (m, 1H).

Step C. 2-(4-trifluoromethyl-phenyl)-cyclopropanecarboxylic acid

To a solution of Compound 28b (3.6 g, 13.2 mmol) in tetrahydrofuran (45 mL) was added a solution of potassium-t-butoxide (1M in tetrahydrofuran, 50 mL, 50 mmol). To the reaction was added water (1.5 mL, 83.3 mmol), and the reaction was stirred at room temperature under an argon atmosphere. After 18 h, ice was added to the reaction until it became homogeneous. To the solution was added ethyl ether, and the layers were seated. The aqueous layer was cooled and acidified with 1 M HCl until the pH was 4. The aqueous layer was extracted with ethyl acetate. The ethyl acetate layer was washed successively with water and brine. The organic layer was dried over magnesium sulfate, filtered and the filtrate was concentrated to provide the title Compound 28c (2.2 g, 73%). $^1$H-NMR (400 MHz, DMSO d6) δ (ppm) 12.4 (s, 1H) 7.62 (d, J=8.08 Hz, 2H) 7.40 (d, J=8.08 Hz, 2H) 2.46-2.54 (m, 1H) 1.88-1.96 (m, 1H) 1.46-1.52 (m, 1H) 1.38-1.44 (m, 1H)

Step D. 5-bromo-2-[2-(4-trifluoromethyl-phenyl)-cyclopropyl]-1H-benzimidazole Using the procedure of Example 1, the title Compound 28d was prepared from Compound 28c and 4-bromobenzene-1,2-diamine. $^1$H-NMR (400 MHz, DMSO d6) δ (ppm) 7.96 (s, 1H) 7.68-7.75 (m, 3H) 7.60-7.64 (dd, J=1.5, 8.6Hz, 1H) 7.46-7.56 (m, 4H) 7.10-7.14 (d, J=8.4Hz, 2H) 2.96-3.02 (m, 1H) 2.70-2.78 (m, 1H) 2.10-2.16 (m, 1H) 2.00-2.08 (m, 1H).

Step E. 2-(2-{2-[2-(4-trifluoromethyl-phenyl)-cyclopropyl]-1H-benzimidazol-5-yl}-phenyl)-propan-2-ol Using the procedure of Example 10, the title Compound 471 was prepared from Compound 28d and Compound 10e. $^1$H-NMR (400 MHz, CD$_3$OD) δ (ppm) 12.4 (s, 0.5H) 12.32 (s, 0.5H) 7.88 (m, 1H) 7.65 (d, 2H, J=8.084 Hz) 7.46 (m, 2H) 7.35 (m, 2H) 7.20 (m, 1H) 6.95 (m, 2H) 4.85 (s, 1H) 2.70 (m, 1H) 2.46 (m, 1H) 1.90 (m, 1H) 1.70 (m, 1H) 1.20 (d, 6H). MS (ESI, pos. ion) m/z: 437.2 (M+1).

Using the procedures described in Example 28 and reagents, starting materials and conditions known to those skilled in the art, the following compounds representative of the present invention were prepared from the corresponding vinyl derivatives:

| Cpd | Name and Data |
|---|---|
| 198 | 2-(2-{2-[2-(4-chloro-phenyl)-cyclopropyl]-1H-benzimidazol-5-yl}-phenyl)-propan-2-ol, <br> $^1$H-NMR(400MHz, CD$_3$OD) δ (ppm) 7.83-7.86(m, 1H) 7.44-7.49(bs, 1H) 7.31-7.36(m, 4H) 7.21-7.26(m, 3H) 7.055-7.13(m, 2H) 2.60-2.65(m, 1H) 2.40-2.44(m, 1H) 1.84-1.90(m, 1H) 1.62-1.70(m, 1H) 1.32(s, 6H). MS(ESI, pos. ion) m/z: 403.2(M+1). |
| 234 | 2-(2-{2-[2-(3-trifluoromethyl-phenyl)-cyclopropyl]-1H-benzimidazol-5-yl}-phenyl)-propan-2-ol <br> $^1$H-NMR(400MHz, CD3OD) δ (ppm) 7.71-7.74(dd, J=1.01, 8.08 Hz, 1H) 7.40-7.45(m, 4H) 7.33-7.38(d, J=8.34 Hz) 7.21-7.26(m, 2H) 7.08-7.13(ddd, J=1.52, 7.58 Hz, 1H) 6.99-7.02(dd, J=1.52, 8.34 Hz) 6.93-6.97(dd, J=1.52, 7.58 Hz, 1H) 2.60-2.66(m, 1H) 2.37-2.42(m, 1H) 1.78-1.84(m, 1H) 1.59-1.65(m, 1H) 1.22(s, 6H). MS(ESI, pos. ion) m/z: 437.3(M+1). |
| 467 | N-(2-{2-[2-(4-trifluoromethyl-phenyl)-cyclopropyl]-1H-benzimidazol-5-yl}-phenyl)-methanesulfonamide <br> $^1$H-NMR(400MHz, CD$_3$OD) δ (ppm) 7.52-7.62(m, 5H) 7.33-7.41(m, 4H) 7.24-7.32(m, 2H) 2.70(m, 4H) 2.48-2.53(m, 1H) 1.90-1.96(m, 1H) 1.69-1.75(m, 1H). MS(ESI, pos. ion) m/z: 472.2(M+1), |
| 472 | 2-{2-[2-(4-trifluoromethyl-phenyl)-cyclopropyl]-1H-benzimidazol-5-yl}-phenol <br> $^1$H-NMR(400MHz, CD$_3$OD) δ (ppm) 7.70(bs, 1H) 7.61(d, 2H, J=8.34 Hz) 7.51(m, 3H) 7.42(m, 3H) 7.30(m, 1H) 7.15(m, 1H) 6.93(m, 2H) 2.72(m,1H) 2.50(m, 1H) 1.93(m, 1H) 1.74(m, 1H). MS(ESI, pos. ion) m/z: 395.2(M+1), |
| 474 | (2-{2-[2-(4-trifluoromethyl-phenyl)-cyclopropyl]-1H-benzimidazol-5-yl}-phenyl)-methanol <br> $^1$H-NMR(400MHz, CD$_3$OD) δ (ppm) 7.62(m, 3H) 7.50(m, 4H) 7.35(m, 3H) 7.20(m, 1H) 4.50(s, 2H) 2.73(m, 1H) 2.52(m, 1H) 1.95(m, 1H) 1.78(m, 1H). MS(ESI, pos. ion) m/z: 409.1(M+1). |
| 494 | 2-(2-{2-[2-(4-methoxy-phenyl)-cyclopropyl]-1H-benzimidazol-5-yl}-phenyl)-propan-2-ol <br> $^1$H-NMR(400MHz, CD$_3$OD) δ (ppm) 7.83-7.86(m, 1H) 7.44-7.49(d, J=8.08 Hz, 1H) 7.34-7.40(m, 2H) 7.14-7.28(m, 3H) 7.12-7.18(m, 2H) 3.80(s, 3H) 2.60-2.65(m, 1H) 2.31-2.35(m, 1H) 1.78-1.82(m, 1H) 1.62-1.70(m, 1H) 1.34(s, 6H). MS(ESI, pos. ion) m/z: 399.1(M+1). |
| 497 | 2-(2-{2-[2-(4-trifluoromethoxy-phenyl)-cyclopropyl]-1H-benzimidazol-5-yl}-phenyl)-propan-2-ol <br> $^1$H-NMR(400MHz, DMSO d6) δ (ppm)12.30-12.40(d, 1H) 7.84-7.87(d, J=7.83 Hz, 1H) 7.45-7.48(d, J=7.83 Hz, 1H) 7.29-7.40(m, 6H) 7.17-7.23(m, 1H) 6.96-7.10(m, 2H) 2.60-2.67(m, 1H) 2.38-2.43(m, 1H) 1.81-1.86(m, 1H) 1.62-1.68(m, 1H) 1.20(s, 6H). MS(ESI, pos. ion) m/z: 453.3(M+1). |
| 498 | 2-{2-[2-(4-trifluoromethyl-phenyl)-cyclopropyl]-1H-benzimidazol-5-yl}-benzamide <br> $^1$H-NMR(400MHz, DMSO d6) δ (ppm)12.5(bs, 1H) 7.68-7.72(d, J=8.08 Hz, 2H) 7.40-7.60(m, 7H) 7.28(s, 1H) 7.21-7.25(dd, J=1.77, 8.34 Hz, 1H) 2.70-2.78(m, 1H) 2.44-2.53(m, 1H) 1.90-1.99(m, 1H) 1.70-1.80(m, 1H). MS (ESI, pos. ion) m/z: 422.2(M+1). |
| 499 | N-tert-butyl-2-{2-[2-(4-trifluoromethyl-phenyl)-cyclopropyl]-1H-benzimidazol-5-yl}-benzenesulfonamide <br> $^1$H-NMR(400MHz, DMSO d6) δ (ppm) 12.40(s, 1H)8.2-8.3(d, J=9.34 Hz, 1H) 7.30-7.70(m, 9H) 7.10-7.15(m, 1H) 6.28-6.32(m, 1H) 2.64-2.72(m, 1H) 1.90-1.94(m, 1H) 1.70-1.75(m, 1H) 0.90(s, 9H). MS(ESI, pos. ion) m/z: 514.2(M+1). |
| 500 | 5-(2-methanesulfonyl-phenyl)-2-[2-(4-trifluoromethyl-phenyl)-cyclopropyl]-1H-benzimidazole <br> $^1$H-NMR(400MHz, DMSO d6) δ (ppm) 8.12-8.15(dd, J=1.26, 7.83 Hz, 1H) 7.70-7.83(m, 6H) 7.53-7.57(d, J=8.08 Hz, 2H) 7.42-7.47(ddd, J=1.26, 7.32 Hz, 2H) 2.93-3.00(m, 1H) 2.66-2.74(m, 1H) 2.06-2.13(m, 1H) 1.97-2.03(m, 1H). MS(ESI, pos. ion) m/z: 457.1(M+1). |

PROPHETIC EXAMPLE 29

Using the procedures of Examples 27 or 28, and reagents, starting materials and conditions known to those skilled in the art, the following prophetic compounds representative of the present invention may be prepared.

| Cpd | Name and Data |
|---|---|
| 189 | 2-{2-[2-(4-trifluoromethoxy-phenyl)-cyclopropyl]-1H-benzimidazol-5-yl}-benzenesulfonamide, |
| 191 | 2-{2-[2-(4-trifluoromethanesulfonyl-phenyl)-cyclopropyl]-1H-benzimidazol-5-yl}-benzenesulfonamide, |
| 192 | C,C,C-trifluoro-N-(2-{2-[2-(4-trifluoromethoxy-phenyl)-cyclopropyl]-1H-benzimidazol-5-yl}-phenyl)-methanesulfonamide, |
| 193 | C,C,C-trifluoro-N-(2-{2-[2-(4-trifluoromethyl-phenyl)-cyclopropyl]-1H-benzimidazol-5-yl}-phenyl)-methanesulfonamide, |
| 194 | C,C,C-trifluoro-N-(2-{2-[2-(4-trifluoromethanesulfonyl-phenyl)-cyclopropyl]-1H-benzimidazol-5-yl}-phenyl)-methanesulfonamide, |
| 195 | 1-(2-{2-[2-(4-chloro-phenyl)-cyclopropyl]-1H-benzimidazol-5-yl}-phenyl)-ethanone, |
| 196 | 1-(2-{2-[2-(4-chloro-phenyl)-cyclopropyl]-1H-benzimidazol-5-yl}-phenyl)-ethanol, |
| 197 | N-(2-{2-[2-(4-chloro-phenyl)-cyclopropyl]-1H-benzimidazol-5-yl}-phenyl)-methanesulfonamide, |
| 199 | 2-{2-[2-(4-chloro-phenyl)-cyclopropyl]-1H-benzimidazol-5-yl}-benzenesulfonamide, |
| 200 | N-(2-{2-[2-(4-chloro-phenyl)-cyclopropyl]-1H-benzimidazol-5-yl}-phenyl)-C,C,C-trifluoro-methanesulfonamide, |
| 201 | 1-(2-{2-[2-(4-methanesulfonyl-phenyl)-cyclopropyl]-1H-benzimidazol-5-yl}-phenyl)-ethanone, |
| 202 | 1-(2-{2-[2-(4-methanesulfonyl-phenyl)-cyclopropyl]-1H-benzimidazol-5-yl}-phenyl)-ethanol, |
| 203 | N-(2-{2-[2-(4-methanesulfonyl-phenyl)-cyclopropyl]-1H-benzimidazol-5-yl}-phenyl)-methanesulfonamide, |
| 204 | 2-(2-{2-[2-(4-methanesulfonyl-phenyl)-cyclopropyl]-1H-benzimidazol-5-yl}-phenyl)-propan-2-ol, |
| 205 | 2-{2-[2-(4-methanesulfonyl-phenyl)-cyclopropyl]-1H-benzimidazol-5-yl}-benzenesulfonamide, |
| 206 | C,C,C-trifluoro-N-(2-{2-[2-(4-methanesulfonyl-phenyl)-cyclopropyl]-1H-benzimidazol-5-yl}-phenyl)-methanesulfonamide, |
| 207 | 1-[2-(2-{2-[4-(2,2,2-trifluoro-1-trifluoromethyl-ethoxy)-phenyl]-cyclopropyl}-1H-benzimidazol-5-yl)-phenyl]-ethanone, |
| 208 | 1-[2-(2-{2-[4-(2,2,2-trifluoro-1-trifluoromethyl-ethoxy)-phenyl]-cyclopropyl}-1H-benzimidazol-5-yl)-phenyl]-ethanol, |
| 209 | N-[2-(2-{2-[4-(2,2,2-trifluoro-1-trifluoromethyl-ethoxy)-phenyl]-cyclopropyl}-1H-benzimidazol-5-yl)-phenyl]-methanesulfonamide, |
| 210 | 2-[2-(2-{2-[4-(2,2,2-trifluoro-1-trifluoromethyl-ethoxy)-phenyl]-cyclopropyl}-1H-benzimidazol-5-yl)-phenyl]-propan-2-ol, |
| 211 | 2-(2-{2-[4-(2,2,2-trifluoro-1-trifluoromethyl-ethoxy)-phenyl]-cyclopropyl}-1H-benzimidazol-5-yl)-benzenesulfonamide, |
| 212 | C,C,C-trifluoro-N-[2-(2-{2-[4-(2,2,2-trifluoro-1-trifluoromethyl-ethoxy)-phenyl]-cyclopropyl}-1H-benzimidazol-5-yl)-phenyl]-methanesulfonamide, |
| 213 | 1-[2-(2-{2-[4-(2,2,2-trifluoro-ethoxy)-phenyl]-cyclopropyl}-1H-benzimidazol-5-yl)-phenyl]-ethanone, |
| 214 | 1-[2-(2-{2-[4-(2,2,2-trifluoro-ethoxy)-phenyl]-cyclopropyl}-1H-benzimidazol-5-yl)-phenyl]-ethanol, |
| 215 | N-[2-(2-{2-[4-(2,2,2-trifluoro-ethoxy)-phenyl]-cyclopropyl}-1H-benzimidazol-5-yl)-phenyl]-methanesulfonamide, |
| 216 | 2-[2-(2-{2-[4-(2,2,2-trifluoro-ethoxy)-phenyl]-cyclopropyl}-1H-benzimidazol-5-yl)-phenyl]-propan-2-ol, |
| 217 | 2-(2-{2-[4-(2,2,2-trifluoro-ethoxy)-phenyl]-cyclopropyl}-1H-benzimidazol-5-yl)-benzenesulfonamide, |
| 218 | C,C,C-trifluoro-N-[2-(2-{2-[4-(2,2,2-trifluoro-ethoxy)-phenyl]-cyclopropyl}-1H-benzimidazol-5-yl)-phenyl]-methanesulfonamide, |
| 219 | 1-[2-(2-{2-[4-(2,2,3,3,3-pentafluoro-propoxy)-phenyl]-cyclopropyl}-1H-benzimidazol-5-yl)-phenyl]-ethanone, |
| 220 | 1-[2-(2-{2-[4-(2,2,3,3,3-pentafluoro-propoxy)-phenyl]-cyclopropyl}-1H-benzimidazol-5-yl)-phenyl]-ethanol, |
| 221 | N-[2-(2-{2-[4-(2,2,3,3,3-pentafluoro-propoxy)-phenyl]-cyclopropyl}-1H-benzimidazol-5-yl)-phenyl]-methanesulfonamide, |
| 222 | 2-[2-(2-{2-[4-(2,2,3,3,3-pentafluoro-propoxy)-phenyl]-cyclopropyl}-1H-benzimidazol-5-yl)-phenyl]-propan-2-ol, |
| 223 | 2-(2-{2-[4-(2,2,3,3,3-pentafluoro-propoxy)-phenyl]-cyclopropyl}-1H-benzimidazol-5-yl)-benzenesulfonamide, |
| 224 | C,C,C-trifluoro-N-[2-(2-{2-[4-(2,2,3,3,3-pentafluoro-propoxy)-phenyl]-cyclopropyl}-1H-benzimidazol-5-yl)-phenyl]-methanesulfonamide, |
| 225 | 1-(2-{2-[2-(3-chloro-phenyl)-cyclopropyl]-1H-benzimidazol-5-yl}-phenyl)-ethanone, |

| Cpd | Name and Data |
|---|---|
| 226 | 1-(2-{2-[2-(3-chloro-phenyl)-cyclopropyl]-1H-benzimidazol-5-yl}-phenyl)-ethanol, |
| 227 | N-(2-{2-[2-(3-chloro-phenyl)-cyclopropyl]-1H-benzimidazol-5-yl}-phenyl)-methanesulfonamide, |
| 228 | 2-(2-{2-[2-(3-chloro-phenyl)-cyclopropyl]-1H-benzimidazol-5-yl}-phenyl)-propan-2-ol, |
| 229 | 2-{2-[2-(3-chloro-phenyl)-cyclopropyl]-1H-benzimidazol-5-yl}-benzenesulfonamide, |
| 230 | N-(2-{2-[2-(3-chloro-phenyl)-cyclopropyl]-1H-benzimidazol-5-yl}-phenyl)-C,C,C-trifluoro-methanesulfonamide, |
| 231 | 1-(2-{2-[2-(3-trifluoromethyl-phenyl)-cyclopropyl]-1H-benzimidazol-5-yl}-phenyl)-ethanone, |
| 232 | 1-(2-{2-[2-(3-trifluoromethyl-phenyl)-cyclopropyl]-1H-benzimidazol-5-yl}-phenyl)-ethanol, |
| 233 | N-(2-{2-[2-(3-trifluoromethyl-phenyl)-cyclopropyl]-1H-benzimidazol-5-yl}-phenyl)-methanesulfonamide, |
| 235 | 2-{2-[2-(3-trifluoromethyl-phenyl)-cyclopropyl]-1H-benzimidazol-5-yl}-benzenesulfonamide, |
| 236 | C,C,C-trifluoro-N-(2-{2-[2-(3-trifluoromethyl-phenyl)-cyclopropyl]-1H-benzimidazol-5-yl}-phenyl)-methanesulfonamide, |
| 237 | N-(4-{2-[5-(2-acetyl-phenyl)-1H-benzimidazol-2-yl]-cyclopropyl}-phenyl)-methanesulfonamide, |
| 238 | N-[4-(2-{5-[2-(1-hydroxy-ethyl)-phenyl]-1H-benzimidazol-2-yl}-cyclopropyl)-phenyl]-methanesulfonamide, |
| 239 | N-(2-{2-[2-(4-methanesulfonylamino-phenyl)-cyclopropyl]-1H-benzimidazol-5-yl}-phenyl)-methanesulfonamide, |
| 240 | N-[4-(2-{5-[2-(1-hydroxy-1-methyl-ethyl)-phenyl]-1H-benzimidazol-2-yl}-cyclopropyl)-phenyl]-methanesulfonamide, |
| 241 | 2-{2-[2-(4-methanesulfonylamino-phenyl)-cyclopropyl]-1H-benzimidazol-5-yl}-benzenesulfonamide, |
| 242 | C,C,C-trifluoro-N-(2-{2-[2-(4-methanesulfonylamino-phenyl)-cyclopropyl]-1H-benzimidazol-5-yl}-phenyl)-methanesulfonamide, |
| 243 | N-(4-{2-[5-(2-acetyl-phenyl)-1H-benzimidazol-2-yl]-cyclopropyl}-phenyl)-C,C,C-trifluoro-methanesulfonamide, |
| 244 | C,C,C-trifluoro-N-[4-(2-{5-[2-(1-hydroxy-ethyl)-phenyl]-1H-benzimidazol-2-yl}-cyclopropyl)-phenyl]-methanesulfonamide, |
| 245 | C,C,C-trifluoro-N-(4-{2-[5-(2-methanesulfonylamino-phenyl)-1H-benzimidazol-2-yl]-cyclopropyl}-phenyl)-methanesulfonamide, |
| 246 | C,C,C-trifluoro-N-[4-(2-{5-[2-(1-hydroxy-1-methyl-ethyl)-phenyl]-1H-benzimidazol-2-yl}-cyclopropyl)-phenyl]-methanesulfonamide, |
| 247 | 2-{2-[2-(4-trifluoromethanesulfonylamino-phenyl)-cyclopropyl]-1H-benzimidazol-5-yl}-benzenesulfonamide, and |
| 248 | C,C,C-trifluoro-N-(2-{2-[2-(4-trifluoromethanesulfonylamino-phenyl)-cyclopropyl]-1H-benzimidazol-5-yl}-phenyl)-methanesulfonamide. |

EXAMPLE 30

2-[2-(2-phenylethynyl-1H-benzimidazol-5-yl)-phenyl]-propan-2-ol (Cpd 489)

Step A. (E)-5-bromo-2-(2-chloro-2-phenyl-vinyl)-1H-benzimidazole

A mixture of 4-bromo-benzene-1,2-diamine dihydrochloride (1.3 g, 5 mmol), phenylpropiolic acid (0.73 g, 5 mmol) in 4 mL of ethylene glycol was heated to reflux for 5 h. The mixture was cooled to rt and poured into water. The mixture was neutralized with 2N sodium hydroxide and filtered. The solid was suspended in water and extracted with ethyl acetate. The organic layers were combined, dried with anhydrous sodium sulfate, and filtered. The filtrate was concentrated to yield a red oil. The residue was purified using preative TLC plates twice (silica gel, 20×20 cm, 2000 microns, EtOAc:hexanes 3:7 and silica gel, 20×20 cm, 2000 microns, EtOAc:dichloromethane 3:97) to provide a mixture of cis and trans isomers of the title Compound 30a (0.345 g). $^1$H NMR (400 MHz, DMSO-$d_6$) δ (ppm): 12.59 (m, 1H), 7.86-7.78 (m, 3H), 7.64-7.56 (m, 1H), 7.54-7.49 (m, 3H), 7.46 (s, 1H), 7.40-7.34 (m, 1H). Mass Spectrum (LCMS, APCl pos.) Calcd. For $C_{15}H_{10}BrClN_2$:333.0 (M+H), Found 333.1.

Step B. 2-[2-(2-phenylethynyl-1H-benzimidazol-5-yl)-phenyl]-propan-2-ol

A mixture of Compound 30a (25 mg, 0.075 mmol), Compound 10e (18 mg, 0.113 mmol) and Pd(dppf)Cl$_2$CH$_2$Cl$_2$ (12 mg, 0.015 mmol) in 3 mL of DME and sodium carbonate solution (1.0 M, 0.6 mL) was heated at 150° C. for 1 h in a Biotage Initiator™ microwave synthesizer. The mixture was filtered through a pad of silica gel. The reaction was repeated total three times. The residues were combined and purified using preative TLC plates twice (silica gel, 20×20 cm, 2000 microns, EtOAc:hexanes 3:7 and then silica gel, 20×20 cm, 2000 microns, EtOAc:hexanes:methanol 2:8:1) to provide the title Compound 489 (8.4 mg). $^1$H NMR (400 MHz, CD$_3$OD) δ (ppm): 7.78 (dd, 1H, J=8.1, 1.1 Hz, 1H), 7.62-7.60 (m, 2H), 7.52 (d, 1H, J=8.3 Hz), 7.46-7.38 (m, 4H), 7.31 (dt, 1H, J=1.5, 8.0 Hz), 7.21-7.17 (m, 2H), 7.02 (dd, J=7.5, 1.3 Hz, 1H), 1.30 (s, 6H). Mass Spectrum (LCMS, APCl pos.) Calcd. For $C_{24}H_{20}N_2O$: 353.2 (M+H), Found 353.3.

EXAMPLE 31

2-(2-phenylethynyl-1H-benzimidazol-5-yl)-benzenesulfonamide (Cpd 490)

Step A. N-tert-butyl-2-(2-phenylethynyl-1H-benzimidazol-5-yl)-benzenesulfonamide A mixture of Compound 30a (25 mg, 0.075 mmol), 2-(tert-butylamino)sulfonylphenyl boronic acid (29 mg, 0.113 mmol), and Pd(dppf)Cl$_2$.CH$_2$Cl$_2$ (12 mg, 0.015 mmol) in 3 mL of DME and sodium carbonate solution (1.0 M, 0.6 mL) was heated at 150° C. for 1 h in a Biotage Initiator™ microwave synthesizer. The mixture was filtered through a pad silica gel. The residue was purified by preative TLC (silica gel, 20×20 cm, 2000 microns, EtOAc:hexanes 3:7) to provide the title Compound 31a (12.8 mg). Mass Spectrum (LCMS, APCl pos.) Calcd. For C$_{25}$H$_{23}$N$_3$O$_2$S: 430.2 (M+H), Found 430.3.

Step B. 2-(2-phenylethynyl-1H-benzimidazol-5-yl)-benzenesulfonamide

A mixture of Compound 31a (14.9 mg, 0.034 mmol) in trifluoroacetic acid and 1,2-dichloroethane (2 mL, 1:1) was heated at 90° C. for 3 h. The reaction was cooled to rt, and concentrated under reduced pressure. The residue was dissolved in dichloromethane, and washed with saturated sodium bicarbonate solution. The aqueous layer was extracted twice with ethyl acetate. The organic layers were combined, dried with anhydrous magnesium sulfate, filtered, and the filtrate was removed under reduced pressure. The residue was purified using preative TLC plates (silica gel, 20×20 cm, 2000 microns, EtOAc:hexanes:methanol 5:5:1) to provide the title Compound 490 (12.1 mg). $^1$H NMR (400 MHz, CD$_3$OD) δ (ppm): 8.11 (dd, 1H, J=8.0, 1.2 Hz), 7.67-7.56 (m, 5H), 7.52 (ddd, 1H, J=7.6, 6.4, 1.4 Hz), 7.48-7.33 (m, 5H). Mass Spectrum (LCMS, ESI pos.) Calcd. For C$_{21}$H$_{15}$N$_3$O$_2$S: 374.1 (M+H), Found 374.2.

Using the procedures described in Examples 30 and 31, and reagents, starting materials and conditions known to those skilled in the art, the following compounds representative of the present invention were prepared from the corresponding vinyl derivatives:

| Cpd | Name and Data |
|---|---|
| 250 | 2-[2-(4-trifluoromethyl-phenylethynyl)-1H-benzimidazol-5-yl]-benzenesulfonamide<br>$^1$H NMR(400MHz, CD$_3$OD) δ (ppm): 8.04(dd, 1H, J=8.0, 1.2 Hz), 7.76(d, J2H,=8.2 Hz), 7.69(d, 2H, J=8.2 Hz), 7.58-7.53(m, 2H), 7.54(dt, 1H, J=1.4, 7.5 Hz), 7.46(dt, 1H, J=1.4, 7.7 Hz), 7.31(dd, 1H, J=7.5, 1.3 Hz), 7.30(dd, 1H, J=8.4, 0.9 Hz). Mass Spectrum(LCMS, ESI pos.) Calcd. For C$_{22}$H$_{14}$F$_3$N$_3$O$_2$S: 442.1(M+H), Found 442.2. |
| 294 | 2-{2-[2-(3-trifluoromethyl-phenylethynyl)-1H-benzimidazol-5-yl]-phenyl}-propan-2-ol<br>$^1$H NMR(400MHz, CD$_3$OD) δ (ppm): 7.94(s, 1H), 7.89(d, 1H, J=7.7 Hz), 7.80-7.74(m, 2H), 7.66(t, 1H, J=7.8 Hz, 1H), 7.60-7.39(m, 2H), 7.33(m, 1H), 7.28-7.18(m, 2H), 7.04(dd, 1H, J=7.5, 1.4 Hz, 1H), 1.32(s, 6H). Mass Spectrum(LCMS, ESI pos.) Calcd. For C$_{25}$H$_{19}$F$_3$N$_2$O: 421.1(M+H), Found 421.3. |
| 295 | 2-[2-(3-trifluoromethyl-phenylethynyl)-1H-benzimidazol-5-yl]-benzenesulfonamide<br>$^1$H NMR(400MHz, CD$_3$OD) δ (ppm): 8.11(dd, 1H, J=8.0, 1.2 Hz), 7.94(s, 1H), 7.89(dm, 1H, J=7.6 Hz), 7.77(dm, 1H, J=7.9 Hz), 7.67-7.58(m, 4H), 7.52(m, 1H), 7.38(dd, J=7.5, 1.3 Hz, 1H), 7.37(br s, 1H). Mass Spectrum(LCMS, ESI pos.) Calcd. For C$_{22}$H$_{14}$F$_3$N$_3$O$_2$S: 442.1(M+H), Found 442.2 |
| 492 | 2-{2-[2-(4-trifluoromethyl-phenylethynyl)-1H-benzimidazol-5-yl]-phenyl}-propan-2-ol<br>$^1$H NMR(400MHz, CD$_3$OD) δ (ppm): 7.83(d, 2H, J=8.2 Hz), 7.79(dd, 1H, J=8.2 1.1 Hz, 1H), 7.76(d, 2H, J=8.3 Hz), 7.64-7.37(m, 2H), 7.33(m, 1H), 7.22(br d, 1H, J=7.2 Hz), 7.20(dt, 1H, J=1.3, 7.4 Hz), 7.04(dd, 1H, J=7.5, 1.4 Hz), 1.32(s, 6H). Mass Spectrum(LCMS, ESI pos.) Calcd. For C$_{25}$H$_{19}$F$_3$N$_2$O: 421.1(M+H), Found 421.3.<br>Preparation of (4-trifluoromethylphenyl)propynoic acid. To a solution of 4-ethynyl-α,α,α-trifluorotoluene (5 g, 29 mmol) in anhydrous THF (25 mL), was slowly added n-butyllithium 2.6M in hexanes (14.5 mL, 47 mmol). The mixture was stirred at −78° C. for 30 min and then at 0° C. for an additional 30 min. The mixture was cooled to −78° C. and transferred via a cannula to a saturated solution of carbon dioxide in anhydrous THF (25 mL) at −78° C. The mixture was stirred and allowed to warm to rt over 18 h. The mixture was quenched with saturated sodium chloride solution, and the two layers were separated. The aqueous layer was washed with hexanes and then acidified with 2 N hydrochloric acid. The aqueous layer was extracted twice with ethyl acetate. The organic layers were combined and dried with anhydrous sodium sulfate and magnesium sulfate. The mixture was filtered and the filtrate was concentrated under reduced pressure to yield the title Compound 31b as a white solid (5.4 g, 87%). $^1$H NMR (400MHz, DMSO-d$_6$) δ (ppm): 7.81(s, 4H). Compound 31b was carried forward using the procedure of Example 31 to provide the title Compound 492. |

PROPHETIC EXAMPLE 32

Using the procedures of Examples 30 or 31, the corresponding bromobenzimidazole and, when not commercially available, the arylacetylenic acid precursors prepared as described in Reaction Scheme KK and reagents, starting materials and conditions known to those skilled in the art, the following prophetic compounds representative of the present invention may be prepared. Alternatively, the following compounds may be prepared from their corresponding vinyl compounds by hydrogenation:

| Cpd | Name and Data |
|---|---|
| 249 | 2-[2-(4-trifluoromethoxy-phenylethynyl)-1H-benzimidazol-5-yl]-benzenesulfonamide, |
| 251 | 2-[2-(4-trifluoromethanesulfonyl-phenylethynyl)-1H-benzimidazol-5-yl]-benzenesulfonamide, |
| 252 | C,C,C-trifluoro-N-{2-[2-(4-trifluoromethoxy-phenylethynyl)-1H-benzimidazol-5-yl]-phenyl}-methanesulfonamide, |
| 253 | C,C,C-trifluoro-N-{2-[2-(4-trifluoromethyl-phenylethynyl)-1H-benzimidazol-5-yl]-phenyl}-methanesulfonamide, |
| 254 | C,C,C-trifluoro-N-{2-[2-(4-trifluoromethanesulfonyl-phenylethynyl)-1H-benzimidazol-5-yl]-phenyl}-methanesulfonamide, |
| 255 | 1-{2-[2-(4-chloro-phenylethynyl)-1H-benzimidazol-5-yl]-phenyl}-ethanone, |
| 256 | 1-{2-[2-(4-chloro-phenylethynyl)-1H-benzimidazol-5-yl]-phenyl}-ethanol, |
| 257 | N-{2-[2-(4-chloro-phenylethynyl)-1H-benzimidazol-5-yl]-phenyl}-methanesulfonamide, |
| 258 | 2-{2-[2-(4-chloro-phenylethynyl)-1H-benzimidazol-5-yl]-phenyl}-propan-2-ol, |
| 259 | 2-[2-(4-chloro-phenylethynyl)-1H-benzimidazol-5-yl]-benzenesulfonamide, |
| 260 | N-{2-[2-(4-chloro-phenylethynyl)-1H-benzimidazol-5-yl]-phenyl}-C,C,C-trifluoro-methanesulfonamide, |
| 261 | 1-{2-[2-(4-methanesulfonyl-phenylethynyl)-1H-benzimidazol-5-yl]-phenyl}-ethanone, |
| 262 | 1-{2-[2-(4-methanesulfonyl-phenylethynyl)-1H-benzimidazol-5-yl]-phenyl}-ethanol, |
| 263 | N-{2-[2-(4-methanesulfonyl-phenylethynyl)-1H-benzimidazol-5-yl]-phenyl}-methanesulfonamide, |
| 264 | 2-{2-[2-(4-methanesulfonyl-phenylethynyl)-1H-benzimidazol-5-yl]-phenyl}-propan-2-ol, |
| 265 | 2-[2-(4-methanesulfonyl-phenylethynyl)-1H-benzimidazol-5-yl]-benzenesulfonamide, |
| 266 | C,C,C-trifluoro-N-{2-[2-(4-methanesulfonyl-phenylethynyl)-1H-benzimidazol-5-yl]-phenyl}-methanesulfonamide, |
| 267 | 1-(2-{2-[4-(2,2,2-trifluoro-1-trifluoromethyl-ethoxy)-phenylethynyl]-1H-benzimidazol-5-yl}-phenyl)-ethanone, |
| 268 | 1-(2-{2-[4-(2,2,2-trifluoro-1-trifluoromethyl-ethoxy)-phenylethynyl]-1H-benzimidazol-5-yl}-phenyl)-ethanol, |
| 269 | N-(2-{2-[4-(2,2,2-trifluoro-1-trifluoromethyl-ethoxy)-phenylethynyl]-1H-benzimidazol-5-yl}-phenyl)-methanesulfonamide, |
| 270 | 2-(2-{2-[4-(2,2,2-trifluoro-1-trifluoromethyl-ethoxy)-phenylethynyl]-1H-benzimidazol-5-yl}-phenyl)-propan-2-ol, |
| 271 | 2-{2-[4-(2,2,2-trifluoro-1-trifluoromethyl-ethoxy)-phenylethynyl]-1H-benzimidazol-5-yl}-benzenesulfonamide, |
| 272 | C,C,C-trifluoro-N-(2-{2-[4-(2,2,2-trifluoro-1-trifluoromethyl-ethoxy)-phenylethynyl]-1H-benzimidazol-5-yl}-phenyl)-methanesulfonamide, |
| 273 | 1-(2-{2-[4-(2,2,2-trifluoro-ethoxy)-phenylethynyl]-1H-benzimidazol-5-yl}-phenyl)-ethanone, |
| 274 | 1-(2-{2-[4-(2,2,2-trifluoro-ethoxy)-phenylethynyl]-1H-benzimidazol-5-yl}-phenyl)-ethanol, |
| 275 | N-(2-{2-[4-(2,2,2-trifluoro-ethoxy)-phenylethynyl]-1H-benzimidazol-5-yl}-phenyl)-methanesulfonamide, |
| 276 | 2-(2-{2-[4-(2,2,2-trifluoro-ethoxy)-phenylethynyl]-1H-benzimidazol-5-yl}-phenyl)-propan-2-ol, |
| 277 | 2-{2-[4-(2,2,2-trifluoro-ethoxy)-phenylethynyl]-1H-benzimidazol-5-yl}-benzenesulfonamide, |
| 278 | C,C,C-trifluoro-N-(2-{2-[4-(2,2,2-trifluoro-ethoxy)-phenylethynyl]-1H-benzimidazol-5-yl}-phenyl)-methanesulfonamide, |
| 279 | 1-(2-{2-[4-(2,2,3,3,3-pentafluoro-propoxy)-phenylethynyl]-1H-benzimidazol-5-yl}-phenyl)-ethanone, |
| 280 | 1-(2-{2-[4-(2,2,3,3,3-pentafluoro-propoxy)-phenylethynyl]-1H-benzimidazol-5-yl}-phenyl)-ethanol, |
| 281 | N-(2-{2-[4-(2,2,3,3,3-pentafluoro-propoxy)-phenylethynyl]-1H-benzimidazol-5-yl}-phenyl)-methanesulfonamide, |
| 282 | 2-(2-{2-[4-(2,2,3,3,3-pentafluoro-propoxy)-phenylethynyl]-1H-benzimidazol-5-yl}-phenyl)-propan-2-ol, |
| 283 | 2-{2-[4-(2,2,3,3,3-pentafluoro-propoxy)-phenylethynyl]-1H-benzimidazol-5-yl}-benzenesulfonamide, |
| 284 | C,C,C-trifluoro-N-(2-{2-[4-(2,2,3,3,3-pentafluoro-propoxy)-phenylethynyl]-1H-benzimidazol-5-yl}-phenyl)-methanesulfonamide, |
| 285 | 1-{2-[2-(3-chloro-phenylethynyl)-1H-benzimidazol-5-yl]-phenyl}-ethanone, |

-continued

| Cpd | Name and Data |
|---|---|
| 286 | 2-{2-[2-(3-chloro-phenylethynyl)-1H-benzimidazol-5-yl]-phenyl}-propan-2-ol, |
| 287 | N-{2-[2-(3-chloro-phenylethynyl)-1H-benzimidazol-5-yl]-phenyl}-methanesulfonamide, |
| 288 | 1-{2-[2-(3-chloro-phenylethynyl)-1H-benzimidazol-5-yl]-phenyl}-ethanol, |
| 289 | 2-[2-(3-chloro-phenylethynyl)-1H-benzimidazol-5-yl]-benzenesulfonamide, |
| 290 | N-{2-[2-(3-chloro-phenylethynyl)-1H-benzimidazol-5-yl]-phenyl}-C,C,C-trifluoro-methanesulfonamide, |
| 291 | 1-{2-[2-(3-trifluoromethyl-phenylethynyl)-1H-benzimidazol-5-yl]-phenyl}-ethanone, |
| 292 | 1-{2-[2-(3-trifluoromethyl-phenylethynyl)-1H-benzimidazol-5-yl]-phenyl}-ethanol, |
| 293 | N-{2-[2-(3-trifluoromethyl-phenylethynyl)-1H-benzimidazol-5-yl]-phenyl}-methanesulfonamide, |
| 296 | C,C,C-trifluoro-N-{2-[2-(3-trifluoromethyl-phenylethynyl)-1H-benzimidazol-5-yl]-phenyl}-methanesulfonamide, |
| 297 | N-{4-[5-(2-acetyl-phenyl)-1H-benzimidazol-2-yl-ethynyl]-phenyl}-methanesulfonamide, |
| 298 | N-(4-{5-[2-(1-hydroxy-ethyl)-phenyl]-1H-benzimidazol-2-yl-ethynyl}-phenyl)-methanesulfonamide, |
| 299 | N-{2-[2-(4-methanesulfonylamino-phenylethynyl)-1H-benzimidazol-5-yl]-phenyl}-methanesulfonamide, |
| 300 | N-(4-{5-[2-(1-hydroxy-1-methyl-ethyl)-phenyl]-1H-benzimidazol-2-yl-ethynyl}-phenyl)-methanesulfonamide, |
| 301 | 2-[2-(4-methanesulfonylamino-phenylethynyl)-1H-benzimidazol-5-yl]-benzenesulfonamide, |
| 302 | C,C,C-trifluoro-N-{2-[2-(4-methanesulfonylamino-phenylethynyl)-1H-benzimidazol-5-yl]-phenyl}-methanesulfonamide, |
| 303 | N-{4-[5-(2-acetyl-phenyl)-1H-benzimidazol-2-yl-ethynyl]-phenyl}-C,C,C-trifluoro-methanesulfonamide, |
| 304 | C,C,C-trifluoro-N-(4-{5-[2-(1-hydroxy-ethyl)-phenyl]-1H-benzimidazol-2-yl-ethynyl}-phenyl)-methanesulfonamide, |
| 305 | C,C,C-trifluoro-N-{4-[5-(2-methanesulfonylamino-phenyl)-1H-benzimidazol-2-yl-ethynyl]-phenyl}-methanesulfonamide, |
| 306 | C,C,C-trifluoro-N-(4-{5-[2-(1-hydroxy-1-methyl-ethyl)-phenyl]-1H-benzimidazol-2-yl-ethynyl}-phenyl)-methanesulfonamide, |
| 307 | 2-[2-(4-trifluoromethanesulfonylamino-phenylethynyl)-1H-benzimidazol-5-yl]-benzenesulfonamide, and |
| 308 | C,C,C-trifluoro-N-{2-[2-(4-trifluoromethanesulfonylamino-phenylethynyl)-1H-benzimidazol-5-yl]-phenyl}-methanesulfonamide. |

EXAMPLE 33

(E)-2-{2-[2-(2-quinolin-6-yl-vinyl)-1H-benzimidazol-5-yl]-phenyl}-propan-2-ol(Cpd. 449)

Step A. 5-bromo-2-chloromethyl-1H-benzimidazole

A mixture of 4-bromo-benzene-1,2-diamine (200 mg, 1.07 mmol) and 2-chloroacetimidic acid ethyl ester hydrochloride salt (168 mg, 1.07 mmol; prepared according to the procedure described in J. Med. Chem. 1986, 29, 2280) in anhydrous ethanol (200 proof, 5 mL) was stirred at room temperature for 4 h. The reaction mixture was concentrated under reduced pressure and extracted with ethyl acetate and water. The organic layer was dried over $Na_2SO_4$, filtered, and the filtrate was concentrated in vacuo to provide the title Compound 33a as an off-white solid (240 mg, 92% yield). $^1$H NMR (400MHz, $CDCl_3$) δ (ppm): 7.75 (d, 1H, J=1.4 Hz), 7.47 (d, 1H, J=8.6 Hz), 7.42 (dd, 1H, J=8.6 Hz, J=1.3 Hz), 4.84 (s, 2H) Mass Spectrum (LCMS, ESI pos.) Calcd. For $C_{18}H_{20}ClN_3O_2S$: 247.50 (M+H), Found 247.0.

Step B. (5-bromo-1H-benzimidazol-2-ylmethyl)-triphenyl-phosphonium chloride

A mixture of Compound 33a (240 mg, 0.98 mmol) and triphenylphosphine (385 mg, 1.47 mmol), in 1,2-dichloroethane (10 mL) was heated at 140° C. for 1 h. The reaction mixture was concentrated under reduced pressure to provide the title Compound 33b, which was used in the next step without further purification.

Step C. (E)-6-[2-(5-bromo-1H-benzimidazol-2-yl)-vinyl]-quinoline

A mixture of Compound 33b (100 mg, 0.204 mmol), 6-quinolinecarboxaldehyde (32 mg, 0.29 mmol) and DBU (39.6 uL, 0.265 mmol) in ethanol:tetrahydrofuran (1:1, 2 mL) was stirred at room temperature for 12 h. The reaction mixture was concentrated under reduced pressure, and the residue was purified by reverse phase preative HPLC (10-100% gradient acetonitrile/water over 10 min) to provide the title Compound 33c as an off-white solid (50 mg, 72% yield). Calcd. For $C_{18}H_{12}BrN_3$:350.21 (M+H), Found 350.2.

Step D. (E)-2-{2-[2-(2-quinolin-6-yl-vinyl)-1H-benzimidazol-5-yl]-phenyl}-propan-2-ol A mixture of Compound 33c (50.0 mg, 0.143 mmol), Compound 10e (46 mg, 0.29 mmol), $PdCl_2$(dppf) (23.4 mg, 0.029 mmol) and 1M sodium bicarbonate solution (1.15 mL, 1.15 mmol) in 1,2-dimethoxyethane (1 mL) was heated at reflux for 12 h. The reaction mixture was concentrated under reduced pressure. The residue was purified by chromatography (silica, EtOAc) to provide the title Compound 449 as an off-white solid (11.8 mg, 20% yield). $^1$H NMR (400 MHz, CD$_3$OD) δ (ppm): 9.01 (br s, 1H), 8.68 (d, 1H, J=8.1 Hz), 8.35 (m, 2H), 8.12-8.21 (m, 2H), 7.76 (m, 3H), 7.67 (s, 1H), 7.53 (m, 2H), 7.38-7.43 (m, 1H), 7.28 (m, 1H), 7.09 (m, 1H), 1.42 (s, 6H). Calcd. For C$_{27}$H$_{23}$N$_3$O: 406.5 (M+H), Found 406.3.

Using the procedures described in Example 33 and reagents, starting materials and conditions known to those skilled in the art, the following compounds representative of the present invention were prepared:

EXAMPLE 34

2-{2-[2-(4-trifluoromethyl-phenyl)-ethyl]-1H-benzimidazol-5-yl}-benzylamine (Cpd 486)

Step A. (E)-2-{2-[2-(4-trifluoromethyl-phenyl)-vinyl]-1H-benzimidazol-5-yl}-benzonitrile A mixture of Compound 10c (52 mg, 0.14 mmol), 2-cyanophenylboronic acid (38 mg, 0.26 mmol), Pd(dppf)

| Cpd | Name and Data |
|---|---|
| 448 | (E)-1-[4-(2-{5-[2-(1-hydroxy-1-methyl-ethyl)-phenyl]-1H-benzimidazol-2-yl}-vinyl)-phenyl]-ethanone<br>The title compound was prepared from Compound 33b (100 mg, 0.204 mmol) and 4-acetylbenzaldehyde (30.2 mg, 0.204 mmol) as an off-white solid (3.75 mg, 10% yield). $^1$H NMR(400MHz, CD$_3$OD) δ (ppm): 8.06(d, 1H, J=8.8 Hz), 7.96(m, 1H), 7.80(m, 3H), 7.68(m, 1H), 7.55(m, 1H), 7.43(m, 1H), 7.34(m, 2H), 7.17-7.24(m, 2H), 7.07(m, 1H), 2.63(s, 3H), 1.35(s, 6H). Mass Spectrum (LCMS, ESI pos.) Calcd. For C$_{26}$H$_{24}$N$_2$O$_2$: 397.5(M+H), Found 397.3. |
| 450 | (E)-N-isopropyl-4-{2-[5-(2-methylsulfamoyl-phenyl)-1H-benzimidazol-2-yl]-vinyl}-benzamide<br>The title compound was prepared from [5-(2-methylsulfamoyl-phenyl)-1H-benzimidazol-2-ylmethyl]-triphenyl-phosphonium chloride Compound 33c (90 mg, 0.15 mmol) and 4-carboxyaldehyde-N-isopropylbenzamide (24.3 mg, 0.15 mmol) as an off-white solid (10.5 mg, 15% yield). $^1$H NMR(400MHz, CD$_3$OD) δ (ppm): 8.06(dd, 1H, J=8.1, Hz, J=1.5 Hz), 7.87(m, 2H), 7.55-7.74(m, 7H), 7.43(dd, 1H, J=8.1 Hz, J=1.5Hz), 7.29(m, 2H), 4.22(m, 1H), 2.37(s, 3H), 1.26(s, 6H). Mass Spectrum(LCMS, ESI pos.) Calcd. For C$_{26}$H$_{26}$N$_4$O$_3$S: 475.5(M+H), Found 475.2. |
| 451 | (E)-2-{2-[2-(4-cyano-phenyl)-vinyl]-1H-benzimidazol-5-yl}-N-methyl-benzenesulfonamide<br>The title compound was prepared from Compound 33c (90 mg, 0.15 mmol) and 4-cyanobenzaldehyde (19.6 mg, 0.15 mmol) as an off-white solid (7.4 mg, 12% yield). $^1$H NMR(400MHz, CD$_3$OD) δ (ppm): 8.07(dd, 1H, J=8.0 Hz, J=1.0 Hz), 7.49-7.69(m. 8H), 7.37(m, 2H), 7.20(m, 2H), 2.32(s, 3H). Mass Spectrum (LCMS, ESI pos.) Calcd. For C$_{23}$H$_{18}$N$_4$O$_2$S: 415.5(M+H), Found 415.2. |
| 452 | (E)-N-(4-{2-[5-(2-methylsulfamoyl-phenyl)-1H-benzimidazol-2-yl]-vinyl}-phenyl)-acetamide<br>The title compound was prepared from Compound 33c (90 mg, 0.15 mmol) and 4-acetamidobenzaldehyde (24.3 mg, 0.15 mmol) as an off-white solid (11.3 mg, 17% yield). $^1$H NMR(400MHz, CD$_3$OD) δ (ppm): 8.04(dd, 1H, J=8.0 Hz, J=1.3 Hz), 7.63(td, 1H, J=7.4 Hz, J=1.4 Hz), 7.55(m, 5H), 7.26-7.39(m, 5H), 7.19(dd, 1H, J=8.1 Hz, J=1.5 Hz), 2.22(s, 3H), 2.03(s, 3H). Mass Spectrum (LCMS, ESI pos.) Calcd. For C$_{24}$H$_{22}$N$_4$O$_3$S: 447.5(M+H), Found 447.2. |
| 453 | (E)-4-{2-[5-(2-methylsulfamoyl-phenyl)-1H-benzimidazol-2-yl]-vinyl}-benzoic acid<br>The title compound was prepared from Compound 33c (90 mg, 0.15 mmol) and 4-carboxybenzaldehyde (22.4 mg, 0.15 mmol) as an off-white solid (3.4 mg, 5% yield). $^1$H NMR(400MHz, CD$_3$OD) δ (ppm): 8.02(m, 2H), 7.53-7.77(m, 6H), 7.18-7.45(m, 5H), 2.36(s, 3H). Mass Spectrum(LCMS, ESI pos.) Calcd. For C$_{23}$H$_{19}$N$_3$O$_4$S: 434.5(M+H), Found 434.2. |
| 454 | (E)-2-{2-[2-(1H-indol-6-yl)-vinyl]-1H-benzimidazol-5-yl}-N-methyl-benzenesulfonamide<br>The title compound was prepared from Compound 33c (90 mg, 0.15 mmol) and indole-6-carboxaldehyde (21.6 mg, 0.15 mmol) as an off-white solid (6.5 mg, 10% yield). $^1$H NMR(400MHz, CD$_3$OD) δ (ppm): 8.06(m, 1H), 7.05-7.73(m, 11H), 6.48(m, 2H), 2.36(m, 3H). Mass Spectrum(LCMS, ESI pos.) Calcd. For C$_{24}$H$_{20}$N$_4$O$_2$S: 429.5(M+H), Found 429.2. |
| 455 | (E)-2-{2-[2-(2,4-bis-trifluoromethyl-phenyl)-vinyl]-1H-benzimidazol-5-yl}-N-methyl-benzenesulfonamide<br>The title compound was prepared from Compound 33c (90 mg, 0.15 mmol) and 2,4-bis(trifluoromethyl)benzaldehyde (24.4 uL, 0.15 mmol) as an off-white solid (8.62mg, 11% yield). $^1$H NMR(400MHz, CD$_3$OD) δ (ppm): 7.14-8.17(m, 12H), 2.44(s, 3H). Mass Spectrum(LCMS, ESI pos.) Calcd. For C$_{24}$H$_{17}$F$_6$N$_3$O$_2$S: 526.5(M+H), Found 526.3. |
| 456 | (E)-2-{2-[2-(4-acetyl-phenyl)-vinyl]-1H-benzimidazol-5-yl}-N-methyl-benzenesulfonamide<br>The title compound was prepared from Compound 33c (90 mg, 0.15 mmol) and 4-acetylbenzaldehyde (22.1 mg, 0.15 mmol) as an off-white solid (8.32 mg, 13% yield). $^1$H NMR(400MHz, CD$_3$OD) δ (ppm): 8.06(m, 3H), 7.56-7.79(m, 9H), 7.44(m, 1H), 2.62(s, 3H), 2.37(s, 3H). Mass Spectrum(LCMS, ESI pos.) Calcd. For C$_{24}$H$_{21}$N$_3$O$_3$S: 432.5(M+H), Found 432.2. |

Cl₂CH₂Cl₂ (36 mg, 0.044 mmol), tetrabutylammonium bromide (55 mg, 0.17 mmol), and sodium carbonate (1 mL, 1.0 M) in DME (5 mL) was heated at 90° C. for 18 h. The mixture was cooled to rt, filtered through a pad of Celite and concentrated under reduced pressure. The residue was purified using preative TLC plates (silica gel, 20×20 cm, 2000 microns, EtOAc:hexanes 1:1 and hexanes:dichloromethane:methanol 6:14:1) to provide the title Compound 34a (20 mg, 37%). $^1$H NMR (400 MHz, CD₃OD+CDCl₃) δ (ppm): 7.72-7.47 (m, 10H), 7.40-7.30 (m, 3H), 7.14 (d, 1H, J=16.55 Hz). Mass Spectrum (LCMS, APCl pos.) Calcd. For C₂₃H₁₄F₃N₃: 0.390.1 (M+H), Found 390.3.

Step B. 2-{2-[2-(4-Trifluoromethyl-phenyl)-ethyl]-1H-benzimidazol-5-yl}-benzylamine A mixture of Compound 34a (20 mg, 0.051 mmol), Raney®-Nickel, ammonium hydroxide (0.1 mL) in ethanol was hydrogenated under 50 psi for 18 h. The mixture was filtered through a pad of Celite and washed with ethanol. The filtrate was concentrated under reduced pressure. The residue was purified using preative TLC plates (silica gel, 20×20 cm, 2000 microns, NH₃ in methanol:EtOAc 1:9) to provide the title Compound 486 (6.3 mg, 31%). $^1$H NMR (400 MHz, CD₃OD) δ (ppm): 7.57-7.52 (m, 4H), 7.46-7.34 (m, 6H), 7.14 (dd, J=8.2, 1.5 Hz, 1H), 4.05 (s, 2H), 3.24 (s, 4H). Mass Spectrum (LCMS, APCl pos.) Calcd. For C₂₃H₂₀F₃N₃: 396.2 (M+H), Found 396.2.

EXAMPLE 35

(Z)-2-(2-{2-[2-(4-Trifluoromethyl-phenyl)-vinyl]-1H-benzimidazol-5-yl}-phenyl)-propan-2-ol (Cpd 469)

A solution of Compound 18 (0.030 g, 0.07 mmol) in DMSO (5 mL) was stirred at room temperature for 5 days under a 60 W light bulb. The reaction was then applied to a 2000 micron prep TLC plate (20×20 cm) and developed using ethyl acetate:hexanes 4:6. The desired band was extracted with MeOH, filtered and concentrated to provide the title Compound 469 (0.001 g). $^1$H-NMR (400 MHz, DMSO d6) δ (ppm) 7.71 (dd, J=1.01, 8.34 Hz,1H) 7.53 (s, 4H) 7.37-7.41 (m, 1H) 7.21-7.28 (m, 2H) 7.11 (dt, J=1.26, 7.33 Hz, 1H) 7.05 (dd, J=1.52, 8.34 Hz, 1H), 6.94-7.10 (m, 4H) 6.67 (d, 12.6 Hz, 1H) 1.23 (s, 6H). MS (ESI, pos. ion) m/z: 423.2 (M+1).

EXAMPLE 36

(E)-N-(2-{3-methyl-2-[2-(4-trifluoromethyl-phenyl)-vinyl]-3H-benzimidazol-5-yl}-phenyl)-methane-sulfonamide (Cpd 443)

(E)-N-(2-{1-methyl-2-[2-(4-trifluoromethyl-phenyl)-vinyl]-1H-benzimidazol-5-yl}-phenyl)-methane-sulfonamide (Cpd 477)

Step A. (E)-5-bromo-1-methyl-2-[2-(4-trifluoromethyl-phenyl)-vinyl]-1H-benzimidazole and (E)-6-bromo-1-methyl-2-[2-(4-trifluoromethyl-phenyl)-vinyl]-1H-benzimidazole To a solution of sodium hydride (60% suspension in oil, 0.131 g, 3.2 mmol) in anhydrous tetrahydrofuran (10 mL) was added Compound 10c (1 g, 2.7 mmol). The solution was stirred at room temperature under an argon atmosphere. After five minutes methyl iodide was added (0.205 mL, 3.2 mmol), and the solution was stirred at room temperature for 3 h. The reaction mixture was partitioned between ethyl acetate (10 mL) and ice water (20 mL). The organic fraction was washed with brine, dried over magnesium sulfate, then filtered and concentrated to give a 1:1 mixture of the title Compound 36a and 36b (0.38 g).

Step B. (E)-N-(2-{3-methyl-2-[2-(4-trifluoromethyl-phenyl)-vinyl]-3H-benzimidazol-5-yl}-phenyl)-methanesulfonamide and (E)-N-(2-{1-methyl-2-[2-(4-trifluoromethyl-phenyl)-vinyl]-1H-benzimidazol-5-yl}-phenyl)-methanesulfonamide Using the procedure of Example 1, Step B, the title compounds were prepared from a mixture of (E)-5-bromo-1-methyl-2-[2-(4-trifluoromethyl-phenyl)-vinyl]-1H-benzimidazole and (E)-6-bromo-1-methyl-2-[2-(4-trifluoromethyl-phenyl)-vinyl]-1H-benzimidazole and 2-methylsulfonylaminophenyl boronic acid.

Cpd 443: $^1$H-NMR (400 MHz, CD₃OD) δ (ppm) 7.82-7.80 (m, 3H) 7.75 (d, J=8.1 Hz, 3H) 7.52-7.62 (m, 3H) 7.34-7.42 (m, 4H) 4.00 (s, 3H) 2.76 (s, 3H). MS (ESI, pos. ion) m/z: 472.1 (M+1).

Cpd 477: $^1$H-NMR (400 MHz, CD₃OD) δ (ppm) 7.88-7.95 (m, 3H) 7.72-7.77 (m, 3H) 7.56-7.67 (m, 4H) 7.40-7.44 (m, 3H) 4.10 (s, 3H) 2.73 (s, 3H). MS (ESI, pos. ion) m/z: 472.1 (M+1).

EXAMPLE 37

(E)-2-hydroxy-1-(2-{2-[2-(4-trifluoromethyl-phenyl)-vinyl]-1H-benzimidazol-5-yl}-phenyl)-ethanone (Cpd 311)

Step A. (E)-2-[2-(4-trifluoromethyl-phenyl)-vinyl]-5-[2-(1-trimethylsilanyloxy-vinyl)-phenyl]-1H-benz-imidazole To a solution of Compound 15 (0.20 g, 0.492 mmol) in 16 mL 1,2-dichloroethane was added TBSOTf (0.19 mL, 1.08 mmol) and Et₃N (0.27 mL, 1.97 mmol) at 0° C. After 5 min., the mixture was warmed to 25° C. and stirred for 8 hours. The reaction was concentrated and the residue was purified by chromatography (silica gel, hexanes:EtOAc, 4:1) to provide the title Compound 37a as a colorless oil.

Step B. (E)-2-[2-(4-trifluoromethyl-phenyl)-vinyl]-5-[2-(2-trimethylsilanyloxy-oxiranyl)-phenyl]-1H-benzimidazole A mixture of Compound 37a (0.124 g, 0.238 mmol) and mCPBA (0.053 g, 0.238 mmol) in 10 mL CH₂Cl₂ was stirred for two hours. The reaction was concentrated and the residue was purified by chromatography (silica gel, hexanes: EtOAc, 4:1) to provide the title Compound 37b as a yellow oil.

Step C. (E)-2-hydroxy-1-(2-{2-[2-(4-trifluoromethyl-phenyl)-vinyl]-1H-benzimidazol-5-yl}-phenyl)-ethanone A mixture of Compound 37b (0.026 g, 0.048 mmol) and p-toluenesulfonic acid monohydrate (p-TsOHH₂O, 0.018 g, 0.0968 mmol) in 4 mL THF was stirred for four hours. The reaction was concentrated and the residue was purified by chromatography (silica gel, hexanes:EtOAc, 1:2) to provide the title Compound 311 as a brown solid. $^1$H-NMR (400 MHz, CD₃OD) δ (ppm): 7.85 (d, 2H, J=8.8 Hz) 7.74 (d, 2H, J=7.6 Hz) 7.71 (d, 1H, J=16.4 Hz) 7.63–7.47 (m, 6H) 7.33 (d, 1H, J=16.0 Hz) 7.25 (dd, 1H, J=1.6 and 8.4 Hz) 4.08 (s, 2H) MS (ESI, pos. ion) m/z: 423.3 (M+1).

EXAMPLE 38

2-(2-{2-[(1R,2R)-2-(4-trifluoromethyl-phenyl)-cyclopropyl]-1H-benzimidazol-5-yl}-phenyl)-propan-2-ol (Cpd 501)

Step A. (1R,2R)-2-(4-trifluoromethyl-phenyl)-cyclopropanecarboxylic acid ethyl ester To a suspension of copper(I)trifluoromethanesulfonate toluene complex (31.0 mg, 0.12 mmol) in anhydrous CHCl$_3$ (3.0 mL) was added a solution of 2,2-bis-[(4S)-(1,1-dimethylethyl)-1,3-oxazolin-2-yl]propane (35 mg, 0.12 mmol) in chloroform (1.2 mL). After stirring at ambient temperature for 1 h, the resulting green solution was filtered through glass wool under argon atmosphere into a flask previously charged with a solution of 4-(trifluoromethyl)-styrene (0.887 mL, 6.00 mmol) in chloroform (0.9 mL). To this solution was added a solution of ethyl diazoacetate (1.56 mL, 15.0 mmol) in chloroform (12.0 mL) at ambient temperature through a dropping funnel over a period of 6 h. The resulting mixture was stirred for 24 h, concentrated to dryness, and purified by flash chromatography on a silica gel column (45 mm×140 mm silica gel), eluting with ethyl acetate/hexane (1, 1.5, 2%) to provide the title Compound 38a (892 mg, 58% yield, 98% ee) as a colorless liquid, and cis isomer (1R,2S)-2-(4-trifluoromethyl-phenyl)-cyclopropanecarboxylic acid ethyl ester Compound 38b (128 mg, 5% yield calculated based on 34 wt % contamination of ethyl fumarate as analyzed by 1NMR). The enantiomeric excess of the product was determined as described in Step E below.

$^1$H-NMR of Compound 38a (400 MHz, CDCl$_3$) δ (ppm): 7.53 (d, 2H, J=8.3 Hz), 7.23 (d, 2 H, J=8.1 Hz), 4.18 (q, 2 H, J=7.1 Hz), 2.55 (dd, 1H, J=2.6, 4.3 & 6.6 Hz), 1.94 (ddd, 1H, J=4.3, 5.6, & 9.6 Hz), 1.6–1.53 (m, 1H), 1.34 (1H, ddd, 4.8, 6.7, & 1.1 Hz), 1.29 (t, 2H, J=7.0 Hz).

$^1$H-NMR of Compound 38b (400 MHz, CDCl$_3$) δ (ppm): 7.51 (d, 2H, J=7.9 Hz), 7.37 (d, 2H, J=7.8 Hz), 3.92–3.86 (m, 2H), 2.62–2.56 (m, 1H), 2.14 (ddd, 1H, J=5.8, 8.1 & 9.3 Hz), 1.73 (td, 1H, J=5.3 & 7.6 Hz), 1.39 (ddd, 1H, J=5.1, 7.8 & 8.6 Hz), 0.99 (t, 3H, J=7.1 Hz).

Step B. (1R,2R)-2-(4-trifluoromethyl-phenyl)-cyclopropanecarboxylic acid

To a solution of Compound 38a (750 mg, 2.91 mmol) in ethanol (7.27 mL) was added a 1M aqueous solution of NaOH (7.27 mL). The resulting mixture was stirred at ambient temperature for 16 h, concentrated to about 4 g, acidified with 2M HCl to pH 3, and extracted with ethyl acetate (15 mL×2). The extracts were combined, washed with brine, dried over Na$_2$SO$_4$, concentrated to provide the title Compound 38c (611 mg, 91% yield) as a white solid. $^1$H-NMR (400 MHz, CDCl$_3$ with a drop of CD$_3$OD) δ (ppm): 7.51 (d, 2H, J=8.3 Hz), 7.18 (d, 2H, J=8.1 Hz), 2.57 (ddd, 1H, J=4.2, 6.6, & 10.3 Hz), 1.90 (ddd, 1H, J=4.0, 5.3, & 8.3 Hz), 1.65 (dt, 1H, J=4.9 & 9.3 Hz), 1.35 (ddd, 1H, J=4.9, 6.4, & 11.1 Hz).

Step C: 2-(2-{2-[(1R,2R)-2-(4-trifluoromethyl-phenyl)-cyclopropyl]-1H-benzimidazol-5-yl}-phenyl)-propan-2-ol Using the procedure of Example 10, Steps B and E, the title Compound 501 was prepared from Compound 38c. $^1$H-NMR (400 MHz, DMSO-d6) δ (ppm): 12.40 (s, 0.5H), 12.32 (s, 0.5H), 7.87-7.84 (m, 1H), 7.66 (d, 2H, J=8.0 Hz), 7.49-7.17 (m, 6H), 7.00-6.96 (m, 2H), 4.84 (s, 1H), 2.72-2.67 (m, 1H), 2.50-2.46 (m, 1H), 1.92-1.86 (m, 1H), 1.74-1.68 (m, 1H), 1.19 (s, 3H), 1.18 (s, 3H). Mass Spectrum (LCMS, ESI pos.) Calcd for $C_{26}H_{24}F_3N_2O$: 437.2. Found 437.3.

Step D: (1R,2R)-2-(4-trifluoromethyl-phenyl)-cyclopropanecarboxylic acid methoxy-methyl-amide To a mixture of Compound 38c (50 mg, 0.216 mmol), N,O-dimethylhydroxylamine hydrochloride (30 mg, 0.30 mmol), BOP (134 mg, 0.30 mmol), and DMF (0.4 mL) was added DIEA (0.15 mL). The resulting mixture was stirred at ambient temperature for 48 h, concentrated to dryness, and partitioned between saturated NaHCO$_3$ (2 mL) and ethyl acetate (4 mL). The ethyl acetate layer was separated, and the aqueous layer was extracted with ethyl acetate (5 mL×2). All ethyl acetate layers were combined, washed with brine, dried over Na$_2$SO$_4$, concentrated, and purified by prep-TLC, developed with 10% ethyl acetate/DCM to provide Compound 38d (46 mg, 78% yield) as a white solid. $^1$H-NMR (400 MHz, CDCl$_3$) δ (ppm): 7.52 (d, 2H, J=8.4 Hz), 7.23 (d, 2H, J=8.1 Hz), 3.70 (s, 3H), 3.24 (s, 3H), 2.56-2.52 (m, 1H), 2.45 (bs, 1H), 2.17-1.67 (m, 1H), 1.34 (ddd, 1H, J=4.6, 6.3, & 8.7 Hz).

Step E: Determination of ee

To a solution of Compound 38d (0.8 mg) in CDCl$_3$ (0.6 mL) was added (R)-(−)-2,2,2-trifluoro-1-(9-anthryl)ethanol portion-wise and the amount of addition was monitored by $^1$HNMR until base line resolution of the resulting methoxy singlets was achieved. Thus, the enantiomer methoxy singlets were around 3.47 and 3.45 ppm. The integration of these singlets was 99 and 1, respectively; thus providing an ee value of 99%.

Using the procedure described in Example 38 and reagents, starting materials and conditions known to those skilled in the art, the following compounds representative of the present invention were prepared:

| Cpd | Name and Data |
| --- | --- |
| 502 | 2-{2-[(1R,2R)-2-(4-trifluoromethyl-phenyl)-cyclopropyl]-1H-benzimidazol-5-yl}-benzenesulfonamide<br>Using the procedure of Example 38, the title compound was prepared from Compound 38c and 2-(t-butylamino)sulfonylphenyl boronic acid.<br>$^1$H-NMR(400MHz, CDCl$_3$) δ (ppm): 12.42(s, 0.5H), 12.40(s, 0.5H), 8.04(dd, 1H, J=1.3 & 7.8 Hz), 7.66(d, 2H, J=8.3 Hz), 7.63-7.34(m, 7H), 7.17-7.11(m, 1H), 7.06(s, 1H), 7.03(s, 1H), 2.71-2.65(m, 1H), 2.50-2.46(m, 1H), 1.92-1.87(m, 1H), 1.75-1.70(m, 1H). Mass Spectrum(LCMS, ESI pos.) Calcd for $C_{23}H_{19}F_3N_3O_2S$: 458.1(M+1). Found 458.2. |

| Cpd | Name and Data |
|---|---|
| 503 | 2-(2-{2-[(1S,2S)-2-(4-trifluoromethyl-phenyl)-cyclopropyl]-1H-benzimidazol-5-yl}-phenyl)-propan-2-ol monosodium salt
Using the procedure of Example 38, the title compound was prepared from 2,2-bis-[(4R)-(1,1-dimethylethyl)-1,3-oxazolin-2-yl]propane and 4-(trifluoromethyl)-styrene.
To a suspension of N,N'-bis-[(2R)-3,3-dimethyl-1-hydroxybutyl]-2,2-dimethyl-1,3-propanediamide (83 mg, 0.25 mmol, prepared according to the procedure described in J. Am. Chem. Soc. 1991, 113, 726) in DCM (2.5 mL) was added (diethylamino)sulfur trifluoride (0.066 mL, 0.50 mmol, as described in J. Org. Chem. 2002, 67, 8566 for the formation of oxazoline from hydroxyamide) dropwise at ambient temperature. The resulting mixture was stirred at ambient temperature for 16h, and poured into saturated NaHCO$_3$ (4.0 mL). The mixture was extracted with DCM (3 × 5 mL). The extracts were combined and dried over Na$_2$SO$_4$, then concentrated and flash chromatographed with ethyl acetate/DCM (0, 5, 10, and 20%) to provide 2,2-bis-[2-((4R)-(1,1-dimethylethyl)-1,3-oxazolinyl)]propane (53mg, 72% yield) as a white solid. $^1$H-NMR was identical to the literature as reported by Evans.
$^1$H-NMR(400MHz, DMSO-d6) δ (ppm): 7.82(dd, 1H, J=1.5 & 8.1 Hz), 7.61(d, 2H, J=8.1 Hz), 7.37(d, 2H, J=8.1 Hz), 7.24(dt, 1H, J=1.8 & 7.3 Hz), 7.15-7.11(m, 2H), 7.00(d, 1H, J=1.5 Hz), 6.98(dd, 1H, J=1.5 & 7.3 Hz), 6.52(d, 1H, J=7.8 Hz), 4.63(bs, 1H), 2.52-2.47(m, 1H), 2.33(ddd, 1H, J=4.1, 5.8 & 8.8 Hz), 1.75(ddd, 1H, J=3.7, 5.8, & 8.8 Hz), 1.45-1.40(m, 1H), 1.22(s, 6H). Mass Spectrum(LCMS, ESI pos.) Calcd for C$_{26}$H$_{24}$F$_3$N$_2$O: 437.2. Found 437.2.
Analogous to Example 38, step A, both the trans isomer (1S,2S)-2-(4-trifluoromethyl-phenyl)-cyclopropanecarboxylic acid ethyl ester Compound 38e and the cis isomer (1S,2R)-2-(4-trifluoromethyl-phenyl)-cyclopropanecarboxylic acid ethyl ester Compound 38f were isolated. |
| 504 | 2-{2-[(1S,2S)-2-(4-trifluoromethyl-phenyl)-cyclopropyl]-1H-benzimidazol-5-yl}-benzenesulfonamide
Using the procedure described for Compound 503, the title compound was prepared from Compound 38e, 4-(trifluoromethyl)-styrene and 2-(t-butylamino)sulfonylphenyl boronic acid.
$^1$H-NMR(400MHz, DMSO-d6) δ (ppm): 12.41(s, 0.5H), 12.40(s, 0.5H), 8.04(dd, 1H, J=1.3 & 7.8 Hz), 7.66(d, 2H, J=8.3 Hz), 7.63-7.34(m, 7H), 7.17-7.11(m, 1H), 7.06(s, 1H), 7.03(s, 1H), 2.71-2.65(m, 1H), 2.50-2.46(m, 1H), 1.92-1.87(m, 1H), 1.75-1.70(m, 1H). MS(ESI, pos. ion) m/z: 458.2(M+1). Mass Spectrum(LCMS, ESI pos.) Calcd for C$_{23}$H$_{19}$F$_3$N$_3$O$_2$S: 458.1(M+1). Found 458.2. |
| 505 | 2-(2-{2-[(1S,2R)-2-(4-trifluoromethyl-phenyl)-cyclopropyl]-1H-benzimidazol-5-yl}-phenyl)-propan-2-ol
Using the procedure described for Compound 503, the title compound was prepared from Compound 38f.
1H-NMR(400MHz, CD$_3$OD) δ (ppm): 7.79(dd, 1H, J=1.0 & 8.1 Hz), 7.36-7.15(m, 8H), 7.01(t, 1H, J=1.5 Hz), 6.99(d, 1H, J=1.5 Hz), 2.83-2.73(m, 2H), 2.08-2.03(m, 1H), 1.71(td, 1H, J=8.6 & 5.6 Hz), 1.23(s, 3H), 1.22(s, 3H). Mass Spectrum(LCMS, ESI pos.) Calcd for C$_{26}$H$_{24}$F$_3$N$_2$O: 437.2. Found 437.3.
Determination of ee: To a mixture of (1S,2R)-2-(4-trifluoromethyl-phenyl)-cyclopropanecarboxylic acid (14 mg, 0.0.061 mmol), (S)-(−)-α-methylbenzylamine (10.0 mg, 0.0609 mmol), BOP (27 mg, 0.0609 mmol), and DMF (0.2 mL) was added DIEA (0.023 mL, 0.13 mmol). The resulting solution was stirred at room temperature for 48 h, concentrated to dryness, and partitioned between saturated NaHCO$_3$ (1 mL) and ethyl acetate (3 mL). Ethyl acetate layer was separated, and aqueous was extracted with ethyl acetate (5 mL × 2). All ethyl acetate layers were combined, washed with brine, dried over Na$_2$SO$_4$, concentrated, and purified by prep-TLC, developed with 10% ethyl acetate/DCM to give the title compound (10.1mg, 70% yield) as a white solid.
1H-NMR(400MHz, C$_6$D$_6$) δ (ppm): 7.26(d, 2H, J=8.1 Hz), 7.03-6.95(m, 5H), 6.68-6.65(m, 2H), 4.96-4.89(m, 1H), 4.79(bd, 1H, J=7.6 Hz), 1.80-1.73(m, 2H), 1.23-1.17(m, 1H), 1.00(d, 3H, J=6.8 Hz), 0.82-0.79(m, 1H).). In the 1H-NMR doublet of the Me in (1R, 2S, 1'S)-N-(1'-phenethyl)-2-(4-trifluoromethyl-phenyl)-cyclopropanecarboxamide appeared at 0.85ppm. Integration of this methyl doublet and that of the title compound was 2.5 and 97.5, respectively. |
| 506 | 2-{2-[(1R,2S)-2-(4-trifluoromethyl-phenyl)-cyclopropyl]-1H-benzimidazol-5-yl}-benzenesulfonamide
Using the procedure of Example 38, the title compound was prepared from Compound 38b and 2-(t-butylamino)sulfonylphenyl boronic acid.
1H-NMR(400MHz, CD$_3$OD) δ (ppm): 8.09(dd, 1H, J=1.3 & 7.9 Hz), 7.59(dt, 1H, J=1.6 & 7.6 Hz), 7.51(dt, 1H, J=1.5 & 7.8 Hz), 7.47(bs, 1H), 7.42-7.29(m, 6H), 7.19(dd, 1H, J=1.7 & 8.3 Hz), 2.84-2.74(m, 2H), 2.05(q, 1H, J=6.3 Hz), 1.72(td, 1H, J=8.5 & 5.7 Hz). Mass Spectrum(LCMS, ESI pos.) Calcd for C$_{23}$H$_{19}$F$_3$N$_3$O$_2$S: 458.1(M+1). Found 458.2. |
| 507 | 2-(2-{2-[(1R,2S)-2-(4-trifluoromethyl-phenyl)-cyclopropyl]-1H-benzimidazol-5-yl}-phenyl)-propan-2-ol
Using the procedure of Example 38, the title compound was prepared using Compound 38b.
1H-NMR(400MHz, CD$_3$OD) δ (ppm): 7.79(dd, 1H, J=1.0 & 8.1 Hz), 7.36-7.15(m, 8H), 7.01(t, 1H, J=1.5 Hz), 6.99(d, 1H, J=1.5 Hz), 2.83-2.73(m, 2H), 2.08-2.03(m, 1H), 1.71(td, 1H, J=8.6 & 5.6 Hz), 1.23(s, 3H), 1.22(s, 3H). |

| Cpd | Name and Data |
|---|---|
|  | Mass Spectrum(LCMS, ESI pos.) Calcd for $C_{26}H_{24}F_3N_2O$: 437.2. Found 437.3.<br>Determination of ee: Using the procedure described for Compound 506, the amide intermediate of Compound 507 was prepared from (1R,2S)-2-(4-trifluoromethyl-phenyl)-cyclopropanecarboxylic acid Compound 38 g and (S)-(−)-α-methylbenzylamine.<br>1H-NMR(400MHz, $C_6D_6$) δ (ppm): 7.37(d, 2H, J=8.1 Hz), 7.35-7.02(m, 5H), 6.97-6.95(m, 2H), 4.95-4.88(m, 1H), 4.82(bd, 1H, J=7.8 Hz), 1.81-1.75(m, 1H), 1.70(ddd, 1H, J=4.8, 5.8 & 7.3 Hz), 1.14(ddd, 1H, J=5.6, 7.8 & 9.0 Hz), 0.85(d, 3H, J=6.6 Hz), 0.80-0.75(m, 1H).<br>In the 1H-NMR doublet of the Me in (1S, 2R, 1'S)-N-(1'-phenethyl)-2-(4-trifluoromethyl-phenyl)-cyclopropanecarboxamide appeared at 1.00ppm. Integration of this methyl doublet and that of the title compound was 3 and 97, respectively. |
| 508 | 2-{2-[(1S,2R)-2-(4-trifluoromethyl-phenyl)-cyclopropyl]-1H-benzimidazol-5-yl}-benzenesulfonamide<br>Using the procedure described for Compound 503, the title compound was prepared from Compound 38f and 2-(t-butylamino)sulfonylphenyl boronic acid.<br>1H-NMR(400MHz, $CD_3OD$) δ (ppm): 8.09(dd, 1H, J=1.3 & 7.9 Hz), 7.59(dt, 1H, J=1.6 & 7.6 Hz), 7.51(dt, 1H, J=1.5 & 7.8 Hz), 7.47(bs, 1H), 7.42-7.29(m, 6H), 7.19(dd, 1H, J=1.7 & 8.3 Hz), 2.84-2.74(m, 2H), 2.05(q, 1H, J=6.3 Hz), 1.72(td, 1H, J=8.5 & 5.7 Hz). Mass Spectrum(LCMS, ESI pos.) Calcd for $C_{23}H_{19}F_3N_3O_2S$: 458.1(M+1). Found 458.2. |

BIOLOGICAL EXAMPLES

Example 1

Human VR1 (hVR1) Binding Assay

Compounds of the present invention were tested for their ability to inhibit the binding of [$^3$H] RTX to hVR1 receptors in a [$^3$H] RTX binding assay as previously described (Zhang, Sui-Po. *Improved ligand binding assays for vanilloid receptors*. PCT Int. Appl. (2002), WO 0233411 A1 20020425 AN 2002:315209, and Elfrida G. R. et al., *J. Pharmacol. Exp. Ther.*, 2002, 300(1): 9-17.)

HEK293 cells were transfected with hVR1 vanilloid receptors and washed with Hank's balanced Salt Solution, dissociated with cell dissociation buffer (Sigma), and then centrifuged at 1000×g for 5 min. Cell pellets were homogenized in cold 20 mM HEPES buffer (pH=7.4), containing 5.8 mM NaCl, 320 mM sucrose, 2 mM $MgCl_2$, 0.75 $CaCl_2$ and 5 mM KCl and centrifuged at 1000×g for 15 min. The resultant supernatant was then centrifuged at 40,000×g for 15 min. The pelleted membranes were stored in a freezer at −80° C.

Approximately 120 μg protein/ml from membranes were incubated with indicated concentrations of [$^3$H]RTX in 0.5 ml of the HEPES buffer (pH 7.4) containing 0.25 mg/mL fatty acid-free bovine serum albumin at 37° C. for 60 min. The reaction mixture was then cooled to 4° C., and 0.1 mg of $α_1$-acid glycoprotein was added to each sample, which was then incubated at 4° C. for 15 min. The samples were centrifuged at 18,500×g for 15 min. The tip of the microcentrifuge tube containing the pellet was cut off. Bound radioactivity was quantified by scintillation counting. Non-specific binding was measured in the presence of 200 nM unlabeled RTX.

Data were calculated according to the equation:

% inhibition=100%×[(total binding−binding)/(total binding−non specific binding)]

$K_i$ values were calculated using a Prism program.

TABLE 1

| Cpd | Ki (nM) |
|---|---|
| 1 | 9.7 |
| 3 | 20 |
| 4 | 31 |
| 5 | 17 |
| 9 | 0.9 |
| 14 | 380 |
| 15 | 41 |
| 17 | 8.7 |
| 18 | 6.5 |
| 27 | 1800 |
| 32 | 100 |
| 36 | 820 |
| 40 | 81 |
| 50 | 16 |
| 51 | 6.4 |
| 56 | 120 |
| 69 | 6 |
| 70 | 8.6 |
| 71 | 22 |
| 78 | 6.4 |
| 79 | 18 |
| 310 | 10 |
| 312 | 19 |
| 319 | 6 |
| 407 | 5.7 |
| 434 | 39 |

Example 2

Human VR1 (hVR1) Functional Assay

The functional activity of the test compounds was determined by measuring changes in intracellular calcium concentration using a $Ca^{++}$-sensitive fluorescent dye and FLIPR™ technology. Increases in $Ca^{++}$ concentration were readily detected upon challenge with capsaicin.

HEK293 cells expressing hVR1 were grown on poly-D-lysine coated 384 well black-walled plates (BD 354663) and 1 day later loaded with Calcium 3 Dye for 35 min at 37° C., 5% $CO_2$ and then for 25 min at room temperature, and subsequently tested for agonist-induced increases in intracellular $Ca^{2+}$ levels using FLIPR™ technology. Cells were challenged with test compounds (at varying concentrations) and intracellular $Ca^{2+}$ was measured for 5 min prior to the addition of capsaicin to all wells to achieve a final concentration of 0.030 μM eliciting about 80% maximal response. $IC_{50}$ values were determined from concentration-response studies, which were generated using the average of quadruplicate wells for each data point.

For those compounds tested, an $IC_{50}$ (nM) value and percent inhibition value is shown in Table 2. Except where indicated, the percent inhibition values were obtained at a test concentration of 1 μM; otherwise: [1]the test concentration was 5 μM. The percent inhibition value is provided for those compounds where an $IC_{50}$ value was not obtained. The term "NA" means that the data is "not available" because it was not obtained for a particular compound.

TABLE 2

| Cpd | % Inh | $IC_{50}$ |
| --- | --- | --- |
| 1 | 100 | 27 |
| 2 | 100 | 12 |
| 3 | NA | 140 |
| 4 | 78 | 400 |
| 5 | 100 | 71 |
| 6 | 12 | NA |
| 7 | 10 | NA |
| 8 | 10 | NA |
| 9 | 99 | 2 |
| 10 | 94 | 280 |
| 11 | 100 | 210 |
| 12 | 100 | 10 |
| 13 | 82 | 310 |
| 14 | 49 | 1000 |
| 15 | 100 | 120 |
| 16 | 100 | 45 |
| 17 | 100 | 8 |
| 18 | 100 | 4 |
| 19 | 32 | NA |
| 20 | NA | 320 |
| 22 | NA | 18 |
| 24 | 8 | NA |
| 25 | 4 | NA |
| 26 | 6 | NA |
| 27 | 100 | 260 |
| 28 | 96 | 250 |
| 29 | 6 | NA |
| 30 | 10 | NA |
| 31 | NA | 13 |
| 32 | 77 | 380 |
| 33 | NA | 1700 |
| 34 | [1]75 | NA |
| 35 | 100 | 41 |
| 36 | 44 | NA |
| 37 | 18 | NA |
| 38 | 89 | 270 |
| 39 | 98 | 200 |
| 40 | 99 | 54 |
| 41 | 90 | 280 |
| 42 | 100 | 22 |
| 43 | 58 | 890 |
| 44 | 95 | 300 |
| 45 | 100 | 16 |
| 46 | 100 | 46 |
| 47 | 100 | 20 |
| 48 | 33 | NA |
| 49 | 16 | NA |
| 50 | 100 | 100 |
| 51 | 100 | 66 |
| 52 | 28 | NA |
| 53 | 98 | 47 |
| 54 | 20 | NA |
| 55 | 14 | NA |
| 56 | 100 | 110 |
| 57 | 15 | NA |
| 58 | 87 | 95 |
| 59 | 80 | 440 |
| 60 | 7 | NA |
| 61 | 100 | 75 |
| 62 | 100 | 200 |
| 63 | 97 | 260 |
| 64 | 41 | NA |
| 65 | 0 | NA |
| 66 | 98 | 48 |
| 67 | 98 | 130 |
| 68 | NA | 329 |
| 69 | 98 | 6 |
| 70 | 100 | 7 |
| 71 | 99 | 22 |
| 77 | 100 | 76 |
| 78 | 99 | 5 |
| 79 | 100 | 7 |
| 83 | NA | >500 |
| 84 | 100 | 40 |
| 85 | 16 | NA |
| 95 | 81 | 301 |
| 101 | NA | >500 |
| 113 | 48 | NA |
| 114 | 99 | 3 |
| 129 | 96 | 34 |
| 130 | 100 | 6 |
| 131 | 96 | 31 |
| 139 | 98 | 31 |
| 145 | 19 | NA |
| 175 | 100 | 16 |
| 190 | 94 | 38 |
| 198 | 95 | 10 |
| 234 | 7 | NA |
| 250 | 98 | 19 |
| 294 | 101 | 9.1 |
| 295 | 100 | 16 |
| 309 | 73 | NA |
| 310 | 100 | 6 |
| 311 | 99 | 54 |
| 312 | 100 | 6 |
| 314 | 100 | 18 |
| 315 | 100 | 11 |
| 316 | 101 | 12 |
| 317 | 101 | 11 |
| 318 | 100 | 50 |
| 319 | 100 | 10 |
| 320 | 100 | 13 |
| 321 | 100 | 18 |
| 322 | 101 | 14 |
| 323 | 97 | 40 |
| 324 | 98 | 33 |
| 325 | 73 | NA |
| 326 | 89 | 157 |
| 327 | 77 | 343 |
| 328 | 99 | 35 |
| 329 | 98 | 27 |
| 330 | 85 | 131 |
| 331 | 97 | 43 |
| 332 | 98 | 49 |
| 333 | 98 | 27 |
| 334 | 94 | 178 |
| 335 | 100 | 47 |
| 336 | 89 | 240 |
| 337 | 96 | 14 |
| 338 | 96 | 104 |
| 339 | 99 | 27 |
| 340 | 98 | 62 |
| 341 | 99 | 6 |
| 342 | 98 | 24 |
| 343 | 82 | 243 |
| 344 | 101 | 24 |
| 345 | 101 | 13 |
| 346 | 87 | 264 |
| 347 | 100 | 44 |
| 348 | 86 | 162 |
| 349 | 99 | 59 |
| 350 | 100 | 33 |
| 351 | NA | >500 |
| 357 | 100 | 8 |
| 358 | 99 | 9 |
| 359 | 98 | 24 |
| 360 | 98 | 46 |
| 361 | 97 | 27 |

TABLE 2-continued

| Cpd | % Inh | IC$_{50}$ |
|---|---|---|
| 362 | 99 | 8 |
| 363 | 98 | 12 |
| 364 | 97 | 65 |
| 365 | 99 | 17 |
| 366 | 99 | 35 |
| 367 | 98 | 53 |
| 368 | 99 | 15 |
| 369 | 99 | 8 |
| 370 | 98 | 13 |
| 371 | 98 | 18 |
| 372 | 97 | 71 |
| 373 | 99 | 20 |
| 374 | 99 | 34 |
| 375 | 97 | 139 |
| 376 | 100 | 28 |
| 378 | 100 | 12 |
| 379 | 99 | 40 |
| 380 | 99 | 12 |
| 383 | 96 | 11 |
| 384 | 98 | 7 |
| 385 | 97 | 21 |
| 386 | 96 | 43 |
| 387 | 98 | 41 |
| 388 | 99 | 54 |
| 389 | 23 | NA |
| 390 | 96 | 7 |
| 391 | 95 | 8 |
| 392 | 97 | 10 |
| 393 | 98 | 10 |
| 394 | 98 | 6 |
| 395 | 99 | 15 |
| 396 | 99 | 13 |
| 397 | 99 | 23 |
| 398 | 97 | 3 |
| 399 | 97 | 3 |
| 402 | 93 | 38 |
| 404 | 94 | 47 |
| 405 | 95 | 20 |
| 406 | 97 | 170 |
| 407 | 96 | 9 |
| 408 | 64 | NA |
| 409 | 43 | NA |
| 410 | 91 | 156 |
| 411 | 85 | 350 |
| 412 | 86 | 190 |
| 413 | 82 | 240 |
| 414 | 98 | 140 |
| 415 | 95 | 150 |
| 416 | 96 | 120 |
| 417 | 100 | 11 |
| 418 | 100 | 18 |
| 419 | 93 | 32 |
| 420 | 93 | 15 |
| 421 | 95 | 10 |
| 422 | 98 | 7 |
| 423 | 99 | 11 |
| 424 | 99 | 11 |
| 425 | 2 | NA |
| 426 | 99 | 22 |
| 427 | 98 | 13 |
| 428 | 100 | 7 |
| 429 | 98 | 6 |
| 430 | 100 | 9 |
| 431 | 97 | 35 |
| 432 | 98 | 15 |
| 433 | 98 | 10 |
| 434 | 98 | 7 |
| 435 | 97 | 20 |
| 436 | 96 | 10 |
| 437 | 97 | 24 |
| 438 | 96 | 71 |
| 439 | 97 | 23 |
| 440 | 98 | 40 |
| 441 | 40 | NA |
| 442 | 96 | 4 |
| 444 | 98 | 28 |
| 445 | 96 | 20 |
| 446 | 97 | 76 |
| 447 | 98 | 44 |
| 448 | 99 | 17 |
| 449 | 100 | 9 |
| 450 | 27 | NA |
| 451 | 101 | 28 |
| 452 | 5 | NA |
| 453 | 22 | NA |
| 454 | 36 | NA |
| 455 | 100 | 17 |
| 456 | 100 | 45 |
| 457 | 22 | NA |
| 458 | 15 | NA |
| 459 | 0 | NA |
| 460 | 21 | NA |
| 461 | 99 | 5 |
| 462 | 98 | 97 |
| 463 | 100 | 14 |
| 464 | 100 | 3 |
| 465 | 75 | 363 |
| 466 | 98 | 71 |
| 467 | 86 | 182 |
| 468 | 97 | 8 |
| 469 | 99 | 7 |
| 470 | 97 | 45 |
| 471 | 100 | 10 |
| 472 | NA | >500 |
| 473 | NA | >500 |
| 474 | NA | >500 |
| 475 | NA | 77 |
| 476 | NA | 68 |
| 477 | 44 | NA |
| 478 | NA | >500 |
| 479 | 12 | NA |
| 480 | NA | >500 |
| 481 | 42 | NA |
| 482 | 100 | 13 |
| 483 | 21 | NA |
| 484 | NA | >500 |
| 485 | NA | >500 |
| 486 | NA | >500 |
| 487 | 20 | NA |
| 488 | 4 | NA |
| 489 | 96 | 2 |
| 490 | 99 | 26 |
| 491 | NA | 77 |
| 492 | 99 | 5 |
| 494 | 93 | 52 |
| 497 | 94 | 39 |
| 498 | 100 | 19 |
| 499 | 7 | NA |
| 500 | 97 | 19 |
| 501 | 99 | 85 |
| 502 | 82 | 190 |
| 503 | 93 | 10 |
| 504 | 95 | 22 |

Example 3

Chemically-Induced Models of Inflammatory Pain

Compounds of the present invention were tested in animal models of inflammation and inflammatory pain. To assess the ability of test compounds to reverse thermal hyperalgesia, baseline response latencies on a radiant heat (RH) paw stimulator were obtained before an intraplantar injection of 100 μL (1 μg/μL) CFA (1:1 CFA:saline) in male Sprague-Dawley rats. Only withdrawal responses that were quick hind paw movements (with or without licking of the hind paw) were recorded. Paw movements associated with locomotion or a shifting of weight were not considered a withdrawal response. The stimulus intensity that produced 10-15 sec baseline withdrawal latencies was used and a maximum cut-off of 20 sec was imposed. Hypersensitivity was evaluated 24 hr after CFA. Only rats that exhibited at least a 25% reduction in response latency from baseline (i.e. hyperalgesia) were included in further analysis.

Following the post-inflammogen latency assessment, rats were orally dosed (2.5 mL/kg) with test compound (10 mg/kg) or vehicle (20% hydroxypropyl beta cyclodextran). To determine the time of peak effect, latencies were redetermined 30, 60, 100, 180 and 300 min after compound administration.

Data are presented as the maximal percent reversal of hypersensitivity obtained during the 300 min test, which was calculated for each animal according to the formula:

% reversal=100%×(treatment response–post-inflammogen response)/(pre-inflammogen response–post-inflammogen response)

TABLE 3

| Cpd | % Reversal |
|-----|-----------|
| 17  | 104 |
| 18  | 133 |
| 22  | 18  |
| 23  | 31  |
| 31  | 72  |
| 47  | 58  |
| 70  | 76  |
| 78  | 19  |
| 114 | 56  |
| 310 | 23  |
| 464 | 65  |

Example 4

Incision-Induced Model of Postoperative Surgery

Compounds of the present invention were tested in animal models of postoperative surgery, as previously described (Brennan, T. J. et al., *Pain,* 1996, 64: 493-501). Male Sprague-Dawley rats were anaesthetized with 2-3% isoflurane and the plantar surface of the hindpaw was sterilized using three alternating betadine and alcohol scrubs. A 1 cm longitudinal incision through the skin of the plantar paw was made using a number 10 scalpel beginning 0.5 cm from the proximal heel and extending toward the toes. The plantaris muscle was excised using a forcep and incised longitudinally. The skin was then sutured in two locations using 5-0 silk. The wound site was then covered with antibiotic ointment and the animals were returned to their individual home cages. Changes in thermal sensitivity were evaluated before surgery and 24 hr after surgery. Vehicle (20% HPβCD) or test compound was orally administered and thermal sensitivity was re-assessed 30, 60, 100, 180 and 300 min later.

Data are presented as the maximal percent reversal of hypersensitivity obtained during the 300 min test, which was calculated for each animal according to the formula:

% reversal=100% (treatment response–post-inflammogen response)/(pre-inflammogen response–post-inflammogen response)

TABLE 4

| Cpd | % Reversal |
|-----|-----------|
| 18  | 132 |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

All publications disclosed in the above specification are hereby incorporated by reference in full.

The invention claimed is:
1. A compound of Formula (I):

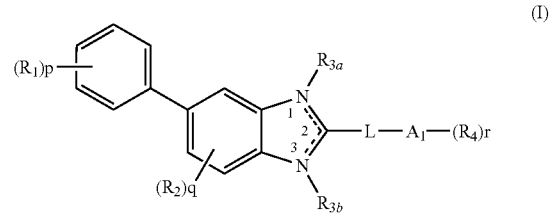

or a salt, stereoisomer, tautomer or ester thereof, wherein:
the dashed lines between positions 1, 2 and 3 in Formula (I) indicate the positions of a tautomeric double bond,
wherein when a double bond is formed between positions 1 and 2, then $R_{3b}$ is present, and
wherein, when a double bond is formed between positions 2 and 3, then $R_{3a}$ is present;
p is 1 or 2;
q is 0 or 1;
r is 0, 1, 2 or 3;
L is $C_{2-3}$alkenyl, $C_{2-3}$alkynyl or cyclopropyl;
$A_1$ is selected from the group consisting of phenyl, biphenyl, naphthyl, pyridinyl, quinolinyl and indole;
$R_1$ is each selected from the group consisting of hydroxy, cyano, halogen, formyl, carboxy, $C_{1-6}$alkyl, halo$C_{1-6}$alkyl, $C_{1-6}$alkoxy, halo$C_{1-6}$alkoxy, $C_{1-6}$alkylcarbonyl, $C_{1-6}$alkoxycarbonyl, $C_{1-6}$alkylthio, $C_{1-6}$alkylsulfonyl, $C_{3-8}$cycloalkyl, $C_{3-8}$cycloalkyl-$C_{1-4}$alkyl, $C_{3-8}$cycloalkyl-$C_{1-4}$alkoxy, $C_{3-8}$cycloalkyl-oxy, amino, $(C_{1-6}$alkyl$)_{1-2}$amino, $(C_{3-8}$cycloalkyl$)_{1-2}$amino, $(C_{3-8}$cycloalkyl-$C_{1-4}$ alkyl$)_{1-2}$amino, aminocarbonyl, $(C_{1-6}$alkyl$)_{1-2}$aminocarbonyl, $C_{1-6}$alkylcarbonylamino, $C_{1-6}$alkoxycarbonylamino, aminocarbonylamino, $(C_{1-6}$alkyl$)_{1-2}$aminocarbonylamino, $C_{1-6}$alkylsulfonylamino, $C_{1-6}$alkylsulfinylamino, aminosulfonyl, $(C_{1-4}$ alkyl$)_{1-2}$aminosulfonyl, aminosulfonylamino and $(C_{1-6}$alkyl$)_{1-2}$-aminosulfonylamino,
wherein alkyl is optionally substituted with $C_{1-8}$alkoxy, amino, $(C_{1-4}$alkyl$)_{1-2}$amino, $C_{1-6}$alkylcarbonylamino, $C_{1-6}$alkoxycarbonylamino, aminocarbonylamino, $(C_{1-6}$alkyl$)_{1-2}$-aminocarbonylamino, $C_{1-6}$alkylsulfonylamino, aminosulfonylamino, $(C_{1-6}$alkyl$)_{1-2}$aminosulfonylamino hydroxy and phenyl,
wherein phenyl is optionally substituted with one, two or three substituents independently selected from the group consisting of halogen, cyano, nitro, $C_{1-6}$alkyl, $C_{1-6}$alkoxy, $C_{1-6}$alkylthio and $C_{1-6}$alkylsulfonyl, and
wherein, each instance of alkyl and alkoxy is optionally perfluorinated;
$R_2$ is selected from the group consisting of halogen, $C_{1-4}$alkyl, $C_{1-4}$-alkoxy, $C_{1-4}$alkylsulfonyl, nitro, amino, $(C_{1-4}$alkyl$)_{1-2}$amino and cyano,
wherein each instance of alkyl and alkoxy is optionally perfluorinated;
$R_{3a}$ and $R_{3b}$ are each selected from the group consisting of hydrogen and optionally perfluorinated $C_{1-4}$alkyl; and R$_4$ is each selected from the group consisting of halogen, nitro, cyano, carboxy, C$_{1-6}$alkyl, C$_{1-6}$alkoxy, haloC$_{1-6}$alkyl, haloC$_{1-6}$alkoxy, C$_{1-6}$alkoxy-C$_{1-6}$alkyl, C$_{1-6}$alkylcarbonyl, C$_{1-6}$alkylthio, haloC$_{1-6}$alkylthio, C$_{1-6}$alkylsulfonyl, haloC$_{1-6}$alkylsulfonyl, C$_{3-8}$cycloalkyl, C$_{3-8}$cycloalkyl-C$_{1-4}$alkyl, C$_{3-8}$cycloalkyl-C$_{1-4}$alkoxy, C$_{3-8}$cycloalkyl-oxy, amino, (C$_{1-6}$alkyl)$_{1-2}$amino, (C$_{3-8}$cycloalkyl)$_{1-2}$amino, (C$_{3-8}$cycloalkyl-C$_{1-4}$alkyl)$_{1-2}$amino, aminocarbonyl, (C$_{1-6}$alkyl)$_{1-2}$aminocarbonyl, C$_{1-6}$alkylcarbonylamino, C$_{1-6}$alkoxycarbonylamino, aminocarbonylamino, (C$_{1-6}$alkyl)$_{1-2}$-aminocarbonylamino, C$_{1-6}$alkylsulfonylamino, haloC$_{1-6}$alkylsulfonylamino, C$_{1-6}$alkylsulfinylamino, aminosulfonyl and (C$_{1-4}$ alkyl)$_{1-2}$aminosulfonyl, wherein each instance of alkyl is optionally substituted with one, two or three substituents independently selected from the group consisting of C$_{1-8}$alkoxy, amino, (C$_{1-4}$alkyl)$_{1-2}$amino, C$_{1-6}$alkylcarbonylamino, C$_{1-6}$alkoxycarbonylamino, aminocarbonylamino, (C$_{1-6}$alkyl)$_{1-2}$aminocarbonylamino, C$_{1-6}$alkylsulfonylamino, oxo and hydroxy, and wherein, each instance of alkyl and alkoxy is optionally perfluorinated.

2. The compound of claim 1, wherein q is 0.

3. The compound of claim 1, wherein A$_1$ is selected from the group consisting of phenyl, biphenyl, naphthyl, quinolinyl and indole.

4. The compound of claim 1, wherein

R$_1$ is each selected from the group consisting of hydroxy, halogen, formyl, C$_{1-6}$alkyl, haloC$_{1-6}$alkyl, haloC$_{1-6}$alkoxy, C$_{1-6}$alkylcarbonyl, C$_{1-6}$alkoxycarbonyl, C$_{1-6}$alkylthio, C$_{1-6}$alkylsulfonyl, amino, aminocarbonyl, C$_{1-6}$alkylcarbonylamino, C$_{1-6}$alkoxycarbonylamino, C$_{1-6}$alkylsulfonylamino, aminosulfonyl, (C$_{1-4}$ alkyl)$_{1-2}$aminosulfonyl and aminosulfonylamino, wherein alkyl is optionally substituted with amino, (C$_{1-4}$alkyl)$_{1-2}$-amino, aminosulfonylamino or hydroxy, and wherein, alkyl is optionally perfluorinated.

5. The compound of claim 1, wherein R$_2$ is selected from the group consisting of halogen and C$_{1-4}$alkyl, wherein alkyl is optionally perfluorinated.

6. The compound of claim 1, wherein R$_{3a}$ and R$_{3b}$ are each selected from the group consisting of hydrogen and C$_{1-4}$alkyl.

7. The compound of claim 1, wherein R$_4$ is each selected from the group consisting of halogen, carboxy, C$_{1-6}$alkyl, C$_{1-6}$alkoxy, haloC$_{1-6}$alkyl, haloC$_{1-6}$alkoxy, C$_{1-6}$alkylcarbonyl, haloC$_{1-6}$alkylthio, C$_{1-6}$alkylsulfonyl, haloC$_{1-6}$alkylsulfonyl, (C$_{1-6}$ alkyl)$_{1-2}$amino, (C$_{1-6}$ alkyl)$_{1-2}$aminocarbonyl, C$_{1-6}$alkylcarbonylamino, C$_{1-6}$alkylsulfonylamino and haloC$_{1-6}$alkylsulfonylamino, wherein alkyl and alkoxy are optionally perfluorinated.

8. The compound of claim 1, wherein
p is 1 or 2;
q is 0;
r is 0, 1, 2 or 3;
L is C$_{2-3}$alkenyl, C$_{2-3}$alkynyl or cyclopropyl;
A$_1$ is selected from the group consisting of phenyl, biphenyl, naphthyl, quinolinyl and indole;
R$_1$ is each selected from the group consisting of hydroxy, halogen, formyl, C$_{1-6}$alkyl, haloC$_{1-6}$alkyl, haloC$_{1-6}$alkoxy, C$_{1-6}$alkylcarbonyl, C$_{1-6}$alkoxycarbonyl, C$_{1-6}$alkylthio, C$_{1-6}$alkylsulfonyl, amino, aminocarbonyl, C$_{1-6}$alkylcarbonylamino, C$_{1-6}$alkoxycarbonylamino, C$_{1-6}$alkylsulfonylamino, aminosulfonyl, (C$_{1-4}$ alkyl)$_{1-2}$aminosulfonyl and aminosulfonylamino, wherein alkyl is optionally substituted with amino, (C$_{1-4}$ alkyl)$_{1-2}$-amino, aminosulfonylamino or hydroxy, and wherein, alkyl is optionally perfluorinated;

R$_2$ is selected from the group consisting of halogen and C$_{1-4}$-alkyl, wherein alkyl is optionally perfluorinated;

R$_{3a}$ and R$_{3b}$ are each selected from the group consisting of hydrogen and C$_{1-4}$alkyl; and R$_4$ is each selected from the group consisting of halogen, carboxy, C$_{1-6}$alkyl, C$_{1-6}$alkoxy, haloC$_{1-6}$alkyl, haloC$_{1-6}$alkoxy, C$_{1-6}$alkylcarbonyl, haloC$_{1-6}$alkylthio, C$_{1-6}$alkylsulfonyl, haloC$_{1-6}$alkylsulfonyl, (C$_{1-6}$alkyl)$_{1-2}$amino, (C$_{1-6}$alkyl)$_{1-2}$aminocarbonyl, C$_{1-6}$alkylcarbonylamino, C$_{1-6}$alkylsulfonylamino and haloC$_{1-6}$alkylsulfonylamino, wherein alkyl and alkoxy are optionally perfluorinated.

9. A compound selected from the group consisting of:
(E)-1-(2-{2-[2-(4-tert-butyl-phenyl)-vinyl]-1H-benzimidazol-5-yl}-phenyl)-ethanone,
(E)-1-(2-{2-[2-(4-tert-butyl-phenyl)-vinyl]-1H-benzimidazol-5-yl}-phenyl)-ethanol,
(E)-2-{2-[2-(4-tert-butyl-phenyl)-vinyl]-1H-benzimidazol-5-yl}-phenol,
(E)-N-(2-{2-[2-(4-tert-butyl-phenyl)-vinyl]-1H-benzimidazol-5-yl}-phenyl)-acetamide,
(E)-2-{2-[2-(4-tert-butyl-phenyl)-vinyl]-1H-benzimidazol-5-yl}-benzamide,
(E)-3-{2-[2-(4-tert-butyl-phenyl)-vinyl]-1H-benzimidazol-5-yl}-benzamide,
(E)-4-{2-[2-(4-tert-butyl-phenyl)-vinyl]-1H-benzimidazol-5-yl}-benzamide,
(E)-N-(4-{2-[2-(4-tert-butyl-phenyl)-vinyl]-1H-benzimidazol-5-yl}-phenyl)-acetamide,
(E)-N-(2-{2-[2-(4-tert-butyl-phenyl)-vinyl]-1H-benzimidazol-5-yl}-phenyl)-methanesulfonamide,
(E)-(2-{2-[2-(4-tert-butyl-phenyl)-vinyl]-1H-benzimidazol-5-yl}-phenyl)-carbamic acid tert-butyl ester,
(E)-2-{2-[2-(4-tert-butyl-phenyl)-vinyl]-1H-benzimidazol-5-yl}-phenylamine,
(E)-(2-{2-[2-(4-tert-butyl-phenyl)-vinyl]-1H-benzimidazol-5-yl}-phenyl)-methanol,
(E)-2-{2-[2-(4-trifluoromethyl-phenyl)-vinyl]-1H-benzimidazol-5-yl}-benzamide,
(E)-2-{2-[2-(4-trifluoromethyl-phenyl)-vinyl]-1H-benzimidazol-5-yl}-phenol,
(E)-1-(2-{2-[2-(4-trifluoromethyl-phenyl)-vinyl]-1H-benzimidazol-5-yl}-phenyl)-ethanone,
(E)-1-(2-{2-[2-(4-trifluoromethyl-phenyl)-vinyl]-1H-benzimidazol-5-yl}-phenyl)-ethanol,
(E)-N-(2-{2-[2-(4-trifluoromethyl-phenyl)-vinyl]-1H-benzimidazol-5-yl}-phenyl)-methanesulfonamide,
(E)-2-(2-{2-[2-(4-trifluoromethyl-phenyl)-vinyl]-1H-benzimidazol-5-yl}-phenyl)-propan-2-ol,
(E)-2-{2-[2-(4-trifluoromethoxy-phenyl)-vinyl]-1H-benzimidazol-5-yl}-benzamide,
(E)-1-(2-{2-[2-(4-trifluoromethoxy-phenyl)-vinyl]-1H-benzimidazol-5-yl}-phenyl)-ethanone,
(E)-1-(2-{2-[2-(4-trifluoromethoxy-phenyl)-vinyl]-1H-benzimidazol-5-yl}-phenyl)-ethanol,
(E)-N-(2-{2-[2-(4-trifluoromethoxy-phenyl)-vinyl]-1H-benzimidazol-5-yl}-phenyl)-methanesulfonamide,
(E)-2-(2-{2-[2-(4-trifluoromethoxy-phenyl)-vinyl]-1H-benzimidazol-5-yl}-phenyl)-propan-2-ol,
(E)-N-(2-{2-[2-(3,4-difluoro-phenyl)-vinyl]-1H-benzimidazol-5-yl}-phenyl)-acetamide,
(E)-N-(3-{2-[2-(3,4-difluoro-phenyl)-vinyl]-1H-benzimidazol-5-yl}-phenyl)-acetamide, (E)-2-{2-[2-(3,4-difluoro-phenyl)-vinyl]-1H-benzimidazol-5-yl}-benzamide,
(E)-1-(2-{2-[2-(3,4-difluoro-phenyl)-vinyl]-1H-benzimidazol-5-yl}-phenyl)-ethanone,
(E)-N-(2-{2-[2-(3,4-difluoro-phenyl)-vinyl]-1H-benzimidazol-5-yl}-phenyl)-methanesulfonamide,
(E)-(2-{2-[2-(4-trifluoromethylsulfanyl-phenyl)-vinyl]-1H-benzimidazol-5-yl}-phenyl)-methanol,
(E)-2-{2-[2-(4-trifluoromethylsulfanyl-phenyl)-vinyl]-1H-benzimidazol-5-yl}-phenol,
(E)-N-(2-{2-[2-(4-trifluoromethylsulfanyl-phenyl)-vinyl]-1H-benzimidazol-5-yl}-phenyl)-acetamide,
(E)-2-{2-[2-(4-trifluoromethylsulfanyl-phenyl)-vinyl]-1H-benzimidazol-5-yl}-benzamide,
(E)-1-(2-{2-[2-(4-trifluoromethylsulfanyl-phenyl)-vinyl]-1H-benzimidazol-5-yl}-phenyl)-ethanone,
(E)-1-(2-{2-[2-(4-trifluoromethanesulfonyl-phenyl)-vinyl]-1H-benzimidazol-5-yl}-phenyl)-ethanone,
(E)-2-{2-[2-(4-trifluoromethanesulfonyl-phenyl)-vinyl]-1H-benzimidazol-5-yl}-phenol,
(E)-(2-{2-[2-(4-trifluoromethanesulfonyl-phenyl)-vinyl]-1H-benzimidazol-5-yl}-phenyl)-methanol,
(E)-N-(2-{2-[2-(4-trifluoromethanesulfonyl-phenyl)-vinyl]-1H-benzimidazol-5-yl}-phenyl)-acetamide,
(E)-2-{2-[2-(4-trifluoromethanesulfonyl-phenyl)-vinyl]-1H-benzimidazol-5-yl}-benzamide,
(E)-1-(2-{2-[2-(4-trifluoromethanesulfonyl-phenyl)-vinyl]-1H-benzimidazol-5-yl}-phenyl)-ethanol,
1-(2-{2-[2-(4-trifluoromethanesulfonyl-phenyl)-ethyl]-1H-benzimidazol-5-yl}-phenyl)-ethanol,
(E)-2-(2-{2-[2-(4-trifluoromethanesulfonyl-phenyl)-vinyl]-1H-benzimidazol-5-yl}-phenyl)-propan-2-ol,
(E)-2-{2-[2-(4-tert-butyl-phenyl)-vinyl]-6-trifluoromethyl-1H-benzimidazol-5-yl}-phenol,
(E)-3-{2-[2-(4-tert-butyl-phenyl)-vinyl]-6-trifluoromethyl-1H-benzimidazol-5-yl}-phenol,
(E)-N-(2-{2-[2-(4-tert-butyl-phenyl)-vinyl]-6-trifluoromethyl-1H-benzimidazol-5-yl}-phenyl)-acetamide,
(E)-(2-{2-[2-(4-tert-butyl-phenyl)-vinyl]-6-trifluoromethyl-1H-benzimidazol-5-yl}-phenyl)-methanol,
(E)-2-[2-(4-tert-butyl-phenyl)-vinyl]-5-(2-fluoro-phenyl)-6-trifluoromethyl-1H-benzimidazole,
(E)-2-{2-[2-(4-tert-butyl-phenyl)-vinyl]-6-trifluoromethyl-1H-benzimidazol-5-yl}-benzamide,
(E)-(2-{2-[2-(4-tert-butyl-phenyl)-vinyl]-6-trifluoromethyl-1H-benzimidazol-5-yl}-phenyl)-carbamic acid tert-butyl ester,
(E)-N-(2-{2-[2-(4-tert-butyl-phenyl)-vinyl]-6-trifluoromethyl-1H-benzimidazol-5-yl}-phenyl)-methanesulfonamide,
(E)-N-(2-{6-trifluoromethyl-2-[2-(4-trifluoromethyl-phenyl)-vinyl]-1H-benzimidazol-5-yl}-phenyl)-acetamide,
(E)-1-(2-{6-trifluoromethyl-2-[2-(4-trifluoromethyl-phenyl)-vinyl]-1H-benzimidazol-5-yl}-phenyl)-ethanone,
(E)-(2-{6-trifluoromethyl-2-[2-(4-trifluoromethyl-phenyl)-vinyl]-1H-benzimidazol-5-yl}-phenyl)-methanol,
(E)-2-{6-fluoro-2-[2-(4-trifluoromethyl-phenyl)-vinyl]-1H-benzimidazol-5-yl}-phenol,
(E)-3-{6-fluoro-2-[2-(4-trifluoromethyl-phenyl)-vinyl]-1H-benzimidazol-5-yl}-phenol,
(E)-(2-{6-fluoro-2-[2-(4-trifluoromethyl-phenyl)-vinyl]-1H-benzimidazol-5-yl}-phenyl)-methanol,
(E)-1-(2-{6-fluoro-2-[2-(4-trifluoromethyl-phenyl)-vinyl]-1H-benzimidazol-5-yl}-phenyl)-ethanone,
(E)-2-{6-fluoro-2-[2-(4-trifluoromethyl-phenyl)-vinyl]-1H-benzimidazol-5-yl}-benzamide,
(E)-N-(2-{6-fluoro-2-[2-(4-trifluoromethyl-phenyl)-vinyl]-1H-benzimidazol-5-yl}-phenyl)-acetamide,
(E)-N-(2-{6-fluoro-2-[2-(4-trifluoromethyl-phenyl)-vinyl]-1H-benzimidazol-5-yl}-phenyl)-methanesulfonamide,
(E)-(2-{6-chloro-2-[2-(4-trifluoromethyl-phenyl)-vinyl]-1H-benzimidazol-5-yl}-phenyl)-methanol,
(E)-1-(2-{6-chloro-2-[2-(4-trifluoromethyl-phenyl)-vinyl]-1H-benzimidazol-5-yl}-phenyl)-ethanone,
(E)-2-{6-chloro-2-[2-(4-trifluoromethyl-phenyl)-vinyl]-1H-benzimidazol-5-yl}-phenol,
(E)-2-{2-[2-(4-trifluoromethoxy-phenyl)-vinyl]-1H-benzimidazol-5-yl}-benzenesulfonamide,
(E)-2-{2-[2-(4-trifluoromethyl-phenyl)-vinyl]-1H-benzimidazol-5-yl}-benzenesulfonamide,
(E)-2-{2-[2-(4-trifluoromethanesulfonyl-phenyl)-vinyl]-1H-benzimidazol-5-yl}-benzenesulfonamide,
(E)-C,C,C-trifluoro-N-(2-{2-[2-(4-trifluoromethoxy-phenyl)-vinyl]-1H-benzimidazol-5-yl}-phenyl)-methanesulfonamide,
(E)-C,C,C-trifluoro-N-(2-{2-[2-(4-trifluoromethyl-phenyl)-vinyl]-1H-benzimidazol-5-yl}-phenyl)-methanesulfonamide,
(E)-C,C,C-trifluoro-N-(2-{2-[2-(4-trifluoromethanesulfonyl-phenyl)-vinyl]-1H-benzimidazol-5-yl}-phenyl)-methanesulfonamide,
(E)-1-(2-{2-[2-(4-chloro-phenyl)-vinyl]-1H-benzimidazol-5-yl}-phenyl)-ethanone,
(E)-1-(2-{2-[2-(4-chloro-phenyl)-vinyl]-1-benzimidazol-5-yl}-phenyl)-ethanol,
(E)-N-(2-{2-[2-(4-chloro-phenyl)-vinyl]-1H-benzimidazol-5-yl}-phenyl)-methanesulfonamide,
(E)-2-(2-{2-[2-(4-chloro-phenyl)-vinyl]-1H-benzimidazol-5-yl}-phenyl)-propan-2-ol,
(E)-2-{2-[2-(4-chloro-phenyl)-vinyl]-1-benzimidazol-5-yl}-benzenesulfonamide,
(E)-N-(2-{2-[2-(4-chloro-phenyl)-vinyl]-1H-benzimidazol-5-yl}-phenyl)-C,C,C-trifluoro-methanesulfonamide,
(E)-1-(2-{2-[2-(4-methanesulfonyl-phenyl)-vinyl]-1H-benzimidazol-5-yl}-phenyl)-ethanone,
(E)-1-(2-{2-[2-(4-methanesulfonyl-phenyl)-vinyl]-1H-benzimidazol-5-yl}-phenyl)-ethanol,
(E)-N-(2-{2-[2-(4-methanesulfonyl-phenyl)-vinyl]-1H-benzimidazol-5-yl}-phenyl)-methanesulfonamide,
(E)-2-(2-{2-[2-(4-methanesulfonyl-phenyl)-vinyl]-1H-benzimidazol-5-yl}-phenyl)-propan-2-ol,
(E)-2-{2-[2-(4-methanesulfonyl-phenyl)-vinyl]-1H-benzimidazol-5-yl}-benzenesulfonamide,
(E)-C,C,C-trifluoro-N-(2-{2-[2-(4-methanesulfonyl-phenyl)-vinyl]-1H-benzimidazol-5-yl}-phenyl)-methanesulfonamide,
(E)-1-[2-(2-{2-[4-(2,2,2-trifluoro-1-trifluoromethyl-ethoxy)-phenyl]-vinyl}-1H-benzimidazol-5-yl)-phenyl]-ethanone,
(E)-1-[2-(2-{2-[4-(2,2,2-trifluoro-1-trifluoromethyl-ethoxy)-phenyl]-vinyl}-1H-benzimidazol-5-yl)-phenyl]-ethanol,
(E)-N-[2-(2-{2-[4-(2,2,2-trifluoro-1-trifluoromethyl-ethoxy)-phenyl]-vinyl}-1H-benzimidazol-5-yl)-phenyl]-methanesulfonamide,
(E)-2-[2-(2-{2-[4-(2,2,2-trifluoro-1-trifluoromethyl-ethoxy)-phenyl]-vinyl}-1H-benzimidazol-5-yl)-phenyl]-propan-2-ol,
(E)-2-(2-{2-[4-(2,2,2-trifluoro-1-trifluoromethyl-ethoxy)-phenyl]-vinyl}-1H-benzimidazol-5-yl)-benzenesulfonamide, (E)-C,C,C-trifluoro-N-[2-(2-{2-[4-(2,2,2-trifluoro-1-trifluoromethyl-ethoxy)-phenyl]-vinyl}-1H-benzimidazol-5-yl)-phenyl]-methanesulfonamide,
(E)-1-[2-(2-{2-[4-(2,2,2-trifluoro-ethoxy)-phenyl]-vinyl}-1H-benzimidazol-5-yl)-phenyl]-ethanone,
(E)-1-[2-(2-{2-[4-(2,2,2-trifluoro-ethoxy)-phenyl]-vinyl}-1H-benzimidazol-5-yl)-phenyl]-ethanol,
(E)-N-[2-(2-{2-[4-(2,2,2-trifluoro-ethoxy)-phenyl]-vinyl}-1H-benzimidazol-5-yl)-phenyl]-methanesulfonamide,
(E)-2-[2-(2-{2-[4-(2,2,2-trifluoro-ethoxy)-phenyl]-vinyl}-1H-benzimidazol-5-yl)-phenyl]-propan-2-ol,
(E)-2-(2-{2-[4-(2,2,2-trifluoro-ethoxy)-phenyl]-vinyl}-1H-benzimidazol-5-yl)-benzenesulfonamide,
(E)-C,C,C-trifluoro-N-[2-(2-{2-[4-(2,2,2-trifluoro-ethoxy)-phenyl]-vinyl}-1H-benzimidazol-5-yl)-phenyl]-methanesulfonamide,
(E)-1-[2-(2-{2-[4-(2,2,3,3,3-pentafluoro-propoxy)-phenyl]-vinyl}-1H-benzimidazol-5-yl)-phenyl]-ethanone,
(E)-1-[2-(2-{2-[4-(2,2,3,3,3-pentafluoro-propoxy)-phenyl]-vinyl}-1H-benzimidazol-5-yl)-phenyl]-ethanol,
(E)-N-[2-(2-{2-[4-(2,2,3,3,3-pentafluoro-propoxy)-phenyl]-vinyl}-1H-benzimidazol-5-yl)-phenyl]-methanesulfonamide,
(E)-2-[2-(2-{2-[4-(2,2,3,3,3-pentafluoro-propoxy)-phenyl]-vinyl}-1H-benzimidazol-5-yl)-phenyl]-propan-2-ol,
(E)-2-(2-{2-[4-(2,2,3,3,3-pentafluoro-propoxy)-phenyl]-vinyl}-1H-benzimidazol-5-yl)-benzenesulfonamide,
(E)-C,C,C-trifluoro-N-[2-(2-{2-[4-(2,2,3,3,3-pentafluoro-propoxy)-phenyl]-vinyl}-1H-benzimidazol-5-yl)-phenyl]-methanesulfonamide,
(E)-1-(2-{2-[2-(3-chloro-phenyl)-vinyl]-1H-benzimidazol-5-yl}-phenyl)-ethanone,
(E)-1-(2-{2-[2-(3-chloro-phenyl)-vinyl]-1H-benzimidazol-5-yl}-phenyl)-ethanol,
(E)-N-(2-{2-[2-(3-chloro-phenyl)-vinyl]-1H-benzimidazol-5-yl}-phenyl)-methanesulfonamide,
(E)-2-(2-{2-[2-(3-chloro-phenyl)-vinyl]-1H-benzimidazol-5-yl}-phenyl)-propan-2-ol,
(E)-2-{2-[2-(3-chloro-phenyl)-vinyl]-1H-benzimidazol-5-yl}-benzenesulfonamide,
(E)-N-(2-{2-[2-(3-chloro-phenyl)-vinyl]-1H-benzimidazol-5-yl}-phenyl)-C,C,C-trifluoro-methanesulfonamide,
(E)-1-(2-{2-[2-(3-trifluoromethyl-phenyl)-vinyl]-1H-benzimidazol-5-yl}-phenyl)-ethanone,
(E)-1-(2-{2-[2-(3-trifluoromethyl-phenyl)-vinyl]-1H-benzimidazol-5-yl}-phenyl)-ethanol,
(E)-N-(2-{2-[2-(3-trifluoromethyl-phenyl)-vinyl]-1H-benzimidazol-5-yl}-phenyl)-methanesulfonamide,
(E)-2-(2-{2-[2-(3-trifluoromethyl-phenyl)-vinyl]-1H-benzimidazol-5-yl}-phenyl)-propan-2-ol,
(E)-2-{2-[2-(3-trifluoromethyl-phenyl)-vinyl]-1H-benzimidazol-5-yl}-benzenesulfonamide,
(E)-C,C,C-trifluoro-N-(2-{2-[2-(3-trifluoromethyl-phenyl)-vinyl]-1H-benzimidazol-5-yl}-phenyl)-methanesulfonamide,
(E)-N-(4-{2-[5-(2-acetyl-phenyl)-1H-benzimidazol-2-yl]-vinyl}-phenyl)-methanesulfonamide,
(E)-N-[4-(2-{5-[2-(1-hydroxy-ethyl)-phenyl]-1H-benzimidazol-2-yl}-vinyl)-phenyl]-methanesulfonamide,
(E)-N-(2-{2-[2-(4-methanesulfonylamino-phenyl)-vinyl]-1H-benzimidazol-5-yl}-phenyl)-methanesulfonamide,
(E)-N-[4-(2-{5-[2-(1-hydroxy-1-methyl-ethyl)-phenyl]-1H-benzimidazol-2-yl}-vinyl)-phenyl]-methanesulfonamide,
(E)-2-{2-[2-(4-methanesulfonylamino-phenyl)-vinyl]-1H-benzimidazol-5-yl}-benzenesulfonamide,
(E)-C,C,C-trifluoro-N-(2-{2-[2-(4-methanesulfonylamino-phenyl)-vinyl]-1H-benzimidazol-5-yl}-phenyl)-methanesulfonamide,
(E)-N-(4-{2-[5-(2-acetyl-phenyl)-1H-benzimidazol-2-yl]-vinyl}-phenyl)-C,C,C-trifluoro-methanesulfonamide,
(E)-C,C,C-trifluoro-N-[4-(2-{5-[2-(1-hydroxy-ethyl)-phenyl]-1H-benzimidazol-2-yl}-vinyl)-phenyl]-methanesulfonamide,
(E)-C,C,C-trifluoro-N-(4-{2-[5-(2-methanesulfonylamino-phenyl)-1H-benzimidazol-2-yl]-vinyl}-phenyl)-methanesulfonamide,
(E)-C,C,C-trifluoro-N-[4-(2-{5-[2-(1-hydroxy-1-methyl-ethyl)-phenyl]-1H-benzimidazol-2-yl}-vinyl)-phenyl]-methanesulfonamide,
(E)-2-{2-[2-(4-trifluoromethanesulfonylamino-phenyl)-vinyl]-1H-benzimidazol-5-yl}-benzenesulfonamide,
(E)-C,C,C-trifluoro-N-(4-{2-[5-(2-trifluoromethanesulfonylamino-phenyl)-1H-benzimidazol-2-yl]-vinyl}-phenyl)-methanesulfonamide,
2-{2-[2-(4-trifluoromethoxy-phenyl)-cyclopropyl]-1H-benzimidazol-5-yl}-benzenesulfonamide,
2-{2-[2-(4-trifluoromethyl-phenyl)-cyclopropyl]-1H-benzimidazol-5-yl}-benzenesulfonamide,
2-{2-[2-(4-trifluoromethanesulfonyl-phenyl)-cyclopropyl]-1H-benzimidazol-5-yl}-benzenesulfonamide,
C,C,C-trifluoro-N-(2-{2-[2-(4-trifluoromethoxy-phenyl)-cyclopropyl]-1H-benzimidazol-5-yl}-phenyl)-methanesulfonamide,
C,C,C-trifluoro-N-(2-{2-[2-(4-trifluoromethyl-phenyl)-cyclopropyl]-1H-benzimidazol-5-yl}-phenyl)-methanesulfonamide,
C,C,C-trifluoro-N-(2-{2-[2-(4-trifluoromethanesulfonyl-phenyl)-cyclopropyl]-1H-benzimidazol-5-yl}-phenyl)-methanesulfonamide,
1-(2-{2-[2-(4-chloro-phenyl)-cyclopropyl]-1H-benzimidazol-5-yl}-phenyl)-ethanone,
1-(2-{2-[2-(4-chloro-phenyl)-cyclopropyl]-1H-benzimidazol-5-yl}-phenyl)-ethanol,
N-(2-{2-[2-(4-chloro-phenyl)-cyclopropyl]-1H-benzimidazol-5-yl}-phenyl)-methanesulfonamide,
2-(2-{2-[2-(4-chloro-phenyl)-cyclopropyl]-1H-benzimidazol-5-yl}-phenyl)-propan-2-ol,
2-{2-[2-(4-chloro-phenyl)-cyclopropyl]-1H-benzimidazol-5-yl}-benzenesulfonamide,
N-(2-{2-[2-(4-chloro-phenyl)-cyclopropyl]-1H-benzimidazol-5-yl}-phenyl)-C,C,C-trifluoro-methanesulfonamide,
1-(2-{2-[2-(4-methanesulfonyl-phenyl)-cyclopropyl]-1H-benzimidazol-5-yl}-phenyl)-ethanone,
1-(2-{2-[2-(4-methanesulfonyl-phenyl)-cyclopropyl]-1H-benzimidazol-5-yl}-phenyl)-ethanol,
N-(2-{2-[2-(4-methanesulfonyl-phenyl)-cyclopropyl]-1H-benzimidazol-5-yl}-phenyl)-methanesulfonamide,
2-(2-{2-[2-(4-methanesulfonyl-phenyl)-cyclopropyl]-1H-benzimidazol-5-yl}-phenyl)-propan-2-ol,
2-{2-[2-(4-methanesulfonyl-phenyl)-cyclopropyl]-1H-benzimidazol-5-yl}-benzenesulfonamide,
C,C,C-trifluoro-N-(2-{2-[2-(4-methanesulfonyl-phenyl)-cyclopropyl]-1H-benzimidazol-5-yl}-phenyl)-methanesulfonamide, 1-[2-(2-{2-[4-(2,2,2-trifluoro-1-trifluoromethyl-ethoxy)-phenyl]-cyclopropyl"-1H-benzimidazol-5-yl)-phenyl]-ethanone,
1-[2-(2-{2-[4-(2,2,2-trifluoro-1-trifluoromethyl-ethoxy)-phenyl]-cyclopropyl"-1H-benzimidazol-5-yl)-phenyl]-ethanol,
N-[2-(2-{2-[4-(2,2,2-trifluoro-1-trifluoromethyl-ethoxy)-phenyl]-cyclopropyl"-1H-benzimidazol-5-yl)-phenyl]-methanesulfonamide,
2-[2-(2-{2-[4-(2,2,2-trifluoro-1-trifluoromethyl-ethoxy)-phenyl]-cyclopropyl"-1H-benzimidazol-5-yl)-phenyl]-propan-2-ol,
2-(2-{2-[4-(2,2,2-trifluoro-1-trifluoromethyl-ethoxy)-phenyl]-cyclopropyl}-1H-benzimidazol-5-yl)-benzenesulfonamide,
C,C,C-trifluoro-N-[2-(2-{2-[4-(2,2,2-trifluoro-1-trifluoromethyl-ethoxy)-phenyl]-cyclopropyl}-1H-benzimidazol-5-yl)-phenyl]-methanesulfonamide,
1-[2-(2-{2-[4-(2,2,2-trifluoro-ethoxy)-phenyl]-cyclopropyl}-1H-benzimidazol-5-yl)-phenyl]-ethanone,
1-[2-(2-{2-[4-(2,2,2-trifluoro-ethoxy)-phenyl]-cyclopropyl}-1H-benzimidazol-5-yl)-phenyl]-ethanol,
N-[2-(2-{2-[4-(2,2,2-trifluoro-ethoxy)-phenyl]-cyclopropyl}-1H-benzimidazol-5-yl)-phenyl]-methanesulfonamide,
2-[2-(2-{2-[4-(2,2,2-trifluoro-ethoxy)-phenyl]-cyclopropyl}-1H-benzimidazol-5-yl)-phenyl]-propan-2-ol,
2-(2-{2-[4-(2,2,2-trifluoro-ethoxy)-phenyl]-cyclopropyl}-1H-benzimidazol-5-yl)-benzenesulfonamide,
C,C,C-trifluoro-N-[2-(2-{2-[4-(2,2,2-trifluoro-ethoxy)-phenyl]-cyclopropyl}-1H-benzimidazol-5-yl)-phenyl]-methanesulfonamide,
1-[2-(2-{2-[4-(2,2,3,3,3-pentafluoro-propoxy)-phenyl]-cyclopropyl}-1H-benzimidazol-5-yl)-phenyl]-ethanone,
1-[2-(2-{2-[4-(2,2,3,3,3-pentafluoro-propoxy)-phenyl]-cyclopropyl}-1H-benzimidazol-5-yl)-phenyl]-ethanol,
N-[2-(2-{2-[4-(2,2,3,3,3-pentafluoro-propoxy)-phenyl]-cyclopropyl}-1H-benzimidazol-5-yl)-phenyl]-methanesulfonamide,
2-[2-(2-{2-[4-(2,2,3,3,3-pentafluoro-propoxy)-phenyl]-cyclopropyl}-1H-benzimidazol-5-yl)-phenyl]-propan-2-ol,
2-(2-{2-[4-(2,2,3,3,3-pentafluoro-propoxy)-phenyl]-cyclopropyl}-1H-benzimidazol-5-yl)-benzenesulfonamide,
C,C,C-trifluoro-N-[2-(2-{2-[4-(2,2,3,3,3-pentafluoro-propoxy)-phenyl]-cyclopropyl}-1H-benzimidazol-5-yl)-phenyl]-methanesulfonamide,
1-(2-{2-[2-(3-chloro-phenyl)-cyclopropyl]-1H-benzimidazol-5-yl}-phenyl)-ethanone,
1-(2-{2-[2-(3-chloro-phenyl)-cyclopropyl]-1H-benzimidazol-5-yl}-phenyl)-ethanol,
N-(2-{2-[2-(3-chloro-phenyl)-cyclopropyl]-1H-benzimidazol-5-yl}-phenyl)-methanesulfonamide,
2-(2-{2-[2-(3-chloro-phenyl)-cyclopropyl]-1H-benzimidazol-5-yl}-phenyl)-propan-2-ol,
2-{2-[2-(3-chloro-phenyl)-cyclopropyl]-1H-benzimidazol-5-yl}-benzenesulfonamide,
N-(2-{2-[2-(3-chloro-phenyl)-cyclopropyl]-1H-benzimidazol-5-yl}-phenyl)-C,C,C-trifluoro-methanesulfonamide,
1-(2-{2-[2-(3-trifluoromethyl-phenyl)-cyclopropyl]-1H-benzimidazol-5-yl}-phenyl)-ethanone,
1-(2-{2-[2-(3-trifluoromethyl-phenyl)-cyclopropyl]-1H-benzimidazol-5-yl}-phenyl)-ethanol,
N-(2-{2-[2-(3-trifluoromethyl-phenyl)-cyclopropyl]-1H-benzimidazol-5-yl}-phenyl)-methanesulfonamide,
2-(2-{2-[2-(3-trifluoromethyl-phenyl)-cyclopropyl]-1H-benzimidazol-5-yl}-phenyl)-propan-2-ol,
2-{2-[2-(3-trifluoromethyl-phenyl)-cyclopropyl]-1H-benzimidazol-5-yl}-benzenesulfonamide,
C,C,C-trifluoro-N-(2-{2-[2-(3-trifluoromethyl-phenyl)-cyclopropyl]-1H-benzimidazol-5-yl}-phenyl)-methanesulfonamide,
N-(4-{2-[5-(2-acetyl-phenyl)-1H-benzimidazol-2-yl]-cyclopropyl}-phenyl)-methanesulfonamide,
N-[4-(2-{5-[2-(1-hydroxy-ethyl)-phenyl]-1H-benzimidazol-2-yl}-cyclopropyl)-phenyl]-methanesulfonamide,
N-(2-{2-[2-(4-methanesulfonylamino-phenyl)-cyclopropyl]-1H-benzimidazol-5-yl}-phenyl)-methanesulfonamide,
N-[4-(2-{5-[2-(1-hydroxy-1-methyl-ethyl)-phenyl]-1H-benzimidazol-2-yl}-cyclopropyl)-phenyl]-methanesulfonamide,
2-{2-[2-(4-methanesulfonylamino-phenyl)-cyclopropyl]-1H-benzimidazol-5-yl}-benzenesulfonamide,
C,C,C-trifluoro-N-(2-{2-[2-(4-methanesulfonylamino-phenyl)-cyclopropyl]-1H-benzimidazol-5-yl}-phenyl)-methanesulfonamide,
N-(4-{2-[5-(2-acetyl-phenyl)-1H-benzimidazol-2-yl]-cyclopropyl}-phenyl)-C,C,C-trifluoro-methanesulfonamide,
C,C,C-trifluoro-N-[4-(2-{5-[2-(1-hydroxy-ethyl)-phenyl]-1H-benzimidazol-2-yl}-cyclopropyl)-phenyl]-methanesulfonamide,
C,C,C-trifluoro-N-(4-{2-[5-(2-methanesulfonylamino-phenyl)-1H-benzimidazol-2-yl]-cyclopropyl}-phenyl)-methanesulfonamide,
C,C,C-trifluoro-N-[4-(2-{5-[2-(1-hydroxy-1-methyl-ethyl)-phenyl]-1H-benzimidazol-2-yl]-cyclopropyl)-phenyl}-methanesulfonamide,
2-{2-[2-(4-trifluoromethanesulfonylamino-phenyl)-cyclopropyl]-1H-benzimidazol-5-yl}-benzenesulfonamide,
C,C,C-trifluoro-N-(2-{2-[2-(4-trifluoromethanesulfonylamino-phenyl)-cyclopropyl]-1H-benzimidazol-5-yl}-phenyl)-methanesulfonamide,
2-[2-(4-trifluoromethoxy-phenylethynyl)-1H-benzimidazol-5-yl]-benzenesulfonamide,
2-[2-(4-trifluoromethyl-phenylethynyl)-1H-benzimidazol-5-yl]-benzenesulfonamide,
2-[2-(4-trifluoromethanesulfonyl-phenylethynyl)-1H-benzimidazol-5-yl]-benzenesulfonamide,
C,C,C-trifluoro-N-{2-[2-(4-trifluoromethoxy-phenylethynyl)-1H-benzimidazol-5-yl]-phenyl}-methanesulfonamide,
C,C,C-trifluoro-N-{2-[2-(4-trifluoromethyl-phenylethynyl)-1H-benzimidazol-5-yl]-phenyl}-methanesulfonamide,
C,C,C-trifluoro-N-{2-[2-(4-trifluoromethanesulfonyl-phenylethynyl)-1H-benzimidazol-5-yl]-phenyl}-methanesulfonamide,
1-{2-[2-(4-chloro-phenylethynyl)-1H-benzimidazol-5-yl]-phenyl}-ethanone,
1-{2-[2-(4-chloro-phenylethynyl)-1H-benzimidazol-5-yl]-phenyl}-ethanol,
N-{2-[2-(4-chloro-phenylethynyl)-1H-benzimidazol-5-yl]-phenyl"-methanesulfonamide,
2-{2-[2-(4-chloro-phenylethynyl)-1H-benzimidazol-5-yl]-phenyl}-propan-2-ol,
2-[2-(4-chloro-phenylethynyl)-1H-benzimidazol-5-yl]-benzenesulfonamide, N-{2-[2-(4-chloro-phenylethynyl)-1H-benzimidazol-5-yl]-phenyl}-C,C,C-trifluoro-methanesulfonamide,
1-{2-[2-(4-methanesulfonyl-phenylethynyl)-1H-benzimidazol-5-yl]-phenyl"-ethanone,
1-{2-[2-(4-methanesulfonyl-phenylethynyl)-1H-benzimidazol-5-yl]-phenyl"-ethanol,
N-{2-[2-(4-methanesulfonyl-phenylethynyl)-1H-benzimidazol-5-yl]-phenyl"-methanesulfonamide,
2-{2-[2-(4-methanesulfonyl-phenylethynyl)-1H-benzimidazol-5-yl]-phenyl"-propan-2-ol,
2-[2-(4-methanesulfonyl-phenylethynyl)-1H-benzimidazol-5-yl]-benzenesulfonamide,
C,C,C-trifluoro-N-{2-[2-(4-methanesulfonyl-phenylethynyl)-1H-benzimidazol-5-yl]-phenyl}-methanesulfonamide,
1-(2-{2-[4-(2,2,2-trifluoro-1-trifluoromethyl-ethoxy)-phenylethynyl]-1H-benzimidazol-5-yl}-phenyl)-ethanone,
1-(2-{2-[4-(2,2,2-trifluoro-1-trifluoromethyl-ethoxy)-phenylethynyl]-1H-benzimidazol-5-yl}-phenyl)-ethanol,
N-(2-{2-[4-(2,2,2-trifluoro-1-trifluoromethyl-ethoxy)-phenylethynyl]-1H-benzimidazol-5-yl}-phenyl)-methanesulfonamide,
2-(2-{2-[4-(2,2,2-trifluoro-1-trifluoromethyl-ethoxy)-phenylethynyl]-1H-benzimidazol-5-yl}-phenyl)-propan-2-ol,
2-{2-[4-(2,2,2-trifluoro-1-trifluoromethyl-ethoxy)-phenylethynyl]-1H-benzimidazol-5-yl}-benzenesulfonamide,
C,C,C-trifluoro-N-(2-{2-[4-(2,2,2-trifluoro-1-trifluoromethyl-ethoxy)-phenylethynyl]-1H-benzimidazol-5-yl}-phenyl)-methanesulfonamide,
1-(2-{2-[4-(2,2,2-trifluoro-ethoxy)-phenylethynyl]-1H-benzimidazol-5-yl}-phenyl)-ethanone,
1-(2-{2-[4-(2,2,2-trifluoro-ethoxy)-phenylethynyl]-1H-benzimidazol-5-yl}-phenyl)-ethanol,
N-(2-{2-[4-(2,2,2-trifluoro-ethoxy)-phenylethynyl]-1H-benzimidazol-5-yl}-phenyl)-methanesulfonamide,
2-(2-{2-[4-(2,2,2-trifluoro-ethoxy)-phenylethynyl]-1H-benzimidazol-5-yl}-phenyl)-propan-2-ol,
2-{2-[4-(2,2,2-trifluoro-ethoxy)-phenylethynyl]-1H-benzimidazol-5-yl}-benzenesulfonamide,
C,C,C-trifluoro-N-(2-{2-[4-(2,2,2-trifluoro-ethoxy)-phenylethynyl]-1H-benzimidazol-5-yl}-phenyl)-methanesulfonamide,
1-(2-{2-[4-(2,2,3,3,3-pentafluoro-propoxy)-phenylethynyl]-1H-benzimidazol-5-yl}-phenyl)-ethanone,
1-(2-{2-[4-(2,2,3,3,3-pentafluoro-propoxy)-phenylethynyl]-1H-benzimidazol-5-yl}-phenyl)-ethanol,
N-(2-{2-[4-(2,2,3,3,3-pentafluoro-propoxy)-phenylethynyl]-1H-benzimidazol-5-yl}-phenyl)-methanesulfonamide,
2-(2-{2-[4-(2,2,3,3,3-pentafluoro-propoxy)-phenylethynyl]-1H-benzimidazol-5-yl}-phenyl)-propan-2-ol,
2-{2-[4-(2,2,3,3,3-pentafluoro-propoxy)-phenylethynyl]-1H-benzimidazol-5-yl}-benzenesulfonamide,
C,C,C-trifluoro-N-(2-{2-[4-(2,2,3,3,3-pentafluoro-propoxy)-phenylethynyl]-1H-benzimidazol-5-yl}-phenyl)-methanesulfonamide,
1-{2-[2-(3-chloro-phenylethynyl)-1H-benzimidazol-5-yl]-phenyl}-ethanone,
2-{2-[2-(3-chloro-phenylethynyl)-1H-benzimidazol-5-yl]-phenyl}-propan-2-ol,
N-{2-[2-(3-chloro-phenylethynyl)-1H-benzimidazol-5-yl]-phenyl"-methanesulfonamide,
1-{2-[2-(3-chloro-phenylethynyl)-1H-benzimidazol-5-yl]-phenyl}-ethanol,
2-[2-(3-chloro-phenylethynyl)-1H-benzimidazol-5-yl]-benzenesulfonamide,
N-{2-[2-(3-chloro-phenylethynyl)-1H-benzimidazol-5-yl]-phenyl}-C,C,C-trifluoro-methanesulfonamide,
1-{2-[2-(3-trifluoromethyl-phenylethynyl)-1H-benzimidazol-5-yl]-phenyl"-ethanone,
1-{2-[2-(3-trifluoromethyl-phenylethynyl)-1H-benzimidazol-5-yl]-phenyl"-ethanol,
N-{2-[2-(3-trifluoromethyl-phenylethynyl)-1H-benzimidazol-5-yl]-phenyl"-methanesulfonamide,
2-{2-[2-(3-trifluoromethyl-phenylethynyl)-1H-benzimidazol-5-yl]-phenyl"-propan-2-ol,
2-[2-(3-trifluoromethyl-phenylethynyl)-1H-benzimidazol-5-yl]-benzenesulfonamide,
C,C,C-trifluoro-N-{2-[2-(3-trifluoromethyl-phenylethynyl)-1H-benzimidazol-5-yl]-phenyl}-methanesulfonamide,
N-{4-[5-(2-acetyl-phenyl)-1H-benzimidazol-2-yl-ethynyl]-phenyl"-methanesulfonamide,
N-(4-{5-[2-(1-hydroxy-ethyl)-phenyl]-1H-benzimidazol-2-yl-ethynyl}-phenyl)-methanesulfonamide,
N-{2-[2-(4-methanesulfonylamino-phenylethynyl)-1H-benzimidazol-5-yl]-phenyl}-methanesulfonamide,
N-(4-{5-[2-(1-hydroxy-1-methyl-ethyl)-phenyl]-1H-benzimidazol-2-yl-ethynyl"-phenyl)-methanesulfonamide,
2-[2-(4-methanesulfonylamino-phenylethynyl)-1H-benzimidazol-5-yl]-benzenesulfonamide,
C,C,C-trifluoro-N-{2-[2-(4-methanesulfonylamino-phenylethynyl)-1H-benzimidazol-5-yl]-phenyl}-methanesulfonamide,
N-{4-[5-(2-acetyl-phenyl)-1H-benzimidazol-2-yl-ethynyl]-phenyl}-C,C,C-trifluoro-methanesulfonamide,
C,C,C-trifluoro-N-(4-{5-[2-(1-hydroxy-ethyl)-phenyl]-1H-benzimidazol-2-yl-ethynyl"-phenyl)-methanesulfonamide,
C,C,C-trifluoro-N-{4-[5-(2-methanesulfonylamino-phenyl)-1H-benzimidazol-2-yl-ethynyl]-phenyl}-methanesulfonamide,
C,C,C-trifluoro-N-(4-{5-[2-(1-hydroxy-1-methyl-ethyl)-phenyl]-1H-benzimidazol-2-yl-ethynyl}-phenyl)-methanesulfonamide,
2-[2-(4-trifluoromethanesulfonylamino-phenylethynyl)-1H-benzimidazol-5-yl]-benzenesulfonamide,
C,C,C-trifluoro-N-{2-[2-(4-trifluoromethanesulfonylamino-phenylethynyl)-1H-benzimidazol-5-yl]-phenyl}-methanesulfonamide,
(E)-N-tert-butyl-2-{2-[2-(4-trifluoromethyl-phenyl)-vinyl]-1H-benzimidazol-5-yl}-benzenesulfonamide,
(E)-N-methyl-2-{2-[2-(4-trifluoromethyl-phenyl)-vinyl]-1H-benzimidazol-5-yl}-benzenesulfonamide,
(E)-2-hydroxy-1-(2-{2-[2-(4-trifluoromethyl-phenyl)-vinyl]-1H-benzimidazol-5-yl}-phenyl)-ethanone,
(E)-2-{2-[2-(4-bromo-phenyl)-vinyl]-1H-benzimidazol-5-yl}-N-methyl-benzenesulfonamide,
(E)-N-methyl-2-[2-(2-p-tolyl-vinyl)-1H-benzimidazol-5-yl]-benzenesulfonamide,
(E)-2-{2-[2-(4-fluoro-phenyl)-vinyl]-1H-benzimidazol-5-yl}-N-methyl-benzenesulfonamide,
(E)-2-{2-[2-(3,4-dichloro-phenyl)-vinyl]-1H-benzimidazol-5-yl}-N-methyl-benzenesulfonamide,
(E)-2-{2-[2-(3-bromo-4-fluoro-phenyl)-vinyl]-1H-benzimidazol-5-yl}-N-methyl-benzenesulfonamide,
(E)-2-{2-[2-(4-dimethylamino-phenyl)-vinyl]-1H-benzimidazol-5-yl}-N-methyl-benzenesulfonamide, (E)-2-{2-[2-(3-fluoro-4-trifluoromethyl-phenyl)-vinyl]-1H-benzimidazol-5-yl}-N-methyl-benzenesulfonamide,
(E)-2-{2-[2-(2-fluoro-4-trifluoromethyl-phenyl)-vinyl]-1H-benzimidazol-5-yl}-N-methyl-benzenesulfonamide,
(E)-2-{2-[2-(3-chloro-4-fluoro-phenyl)-vinyl]-1H-benzimidazol-5-yl}-N-methyl-benzenesulfonamide,
(E)-2-{2-[2-(3-fluoro-5-trifluoromethyl-phenyl)-vinyl]-1H-benzimidazol-5-yl}-N-methyl-benzenesulfonamide,
(E)-N-methyl-2-{2-[2-(2,3,4-trifluoro-phenyl)-vinyl]-1H-benzimidazol-5-yl}-benzenesulfonamide,
(E)-N-methyl-2-{2-[2-(2,4,5-trifluoro-phenyl)-vinyl]-1H-benzimidazol-5-yl}-benzenesulfonamide,
(E)-2-{2-[2-(2,3-difluoro-phenyl)-vinyl]-1H-benzimidazol-5-yl}-N-methyl-benzenesulfonamide,
(E)-2-{2-[2-(2,5-difluoro-phenyl)-vinyl]-1H-benzimidazol-5-yl}-N-methyl-benzenesulfonamide,
(E)-2-{2-[2-(2,6-difluoro-phenyl)-vinyl]-1H-benzimidazol-5-yl}-N-methyl-benzenesulfonamide,
(E)-2-{2-[2-(3,5-difluoro-phenyl)-vinyl]-1H-benzimidazol-5-yl}-N-methyl-benzenesulfonamide,
(E)-2-{2-[2-(3,4-difluoro-phenyl)-vinyl]-1H-benzimidazol-5-yl}-N-methyl-benzenesulfonamide,
(E)-2-{2-[2-(4-fluoro-2-trifluoromethyl-phenyl)-vinyl]-1H-benzimidazol-5-yl}-N-methyl-benzenesulfonamide,
(E)-2-{2-[2-(4-fluoro-3-trifluoromethyl-phenyl)-vinyl]-1H-benzimidazol-5-yl}-N-methyl-benzenesulfonamide,
(E)-2-{2-[2-(2-fluoro-3-trifluoromethyl-phenyl)-vinyl]-1H-benzimidazol-5-yl}-N-methyl-benzenesulfonamide,
(E)-2-{2-[2-(3,5-bis-trifluoromethyl-phenyl)-vinyl]-1H-benzimidazol-5-yl}-N-methyl-benzenesulfonamide,
(E)-2-{2-[2-(2,5-bis-trifluoromethyl-phenyl)-vinyl]-1H-benzimidazol-5-yl}-N-methyl-benzenesulfonamide,
(E)-2-{2-[2-(3-chloro-2-fluoro-phenyl)-vinyl]-1H-benzimidazol-5-yl}-N-methyl-benzenesulfonamide,
(E)-2-{2-[2-(2-chloro-6-fluoro-phenyl)-vinyl]-1H-benzimidazol-5-yl}-N-methyl-benzenesulfonamide,
(E)-2-{2-[2-(2,4-dichloro-phenyl)-vinyl]-1H-benzimidazol-5-yl}-N-methyl-benzenesulfonamide,
(E)-2-{2-[2-(3-bromo-phenyl)-vinyl]-1H-benzimidazol-5-yl}-N-methyl-benzenesulfonamide,
(E)-2-{2-[2-(4-chloro-2-fluoro-phenyl)-vinyl]-1H-benzimidazol-5-yl}-N-methyl-benzenesulfonamide,
(E)-2-{2-[2-(4-chloro-2-methanesulfonyl-phenyl)-vinyl]-1H-benzimidazol-5-yl}-N-methyl-benzenesulfonamide,
(E)-N-methyl-2-{2-[2-(4-trifluoromethylsulfanyl-phenyl)-vinyl]-1H-benzimidazol-5-yl}-benzenesulfonamide,
(E)-N-methyl-2-{2-[2-(4-trifluoromethanesulfonyl-phenyl)-vinyl]-1H-benzimidazol-5-yl}-benzenesulfonamide,
(E)-N-methyl-2-{2-[2-(2-trifluoromethyl-phenyl)-vinyl]-1H-benzimidazol-5-yl}-benzenesulfonamide,
(E)-N-methyl-2-{2-[2-(3-trifluoromethoxy-phenyl)-vinyl]-1H-benzimidazol-5-yl}-benzenesulfonamide,
(E)-N-methyl-2-{2-[2-(4-trifluoromethoxy-phenyl)-vinyl]-1H-benzimidazol-5-yl}-benzenesulfonamide,
(E)-2-{2-[2-(2-chloro-phenyl)-vinyl]-1H-benzimidazol-5-yl}-N-methyl-benzenesulfonamide,
(E)-2-{2-[2-(4-chloro-phenyl)-vinyl]-1H-benzimidazol-5-yl}-N-methyl-benzenesulfonamide,
(E)-2-{2-[2-(2-bromo-phenyl)-vinyl]-1H-benzimidazol-5-yl}-N-methyl-benzenesulfonamide,
(E)-2-{2-[2-(2,4-difluoro-phenyl)-vinyl]-1H-benzimidazol-5-yl}-N-methyl-benzenesulfonamide,
N-methyl-2-{2-[2-(3-trifluoromethyl-phenyl)-ethyl]-1H-benzimidazol-5-yl}-benzenesulfonamide,
(E)-2-{2-[2-(4-methanesulfonyl-phenyl)-vinyl]-1H-benzimidazol-5-yl}-N-methyl-benzenesulfonamide,
(E)-2-{2-[2-(2,4-difluoro-phenyl)-vinyl]-1H-benzimidazol-5-yl}-benzenesulfonamide,
(E)-2-{2-[2-(3,4-difluoro-phenyl)-vinyl]-1H-benzimidazol-5-yl}-benzenesulfonamide,
(E)-2-{2-[2-(2,3-difluoro-phenyl)-vinyl]-1H-benzimidazol-5-yl}-benzenesulfonamide,
(E)-2-{2-[2-(2,5-difluoro-phenyl)-vinyl]-1H-benzimidazol-5-yl}-benzenesulfonamide,
(E)-2-{2-[2-(3,5-difluoro-phenyl)-vinyl]-1H-benzimidazol-5-yl}-benzenesulfonamide,
(E)-2-{2-[2-(3-trifluoromethoxy-phenyl)-vinyl]-1H-benzimidazol-5-yl}-benzenesulfonamide,
(E)-2-{2-[2-(4-bromo-phenyl)-vinyl]-1H-benzimidazol-5-yl}-benzenesulfonamide,
(E)-2-{2-[2-(2-trifluoromethyl-phenyl)-vinyl]-1H-benzimidazol-5-yl}-benzenesulfonamide,
(E)-2-{2-[2-(2-chloro-phenyl)-vinyl]-1H-benzimidazol-5-yl}-benzenesulfonamide,
(E)-2-{2-[2-(2-bromo-phenyl)-vinyl]-1H-benzimidazol-5-yl}-benzenesulfonamide,
(E)-2-{2-[2-(4-fluoro-2-trifluoromethyl-phenyl)-vinyl]-1H-benzimidazol-5-yl}-benzenesulfonamide,
(E)-2-{2-[2-(2-fluoro-3-trifluoromethyl-phenyl)-vinyl]-1H-benzimidazol-5-yl}-benzenesulfonamide,
(E)-2-{2-[2-(4-fluoro-3-trifluoromethyl-phenyl)-vinyl]-1H-benzimidazol-5-yl}-benzenesulfonamide,
(E)-2-{2-[2-(2,3,4-trifluoro-phenyl)-vinyl]-1H-benzimidazol-5-yl}-benzenesulfonamide,
(E)-2-{2-[2-(2,4,5-trifluoro-phenyl)-vinyl]-1H-benzimidazol-5-yl}-benzenesulfonamide,
(E)-2-{2-[2-(2,6-difluoro-phenyl)-vinyl]-1H-benzimidazol-5-yl}-benzenesulfonamide,
(E)-2-{2-[2-(3,5-bis-trifluoromethyl-phenyl)-vinyl]-1H-benzimidazol-5-yl}-benzenesulfonamide,
(E)-2-{2-[2-(2,5-bis-trifluoromethyl-phenyl)-vinyl]-1H-benzimidazol-5-yl}-benzenesulfonamide,
(E)-2-{2-[2-(4-chloro-2-methanesulfonyl-phenyl)-vinyl]-1H-benzimidazol-5-yl}-benzenesulfonamide,
(E)-2-{2-[2-(3-bromo-phenyl)-vinyl]-1H-benzimidazol-5-yl}-benzenesulfonamide,
(E)-2-{2-[2-(4-chloro-3-trifluoromethyl-phenyl)-vinyl]-1H-benzimidazol-5-yl}-benzenesulfonamide,
(E)-2-{2-[2-(5-bromo-2-fluoro-phenyl)-vinyl]-1H-benzimidazol-5-yl}-benzenesulfonamide,
(E)-2-{2-[2-(4-trifluoromethylsulfanyl-phenyl)-vinyl]-1H-benzimidazol-5-yl}-benzenesulfonamide,
(E)-N-(2-{2-[2-(4-bromo-phenyl)-vinyl]-1H-benzimidazol-5-yl}-phenyl)-methanesulfonamide,
(E)-N-(2-{2-[2-(4-isopropyl-phenyl)-vinyl]-1H-benzimidazol-5-yl}-phenyl)-methanesulfonamide,
(E)-N-(2-{2-[2-(3-chloro-4-fluoro-phenyl)-vinyl]-1H-benzimidazol-5-yl}-phenyl)-methanesulfonamide,
(E)-N-(2-{2-[2-(3-bromo-4-fluoro-phenyl)-vinyl]-1H-benzimidazol-5-yl}-phenyl)-methanesulfonamide,
(E)-N-(2-{2-[2-(4-difluoromethoxy-phenyl)-vinyl]-1H-benzimidazol-5-yl}-phenyl)-methanesulfonamide,
(E)-N-(2-{2-[2-(3-fluoro-5-trifluoromethyl-phenyl)-vinyl]-1H-benzimidazol-5-yl}-phenyl)-methanesulfonamide, (E)-N-{2-[2-(2-p-tolyl-vinyl)-1H-benzimidazol-5-yl]-phenyl"-methanesulfonamide,
(E)-N-(2-{2-[2-(4-dimethylamino-phenyl)-vinyl]-1H-benzimidazol-5-yl}-phenyl)-methanesulfonamide,
(E)-N-(2-{2-[2-(4-ethoxy-phenyl)-vinyl]-1H-benzimidazol-5-yl}-phenyl)-methanesulfonamide,
(E)-N-{2-[2-(2-naphthalen-2-yl-vinyl)-1H-benzimidazol-5-yl]-phenyl"-methanesulfonamide,
(E)-N-(2-{2-[2-(3,4-dichloro-phenyl)-vinyl]-1H-benzimidazol-5-yl}-phenyl)-methanesulfonamide,
(E)-N-(2-{2-[2-(3-fluoro-4-trifluoromethyl-phenyl)-vinyl]-1H-benzimidazol-5-yl}-phenyl)-methanesulfonamide,
(E)-N-(2-{2-[2-(2-fluoro-4-trifluoromethyl-phenyl)-vinyl]-1H-benzimidazol-5-yl}-phenyl)-methanesulfonamide,
(E)-5-(2-methanesulfonyl-phenyl)-2-[2-(4-trifluoromethyl-phenyl)-vinyl]-1H-benzimidazole,
(E)-2-{2-[2-(3-fluoro-4-trifluoromethyl-phenyl)-vinyl]-1H-benzimidazol-5-yl}-benzenesulfonamide,
(E)-2-{2-[2-(2-fluoro-4-trifluoromethyl-phenyl)-vinyl]-1H-benzimidazol-5-yl}-benzenesulfonamide,
(E)-2-{2-[2-(3-ethoxy-phenyl)-vinyl]-1H-benzimidazol-5-yl}-benzenesulfonamide,
(E)-2-(2-styryl-1H-benzimidazol-5-yl)-benzenesulfonamide,
(E)-2-{2-[2-(3,4-dichloro-phenyl)-vinyl]-1H-benzimidazol-5-yl}-benzenesulfonamide,
(E)-2-{2-[2-(4-chloro-2-fluoro-phenyl)-vinyl]-1H-benzimidazol-5-yl}-benzenesulfonamide,
(E)-2-{2-[2-(4-isopropyl-phenyl)-vinyl]-1H-benzimidazol-5-yl}-benzenesulfonamide,
(E)-2-[2-(2-p-tolyl-vinyl)-1H-benzimidazol-5-yl]-benzenesulfonamide,
(E)-2-{2-[2-(3-chloro-2-fluoro-phenyl)-vinyl]-1H-benzimidazol-5-yl}-benzenesulfonamide,
(E)-2-{2-[2-(3-chloro-4-fluoro-phenyl)-vinyl]-1H-benzimidazol-5-yl}-benzenesulfonamide,
(E)-2-[2-(2-naphthalen-2-yl-vinyl)-1H-benzimidazol-5-yl]-benzenesulfonamide,
(E)-2-{2-[2-(4-fluoro-phenyl)-vinyl]-1H-benzimidazol-5-yl}-benzenesulfonamide,
(E)-2-{2-[2-(4-difluoromethyl-phenyl)-vinyl]-1H-benzimidazol-5-yl}-benzenesulfonamide,
(E)-2-{2-[2-(3-fluoro-5-trifluoromethyl-phenyl)-vinyl]-1H-benzimidazol-5-yl}-benzenesulfonamide,
(E)-2-{2-[2-(2,4-dichloro-phenyl)-vinyl]-1H-benzimidazol-5-yl}-benzenesulfonamide,
(E)-2-{2-[2-(2-chloro-6-fluoro-phenyl)-vinyl]-1H-benzimidazol-5-yl}-benzenesulfonamide,
(E)-2-{2-[2-(3-bromo-4-fluoro-phenyl)-vinyl]-1H-benzimidazol-5-yl}-benzenesulfonamide,
(E)-2-{2-[2-(4-ethoxy-phenyl)-vinyl]-1H-benzimidazol-5-yl}-benzenesulfonamide,
(E)-4-fluoro-2-{2-[2-(4-trifluoromethyl-phenyl)-vinyl]-1H-benzimidazol-5-yl}-benzenesulfonamide,
(E)-N-(2-{3-methyl-2-[2-(4-trifluoromethyl-phenyl)-vinyl]-3H-benzimidazol-5-yl}-phenyl)-methanesulfonamide,
(E)-4-trifluoromethyl-2-{2-[2-(4-trifluoromethyl-phenyl)-vinyl]-1H-benzimidazol-5-yl}-benzenesulfonamide,
(E)-5-trifluoromethyl-2-{2-[2-(4-trifluoromethyl-phenyl)-vinyl]-1H-benzimidazol-5-yl}-benzenesulfonamide,
(E)-2-{2-[2-(2-quinolin-6-yl-vinyl)-1H-benzimidazol-5-yl]-phenyl}-propan-2-ol,
(E)-N-isopropyl-4-{2-[5-(2-methylsulfamoyl-phenyl)-1H-benzimidazol-2-yl]-vinyl}-benzamide,
(E)-2-{2-[2-(4-cyano-phenyl)-vinyl]-1H-benzimidazol-5-yl}-N-methyl-benzenesulfonamide,
(E)-N-(4-{2-[5-(2-methylsulfamoyl-phenyl)-1H-benzimidazol-2-yl]-vinyl"-phenyl)-acetamide,
(E)-4-{2-[5-(2-methylsulfamoyl-phenyl)-1H-benzimidazol-2-yl]-vinyl}-benzoic acid,
(E)-2-{2-[2-(1H-indol-6-yl)-vinyl]-1H-benzimidazol-5-yl}-N-methyl-benzenesulfonamide,
(E)-2-{2-[2-(2,4-bis-trifluoromethyl-phenyl)-vinyl]-1H-benzimidazol-5-yl}-N-methyl-benzenesulfonamide,
(E)-2-{2-[2-(4-acetyl-phenyl)-vinyl]-1H-benzimidazol-5-yl}-N-methyl-benzenesulfonamide,
(E)-2,2,2-trifluoro-N-(2-{2-[2-(4-trifluoromethyl-phenyl)-vinyl]-1H-benzimidazol-5-yl}-phenyl)-acetamide,
(E)-2,2,2-trifluoro-ethanesulfonic acid (2-{2-[2-(4-trifluoromethyl-phenyl)-vinyl]-1H-benzimidazol-5-yl}-phenyl)-amide,
(E)-2,2-dimethyl-N-(2-{2-[2-(4-trifluoromethyl-phenyl)-vinyl]-1H-benzimidazol-5-yl}-phenyl)-propionamide,
(E)-ethanesulfonic acid (2-{2-[2-(4-trifluoromethyl-phenyl)-vinyl]-1H-benzimidazol-5-yl}-phenyl)-amide,
(E)-(2-{2-[2-(4-trifluoromethyl-phenyl)-vinyl]-1H-benzimidazol-5-yl}-phenyl)-carbamic acid methyl ester,
(E)-2-(2-{2-[2-(4-tert-butyl-phenyl)-vinyl]-1H-benzimidazol-5-yl}-phenyl)-propan-2-ol,
(E)-2-{2-[2-(4-trifluoromethyl-phenyl)-vinyl]-1H-benzimidazol-5-yl}-phenylamine,
(E)-2-{2-[2-(4-trifluoromethyl-phenyl)-vinyl]-1H-benzimidazol-5-yl}-benzoic acid ethyl ester,
N-(2-{2-[2-(4-trifluoromethyl-phenyl)-cyclopropyl]-1H-benzimidazol-5-yl}-phenyl)-methanesulfonamide,
(E)-2-[2-(2-styryl-1H-benzimidazol-5-yl)-phenyl]-propan-2-ol,
(Z)-2-(2-{2-[2-(4-trifluoromethyl-phenyl)-vinyl]-1H-benzimidazol-5-yl}-phenyl)-propan-2-ol,
(E)-5-(2-aminosulfonylamino-phenyl)-2-[2-(4-trifluoromethyl-phenyl)-vinyl]-1H-benzimidazole,
2-(2-{2-[2-(4-trifluoromethyl-phenyl)-cyclopropyl]-1H-benzimidazol-5-yl}-phenyl)-propan-2-ol,
2-{2-[2-(4-trifluoromethyl-phenyl)-cyclopropyl]-1H-benzimidazol-5-yl}-phenol,
(2-{2-[2-(4-trifluoromethyl-phenyl)-cyclopropyl]-1H-benzimidazol-5-yl}-phenyl)-carbamic acid tert-butyl ester,
(2-{2-[2-(4-trifluoromethyl-phenyl)-cyclopropyl]-1H-benzimidazol-5-yl}-phenyl)-methanol,
(E)-N-{2-[2-(2-biphenyl-4-yl-vinyl)-1H-benzimidazol-5-yl]-phenyl"-methanesulfonamide,
(E)-(2-{2-[2-(4-trifluoromethyl-phenyl)-vinyl]-1H-benzimidazol-5-yl}-phenyl)-methanol,
(E)-N-(2-{1-methyl-2-[2-(4-trifluoromethyl-phenyl)-vinyl]-1H-benzimidazol-5-yl}-phenyl)-methanesulfonamide,
(E)-N-(2-{2-[2-(4-trifluoromethyl-phenyl)-vinyl]-1H-benzimidazol-5-yl}-phenyl)-acetamide,
(E)-(2-{2-[2-(4-trifluoromethyl-phenyl)-vinyl]-1H-benzimidazol-5-yl}-phenyl)-carbamic acid tert-butyl ester,
(E)-5-(2-methylsulfanyl-phenyl)-2-[2-(4-trifluoromethyl-phenyl)-vinyl]-1H-benzimidazole,
(E)-2-[2-(4-trifluoromethanesulfonyl-phenyl)-vinyl]-5-(2-trifluoromethyl-phenyl)-1H-benzimidazole,
(E)-2-(2-{2-[2-(2-trifluoromethyl-phenyl)-vinyl]-1H-benzimidazol-5-yl}-phenyl)-propan-2-ol, (E)-dimethyl-(2-{2-[2-(4-trifluoromethyl-phenyl)-vinyl]-1H-benzimidazol-5-yl}-benzyl)-amine,
(E)-2-{2-[2-(4-trifluoromethyl-phenyl)-vinyl]-1H-benzimidazol-5-yl}-benzaldehyde,
(E)-methyl-(2-{2-[2-(4-trifluoromethyl-phenyl)-vinyl]-1H-benzimidazol-5-yl}-benzyl)-amine,
(E)-5-(2-trifluoromethyl-phenyl)-2-[2-(4-trifluoromethyl-phenyl)-vinyl]-1H-benzimidazole,
(E)-5-(2-trifluoromethoxy-phenyl)-2-[2-(4-trifluoromethyl-phenyl)-vinyl]-1H-benzimidazole,
2-[2-(2-phenylethynyl-1H-benzimidazol-5-yl)-phenyl]-propan-2-ol,
2-(2-phenylethynyl-1H-benzimidazol-5-yl)-benzenesulfonamide,
(E)-5-(2-aminosulfonylamino-methylphenyl)-2-[2-(4-trifluoromethyl-phenyl)-vinyl]-1H-benzimidazole,
2-{2-[2-(4-trifluoromethyl-phenylethynyl)-1H-benzimidazol-5-yl]-phenyl"-propan-2-ol,
2-(2-{2-[2-(4-methoxy-phenyl)-cyclopropyl]-1H-benzimidazol-5-yl}-phenyl)-propan-2-ol,
2-(2-{2-[2-(4-trifluoromethoxy-phenyl)-cyclopropyl]-1H-benzimidazol-5-yl}-phenyl)-propan-2-ol,
2-{2-[2-(4-trifluoromethyl-phenyl)-cyclopropyl]-1H-benzimidazol-5-yl}-benzamide,
N-tert-butyl-2-{2-[2-(4-trifluoromethyl-phenyl)-cyclopropyl]-1H-benzimidazol-5-yl}-benzenesulfonamide,
5-(2-methanesulfonyl-phenyl)-2-[2-(4-trifluoromethyl-phenyl)-cyclopropyl]-1H-benzimidazole,
2-(2-{2-[(1R,2R)-2-(4-trifluoromethyl-phenyl)-cyclopropyl]-1H-benzimidazol-5-yl}-phenyl)-propan-2-ol,
2-{2-[(1R,2R)-2-(4-trifluoromethyl-phenyl)-cyclopropyl]-1H-benzimidazol-5-yl}-benzenesulfonamide,
2-(2-{2-[(1S,2S)-2-(4-trifluoromethyl-phenyl)-cyclopropyl]-1H-benzimidazol-5-yl}-phenyl)-propan-2-ol,
2-{2-[(1S,2S)-2-(4-trifluoromethyl-phenyl)-cyclopropyl]-1H-benzimidazol-5-yl}-benzenesulfonamide,
2-(2-{2-[(1S,2R)-2-(4-trifluoromethyl-phenyl)-cyclopropyl]-1H-benzimidazol-5-yl}-phenyl)-propan-2-ol,
2-{2-[(1R,2S)-2-(4-trifluoromethyl-phenyl)-cyclopropyl]-1H-benzimidazol-5-yl}-benzenesulfonamide,
2-(2-{2-[(1R,2S)-2-(4-trifluoromethyl-phenyl)-cyclopropyl]-1H-benzimidazol-5-yl}-phenyl)-propan-2-ol, and
2-{2-[(1S,2R)-2-(4-trifluoromethyl-phenyl)-cyclopropyl]-1H-benzimidazol-5-yl}-benzenesulfonamide.

10. The compound of claim 9, wherein the compound is selected from the group consisting of:
(E)-1-(2-{2-[2-(4-tert-butyl-phenyl)-vinyl]-1H-benzimidazol-5-yl}-phenyl)-ethanone,
(E)-1-(2-{2-[2-(4-tert-butyl-phenyl)-vinyl]-1H-benzimidazol-5-yl}-phenyl)-ethanol,
(E)-2-{2-[2-(4-tert-butyl-phenyl)-vinyl]-1H-benzimidazol-5-yl}-phenol,
(E)-N-(2-{2-[2-(4-tert-butyl-phenyl)-vinyl]-1H-benzimidazol-5-yl}-phenyl)-acetamide,
(E)-2-{2-[2-(4-tert-butyl-phenyl)-vinyl]-1H-benzimidazol-5-yl}-benzamide,
(E)-3-{2-[2-(4-tert-butyl-phenyl)-vinyl]-1H-benzimidazol-5-yl}-benzamide,
(E)-4-{2-[2-(4-tert-butyl-phenyl)-vinyl]-1H-benzimidazol-5-yl}-benzamide,
(E)-N-(4-{2-[2-(4-tert-butyl-phenyl)-vinyl]-1H-benzimidazol-5-yl}-phenyl)-acetamide,
(E)-N-(2-{2-[2-(4-tert-butyl-phenyl)-vinyl]-1H-benzimidazol-5-yl}-phenyl)-methanesulfonamide,
(E)-(2-{2-[2-(4-tert-butyl-phenyl)-vinyl]-1H-benzimidazol-5-yl}-phenyl)-carbamic acid tert-butyl ester,
(E)-2-{2-[2-(4-tert-butyl-phenyl)-vinyl]-1H-benzimidazol-5-yl}-phenylamine,
(E)-(2-{2-[2-(4-tert-butyl-phenyl)-vinyl]-1H-benzimidazol-5-yl}-phenyl)-methanol,
(E)-2-{2-[2-(4-trifluoromethyl-phenyl)-vinyl]-1H-benzimidazol-5-yl}-benzamide,
(E)-2-{2-[2-(4-trifluoromethyl-phenyl)-vinyl]-1H-benzimidazol-5-yl}-phenol,
(E)-1-(2-{2-[2-(4-trifluoromethyl-phenyl)-vinyl]-1H-benzimidazol-5-yl}-phenyl)-ethanone,
(E)-1-(2-{2-[2-(4-trifluoromethyl-phenyl)-vinyl]-1H-benzimidazol-5-yl}-phenyl)-ethanol,
(E)-N-(2-{2-[2-(4-trifluoromethyl-phenyl)-vinyl]-1H-benzimidazol-5-yl}-phenyl)-methanesulfonamide,
(E)-2-(2-{2-[2-(4-trifluoromethyl-phenyl)-vinyl]-1H-benzimidazol-5-yl}-phenyl)-propan-2-ol,
(E)-2-{2-[2-(4-trifluoromethoxy-phenyl)-vinyl]-1H-benzimidazol-5-yl}-benzamide,
(E)-1-(2-{2-[2-(4-trifluoromethoxy-phenyl)-vinyl]-1H-benzimidazol-5-yl}-phenyl)-ethanone,
(E)-1-(2-{2-[2-(4-trifluoromethoxy-phenyl)-vinyl]-1H-benzimidazol-5-yl}-phenyl)-ethanol,
(E)-N-(2-{2-[2-(4-trifluoromethoxy-phenyl)-vinyl]-1H-benzimidazol-5-yl}-phenyl)-methanesulfonamide,
(E)-2-(2-{2-[2-(4-trifluoromethoxy-phenyl)-vinyl]-1H-benzimidazol-5-yl}-phenyl)-propan-2-ol,
(E)-N-(2-{2-[2-(3,4-difluoro-phenyl)-vinyl]-1H-benzimidazol-5-yl}-phenyl)-acetamide,
(E)-N-(3-{2-[2-(3,4-difluoro-phenyl)-vinyl]-1H-benzimidazol-5-yl}-phenyl)-acetamide,
(E)-2-{2-[2-(3,4-difluoro-phenyl)-vinyl]-1H-benzimidazol-5-yl}-benzamide,
(E)-1-(2-{2-[2-(3,4-difluoro-phenyl)-vinyl]-1H-benzimidazol-5-yl}-phenyl)-ethanone,
(E)-N-(2-{2-[2-(3,4-difluoro-phenyl)-vinyl]-1H-benzimidazol-5-yl}-phenyl)-methanesulfonamide,
2-{2-[3-(4-tert-butyl-phenyl)-propyl]-1H-benzimidazol-5-yl}-phenol,
(E)-(2-{2-[2-(4-trifluoromethylsulfanyl-phenyl)-vinyl]-1H-benzimidazol-5-yl}-phenyl)-methanol,
(E)-2-{2-[2-(4-trifluoromethylsulfanyl-phenyl)-vinyl]-1H-benzimidazol-5-yl}-phenol,
(E)-N-(2-{2-[2-(4-trifluoromethylsulfanyl-phenyl)-vinyl]-1H-benzimidazol-5-yl}-phenyl)-acetamide,
(E)-2-{2-[2-(4-trifluoromethylsulfanyl-phenyl)-vinyl]-1H-benzimidazol-5-yl}-benzamide,
(E)-1-(2-{2-[2-(4-trifluoromethylsulfanyl-phenyl)-vinyl]-1H-benzimidazol-5-yl}-phenyl)-ethanone,
(E)-1-(2-{2-[2-(4-trifluoromethanesulfonyl-phenyl)-vinyl]-1H-benzimidazol-5-yl}-phenyl)-ethanone,
(E)-2-{2-[2-(4-trifluoromethanesulfonyl-phenyl)-vinyl]-1H-benzimidazol-5-yl}-phenol,
(E)-(2-{2-[2-(4-trifluoromethanesulfonyl-phenyl)-vinyl]-1H-benzimidazol-5-yl}-phenyl)-methanol,
(E)-N-(2-{2-[2-(4-trifluoromethanesulfonyl-phenyl)-vinyl]-1H-benzimidazol-5-yl}-phenyl)-acetamide,
(E)-2-{2-[2-(4-trifluoromethanesulfonyl-phenyl)-vinyl]-1H-benzimidazol-5-yl}-benzamide,
(E)-1-(2-{2-[2-(4-trifluoromethanesulfonyl-phenyl)-vinyl]-1H-benzimidazol-5-yl}-phenyl)-ethanol,
(E)-2-(2-{2-[2-(4-trifluoromethanesulfonyl-phenyl)-vinyl]-1H-benzimidazol-5-yl}-phenyl)-propan-2-ol,
(E)-2-{2-[2-(4-tert-butyl-phenyl)-vinyl]-6-trifluoromethyl-1H-benzimidazol-5-yl}-phenol,
(E)-3-{2-[2-(4-tert-butyl-phenyl)-vinyl]-6-trifluoromethyl-1H-benzimidazol-5-yl}-phenol, (E)-N-(2-{2-[2-(4-tert-butyl-phenyl)-vinyl]-6-trifluorom-
ethyl-1H-benzimidazol-5-yl}-phenyl)-acetamide,
(E)-(2-{2-[2-(4-tert-butyl-phenyl)-vinyl]-6-trifluorom-
ethyl-1H-benzimidazol-5-yl}-phenyl)-methanol,
(E)-2-[2-(4-tert-butyl-phenyl)-vinyl]-5-(2-fluoro-phe-
nyl)-6-trifluoromethyl-1H-benzimidazole,
(E)-2-{2-[2-(4-tert-butyl-phenyl)-vinyl]-6-trifluorom-
ethyl-1H-benzimidazol-5-yl}-benzamide,
(E)-(2-{2-[2-(4-tert-butyl-phenyl)-vinyl]-6-trifluorom-
ethyl-1H-benzimidazol-5-yl}-phenyl)-carbamic acid
tert-butyl ester,
(E)-N-(2-{2-[2-(4-tert-butyl-phenyl)-vinyl]-6-trifluorom-
ethyl-1H-benzimidazol-5-yl}-phenyl)-methane-
sulfonamide,
(E)-N-(2-{6-trifluoromethyl-2-[2-(4-trifluoromethyl-phe-
nyl)-vinyl]-1H-benzimidazol-5-yl}-phenyl)-aceta-
mide,
(E)-1-(2-{6-trifluoromethyl-2-[2-(4-trifluoromethyl-phe-
nyl)-vinyl]-1H-benzimidazol-5-yl}-phenyl)-ethanone,
(E)-(2-{6-trifluoromethyl-2-[2-(4-trifluoromethyl-phe-
nyl)-vinyl]-1H-benzimidazol-5-yl}-phenyl)-methanol,
(E)-2-{6-fluoro-2-[2-(4-trifluoromethyl-phenyl)-vinyl]-
1H-benzimidazol-5-yl}-phenol,
(E)-3-{6-fluoro-2-[2-(4-trifluoromethyl-phenyl)-vinyl]-
1H-benzimidazol-5-yl}-phenol,
(E)-(2-{6-fluoro-2-[2-(4-trifluoromethyl-phenyl)-vinyl]-
1H-benzimidazol-5-yl}-phenyl)-methanol,
(E)-1-(2-{6-fluoro-2-[2-(4-trifluoromethyl-phenyl)-vi-
nyl]-1H-benzimidazol-5-yl}-phenyl)-ethanone,
(E)-2-{6-fluoro-2-[2-(4-trifluoromethyl-phenyl)-vinyl]-
1H-benzimidazol-5-yl}-benzamide,
(E)-N-(2-{6-fluoro-2-[2-(4-trifluoromethyl-phenyl)-vi-
nyl]-1H-benzimidazol-5-yl}-phenyl)-acetamide,
(E)-N-(2-{6-fluoro-2-[2-(4-trifluoromethyl-phenyl)-vi-
nyl]-1H-benzimidazol-5-yl}-phenyl)-methanesulfona-
mide,
(E)-(2-{6-chloro-2-[2-(4-trifluoromethyl-phenyl)-vinyl]-
1H-benzimidazol-5-yl}-phenyl)-methanol,
(E)-1-(2-{6-chloro-2-[2-(4-trifluoromethyl-phenyl)-vi-
nyl]-1H-benzimidazol-5-yl}-phenyl)-ethanone,
(E)-2-{6-chloro-2-[2-(4-trifluoromethyl-phenyl)-vinyl]-
1H-benzimidazol-5-yl}-phenol,
(E)-2-{2-[2-(4-trifluoromethoxy-phenyl)-vinyl]-1H-ben-
zimidazol-5-yl}-benzenesulfonamide,
(E)-2-{2-[2-(4-trifluoromethyl-phenyl)-vinyl]-1H-benz-
imidazol-5-yl}-benzenesulfonamide,
(E)-2-{2-[2-(4-trifluoromethanesulfonyl-phenyl)-vinyl]-
1H-benzimidazol-5-yl}-benzenesulfonamide,
(E)-N-(2-{2-[2-(4-chloro-phenyl)-vinyl]-1H-benzimida-
zol-5-yl}-phenyl)-methanesulfonamide,
(E)-2-(2-{2-[2-(4-chloro-phenyl)-vinyl]-1H-benzimida-
zol-5-yl}-phenyl)-propan-2-ol,
(E)-2-{2-[2-(4-chloro-phenyl)-vinyl]-1-benzimidazol-5-
yl}-benzenesulfonamide,
(E)-N-(2-{2-[2-(4-methanesulfonyl-phenyl)-vinyl]-1H-
benzimidazol-5-yl}-phenyl)-methanesulfonamide,
(E)-2-(2-{2-[2-(4-methanesulfonyl-phenyl)-vinyl]-1H-
benzimidazol-5-yl}-phenyl)-propan-2-ol,
(E)-2-{2-[2-(4-methanesulfonyl-phenyl)-vinyl]-1H-benz-
imidazol-5-yl}-benzenesulfonamide,
(E)-N-[2-(2-{2-[4-(2,2,2-trifluoro-ethoxy)-phenyl]-vi-
nyl}-1H-benzimidazol-5-yl)-phenyl]-methanesulfona-
mide,
(E)-N-[2-(2-{2-[4-(2,2,3,3,3-pentafluoro-propoxy)-phe-
nyl]-vinyl}-1H-benzimidazol-5-yl)-phenyl]-methane-
sulfonamide, (E)-N-(2-{2-[2-(3-trifluoromethyl-phenyl)-vinyl]-1H-
benzimidazol-5-yl}-phenyl)-methanesulfonamide,
(E)-2-(2-{2-[2-(3-trifluoromethyl-phenyl)-vinyl]-1H-
benzimidazol-5-yl}-phenyl)-propan-2-ol,
2-{2-[2-(4-trifluoromethyl-phenyl)-cyclopropyl]-1H-
benzimidazol-5-yl}-benzenesulfonamide,
2-(2-{2-[2-(4-chloro-phenyl)-cyclopropyl]-1H-benzimi-
dazol-5-yl}-phenyl)-propan-2-ol,
2-(2-{2-[2-(3-trifluoromethyl-phenyl)-cyclopropyl]-1H-
benzimidazol-5-yl}-phenyl)-propan-2-ol,
2-[2-(4-trifluoromethyl-phenylethynyl)-1H-benzimida-
zol-5-yl]-benzenesulfonamide,
2-{2-[2-(3-trifluoromethyl-phenylethynyl)-1H-benzimi-
dazol-5-yl]-phenyl"-propan-2-ol,
2-[2-(3-trifluoromethyl-phenylethynyl)-1H-benzimida-
zol-5-yl]-benzenesulfonamide,
(E)-N-tert-butyl-2-{2-[2-(4-trifluoromethyl-phenyl)-vi-
nyl]-1H-benzimidazol-5-yl}-benzenesulfonamide,
(E)-N-methyl-2-{2-[2-(4-trifluoromethyl-phenyl)-vinyl]-
1H-benzimidazol-5-yl}-benzenesulfonamide,
(E)-2-hydroxy-1-(2-{2-[2-(4-trifluoromethyl-phenyl)-vi-
nyl]-1H-benzimidazol-5-yl}-phenyl)-ethanone,
(E)-2-{2-[2-(4-bromo-phenyl)-vinyl]-1H-benzimidazol-
5-yl}-N-methyl-benzenesulfonamide,
(E)-N-methyl-2-[2-(2-p-tolyl-vinyl)-1H-benzimidazol-5-
yl]-benzenesulfonamide,
(E)-2-{2-[2-(4-fluoro-phenyl)-vinyl]-1H-benzimidazol-
5-yl}-N-methyl-benzenesulfonamide,
(E)-2-{2-[2-(3,4-dichloro-phenyl)-vinyl]-1H-benzimida-
zol-5-yl}-N-methyl-benzenesulfonamide,
(E)-2-{2-[2-(3-bromo-4-fluoro-phenyl)-vinyl]-1H-benz-
imidazol-5-yl}-N-methyl-benzenesulfonamide,
(E)-2-{2-[2-(4-dimethylamino-phenyl)-vinyl]-1H-benz-
imidazol-5-yl}-N-methyl-benzenesulfonamide,
(E)-2-{2-[2-(3-fluoro-4-trifluoromethyl-phenyl)-vinyl]-
1H-benzimidazol-5-yl}-N-methyl-benzenesulfona-
mide,
(E)-2-{2-[2-(2-fluoro-4-trifluoromethyl-phenyl)-vinyl]-
1H-benzimidazol-5-yl}-N-methyl-benzenesulfona-
mide,
(E)-2-{2-[2-(3-chloro-4-fluoro-phenyl)-vinyl]-1H-benz-
imidazol-5-yl}-N-methyl-benzenesulfonamide,
(E)-2-{2-[2-(3-fluoro-5-trifluoromethyl-phenyl)-vinyl]-
1H-benzimidazol-5-yl}-N-methyl-benzenesulfona-
mide,
(E)-N-methyl-2-{2-[2-(2,3,4-trifluoro-phenyl)-vinyl]-
1H-benzimidazol-5-yl}-benzenesulfonamide,
(E)-N-methyl-2-{2-[2-(2,4,5-trifluoro-phenyl)-vinyl]-
1H-benzimidazol-5-yl}-benzenesulfonamide,
(E)-2-{2-[2-(2,3-difluoro-phenyl)-vinyl]-1H-benzimida-
zol-5-yl}-N-methyl-benzenesulfonamide,
(E)-2-{2-[2-(2,5-difluoro-phenyl)-vinyl]-1H-benzimida-
zol-5-yl}-N-methyl-benzenesulfonamide,
(E)-2-{2-[2-(2,6-difluoro-phenyl)-vinyl]-1H-benzimida-
zol-5-yl}-N-methyl-benzenesulfonamide,
(E)-2-{2-[2-(3,5-difluoro-phenyl)-vinyl]-1H-benzimida-
zol-5-yl}-N-methyl-benzenesulfonamide,
(E)-2-{2-[2-(3,4-difluoro-phenyl)-vinyl]-1H-benzimida-
zol-5-yl}-N-methyl-benzenesulfonamide,
(E)-2-{2-[2-(4-fluoro-2-trifluoromethyl-phenyl)-vinyl]-
1H-benzimidazol-5-yl}-N-methyl-benzenesulfona-
mide,
(E)-2-{2-[2-(4-fluoro-3-trifluoromethyl-phenyl)-vinyl]-
1H-benzimidazol-5-yl}-N-methyl-benzenesulfona-
mide, (E)-2-{2-[2-(2-fluoro-3-trifluoromethyl-phenyl)-vinyl]-1H-benzimidazol-5-yl}-N-methyl-benzenesulfonamide,
(E)-2-{2-[2-(3,5-bis-trifluoromethyl-phenyl)-vinyl]-1H-benzimidazol-5-yl}-N-methyl-benzenesulfonamide,
(E)-2-{2-[2-(2,5-bis-trifluoromethyl-phenyl)-vinyl]-1H-benzimidazol-5-yl}-N-methyl-benzenesulfonamide,
(E)-2-{2-[2-(3-chloro-2-fluoro-phenyl)-vinyl]-1H-benzimidazol-5-yl}-N-methyl-benzenesulfonamide,
(E)-2-{2-[2-(2-chloro-6-fluoro-phenyl)-vinyl]-1H-benzimidazol-5-yl}-N-methyl-benzenesulfonamide,
(E)-2-{2-[2-(2,4-dichloro-phenyl)-vinyl]-1H-benzimidazol-5-yl}-N-methyl-benzenesulfonamide,
(E)-2-{2-[2-(3-bromo-phenyl)-vinyl]-1H-benzimidazol-5-yl}-N-methyl-benzenesulfonamide,
(E)-2-{2-[2-(4-chloro-2-fluoro-phenyl)-vinyl]-1H-benzimidazol-5-yl}-N-methyl-benzenesulfonamide,
(E)-2-{2-[2-(4-chloro-2-methanesulfonyl-phenyl)-vinyl]-1H-benzimidazol-5-yl}-N-methyl-benzenesulfonamide,
(E)-N-methyl-2-{2-[2-(4-trifluoromethylsulfanyl-phenyl)-vinyl]-1H-benzimidazol-5-yl}-benzenesulfonamide,
(E)-N-methyl-2-{2-[2-(4-trifluoromethanesulfonyl-phenyl)-vinyl]-1H-benzimidazol-5-yl}-benzenesulfonamide,
(E)-N-methyl-2-{2-[2-(2-trifluoromethyl-phenyl)-vinyl]-1H-benzimidazol-5-yl}-benzenesulfonamide,
(E)-N-methyl-2-{2-[2-(3-trifluoromethoxy-phenyl)-vinyl]-1H-benzimidazol-5-yl}-benzenesulfonamide,
(E)-N-methyl-2-{2-[2-(4-trifluoromethoxy-phenyl)-vinyl]-1H-benzimidazol-5-yl}-benzenesulfonamide,
(E)-2-{2-[2-(2-chloro-phenyl)-vinyl]-1H-benzimidazol-5-yl}-N-methyl-benzenesulfonamide,
(E)-2-{2-[2-(4-chloro-phenyl)-vinyl]-1H-benzimidazol-5-yl}-N-methyl-benzenesulfonamide,
(E)-2-{2-[2-(2-bromo-phenyl)-vinyl]-1H-benzimidazol-5-yl}-N-methyl-benzenesulfonamide,
(E)-2-{2-[2-(2,4-difluoro-phenyl)-vinyl]-1H-benzimidazol-5-yl}-N-methyl-benzenesulfonamide,
(E)-2-{2-[2-(4-methanesulfonyl-phenyl)-vinyl]-1H-benzimidazol-5-yl}-N-methyl-benzenesulfonamide,
(E)-2-{2-[2-(2,4-difluoro-phenyl)-vinyl]-1H-benzimidazol-5-yl}-benzenesulfonamide,
(E)-2-{2-[2-(3,4-difluoro-phenyl)-vinyl]-1H-benzimidazol-5-yl}-benzenesulfonamide,
(E)-2-{2-[2-(2,3-difluoro-phenyl)-vinyl]-1H-benzimidazol-5-yl}-benzenesulfonamide,
(E)-2-{2-[2-(2,5-difluoro-phenyl)-vinyl]-1H-benzimidazol-5-yl}-benzenesulfonamide,
(E)-2-{2-[2-(3,5-difluoro-phenyl)-vinyl]-1H-benzimidazol-5-yl}-benzenesulfonamide,
(E)-2-{2-[2-(3-trifluoromethoxy-phenyl)-vinyl]-1H-benzimidazol-5-yl}-benzenesulfonamide,
(E)-2-{2-[2-(4-bromo-phenyl)-vinyl]-1H-benzimidazol-5-yl}-benzenesulfonamide,
(E)-2-{2-[2-(2-trifluoromethyl-phenyl)-vinyl]-1H-benzimidazol-5-yl}-benzenesulfonamide,
(E)-2-{2-[2-(2-chloro-phenyl)-vinyl]-1-benzimidazol-5-yl}-benzenesulfonamide,
(E)-2-{2-[2-(2-bromo-phenyl)-vinyl]-1H-benzimidazol-5-yl}-benzenesulfonamide,
(E)-2-{2-[2-(4-fluoro-2-trifluoromethyl-phenyl)-vinyl]-1H-benzimidazol-5-yl}-benzenesulfonamide,
(E)-2-{2-[2-(2-fluoro-3-trifluoromethyl-phenyl)-vinyl]-1H-benzimidazol-5-yl}-benzenesulfonamide,
(E)-2-{2-[2-(4-fluoro-3-trifluoromethyl-phenyl)-vinyl]-1H-benzimidazol-5-yl}-benzenesulfonamide,
(E)-2-{2-[2-(2,3,4-trifluoro-phenyl)-vinyl]-1H-benzimidazol-5-yl}-benzenesulfonamide,
(E)-2-{2-[2-(2,4,5-trifluoro-phenyl)-vinyl]-1H-benzimidazol-5-yl}-benzenesulfonamide,
(E)-2-{2-[2-(2,6-difluoro-phenyl)-vinyl]-1H-benzimidazol-5-yl}-benzenesulfonamide,
(E)-2-{2-[2-(3,5-bis-trifluoromethyl-phenyl)-vinyl]-1H-benzimidazol-5-yl}-benzenesulfonamide,
(E)-2-{2-[2-(2,5-bis-trifluoromethyl-phenyl)-vinyl]-1H-benzimidazol-5-yl}-benzenesulfonamide,
(E)-2-{2-[2-(4-chloro-2-methanesulfonyl-phenyl)-vinyl]-1H-benzimidazol-5-yl}-benzenesulfonamide,
(E)-2-{2-[2-(3-bromo-phenyl)-vinyl]-1H-benzimidazol-5-yl}-benzenesulfonamide,
(E)-2-{2-[2-(4-chloro-3-trifluoromethyl-phenyl)-vinyl]-1H-benzimidazol-5-yl}-benzenesulfonamide,
(E)-2-{2-[2-(5-bromo-2-fluoro-phenyl)-vinyl]-1H-benzimidazol-5-yl}-benzenesulfonamide,
(E)-2-{2-[2-(4-trifluoromethylsulfanyl-phenyl)-vinyl]-1H-benzimidazol-5-yl}-benzenesulfonamide,
(E)-N,N-dimethyl-2-{2-[2-(4-trifluoromethyl-phenyl)-vinyl]-1H-benzimidazol-5-yl}-benzenesulfonamide,
(E)-N-(2-{2-[2-(4-bromo-phenyl)-vinyl]-1H-benzimidazol-5-yl}-phenyl)-methanesulfonamide,
(E)-N-(2-{2-[2-(4-isopropyl-phenyl)-vinyl]-1H-benzimidazol-5-yl}-phenyl)-methanesulfonamide,
(E)-N-(2-{2-[2-(3-chloro-4-fluoro-phenyl)-vinyl]-1H-benzimidazol-5-yl}-phenyl)-methanesulfonamide,
(E)-N-(2-{2-[2-(3-bromo-4-fluoro-phenyl)-vinyl]-1H-benzimidazol-5-yl}-phenyl)-methanesulfonamide,
(E)-N-(2-{2-[2-(4-difluoromethoxy-phenyl)-vinyl]-1H-benzimidazol-5-yl}-phenyl)-methanesulfonamide,
(E)-N-(2-{2-[2-(3-fluoro-5-trifluoromethyl-phenyl)-vinyl]-1H-benzimidazol-5-yl}-phenyl)-methanesulfonamide,
(E)-N-{2-[2-(2-p-tolyl-vinyl)-1H-benzimidazol-5-yl]-phenyl"-methanesulfonamide,
(E)-N-(2-{2-[2-(4-dimethylamino-phenyl)-vinyl]-1H-benzimidazol-5-yl}-phenyl)-methanesulfonamide,
(E)-N-(2-{2-[2-(4-ethoxy-phenyl)-vinyl]-1H-benzimidazol-5-yl}-phenyl)-methanesulfonamide,
(E)-N-{2-[2-(2-naphthalen-2-yl-vinyl)-1H-benzimidazol-5-yl]-phenyl"-methanesulfonamide,
(E)-N-(2-{2-[2-(3,4-dichloro-phenyl)-vinyl]-1H-benzimidazol-5-yl}-phenyl)-methanesulfonamide,
(E)-N-(2-{2-[2-(3-fluoro-4-trifluoromethyl-phenyl)-vinyl]-1H-benzimidazol-5-yl}-phenyl)-methanesulfonamide,
(E)-N-(2-{2-[2-(2-fluoro-4-trifluoromethyl-phenyl)-vinyl]-1H-benzimidazol-5-yl}-phenyl)-methanesulfonamide,
(E)-5-(2-methanesulfonyl-phenyl)-2-[2-(4-trifluoromethyl-phenyl)-vinyl]-1H-benzimidazole,
(E)-2-{2-[2-(3-fluoro-4-trifluoromethyl-phenyl)-vinyl]-1H-benzimidazol-5-yl}-benzenesulfonamide,
(E)-2-{2-[2-(2-fluoro-4-trifluoromethyl-phenyl)-vinyl]-1H-benzimidazol-5-yl}-benzenesulfonamide,
(E)-2-{2-[2-(3-ethoxy-phenyl)-vinyl]-1H-benzimidazol-5-yl}-benzenesulfonamide,
(E)-2-(2-styryl-1H-benzimidazol-5-yl)-benzenesulfonamide,
(E)-2-{2-[2-(3,4-dichloro-phenyl)-vinyl]-1H-benzimidazol-5-yl}-benzenesulfonamide,
(E)-2-{2-[2-(4-chloro-2-fluoro-phenyl)-vinyl]-1H-benzimidazol-5-yl}-benzenesulfonamide, (E)-2-{2-[2-(4-isopropyl-phenyl)-vinyl]-1H-benzimidazol-5-yl}-benzenesulfonamide,
(E)-2-[2-(2-p-tolyl-vinyl)-1H-benzimidazol-5-yl]-benzenesulfonamide,
(E)-2-{2-[2-(3-chloro-2-fluoro-phenyl)-vinyl]-1H-benzimidazol-5-yl}-benzenesulfonamide,
(E)-2-{2-[2-(3-chloro-4-fluoro-phenyl)-vinyl]-1H-benzimidazol-5-yl}-benzenesulfonamide,
(E)-2-[2-(2-naphthalen-2-yl-vinyl)-1H-benzimidazol-5-yl]-benzenesulfonamide,
(E)-2-{2-[2-(4-fluoro-phenyl)-vinyl]-1H-benzimidazol-5-yl}-benzenesulfonamide,
(E)-2-{2-[2-(4-difluoromethyl-phenyl)-vinyl]-1H-benzimidazol-5-yl}-benzenesulfonamide,
(E)-2-{2-[2-(3-fluoro-5-trifluoromethyl-phenyl)-vinyl]-1H-benzimidazol-5-yl}-benzenesulfonamide,
(E)-2-{2-[2-(2,4-dichloro-phenyl)-vinyl]-1H-benzimidazol-5-yl}-benzenesulfonamide,
(E)-2-{2-[2-(2-chloro-6-fluoro-phenyl)-vinyl]-1H-benzimidazol-5-yl}-benzenesulfonamide,
(E)-2-{2-[2-(3-bromo-4-fluoro-phenyl)-vinyl]-1H-benzimidazol-5-yl}-benzenesulfonamide,
(E)-2-{2-[2-(4-ethoxy-phenyl)-vinyl]-1H-benzimidazol-5-yl}-benzenesulfonamide,
(E)-4-fluoro-2-{2-[2-(4-trifluoromethyl-phenyl)-vinyl]-1H-benzimidazol-5-yl}-benzenesulfonamide,
(E)-N-(2-{3-methyl-2-[2-(4-trifluoromethyl-phenyl)-vinyl]-3H-benzimidazol-5-yl}-phenyl)-methanesulfonamide,
(E)-4-trifluoromethyl-2-{2-[2-(4-trifluoromethyl-phenyl)-vinyl]-1H-benzimidazol-5-yl}-benzenesulfonamide,
(E)-5-trifluoromethyl-2-{2-[2-(4-trifluoromethyl-phenyl)-vinyl]-1H-benzimidazol-5-yl}-benzenesulfonamide,
(E)-1-[4-(2-{5-[2-(1-hydroxy-1-methyl-ethyl)-phenyl]-1H-benzimidazol-2-yl}-vinyl)-phenyl]-ethanone,
(E)-2-{2-[2-(2-quinolin-6-yl-vinyl)-1H-benzimidazol-5-yl]-phenyl}-propan-2-ol,
(E)-N-isopropyl-4-{2-[5-(2-methylsulfamoyl-phenyl)-1H-benzimidazol-2-yl]-vinyl}-benzamide,
(E)-2-{2-[2-(4-cyano-phenyl)-vinyl]-1H-benzimidazol-5-yl}-N-methyl-benzenesulfonamide,
(E)-N-(4-{2-[5-(2-methylsulfamoyl-phenyl)-1H-benzimidazol-2-yl]-vinyl"-phenyl)-acetamide,
(E)-4-{2-[5-(2-methylsulfamoyl-phenyl)-1H-benzimidazol-2-yl]-vinyl}-benzoic acid,
(E)-2-{2-[2-(1H-indol-6-yl)-vinyl]-1H-benzimidazol-5-yl}-N-methyl-benzenesulfonamide,
(E)-2-{2-[2-(2,4-bis-trifluoromethyl-phenyl)-vinyl]-1H-benzimidazol-5-yl}-N-methyl-benzenesulfonamide,
(E)-2-{2-[2-(4-acetyl-phenyl)-vinyl]-1H-benzimidazol-5-yl}-N-methyl-benzene sulfonamide,
(E)-2,2,2-trifluoro-N-(2-{2-[2-(4-trifluoromethyl-phenyl)-vinyl]-1H-benzimidazol-5-yl}-phenyl)-acetamide,
(E)-2,2,2-trifluoro-ethanesulfonic acid (2-{2-[2-(4-trifluoromethyl-phenyl)-vinyl]-1H-benzimidazol-5-yl}-phenyl)-amide,
(E)-2,2-dimethyl-N-(2-{2-[2-(4-trifluoromethyl-phenyl)-vinyl]-1H-benzimidazol-5-yl}-phenyl)-propionamide,
(E)-ethanesulfonic acid (2-{2-[2-(4-trifluoromethyl-phenyl)-vinyl]-1H-benzimidazol-5-yl}-phenyl)-amide,
(E)-(2-{2-[2-(4-trifluoromethyl-phenyl)-vinyl]-1H-benzimidazol-5-yl}-phenyl)-carbamic acid methyl ester,
(E)-2-(2-{2-[2-(4-tert-butyl-phenyl)-vinyl]-1H-benzimidazol-5-yl}-phenyl)-propan-2-ol,
(E)-2-{2-[2-(4-trifluoromethyl-phenyl)-vinyl]-1H-benzimidazol-5-yl}-phenylamine,
(E)-2-{2-[2-(4-trifluoromethyl-phenyl)-vinyl]-1H-benzimidazol-5-yl}-benzoic acid ethyl ester,
N-(2-{2-[2-(4-trifluoromethyl-phenyl)-cyclopropyl]-1H-benzimidazol-5-yl}-phenyl)-methanesulfonamide,
(E)-2-[2-(2-styryl-1H-benzimidazol-5-yl)-phenyl]-propan-2-ol,
(Z)-2-(2-{2-[2-(4-trifluoromethyl-phenyl)-vinyl]-1H-benzimidazol-5-yl}-phenyl)-propan-2-ol,
(E)-5-(2-aminosulfonylamino-phenyl)-2-[2-(4-trifluoromethyl-phenyl)-vinyl]-1H-benzimidazole,
2-(2-{2-[2-(4-trifluoromethyl-phenyl)-cyclopropyl]-1H-benzimidazol-5-yl}-phenyl)-propan-2-ol,
2-{2-[2-(4-trifluoromethyl-phenyl)-cyclopropyl]-1H-benzimidazol-5-yl}-phenol,
(2-{2-[2-(4-trifluoromethyl-phenyl)-cyclopropyl]-1H-benzimidazol-5-yl}-phenyl)-carbamic acid tert-butyl ester,
(2-{2-[2-(4-trifluoromethyl-phenyl)-cyclopropyl]-1H-benzimidazol-5-yl}-phenyl)-methanol,
(E)-N-{2-[2-(2-biphenyl-4-yl-vinyl]-1H-benzimidazol-5-yl]-phenyl"-methanesulfonamide,
(E)-(2-{2-[2-(4-trifluoromethyl-phenyl)-vinyl]-1H-benzimidazol-5-yl}-phenyl)-methanol,
(E)-N-(2-{1-methyl-2-[2-(4-trifluoromethyl-phenyl)-vinyl]-1H-benzimidazol-5-yl}-phenyl)-methanesulfonamide,
(E)-N-(2-{2-[2-(4-trifluoromethyl-phenyl)-vinyl]-1H-benzimidazol-5-yl}-phenyl)-acetamide,
(E)-(2-{2-[2-(4-trifluoromethyl-phenyl)-vinyl]-1H-benzimidazol-5-yl}-phenyl)-carbamic acid tert-butyl ester,
(E)-5-(2-methylsulfanyl-phenyl)-2-[2-(4-trifluoromethyl-phenyl)-vinyl]-1H-benzimidazole,
(E)-2-[2-(4-trifluoromethanesulfonyl-phenyl)-vinyl]-5-(2-trifluoromethyl-phenyl)-1H-benzimidazole,
(E)-2-(2-{2-[2-(2-trifluoromethyl-phenyl)-vinyl]-1H-benzimidazol-5-yl}-phenyl)-propan-2-ol,
(E)-dimethyl-(2-{2-[2-(4-trifluoromethyl-phenyl)-vinyl]-1H-benzimidazol-5-yl}-benzyl)-amine,
(E)-2-{2-[2-(4-trifluoromethyl-phenyl)-vinyl]-1H-benzimidazol-5-yl}-benzaldehyde,
(E)-methyl-(2-{2-[2-(4-trifluoromethyl-phenyl)-vinyl]-1H-benzimidazol-5-yl}-benzyl)-amine,
(E)-5-(2-trifluoromethyl-phenyl)-2-[2-(4-trifluoromethyl-phenyl)-vinyl]-1H-benzimidazole,
(E)-5-(2-trifluoromethoxy-phenyl)-2-[2-(4-trifluoromethyl-phenyl)-vinyl]-1H-benzimidazole,
2-[2-(2-phenylethynyl-1H-benzimidazol-5-yl)-phenyl]-propan-2-ol,
2-(2-phenylethynyl-1H-benzimidazol-5-yl)-benzenesulfonamide,
(E)-5-(2-aminosulfonylamino-methylphenyl)-2-[2-(4-trifluoromethyl-phenyl)-vinyl]-1H-benzimidazole,
2-{2-[2-(4-trifluoromethyl-phenylethynyl)-1H-benzimidazol-5-yl]-phenyl"-propan-2-ol,
2-(2-{2-[2-(4-methoxy-phenyl)-cyclopropyl]-1H-benzimidazol-5-yl}-phenyl)-propan-2-ol,
2-(2-{2-[2-(4-trifluoromethoxy-phenyl)-cyclopropyl]-1H-benzimidazol-5-yl}-phenyl)-propan-2-ol,
2-{2-[2-(4-trifluoromethyl-phenyl)-cyclopropyl]-1H-benzimidazol-5-yl}-benzamide,
N-tert-butyl-2-{2-[2-(4-trifluoromethyl-phenyl)-cyclopropyl]-1H-benzimidazol-5-yl}-benzenesulfonamide,
5-(2-methanesulfonyl-phenyl)-2-[2-(4-trifluoromethyl-phenyl)-cyclopropyl]-1H-benzimidazole, 2-(2-{2-[(1R,2R)-2-(4-trifluoromethyl-phenyl)-cyclopropyl]-1H-benzimidazol-5-yl}-phenyl)-propan-2-ol,
2-{2-[(1R,2R)-2-(4-trifluoromethyl-phenyl)-cyclopropyl]-1H-benzimidazol-5-yl}-benzenesulfonamide,
2-(2-{2-[(1S,2S)-2-(4-trifluoromethyl-phenyl)-cyclopropyl]-1H-benzimidazol-5-yl}-phenyl)-propan-2-ol,
2-{2-[(1S,2S)-2-(4-trifluoromethyl-phenyl)-cyclopropyl]-1H-benzimidazol-5-yl}-benzenesulfonamide,
2-(2-{2-[(1S,2R)-2-(4-trifluoromethyl-phenyl)-cyclopropyl]-1H-benzimidazol-5-yl}-phenyl)-propan-2-ol,
2-{2-[(1R,2S)-2-(4-trifluoromethyl-phenyl)-cyclopropyl]-1H-benzimidazol-5-yl}-benzenesulfonamide,
2-(2-{2-[(1R,2S)-2-(4-trifluoromethyl-phenyl)-cyclopropyl]-1H-benzimidazol-5-yl}-phenyl)-propan-2-ol, and
2-{2-[(1S,2R)-2-(4-trifluoromethyl-phenyl)-cyclopropyl]-1H-benzimidazol-5-yl}-benzenesulfonamide.

11. The compound of claim 9, wherein the compound is selected from the group consisting of:

(E)-C,C,C-trifluoro-N-(2-{2-[2-(4-trifluoromethoxy-phenyl)-vinyl]-1H-benzimidazol-5-yl}-phenyl)-methanesulfonamide,
(E)-C,C,C-trifluoro-N-(2-{2-[2-(4-trifluoromethyl-phenyl)-vinyl]-1H-benzimidazol-5-yl}-phenyl)-methanesulfonamide,
(E)-C,C,C-trifluoro-N-(2-{2-[2-(4-trifluoromethanesulfonyl-phenyl)-vinyl]-1H-benzimidazol-5-yl}-phenyl)-methanesulfonamide,
(E)-1-(2-{2-[2-(4-chloro-phenyl)-vinyl]-1H-benzimidazol-5-yl}-phenyl)-ethanone,
(E)-1-(2-{2-[2-(4-chloro-phenyl)-vinyl]-1H-benzimidazol-5-yl}-phenyl)-ethanol,
(E)-N-(2-{2-[2-(4-chloro-phenyl)-vinyl]-1H-benzimidazol-5-yl}-phenyl)-C,C,C-trifluoro-methanesulfonamide,
(E)-1-(2-{2-[2-(4-methanesulfonyl-phenyl)-vinyl]-1H-benzimidazol-5-yl}-phenyl)-ethanone,
(E)-1-(2-{2-[2-(4-methanesulfonyl-phenyl)-vinyl]-1H-benzimidazol-5-yl}-phenyl)-ethanol,
(E)-C,C,C-trifluoro-N-(2-{2-[2-(4-methanesulfonyl-phenyl)-vinyl]-1H-benzimidazol-5-yl}-phenyl)-methanesulfonamide,
(E)-1-[2-(2-{2-[4-(2,2,2-trifluoro-1-trifluoromethyl-ethoxy)-phenyl]-vinyl}-1H-benzimidazol-5-yl)-phenyl]-ethanone,
(E)-1-[2-(2-{2-[4-(2,2,2-trifluoro-1-trifluoromethyl-ethoxy)-phenyl]-vinyl}-1H-benzimidazol-5-yl)-phenyl]-ethanol,
(E)-N-[2-(2-{2-[4-(2,2,2-trifluoro-1-trifluoromethyl-ethoxy)-phenyl]-vinyl}-1H-benzimidazol-5-yl)-phenyl]-methanesulfonamide,
(E)-2-[2-(2-{2-[4-(2,2,2-trifluoro-1-trifluoromethyl-ethoxy)-phenyl]-vinyl}-1H-benzimidazol-5-yl)-phenyl]-propan-2-ol,
(E)-2-(2-{2-[4-(2,2,2-trifluoro-1-trifluoromethyl-ethoxy)-phenyl]-vinyl}-1H-benzimidazol-5-yl)-benzenesulfonamide,
(E)-C,C,C-trifluoro-N-[2-(2-{2-[4-(2,2,2-trifluoro-1-trifluoromethyl-ethoxy)-phenyl]-vinyl}-1H-benzimidazol-5-yl)-phenyl]-methanesulfonamide,
(E)-1-[2-(2-{2-[4-(2,2,2-trifluoro-ethoxy)-phenyl]-vinyl}-1H-benzimidazol-5-yl)-phenyl]-ethanone,
(E)-1-[2-(2-{2-[4-(2,2,2-trifluoro-ethoxy)-phenyl]-vinyl}-1H-benzimidazol-5-yl)-phenyl]-ethanol,
(E)-2-[2-(2-{2-[4-(2,2,2-trifluoro-ethoxy)-phenyl]-vinyl}-1H-benzimidazol-5-yl)-phenyl]-propan-2-ol,
(E)-2-(2-{2-[4-(2,2,2-trifluoro-ethoxy)-phenyl]-vinyl}-1H-benzimidazol-5-yl)-benzenesulfonamide,
(E)-C,C,C-trifluoro-N-[2-(2-{2-[4-(2,2,2-trifluoro-ethoxy)-phenyl]-vinyl}-1H-benzimidazol-5-yl)-phenyl]-methanesulfonamide,
(E)-1-[2-(2-{2-[4-(2,2,3,3,3-pentafluoro-propoxy)-phenyl]-vinyl}-1H-benzimidazol-5-yl)-phenyl]-ethanone,
(E)-1-[2-(2-{2-[4-(2,2,3,3,3-pentafluoro-propoxy)-phenyl]-vinyl}-1H-benzimidazol-5-yl)-phenyl]-ethanol,
(E)-2-[2-(2-{2-[4-(2,2,3,3,3-pentafluoro-propoxy)-phenyl]-vinyl}-1H-benzimidazol-5-yl)-phenyl]-propan-2-ol,
(E)-2-(2-{2-[4-(2,2,3,3,3-pentafluoro-propoxy)-phenyl]-vinyl}-1H-benzimidazol-5-yl)-benzenesulfonamide,
(E)-C,C,C-trifluoro-N-[2-(2-{2-[4-(2,2,3,3,3-pentafluoro-propoxy)-phenyl]-vinyl}-1H-benzimidazol-5-yl)-phenyl]-methanesulfonamide,
(E)-1-(2-{2-[2-(3-chloro-phenyl)-vinyl]-1H-benzimidazol-5-yl}-phenyl)-ethanone,
(E)-1-(2-{2-[2-(3-chloro-phenyl)-vinyl]-1H-benzimidazol-5-yl}-phenyl)-ethanol,
(E)-N-(2-{2-[2-(3-chloro-phenyl)-vinyl]-1H-benzimidazol-5-yl}-phenyl)-methanesulfonamide,
(E)-2-(2-{2-[2-(3-chloro-phenyl)-vinyl]-1H-benzimidazol-5-yl}-phenyl)-propan-2-ol,
(E)-2-{2-[2-(3-chloro-phenyl)-vinyl]-1H-benzimidazol-5-yl}-benzenesulfonamide,
(E)-N-(2-{2-[2-(3-chloro-phenyl)-vinyl]-1H-benzimidazol-5-yl}-phenyl)-C,C,C-trifluoro-methanesulfonamide,
(E)-1-(2-{2-[2-(3-trifluoromethyl-phenyl)-vinyl]-1H-benzimidazol-5-yl}-phenyl)-ethanone,
(E)-1-(2-{2-[2-(3-trifluoromethyl-phenyl)-vinyl]-1H-benzimidazol-5-yl}-phenyl)-ethanol,
(E)-2-{2-[2-(3-trifluoromethyl-phenyl)-vinyl]-1H-benzimidazol-5-yl}-benzenesulfonamide,
(E)-C,C,C-trifluoro-N-(2-{2-[2-(3-trifluoromethyl-phenyl)-vinyl]-1H-benzimidazol-5-yl}-phenyl)-methanesulfonamide,
(E)-N-(4-{2-[5-(2-acetyl-phenyl)-1H-benzimidazol-2-yl]-vinyl}-phenyl)-methanesulfonamide,
(E)-N-[4-(2-{5-[2-(1-hydroxy-ethyl)-phenyl]-1H-benzimidazol-2-yl}-vinyl)-phenyl]-methanesulfonamide,
(E)-N-(2-{2-[2-(4-methanesulfonylamino-phenyl)-vinyl]-1H-benzimidazol-5-yl}-phenyl)-methanesulfonamide,
(E)-N-[4-(2-{5-[2-(1-hydroxy-1-methyl-ethyl)-phenyl]-1H-benzimidazol-2-yl}-vinyl)-phenyl]-methanesulfonamide,
(E)-2-{2-[2-(4-methanesulfonylamino-phenyl)-vinyl]-1H-benzimidazol-5-yl}-benzenesulfonamide,
(E)-C,C,C-trifluoro-N-(2-{2-[2-(4-methanesulfonylamino-phenyl)-vinyl]-1H-benzimidazol-5-yl}-phenyl)-methanesulfonamide,
(E)-N-(4-{2-[5-(2-acetyl-phenyl)-1H-benzimidazol-2-yl]-vinyl}-phenyl)-C,C,C-trifluoro-methanesulfonamide,
(E)-C,C,C-trifluoro-N-[4-(2-{5-[2-(1-hydroxy-ethyl)-phenyl]-1H-benzimidazol-2-yl}-vinyl)-phenyl]-methanesulfonamide,
(E)-C,C,C-trifluoro-N-(4-{2-[5-(2-methanesulfonylamino-phenyl)-1H-benzimidazol-2-yl]-vinyl}-phenyl)-methanesulfonamide,
(E)-C,C,C-trifluoro-N-[4-(2-{5-[2-(1-hydroxy-1-methyl-ethyl)-phenyl]-1H-benzimidazol-2-yl}-vinyl)-phenyl]-methanesulfonamide,
(E)-2-{2-[2-(4-trifluoromethanesulfonylamino-phenyl)-vinyl]-1H-benzimidazol-5-yl}-benzenesulfonamide, (E)-C,C,C-trifluoro-N-(4-{2-[5-(2-trifluoromethane-sulfonylamino-phenyl)-1H-benzimidazol-2-yl]-vinyl}-phenyl)-methanesulfonamide,
2-{2-[2-(4-trifluoromethoxy-phenyl)-cyclopropyl]-1H-benzimidazol-5-yl}-benzenesulfonamide,
2-{2-[2-(4-trifluoromethanesulfonyl-phenyl)-cyclopropyl]-1H-benzimidazol-5-yl}-benzenesulfonamide,
C,C,C-trifluoro-N-(2-{2-[2-(4-trifluoromethoxy-phenyl)-cyclopropyl]-1H-benzimidazol-5-yl}-phenyl)-methanesulfonamide,
C,C,C-trifluoro-N-(2-{2-[2-(4-trifluoromethyl-phenyl)-cyclopropyl]-1H-benzimidazol-5-yl}-phenyl)-methanesulfonamide,
C,C,C-trifluoro-N-(2-{2-[2-(4-trifluoromethanesulfonyl-phenyl)-cyclopropyl]-1H-benzimidazol-5-yl}-phenyl)-methanesulfonamide,
1-(2-{2-[2-(4-chloro-phenyl)-cyclopropyl]-1H-benzimidazol-5-yl}-phenyl)-ethanone,
1-(2-{2-[2-(4-chloro-phenyl)-cyclopropyl]-1H-benzimidazol-5-yl}-phenyl)-ethanol,
N-(2-{2-[2-(4-chloro-phenyl)-cyclopropyl]-1H-benzimidazol-5-yl}-phenyl)-methanesulfonamide,
2-{2-[2-(4-chloro-phenyl)-cyclopropyl]-1H-benzimidazol-5-yl}-benzenesulfonamide,
N-(2-{2-[2-(4-chloro-phenyl)-cyclopropyl]-1H-benzimidazol-5-yl}-phenyl)-C,C,C-trifluoro-methanesulfonamide,
1-(2-{2-[2-(4-methanesulfonyl-phenyl)-cyclopropyl]-1H-benzimidazol-5-yl}-phenyl)-ethanone,
1-(2-{2-[2-(4-methanesulfonyl-phenyl)-cyclopropyl]-1H-benzimidazol-5-yl}-phenyl)-ethanol,
N-(2-{2-[2-(4-methanesulfonyl-phenyl)-cyclopropyl]-1H-benzimidazol-5-yl}-phenyl)-methanesulfonamide,
2-(2-{2-[2-(4-methanesulfonyl-phenyl)-cyclopropyl]-1H-benzimidazol-5-yl}-phenyl)-propan-2-ol,
2-{2-[2-(4-methanesulfonyl-phenyl)-cyclopropyl]-1H-benzimidazol-5-yl}-benzenesulfonamide,
C,C,C-trifluoro-N-(2-{2-[2-(4-methanesulfonyl-phenyl)-cyclopropyl]-1H-benzimidazol-5-yl}-phenyl)-methanesulfonamide,
1-[2-(2-{2-[4-(2,2,2-trifluoro-1-trifluoromethyl-ethoxy)-phenyl]-cyclopropyl}-1H-benzimidazol-5-yl)-phenyl]-ethanone,
1-[2-(2-{2-[4-(2,2,2-trifluoro-1-trifluoromethyl-ethoxy)-phenyl]-cyclopropyl}-1H-benzimidazol-5-yl)-phenyl]-ethanol,
N-[2-(2-{2-[4-(2,2,2-trifluoro-1-trifluoromethyl-ethoxy)-phenyl]-cyclopropyl}-1H-benzimidazol-5-yl)-phenyl]-methanesulfonamide,
2-[2-(2-{2-[4-(2,2,2-trifluoro-1-trifluoromethyl-ethoxy)-phenyl]-cyclopropyl}-1H-benzimidazol-5-yl)-phenyl]-propan-2-ol,
2-(2-{2-[4-(2,2,2-trifluoro-1-trifluoromethyl-ethoxy)-phenyl]-cyclopropyl}-1H-benzimidazol-5-yl)-benzenesulfonamide,
C,C,C-trifluoro-N-[2-(2-{2-[4-(2,2,2-trifluoro-1-trifluoromethyl-ethoxy)-phenyl]-cyclopropyl}-1H-benzimidazol-5-yl)-phenyl]-methanesulfonamide,
1-[2-(2-{2-[4-(2,2,2-trifluoro-ethoxy)-phenyl]-cyclopropyl}-1H-benzimidazol-5-yl)-phenyl]-ethanone,
1-[2-(2-{2-[4-(2,2,2-trifluoro-ethoxy)-phenyl]-cyclopropyl}-1H-benzimidazol-5-yl)-phenyl]-ethanol,
N-[2-(2-{2-[4-(2,2,2-trifluoro-ethoxy)-phenyl]-cyclopropyl}-1H-benzimidazol-5-yl)-phenyl]-methanesulfonamide,
2-[2-(2-{2-[4-(2,2,2-trifluoro-ethoxy)-phenyl]-cyclopropyl}-1H-benzimidazol-5-yl)-phenyl]-propan-2-ol,
2-(2-{2-[4-(2,2,2-trifluoro-ethoxy)-phenyl]-cyclopropyl}-1H-benzimidazol-5-yl)-benzenesulfonamide,
C,C,C-trifluoro-N-[2-(2-{2-[4-(2,2,2-trifluoro-ethoxy)-phenyl]-cyclopropyl}-1H-benzimidazol-5-yl)-phenyl]-methanesulfonamide,
1-[2-(2-{2-[4-(2,2,3,3,3-pentafluoro-propoxy)-phenyl]-cyclopropyl}-1H-benzimidazol-5-yl)-phenyl]-ethanone,
1-[2-(2-{2-[4-(2,2,3,3,3-pentafluoro-propoxy)-phenyl]-cyclopropyl}-1H-benzimidazol-5-yl)-phenyl]-ethanol,
N-[2-(2-{2-[4-(2,2,3,3,3-pentafluoro-propoxy)-phenyl]-cyclopropyl}-1H-benzimidazol-5-yl)-phenyl]-methanesulfonamide,
2-[2-(2-{2-[4-(2,2,3,3,3-pentafluoro-propoxy)-phenyl]-cyclopropyl}-1H-benzimidazol-5-yl)-phenyl]-propan-2-ol,
2-(2-{2-[4-(2,2,3,3,3-pentafluoro-propoxy)-phenyl]-cyclopropyl}-1H-benzimidazol-5-yl)-benzenesulfonamide,
C,C,C-trifluoro-N-[2-(2-{2-[4-(2,2,3,3,3-pentafluoro-propoxy)-phenyl]-cyclopropyl}-1H-benzimidazol-5-yl)-phenyl]-methanesulfonamide,
1-(2-{2-[2-(3-chloro-phenyl)-cyclopropyl]-1H-benzimidazol-5-yl}-phenyl)-ethanone,
1-(2-{2-[2-(3-chloro-phenyl)-cyclopropyl]-1H-benzimidazol-5-yl}-phenyl)-ethanol,
N-(2-{2-[2-(3-chloro-phenyl)-cyclopropyl]-1H-benzimidazol-5-yl}-phenyl)-methanesulfonamide,
2-(2-{2-[2-(3-chloro-phenyl)-cyclopropyl]-1H-benzimidazol-5-yl}-phenyl)-propan-2-ol,
2-{2-[2-(3-chloro-phenyl)-cyclopropyl]-1H-benzimidazol-5-yl}-benzenesulfonamide,
N-(2-{2-[2-(3-chloro-phenyl)-cyclopropyl]-1H-benzimidazol-5-yl}-phenyl)-C,C,C-trifluoro-methanesulfonamide,
1-(2-{2-[2-(3-trifluoromethyl-phenyl)-cyclopropyl]-1H-benzimidazol-5-yl}-phenyl)-ethanone,
1-(2-{2-[2-(3-trifluoromethyl-phenyl)-cyclopropyl]-1H-benzimidazol-5-yl}-phenyl)-ethanol,
N-(2-{2-[2-(3-trifluoromethyl-phenyl)-cyclopropyl]-1H-benzimidazol-5-yl}-phenyl)-methanesulfonamide,
2-{2-[2-(3-trifluoromethyl-phenyl)-cyclopropyl]-1H-benzimidazol-5-yl}-benzenesulfonamide,
C,C,C-trifluoro-N-(2-{2-[2-(3-trifluoromethyl-phenyl)-cyclopropyl]-1H-benzimidazol-5-yl}-phenyl)-methanesulfonamide,
N-(4-{2-[5-(2-acetyl-phenyl)-1H-benzimidazol-2-yl]-cyclopropyl}-phenyl)-methanesulfonamide,
N-[4-(2-{5-[2-(1-hydroxy-ethyl)-phenyl]-1H-benzimidazol-2-yl}-cyclopropyl)-phenyl]-methanesulfonamide,
N-(2-{2-[2-(4-methanesulfonylamino-phenyl)-cyclopropyl]-1H-benzimidazol-5-yl}-phenyl)-methanesulfonamide,
N-[4-(2-{5-[2-(1-hydroxy-1-methyl-ethyl)-phenyl]-1H-benzimidazol-2-yl}-cyclopropyl)-phenyl]-methanesulfonamide,
2-{2-[2-(4-methanesulfonylamino-phenyl)-cyclopropyl]-1H-benzimidazol-5-yl}-benzenesulfonamide,
C,C,C-trifluoro-N-(2-{2-[2-(4-methanesulfonylamino-phenyl)-cyclopropyl]-1H-benzimidazol-5-yl}-phenyl)-methanesulfonamide,
N-(4-{2-[5-(2-acetyl-phenyl)-1H-benzimidazol-2-yl]-cyclopropyl}-phenyl)-C,C,C-trifluoro-methanesulfonamide,
C,C,C-trifluoro-N-[4-(2-{5-[2-(1-hydroxy-ethyl)-phenyl]-1H-benzimidazol-2-yl}-cyclopropyl)-phenyl]-methanesulfonamide, C,C,C-trifluoro-N-(4-{2-[5-(2-methanesulfonylamino-phenyl)-1H-benzimidazol-2-yl]-cyclopropyl}-phenyl)-methanesulfonamide,
C,C,C-trifluoro-N-[4-(2-{5-[2-(1-hydroxy-1-methyl-ethyl)-phenyl]-1H-benzimidazol-2-yl}-cyclopropyl)-phenyl]-methanesulfonamide,
2-{2-[2-(4-trifluoromethanesulfonylamino-phenyl)-cyclopropyl]-1H-benzimidazol-5-yl}-benzenesulfonamide,
C,C,C-trifluoro-N-(2-{2-[2-(4-trifluoromethanesulfonylamino-phenyl)-cyclopropyl]-1H-benzimidazol-5-yl}-phenyl)-methanesulfonamide,
2-[2-(4-trifluoromethoxy-phenylethynyl)-1H-benzimidazol-5-yl]-benzenesulfonamide,
2-[2-(4-trifluoromethanesulfonyl-phenylethynyl)-1H-benzimidazol-5-yl]-benzenesulfonamide,
C,C,C-trifluoro-N-{2-[2-(4-trifluoromethoxy-phenyl-ethynyl)-1H-benzimidazol-5-yl]-phenyl}-methanesulfonamide,
C,C,C-trifluoro-N-{2-[2-(4-trifluoromethyl-phenylethynyl)-1H-benzimidazol-5-yl]-phenyl}-methanesulfonamide,
C,C,C-trifluoro-N-{2-[2-(4-trifluoromethanesulfonyl-phenylethynyl)-1H-benzimidazol-5-yl]-phenyl}-methanesulfonamide,
1-{2-[2-(4-chloro-phenylethynyl)-1H-benzimidazol-5-yl]-phenyl}-ethanone,
1-{2-[2-(4-chloro-phenylethynyl)-1H-benzimidazol-5-yl]-phenyl}-ethanol,
N-{2-[2-(4-chloro-phenylethynyl)-1H-benzimidazol-5-yl]-phenyl}-methanesulfonamide,
2-{2-[2-(4-chloro-phenylethynyl)-1H-benzimidazol-5-yl]-phenyl}-propan-2-ol,
2-[2-(4-chloro-phenylethynyl)-1H-benzimidazol-5-yl]-benzenesulfonamide,
N-{2-[2-(4-chloro-phenylethynyl)-1H-benzimidazol-5-yl]-phenyl}-C,C,C-trifluoro-methanesulfonamide,
1-{2-[2-(4-methanesulfonyl-phenylethynyl)-1H-benzimidazol-5-yl]-phenyl}-ethanone,
1-{2-[2-(4-methanesulfonyl-phenylethynyl)-1H-benzimidazol-5-yl]-phenyl}-ethanol,
N-{2-[2-(4-methanesulfonyl-phenylethynyl)-1H-benzimidazol-5-yl]-phenyl}-methanesulfonamide,
2-{2-[2-(4-methanesulfonyl-phenylethynyl)-1H-benzimidazol-5-yl]-phenyl}-propan-2-ol,
2-[2-(4-methanesulfonyl-phenylethynyl)-1H-benzimidazol-5-yl]-benzenesulfonamide,
C,C,C-trifluoro-N-{2-[2-(4-methanesulfonyl-phenylethynyl)-1H-benzimidazol-5-yl]-phenyl}-methanesulfonamide,
1-(2-{2-[4-(2,2,2-trifluoro-1-trifluoromethyl-ethoxy)-phenylethynyl]-1H-benzimidazol-5-yl}-phenyl)-ethanone,
1-(2-{2-[4-(2,2,2-trifluoro-1-trifluoromethyl-ethoxy)-phenylethynyl]-1H-benzimidazol-5-yl}-phenyl)-ethanol,
N-(2-{2-[4-(2,2,2-trifluoro-1-trifluoromethyl-ethoxy)-phenylethynyl]-1H-benzimidazol-5-yl}-phenyl)-methanesulfonamide,
2-(2-{2-[4-(2,2,2-trifluoro-1-trifluoromethyl-ethoxy)-phenylethynyl]-1H-benzimidazol-5-yl}-phenyl)-propan-2-ol,
2-{2-[4-(2,2,2-trifluoro-1-trifluoromethyl-ethoxy)-phenylethynyl]-1H-benzimidazol-5-yl}-benzenesulfonamide,
C,C,C-trifluoro-N-(2-{2-[4-(2,2,2-trifluoro-1-trifluoromethyl-ethoxy)-phenylethynyl]-1H-benzimidazol-5-yl}-phenyl)-methanesulfonamide,
1-(2-{2-[4-(2,2,2-trifluoro-ethoxy)-phenylethynyl]-1H-benzimidazol-5-yl}-phenyl)-ethanone,
1-(2-{2-[4-(2,2,2-trifluoro-ethoxy)-phenylethynyl]-1H-benzimidazol-5-yl}-phenyl)-ethanol,
N-(2-{2-[4-(2,2,2-trifluoro-ethoxy)-phenylethynyl]-1H-benzimidazol-5-yl}-phenyl)-methanesulfonamide,
2-(2-{2-[4-(2,2,2-trifluoro-ethoxy)-phenylethynyl]-1H-benzimidazol-5-yl}-phenyl)-propan-2-ol,
2-{2-[4-(2,2,2-trifluoro-ethoxy)-phenylethynyl]-1H-benzimidazol-5-yl}-benzenesulfonamide,
C,C,C-trifluoro-N-(2-{2-[4-(2,2,2-trifluoro-ethoxy)-phenylethynyl]-1H-benzimidazol-5-yl}-phenyl)-methanesulfonamide,
1-(2-{2-[4-(2,2,3,3,3-pentafluoro-propoxy)-phenylethynyl]-1H-benzimidazol-5-yl}-phenyl)-ethanone,
1-(2-{2-[4-(2,2,3,3,3-pentafluoro-propoxy)-phenylethynyl]-1H-benzimidazol-5-yl}-phenyl)-ethanol,
N-(2-{2-[4-(2,2,3,3,3-pentafluoro-propoxy)-phenylethynyl]-1H-benzimidazol-5-yl}-phenyl)-methanesulfonamide,
2-(2-{2-[4-(2,2,3,3,3-pentafluoro-propoxy)-phenylethynyl]-1H-benzimidazol-5-yl}-phenyl)-propan-2-ol,
2-{2-[4-(2,2,3,3,3-pentafluoro-propoxy)-phenylethynyl]-1H-benzimidazol-5-yl}-benzenesulfonamide,
C,C,C-trifluoro-N-(2-{2-[4-(2,2,3,3,3-pentafluoro-propoxy)-phenylethynyl]-1H-benzimidazol-5-yl}-phenyl)-methanesulfonamide,
1-{2-[2-(3-chloro-phenylethynyl)-1H-benzimidazol-5-yl]-phenyl}-ethanone,
2-{2-[2-(3-chloro-phenylethynyl)-1H-benzimidazol-5-yl]-phenyl}-propan-2-ol,
N-{2-[2-(3-chloro-phenylethynyl)-1H-benzimidazol-5-yl]-phenyl}-methanesulfonamide,
1-{2-[2-(3-chloro-phenylethynyl)-1H-benzimidazol-5-yl]-phenyl}-ethanol,
2-[2-(3-chloro-phenylethynyl)-1H-benzimidazol-5-yl]-benzenesulfonamide,
N-{2-[2-(3-chloro-phenylethynyl)-1H-benzimidazol-5-yl]-phenyl}-C,C,C-trifluoro-methanesulfonamide,
1-{2-[2-(3-trifluoromethyl-phenylethynyl)-1H-benzimidazol-5-yl]-phenyl}-ethanone,
1-{2-[2-(3-trifluoromethyl-phenylethynyl)-1H-benzimidazol-5-yl]-phenyl}-ethanol,
N-{2-[2-(3-trifluoromethyl-phenylethynyl)-1H-benzimidazol-5-yl]-phenyl}-methanesulfonamide,
C,C,C-trifluoro-N-{2-[2-(3-trifluoromethyl-phenylethynyl)-1H-benzimidazol-5-yl]-phenyl}-methanesulfonamide,
N-{4-[5-(2-acetyl-phenyl)-1H-benzimidazol-2-yl-ethynyl]-phenyl}-methanesulfonamide,
N-(4-{5-[2-(1-hydroxy-ethyl)-phenyl]-1H-benzimidazol-2-yl-ethynyl}-phenyl)-methanesulfonamide,
N-{2-[2-(4-methanesulfonylamino-phenylethynyl)-1H-benzimidazol-5-yl]-phenyl}-methanesulfonamide,
N-(4-{5-[2-(1-hydroxy-1-methyl-ethyl)-phenyl]-1H-benzimidazol-2-yl-ethynyl}-phenyl)-methanesulfonamide,
2-[2-(4-methanesulfonylamino-phenylethynyl)-1H-benzimidazol-5-yl]-benzenesulfonamide,
C,C,C-trifluoro-N-{2-[2-(4-methanesulfonylamino-phenylethynyl)-1H-benzimidazol-5-yl]-phenyl}-methanesulfonamide,
N-{4-[5-(2-acetyl-phenyl)-1H-benzimidazol-2-yl-ethynyl]-phenyl}-C,C,C-trifluoro-methanesulfonamide, C,C,C-trifluoro-N-(4-{5-[2-(1-hydroxy-ethyl)-phenyl]-
1H-benzimidazol-2-yl-ethynyl}-phenyl)-methane-
sulfonamide,
C,C,C-trifluoro-N-{4-[5-(2-methanesulfonylamino-phe-
nyl)-1H-benzimidazol-2-yl-ethynyl]-phenyl}-methane
sulfonamide,
C,C,C-trifluoro-N-(4-{5-[2-(1-hydroxy-1-methyl-ethyl)-
phenyl]-1H-benzimidazol-2-yl-ethynyl}-phenyl)-
methanesulfonamide,
2-[2-(4-trifluoromethanesulfonylamino-phenylethynyl)-
1H-benzimidazol-5-yl]-benzenesulfonamide, and
C,C,C-trifluoro-N-{2-[2-(4-trifluoromethanesulfony-
lamino-phenylethynyl)-1H-benzimidazol-5-yl]-phe-
nyl}-methanesulfonamide.

12. A salt of the compound of Formula (I) as claimed in claim 1, wherein the salt is selected from the group consisting of acetate, adipate, benzenesulfonate, benzoate, bicarbonate, bisulfate, bitartrate, borate, bromide, calcium, camsylate (or camphorsulphonate), carbonate, chloride, choline, clavulanate, citrate, dihydrochloride, disodium, edetate, fumarate, gluconate, glutamate, hydrabamine, hydrobromine, hydrochloride, iodide, isothionate, lactate, malate, maleate, mandelate, mesylate, nitrate, oleate, pamoate, palmitate, phosphate/diphosphate, salicylate, sodium, stearate, sulfate, succinate, tartrate, tromethane, tosylate, trichloroacetate and trifluoroacetate.

13. The salt of claim 12, wherein the salt is selected from the group consisting of disodium, hydrochloride and sodium.

14. A pharmaceutical composition comprising the compound of claim 1 and one or more pharmaceutically acceptable carriers, excipients or diluents.

15. A method of treating a patient suffering from pain, wherein the pain is due to disease that causes inflammatory pain, burning pain or post-operative pain, said method comprising administering to the patient an effective amount of the compound of claim 1.

16. The method of claim 15, wherein the effective amount of the compound of claim 1 is in a range of from about 0.001 mg/kg/day to about 300 mg/kg/day.

17. A process for preparing the compound of claim 1 comprising the steps of:

Step A. reacting an aldehyde QQ1 with malonic acid and a catalytic amount of piperidine in pyridine at elevated temperatures to provide an acid QQ2:

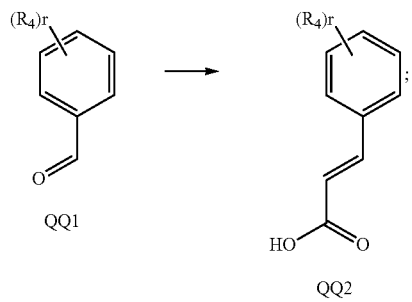

Step B. reacting the acid QQ2 with oxalyl chloride and a catalytic amount of DMF in a solvent such as methylene chloride to provide an acid chloride QQ3:

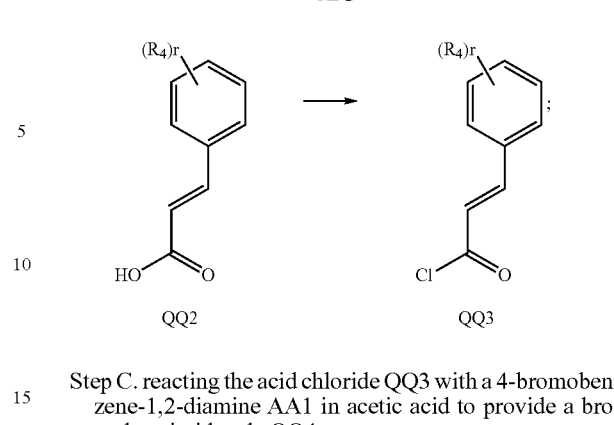

Step C. reacting the acid chloride QQ3 with a 4-bromobenzene-1,2-diamine AA1 in acetic acid to provide a bromobenzimidazole QQ4:

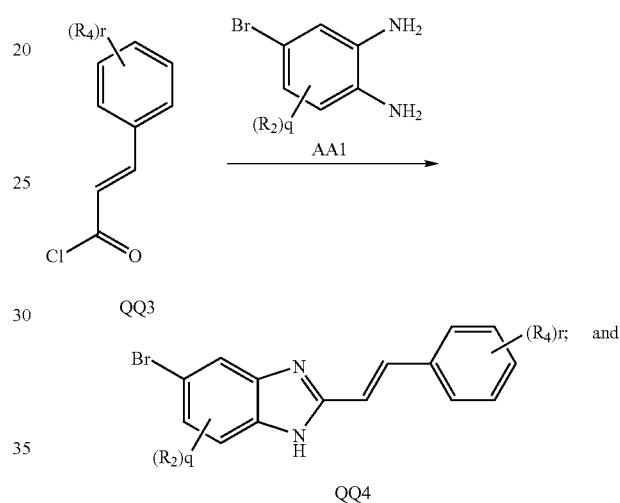

Step D. reacting the bromobenzimidazole QQ4 with a suitably substituted phenyl boronic acid in the presence of a reagent and a catalytic amount of a palladium catalyst in a solvent to give an alcohol substituted benzimidazole QQ5, representative of a compound of Formula (I):

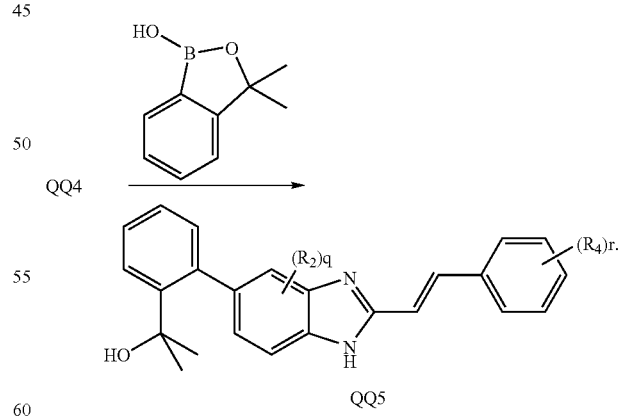

* * * * *